US009040558B2

(12) United States Patent
Baruah et al.

(10) Patent No.: US 9,040,558 B2
(45) Date of Patent: *May 26, 2015

(54) SUBSTITUTED BENZYLAMINO QUINOLINES AS CHOLESTEROL ESTER-TRANSFER PROTEIN INHIBITORS

(75) Inventors: Anima Baruah, Hyderabad (IN); Dibyendu De, Suwanee, GA (US); Ish Kumar Khanna, Alpharetta, GA (US); Sivaram Pillarisetti, Norcross, GA (US); Santanu Maitra, Hyderabad (IN); Christopher W. Alexander, Atlanta, GA (US); Jennepalli Sreenu, Hyderabad (IN); Indu Dager, Uttar Pradesh (IN); Shanavas Alikunju, Secunderabad (IN)

(73) Assignee: DR. REDDY'S LABORATORIES LTD., Hyderabad (IN)

( * ) Notice: Subject to any disclaimer, the term of this patent is extended or adjusted under 35 U.S.C. 154(b) by 1560 days.

This patent is subject to a terminal disclaimer.

(21) Appl. No.: 11/320,120

(22) Filed: Dec. 28, 2005

(65) Prior Publication Data
US 2006/0178514 A1    Aug. 10, 2006

Related U.S. Application Data

(60) Provisional application No. 60/640,798, filed on Dec. 31, 2004.

(51) Int. Cl.

| | |
|---|---|
| *C07D 239/78* | (2006.01) |
| *A61K 31/47* | (2006.01) |
| *A61K 31/4709* | (2006.01) |
| *C07D 221/04* | (2006.01) |
| *C07D 401/12* | (2006.01) |
| *C07D 213/73* | (2006.01) |
| *C07D 213/74* | (2006.01) |
| *C07D 215/38* | (2006.01) |
| *C07D 241/20* | (2006.01) |
| *C07D 498/04* | (2006.01) |
| *C07D 417/12* | (2006.01) |
| *C07D 471/04* | (2006.01) |
| *C07D 215/14* | (2006.01) |
| *C07D 403/12* | (2006.01) |
| *C07D 401/04* | (2006.01) |
| *C07D 413/12* | (2006.01) |

(52) U.S. Cl.
CPC ............ *C07D 213/73* (2013.01); *C07D 239/78* (2013.01); *C07D 213/74* (2013.01); *C07D 215/38* (2013.01); *C07D 221/04* (2013.01); *C07D 241/20* (2013.01); *C07D 401/12* (2013.01); *C07D 413/12* (2013.01); *C07D 417/12* (2013.01); *C07D 471/04* (2013.01); *C07D 498/04* (2013.01)

(58) Field of Classification Search
CPC ... C07D 239/78; A61K 31/47; A61K 31/4709
USPC ........... 546/162, 157, 159; 514/313, 312, 314
See application file for complete search history.

(56) References Cited

U.S. PATENT DOCUMENTS

| | | | |
|---|---|---|---|
| 2,858,309 A | 10/1958 | Druey et al. | |
| 2,965,643 A | 12/1960 | Druey et al. | |
| 3,546,295 A | 12/1970 | Maravetz | |
| 5,086,073 A | 2/1992 | White et al. | |
| 5,260,331 A | 11/1993 | White et al. | |
| 5,348,953 A | 9/1994 | Doherty et al. | |
| 5,422,355 A | 6/1995 | White et al. | |
| 5,456,923 A | 10/1995 | Nakamichi et al. | |
| 5,474,989 A | 12/1995 | Hashimoto et al. | |
| 5,482,967 A * | 1/1996 | Natsugari et al. | 514/457 |
| 5,491,152 A | 2/1996 | Wilde et al. | |
| 5,977,170 A | 11/1999 | Commons et al. | |
| 5,985,326 A | 11/1999 | Butler | |
| 6,008,362 A | 12/1999 | Commons et al. | |
| 6,121,271 A | 9/2000 | Dollings et al. | |
| 6,350,786 B1 | 2/2002 | Albano et al. | |
| 6,432,987 B2 | 8/2002 | Gunther et al. | |
| 6,548,555 B1 | 4/2003 | Curatolo et al. | |
| 6,576,644 B2 * | 6/2003 | Bi et al. | 514/313 |
| 6,638,522 B1 | 10/2003 | Mulye | |

(Continued)

FOREIGN PATENT DOCUMENTS

| | | |
|---|---|---|
| AU | 660026 B2 | 6/1995 |
| CA | 2395259 A1 | 7/2001 |

(Continued)

OTHER PUBLICATIONS

Al-Dabbagh and Smith, "Species differences in oxidative drug metabolism: some basic considerations," Archives of toxicology. Supplement. Archiv fur Toxikologie. supplement, vol. 7, pp. 219-231 (1984).*
Hans Bundgaard, Design of Prodrugs, p. 1. © 1985 Elsevier Science Publishers.*
Richard B. Silverman, The Organic Chemistry of Drug Design and Drug Action, pp. 352-400. © 1992 Academic Press, Inc.*
Vippagunta et. al. (Advanced Drug Delivery reviews, 2001, 48, pp. 3-26).*
Kerns, Edward et al, Drug-like Properties: Concepts, Structure Design and Methods: from ADME to Toxicity Optimization, (Elsevier, 2008) pp. 92-93.*
Goosen et al., Pharmaceutical Research vol. 19, No. 1, 13-19 (Jan. 2002).*
Fourie, International Journal of Pharmaceutics vol. 279, Issues 1-2, Jul. 26, 2004, pp. 59-66.*
Edwards, J. Med. Chem. 39 (1996), pp. 1112-1124.*
Rautio, Eur. J. Pharm. Sci. 11:157-163 (2000).*
Anzini et. al. (J. Med. Chem., 2001, 44, pp. 1134-1150).*

(Continued)

*Primary Examiner* — Susanna Moore
(74) *Attorney, Agent, or Firm* — Pergament Gilman & Cepeda LLP; Milagros A. Cepeda; Edward D. Pergament

(57) ABSTRACT

The invention is directed to novel substituted benzylamino quinolines, compounds comprising substituted benzylamino quinolines, methods of making substituted benzylamino quinolines, the use of substituted benzylamino quinolines for treating or preventing a variety of conditions or diseases associated with lipoprotein metabolism, and the use of substituted benzylamino quinolines as cholesterol ester-transfer protein inhibitors.

28 Claims, No Drawings

(56) References Cited

U.S. PATENT DOCUMENTS

| | | | |
|---|---|---|---|
| 6,710,089 B2 | 3/2004 | Sikorski et al. | |
| 6,713,499 B2 | 3/2004 | Flohr et al. | |
| 6,723,753 B2 | 4/2004 | Sikorski et al. | |
| 6,730,679 B1 | 5/2004 | Roy et al. | |
| 7,008,640 B2 | 3/2006 | Watanabe et al. | |
| 7,034,013 B2 | 4/2006 | Thompson et al. | |
| 7,037,528 B2 | 5/2006 | Kipp et al. | |
| 7,078,057 B2 | 7/2006 | Kerkhof | |
| 7,081,255 B2 | 7/2006 | Baert et al. | |
| 8,030,359 B2 | 10/2011 | Geers et al. | |
| 2002/0177587 A1* | 11/2002 | Bi et al. | 514/210.21 |
| 2003/0054037 A1 | 3/2003 | Babcock et al. | |
| 2003/0072801 A1 | 4/2003 | Curatolo et al. | |
| 2003/0104063 A1 | 6/2003 | Babcock et al. | |
| 2003/0114454 A1 | 6/2003 | Sikorski et al. | |
| 2003/0170309 A1 | 9/2003 | Babcock et al. | |
| 2003/0198674 A1 | 10/2003 | Curatolo et al. | |
| 2004/0039018 A1 | 2/2004 | Ruggeri | |
| 2004/0053842 A1 | 3/2004 | Nguyen et al. | |
| 2004/0185102 A1 | 9/2004 | Friesen et al. | |
| 2005/0038007 A1 | 2/2005 | Curatolo et al. | |
| 2005/0049239 A1 | 3/2005 | Huang et al. | |
| 2005/0059810 A1 | 3/2005 | Maeda et al. | |
| 2006/0178514 A1 | 8/2006 | Baruah et al. | |
| 2009/0118328 A1 | 5/2009 | Friesen et al. | |
| 2009/0227580 A1 | 9/2009 | Kishida et al. | |
| 2010/0249148 A1 | 9/2010 | Ohgiya et al. | |

FOREIGN PATENT DOCUMENTS

| | | | |
|---|---|---|---|
| DE | 294706 A5 | 10/1991 | |
| DE | 19615262 A1 | 10/1997 | |
| DE | 19845202 A1 | 4/2000 | |
| DE | 19930075 A1 | 1/2001 | |
| DE | 19962300 A1 | 6/2001 | |
| EP | 0298666 A2 | 1/1989 | |
| EP | 0553016 A1 | 7/1993 | |
| EP | 0585500 A1 | 3/1994 | |
| EP | 0585913 A2 | 3/1994 | |
| EP | 0604798 A1 | 7/1994 | |
| EP | 0802188 A1 | 10/1997 | |
| EP | 1108426 A2 | 6/2001 | |
| EP | 1741424 A2 | 1/2007 | |
| GB | 2 087 390 | * | 5/1982 |
| JP | 01104052 A2 | 4/1989 | |
| JP | 07285962 A2 | 10/1995 | |
| JP | 08092224 A2 | 4/1996 | |
| JP | 08092225 A2 | 4/1996 | |
| JP | 11209366 A2 | 8/1999 | |
| JP | 2001163779 A2 | 6/2001 | |
| WO | WO-93/00332 A1 | 1/1993 | |
| WO | WO-93/10099 A1 | 5/1993 | |
| WO | WO-94/05648 A1 | 3/1994 | |
| WO | WO-94/13636 A1 | 6/1994 | |
| WO | WO-95/05363 A1 | 2/1995 | |
| WO | WO 96/02509 | * | 2/1996 |
| WO | WO-96/16650 A1 | 6/1996 | |
| WO | 9804528 A2 | 2/1998 | |
| WO | WO-98/09946 A1 | 3/1998 | |
| WO | WO-98/27053 A1 | 6/1998 | |
| WO | WO-98/57925 A1 | 12/1998 | |
| WO | WO-98/57927 A1 | 12/1998 | |
| WO | WO-98/57928 A1 | 12/1998 | |
| WO | WO-99/19300 A1 | 4/1999 | |
| WO | WO-99/51224 A1 | 10/1999 | |
| WO | WO-00/17165 A1 | 3/2000 | |
| WO | WO-00/19969 A1 | 4/2000 | |
| WO | WO-00/50398 A2 | 8/2000 | |
| WO | WO-01/00623 A1 | 1/2001 | |
| WO | WO-01/02350 A2 | 1/2001 | |
| WO | WO-01/22954 A2 | 4/2001 | |
| WO | WO-01/47913 A2 | 7/2001 | |
| WO | WO-01/56560 A1 | 8/2001 | |
| WO | WO-01/60369 A1 | 8/2001 | |
| WO | WO-01/60458 A2 | 8/2001 | |
| WO | WO-01/85671 A2 | 11/2001 | |
| WO | WO-02/11710 A2 | 2/2002 | |
| WO | WO-02/22584 A1 | 3/2002 | |
| WO | WO-02/42273 A2 | 5/2002 | |
| WO | WO-02/068417 A2 | 9/2002 | |
| WO | WO-02/070462 A1 | 9/2002 | |
| WO | WO-02/090349 A1 | 11/2002 | |
| WO | WO-03/000295 A2 | 1/2003 | |
| WO | WO-03/030909 A1 | 4/2003 | |
| WO | WO-03/063832 A1 | 8/2003 | |
| WO | WO-03/087088 A2 | 10/2003 | |
| WO | WO-2004/020393 A1 | 3/2004 | |
| WO | WO-2004/073709 A1 | 9/2004 | |
| WO | WO-2004/078128 A2 | 9/2004 | |
| WO | WO-2004/078169 A1 | 9/2004 | |
| WO | WO-2005/000811 A1 | 1/2005 | |
| WO | WO-2005/021525 A1 | 3/2005 | |
| WO | WO-2005/030185 A2 | 4/2005 | |
| WO | 2005100298 A1 | 10/2005 | |
| WO | WO-2005/095395 A2 | 10/2005 | |
| WO | WO-2005/095409 A2 | 10/2005 | |
| WO | WO-2005/097806 A1 | 10/2005 | |
| WO | 2006056854 A1 | 6/2006 | |
| WO | 2007/075194 A1 | 7/2007 | |
| ZA | 9204659 | 3/1993 | |

OTHER PUBLICATIONS

U.S. Patent and Trademark Office, Office Action/Election/Restrictions, mailed Apr. 1, 2009, U.S. Appl. No. 11/478,547, filed Jun. 28, 2006, Anima Baruah.

Response to Restriction Requirement, filed May 1, 2009 with the U.S. Patent and Trademark Office, in response to the outstanding Office Action/Election/Restrictions, mailed Apr. 1, 2009, U.S. Appl. No. 11/478,547, filed Jun. 28, 2006, Anima Baruah.

U.S. Patent and Trademark Office, Non-Final Office Action, mailed Jul. 9, 2009, U.S. Appl. No. 11/478,547, filed Jun. 28, 2006, Anima Baruah.

Response to Non-Final Office Action, filed Jan. 8, 2010 with the U.S. Patent and Trademark Office, in response to the outstanding Non-Final Office Action, mailed Jul. 9, 2009, U.S. Appl. No. 11/478,547, filed Jun. 28, 2006, Anima Baruah.

U.S. Patent and Trademark Office, Non-Final Office Action, mailed Apr. 28, 2010, U.S. Appl. No. 11/478,547, filed Jun. 28, 2006, Anima Baruah.

Intellectual Property Office of New Zealand, Ministry of Economic Development, Examination Report, mailed Mar. 1, 2010, New Zealand Patent Application No. 569415, Reddy US Therapeutics, Inc.

Institute of Mexican Industrial Property, Official Action, mailed Mar. 19, 2010, Mexican Patent Application No. MX/a/2007/007919, Reddy US Therapeutics, Inc.

European Patent Office, Extended European Search Report, date of completion of the search Jun. 11, 2010, mailed Jun. 22, 2010, European Patent Application No. 06 77 4300, Applicant Dr. Reddy's Laboratories Ltd.

The Patent Office of the People's Republic of China, Office Action issued Aug. 11, 2010, Chinese Patent Application No. 200580048913.X, Applicant: Reddy US Therapeutics, Inc.

Gordon, D., et al., "High Density Lipoprotein Cholesterol and Cardiovascular Disease", Circulation, 1989, vol. 79(1), pp. 8-15, American Heart Association.

Despres, J., et al., "HDL-Cholesterol as a Marker of Coronary Heart Disease Risk: The Quebec Cardiovascular Study", Atherosclerosis, 2000, vol. 153, (2) pp. 263-272, Elsevier.

Berge, S., et al., "Pharmaceutical Salts", J. Pharma Sci., 1977, vol. 66(1), pp. 1-19.

Wilman, D., "Prodrugs in Cancer Chemotherapy", Biochem Soc Trans, 615th Meeting, 1986, vol. 14, pp. 375-385.

Stella, et al., "Prodrugs: A Chemical Approach to Targeted Drug Delivery", Directed Drug Delivery, 1985, pp. 247-267.

Ali, M. et al., "An Efficient and Facile Synthesis of 2-Chloro-3-formyl Quinolines from Acetanilides in. Micellar Media . . . ", Synlett, 2001, No. 2, pp. 251-253.

(56) References Cited

OTHER PUBLICATIONS

Paine, III, J., "A Convenient Synthesis of Nicotinate Esters from 3-Cyanopyridones", J. Heterocyclic Chemistry, 1987, No. 24, pp. 351-355.
Boatman, S., et al., "Alkylations at the Methyl or Alpha-Methylene Group of 6- or 4-Alkyl-3-cyano-2(1)-pyridones . . . ", J. Organic Chemistry, 1965, vol. 30(11), 1), pp. 3593-4359.
Capelli, A., et al., "Design, Synthesis, Structural Studies, Biological Evaluation, and Computational Simulations . . . ", J. Med Chem, 2004, vol. 47(10), pp. 2574-2586.
Izumi, T., et al., "1H-Imidazo[4,5-c]quinoline Derivatives . . . ", Biorganic & Medicinal Chemistry, 2003, vol. 11(12), 2541-2550.
Yin, J. et al., "Palladium-Catalyzed Intermolecular Coupling of Aryl Halides and Amides", Organic Letters, 2000, vol. 2(8), pp. 1101-1104.
Frazen, R., "The Suzuki, the Heck and the Stille Reaction . . . ", Canadian J of Chem, 2000, vol. 78(7), pp. 957-962.
Negishi, E., et al., "Cyclic Carbopalladation. A Versatile Synthetic Methodology . . . ", Chemical Reviews, 1996, vol. 96(1), pp. 365-394.
McGee, Jr., K., et al., "Fusiococcin Synthesis by Intramolecular [4+4] Photocycloaddition . . . ", Synthesis 2001, pp. 1185-1196.
Bisgaier, C., et al., "Use of Fluorescent Cholesteryl Ester Microemulsions . . . ", J. Lipid Res., 1993, vol. 34(9), pp. 1625-1634.
Epps, D., et al., "Method for Measuring the Activities of Cholesteryl Ester Transfer Protein . . . ", Chem Phys Lipids, 1995, vol. 77(1), pp. 51-63.
Scully, J., "Some Amide Derivatives of Certain Aminomethylpyridines", J. American Chem Soc., 1958, vol. 75, pp. 3400-3403.
INPADOC/Family and Legal Status Search Results, obtained from Dialog Database #345, Jun. 14, 2006, 19 pgs.
Obtained from DELPHION website (www.delphion.com), 5 pgs. (1993).
International Search Report and Written Opinion dated Feb. 25, 2013, for corresponding International Patent Application No. PCT/IB2012/002435.
International Search Report and Written Opinion dated May 8, 2013, for corresponding International Patent Application No. PCT/IB2012/002056.
International Search Report and Written Opinion dated Mar. 27, 2014, for corresponding International Patent Application No. PCT/IB2013/002909.
Toshiya Kai et al., "Oral Absorption Improvement of Poorly Soluble Drug Using Solid Dispersion Technique", Chem. Pharm. Bull., Mar. 1996, pp. 568-571, vol. 43-issue No. 3, Pharmaceutical Society of Japan.
Tomaz Einfalt et al., "Methods of amorphization and investigation of the amorphous state", Acta Pharm., 2013, pp. 305-334, vol. 63.
Tae-Wan Kim et al., "Modified Release of Coated Sugar Spheres Using Drug-Containing Polymeric Dispersions", Arch Pharm Res, 2007, pp. 124-130, vol. 30-issue No. 1.
Tae-Wan Kim et al., "Characterization of Dual Layered Pellets for Sustained Release of Poorly Water-Soluble Drug", Chem. Pharm. Bull., Jul. 2007, pp. 975-979, vol. 55-issue No. 7, Pharmaceutical Society of Japan.
International Search Report and Written Opinion dated Oct. 23, 2006, for corresponding International Patent Application No. PCT/US06/25427.

* cited by examiner

SUBSTITUTED BENZYLAMINO QUINOLINES AS CHOLESTEROL ESTER-TRANSFER PROTEIN INHIBITORS

RELATED APPLICATION DATA

This application claims the benefit of U.S. Provisional Patent Application Ser. No. 60/640,798, filed Dec. 31, 2004, which is incorporated herein by reference in its entirety.

FIELD OF THE INVENTION

The present invention relates to benzylamine compounds, methods and compositions for making and using the benzylamine compounds, and compositions and methods for treating or preventing conditions or diseases associated with lipoprotein metabolism.

BACKGROUND OF THE INVENTION

Cholesteryl ester-transfer protein (CETP) is an important player in metabolism of lipoproteins such as, for example, a high density lipoprotein (HDL). CETP is a 70 kDa plasma glycoprotein that is physically associated with HDL particles. It facilitates the transport of cholesteryl ester from HDL to apolipoprotein B-containing lipoproteins. This transfer is accompanied by transfer of triglycerides in the opposite direction. Thus, a decrease in CETP activity can result in an increase in the level of HDL cholesterol and a decrease in the level of very low density lipoprotein (VLDL) and low density lipoprotein (LDL). CETP can therefore simultaneously affect the concentrations of pro-atherogenic (e.g., LDL) and anti-atherogenic (e.g., HDL) lipoproteins.

Human and clinical studies have shown that inhibitors of CETP can be effective in elevating HDL levels by 30-60%. And, epidemiological studies have shown that decreased high-density lipoprotein cholesterol (HDL-C) is a powerful risk factor for coronary artery disease (CAD). Gordon et al., Circulation, 79, pp. 8-15, 1989; Despres et al., Atherosclerosis 153: 263-272, 2000. Elevating HDL-C has been shown to decrease this risk and it is estimated that each 1 mg/dl (0.02 mmol/l) elevation of HDL-C is associated with a 2-3% reduction in coronary heart disease (CHD) risk, a magnitude comparable to that for low density lipoprotein (LDL) lowering. It has been recommended that serum HDL-C levels of >40 mg/dl be considered as a therapeutic target in primary and secondary prevention. This goal appears to be particularly important in patients with low serum HDL-C levels and ischemic heart disease (IHD) or its equivalents, even if the therapeutic target for serum low-density lipoprotein cholesterol (LDL-C) levels (<100 mg/dl) has been achieved.

It is believed that the anti-atherogenic role of HDL is in part due its ability to promote the efflux of free cholesterol from cells and to transport it to the liver, a process termed reverse cholesterol transport. HDL could protect against atherosclerosis by several other mechanisms. For example, several studies showed HDL to have antioxidant and anti-inflammatory effects. Oxidative products of lipid metabolism induce inflammatory cell recruitment in vascular cells. HDL particles carry enzymes that retard LDL oxidation, including paraoxonase, platelet-activating factor acetylhydrolase, and lecithin-cholesterol acyltransferase. These enzymes degrade pro-inflammatory, oxidized phospholipids, limiting their accumulation in LDL. In addition, apoA-I can bind oxidized lipids and remove them from LDL. Further, HDL also can act as a carrier vehicle for small molecules, including bacterial lipopolysaccharide (LPS) thus regulating the inflammatory effects of LPS. In animal models of endotoxic shock, HDL attenuates organ injury and adhesion molecule expression. Thus elevating HDL is not only anti-atherogenic but it could also potentially be anti-inflammatory.

Existing therapies such as, for example, HDL-elevating therapies and anti-atherosclerosis therapies have limitations including serious toleration issues. There is a present need to find alternative therapies including methods of preventing or treating conditions or diseases associated with lipoprotein metabolism such as, for example, atherosclerosis.

SUMMARY OF THE INVENTION

The present invention is directed to novel benzylamine compounds, novel compositions comprising these benzylamine compounds, and novel methods employing such benzylamine compounds and their compositions. Disclosed herein are methods for making benzylamine compounds compounds, compositions comprising these benzylamines, and methods and compositions for using these benzylamines. The benzylamine compounds and compositions comprising these compounds have utility in treatment of a variety of diseases. Certain aspects of benzylamine compounds have been disclosed in PCT Publication WO 2004/020393, and in U.S. Pat. Nos. 6,710,089 and 6,723,753.

In one aspect, the present invention provides for compounds and compositions comprising these compounds, in which the compounds have the following formula:

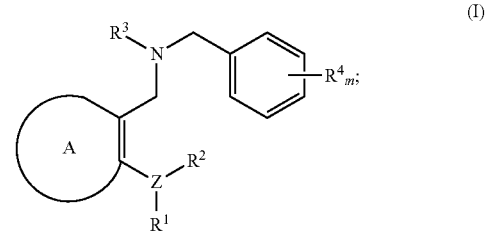

or a salt, including a pharmaceutically acceptable or a non-pharmaceutically acceptable salt, a prodrug, a diastereomeric mixture, an enantiomer, a tautomer, a racemic mixture, or any combination thereof, wherein:

A is a substituted or an unsubstituted, monocyclic or bicyclic, heterocyclic moiety, comprising from 5 to 10 ring atoms, inclusive, and comprising at least one heteroatom or heterogroup selected independently from O, N, S, $NR^{10}$, $SO_2$, or CO;

$R^1$ and $R^2$ are selected independently from: 1) hydrogen; 2) a substituted or an unsubstituted alkyl, cycloalkyl, haloalkyl, aryl, heterocyclyl, heteroaryl, any of which having up to 12 carbon atoms, wherein any heterocyclyl or heteroaryl comprises at least one heteroatom or heterogroup selected independently from O, N, S, $NR^{10}$, $SO_2$, or CO; 3) $CO_2R^6$, $COR^8$, $SO_2R^8$, $SO_2NR^6R^7$, or $CONR^6R^7$; or 4) $(CHR^x)_nR^5$ or $(CH_2)_n R^d CO_2R^e$, wherein n, in each occurrence, is 1, 2, or 3; $R^x$, in each occurrence, is selected independently from an alkyl or an alkoxy, either of which having up to 12 carbon atoms, or hydrogen; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen;

or $R^1$ and $R^2$ together form a substituted or an unsubstituted monocyclic or bicyclic moiety comprising up to 12 carbon atoms, and optionally comprising 1, 2, or 3 heteroatoms or heterogroups in addition to Z, selected independently from O, N, S, $NR^{10}$, $SO_2$, or CO;

$R^3$ is selected from: 1) hydrogen or cyano; 2) a substituted or an unsubstituted alkyl having up to 12 carbon atoms; 3) a substituted or an unsubstituted aryl, or a substituted or an unsubstituted 5-, 6-, or 7-membered heterocyclyl or heteroaryl, any of which having up to 12 carbon atoms, comprising 1, 2, or 3 heteroatoms or heterogroups selected independently from O, N, S, $NR^{10}$, $SO_2$, or CO; or 4) $CO_2R^6$, $COR^8$, $SO_2R^8$, $SO_2NR^6R^7$, $CONR^6R^7$, $C(S)NR^6R^7$, $C(S)NC(O)OR^8$, or $C(S)SR^8$;

wherein when $R^3$ is an alkyl, an aryl, a heterocyclyl, or a heteroaryl, $R^3$ is optionally substituted with up to three substituents selected independently from a halide, a hydroxyl, a cyano, an alkoxy having up to 12 carbon atoms, or $R^{11}$;

$R^4$, in each occurrence, is selected independently from: 1) halogen, cyano, or hydroxy; 2) an alkyl, a cycloalkyl, a cycloalkoxy, an alkoxy, a haloalkyl, or a haloalkoxy, any of which having up to 12 carbon atoms; 3) a substituted or an unsubstituted aryl, aralkyl, aryloxy, heteroaryl, or heteroaryloxy, any of which having up to 12 carbon atoms, wherein any heteroaryl or heteroaryloxy comprises at least one heteroatom or heterogroup selected independently from O, N, S, or $NR^{10}$; or 4) $CO_2R^6$, $COR^8$, $SO_2R^8$, $SO_2NR^6R^7$, $CONR^6R^7$, or $(CH_2)_qNR^6R^7$, wherein q is an integer from 0 to 5, inclusive;

m is an integer from 0 to 3, inclusive;

or $R^4_m$ is a fused cyclic moiety comprising from 3 to 5 additional ring carbon atoms, inclusive, and optionally comprising at least one heteroatom or heterogroup selected independently from O, N, S, $NR^{10}$, $SO_2$, or CO;

$R^5$, in each occurrence, is selected independently from: 1) an alkoxy, a haloalkoxy, or a cycloalkyl, any of which having up to 12 carbon atoms; 2) a substituted or an unsubstituted aryl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO; 3) hydroxyl, $NR^6R^7$, $CO_2R^6$, $COR^8$, or $SO_2R^8$; or 4) a substituted or an unsubstituted heterocycloalkyl comprising from 3 to 7 ring carbon atoms, and from 1 to 3 heteroatoms or heterogroups, inclusive, selected independently from O, N, S, $NR^{10}$, $SO_2$, or CO;

$R^6$ and $R^7$, in each occurrence, are selected independently from: 1) hydrogen; 2) an alkyl, a cycloalkyl, or a haloalkyl, any of which having up to 12 carbon atoms; or 3) a substituted of an unsubstituted aryl, aralkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

or $R^6$ and $R^7$ together form a substituted or an unsubstituted cyclic moiety having from 3 to 7 ring carbon atoms, and optionally comprising 1, 2, or 3 heteroatoms in addition to the nitrogen atom to which $R^6$ and $R^7$ are bonded, selected independently from O, N, S, or $NR^{10}$;

$R^8$, in each occurrence, is selected independently from: 1) an alkyl, a cycloalkyl, or a haloalkyl, any of which having up to 12 carbon atoms; or 2) a substituted of an unsubstituted aryl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

$R^{10}$, in each occurrence, is selected independently from: 1) hydrogen; or 2) an alkyl, a cycloalkyl, a haloalkyl, an aryl, or an aralkyl, any of which having up to 12 carbon atoms;

Z is N or CH; or the $ZR^1$ moiety is S, CO, or $SO_2$; or the $ZR^1R^2$ moiety is —C≡$CR^2$;

$R^{11}$ is selected independently from:

1) an alkyl, a haloalkyl, a cycloalkyl, or an alkoxycarbonyl, any of which having up to 12 carbon atoms;

2) a substituted or an unsubstituted heteroaryl or heterocyclyl, any of which having up to 12 carbon atoms, comprises at least one heteroatom or heterogroup selected independently from O, N, S, $NR^{10}$, $SO_2$, or CO, wherein any substituted heteroaryl or heterocyclyl is substituted with up to three substituents selected independently from an alkyl having up to 12 carbon atoms or a hydroxyl; or 3) —CO—$Z^2$—$R^{13}$, —CO—$R^{12}$, —CO—$Z^2$—$(CH_2)_r$—CO—$Z^2$—$R^{13}$, —$NR^{15}R^{16}$, —$Z^2$—CO—$(CH_2)_r$—$Z^2$—$R^{13}$, —$Z^2$—CO—$(CH_2)_r$—CO—$Z^2$—$R^{13}$, —O—$(CH_2)_r$—CO—$Z^2$—$R^{13}$, —O—$(CH_2)_r$—$R^{14}$, —O—$R^{12}$—$(CH_2)_r$—$R^{13}$, —O—$R^{14}$—CO—O—$R^{13}$, —O—$(CH_2)_r$—$R^{12}$, —O—$(CH_2)_r$—NR'R", —O—$(CH_2)_r$—$CO_2$—$(CH_2)_r$—$R^{13}$, —O—$(CH_2)_r$—CONR'R", —O—$(CH_2)_r$—$SR^8$, —O—$(CH_2)_r$—$CO_2$—$R^{13}$, —O—$(CH_2)_r$—O—$(CH_2)_r$—$OR^{13}$, —O—$(CH_2)_r$—CONR'R", —O—$(CH_2)_r$—CONH—$(CH_2)_r$—$OR^{13}$, —O—$(CH_2)_r$—$SO_2R^8$, —O—$(CH_2)_r$—$R^{13}$, —O—$(CH_2)_r$—$OR^{13}$, —O—$(CH_2)_r$—O—$(CH_2)_r$—$OR^{13}$, —S—$(CH_2)_r$—CONR'R", —$SO_2$—$(CH_2)_r$—$OR^{13}$, —$SO_2$—$(CH_2)_r$—CONR'R", —$(CH_2)_r$—O—CO—$R^8$, —$(CH_2)_r$—$R^{12}$, —$(CH_2)_r$—$R^{13}$, —$(CH_2)_r$—CO—$Z^2$—$R^{13}$, —$(CH_2)_r$—$Z^2$—$R^{13}$, or -alkenylene-$CO_2$—$(CH_2)_r$—$R^{13}$;

r, in each occurrence, is independently 1, 2, or 3;

$R^{12}$, in each occurrence, is independently selected from a substituted or an unsubstituted heterocyclyl having up to 12 carbon atoms, comprising at least one heteroatom or heterogroup selected independently from O, N, S, $NR^{10}$, $SO_2$, or CO, wherein any substituted heterocyclyl is substituted with up to three substituents selected independently from an acyl, an alkyl, or an alkoxycarbonyl, any of which having up to 12 carbon atoms, or —COOH;

$R^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from O, N, S, $NR^{10}$, $SO_2$, or CO;

$R^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from O, N, S, $NR^{10}$, $SO_2$, or CO;

$Z^2$, in each occurrence, is selected independently from $NR^{10}$ or O;

R' and R", in each occurrence, are independently selected from hydrogen or an alkyl having up to 12 carbon atoms; and $R^{15}$ and $R^{16}$, in each occurrence, are independently selected from: 1) hydrogen; 2) an alkyl having up to 12 carbon atoms; or 3) —$(CH_2)_r$—O—$R^{13}$, —$(CH_2)_r$—$R^{14}$, —$COR^{13}$, —$(CH_2)_r$—CO—$Z^2$—$R^{13}$, —$CO_2R^{13}$, —$CO_2$—$(CH_2)_r$—$R^{13}$, —$CO_2$—$(CH_2)_r$—$R^{12}$, —$CO_2$—$(CH_2)_r$—CO—$Z^2$—

$R^{13}$, $-CO_2-(CH_2)_r-OR^{13}$, $-CO-(CH_2)_r-O-(CH_2)_r-O-(CH_2)_r-R^{13}$, $-CO-(CH_2)_r-O(CH_2)_r-OR^{13}-$, or $-CO-NH-(CH_2)_r-OR^{13}$;

or $R^{15}$ and $R^{16}$ together form a substituted or an unsubstituted cyclic moiety comprising up to 12 carbon atoms, optionally comprising at least one additional heteroatom or heterogroup selected independently from O, N, S, $NR^{10}$, $SO_2$, or CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from O, N, S, or $NR^{10}$; or 3) $COOR^{13}$, $-Z^2-(CH_2)_r-R^{13}$, $-COR^{13}$, $-CO_2-(CH_2)_r-R^{13}$, $-CO(CH_2)_r-O-R^{13}$, $-(CH_2)_r-CO_2-R^{13}$, $-SO_2R^8$, $-SO_2NR'R''$, or $-NR'R''$;

wherein the $-(CH_2)_r-$ linking moiety, in any occurrence, is optionally substituted with at least one group selected independently from hydroxyl, amino, or an alkyl having up to 3 carbon atoms;

A is optionally substituted with 1, 2, or 3 substituents selected independently from: 1) halogen, cyano, or hydroxyl; 2) an alkyl, an alkenyl, an alkynyl, a haloalkyl, a cycloalkyl, an alkoxy, a cycloalkoxy, a haloalkoxy, an aryl, an aryloxy, an aralkyl, a heteroaryl, a heterocyclyl, or a heteroaryloxy, any of which having up to 12 carbon atoms, wherein any heteroaryl, heterocyclyl, or heteroaryloxy comprises at least one heteroatom or heterogroup selected independently from O, N, S, $NR^{10}$, $SO_2$, or CO; 3) $CO_2R^6$, $COR^8$, $SO_2R^8$, $SO_2NR^6R^7$, or $CONR^6R^7$; 4) $(CH_2)_qNR^6R^7$, wherein q is an integer from 0 to 5, inclusive; or 5) $(CH_2)_qCO_2(CH_2)_q$, wherein q is an integer selected independently from 0 to 3, inclusive;

when $R^1$ and $R^2$ do not form a monocyclic or bicyclic moiety, $R^1$ and $R^2$ are optionally and independently substituted with 1 or 2 substituents selected independently from: 1) an alkyl, a cycloalkyl, a haloalkyl, an alkoxy, an aryl, a heteroaryl, or a heterocyclyl, any of which having up to 12 carbon atoms, wherein any heteroaryl or heterocyclyl comprises at least one heteroatom or heterogroup selected independently from O, N, S, $NR^{10}$, $SO_2$, or CO; or 2) halogen, cyano, or hydroxyl;

when $R^1$ and $R^2$ together form a monocyclic or a bicyclic moiety, the cyclic moiety is optionally substituted with at least one substituent selected independently from: 1) halogen, cyano, or hydroxyl; 2) an alkyl, a haloalkyl, a cycloalkyl, an alkoxy, a cycloalkyl-substituted alkyl, an alkoxyalkyl, a cycloalkoxy, a haloalkoxy, an aryl, an aryloxy, an aralkyl, a heteroaryl or a heteroaryloxy, any of which having up to 12 carbon atoms, wherein any heteroaryl or heteroaryloxy comprises at least one heteroatom or heterogroup selected independently from O, N, S, or $NR^{10}$; or 3) $CO_2R^6$, $COR^8$, $SO_2R^8$, $SO_2NR^1R^7$, or $CONR^6R^7$; or 4) $(CH_2)_qCO_2(CH_2)_q$, wherein q is selected independently from an integer from 0 to 3, inclusive; and $R^4$, $R^5$, $R^6$, $R^7$, and $R^8$ are optionally and independently substituted with at least one substituent selected independently from: 1) halide, hydroxy, cyano, or $NR^6R^7$; or 2) an alkyl or an alkoxy, any of which having up to 12 carbon atoms.

Throughout this disclosure, unless otherwise specified, any representation of an atom or a group as a substituent on any portion of a monocyclic or bicyclic moiety such as A, is intended to denote all possible regioisomers, including regioisomers in which that atom or group is bonded to either ring of a bicyclic moiety A. For example, when a substituent such as $R^a$ is represented as bonded to any position on the carbocyclic ring of a quinoline moiety, such a representation is intended to encompass regioisomers in which $R^a$ is bonded to the heterocyclic ring as well.

Accordingly, the notation

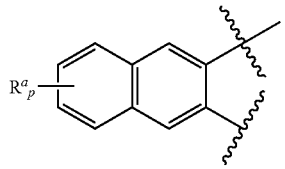

is used to encompass all regioisomers in which $R^a$ moieties can be bonded to the carbocycle as shown, those in which an $R^a$ moiety is bonded to the available carbon on the heterocycle, and those in which $R^a$ moieties can be bonded to both the carbocycle and the heterocycle. Further, throughout this disclosure, unless otherwise specified, any heterocyclyl, any heterocycloalkyl, any heteroaryl, and any heteroaryloxy comprises at least one heteroatom or heterogroup selected independently from O, N, S, $NR^{10}$, $SO_2$, or CO, as the context allows or requires.

Also in this aspect of the present invention, and throughout this disclosure, whenever two R-groups such as $R^1$ and $R^2$ are acyclic, that is, when $R^1$ and $R^2$ do not form a monocyclic or bicyclic moiety, substituents on $R^1$ are selected independently from substituents on $R^2$. Whenever two R-groups such as $R^1$ and $R^2$ form a cyclic moiety, any subsitutent selected constitutes a subsitutent on the cyclic $R^1$-A-$R^2$ moiety or core. In all cases, whenever more than one substituent is selected for any group, each substituent is selected independently of any other substituent.

In yet another aspect, the present invention is also directed to methods or processes for the preparation of the benzylamine compounds disclosed herein, including compounds of the general formula (I). In another aspect, this invention is also directed to compositions comprising the benzylamine compounds disclosed herein, including compounds of the general formula (I). When the composition is a pharmaceutical compositions, the composition also comprises a pharmaceutically acceptable carrier and at least one compound according to this invention, and further comprises: optionally, a pharmaceutically acceptable auxiliary; optionally, a pharmaceutically acceptable preservative; optionally, a pharmaceutically acceptable excipient; optionally, a pharmaceutically acceptable diluent; and optionally, a pharmaceutically acceptable solvate.

The present invention also is directed to a method for treating a condition or disease in a mammalian subject, including a human. In some aspects, the method comprises administering to the subject a composition comprising a therapeutically-effective amount of at least one compound disclosed herein, or their pharmaceutically-acceptable salts thereof. Besides being useful for treating a human subject, the methods and compositions of the present invention are useful for treating a variety of mammals such as, for example, companion animals such as cats or dogs, primates, ruminant animals, and rodents.

The present invention also is directed to a method for treating or preventing a condition or disease in a human or an animal subject, the method comprising administering to the subject a composition comprising a prophylactically- or therapeutically-effective amount of at least one compound disclosed herein, or their pharmaceutically-acceptable salts thereof. In some aspects, for example, this invention provides methods for the treatment and/or prevention of conditions or disease states in a human or anminal, such as dyslipidemia, atherosclerosis, peripheral vascular disease, hypertryglyceridemia, hypercholesterolemia, hyperbetalipoproteinemia, hypoalphalipoprotenemia, cardiovascular disorders such as angina, ischemia, stroke, myocardial infarction (MI), reperfusion injury, restenosis and hypertension, and diabetic vascular diseases such as diabetic retinopathy, and endotoxemia, comprising administering a therapeutically-effective amount of at least one compound disclosed herein.

DETAILED DESCRIPTION OF THE INVENTION

In accordance with the present invention, novel benzylamine compounds and novel compositions comprising these benzylamine compounds are described. In one aspect, compounds in accordance with the present invention can comprise benzylamine compounds having the following formula:

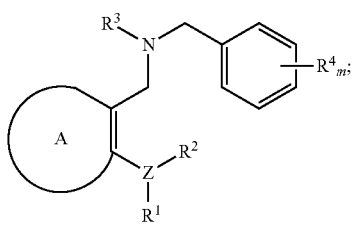

(I)

wherein each substituent is defined as disclosed above.

Further to this aspect of formula (I) presented immediately above, the following substituents of the formula can be selected as indicated here, while unspecified substitutents are selected as disclosed above for this formula: Z is N or CH; or the $ZR^1R^2$ moiety is —C≡$CR^2$.

In another aspect of the formula (I) presented above, the following substituents of the formula can be selected as indicated here, while unspecified substituents are selected as disclosed above for this formula:

$R^1$ and $R^2$ are selected independently from: hydrogen; a C1 to C6 alkyl, that is, an alkyl having up to 6 carbon atoms; a C3 to C6 cycloalkyl, that is, a cycloalkyl having up to 6 carbon atoms; $COR^8$; or $(CH_2)_nR^5$ or $(CH_2)_nR^dCO_2R^e$, wherein n, in each occurrence, is 1 or 2;

or $R^1$ and $R^2$ together form a substituted or an unsubstituted monocyclic or bicyclic moiety comprising up to 12 carbon atoms, and optionally comprising 1 or 2 heteroatoms or heterogroups selected independently from O, N, or $NR^{10}$; wherein any optional substituent on the cyclic moiety selected from: 1) a C3 to C6 cycloalkyl, that is, a cycloalkyl having up to 6 carbon atoms; or 2) a C1 to C2 alkyl, that is, an alkyl having up to 2 carbon atoms.

In yet another aspect of the formula (I) presented above, the following substituents of the formula can be selected as indicated here, while unspecified substitutents are selected as disclosed above for this formula:

$R^3$ is selected from: 1) hydrogen or cyano; 2) a substituted or an unsubstituted alkyl having up to 12 carbon atoms; 3) a substituted or an unsubstituted aryl, or a substituted or an unsubstituted 5-, 6-, or 7-membered heterocyclyl or heteroaryl, comprising 1, 2, or 3 heteroatoms or heterogroups selected independently from O, N, S, $NR^{10}$, $SO_2$, or CO, any of which having up to 12 carbon atoms; or 4) $CO_2R^6$, $COR^8$, $SO_2R^8$, $SO_2NR^6R^7$, $CONR^6R^7$, $C(S)NR^6R^7$, $C(S)NC(O)OR^8$, or $C(S)SR^8$;

wherein when $R^3$ is an alkyl, an aryl, a heterocyclyl, or a heteroaryl, $R^3$ is optionally substituted with up to three substituents selected independently from a halide, a hydroxyl, a cyano, an alkoxy having up to 12 carbon atoms, or $R^{11}$;

$R^{11}$ is selected independently from:
1) an alkyl, a haloalkyl, a cycloalkyl, or an alkoxycarbonyl, any of which having up to 12 carbon atoms;
2) a substituted or an unsubstituted heteroaryl or heterocyclyl, any of which having up to 12 carbon atoms, comprises at least one heteroatom or heterogroup selected independently from O, N, S, $NR^{10}$, $SO_2$, or CO, wherein any substituted heteroaryl or heterocyclyl is substituted with up to three substituents selected independently from an alkyl having up to 12 carbon atoms or a hydroxyl; or
3) —CO—$Z^2$—$R^{13}$, —CO—$R^{12}$, —CO—$Z^2$—$(CH_2)_r$—CO—$Z^2$—$R^{13}$, —$NR^{15}R^{16}$, —$Z^2$—CO—$(CH_2)_r$—$Z^2$—$R^{13}$, —$Z^2$—CO—$(CH_2)_r$—CO—$Z^2$—$R^{11}$, —O—$(CH_2)_r$—CO—$Z^2$—$R^{13}$, —O—$(CH_2)_r$—$R^{14}$, —O—$R^{12}$—$(CH_2)_r$—$R^{13}$, —O—$R^{14}$—CO—O—$R^{13}$, —O—$(CH_2)_r$—$R^{12}$, —O—$(CH_2)_r$—NR'R'', —O—$(CH_2)_r$—$CO_2$—$(CH_2)_r$—$R^{13}$, —O—$(CH_2)_r$—CONR'R'', —O—$(CH_2)_r$—$SR^8$, —O—$(CH_2)_r$—$CO_2$—$R^{13}$, —O—$(CH_2)_r$—O—$(CH_2)_r$—$OR^{13}$, —O—$(CH_2)_r$—CONR'R'', —O—$(CH_2)_r$—CONH—$(CH_2)_r$—$OR^{13}$, —O—$(CH_2)_r$—$SO_2R^8$, —O—$(CH_2)_r$—$R^{12}$, —O—$(CH_2)_r$—$OR^{13}$, —O—$(CH_2)_r$—O—$(CH_2)_r$—$OR^{13}$, —S—$(CH_2)_r$—CONR'R'', —$SO_2$—$(CH_2)_r$—$OR^{13}$, —$SO_2$—$(CH_2)_r$—CONR'R'', —$(CH_2)_r$—O—CO—$R^6$, —$(CH_2)_r$—$R^{12}$, —$(CH_2)_r$—$R^{13}$, —$(CH_2)_r$—N—$(CH_2)_r$—$OR^{13}$, —$(CH_2)_r$—CO—$Z^2$—$R^{13}$, —$(CH_2)_r$—$Z^2$—$R^{13}$, or -alkenylene-$CO_2$—$(CH_2)_r$—$R^{13}$;

r, in each occurrence, is independently 1, 2, or 3;

$R^{12}$, in each occurrence, is independently selected from a substituted or an unsubstituted heterocyclyl having up to 12 carbon atoms, comprising at least one heteroatom or heterogroup selected independently from O, N, S, $NR^{10}$, $SO_2$, or CO, wherein any substituted heterocyclyl is substituted with up to three substituents selected independently from an acyl, an alkyl, or an alkoxycarbonyl, any of which having up to 12 carbon atoms, or —COOH;

$R^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from O, N, S, $NR^{10}$, $SO_2$, or CO;

$R^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from O, N, S, $NR^{10}$, $SO_2$, or CO;

$Z^2$, in each occurrence, is selected independently from $NR^{10}$ or O;

R' and R'', in each occurrence, are independently selected from hydrogen or an alkyl having up to 12 carbon atoms; and $R^{15}$ and $R^{16}$, in each occurrence, are independently selected from: 1) hydrogen; 2) an alkyl having up to 12 carbon atoms; or 3) —$(CH_2)_r$—O—$R^{13}$, —$(CH_2)_r$—$R^{14}$, —$COR^{13}$, —$(CH_2)_r$—CO—$Z^2$—$R^{13}$, —$CO_2R^{13}$, —$CO_2$—$(CH_2)_r$—$R^{13}$, —$CO_2$—$(CH_2)_r$—$R^{12}$, —$CO_2$—$(CH_2)_r$—CO—$Z^2$—$R^{13}$, —$CO_2$—$(CH_2)_r$—$OR^{13}$, —CO—$(CH_2)_r$—O—$(CH_2)_r$—O—$(CH_2)_r$—$R^{13}$, —CO—$(CH_2)_r$—O$(CH_2)_r$—$OR^{13}$—, or —CO—NH—$(CH_2)_r$—$OR^{13}$;

or $R^{15}$ and $R^{16}$ together form a substituted or an unsubstituted cyclic moiety comprising up to 12 carbon atoms, optionally comprising at least one additional heteroatom or heterogroup selected independently from O, N, S, $NR^{10}$, $SO_2$, or CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from O, N, S, or $NR^{10}$; or 3) $COOR^{13}$, $-Z^2-(CH_2)_r-R^{13}$, $-COR^{13}$, $-CO_2-(CH_2)_r-R^{13}$, $-CO(CH_2)_r-O-R^{13}$, $-(CH_2)_r-CO_2-R^{13}$, $-SO_2R^8$, $-SO_2NR'R''$, or $-NR'R''$; and wherein the $-(CH_2)_r-$ linking moiety, in any occurrence, is optionally substituted with at least one group selected independently from hydroxyl, amino, or an alkyl having up to 3 carbon atoms.

In still another aspect of the formula (I) presented above, the following substituents of the formula can be selected as indicated here, while unspecified substitutents are selected as disclosed above for this formula for this formula:

$R^4$, in each occurrence, is selected independently from: 1) a halogen or cyano; or 2) an alkyl or a haloalkyl, either of which having up to 4 carbon atoms; and m is 2 or 3.

In another aspect of this invention, compounds in accordance with the present invention can comprise benzylamine compounds according to formula (I), having the following formula:

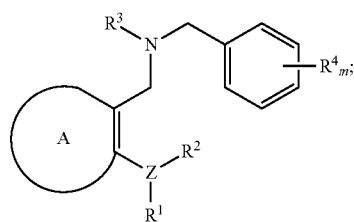

or a salt, including a pharmaceutically acceptable or a non-pharmaceutically acceptable salt, a prodrug, a diastereomeric mixture, an enantiomer, a tautomer, a racemic mixture, or any combination thereof, wherein:

A is selected from a substituted or an unsubstituted, monocyclic or bicyclic moiety selected from:

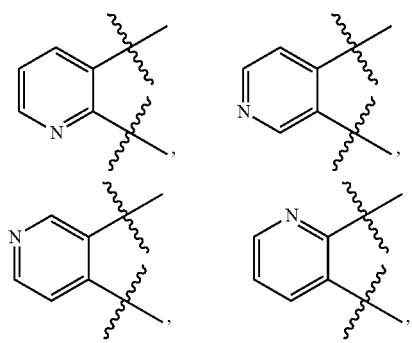

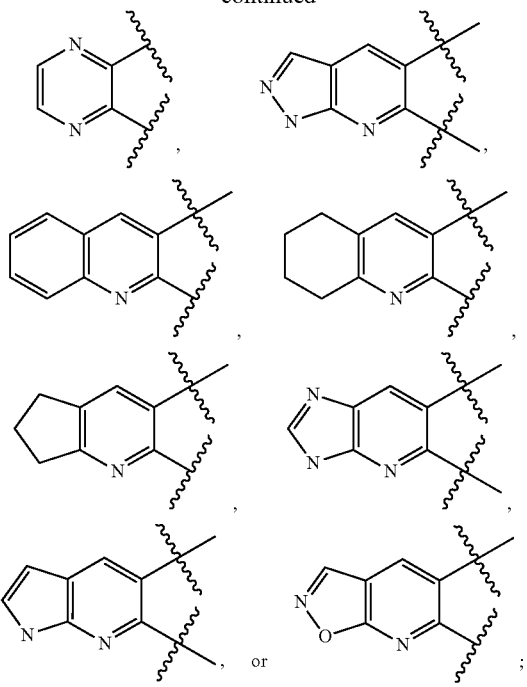

and all other substituents and groups, including substituents to the ring system A, are selected according to the definitions provided above in the formula (I).

Further to this aspect of formula (Ia) presented immediately above, the following substituents of the formula can be selected as indicated here, while unspecified substitutents are selected as disclosed above for this formula: Z is N or CH; or the $ZR^1R^2$ moiety is $-C\equiv CR^2$.

In another aspect of the formula (Ia) presented above, the following substituents of the formula can be selected as indicated here, while unspecified substitutents are selected as disclosed above for this formula:

$R^1$ and $R^2$ are selected independently from: 1) hydrogen; 2) a C1 to C6 alkyl, that is, an alkyl having up to 6 carbon atoms; 3) a C3 to C6 cycloalkyl, that is, a cycloalkyl having up to 6 carbon atoms; 4) $COR^8$; or 5) $(CH_2)_nR^5$ or $(CH_2)_nR^dCO_2R^e$, wherein n, in each occurrence, is 1 or 2; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen;

or $R^1$ and $R^2$ together form a substituted or an unsubstituted monocyclic or bicyclic moiety comprising up to 12 carbon atoms, and optionally comprising 1 or 2 heteroatoms or heterogroups selected independently from O, N, or $NR^{10}$; wherein any optional substituent on the cyclic moiety selected from: 1) a C3 to C6 cycloalkyl, that is, a cycloalkyl having up to 6 carbon atoms; or 2) a C1 to C2 alkyl, that is, an alkyl having up to 2 carbon atoms.

In yet another aspect of the formula (Ia) presented above, the following substituents of the formula can be selected as indicated here, while unspecified substitutents are selected as disclosed above for this formula:

$R^3$ is selected from: 1) hydrogen or cyano; 2) a substituted or an unsubstituted alkyl having up to 12 carbon atoms; 3) a substituted or an unsubstituted aryl, or a substituted or an unsubstituted 5-, 6-, or 7-membered heterocyclyl or heteroaryl, comprising 1, 2, or 3 heteroatoms or heterogroups selected independently from O, N, S, $NR^{10}$, $SO_2$, or CO, any of which having up to 12 carbon atoms; or 4) $CO_2R^6$, $COR^8$, $SO_2R^8$, $SO_2NR^6R^7$, $CONR^6R^7$, $C(S)NR^6R^7$, $C(S)NC(O)OR^8$, or $C(S)SR^8$;

wherein when $R^3$ is a heterocyclyl or a heteroaryl, $R^3$ is optionally substituted with up to three substituents selected independently from a halide, a hydroxyl, a cyano, an alkoxy having up to 12 carbon atoms, or $R^{11}$;

$R^{11}$ is selected independently from:
1) an alkyl, a haloalkyl, a cycloalkyl, or an alkoxycarbonyl, any of which having up to 12 carbon atoms;
2) a substituted or an unsubstituted heteroaryl or heterocyclyl, any of which having up to 12 carbon atoms, comprises at least one heteroatom or heterogroup selected independently from O, N, S, $NR^{10}$, $SO_2$, or CO, wherein any substituted heteroaryl or heterocyclyl is substituted with up to three substituents selected independently from an alkyl having up to 12 carbon atoms or a hydroxyl; or
3) —CO—$Z^2$—$R^{13}$, —CO—$R^{12}$, —CO—$Z^2$—$(CH_2)_r$—CO—$Z^2$—$R^{13}$, —$NR^{15}R^{16}$, —$Z^2$—CO—$(CH_2)_r$—$Z^2$—$R^{13}$, —$Z^2$—CO—$(CH_2)_r$—CO—$Z^2$—$R^{13}$, —O—$(CH_2)_r$—CO—$Z^2$—$R^{13}$, —O—$(CH_2)_r$—$R^{14}$, —O—$R^{12}$—$(CH_2)_r$—$R^{13}$, —O—$R^{14}$—CO—O—$R^{13}$, —O—$(CH_2)_r$—$R^{12}$, —O—$(CH_2)_r$—NR'R'', —O—$(CH_2)_r$—$CO_2$—$(CH_2)_r$—$R^{13}$, —O—$(CH_2)_r$—CONR'R'', —O—$(CH_2)_r$—$SR^8$, —O—$(CH_2)_r$—$CO_2$—$R^{13}$, —O—$(CH_2)_r$—O—$(CH_2)_r$—$OR^{13}$, —O—$(CH_2)_r$—CONR'R'', —O—$(CH_2)_r$—CONH—$(CH_2)_r$—$OR^{13}$, —O—$(CH_2)_r$—$SO_2R^8$, —O—$(CH_2)_r$—$R^{13}$, —O—$(CH_2)_r$—$OR^{13}$, —O—$(CH_2)_r$—O—$(CH_2)_r$—$OR^{13}$, —S—$(CH_2)_r$—CONR'R'', —$SO_2$—$(CH_2)_r$—$OR^{13}$, —$SO_2$—$(CH_2)_r$—CONR'R'', —$(CH_2)_r$—O—CO—$R^8$, —$(CH_2)_r$—$R^{12}$, —$(CH_2)_r$—$R^{13}$, $(CH_2)_r$—$R^{13}$, —$(CH_2)_r$—CO—$Z^2$—$R^{13}$, —$(CH_2)_r$—$Z^2$—$R^{13}$, or -alkenylene-$CO_2$—$(CH_2)_r$—$R^{13}$;

r, in each occurrence, is independently 1, 2, or 3;

$R^{12}$, in each occurrence, is independently selected from a substituted or an unsubstituted heterocyclyl having up to 12 carbon atoms, comprising at least one heteroatom or heterogroup selected independently from O, N, S, $NR^{10}$, $SO_2$, or CO, wherein any substituted heterocyclyl is substituted with up to three substituents selected independently from an acyl, an alkyl, or an alkoxycarbonyl, any of which having up to 12 carbon atoms, or —COOH;

$R^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from O, N, S, $NR^{10}$, $SO_2$, or CO;

$R^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from O, N, S, $NR^{10}$, $SO_2$, or CO;

$Z^2$, in each occurrence, is selected independently from $NR^{10}$ or O;

R' and R'', in each occurrence, are independently selected from hydrogen or an alkyl having up to 12 carbon atoms; and $R^{15}$ and $R^{16}$, in each occurrence, are independently selected from: 1) hydrogen; 2) an alkyl having up to 12 carbon atoms; or 3) —$(CH_2)_r$—O—$R^{13}$, —$(CH_2)_r$—$R^{14}$, —$COR^{13}$, —$(CH_2)_r$—CO—$Z^2$—$R^{13}$, —$CO_2R^{13}$, —$CO_2$—$(CH_2)_r$—$R^{13}$, —$CO_2$—$(CH_2)_r$—$R^{13}$, —$CO_2$—$(CH_2)_r$—CO—$Z^2$—$R^{13}$, —$CO_2$—$(CH_2)_r$—$OR^{13}$, —CO—$(CH_2)_r$—O—$(CH_2)_r$—O—$(CH_2)_r$—$R^{13}$, —CO—$(CH_2)_r$—O$(CH_2)_r$—$OR^{13}$—, or —CO—NH—$(CH_2)_r$—$R^{13}$;

or $R^{15}$ and $R^{16}$ together form a substituted or an unsubstituted cyclic moiety comprising up to 12 carbon atoms, optionally comprising at least one additional heteroatom or heterogroup selected independently from O, N, S, $NR^{10}$, $SO_2$, or CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from O, N, S, or $NR^{10}$; or 3) $COOR^{13}$, —$Z^2$—$(CH_2)_r$—$R^{13}$, —$COR^{13}$, —$CO_2$—$(CH_2)_r$—$R^{13}$, —$CO(CH_2)_r$—O—$R^{13}$, —$(CH_2)_r$—$CO_2$—$R^{13}$, —$SO_2R^8$, —$SO_2NR'R''$, or —NR'R'';

wherein the —$(CH_2)_r$— linking moiety, in any occurrence, is optionally substituted with at least one group selected independently from hydroxyl, amino, or an alkyl having up to 3 carbon atoms.

In still another aspect of the formula (Ia) presented above, the following substituents of the formula can be selected as indicated here, while unspecified substitutents are selected as disclosed above for this formula for this formula:

$R^4$, in each occurrence, is selected independently from: 1) halogen or cyano; or 2) an alkyl or a haloalkyl, any of which having up to 4 carbon atoms; and m is 2 or 3.

In yet another aspect, compounds in accordance with the present invention can comprise benzylamine compounds according to formula (I), having the following formula:

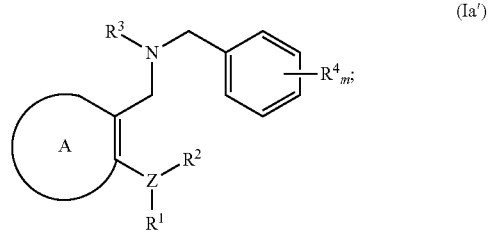

(Ia')

or a salt, including a pharmaceutically acceptable or a non-pharmaceutically acceptable salt, a prodrug, a diastereomeric mixture, an enantiomer, a tautomer, a racemic mixture, or any combination thereof, wherein:

A is selected from a substituted or an unsubstituted, monocyclic or bicyclic moiety selected from:

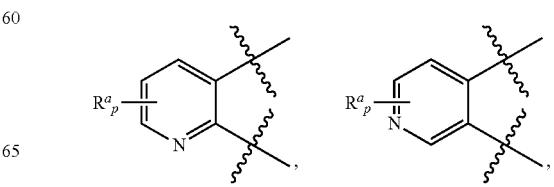

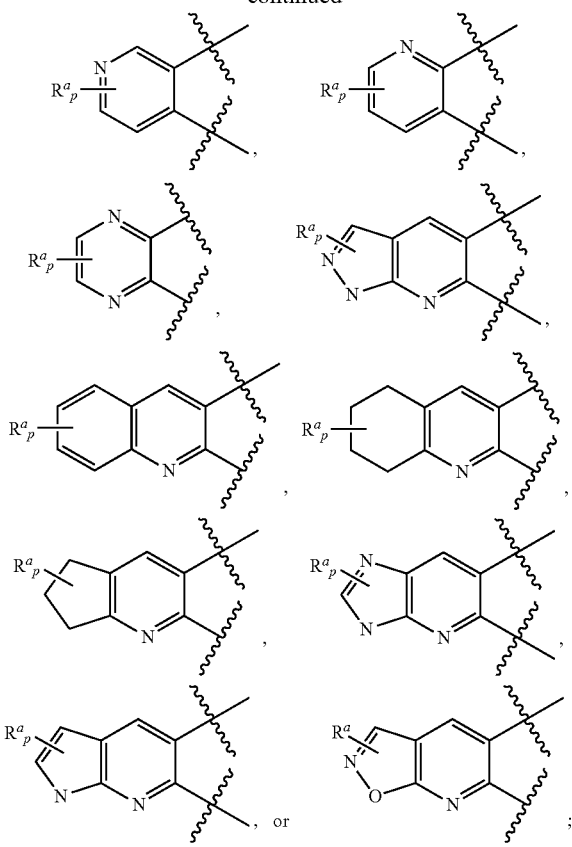

wherein $R^a$, in each occurrence, is selected independently from: 1) a halogen; a hydroxyl, or a cyano; 2) an alkyl or an alkoxy, any of which having up to 12 carbon atoms; or 3) $CO_2R^6$; and p is an integer from 0 to 3, inclusive, as the structure of A allows or requires. In this aspect of the invention, the representation of $R^a$ groups as substituents on any portion of the bicyclic moieties is intended to denote all possible regioisomers, including regioisomers in which $R^a$ groups are bonded to either ring or both rings of the bicyclic moieties.

Further to this aspect of formula (Ia') presented immediately above, the following substituents of the formula can be selected as indicated here, while unspecified substitutents are selected as disclosed above for this formula:

Z is N or CH; or the $ZR^1R^2$ moiety is —C≡$CR^2$.

In another aspect of the formula (Ia') presented above, the following substituents of the formula can be selected as indicated here, while unspecified substitutents are selected as disclosed above for this formula:

$R^1$ and $R^2$ are selected independently from: 1) hydrogen; 2) a C1 to C6 alkyl, that is, an alkyl having up to 6 carbon atoms; 3) a C3 to C6 cycloalkyl, that is, a cycloalkyl having up to 6 carbon atoms; 4) $COR^8$; or 5) $(CH_2)_nR^5$ or $(CH_2)_nR^dCO_2R^e$, wherein n, in each occurrence, is 1 or 2; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen;

or $R^1$ and $R^2$ together form a substituted or an unsubstituted monocyclic or bicyclic moiety comprising up to 12 carbon atoms, and optionally comprising 1 or 2 heteroatoms or heterogroups selected independently from O, N, or $NR^{10}$; wherein any optional substituent on the cyclic moiety selected from: 1) a C3 to C6 cycloalkyl, that is, a cycloalkyl having up to 6 carbon atoms; or 2) a C1 to C2 alkyl, that is, an alkyl having up to 2 carbon atoms.

In yet another aspect of the formula (Ia') presented above, the following substituents of the formula can be selected as indicated here, while unspecified substitutents are selected as disclosed above for this formula:

$R^3$ is selected from: 1) hydrogen or cyano; 2) a substituted or an unsubstituted alkyl having up to 12 carbon atoms; 3) a substituted or an unsubstituted aryl, or a substituted or an unsubstituted 5-, 6-, or 7-membered heterocyclyl or heteroaryl, comprising 1, 2, or 3 heteroatoms or heterogroups selected independently from O, N, S, $NR^{10}$, $SO_2$, or CO, any of which having up to 12 carbon atoms; or 4) $CO_2R^6$, $COR^8$, $SO_2R^8$, $SO_2NR^6R^7$, $CONR^6R^7$, $C(S)NR^6R^7$, $C(S)NC(O)OR^8$, or $C(S)SR^8$;

wherein when $R^3$ is an alkyl, an aryl, a heterocyclyl, or a heteroaryl, $R^3$ is optionally substituted with up to three substituents selected independently from a halide, a hydroxyl, a cyano, an alkoxy having up to 12 carbon atoms, or $R^{11}$;

$R^{11}$ is selected independently from:

1) an alkyl, a haloalkyl, a cycloalkyl, or an alkoxycarbonyl, any of which having up to 12 carbon atoms;

2) a substituted or an unsubstituted heteroaryl or heterocyclyl, any of which having up to 12 carbon atoms, comprises at least one heteroatom or heterogroup selected independently from O, N, S, $NR^{10}$, $SO_2$, or CO, wherein any substituted heteroaryl or heterocyclyl is substituted with up to three substituents selected independently from an alkyl having up to 12 carbon atoms or a hydroxyl; or 3) —CO—$Z^2$—$R^{13}$, —CO—$R^2$, —CO—$Z^2$—$(CH_2)_r$—CO—$Z^2$—$R^{13}$, —$NR^{15}R^{16}$, —$Z^2$—CO—$(CH_2)_r$—$Z^2$—$R^{13}$, —$Z^2$—CO—$(CH_2)_r$—CO—$Z^2$—$R^{13}$, —O—$(CH_2)_r$—CO—$Z^2$—$R^{13}$, —O—$(CH_2)_r$—$R^{14}$, —O—$R^{12}$—$(CH_2)_r$—$R^{13}$, —O—$R^{14}$—CO—O—$R^{13}$, —O—$(CH_2)_r$—$R^{12}$, —O—$(CH_2)_r$—NR'R'', —O—$(CH_2)_r$—$CO_2$—$(CH_2)_r$—$R^{13}$, —O—$(CH_2)_r$—CONR'R'', —O—$(CH_2)_r$—$SR^8$, —O—$(CH_2)_r$—$CO_2$—$R^{13}$, —O—$(CH_2)_r$—O—$(CH_2)_r$—$OR^{13}$, —O—$(CH_2)_r$—CONR'R'', —O—$(CH_2)_r$—CONH—$(CH_2)_r$—$OR^{13}$, —O—$(CH_2)_r$—$SO_2R^8$, —O—$(CH_2)_r$—$R^{13}$—, —O—$(CH_2)_r$—$OR^{13}$, —O—$(CH_2)_r$—O—$(CH_2)_r$—$OR^{11}$, —S—$(CH_2)_r$—CONR'R'', —$SO_2$—$(CH_2)_r$—$OR^{13}$, —$SO_2$—$(CH_2)_r$—CONR'R'', —$(CH_2)_r$—O—CO—$R^8$, —$(CH_2)_r$—$R^{12}$, —$(CH_2)_r$—$R^{13}$, —$(CH_2)_r$—N—$(CH_2)_r$—$OR^{13}$, —$(CH_2)_r$—CO—$Z^2$—$R^{13}$, —$(CH_2)_r$—Z—$R^{13}$, or -alkenylene-$CO_2$—$(CH_2)_r$—$R^{13}$;

r, in each occurrence, is independently 1, 2, or 3;

$R^{12}$, in each occurrence, is independently selected from a substituted or an unsubstituted heterocyclyl having up to 12 carbon atoms, comprising at least one heteroatom or heterogroup selected independently from O, N, S, $NR^{10}$, $SO_2$, or CO, wherein any substituted heterocyclyl is substituted with up to three substituents selected independently from an acyl, an alkyl, or an alkoxycarbonyl, any of which having up to 12 carbon atoms, or —COOH;

$R^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from O, N, S, $NR^{10}$, $SO_2$, or CO;

$R^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from O, N, S, $NR^{10}$, $SO_2$, or CO;

$Z^2$, in each occurrence, is selected independently from $NR^{10}$ or O;

R' and R", in each occurrence, are independently selected from hydrogen or an alkyl having up to 12 carbon atoms; and $R^{15}$ and $R^{16}$, in each occurrence, are independently selected from: 1) hydrogen; 2) an alkyl having up to 12 carbon atoms; or 3) —$(CH_2)_r$—O—$R^{13}$, —$(CH_2)_r$—$R^{14}$, —$COR^{13}$, —$(CH_2)_r$—CO—$Z^2$—$R^{13}$, —$CO_2R^{13}$, —$CO_2$—$(CH_2)_r$—$R^{13}$, —$CO_2$—$(CH_2)_r$—$R^{12}$, —$CO_2$—$(CH_2)_r$—CO—$Z^2$—$R^{13}$, —$CO_2$—$(CH_2)_r$—$OR^{13}$, —CO—$(CH_2)_r$—O—$(CH_2)_r$—O—$(CH_2)_r$—$R^{13}$, —CO—$(CH_2)_r$—O$(CH_2)_r$—$OR^{13}$, or —CO—NH—$(CH_2)_r$—$OR^{13}$;

or $R^{15}$ and $R^{16}$ together form a substituted or an unsubstituted cyclic moiety comprising up to 12 carbon atoms, optionally comprising at least one additional heteroatom or heterogroup selected independently from O, N, S, $NR^{10}$, $SO_2$, or CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from O, N, S, or $NR^{10}$; or 3) $COOR^{13}$, —$Z^2$—$(CH_2)_r$—$R^{13}$, —$COR^{13}$, —$CO_2$—$(CH_2)_r$—$R^{13}$, —$CO(CH_2)_r$—O—$R^{13}$, —$(CH_2)_r$—$CO_2$—$R^{13}$, —$SO_2R^8$, —$SO_2NR'R"$, or —NR'R"; and wherein the —$(CH_2)_r$— linking moiety, in any occurrence, is optionally substituted with at least one group selected independently from hydroxyl, amino, or an alkyl having up to 3 carbon atoms.

In still another aspect of the formula (Ia') presented above, the following substituents of the formula can be selected as indicated here, while unspecified substituents are selected as disclosed above for this formula for this formula:

$R^4$, in each occurrence, is selected independently from: 1) halogen or cyano; or 2) an alkyl or a haloalkyl, any of which having up to 4 carbon atoms; and m is 2 or 3.

Still another aspect of this invention provides benzylamine compounds according to formula (I), and compositions comprising benzylamine compounds, having the following formula:

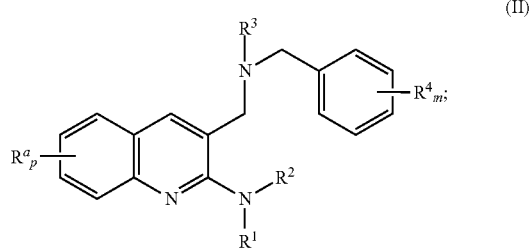

(II)

or a salt, including a pharmaceutically acceptable or a non-pharmaceutically acceptable salt, a prodrug, a diastereomeric mixture, an enantiomer, a tautomer, a racemic mixture thereof, or any combination thereof, wherein:

$R^1$ and $R^2$ are selected independently from: 1) a substituted or an unsubstituted alkyl or a substituted or an unsubstituted cycloalkyl, either of which having up to 12 carbon atoms; 2) $COR^8$ or $CO_2R^6$; or 3) $(CH_2)_nR^5$ or $(CH_2)_nR^dCO_2R^e$, wherein n, in each occurrence, is 1 or 2; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen;

$R^3$ is selected from: 1) hydrogen or cyano; 2) a substituted or an unsubstituted alkyl having up to 12 carbon atoms; 3) a substituted or an unsubstituted, 5-, 6-, or 7-membered heterocyclyl or heteroaryl, any of which having up to 12 carbon atoms, comprising 1, 2, or 3 heteroatoms or heterogroups selected independently from O, N, S, $NR^{10}$, $SO_2$, or CO; or 4) $CO_2R^6$, $C(S)SR^8$, or $C(S)NC(O)OR^8$;

$R^4$, in each occurrence, is selected independently from: 1) halogen or cyano; or 2) an alkyl or a haloalkyl, either of which having up to 12 carbon atoms;

m is an integer from 0 to 3, inclusive;

$R^5$, in each occurrence, is selected independently from: 1) a substituted or an unsubstituted aryl, cycloalkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

$R^6$ is selected from: 1) hydrogen; or 2) a substituted or an unsubstituted alkyl, cycloalkyl, haloalkyl, aryl, aralkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

$R^8$, in each occurrence, is selected independently from a substituted or an unsubstituted alkyl, cycloalkyl, haloalkyl, aryl, heteroaryl, or heterocyclyl, any of which having up to 12 carbon atoms, wherein any heteroaryl or heterocyclyl comprises at least one heteroatom or heterogroup selected independently from O, N, S, $NR^{10}$, $SO_2$, or CO;

$R^{10}$, in each occurrence, is selected independently from: 1) hydrogen; or 2) an alkyl, a cycloalkyl, a haloalkyl, an aryl, or an aralkyl, any of which having up to 12 carbon atoms;

$R^a$, in each occurrence, is selected independently from: 1) halogen, hydroxyl, or cyano; 2) an alkyl, a haloalkyl, an alkoxy, a haloalkoxy, or an aryl, any of which having up to 12 carbon atoms; or 3) $CO_2R^6$;

p is an integer from 0 to 3, inclusive;

$R^3$ is optionally substituted with at least one substituent selected independently from 1) an alkyl or a haloalkyl, any of which having up to 12 carbon atoms; or 2) $CO_2R^9$, wherein $R^9$ is an alkyl having up to 12 carbon atoms; and any group or substituent that is not specified, is selected according to the substituents disclosed herein for structure (I).

Yet another aspect of this invention provides benzylamine compounds according to formula (I), and compositions comprising benzylamine compounds, having the following formula:

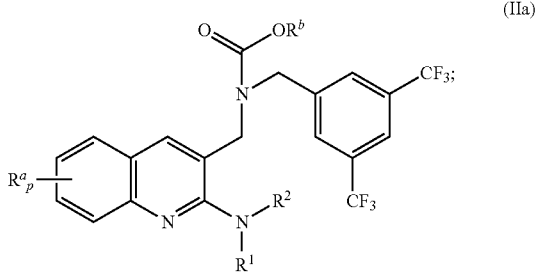

(IIa)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^b$ is selected independently from: 1) hydrogen; or 2) an alkyl or a cycloalkyl, either of which having up to 12 carbon atoms; and any group or substituent that is not specified, is selected according to the substituents disclosed herein for structure (I).

In another aspect, this invention provides benzylamine compounds according to formula (I), and compositions comprising benzylamine compounds, having the following formula:

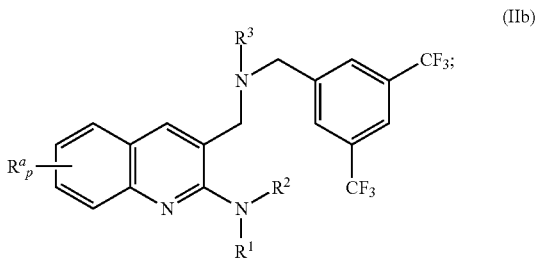

(IIb)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^3$ is selected from a substituted or an unsubstituted group selected from tetrazolyl, 1,3,4-oxadiazolyl, oxazolyl, pyrimidinyl, 4,5-dihydro-oxazolyl, pyridyl, thiazolyl, or isoxazolyl; wherein any optional substitutent on $R^3$ is selected independently from an alkyl or a haloalkyl, any of which having up to 12 carbon atoms; and any group or substituent that is not specified, is selected according to the substituents disclosed herein for structure (I).

In another aspect, this invention provides benzylamine compounds according to formula (I), and compositions comprising benzylamine compounds, having the following formula:

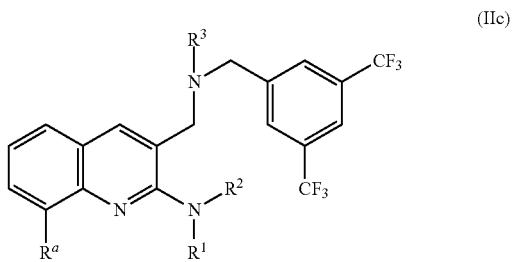

(IIc)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^a$ is selected from methyl, ethyl, or methoxy; and any group or substituent that is not specified, is selected according to the substituents disclosed herein for structure (I).

In another aspect, this invention provides benzylamine compounds according to formula (I), and compositions comprising benzylamine compounds, having the following formula:

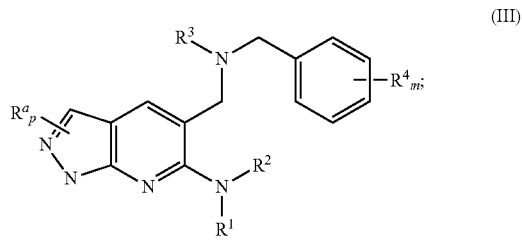

(III)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^1$ and $R^2$ are selected independently from: 1) a substituted or an unsubstituted alkyl or a substituted or an unsubstituted cycloalkyl, either of which having up to 12 carbon atoms; 2) $COR^8$ or $CO_2R^6$; or 3) $(CH_2)_nR^5$ or $(CH_2)_nR^dCO_2R^e$, wherein n, in each occurrence, is 1 or 2; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen;

$R^3$ is selected from: 1) hydrogen or cyano; 2) a substituted or an unsubstituted, 5-, 6-, or 7-membered heterocyclyl or heteroaryl, any of which having up to 12 carbon atoms, comprising 1, 2, or 3 heteroatoms or heterogroups selected independently from O, N, S, $NR^{10}$, $SO_2$, or CO; or 4) $CO_2R^6$;

$R^4$, in each occurrence, is selected independently from: 1) halogen or cyano; or 2) an alkyl or a haloalkyl, either of which having up to 12 carbon atoms;

m is an integer from 0 to 3, inclusive;

$R^5$, in each occurrence, is selected independently from: 1) a substituted or an unsubstituted aryl, cycloalkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO; or 2) a substituted or an unsubstituted heterocycloalkyl comprising from 3 to 7 ring carbon atoms, and from 1 to 3 heteroatoms or heterogroups, inclusive, selected independently from O, N, S, $NR^{10}$, $SO_2$, or CO;

$R^6$ is selected from: 1) hydrogen; or 2) a substituted or an unsubstituted alkyl, cycloalkyl, haloalkyl, aryl, aralkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

$R^8$, in each occurrence, is selected independently from an alkyl, a cycloalkyl, a haloalkyl, an aryl, a heteroaryl, or a heterocyclyl, any of which having up to 12 carbon atoms, wherein any heteroaryl or heterocyclyl comprises at least one heteroatom or heterogroup selected independently from O, N, S, $NR^{10}$, $SO_2$, or CO;

$R^{10}$, in each occurrence, is an selected independently from: 1) hydrogen; or 2) an alkyl, a cycloalkyl, a haloalkyl, an aryl, or an aralkyl, any of which having up to 12 carbon atoms;

$R^a$, in each occurrence, is selected independently from: 1) a hydrogen; 2) an alkyl, a haloalkyl, an aryl, or an alkoxy, any of which having up to 12 carbon atoms; or 3) $CO_2R^6$;

p is an integer from 0 to 2, inclusive;

$R^3$ is optionally substituted with at least one substituent selected independently from: 1) an alkyl or a haloalkyl, any of which having up to 12 carbon atoms; or 2) $CO_2R^9$, wherein $R^9$ is an alkyl having up to 12 carbon atoms; and any group or substituent that is not specified, is selected according to the substituents disclosed herein for structure (I).

In still another aspect, this invention affords benzylamine compounds according to formula (I), and compositions comprising benzylamine compounds, having the following formula:

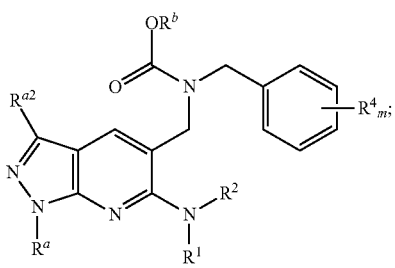

(IIIa)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^a$ is selected from: 1) hydrogen; or 2) an alkyl or an aryl, either of which having up to 12 carbon atoms;

$R^{a2}$ is selected from hydrogen or an alkyl having up to 12 carbon atoms;

$R^b$ is selected from: 1) hydrogen; or 2) an alkyl or a cycloalkyl, either of which having up to 12 carbon atoms; and any group or substituent that is not specified, is selected according to the substituents disclosed herein for structure (I).

Yet still another aspect of this invention affords benzylamine compounds according to formula (I), and compositions comprising benzylamine compounds, having the following formula:

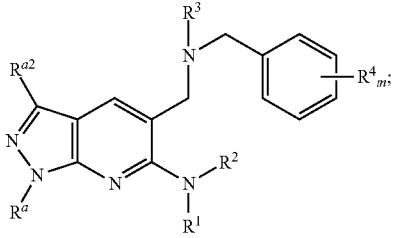

(IIIb)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^a$ is selected from: 1) hydrogen, or 2) an alkyl or an aryl, either of which having up to 12 carbon atoms;

$R^{a2}$ is selected from hydrogen or an alkyl having up to 12 carbon atoms;

$R^3$ is selected from a substituted or an unsubstituted group selected from tetrazolyl, 1,3,4-oxadiazolyl, oxazolyl, pyrimidinyl, 4,5-dihydro-oxazolyl, pyridyl, thiazolyl, or isooxazolyl; wherein any optional substitutent on $R^3$ is selected independently from an alkyl or a haloalkyl, any of which having up to 12 carbon atoms; and any group or substituent that is not specified, is selected according to the substituents disclosed herein for structure (I).

In still another aspect, this invention provides benzylamine compounds according to formula (I), and compositions comprising benzylamine compounds, having the following formula:

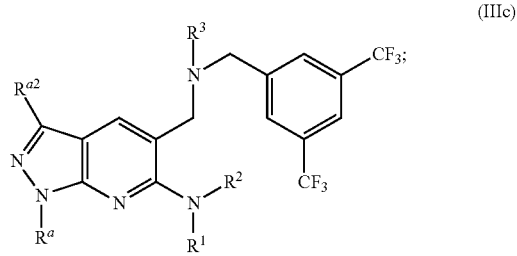

(IIIc)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^3$ is selected from: 1) $CO_2R^6$ or 2) a substituted or an unsubstituted 5-, 6-, or 7-membered heteroaryl having up to 12 carbon atoms, comprising 1, 2, or 3 heteroatoms or heterogroups selected independently from O, N, S, or $NR^{10}$; and any group or substituent that is not specified, is selected according to the substituents disclosed herein for structure (I).

Still a further aspect of this invention affords benzylamine compounds according to formula (I), and compositions comprising benzylamine compounds, having the following formula:

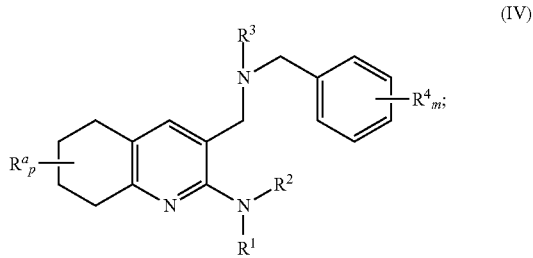

(IV)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^1$ and $R^2$ are selected independently from: 1) a substituted or an unsubstituted alkyl or a substituted or an unsubstituted cycloalkyl, either of which having up to 12 carbon atoms; 2) $COR^8$ or $CO_2R^6$; or 3) $(CH_2)_nR^5$ or $(CH_2)_nR^dCO_2R^e$, wherein n, in each occurrence, is 1, 3, or 3; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen;

$R^3$ is selected from: 1) hydrogen or cyano; 2) a substituted or an unsubstituted, 5-, 6-, or 7-membered heterocyclyl or heteroaryl, any of which having up to 12 carbon atoms, comprising 1, 2, or 3 heteroatoms or heterogroups selected independently from O, N, S, $NR^{10}$, $SO_2$, or CO; or 3) $CO_2R^6$;

$R^4$, in each occurrence, is selected independently from: 1) halogen or cyano; or 2) an alkyl or a haloalkyl, either of which having up to 12 carbon atoms;

m is an integer from 0 to 3, inclusive;

$R^5$, in each occurrence, is selected independently from: 1) a substituted or an unsubstituted aryl, cycloalkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO; or 2) a substituted or an unsubstituted heterocycloalkyl comprising from 3 to 7 ring carbon atoms, and from 1 to 3 heteroatoms or heterogroups, inclusive, selected independently from O, N, S, $NR^{10}$, $SO_2$, or CO;

$R^6$ is selected from: 1) hydrogen; or 2) a substituted of an unsubstituted alkyl, cycloalkyl, haloalkyl, aryl, aralkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

$R^8$, in each occurrence, is selected independently from an alkyl, a cycloalkyl, a haloalkyl, an aryl, a heteroaryl, or a heterocyclyl, any of which having up to 12 carbon atoms, wherein any heteroaryl or heterocyclyl comprises at least one heteroatom or heterogroup selected independently from O, N, S, $NR^{10}$, $SO_2$, or CO;

$R^{10}$, in each occurrence, is selected independently from: 1) hydrogen; or 2) an alkyl, a cycloalkyl, a haloalkyl, an aryl, or an aralkyl, any of which having up to 12 carbon atoms;

$R^a$, in each occurrence, is selected independently from hydrogen or an alkyl having up to 12 carbon atoms;

p is an integer from 0 to 3, inclusive;

$R^3$ is optionally substituted with at least one substituent selected independently from 1) an alkyl or a haloalkyl, any of which having up to 12 carbon atoms; or 2) $CO_2R^9$, wherein $R^9$ is an alkyl having up to 12 carbon atoms; and any group or substituent that is not specified, is selected according to the substituents disclosed herein for structure (I).

Yet a further aspect of this invention affords benzylamine compounds according to formula (I), and compositions comprising benzylamine compounds, having the following formula:

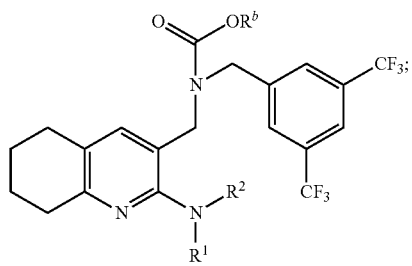

(IVa)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^b$ is selected independently from: 1) hydrogen; or 2) an alkyl or a cycloalkyl, either of which having up to 12 carbon atoms; and any group or substituent that is not specified, is selected according to the substituents disclosed herein for structure (I).

In yet another aspect of the present invention, this disclosure affords benzylamine compounds according to formula (I), and compositions comprising benzylamine compounds, having the following formula:

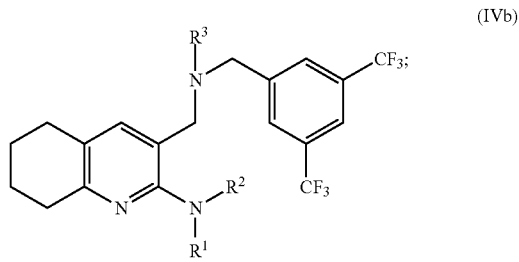

(IVb)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^3$ is selected from a substituted or an unsubstituted group selected from tetrazolyl, 1,3,4-oxadiazolyl, oxazolyl, pyrimidinyl, 4,5-dihydro-oxazolyl, pyridyl, thiazolyl, or isooxazolyl; wherein any optional substitutent on $R^3$ is selected independently from an alkyl or a haloalkyl, any of which having up to 12 carbon atoms; and any group or substituent that is not specified, is selected according to the substituents disclosed herein for structure (I).

In another aspect, this invention provides benzylamine compounds according to formula (I), and compositions comprising benzylamine compounds, having the following formula:

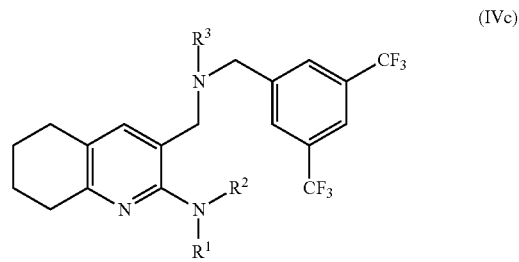

(IVc)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^3$ is selected from: 1) $CO_2R^6$ or 2) a substituted or an unsubstituted 5-, 6-, or 7-membered heteroaryl having up to 12 carbon atoms, comprising 1, 2, or 3 heteroatoms or heterogroups selected independently from O, N, S, or $NR^{10}$; and any group or substituent that is not specified, is selected according to the substituents disclosed herein for structure (I).

Still another aspect of this invention provides benzylamine compounds according to formula (I), and compositions comprising benzylamine compounds, having the following formula:

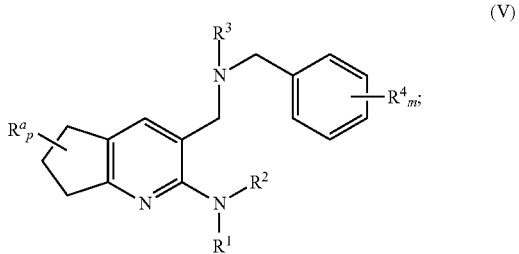

(V)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^1$ and $R^2$ are selected independently from: 1) a substituted or an unsubstituted alkyl or a substituted or an unsubstituted cycloalkyl, either of which having up to 12 carbon atoms; 2) $COR^8$ or $CO_2R^6$; or 3) $(CH_2)_nR^5$ or $(CH_2)_nR^dCO_2R^e$, wherein n, in each occurrence, is 1 or 2; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen;

$R^3$ is selected from: 1) hydrogen or cyano; 2) a substituted or an unsubstituted, 5-, 6-, or 7-membered heterocyclyl or heteroaryl, any of which having up to 12 carbon atoms, comprising 1, 2, or 3 heteroatoms or heterogroups selected independently from O, N, S, $NR^{10}$, $SO_2$, or CO; or 4) $CO_2R^6$;

$R^4$, in each occurrence, is selected independently from: 1) halogen or cyano; or 2) an alkyl or a haloalkyl, any of which having up to 12 carbon atoms;

m is an integer from 0 to 3, inclusive;

$R^5$, in each occurrence, is selected independently from: 1) a substituted or an unsubstituted aryl, cycloalkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO; or 2) a substituted or an unsubstituted heterocycloalkyl comprising from 3 to 7 ring carbon atoms, and from 1 to 3 heteroatoms or heterogroups, inclusive, selected independently from O, N, S, $NR^{10}$, $SO_2$, or CO;

$R^6$ is selected from: 1) hydrogen; or 2) a substituted or an unsubstituted alkyl, cycloalkyl, haloalkyl, aryl, aralkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

$R^8$, in each occurrence, is selected independently from an alkyl, a cycloalkyl, a haloalkyl, an aryl, a heteroaryl, or a heterocyclyl, any of which having up to 12 carbon atoms, wherein any heteroaryl or heterocyclyl comprises at least one heteroatom or heterogroup selected independently from O, N, S, $NR^{10}$, $SO_2$, or CO;

$R^{10}$, in each occurrence, is an selected independently from: 1) hydrogen; or 2) an alkyl, a cycloalkyl, a haloalkyl, an aryl, or an aralkyl, any of which having up to 12 carbon atoms;

$R^a$, in each occurrence, is selected independently from hydrogen or an alkyl having up to 12 carbon atoms;

p is an integer from 0 to 3, inclusive;

$R^3$ is optionally substituted with at least one substituent selected independently from: 1) an alkyl or a haloalkyl, any of which having up to 12 carbon atoms; or 2) $CO_2R^9$, wherein $R^9$ is an alkyl having up to 12 carbon atoms; and any group or substituent that is not specified, is selected according to the substituents disclosed herein for structure (I).

Yet another aspect of this invention provides benzylamine compounds according to formula (I), and compositions comprising benzylamine compounds, having the following formula:

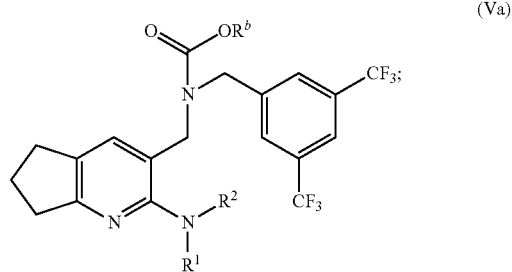

(Va)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^b$ is selected independently from: 1) hydrogen; or 2) an alkyl or a cycloalkyl, either of which having up to 12 carbon atoms; and any group or substituent that is not specified, is selected according to the substituents disclosed herein for structure (I).

A further aspect of this invention provides benzylamine compounds according to formula (I), and compositions comprising benzylamine compounds, having the following formula:

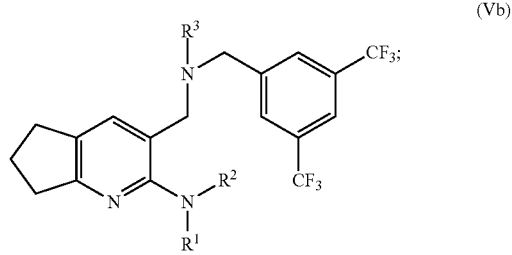

(Vb)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^3$ is selected from a substituted or an unsubstituted tetrazolyl, 1,3,4-oxadiazolyl, oxazolyl, pyrimidinyl, 4,5-dihydro-oxazolyl, pyridyl, thiazolyl, or isooxazolyl; wherein any optional substituent on $R^3$ is selected independently from an alkyl or a haloalkyl, any of which having up to 12 carbon atoms; and any group or substituent that is not specified, is selected according to the substituents disclosed herein for structure (I).

In another aspect, this invention provides benzylamine compounds according to formula (I), and compositions comprising benzylamine compounds, having the following formula:

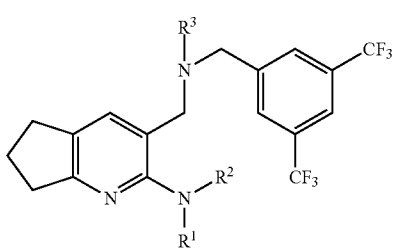

(Vc)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^3$ is selected from: 1) $CO_2R^6$ or 2) a substituted or an unsubstituted 5-, 6-, or 7-membered heteroaryl having up to 12 carbon atoms, comprising 1, 2, or 3 heteroatoms or heterogroups selected independently from O, N, S, or $NR^{10}$; and any group or substituent that is not specified, is selected according to the substituents disclosed herein for structure (I).

Still another aspect of this invention provides benzylamine compounds according to formula (I), and compositions comprising benzylamine compounds, having the following formula:

(VI)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^1$ and $R^2$ are selected independently from: 1) a substituted or an unsubstituted alkyl or a substituted or an unsubstituted cycloalkyl, either of which having up to 12 carbon atoms; 2) $COR^8$ or $CO_2R^6$; or 3) $(CH_2)_nR^5$ or $(CH_2)_nR^dCO_2R^e$, wherein n, in each occurrence, is 1, 2, or 3; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen;

$R^3$ is selected from: 1) hydrogen or cyano; 2) a substituted or an unsubstituted, 5-, 6-, or 7-membered heterocyclyl or heteroaryl, any of which having up to 12 carbon atoms, comprising 1, 2, or 3 heteroatoms or heterogroups selected independently from O, N, S, $NR^{10}$, or CO; or 4) $CO_2R^6$;

$R^4$, in each occurrence, is selected independently from: 1) halogen or cyano; or 2) an alkyl or a haloalkyl, any of which having up to 12 carbon atoms;

m is an integer from 0 to 3, inclusive;

$R^5$, in each occurrence, is selected independently from: 1) a substituted or an unsubstituted aryl, cycloalkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO; or 2) a substituted or an unsubstituted heterocycloalkyl comprising from 3 to 7 ring carbon atoms, and from 1 to 3 heteroatoms or heterogroups, inclusive, selected independently from O, N, S, $NR^{10}$, $SO_2$, or CO;

$R^6$ is selected from: 1) hydrogen; or 2) a substituted or an unsubstituted alkyl, cycloalkyl, haloalkyl, aryl, aralkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

$R^8$, in each occurrence, is selected independently from an alkyl, a cycloalkyl, a haloalkyl, an aryl, a heteroaryl, or a heterocyclyl, any of which having up to 12 carbon atoms, wherein any heteroaryl or heterocyclyl comprises at least one heteroatom or heterogroup selected independently from O, N, S, $NR^{10}$, $SO_2$, or CO;

$R^{10}$, in each occurrence, is an selected independently from: 1) hydrogen; or 2) an alkyl, a cycloalkyl, a haloalkyl, an aryl, or an aralkyl, any of which having up to 12 carbon atoms;

$R^a$, in each occurrence, is selected independently from: 1) halogen, hydroxyl, or cyano; or 2) an alkyl, a haloalkyl, an alkoxy, a haloalkoxy, an aryl, a heteroaryl, or a heterocyclyl, any of which having up to 12 carbon atoms; or 3) $CO_2R^6$;

p is an integer from 0 to 3, inclusive;

$R^3$ is optionally substituted with at least one substituent selected independently from: 1) an alkyl or a haloalkyl, any of which having up to 12 carbon atoms; or 2) $CO_2R^9$, wherein $R^9$ is an alkyl having up to 12 carbon atoms; and any group or substituent that is not specified, is selected according to the substituents disclosed herein for structure (I).

Yet another aspect of this invention provides benzylamine compounds according to formula (I), and compositions comprising benzylamine compounds, having the following formula:

(VIa)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^b$ is selected independently from: 1) hydrogen; or 2) an alkyl or a cycloalkyl, either of which having up to 12 carbon atoms; and any group or substituent that is not specified, is selected according to the substituents disclosed herein for structure (I).

A further aspect of this invention provides benzylamine compounds according to formula (I), and compositions comprising benzylamine compounds, having the following formula:

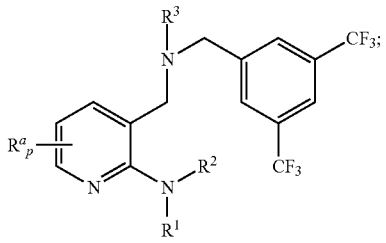

(VIb)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^3$ is selected from a substituted or an unsubstituted tetrazolyl, 1,3,4-oxadiazolyl, oxazolyl, pyrimidinyl, 4,5-dihydrooxazolyl, pyridyl, thiazolyl, or isooxazolyl; wherein any optional substituent on $R^3$ is selected independently from an alkyl or a haloalkyl, any of which having up to 12 carbon atoms; and any group or substituent that is not specified, is selected according to the substituents disclosed herein for structure (I).

In another aspect, this invention provides benzylamine compounds according to formula (I), and compositions comprising benzylamine compounds, having the following formula:

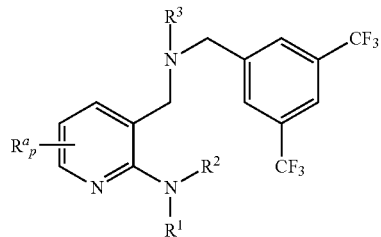

(VIc)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^3$ is selected from: 1) $CO_2R^6$ or 2) a substituted or an unsubstituted 5-, 6-, or 7-membered heteroaryl having up to 12 carbon atoms, comprising 1, 2, or 3 heteroatoms or heterogroups selected independently from O, N, S, or $NR^{10}$; and any group or substituent that is not specified, is selected according to the substituents disclosed herein for structure (I).

Still another aspect of this invention provides benzylamine compounds according to formula (I), and compositions comprising benzylamine compounds, having the following formula:

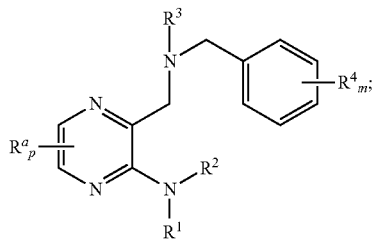

(VII)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^1$ and $R^2$ are selected independently from: 1) a substituted or an unsubstituted alkyl or a substituted or an unsubstituted cycloalkyl, either of which having up to 12 carbon atoms; 2) $COR^8$ or $CO_2R^6$; or 3) $(CH_2)_nR^5$ or $(CH_2)_nR^dCO_2R^e$, wherein n, in each occurrence, is 1, 2, or 3; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen $R^3$ is selected from: 1) hydrogen or cyano; 2) a substituted or an unsubstituted, 5-, 6-, or 7-membered heterocyclyl or heteroaryl, any of which having up to 12 carbon atoms, comprising 1, 2, or 3 heteroatoms or heterogroups selected independently from O, N, S, $NR^{10}$, $SO_2$, or CO; or 4) $CO_2R^6$;

$R^4$, in each occurrence, is selected independently from: 1) halogen or cyano; or 2) an alkyl or a haloalkyl, any of which having up to 12 carbon atoms;

m is an integer from 0 to 3, inclusive;

$R^5$, in each occurrence, is selected independently from: 1) a substituted or an unsubstituted aryl, cycloalkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO; or 2) a substituted or an unsubstituted heterocycloalkyl comprising from 3 to 7 ring carbon atoms, and from 1 to 3 heteroatoms or heterogroups, inclusive, selected independently from O, N, S, $NR^{10}$, $SO_2$, or CO;

$R^6$ is selected from: 1) hydrogen; or 2) a substituted or an unsubstituted alkyl, cycloalkyl, haloalkyl, aryl, aralkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

$R^8$, in each occurrence, is selected independently from an alkyl, a cycloalkyl, a haloalkyl, an aryl, a heteroaryl, or a heterocyclyl, any of which having up to 12 carbon atoms, wherein any heteroaryl or heterocyclyl comprises at least one heteroatom or heterogroup selected independently from O, N, S, $NR^{10}$, $SO_2$, or CO;

$R^{10}$, in each occurrence, is an selected independently from: 1) hydrogen; or 2) an alkyl, a cycloalkyl, a haloalkyl, an aryl, or an aralkyl, any of which having up to 12 carbon atoms;

$R^a$, in each occurrence, is selected independently from: 1) halogen, hydroxyl, or cyano; or 2) an alkyl, a haloalkyl, an alkoxy, a haloalkoxy, an aryl, a heteroaryl, or a heterocyclyl, any of which having up to 12 carbon atoms; or 3) CO$_2$R$^6$;

p is an integer from 0 to 3, inclusive;

R$^3$ is optionally substituted with at least one substituent selected independently from: 1) an alkyl or a haloalkyl, any of which having up to 12 carbon atoms; or 2) CO$_2$R$^9$, wherein R$^9$ is an alkyl having up to 12 carbon atoms; and any group or substituent that is not specified, is selected according to the substituents disclosed herein for structure (I).

Yet another aspect of this invention provides benzylamine compounds according to formula (I), and compositions comprising benzylamine compounds, having the following formula:

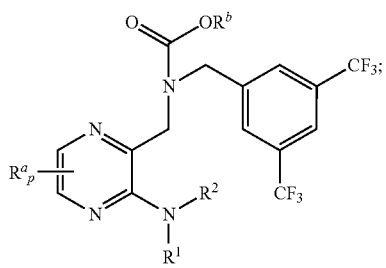

(VIIa)

or a salt, including a pharmaceutically acceptable or a non-pharmaceutically acceptable salt, a prodrug, a diastereomeric mixture, an enantiomer, a tautomer, a racemic mixture, or any combination thereof, wherein:

R$^b$ is selected independently from: 1) hydrogen; or 2) an alkyl or a cycloalkyl, either of which having up to 12 carbon atoms; and any group or substitutent that is not specified, is selected according to the substituents disclosed herein for structure (I).

A further aspect of this invention provides benzylamine compounds according to formula (I), and compositions comprising benzylamine compounds, having the following formula:

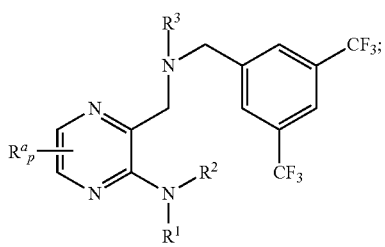

(VIIb)

or a salt, including a pharmaceutically acceptable or a non-pharmaceutically acceptable salt, a prodrug, a diastereomeric mixture, an enantiomer, a tautomer, a racemic mixture, or any combination thereof, wherein:

R$^3$ is selected from a substituted or an unsubstituted tetrazolyl, 1,3,4-oxadiazolyl, oxazolyl, pyrimidinyl, 4,5-dihydro-oxazolyl, pyridyl, thiazolyl, or isooxazolyl; wherein any optional substitutent on R$^3$ is selected independently from an alkyl or a haloalkyl, any of which having up to 12 carbon atoms; and any group or substituent that is not specified, is selected according to the substituents disclosed herein for structure (I).

In another aspect, this invention provides benzylamine compounds according to formula (I), and compositions comprising benzylamine compounds, having the following formula:

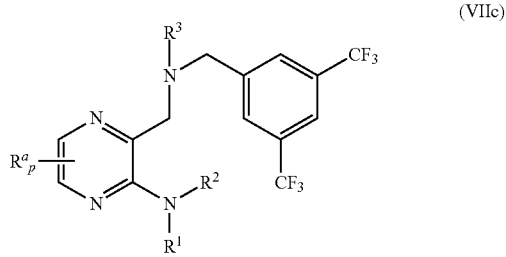

(VIIc)

or a salt, including a pharmaceutically acceptable or a non-pharmaceutically acceptable salt, a prodrug, a diastereomeric mixture, an enantiomer, a tautomer, a racemic mixture, or any combination thereof, wherein:

R$^3$ is selected from: 1) CO$_2$R$^6$ or 2) a substituted or an unsubstituted 5-, 6-, or 7-membered heteroaryl having up to 12 carbon atoms, comprising 1, 2, or 3 heteroatoms or heterogroups selected independently from O, N, S, or NR$^{10}$; and any group or substituent that is not specified, is selected according to the substituents disclosed herein for structure (I).

Still another aspect of this invention provides benzylamine compounds according to formula (I), and compositions comprising benzylamine compounds, having the following formula:

(VIII)

or a salt, including a pharmaceutically acceptable or a non-pharmaceutically acceptable salt, a prodrug, a diastereomeric mixture, an enantiomer, a tautomer, a racemic mixture, or any combination thereof, wherein:

R$^1$ and R$^2$ are selected independently from: 1) a substituted or an unsubstituted alkyl or a substituted or an unsubstituted cycloalkyl, either of which having up to 12 carbon atoms; 2) COR$^8$ or CO$_2$R$^6$; or 3) (CH$_2$)$_n$R$^5$ or (CH$_2$)$_n$R$^d$CO$_2$R$^e$, wherein n, in each occurrence, is 1, 2, or 3; R$^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, NR$^{10}$, SO$_2$, or CO; and Re, in each occurrence, is selected independently from an alkyl or a cycloalkyl, either of which having up to 12 carbon atoms, or hydrogen;

R$^3$ is selected from: 1) hydrogen or cyano; 2) a substituted or an unsubstituted, 5-, 6-, or 7-membered heterocyclyl or heteroaryl, any of which having up to 12 carbon atoms, comprising 1, 2, or 3 heteroatoms or heterogroups selected independently from O, N, S, NR$^{10}$, SO$_2$, or CO; or 4) CO$_2$R$^6$;

R⁴, in each occurrence, is selected independently from: 1) halogen or cyano; or 2) an alkyl or a haloalkyl, any of which having up to 12 carbon atoms;

m is an integer from 0 to 3, inclusive;

R⁵, in each occurrence, is selected independently from: 1) a substituted or an unsubstituted aryl, cycloalkyl, heterocyclyl, or heteroaryl, any of which having up to 12 carbon atoms, wherein any heterocyclyl or heteroaryl comprises at least one heteroatom or heterogroup selected independently from O, N, S, NR¹⁰, SO₂, or CO; or 2) a substituted or an unsubstituted heterocycloalkyl comprising from 3 to 7 ring carbon atoms, and from 1 to 3 heteroatoms or heterogroups, inclusive, selected independently from O, N, S, NR¹⁰, SO₂, or CO;

R⁶ is selected from: 1) hydrogen; or 2) a substituted or an unsubstituted alkyl, cycloalkyl, haloalkyl, aryl, aralkyl, heterocyclyl, or heteroaryl, any of which having up to 12 carbon atoms, wherein any heterocyclyl or heteroaryl comprises at least one heteroatom or heterogroup selected independently from O, N, S, NR¹⁰, SO₂, or CO;

R⁸, in each occurrence, is selected independently from an alkyl, a cycloalkyl, a haloalkyl, an aryl, a heteroaryl, or a heterocyclyl, any of which having up to 12 carbon atoms, wherein any heteroaryl or heterocyclyl comprises at least one heteroatom or heterogroup selected independently from O, N, S, NR¹⁰, SO₂, or CO;

R¹⁰, in each occurrence, is an selected independently from: 1) hydrogen; or 2) an alkyl, a cycloalkyl, a haloalkyl, an aryl, or an aralkyl, any of which having up to 12 carbon atoms;

Rᵃ, in each occurrence, is selected independently from: 1) halogen, hydroxyl, or cyano; or 2) an alkyl, a haloalkyl, an alkoxy, a haloalkoxy, an aryl, a heteroaryl, or a heterocyclyl, any of which having up to 12 carbon atoms; or 3) CO₂R⁶;

R³ is optionally substituted with at least one substituent selected independently from: 1) an alkyl or a haloalkyl, any of which having up to 12 carbon atoms; or 2) CO₂R⁹, wherein R⁹ is an alkyl having up to 12 carbon atoms; and any group or substituent that is not specified, is selected according to the substituents disclosed herein for structure (I).

any group or substituent that is not specified, is selected according to the substituents disclosed herein for structure (I).

Yet another aspect of this invention provides benzylamine compounds according to formula (I), and compositions comprising benzylamine compounds, having the following formula:

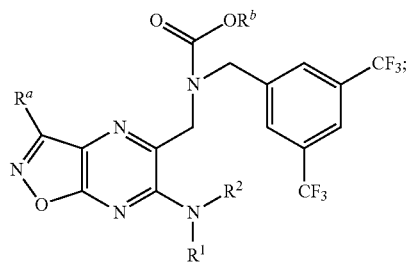

(VIIIa)

or a salt, including a pharmaceutically acceptable or a non-pharmaceutically acceptable salt, a prodrug, a diastereomeric mixture, an enantiomer, a tautomer, a racemic mixture, or any combination thereof, wherein:

Rᵇ is selected independently from: 1) hydrogen; or 2) an alkyl or a cycloalkyl, either of which having up to 12 carbon atoms; and any group or substituent that is not specified, is selected according to the substituents disclosed herein for structure (I).

A further aspect of this invention provides benzylamine compounds according to formula (I), and compositions comprising benzylamine compounds, having the following formula:

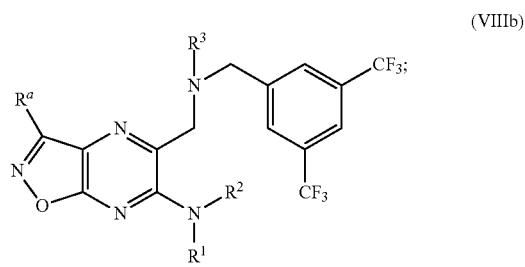

(VIIIb)

or a salt, including a pharmaceutically acceptable or a non-pharmaceutically acceptable salt, a prodrug, a diastereomeric mixture, an enantiomer, a tautomer, a racemic mixture, or any combination thereof, wherein:

R³ is selected from a substituted or an unsubstituted tetrazolyl, 1,3,4-oxadiazolyl, oxazolyl, pyrimidinyl, 4,5-dihydro-oxazolyl, pyridyl, thiazolyl, or isooxazolyl; wherein any optional substitutent on R³ is selected independently from an alkyl or a haloalkyl, any of which having up to 12 carbon atoms; and any group or substituent that is not specified, is selected according to the substituents disclosed herein for structure (I).

In another aspect, this invention provides benzylamine compounds according to formula (I), and compositions comprising benzylamine compounds, having the following formula:

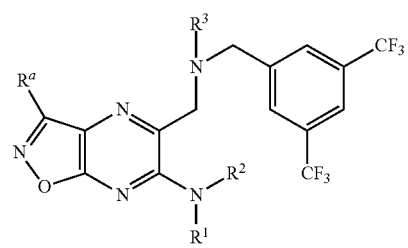

(VIIIc)

or a salt, including a pharmaceutically acceptable or a non-pharmaceutically acceptable salt, a prodrug, a diastereomeric mixture, an enantiomer, a tautomer, a racemic mixture, or any combination thereof, wherein:

Rₐ is hydrogen or an alkyl having up to 2 carbon atoms;

R³ is selected from: 1) CO₂R⁶ or 2) a substituted or an unsubstituted 5-, 6-, or 7-membered heteroaryl having up to 12 carbon atoms, comprising 1, 2, or 3 heteroatoms or heterogroups selected independently from O, N, S, or NR¹⁰; and any group or substituent that is not specified, is selected according to the substituents disclosed herein for structure (I).

In further aspects of this invention, the present invention provides several benzylamine compound genera, each of which is a subgenus of formula (I) disclosed herein. These genera are represented by the formulas (II-1), (IIa-1), (IIb-1), (III-1), (IIIa-1), (IIIb-1), (IV-1), (IVa-1), (IVb-1), (V-1), (Va-1), (Vb-1), (VI-1), (VIa-1), (VIb-1), (VII-1), (VIIa-1), (VIIb-1), (VIII-1), (VIIIa-1), and (VIIIb-1), as illustrated below, and each is characterized by various substituents including, but not limited to, Z, $R^1$, $R^2$, $R^3$, $R^4$, $R^5$, $R^6$, $R^7$, $R^8$, $R^9$, $R^{10}$, $R^a$, $R^b$, $R^x$, and the like. In this aspect, the possible selections for these substituent in each instance are provided in the listing below, and definitions of each of these possible selections, for example, the definitions of $R^{1A}$, $R^{1B}$, $R^{1C}$, and $R^{1D}$ which are possible selections for $R^1$, are further provided below.

The genera represented by the formulas (II-1), (IIa-1), (IIb-1), (III-1), (IIIa-1), (IIIb-1), (IV-1), (IVa-1), (IVb-1), (V-1), (Va-1), (Vb-1), (VI-1), (VIa-1), (VIb-1), (VII-1), (VIIa-1), (VIIb-1), (VIII-1), (VIIIa-1), and (VIIIb-1), are also provided in the tables below. These tables break down each genera into a listing of subgeneric formulas defined by the substituent selections according to the tables. For example, formulas (A-01) through (A-384) in Table A, are applicable to the compounds associated with that table, in this case, (II-1), (III-1), (IIIb-1), (IV-1), (V-1), (VI-1), (VII-1), and (VIII-1), and provide 384 differenet subgenera for each formula (II-1), (III-1), (IIIb-1), (IV-1), (V-1), (VI-1), (VII-1), and (VIII-1). This present invention provides for each of these compounds, methods of making each of these compounds, and methods of using each compound.

Thus, in this aspect, substituent selections are as follows. To the extent that any group or substituent is not specified in any of these formulas, the definition of that group of or substituent provided for formula (I) is applicable.

Z can be selected from $Z^A$, $Z^B$, or $Z^C$.
$R^1$ can be selected from $R^{1A}$, $R^{1B}$, $R^{1C}$, or $R^{1D}$.
$R^2$ can be selected from $R^{2A}$, $R^{2B}$, $R^{2C}$, or $R^{2D}$.
$R^3$ can be selected from $R^{3A}$, $R^{3B}$, $R^{3C}$, or $R^{3D}$.
$R^4$ can be selected from $R^{4A}$, $R^{4B}$, or $R^{4C}$.
$R^5$ can be selected from $R^{5A}$, $R^{5B}$, or $R^{5C}$.
$R^6$ can be selected from $R^{6A}$, $R^{6B}$, $R^{6C}$, $R^{6D}$, or $R^{6E}$.
$R^7$ can be selected from $R^{7A}$, $R^{7B}$, $R^{7C}$, or $R^{7E}$.
$R^8$ can be selected from $R^{8A}$, $R^{8B}$, or $R^{8C}$.
$R^9$ can be selected from $R^{9A}$, $R^{9B}$, $R^{9C}$, or $R^{9D}$.
$R^{10}$ can be selected from $R^{10A}$, $R^{10B}$, or $R^{10C}$.
$R^a$ can be selected from $R^{a1}$ or $R^{a2}$.
$R^b$ can be selected from $R^{b1}$ or $R^{b2}$.
$R^x$ can be selected from $R^{x1}$, $R^{x2}$, $R^{x3}$, or $R^{x4}$.

For each of these substituents selections, the following definitions are provided.

$Z^A$ is N or CH.
$Z^B$ is N.
$Z^C$ is CH.

$R^1A$ is: a) hydrogen; or b) a substituted or an unsubstituted alkyl, cycloalkyl, haloalkyl, aryl, heterocyclyl, heteroaryl, monoalkylamino, dialkylamino, alkoxyalkyl, haloalkoxyalkyl, or aminoalkyl, any of which having up to 12 carbon atoms, wherein any heterocyclyl or heteroaryl comprises at least one heteroatom or heterogroup selected independently from O, N, S, $NR^{10}$, $SO_2$, or CO.

$R^1B$ is a substituted or an unsubstituted heterocyclyl or heteroaryl, any of which having up to 12 carbon atoms, comprising at least one heteroatom or heterogroup selected independently from O, N, S, $NR^{10}$, $SO_2$, or CO.

$R^1C$ is: a) $CO_2R^6$, $COR^8$, $SO_2R^8$, $SO_2NR^6R^7$, or $CONR^6R^7$; or b) $(CHR^x)_nR^5$ or $(CH_2)_nR^dCO_2R^e$, wherein n, in each occurrence, is 1, 2, or 3; $R^x$, in each occurrence, is selected independently from an alkyl or an alkoxy, either of which having up to 12 carbon atoms, or hydrogen; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen.

$R^1D$ and $R^2D$ together form a substituted or an unsubstituted monocyclic or bicyclic moiety comprising up to 12 carbon atoms, and optionally comprising 1, 2, or 3 heteroatoms or heterogroups in addition to Z, selected independently from O, N, S, $NR^{10}$, $SO_2$, or CO.

$R^2A$ is: a) hydrogen; or b) a substituted or an unsubstituted alkyl, cycloalkyl, haloalkyl, aryl, heterocyclyl, heteroaryl, monoalkylamino, dialkylamino, alkoxyalkyl, haloalkoxyalkyl, or aminoalkyl, any of which having up to 12 carbon atoms, wherein any heterocyclyl or heteroaryl comprises at least one heteroatom or heterogroup selected independently from O, N, S, $NR^{10}$, $SO_2$, or CO.

$R^2B$ is a substituted or an unsubstituted heterocyclyl or heteroaryl, any of which having up to 12 carbon atoms, comprising at least one heteroatom or heterogroup selected independently from O, N, S, $NR^{10}$, $SO_2$, or CO.

$R^2C$ is: a) $CO_2R^6$, $COR^8$, $SO_2R^8$, $SO_2NR^6R^7$, or $CONR^6R^7$; or b) $(CHR^x)_nR^5$ or $(CH_2)_nR^dCO_2R^e$, wherein n, in each occurrence, is 1, 2, or 3; $R^x$, in each occurrence, is selected independently from an alkyl or an alkoxy, either of which having up to 12 carbon atoms, or hydrogen; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen.

$R^2D$ and $R^1D$ together form a substituted or an unsubstituted monocyclic or bicyclic moiety comprising up to 12 carbon atoms, and optionally comprising 1, 2, or 3 heteroatoms or heterogroups in addition to Z, selected independently from O, N, S, $NR^{10}$, $SO_2$, or CO.

$R^{3A}$ is: a) hydrogen or cyano; or 2) a substituted or an unsubstituted alkyl having up to 12 carbon atoms.

$R^3B$ is a substituted or an unsubstituted aryl, or a substituted or an unsubstituted 5-, 6-, or 7-membered heterocyclyl or heteroaryl, any of which having up to 12 carbon atoms, comprising 1, 2, or 3 heteroatoms or heterogroups selected independently from O, N, S, $NR^{10}$, $SO_2$, or CO.

$R^{3C}$ is a substituted or an unsubstituted group selected from $CO_2R^6$, $COR^8$, $SO_2R^8$, $SO_2NR^6R^7$, $CONR^6R^7$, $C(S)NR^6R^7$, $C(S)NC(O)OR^8$, or $C(S)SR^8$.

$R^{3D}$ is a substituted or an unsubstituted group selected from 4,5-dihydro-oxazolyl, tetrazolyl, isooxazolyl, pyridyl, pyrimidinyl, oxadiazolyl, thiazoyl, or oxazolyl; wherein any optional substitutent on $R^{3D}$ is selected independently from: a) an alkyl or a haloalkyl, any of which having up to 12 carbon atoms; or b) $CO_2R^9$, wherein $R^9$ is an alkyl having up to 12 carbon atoms.

$R^{4A}$ is: a) halogen, cyano, or hydroxy; or b) an alkyl, a cycloalkyl, a cycloalkoxy, an alkoxy, a haloalkyl, or a haloalkoxy, any of which having up to 12 carbon atoms.

$R^4B$ is a substituted or an unsubstituted aryl, aralkyl, aryloxy, heteroaryl, or heteroaryloxy, any of which having up to 12 carbon atoms, wherein any heteroaryl or heteroaryloxy comprises at least one heteroatom or heterogroup selected independently from O, N, S, or $NR^{10}$.

$R^{4C}$ is: a) a substituted or an unsubstituted group selected from $CO_2R^6$, $COR^8$, $SO_2R^8$, $SO_2NR^6R^7$, or $CONR^6R^7$; or b) $(CH_2)_qNR^6R^7$, wherein q is an integer from 0 to 5, inclusive.

$R^{5A}$ is a substituted or an unsubstituted an alkoxy, a haloalkoxy, or a cycloalkyl, any of which having up to 12 carbon atoms.

$R^{5B}$ is: a) a substituted or an unsubstituted aryl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO; or b) a substituted or an unsubstituted heterocycloalkyl comprising from 3 to 7 ring carbon atoms, and from 1 to 3 heteroatoms or heterogroups, inclusive, selected independently from O, N, S, $NR^{10}$, $SO_2$, or CO.

$R^{5C}$ is hydroxyl, $NR^6R^7$, $CO_2R^6$, $COR^8$, or $SO_2R^8$.

$R^{6A}$ hydrogen.

$R^{6B}$ is an alkyl, a cycloalkyl, or a haloalkyl, any of which having up to 12 carbon atoms.

$R^{6C}$ is a substituted or an unsubstituted aryl, or a substituted or an unsubstituted aralkyl, any of which having up to 12 carbon atoms.

$R^{6D}$ is a substituted or an unsubstituted heterocyclyl, or a substituted or an unsubstituted heteroaryl, any of which having up to 12 carbon atoms, comprising at least one heteroatom or heterogroup selected independently from O, N, S, $NR^{10}$, $SO_2$, or CO.

$R^{6E}$ and $R^{7E}$ together form a substituted or an unsubstituted cyclic moiety having from 3 to 7 ring carbon atoms, and optionally comprising 1, 2, or 3 heteroatoms in addition to the nitrogen atom to which $R^6E$ and $R^7E$ are bonded, selected independently from O, N, S, or $NR^{10}$.

$R^{7A}$ hydrogen.

$R^{7B}$ is an alkyl, a cycloalkyl, or a haloalkyl, any of which having up to 12 carbon atoms.

$R^{7C}$ is a substituted or an unsubstituted aryl, or a substituted or an unsubstituted aralkyl, any of which having up to 12 carbon atoms.

$R^{7D}$ is a substituted or an unsubstituted heterocyclyl, or a substituted or an unsubstituted heteroaryl, any of which having up to 12 carbon atoms, comprising at least one heteroatom or heterogroup selected independently from O, N, S, $NR^{10}$, $SO_2$, or CO.

$R^{7E}$ and $R^{6E}$ together form a substituted or an unsubstituted cyclic moiety having from 3 to 7 ring carbon atoms, and optionally comprising 1, 2, or 3 heteroatoms in addition to the nitrogen atom to which $R^6E$ and $R^7E$ are bonded, selected independently from O, N, S, or $NR^{10}$.

$R^{8A}$ is: a) an alkyl, a cycloalkyl, or a haloalkyl, any of which having up to 12 carbon atoms; or b) a substituted of an unsubstituted aryl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO.

$R^{8B}$ is an alkyl, a cycloalkyl, or a haloalkyl, any of which having up to 12 carbon atoms.

$R^{8C}$ is a substituted of an unsubstituted aryl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO.

$R^{9A}$ is an alkyl having up to 12 carbon atoms.

$R^{9B}$ is an alkyl having up to 8 carbon atoms.

$R^{9C}$ is an alkyl having up to 6 carbon atoms.

$R^{9D}$ is an alkyl having up to 4 carbon atoms.

$R^{10A}$ is hydrogen; or 2) an alkyl, a cycloalkyl, a haloalkyl, an aryl, or an aralkyl, any of which having up to 12 carbon atoms.

$R^{10B}$ is an alkyl, a cycloalkyl, or a haloalkyl, any of which having up to 12 carbon atoms.

$R^{10C}$ is an aryl or an aralkyl, any of which having up to 12 carbon atoms.

$R^{a1}$ is a halogen.

$R^{a2}$ is an alkyl or an alkoxy, any of which having up to 12 carbon atoms.

$R^{b1}$ is an alkyl having up to 12 carbon atoms.

$R^{b2}$ is an alkyl having up to 6 carbon atoms.

$R^{x1}$ is independently: 1) an alkyl or an alkoxy, either of which having up to 12 carbon atoms; or 2) hydrogen.

$R^{x2}$ is an alkyl having up to 12 carbon atoms.

$R^{x3}$ is an alkoxy having up to 12 carbon atoms.

$R^{x4}$ is hydrogen.

In one aspect of the genera represented by the formulas (II-1), (IIa-1), (IIb-1), (III-1), (IIIa-1), (IIIb-1), (IV-1), (IVa-1), (IVb-1), (V-1), (Va-1), (Vb-1), (VI-1), (VIa-1), (VIb-1), (VII-1), (VIIa-1), (VIIb-1), (VIII-1), (VIIIa-1), and (VIIIb-1), any of substituents on substituted or optionally substituted groups can be selected as specified herein for formula (I). In another aspect of the genera represented by the formulas (II-1), (IIa-1), (IIb-1), (III-1), (IIIa-1), (IIIb-1), (IV-1), (IVa-1), (IVb-1), (V-1), (Va-1), (Vb-1), (VI-1), (VIa-1), (VIb-1), (VII-1), (VIIa-1), (VIIb-1), (VIII-1), (VIIIa-1), and (VIIIb-1), any of substituents on substituted or optionally substituted groups can be selected as follows:

Ring A is optionally substituted with 1, 2, or 3 substituents selected independently from: 1) halogen, cyano, or hydroxyl; 2) an alkyl, an alkenyl, an alkynyl, a haloalkyl, a cycloalkyl, an alkoxy, a cycloalkoxy, a haloalkoxy, an aryl, an aryloxy, an aralkyl, a heteroaryl, or a heteroarylaoxy, any of which having up to 12 carbon atoms; or 3) $CO_2R^6$, $COR^8$, $SO_2R^8$, $SO_2NR^6R^7$, or $CONR^6R^7$; 4) $(CH_2)_qNR^6R^7$, wherein q is an integer from 0 to 5, inclusive; or 5) $(CH_2)_qCO_2(CH_2)_q$, wherein q is an integer from 0 to 3, inclusive;

when $R^1$ and $R^2$ do not form a monocyclic or bicyclic moiety, $R^1$ and $R^2$ are optionally and independently substituted with 1 or 2 substituents selected independently from: 1) an alkyl, a cycloalkyl, a haloalkyl, an alkoxy, an aryl, a heteroaryl, or a heterocyclyl, any of which having up to 12 carbon atoms, wherein any heteroaryl or heterocyclyl comprises at least one heteroatom or heterogroup selected independently from O, N, S, $NR^{10}$, $SO_2$, or CO; or 2) halogen, cyano, or hydroxyl;

when $R^1$ and $R^2$ together form a monocyclic or a bicyclic moiety, the cyclic moiety is optionally substituted with at least one substituent selected independently from: 1) halogen, cyano, or hydroxyl; 2) an alkyl, an alkenyl, an alkynyl, a haloalkyl, a cycloalkyl, an alkoxy, a cycloalkylalkyl, an alkoxyalkyl, a cycloalkoxy, a haloalkoxy, an aryl, an aryloxy, an aralkyl, a heteroaryl or a heteroaryloxy, any of which having up to 12 carbon atoms, wherein any heteroaryl or heteroaryloxy comprises at least one heteroatom or heterogroup selected independently from O, N, S, or $NR^{10}$; or 3) $CO_2R^6$, $COR^8$, $SO_2R^8$, $SO_2NR^6R^7$, or $CONR^6R^7$; or 4) $(CH_2)_qCO_2(CH_2)_q$, wherein q is an integer from 0 to 3, inclusive;

$R^3$ is optionally substituted with at least one substituent selected independently from: 1) an alkyl, a haloalkyl, an aryl, or a cycloalkyl, any of which having up to 12 carbon atoms; or 2) $CO_2R^9$, wherein $R^9$ is an alkyl having up to 12 carbon atoms;

$R^4$ and $R^5$ are optionally and independently substituted with at least one substituent selected independently from: 1)

halide, hydroxy, cyano, amino, or oxo; or 2) an alkyl, an alkenyl, a carboxy, a cycloalkyl, an aryl, a heterocyclyl, a heteroaryl, an alkoxy, an alkylthio, an alkyloxycarbonyl, a monoalkylamino, or a dialkylamino, any of which having up to 12 carbon atoms, wherein any heterocyclyl or heteroaryl comprises at least one heteroatom or heterogroup selected independently from O, N, S, $NR^{10}$, $SO_2$, or CO;

$R^6$, $R^7$, and $R^8$ are optionally and independently substituted with 1 or 2 substituents selected independently from an alkyl, a haloalkyl, or an aryl, any of which having up to 12 carbon atoms; and m and p are intergers from 0 to the maximum number allowed by the structure of the moiety to which $R^4$ and $R^a$ are bonded, respectively. In one aspect, m can be an integer from 0 to 3, inclusive. In another aspect, p can be an integer from 0 to 3, inclusive.

In these selections and definitions, unless otherwise indicated, the number of carbon atoms on the substituents refers to the carbon atoms on the base chemical moiety, and does not include the carbon atoms in any optional substituent. Unless otherwise indicated, substituent size is listed in the definitions of the substitutents.

In the following formulas, when more than one substituent of a particular selection occurs within a given molecule, for example when more than one $R^4$, $R^a$, or $R^b$ is present in a given molecule, the selection in the table refers to one of the occurrences of that substituent, wherein any further occurrences of that substituent are selected independently according to the definitions provided herein. For example, when more than one $R^a$ occurs in formula (II-1), according to formula A-01 in table below, at least one occurrence of $R^a$ is $R^{a1}$, and any other occurrences of $R^a$ are selected independently from $R^{a1}$ and $R^{a2}$.

Thus, according to various aspects of this invention, this disclosure provides benzylamine compounds according to formula (I), wherein the compounds have following formula:

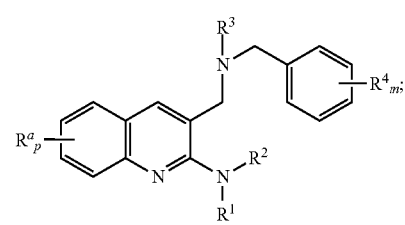
(II-1)

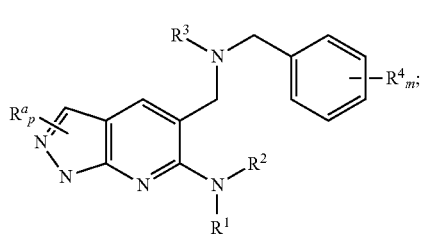
(III-1)

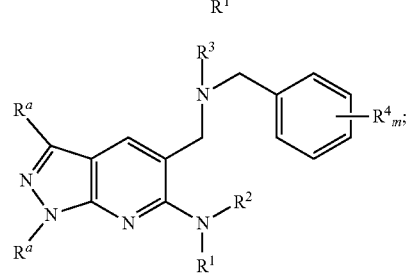
(IIIb-1)

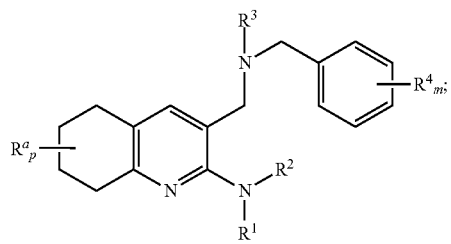
(IV-1)

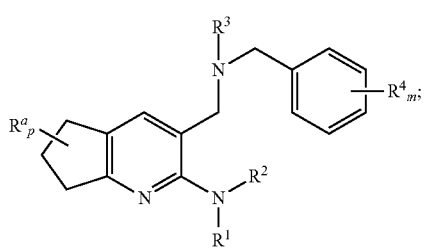
(V-1)

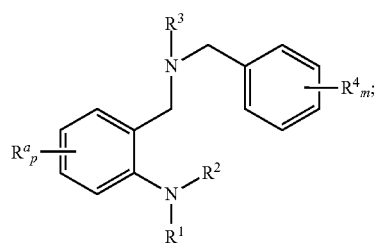
(VI-1)

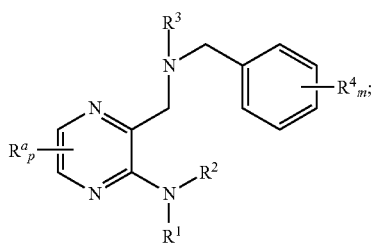
(VII-1)

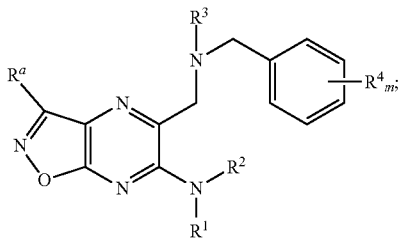
(VIII-1)

or any combination thereof;
or a salt, including a pharmaceutically acceptable or a non-pharmaceutically acceptable salt, a prodrug, a diastereomeric mixture, an enantiomer, a tautomer, a racemic mixture, or any combination thereof, wherein $R^1$, $R^2$, $R^3$, $R^4$, and $R^a$ can be selected according to the following table, to provide formulas (A-01) through (A-384), that are applicable to the compounds (II-1), (III-1), (IIIb-1), (IV-1), (V-1), (VI-1), (VII-1), and (VIII-1) illustrated above.

TABLE 1

Substituent selections for compounds according to this invention, having substituents $R^1$, $R^2$, $R^3$, $R^4$, and $R^a$.

| Formula | $R^1$ | $R^2$ | $R^3$ | $R^4$ | $R^a$ |
|---|---|---|---|---|---|
| A-01 | $R^{1A}$ | $R^{2A}$ | $R^{3A}$ | $R^{4A}$ | $R^{a1}$ |
| A-02 | $R^{1B}$ | $R^{2A}$ | $R^{3A}$ | $R^{4A}$ | $R^{a1}$ |
| A-03 | $R^{1C}$ | $R^{2A}$ | $R^{3A}$ | $R^{4A}$ | $R^{a1}$ |
| A-04 | $R^{1D}$ | $R^{2A}$ | $R^{3A}$ | $R^{4A}$ | $R^{a1}$ |
| A-05 | $R^{1A}$ | $R^{2B}$ | $R^{3A}$ | $R^{4A}$ | $R^{a1}$ |
| A-06 | $R^{1B}$ | $R^{2B}$ | $R^{3A}$ | $R^{4A}$ | $R^{a1}$ |
| A-07 | $R^{1C}$ | $R^{2B}$ | $R^{3A}$ | $R^{4A}$ | $R^{a1}$ |
| A-08 | $R^{1D}$ | $R^{2B}$ | $R^{3A}$ | $R^{4A}$ | $R^{a1}$ |
| A-09 | $R^{1A}$ | $R^{2C}$ | $R^{3A}$ | $R^{4A}$ | $R^{a1}$ |
| A-10 | $R^{1B}$ | $R^{2C}$ | $R^{3A}$ | $R^{4A}$ | $R^{a1}$ |
| A-11 | $R^{1C}$ | $R^{2C}$ | $R^{3A}$ | $R^{4A}$ | $R^{a1}$ |
| A-12 | $R^{1D}$ | $R^{2C}$ | $R^{3A}$ | $R^{4A}$ | $R^{a1}$ |
| A-13 | $R^{1A}$ | $R^{2D}$ | $R^{3A}$ | $R^{4A}$ | $R^{a1}$ |
| A-14 | $R^{1B}$ | $R^{2D}$ | $R^{3A}$ | $R^{4A}$ | $R^{a1}$ |
| A-15 | $R^{1C}$ | $R^{2D}$ | $R^{3A}$ | $R^{4A}$ | $R^{a1}$ |
| A-16 | $R^{1D}$ | $R^{2D}$ | $R^{3A}$ | $R^{4A}$ | $R^{a1}$ |
| A-17 | $R^{1A}$ | $R^{2A}$ | $R^{3B}$ | $R^{4A}$ | $R^{a1}$ |
| A-18 | $R^{1B}$ | $R^{2A}$ | $R^{3B}$ | $R^{4A}$ | $R^{a1}$ |
| A-19 | $R^{1C}$ | $R^{2A}$ | $R^{3B}$ | $R^{4A}$ | $R^{a1}$ |
| A-20 | $R^{1D}$ | $R^{2A}$ | $R^{3B}$ | $R^{4A}$ | $R^{a1}$ |
| A-21 | $R^{1A}$ | $R^{2B}$ | $R^{3B}$ | $R^{4A}$ | $R^{a1}$ |
| A-22 | $R^{1B}$ | $R^{2B}$ | $R^{3B}$ | $R^{4A}$ | $R^{a1}$ |
| A-23 | $R^{1C}$ | $R^{2B}$ | $R^{3B}$ | $R^{4A}$ | $R^{a1}$ |
| A-24 | $R^{1D}$ | $R^{2B}$ | $R^{3B}$ | $R^{4A}$ | $R^{a1}$ |
| A-25 | $R^{1A}$ | $R^{2C}$ | $R^{3B}$ | $R^{4A}$ | $R^{a1}$ |
| A-26 | $R^{1B}$ | $R^{2C}$ | $R^{3B}$ | $R^{4A}$ | $R^{a1}$ |
| A-27 | $R^{1C}$ | $R^{2C}$ | $R^{3B}$ | $R^{4A}$ | $R^{a1}$ |
| A-28 | $R^{1D}$ | $R^{2C}$ | $R^{3B}$ | $R^{4A}$ | $R^{a1}$ |
| A-29 | $R^{1A}$ | $R^{2D}$ | $R^{3B}$ | $R^{4A}$ | $R^{a1}$ |
| A-30 | $R^{1B}$ | $R^{2D}$ | $R^{3B}$ | $R^{4A}$ | $R^{a1}$ |
| A-31 | $R^{1C}$ | $R^{2D}$ | $R^{3B}$ | $R^{4A}$ | $R^{a1}$ |
| A-32 | $R^{1D}$ | $R^{2D}$ | $R^{3B}$ | $R^{4A}$ | $R^{a1}$ |
| A-33 | $R^{1A}$ | $R^{2A}$ | $R^{3C}$ | $R^{4A}$ | $R^{a1}$ |
| A-34 | $R^{1B}$ | $R^{2A}$ | $R^{3C}$ | $R^{4A}$ | $R^{a1}$ |
| A-35 | $R^{1C}$ | $R^{2A}$ | $R^{3C}$ | $R^{4A}$ | $R^{a1}$ |
| A-36 | $R^{1D}$ | $R^{2A}$ | $R^{3C}$ | $R^{4A}$ | $R^{a1}$ |
| A-37 | $R^{1A}$ | $R^{2B}$ | $R^{3C}$ | $R^{4A}$ | $R^{a1}$ |
| A-38 | $R^{1B}$ | $R^{2B}$ | $R^{3C}$ | $R^{4A}$ | $R^{a1}$ |
| A-39 | $R^{1C}$ | $R^{2B}$ | $R^{3C}$ | $R^{4A}$ | $R^{a1}$ |
| A-40 | $R^{1D}$ | $R^{2B}$ | $R^{3C}$ | $R^{4A}$ | $R^{a1}$ |
| A-41 | $R^{1A}$ | $R^{2C}$ | $R^{3C}$ | $R^{4A}$ | $R^{a1}$ |
| A-42 | $R^{1B}$ | $R^{2C}$ | $R^{3C}$ | $R^{4A}$ | $R^{a1}$ |
| A-43 | $R^{1C}$ | $R^{2C}$ | $R^{3C}$ | $R^{4A}$ | $R^{a1}$ |
| A-44 | $R^{1D}$ | $R^{2C}$ | $R^{3C}$ | $R^{4A}$ | $R^{a1}$ |
| A-45 | $R^{1A}$ | $R^{2D}$ | $R^{3C}$ | $R^{4A}$ | $R^{a1}$ |
| A-46 | $R^{1B}$ | $R^{2D}$ | $R^{3C}$ | $R^{4A}$ | $R^{a1}$ |
| A-47 | $R^{1C}$ | $R^{2D}$ | $R^{3C}$ | $R^{4A}$ | $R^{a1}$ |
| A-48 | $R^{1D}$ | $R^{2D}$ | $R^{3C}$ | $R^{4A}$ | $R^{a1}$ |
| A-49 | $R^{1A}$ | $R^{2A}$ | $R^{3D}$ | $R^{4A}$ | $R^{a1}$ |
| A-50 | $R^{1B}$ | $R^{2A}$ | $R^{3D}$ | $R^{4A}$ | $R^{a1}$ |
| A-51 | $R^{1C}$ | $R^{2A}$ | $R^{3D}$ | $R^{4A}$ | $R^{a1}$ |
| A-52 | $R^{1D}$ | $R^{2A}$ | $R^{3D}$ | $R^{4A}$ | $R^{a1}$ |
| A-53 | $R^{1A}$ | $R^{2B}$ | $R^{3D}$ | $R^{4A}$ | $R^{a1}$ |
| A-54 | $R^{1B}$ | $R^{2B}$ | $R^{3D}$ | $R^{4A}$ | $R^{a1}$ |
| A-55 | $R^{1C}$ | $R^{2B}$ | $R^{3D}$ | $R^{4A}$ | $R^{a1}$ |
| A-56 | $R^{1D}$ | $R^{2B}$ | $R^{3D}$ | $R^{4A}$ | $R^{a1}$ |
| A-57 | $R^{1A}$ | $R^{2C}$ | $R^{3D}$ | $R^{4A}$ | $R^{a1}$ |
| A-58 | $R^{1B}$ | $R^{2C}$ | $R^{3D}$ | $R^{4A}$ | $R^{a1}$ |
| A-59 | $R^{1C}$ | $R^{2C}$ | $R^{3D}$ | $R^{4A}$ | $R^{a1}$ |
| A-60 | $R^{1D}$ | $R^{2C}$ | $R^{3D}$ | $R^{4A}$ | $R^{a1}$ |
| A-61 | $R^{1A}$ | $R^{2D}$ | $R^{3D}$ | $R^{4A}$ | $R^{a1}$ |
| A-62 | $R^{1B}$ | $R^{2D}$ | $R^{3D}$ | $R^{4A}$ | $R^{a1}$ |
| A-63 | $R^{1C}$ | $R^{2D}$ | $R^{3D}$ | $R^{4A}$ | $R^{a1}$ |
| A-64 | $R^{1D}$ | $R^{2D}$ | $R^{3D}$ | $R^{4A}$ | $R^{a1}$ |
| A-65 | $R^{1A}$ | $R^{2A}$ | $R^{3A}$ | $R^{4B}$ | $R^{a1}$ |
| A-66 | $R^{1B}$ | $R^{2A}$ | $R^{3A}$ | $R^{4B}$ | $R^{a1}$ |
| A-67 | $R^{1C}$ | $R^{2A}$ | $R^{3A}$ | $R^{4B}$ | $R^{a1}$ |
| A-68 | $R^{1D}$ | $R^{2A}$ | $R^{3A}$ | $R^{4B}$ | $R^{a1}$ |
| A-69 | $R^{1A}$ | $R^{2B}$ | $R^{3A}$ | $R^{4B}$ | $R^{a1}$ |
| A-70 | $R^{1B}$ | $R^{2B}$ | $R^{3A}$ | $R^{4B}$ | $R^{a1}$ |
| A-71 | $R^{1C}$ | $R^{2B}$ | $R^{3A}$ | $R^{4B}$ | $R^{a1}$ |
| A-72 | $R^{1D}$ | $R^{2B}$ | $R^{3A}$ | $R^{4B}$ | $R^{a1}$ |
| A-73 | $R^{1A}$ | $R^{2C}$ | $R^{3A}$ | $R^{4B}$ | $R^{a1}$ |
| A-74 | $R^{1B}$ | $R^{2C}$ | $R^{3A}$ | $R^{4B}$ | $R^{a1}$ |
| A-75 | $R^{1C}$ | $R^{2C}$ | $R^{3A}$ | $R^{4B}$ | $R^{a1}$ |
| A-76 | $R^{1D}$ | $R^{2C}$ | $R^{3A}$ | $R^{4B}$ | $R^{a1}$ |
| A-77 | $R^{1A}$ | $R^{2D}$ | $R^{3A}$ | $R^{4B}$ | $R^{a1}$ |
| A-78 | $R^{1B}$ | $R^{2D}$ | $R^{3A}$ | $R^{4B}$ | $R^{a1}$ |
| A-79 | $R^{1C}$ | $R^{2D}$ | $R^{3A}$ | $R^{4B}$ | $R^{a1}$ |
| A-80 | $R^{1D}$ | $R^{2D}$ | $R^{3A}$ | $R^{4B}$ | $R^{a1}$ |
| A-81 | $R^{1A}$ | $R^{2A}$ | $R^{3B}$ | $R^{4B}$ | $R^{a1}$ |
| A-82 | $R^{1B}$ | $R^{2A}$ | $R^{3B}$ | $R^{4B}$ | $R^{a1}$ |
| A-83 | $R^{1C}$ | $R^{2A}$ | $R^{3B}$ | $R^{4B}$ | $R^{a1}$ |
| A-84 | $R^{1D}$ | $R^{2A}$ | $R^{3B}$ | $R^{4B}$ | $R^{a1}$ |
| A-85 | $R^{1A}$ | $R^{2B}$ | $R^{3B}$ | $R^{4B}$ | $R^{a1}$ |
| A-86 | $R^{1B}$ | $R^{2B}$ | $R^{3B}$ | $R^{4B}$ | $R^{a1}$ |
| A-87 | $R^{1C}$ | $R^{2B}$ | $R^{3B}$ | $R^{4B}$ | $R^{a1}$ |
| A-88 | $R^{1D}$ | $R^{2B}$ | $R^{3B}$ | $R^{4B}$ | $R^{a1}$ |
| A-89 | $R^{1A}$ | $R^{2C}$ | $R^{3B}$ | $R^{4B}$ | $R^{a1}$ |
| A-90 | $R^{1B}$ | $R^{2C}$ | $R^{3B}$ | $R^{4B}$ | $R^{a1}$ |
| A-91 | $R^{1C}$ | $R^{2C}$ | $R^{3B}$ | $R^{4B}$ | $R^{a1}$ |
| A-92 | $R^{1D}$ | $R^{2C}$ | $R^{3B}$ | $R^{4B}$ | $R^{a1}$ |
| A-93 | $R^{1A}$ | $R^{2D}$ | $R^{3B}$ | $R^{4B}$ | $R^{a1}$ |
| A-94 | $R^{1B}$ | $R^{2D}$ | $R^{3B}$ | $R^{4B}$ | $R^{a1}$ |
| A-95 | $R^{1C}$ | $R^{2D}$ | $R^{3B}$ | $R^{4B}$ | $R^{a1}$ |
| A-96 | $R^{1D}$ | $R^{2D}$ | $R^{3B}$ | $R^{4B}$ | $R^{a1}$ |
| A-97 | $R^{1A}$ | $R^{2A}$ | $R^{3C}$ | $R^{4B}$ | $R^{a1}$ |
| A-98 | $R^{1B}$ | $R^{2A}$ | $R^{3C}$ | $R^{4B}$ | $R^{a1}$ |
| A-99 | $R^{1C}$ | $R^{2A}$ | $R^{3C}$ | $R^{4B}$ | $R^{a1}$ |
| A-100 | $R^{1D}$ | $R^{2A}$ | $R^{3C}$ | $R^{4B}$ | $R^{a1}$ |
| A-101 | $R^{1A}$ | $R^{2B}$ | $R^{3C}$ | $R^{4B}$ | $R^{a1}$ |
| A-102 | $R^{1B}$ | $R^{2B}$ | $R^{3C}$ | $R^{4B}$ | $R^{a1}$ |
| A-103 | $R^{1C}$ | $R^{2B}$ | $R^{3C}$ | $R^{4B}$ | $R^{a1}$ |
| A-104 | $R^{1D}$ | $R^{2B}$ | $R^{3C}$ | $R^{4B}$ | $R^{a1}$ |
| A-105 | $R^{1A}$ | $R^{2C}$ | $R^{3C}$ | $R^{4B}$ | $R^{a1}$ |
| A-106 | $R^{1B}$ | $R^{2C}$ | $R^{3C}$ | $R^{4B}$ | $R^{a1}$ |
| A-107 | $R^{1C}$ | $R^{2C}$ | $R^{3C}$ | $R^{4B}$ | $R^{a1}$ |
| A-108 | $R^{1D}$ | $R^{2C}$ | $R^{3C}$ | $R^{4B}$ | $R^{a1}$ |
| A-109 | $R^{1A}$ | $R^{2D}$ | $R^{3C}$ | $R^{4B}$ | $R^{a1}$ |
| A-110 | $R^{1B}$ | $R^{2D}$ | $R^{3C}$ | $R^{4B}$ | $R^{a1}$ |
| A-111 | $R^{1C}$ | $R^{2D}$ | $R^{3C}$ | $R^{4B}$ | $R^{a1}$ |
| A-112 | $R^{1D}$ | $R^{2D}$ | $R^{3C}$ | $R^{4B}$ | $R^{a1}$ |
| A-113 | $R^{1A}$ | $R^{2A}$ | $R^{3D}$ | $R^{4B}$ | $R^{a1}$ |
| A-114 | $R^{1B}$ | $R^{2A}$ | $R^{3D}$ | $R^{4B}$ | $R^{a1}$ |
| A-115 | $R^{1C}$ | $R^{2A}$ | $R^{3D}$ | $R^{4B}$ | $R^{a1}$ |
| A-116 | $R^{1D}$ | $R^{2A}$ | $R^{3D}$ | $R^{4B}$ | $R^{a1}$ |
| A-117 | $R^{1A}$ | $R^{2B}$ | $R^{3D}$ | $R^{4B}$ | $R^{a1}$ |
| A-118 | $R^{1B}$ | $R^{2B}$ | $R^{3D}$ | $R^{4B}$ | $R^{a1}$ |
| A-119 | $R^{1C}$ | $R^{2B}$ | $R^{3D}$ | $R^{4B}$ | $R^{a1}$ |
| A-120 | $R^{1D}$ | $R^{2B}$ | $R^{3D}$ | $R^{4B}$ | $R^{a1}$ |
| A-121 | $R^{1A}$ | $R^{2C}$ | $R^{3D}$ | $R^{4B}$ | $R^{a1}$ |
| A-122 | $R^{1B}$ | $R^{2C}$ | $R^{3D}$ | $R^{4B}$ | $R^{a1}$ |
| A-123 | $R^{1C}$ | $R^{2C}$ | $R^{3D}$ | $R^{4B}$ | $R^{a1}$ |
| A-124 | $R^{1D}$ | $R^{2C}$ | $R^{3D}$ | $R^{4B}$ | $R^{a1}$ |
| A-125 | $R^{1A}$ | $R^{2D}$ | $R^{3D}$ | $R^{4B}$ | $R^{a1}$ |
| A-126 | $R^{1B}$ | $R^{2D}$ | $R^{3D}$ | $R^{4B}$ | $R^{a1}$ |
| A-127 | $R^{1C}$ | $R^{2D}$ | $R^{3D}$ | $R^{4B}$ | $R^{a1}$ |
| A-128 | $R^{1D}$ | $R^{2D}$ | $R^{3D}$ | $R^{4B}$ | $R^{a1}$ |
| A-129 | $R^{1A}$ | $R^{2A}$ | $R^{3A}$ | $R^{4C}$ | $R^{a1}$ |
| A-130 | $R^{1B}$ | $R^{2A}$ | $R^{3A}$ | $R^{4C}$ | $R^{a1}$ |
| A-131 | $R^{1C}$ | $R^{2A}$ | $R^{3A}$ | $R^{4C}$ | $R^{a1}$ |
| A-132 | $R^{1D}$ | $R^{2A}$ | $R^{3A}$ | $R^{4C}$ | $R^{a1}$ |
| A-133 | $R^{1A}$ | $R^{2B}$ | $R^{3A}$ | $R^{4C}$ | $R^{a1}$ |
| A-134 | $R^{1B}$ | $R^{2B}$ | $R^{3A}$ | $R^{4C}$ | $R^{a1}$ |
| A-135 | $R^{1C}$ | $R^{2B}$ | $R^{3A}$ | $R^{4C}$ | $R^{a1}$ |
| A-136 | $R^{1D}$ | $R^{2B}$ | $R^{3A}$ | $R^{4C}$ | $R^{a1}$ |
| A-137 | $R^{1A}$ | $R^{2C}$ | $R^{3A}$ | $R^{4C}$ | $R^{a1}$ |
| A-138 | $R^{1B}$ | $R^{2C}$ | $R^{3A}$ | $R^{4C}$ | $R^{a1}$ |
| A-139 | $R^{1C}$ | $R^{2C}$ | $R^{3A}$ | $R^{4C}$ | $R^{a1}$ |
| A-140 | $R^{1D}$ | $R^{2C}$ | $R^{3A}$ | $R^{4C}$ | $R^{a1}$ |
| A-141 | $R^{1A}$ | $R^{2D}$ | $R^{3A}$ | $R^{4C}$ | $R^{a1}$ |
| A-142 | $R^{1B}$ | $R^{2D}$ | $R^{3A}$ | $R^{4C}$ | $R^{a1}$ |
| A-143 | $R^{1C}$ | $R^{2D}$ | $R^{3A}$ | $R^{4C}$ | $R^{a1}$ |
| A-144 | $R^{1D}$ | $R^{2D}$ | $R^{3A}$ | $R^{4C}$ | $R^{a1}$ |
| A-145 | $R^{1A}$ | $R^{2A}$ | $R^{3B}$ | $R^{4C}$ | $R^{a1}$ |
| A-146 | $R^{1B}$ | $R^{2A}$ | $R^{3B}$ | $R^{4C}$ | $R^{a1}$ |
| A-147 | $R^{1C}$ | $R^{2A}$ | $R^{3B}$ | $R^{4C}$ | $R^{a1}$ |
| A-148 | $R^{1D}$ | $R^{2A}$ | $R^{3B}$ | $R^{4C}$ | $R^{a1}$ |
| A-149 | $R^{1A}$ | $R^{2B}$ | $R^{3B}$ | $R^{4C}$ | $R^{a1}$ |
| A-150 | $R^{1B}$ | $R^{2B}$ | $R^{3B}$ | $R^{4C}$ | $R^{a1}$ |

TABLE 1-continued

Substituent selections for compounds according to this invention, having substituents $R^1$, $R^2$, $R^3$, $R^4$, and $R^a$.

| Formula | $R^1$ | $R^2$ | $R^3$ | $R^4$ | $R^a$ |
|---|---|---|---|---|---|
| A-151 | $R^{1C}$ | $R^{2B}$ | $R^{3B}$ | $R^{4C}$ | $R^{a1}$ |
| A-152 | $R^{1D}$ | $R^{2B}$ | $R^{3B}$ | $R^{4C}$ | $R^{a1}$ |
| A-153 | $R^{1A}$ | $R^{2C}$ | $R^{3B}$ | $R^{4C}$ | $R^{a1}$ |
| A-154 | $R^{1B}$ | $R^{2C}$ | $R^{3B}$ | $R^{4C}$ | $R^{a1}$ |
| A-155 | $R^{1C}$ | $R^{2C}$ | $R^{3B}$ | $R^{4C}$ | $R^{a1}$ |
| A-156 | $R^{1D}$ | $R^{2C}$ | $R^{3B}$ | $R^{4C}$ | $R^{a1}$ |
| A-157 | $R^{1A}$ | $R^{2D}$ | $R^{3B}$ | $R^{4C}$ | $R^{a1}$ |
| A-158 | $R^{1B}$ | $R^{2D}$ | $R^{3B}$ | $R^{4C}$ | $R^{a1}$ |
| A-159 | $R^{1C}$ | $R^{2D}$ | $R^{3B}$ | $R^{4C}$ | $R^{a1}$ |
| A-160 | $R^{1D}$ | $R^{2D}$ | $R^{3B}$ | $R^{4C}$ | $R^{a1}$ |
| A-161 | $R^{1A}$ | $R^{2A}$ | $R^{3C}$ | $R^{4C}$ | $R^{a1}$ |
| A-162 | $R^{1B}$ | $R^{2A}$ | $R^{3C}$ | $R^{4C}$ | $R^{a1}$ |
| A-163 | $R^{1C}$ | $R^{2A}$ | $R^{3C}$ | $R^{4C}$ | $R^{a1}$ |
| A-164 | $R^{1D}$ | $R^{2A}$ | $R^{3C}$ | $R^{4C}$ | $R^{a1}$ |
| A-165 | $R^{1A}$ | $R^{2B}$ | $R^{3C}$ | $R^{4C}$ | $R^{a1}$ |
| A-166 | $R^{1B}$ | $R^{2B}$ | $R^{3C}$ | $R^{4C}$ | $R^{a1}$ |
| A-167 | $R^{1C}$ | $R^{2B}$ | $R^{3C}$ | $R^{4C}$ | $R^{a1}$ |
| A-168 | $R^{1D}$ | $R^{2B}$ | $R^{3C}$ | $R^{4C}$ | $R^{a1}$ |
| A-169 | $R^{1A}$ | $R^{2C}$ | $R^{3C}$ | $R^{4C}$ | $R^{a1}$ |
| A-170 | $R^{1B}$ | $R^{2C}$ | $R^{3C}$ | $R^{4C}$ | $R^{a1}$ |
| A-171 | $R^{1C}$ | $R^{2C}$ | $R^{3C}$ | $R^{4C}$ | $R^{a1}$ |
| A-172 | $R^{1D}$ | $R^{2C}$ | $R^{3C}$ | $R^{4C}$ | $R^{a1}$ |
| A-173 | $R^{1A}$ | $R^{2D}$ | $R^{3C}$ | $R^{4C}$ | $R^{a1}$ |
| A-174 | $R^{1B}$ | $R^{2D}$ | $R^{3C}$ | $R^{4C}$ | $R^{a1}$ |
| A-175 | $R^{1C}$ | $R^{2D}$ | $R^{3C}$ | $R^{4C}$ | $R^{a1}$ |
| A-176 | $R^{1D}$ | $R^{2D}$ | $R^{3C}$ | $R^{4C}$ | $R^{a1}$ |
| A-177 | $R^{1A}$ | $R^{2A}$ | $R^{3D}$ | $R^{4C}$ | $R^{a1}$ |
| A-178 | $R^{1B}$ | $R^{2A}$ | $R^{3D}$ | $R^{4C}$ | $R^{a1}$ |
| A-179 | $R^{1C}$ | $R^{2A}$ | $R^{3D}$ | $R^{4C}$ | $R^{a1}$ |
| A-180 | $R^{1D}$ | $R^{2A}$ | $R^{3D}$ | $R^{4C}$ | $R^{a1}$ |
| A-181 | $R^{1A}$ | $R^{2B}$ | $R^{3D}$ | $R^{4C}$ | $R^{a1}$ |
| A-182 | $R^{1B}$ | $R^{2B}$ | $R^{3D}$ | $R^{4C}$ | $R^{a1}$ |
| A-183 | $R^{1C}$ | $R^{2B}$ | $R^{3D}$ | $R^{4C}$ | $R^{a1}$ |
| A-184 | $R^{1D}$ | $R^{2B}$ | $R^{3D}$ | $R^{4C}$ | $R^{a1}$ |
| A-185 | $R^{1A}$ | $R^{2C}$ | $R^{3D}$ | $R^{4C}$ | $R^{a1}$ |
| A-186 | $R^{1B}$ | $R^{2C}$ | $R^{3D}$ | $R^{4C}$ | $R^{a1}$ |
| A-187 | $R^{1C}$ | $R^{2C}$ | $R^{3D}$ | $R^{4C}$ | $R^{a1}$ |
| A-188 | $R^{1D}$ | $R^{2C}$ | $R^{3D}$ | $R^{4C}$ | $R^{a1}$ |
| A-189 | $R^{1A}$ | $R^{2D}$ | $R^{3D}$ | $R^{4C}$ | $R^{a1}$ |
| A-190 | $R^{1B}$ | $R^{2D}$ | $R^{3D}$ | $R^{4C}$ | $R^{a1}$ |
| A-191 | $R^{1C}$ | $R^{2D}$ | $R^{3D}$ | $R^{4C}$ | $R^{a1}$ |
| A-192 | $R^{1D}$ | $R^{2D}$ | $R^{3D}$ | $R^{4C}$ | $R^{a1}$ |
| A-193 | $R^{1A}$ | $R^{2A}$ | $R^{3A}$ | $R^{4A}$ | $R^{a2}$ |
| A-194 | $R^{1B}$ | $R^{2A}$ | $R^{3A}$ | $R^{4A}$ | $R^{a2}$ |
| A-195 | $R^{1C}$ | $R^{2A}$ | $R^{3A}$ | $R^{4A}$ | $R^{a2}$ |
| A-196 | $R^{1D}$ | $R^{2A}$ | $R^{3A}$ | $R^{4A}$ | $R^{a2}$ |
| A-197 | $R^{1A}$ | $R^{2B}$ | $R^{3A}$ | $R^{4A}$ | $R^{a2}$ |
| A-198 | $R^{1B}$ | $R^{2B}$ | $R^{3A}$ | $R^{4A}$ | $R^{a2}$ |
| A-199 | $R^{1C}$ | $R^{2B}$ | $R^{3A}$ | $R^{4A}$ | $R^{a2}$ |
| A-200 | $R^{1D}$ | $R^{2B}$ | $R^{3A}$ | $R^{4A}$ | $R^{a2}$ |
| A-201 | $R^{1A}$ | $R^{2C}$ | $R^{3A}$ | $R^{4A}$ | $R^{a2}$ |
| A-202 | $R^{1B}$ | $R^{2C}$ | $R^{3A}$ | $R^{4A}$ | $R^{a2}$ |
| A-203 | $R^{1C}$ | $R^{2C}$ | $R^{3A}$ | $R^{4A}$ | $R^{a2}$ |
| A-204 | $R^{1D}$ | $R^{2C}$ | $R^{3A}$ | $R^{4A}$ | $R^{a2}$ |
| A-205 | $R^{1A}$ | $R^{2D}$ | $R^{3A}$ | $R^{4A}$ | $R^{a2}$ |
| A-206 | $R^{1B}$ | $R^{2D}$ | $R^{3A}$ | $R^{4A}$ | $R^{a2}$ |
| A-207 | $R^{1C}$ | $R^{2D}$ | $R^{3A}$ | $R^{4A}$ | $R^{a2}$ |
| A-208 | $R^{1D}$ | $R^{2D}$ | $R^{3A}$ | $R^{4A}$ | $R^{a2}$ |
| A-209 | $R^{1A}$ | $R^{2A}$ | $R^{3B}$ | $R^{4A}$ | $R^{a2}$ |
| A-210 | $R^{1B}$ | $R^{2A}$ | $R^{3B}$ | $R^{4A}$ | $R^{a2}$ |
| A-211 | $R^{1C}$ | $R^{2A}$ | $R^{3B}$ | $R^{4A}$ | $R^{a2}$ |
| A-212 | $R^{1D}$ | $R^{2A}$ | $R^{3B}$ | $R^{4A}$ | $R^{a2}$ |
| A-213 | $R^{1A}$ | $R^{2B}$ | $R^{3B}$ | $R^{4A}$ | $R^{a2}$ |
| A-214 | $R^{1B}$ | $R^{2B}$ | $R^{3B}$ | $R^{4A}$ | $R^{a2}$ |
| A-215 | $R^{1C}$ | $R^{2B}$ | $R^{3B}$ | $R^{4A}$ | $R^{a2}$ |
| A-216 | $R^{1D}$ | $R^{2B}$ | $R^{3B}$ | $R^{4A}$ | $R^{a2}$ |
| A-217 | $R^{1A}$ | $R^{2C}$ | $R^{3B}$ | $R^{4A}$ | $R^{a2}$ |
| A-218 | $R^{1B}$ | $R^{2C}$ | $R^{3B}$ | $R^{4A}$ | $R^{a2}$ |
| A-219 | $R^{1C}$ | $R^{2C}$ | $R^{3B}$ | $R^{4A}$ | $R^{a2}$ |
| A-220 | $R^{1D}$ | $R^{2C}$ | $R^{3B}$ | $R^{4A}$ | $R^{a2}$ |
| A-221 | $R^{1A}$ | $R^{2D}$ | $R^{3B}$ | $R^{4A}$ | $R^{a2}$ |
| A-222 | $R^{1B}$ | $R^{2D}$ | $R^{3B}$ | $R^{4A}$ | $R^{a2}$ |
| A-223 | $R^{1C}$ | $R^{2D}$ | $R^{3B}$ | $R^{4A}$ | $R^{a2}$ |
| A-224 | $R^{1D}$ | $R^{2D}$ | $R^{3B}$ | $R^{4A}$ | $R^{a2}$ |
| A-225 | $R^{1A}$ | $R^{2A}$ | $R^{3C}$ | $R^{4A}$ | $R^{a2}$ |
| A-226 | $R^{1B}$ | $R^{2A}$ | $R^{3C}$ | $R^{4A}$ | $R^{a2}$ |
| A-227 | $R^{1C}$ | $R^{2A}$ | $R^{3C}$ | $R^{4A}$ | $R^{a2}$ |
| A-228 | $R^{1D}$ | $R^{2A}$ | $R^{3C}$ | $R^{4A}$ | $R^{a2}$ |
| A-229 | $R^{1A}$ | $R^{2B}$ | $R^{3C}$ | $R^{4A}$ | $R^{a2}$ |
| A-230 | $R^{1B}$ | $R^{2B}$ | $R^{3C}$ | $R^{4A}$ | $R^{a2}$ |
| A-231 | $R^{1C}$ | $R^{2B}$ | $R^{3C}$ | $R^{4A}$ | $R^{a2}$ |
| A-232 | $R^{1D}$ | $R^{2B}$ | $R^{3C}$ | $R^{4A}$ | $R^{a2}$ |
| A-233 | $R^{1A}$ | $R^{2C}$ | $R^{3C}$ | $R^{4A}$ | $R^{a2}$ |
| A-234 | $R^{1B}$ | $R^{2C}$ | $R^{3C}$ | $R^{4A}$ | $R^{a2}$ |
| A-235 | $R^{1C}$ | $R^{2C}$ | $R^{3C}$ | $R^{4A}$ | $R^{a2}$ |
| A-236 | $R^{1D}$ | $R^{2C}$ | $R^{3C}$ | $R^{4A}$ | $R^{a2}$ |
| A-237 | $R^{1A}$ | $R^{2D}$ | $R^{3C}$ | $R^{4A}$ | $R^{a2}$ |
| A-238 | $R^{1B}$ | $R^{2D}$ | $R^{3C}$ | $R^{4A}$ | $R^{a2}$ |
| A-239 | $R^{1C}$ | $R^{2D}$ | $R^{3C}$ | $R^{4A}$ | $R^{a2}$ |
| A-240 | $R^{1D}$ | $R^{2D}$ | $R^{3C}$ | $R^{4A}$ | $R^{a2}$ |
| A-241 | $R^{1A}$ | $R^{2A}$ | $R^{3D}$ | $R^{4A}$ | $R^{a2}$ |
| A-242 | $R^{1B}$ | $R^{2A}$ | $R^{3D}$ | $R^{4A}$ | $R^{a2}$ |
| A-243 | $R^{1C}$ | $R^{2A}$ | $R^{3D}$ | $R^{4A}$ | $R^{a2}$ |
| A-244 | $R^{1D}$ | $R^{2A}$ | $R^{3D}$ | $R^{4A}$ | $R^{a2}$ |
| A-245 | $R^{1A}$ | $R^{2B}$ | $R^{3D}$ | $R^{4A}$ | $R^{a2}$ |
| A-246 | $R^{1B}$ | $R^{2B}$ | $R^{3D}$ | $R^{4A}$ | $R^{a2}$ |
| A-247 | $R^{1C}$ | $R^{2B}$ | $R^{3D}$ | $R^{4A}$ | $R^{a2}$ |
| A-248 | $R^{1D}$ | $R^{2B}$ | $R^{3D}$ | $R^{4A}$ | $R^{a2}$ |
| A-249 | $R^{1A}$ | $R^{2C}$ | $R^{3D}$ | $R^{4A}$ | $R^{a2}$ |
| A-250 | $R^{1B}$ | $R^{2C}$ | $R^{3D}$ | $R^{4A}$ | $R^{a2}$ |
| A-251 | $R^{1C}$ | $R^{2C}$ | $R^{3D}$ | $R^{4A}$ | $R^{a2}$ |
| A-252 | $R^{1D}$ | $R^{2C}$ | $R^{3D}$ | $R^{4A}$ | $R^{a2}$ |
| A-253 | $R^{1A}$ | $R^{2D}$ | $R^{3D}$ | $R^{4A}$ | $R^{a2}$ |
| A-254 | $R^{1B}$ | $R^{2D}$ | $R^{3D}$ | $R^{4A}$ | $R^{a2}$ |
| A-255 | $R^{1C}$ | $R^{2D}$ | $R^{3D}$ | $R^{4A}$ | $R^{a2}$ |
| A-256 | $R^{1D}$ | $R^{2D}$ | $R^{3D}$ | $R^{4A}$ | $R^{a2}$ |
| A-257 | $R^{1A}$ | $R^{2A}$ | $R^{3A}$ | $R^{4B}$ | $R^{a2}$ |
| A-258 | $R^{1B}$ | $R^{2A}$ | $R^{3A}$ | $R^{4B}$ | $R^{a2}$ |
| A-259 | $R^{1C}$ | $R^{2A}$ | $R^{3A}$ | $R^{4B}$ | $R^{a2}$ |
| A-260 | $R^{1D}$ | $R^{2A}$ | $R^{3A}$ | $R^{4B}$ | $R^{a2}$ |
| A-261 | $R^{1A}$ | $R^{2B}$ | $R^{3A}$ | $R^{4B}$ | $R^{a2}$ |
| A-262 | $R^{1B}$ | $R^{2B}$ | $R^{3A}$ | $R^{4B}$ | $R^{a2}$ |
| A-263 | $R^{1C}$ | $R^{2B}$ | $R^{3A}$ | $R^{4B}$ | $R^{a2}$ |
| A-264 | $R^{1D}$ | $R^{2B}$ | $R^{3A}$ | $R^{4B}$ | $R^{a2}$ |
| A-265 | $R^{1A}$ | $R^{2C}$ | $R^{3A}$ | $R^{4B}$ | $R^{a2}$ |
| A-266 | $R^{1B}$ | $R^{2C}$ | $R^{3A}$ | $R^{4B}$ | $R^{a2}$ |
| A-267 | $R^{1C}$ | $R^{2C}$ | $R^{3A}$ | $R^{4B}$ | $R^{a2}$ |
| A-268 | $R^{1D}$ | $R^{2C}$ | $R^{3A}$ | $R^{4B}$ | $R^{a2}$ |
| A-269 | $R^{1A}$ | $R^{2D}$ | $R^{3A}$ | $R^{4B}$ | $R^{a2}$ |
| A-270 | $R^{1B}$ | $R^{2D}$ | $R^{3A}$ | $R^{4B}$ | $R^{a2}$ |
| A-271 | $R^{1C}$ | $R^{2D}$ | $R^{3A}$ | $R^{4B}$ | $R^{a2}$ |
| A-272 | $R^{1D}$ | $R^{2D}$ | $R^{3A}$ | $R^{4B}$ | $R^{a2}$ |
| A-273 | $R^{1A}$ | $R^{2A}$ | $R^{3B}$ | $R^{4B}$ | $R^{a2}$ |
| A-274 | $R^{1B}$ | $R^{2A}$ | $R^{3B}$ | $R^{4B}$ | $R^{a2}$ |
| A-275 | $R^{1C}$ | $R^{2A}$ | $R^{3B}$ | $R^{4B}$ | $R^{a2}$ |
| A-276 | $R^{1D}$ | $R^{2A}$ | $R^{3B}$ | $R^{4B}$ | $R^{a2}$ |
| A-277 | $R^{1A}$ | $R^{2B}$ | $R^{3B}$ | $R^{4B}$ | $R^{a2}$ |
| A-278 | $R^{1B}$ | $R^{2B}$ | $R^{3B}$ | $R^{4B}$ | $R^{a2}$ |
| A-279 | $R^{1C}$ | $R^{2B}$ | $R^{3B}$ | $R^{4B}$ | $R^{a2}$ |
| A-280 | $R^{1D}$ | $R^{2B}$ | $R^{3B}$ | $R^{4B}$ | $R^{a2}$ |
| A-281 | $R^{1A}$ | $R^{2C}$ | $R^{3B}$ | $R^{4B}$ | $R^{a2}$ |
| A-282 | $R^{1B}$ | $R^{2C}$ | $R^{3B}$ | $R^{4B}$ | $R^{a2}$ |
| A-283 | $R^{1C}$ | $R^{2C}$ | $R^{3B}$ | $R^{4B}$ | $R^{a2}$ |
| A-284 | $R^{1D}$ | $R^{2C}$ | $R^{3B}$ | $R^{4B}$ | $R^{a2}$ |
| A-285 | $R^{1A}$ | $R^{2D}$ | $R^{3B}$ | $R^{4B}$ | $R^{a2}$ |
| A-286 | $R^{1B}$ | $R^{2D}$ | $R^{3B}$ | $R^{4B}$ | $R^{a2}$ |
| A-287 | $R^{1C}$ | $R^{2D}$ | $R^{3B}$ | $R^{4B}$ | $R^{a2}$ |
| A-288 | $R^{1D}$ | $R^{2D}$ | $R^{3B}$ | $R^{4B}$ | $R^{a2}$ |
| A-289 | $R^{1A}$ | $R^{2A}$ | $R^{3C}$ | $R^{4B}$ | $R^{a2}$ |
| A-290 | $R^{1B}$ | $R^{2A}$ | $R^{3C}$ | $R^{4B}$ | $R^{a2}$ |
| A-291 | $R^{1C}$ | $R^{2A}$ | $R^{3C}$ | $R^{4B}$ | $R^{a2}$ |
| A-292 | $R^{1D}$ | $R^{2A}$ | $R^{3C}$ | $R^{4B}$ | $R^{a2}$ |
| A-293 | $R^{1A}$ | $R^{2B}$ | $R^{3C}$ | $R^{4B}$ | $R^{a2}$ |
| A-294 | $R^{1B}$ | $R^{2B}$ | $R^{3C}$ | $R^{4B}$ | $R^{a2}$ |
| A-295 | $R^{1C}$ | $R^{2B}$ | $R^{3C}$ | $R^{4B}$ | $R^{a2}$ |
| A-296 | $R^{1D}$ | $R^{2B}$ | $R^{3C}$ | $R^{4B}$ | $R^{a2}$ |
| A-297 | $R^{1A}$ | $R^{2C}$ | $R^{3C}$ | $R^{4B}$ | $R^{a2}$ |
| A-298 | $R^{1B}$ | $R^{2C}$ | $R^{3C}$ | $R^{4B}$ | $R^{a2}$ |
| A-299 | $R^{1C}$ | $R^{2C}$ | $R^{3C}$ | $R^{4B}$ | $R^{a2}$ |
| A-300 | $R^{1D}$ | $R^{2C}$ | $R^{3C}$ | $R^{4B}$ | $R^{a2}$ |

TABLE 1-continued

Substituent selections for compounds according to this invention, having substituents $R^1$, $R^2$, $R^3$, $R^4$, and $R^a$.

| Formula | $R^1$ | $R^2$ | $R^3$ | $R^4$ | $R^a$ |
|---|---|---|---|---|---|
| A-301 | $R^{1A}$ | $R^{2D}$ | $R^{3C}$ | $R^{4B}$ | $R^{a2}$ |
| A-302 | $R^{1B}$ | $R^{2D}$ | $R^{3C}$ | $R^{4B}$ | $R^{a2}$ |
| A-303 | $R^{1C}$ | $R^{2D}$ | $R^{3C}$ | $R^{4B}$ | $R^{a2}$ |
| A-304 | $R^{1D}$ | $R^{2D}$ | $R^{3C}$ | $R^{4B}$ | $R^{a2}$ |
| A-305 | $R^{1A}$ | $R^{2A}$ | $R^{3D}$ | $R^{4B}$ | $R^{a2}$ |
| A-306 | $R^{1B}$ | $R^{2A}$ | $R^{3D}$ | $R^{4B}$ | $R^{a2}$ |
| A-307 | $R^{1C}$ | $R^{2A}$ | $R^{3D}$ | $R^{4B}$ | $R^{a2}$ |
| A-308 | $R^{1D}$ | $R^{2A}$ | $R^{3D}$ | $R^{4B}$ | $R^{a2}$ |
| A-309 | $R^{1A}$ | $R^{2B}$ | $R^{3D}$ | $R^{4B}$ | $R^{a2}$ |
| A-310 | $R^{1B}$ | $R^{2B}$ | $R^{3D}$ | $R^{4B}$ | $R^{a2}$ |
| A-311 | $R^{1C}$ | $R^{2B}$ | $R^{3D}$ | $R^{4B}$ | $R^{a2}$ |
| A-312 | $R^{1D}$ | $R^{2B}$ | $R^{3D}$ | $R^{4B}$ | $R^{a2}$ |
| A-313 | $R^{1A}$ | $R^{2C}$ | $R^{3D}$ | $R^{4B}$ | $R^{a2}$ |
| A-314 | $R^{1B}$ | $R^{2C}$ | $R^{3D}$ | $R^{4B}$ | $R^{a2}$ |
| A-315 | $R^{1C}$ | $R^{2C}$ | $R^{3D}$ | $R^{4B}$ | $R^{a2}$ |
| A-316 | $R^{1D}$ | $R^{2C}$ | $R^{3D}$ | $R^{4B}$ | $R^{a2}$ |
| A-317 | $R^{1A}$ | $R^{2D}$ | $R^{3D}$ | $R^{4B}$ | $R^{a2}$ |
| A-318 | $R^{1B}$ | $R^{2D}$ | $R^{3D}$ | $R^{4B}$ | $R^{a2}$ |
| A-319 | $R^{1C}$ | $R^{2D}$ | $R^{3D}$ | $R^{4B}$ | $R^{a2}$ |
| A-320 | $R^{1D}$ | $R^{2D}$ | $R^{3D}$ | $R^{4B}$ | $R^{a2}$ |
| A-321 | $R^{1A}$ | $R^{2A}$ | $R^{3A}$ | $R^{4C}$ | $R^{a2}$ |
| A-322 | $R^{1B}$ | $R^{2A}$ | $R^{3A}$ | $R^{4C}$ | $R^{a2}$ |
| A-323 | $R^{1C}$ | $R^{2A}$ | $R^{3A}$ | $R^{4C}$ | $R^{a2}$ |
| A-324 | $R^{1D}$ | $R^{2A}$ | $R^{3A}$ | $R^{4C}$ | $R^{a2}$ |
| A-325 | $R^{1A}$ | $R^{2B}$ | $R^{3A}$ | $R^{4C}$ | $R^{a2}$ |
| A-326 | $R^{1B}$ | $R^{2B}$ | $R^{3A}$ | $R^{4C}$ | $R^{a2}$ |
| A-327 | $R^{1C}$ | $R^{2B}$ | $R^{3A}$ | $R^{4C}$ | $R^{a2}$ |
| A-328 | $R^{1D}$ | $R^{2B}$ | $R^{3A}$ | $R^{4C}$ | $R^{a2}$ |
| A-329 | $R^{1A}$ | $R^{2C}$ | $R^{3A}$ | $R^{4C}$ | $R^{a2}$ |
| A-330 | $R^{1B}$ | $R^{2C}$ | $R^{3A}$ | $R^{4C}$ | $R^{a2}$ |
| A-331 | $R^{1C}$ | $R^{2C}$ | $R^{3A}$ | $R^{4C}$ | $R^{a2}$ |
| A-332 | $R^{1D}$ | $R^{2C}$ | $R^{3A}$ | $R^{4C}$ | $R^{a2}$ |
| A-333 | $R^{1A}$ | $R^{2D}$ | $R^{3A}$ | $R^{4C}$ | $R^{a2}$ |
| A-334 | $R^{1B}$ | $R^{2D}$ | $R^{3A}$ | $R^{4C}$ | $R^{a2}$ |
| A-335 | $R^{1C}$ | $R^{2D}$ | $R^{3A}$ | $R^{4C}$ | $R^{a2}$ |
| A-336 | $R^{1D}$ | $R^{2D}$ | $R^{3A}$ | $R^{4C}$ | $R^{a2}$ |
| A-337 | $R^{1A}$ | $R^{2A}$ | $R^{3B}$ | $R^{4C}$ | $R^{a2}$ |
| A-338 | $R^{1B}$ | $R^{2A}$ | $R^{3B}$ | $R^{4C}$ | $R^{a2}$ |
| A-339 | $R^{1C}$ | $R^{2A}$ | $R^{3B}$ | $R^{4C}$ | $R^{a2}$ |
| A-340 | $R^{1D}$ | $R^{2A}$ | $R^{3B}$ | $R^{4C}$ | $R^{a2}$ |
| A-341 | $R^{1A}$ | $R^{2B}$ | $R^{3B}$ | $R^{4C}$ | $R^{a2}$ |
| A-342 | $R^{1B}$ | $R^{2B}$ | $R^{3B}$ | $R^{4C}$ | $R^{a2}$ |
| A-343 | $R^{1C}$ | $R^{2B}$ | $R^{3B}$ | $R^{4C}$ | $R^{a2}$ |
| A-344 | $R^{1D}$ | $R^{2B}$ | $R^{3B}$ | $R^{4C}$ | $R^{a2}$ |
| A-345 | $R^{1A}$ | $R^{2C}$ | $R^{3B}$ | $R^{4C}$ | $R^{a2}$ |
| A-346 | $R^{1B}$ | $R^{2C}$ | $R^{3B}$ | $R^{4C}$ | $R^{a2}$ |
| A-347 | $R^{1C}$ | $R^{2C}$ | $R^{3B}$ | $R^{4C}$ | $R^{a2}$ |
| A-348 | $R^{1D}$ | $R^{2C}$ | $R^{3B}$ | $R^{4C}$ | $R^{a2}$ |
| A-349 | $R^{1A}$ | $R^{2D}$ | $R^{3B}$ | $R^{4C}$ | $R^{a2}$ |
| A-350 | $R^{1B}$ | $R^{2D}$ | $R^{3B}$ | $R^{4C}$ | $R^{a2}$ |
| A-351 | $R^{1C}$ | $R^{2D}$ | $R^{3B}$ | $R^{4C}$ | $R^{a2}$ |
| A-352 | $R^{1D}$ | $R^{2D}$ | $R^{3B}$ | $R^{4C}$ | $R^{a2}$ |
| A-353 | $R^{1A}$ | $R^{2A}$ | $R^{3C}$ | $R^{4C}$ | $R^{a2}$ |
| A-354 | $R^{1B}$ | $R^{2A}$ | $R^{3C}$ | $R^{4C}$ | $R^{a2}$ |
| A-355 | $R^{1C}$ | $R^{2A}$ | $R^{3C}$ | $R^{4C}$ | $R^{a2}$ |
| A-356 | $R^{1D}$ | $R^{2A}$ | $R^{3C}$ | $R^{4C}$ | $R^{a2}$ |
| A-357 | $R^{1A}$ | $R^{2B}$ | $R^{3C}$ | $R^{4C}$ | $R^{a2}$ |
| A-358 | $R^{1B}$ | $R^{2B}$ | $R^{3C}$ | $R^{4C}$ | $R^{a2}$ |
| A-359 | $R^{1C}$ | $R^{2B}$ | $R^{3C}$ | $R^{4C}$ | $R^{a2}$ |
| A-360 | $R^{1D}$ | $R^{2B}$ | $R^{3C}$ | $R^{4C}$ | $R^{a2}$ |
| A-361 | $R^{1A}$ | $R^{2C}$ | $R^{3C}$ | $R^{4C}$ | $R^{a2}$ |
| A-362 | $R^{1B}$ | $R^{2C}$ | $R^{3C}$ | $R^{4C}$ | $R^{a2}$ |
| A-363 | $R^{1C}$ | $R^{2C}$ | $R^{3C}$ | $R^{4C}$ | $R^{a2}$ |
| A-364 | $R^{1D}$ | $R^{2C}$ | $R^{3C}$ | $R^{4C}$ | $R^{a2}$ |
| A-365 | $R^{1A}$ | $R^{2D}$ | $R^{3C}$ | $R^{4C}$ | $R^{a2}$ |
| A-366 | $R^{1B}$ | $R^{2D}$ | $R^{3C}$ | $R^{4C}$ | $R^{a2}$ |
| A-367 | $R^{1C}$ | $R^{2D}$ | $R^{3C}$ | $R^{4C}$ | $R^{a2}$ |
| A-368 | $R^{1D}$ | $R^{2D}$ | $R^{3C}$ | $R^{4C}$ | $R^{a2}$ |
| A-369 | $R^{1A}$ | $R^{2A}$ | $R^{3D}$ | $R^{4C}$ | $R^{a2}$ |
| A-370 | $R^{1B}$ | $R^{2A}$ | $R^{3D}$ | $R^{4C}$ | $R^{a2}$ |
| A-371 | $R^{1C}$ | $R^{2A}$ | $R^{3D}$ | $R^{4C}$ | $R^{a2}$ |
| A-372 | $R^{1D}$ | $R^{2A}$ | $R^{3D}$ | $R^{4C}$ | $R^{a2}$ |
| A-373 | $R^{1A}$ | $R^{2B}$ | $R^{3D}$ | $R^{4C}$ | $R^{a2}$ |
| A-374 | $R^{1B}$ | $R^{2B}$ | $R^{3D}$ | $R^{4C}$ | $R^{a2}$ |
| A-375 | $R^{1C}$ | $R^{2B}$ | $R^{3D}$ | $R^{4C}$ | $R^{a2}$ |
| A-376 | $R^{1D}$ | $R^{2B}$ | $R^{3D}$ | $R^{4C}$ | $R^{a2}$ |
| A-377 | $R^{1A}$ | $R^{2C}$ | $R^{3D}$ | $R^{4C}$ | $R^{a2}$ |
| A-378 | $R^{1B}$ | $R^{2C}$ | $R^{3D}$ | $R^{4C}$ | $R^{a2}$ |
| A-379 | $R^{1C}$ | $R^{2C}$ | $R^{3D}$ | $R^{4C}$ | $R^{a2}$ |
| A-380 | $R^{1D}$ | $R^{2C}$ | $R^{3D}$ | $R^{4C}$ | $R^{a2}$ |
| A-381 | $R^{1A}$ | $R^{2D}$ | $R^{3D}$ | $R^{4C}$ | $R^{a2}$ |
| A-382 | $R^{1B}$ | $R^{2D}$ | $R^{3D}$ | $R^{4C}$ | $R^{a2}$ |
| A-383 | $R^{1C}$ | $R^{2D}$ | $R^{3D}$ | $R^{4C}$ | $R^{a2}$ |
| A-384 | $R^{1D}$ | $R^{2D}$ | $R^{3D}$ | $R^{4C}$ | $R^{a2}$ |

According to further aspects of this invention, this disclosure provides benzylamine compounds according to formula (I), wherein the compounds have following formula:

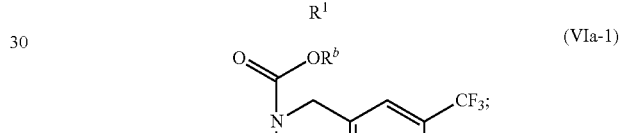

(IIa-1)

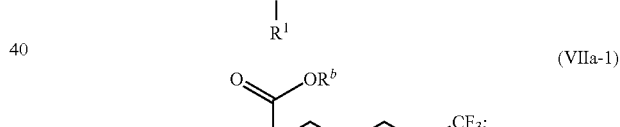

(VIa-1)

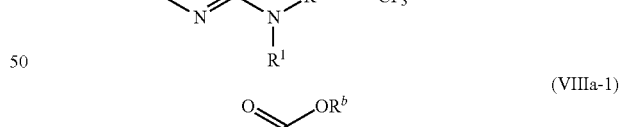

(VIIa-1)

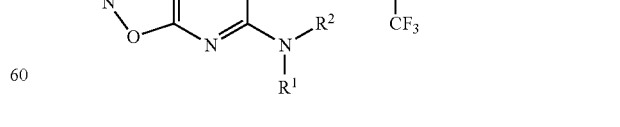

(VIIIa-1)

or any combination thereof;
or a salt, including a pharmaceutically acceptable or a non-pharmaceutically acceptable salt, a prodrug, a diastereomeric mixture, an enantiomer, a tautomer, a racemic mixture, or any combination thereof, wherein $R^1$, $R^2$, $R^a$, and $R^b$ can be selected according to the following table, to provide formulas (B-01) through (B-64), that are applicable to the compounds (IIa-1), (VIa-1), (VIIa-1), and (VIIa-1) illustrated above.

TABLE 2

Substituent selections for compounds according to this invention, having substituents $R^1$, $R^2$, $R^a$, and $R^b$.

| Formula | $R^1$ | $R^2$ | $R^a$ | $R^b$ |
|---|---|---|---|---|
| B-01 | $R^{1A}$ | $R^{2A}$ | $R^{a1}$ | $R^{b1}$ |
| B-02 | $R^{1B}$ | $R^{2A}$ | $R^{a1}$ | $R^{b1}$ |
| B-03 | $R^{1C}$ | $R^{2A}$ | $R^{a1}$ | $R^{b1}$ |
| B-04 | $R^{1D}$ | $R^{2A}$ | $R^{a1}$ | $R^{b1}$ |
| B-05 | $R^{1A}$ | $R^{2B}$ | $R^{a1}$ | $R^{b1}$ |
| B-06 | $R^{1B}$ | $R^{2B}$ | $R^{a1}$ | $R^{b1}$ |
| B-07 | $R^{1C}$ | $R^{2B}$ | $R^{a1}$ | $R^{b1}$ |
| B-08 | $R^{1D}$ | $R^{2B}$ | $R^{a1}$ | $R^{b1}$ |
| B-09 | $R^{1A}$ | $R^{2C}$ | $R^{a1}$ | $R^{b1}$ |
| B-10 | $R^{1B}$ | $R^{2C}$ | $R^{a1}$ | $R^{b1}$ |
| B-11 | $R^{1C}$ | $R^{2C}$ | $R^{a1}$ | $R^{b1}$ |
| B-12 | $R^{1D}$ | $R^{2C}$ | $R^{a1}$ | $R^{b1}$ |
| B-13 | $R^{1A}$ | $R^{2D}$ | $R^{a1}$ | $R^{b1}$ |
| B-14 | $R^{1B}$ | $R^{2D}$ | $R^{a1}$ | $R^{b1}$ |
| B-15 | $R^{1C}$ | $R^{2D}$ | $R^{a1}$ | $R^{b1}$ |
| B-16 | $R^{1D}$ | $R^{2D}$ | $R^{a1}$ | $R^{b1}$ |
| B-17 | $R^{1A}$ | $R^{2A}$ | $R^{a2}$ | $R^{b1}$ |
| B-18 | $R^{1B}$ | $R^{2A}$ | $R^{a2}$ | $R^{b1}$ |
| B-19 | $R^{1C}$ | $R^{2A}$ | $R^{a2}$ | $R^{b1}$ |
| B-20 | $R^{1D}$ | $R^{2A}$ | $R^{a2}$ | $R^{b1}$ |
| B-21 | $R^{1A}$ | $R^{2B}$ | $R^{a2}$ | $R^{b1}$ |
| B-22 | $R^{1B}$ | $R^{2B}$ | $R^{a2}$ | $R^{b1}$ |
| B-23 | $R^{1C}$ | $R^{2B}$ | $R^{a2}$ | $R^{b1}$ |
| B-24 | $R^{1D}$ | $R^{2B}$ | $R^{a2}$ | $R^{b1}$ |
| B-25 | $R^{1A}$ | $R^{2C}$ | $R^{a2}$ | $R^{b1}$ |
| B-26 | $R^{1B}$ | $R^{2C}$ | $R^{a2}$ | $R^{b1}$ |
| B-27 | $R^{1C}$ | $R^{2C}$ | $R^{a2}$ | $R^{b1}$ |
| B-28 | $R^{1D}$ | $R^{2C}$ | $R^{a2}$ | $R^{b1}$ |
| B-29 | $R^{1A}$ | $R^{2D}$ | $R^{a2}$ | $R^{b1}$ |
| B-30 | $R^{1B}$ | $R^{2D}$ | $R^{a2}$ | $R^{b1}$ |
| B-31 | $R^{1C}$ | $R^{2D}$ | $R^{a2}$ | $R^{b1}$ |
| B-32 | $R^{1D}$ | $R^{2D}$ | $R^{a2}$ | $R^{b1}$ |
| B-33 | $R^{1A}$ | $R^{2A}$ | $R^{a1}$ | $R^{b2}$ |
| B-34 | $R^{1B}$ | $R^{2A}$ | $R^{a1}$ | $R^{b2}$ |
| B-35 | $R^{1C}$ | $R^{2A}$ | $R^{a1}$ | $R^{b2}$ |
| B-36 | $R^{1D}$ | $R^{2A}$ | $R^{a1}$ | $R^{b2}$ |
| B-37 | $R^{1A}$ | $R^{2B}$ | $R^{a1}$ | $R^{b2}$ |
| B-38 | $R^{1B}$ | $R^{2B}$ | $R^{a1}$ | $R^{b2}$ |
| B-39 | $R^{1C}$ | $R^{2B}$ | $R^{a1}$ | $R^{b2}$ |
| B-40 | $R^{1D}$ | $R^{2B}$ | $R^{a1}$ | $R^{b2}$ |
| B-41 | $R^{1A}$ | $R^{2C}$ | $R^{a1}$ | $R^{b2}$ |
| B-42 | $R^{1B}$ | $R^{2C}$ | $R^{a1}$ | $R^{b2}$ |
| B-43 | $R^{1C}$ | $R^{2C}$ | $R^{a1}$ | $R^{b2}$ |
| B-44 | $R^{1D}$ | $R^{2C}$ | $R^{a1}$ | $R^{b2}$ |
| B-45 | $R^{1A}$ | $R^{2D}$ | $R^{a1}$ | $R^{b2}$ |
| B-46 | $R^{1B}$ | $R^{2D}$ | $R^{a1}$ | $R^{b2}$ |
| B-47 | $R^{1C}$ | $R^{2D}$ | $R^{a1}$ | $R^{b2}$ |
| B-48 | $R^{1D}$ | $R^{2D}$ | $R^{a1}$ | $R^{b2}$ |
| B-49 | $R^{1A}$ | $R^{2A}$ | $R^{a2}$ | $R^{b2}$ |
| B-50 | $R^{1B}$ | $R^{2A}$ | $R^{a2}$ | $R^{b2}$ |
| B-51 | $R^{1C}$ | $R^{2A}$ | $R^{a2}$ | $R^{b2}$ |
| B-52 | $R^{1D}$ | $R^{2A}$ | $R^{a2}$ | $R^{b2}$ |
| B-53 | $R^{1A}$ | $R^{2B}$ | $R^{a2}$ | $R^{b2}$ |
| B-54 | $R^{1B}$ | $R^{2B}$ | $R^{a2}$ | $R^{b2}$ |
| B-55 | $R^{1C}$ | $R^{2B}$ | $R^{a2}$ | $R^{b2}$ |
| B-56 | $R^{1D}$ | $R^{2B}$ | $R^{a2}$ | $R^{b2}$ |
| B-57 | $R^{1A}$ | $R^{2C}$ | $R^{a2}$ | $R^{b2}$ |
| B-58 | $R^{1B}$ | $R^{2C}$ | $R^{a2}$ | $R^{b2}$ |
| B-59 | $R^{1C}$ | $R^{2C}$ | $R^{a2}$ | $R^{b2}$ |
| B-60 | $R^{1D}$ | $R^{2C}$ | $R^{a2}$ | $R^{b2}$ |
| B-61 | $R^{1A}$ | $R^{2D}$ | $R^{a2}$ | $R^{b2}$ |
| B-62 | $R^{1B}$ | $R^{2D}$ | $R^{a2}$ | $R^{b2}$ |
| B-63 | $R^{1C}$ | $R^{2D}$ | $R^{a2}$ | $R^{b2}$ |
| B-64 | $R^{1D}$ | $R^{2D}$ | $R^{a2}$ | $R^{b2}$ |

According to various aspects of this invention, this disclosure provides benzylamine compounds according to formula (I), wherein the compounds have following formula:

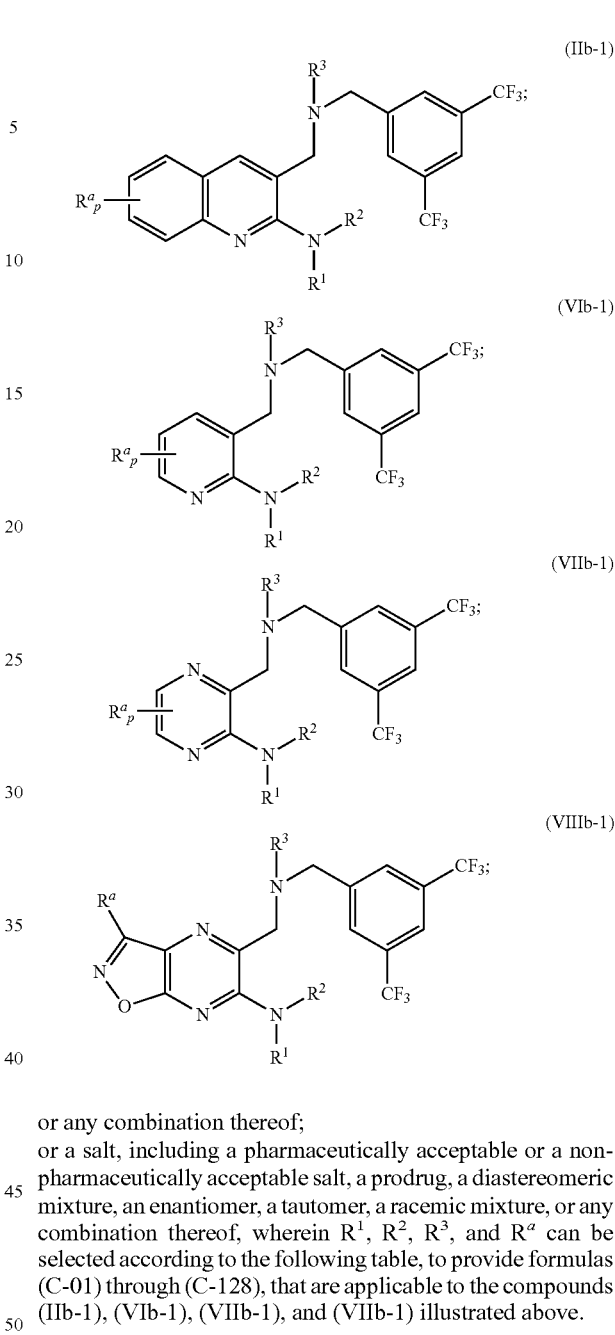

or any combination thereof;

or a salt, including a pharmaceutically acceptable or a non-pharmaceutically acceptable salt, a prodrug, a diastereomeric mixture, an enantiomer, a tautomer, a racemic mixture, or any combination thereof, wherein $R^1$, $R^2$, $R^3$, and $R^a$ can be selected according to the following table, to provide formulas (C-01) through (C-128), that are applicable to the compounds (IIb-1), (VIb-1), (VIIb-1), and (VIIb-1) illustrated above.

TABLE 3

Substituent selections for compounds according to this invention, having substituents $R^1$, $R^2$, $R^3$, and $R^a$.

| Formula | $R^1$ | $R^2$ | $R^3$ | $R^a$ |
|---|---|---|---|---|
| C-01 | $R^{1A}$ | $R^{2A}$ | $R^{3A}$ | $R^{a1}$ |
| C-02 | $R^{1B}$ | $R^{2A}$ | $R^{3A}$ | $R^{a1}$ |
| C-03 | $R^{1C}$ | $R^{2A}$ | $R^{3A}$ | $R^{a1}$ |
| C-04 | $R^{1D}$ | $R^{2A}$ | $R^{3A}$ | $R^{a1}$ |
| C-05 | $R^{1A}$ | $R^{2B}$ | $R^{3A}$ | $R^{a1}$ |
| C-06 | $R^{1B}$ | $R^{2B}$ | $R^{3A}$ | $R^{a1}$ |
| C-07 | $R^{1C}$ | $R^{2B}$ | $R^{3A}$ | $R^{a1}$ |
| C-08 | $R^{1D}$ | $R^{2B}$ | $R^{3A}$ | $R^{a1}$ |
| C-09 | $R^{1A}$ | $R^{2C}$ | $R^{3A}$ | $R^{a1}$ |
| C-10 | $R^{1B}$ | $R^{2C}$ | $R^{3A}$ | $R^{a1}$ |
| C-11 | $R^{1C}$ | $R^{2C}$ | $R^{3A}$ | $R^{a1}$ |
| C-12 | $R^{1D}$ | $R^{2C}$ | $R^{3A}$ | $R^{a1}$ |

TABLE 3-continued

Substituent selections for compounds according to this invention, having substituents $R^1$, $R^2$, $R^3$, and $R^a$.

| Formula | $R^1$ | $R^2$ | $R^3$ | $R^a$ |
|---|---|---|---|---|
| C-13 | $R^{1A}$ | $R^{2D}$ | $R^{3A}$ | $R^{a1}$ |
| C-14 | $R^{1B}$ | $R^{2D}$ | $R^{3A}$ | $R^{a1}$ |
| C-15 | $R^{1C}$ | $R^{2D}$ | $R^{3A}$ | $R^{a1}$ |
| C-16 | $R^{1D}$ | $R^{2D}$ | $R^{3A}$ | $R^{a1}$ |
| C-17 | $R^{1A}$ | $R^{2A}$ | $R^{3B}$ | $R^{a1}$ |
| C-18 | $R^{1B}$ | $R^{2A}$ | $R^{3B}$ | $R^{a1}$ |
| C-19 | $R^{1C}$ | $R^{2A}$ | $R^{3B}$ | $R^{a1}$ |
| C-20 | $R^{1D}$ | $R^{2A}$ | $R^{3B}$ | $R^{a1}$ |
| C-21 | $R^{1A}$ | $R^{2B}$ | $R^{3B}$ | $R^{a1}$ |
| C-22 | $R^{1B}$ | $R^{2B}$ | $R^{3B}$ | $R^{a1}$ |
| C-23 | $R^{1C}$ | $R^{2B}$ | $R^{3B}$ | $R^{a1}$ |
| C-24 | $R^{1D}$ | $R^{2B}$ | $R^{3B}$ | $R^{a1}$ |
| C-25 | $R^{1A}$ | $R^{2C}$ | $R^{3B}$ | $R^{a1}$ |
| C-26 | $R^{1B}$ | $R^{2C}$ | $R^{3B}$ | $R^{a1}$ |
| C-27 | $R^{1C}$ | $R^{2C}$ | $R^{3B}$ | $R^{a1}$ |
| C-28 | $R^{1D}$ | $R^{2C}$ | $R^{3B}$ | $R^{a1}$ |
| C-29 | $R^{1A}$ | $R^{2D}$ | $R^{3B}$ | $R^{a1}$ |
| C-30 | $R^{1B}$ | $R^{2D}$ | $R^{3B}$ | $R^{a1}$ |
| C-31 | $R^{1C}$ | $R^{2D}$ | $R^{3B}$ | $R^{a1}$ |
| C-32 | $R^{1D}$ | $R^{2D}$ | $R^{3B}$ | $R^{a1}$ |
| C-33 | $R^{1A}$ | $R^{2A}$ | $R^{3C}$ | $R^{a1}$ |
| C-34 | $R^{1B}$ | $R^{2A}$ | $R^{3C}$ | $R^{a1}$ |
| C-35 | $R^{1C}$ | $R^{2A}$ | $R^{3C}$ | $R^{a1}$ |
| C-36 | $R^{1D}$ | $R^{2A}$ | $R^{3C}$ | $R^{a1}$ |
| C-37 | $R^{1A}$ | $R^{2B}$ | $R^{3C}$ | $R^{a1}$ |
| C-38 | $R^{1B}$ | $R^{2B}$ | $R^{3C}$ | $R^{a1}$ |
| C-39 | $R^{1C}$ | $R^{2B}$ | $R^{3C}$ | $R^{a1}$ |
| C-40 | $R^{1D}$ | $R^{2B}$ | $R^{3C}$ | $R^{a1}$ |
| C-41 | $R^{1A}$ | $R^{2C}$ | $R^{3C}$ | $R^{a1}$ |
| C-42 | $R^{1B}$ | $R^{2C}$ | $R^{3C}$ | $R^{a1}$ |
| C-43 | $R^{1C}$ | $R^{2C}$ | $R^{3C}$ | $R^{a1}$ |
| C-44 | $R^{1D}$ | $R^{2C}$ | $R^{3C}$ | $R^{a1}$ |
| C-45 | $R^{1A}$ | $R^{2D}$ | $R^{3C}$ | $R^{a1}$ |
| C-46 | $R^{1B}$ | $R^{2D}$ | $R^{3C}$ | $R^{a1}$ |
| C-47 | $R^{1C}$ | $R^{2D}$ | $R^{3C}$ | $R^{a1}$ |
| C-48 | $R^{1D}$ | $R^{2D}$ | $R^{3C}$ | $R^{a1}$ |
| C-49 | $R^{1A}$ | $R^{2A}$ | $R^{3D}$ | $R^{a1}$ |
| C-50 | $R^{1B}$ | $R^{2A}$ | $R^{3D}$ | $R^{a1}$ |
| C-51 | $R^{1C}$ | $R^{2A}$ | $R^{3D}$ | $R^{a1}$ |
| C-52 | $R^{1D}$ | $R^{2A}$ | $R^{3D}$ | $R^{a1}$ |
| C-53 | $R^{1A}$ | $R^{2B}$ | $R^{3D}$ | $R^{a1}$ |
| C-54 | $R^{1B}$ | $R^{2B}$ | $R^{3D}$ | $R^{a1}$ |
| C-55 | $R^{1C}$ | $R^{2B}$ | $R^{3D}$ | $R^{a1}$ |
| C-56 | $R^{1D}$ | $R^{2B}$ | $R^{3D}$ | $R^{a1}$ |
| C-57 | $R^{1A}$ | $R^{2C}$ | $R^{3D}$ | $R^{a1}$ |
| C-58 | $R^{1B}$ | $R^{2C}$ | $R^{3D}$ | $R^{a1}$ |
| C-59 | $R^{1C}$ | $R^{2C}$ | $R^{3D}$ | $R^{a1}$ |
| C-60 | $R^{1D}$ | $R^{2C}$ | $R^{3D}$ | $R^{a1}$ |
| C-61 | $R^{1A}$ | $R^{2D}$ | $R^{3D}$ | $R^{a1}$ |
| C-62 | $R^{1B}$ | $R^{2D}$ | $R^{3D}$ | $R^{a1}$ |
| C-63 | $R^{1C}$ | $R^{2D}$ | $R^{3D}$ | $R^{a1}$ |
| C-64 | $R^{1D}$ | $R^{2D}$ | $R^{3D}$ | $R^{a1}$ |
| C-65 | $R^{1A}$ | $R^{2A}$ | $R^{3A}$ | $R^{a2}$ |
| C-66 | $R^{1B}$ | $R^{2A}$ | $R^{3A}$ | $R^{a2}$ |
| C-67 | $R^{1C}$ | $R^{2A}$ | $R^{3A}$ | $R^{a2}$ |
| C-68 | $R^{1D}$ | $R^{2A}$ | $R^{3A}$ | $R^{a2}$ |
| C-69 | $R^{1A}$ | $R^{2B}$ | $R^{3A}$ | $R^{a2}$ |
| C-70 | $R^{1B}$ | $R^{2B}$ | $R^{3A}$ | $R^{a2}$ |
| C-71 | $R^{1C}$ | $R^{2B}$ | $R^{3A}$ | $R^{a2}$ |
| C-72 | $R^{1D}$ | $R^{2B}$ | $R^{3A}$ | $R^{a2}$ |
| C-73 | $R^{1A}$ | $R^{2C}$ | $R^{3A}$ | $R^{a2}$ |
| C-74 | $R^{1B}$ | $R^{2C}$ | $R^{3A}$ | $R^{a2}$ |
| C-75 | $R^{1C}$ | $R^{2C}$ | $R^{3A}$ | $R^{a2}$ |
| C-76 | $R^{1D}$ | $R^{2C}$ | $R^{3A}$ | $R^{a2}$ |
| C-77 | $R^{1A}$ | $R^{2D}$ | $R^{3A}$ | $R^{a2}$ |
| C-78 | $R^{1B}$ | $R^{2D}$ | $R^{3A}$ | $R^{a2}$ |
| C-79 | $R^{1C}$ | $R^{2D}$ | $R^{3A}$ | $R^{a2}$ |
| C-80 | $R^{1D}$ | $R^{2D}$ | $R^{3A}$ | $R^{a2}$ |
| C-81 | $R^{1A}$ | $R^{2A}$ | $R^{3B}$ | $R^{a2}$ |
| C-82 | $R^{1B}$ | $R^{2A}$ | $R^{3B}$ | $R^{a2}$ |
| C-83 | $R^{1C}$ | $R^{2A}$ | $R^{3B}$ | $R^{a2}$ |
| C-84 | $R^{1D}$ | $R^{2A}$ | $R^{3B}$ | $R^{a2}$ |
| C-85 | $R^{1A}$ | $R^{2B}$ | $R^{3B}$ | $R^{a2}$ |
| C-86 | $R^{1B}$ | $R^{2B}$ | $R^{3B}$ | $R^{a2}$ |
| C-87 | $R^{1C}$ | $R^{2B}$ | $R^{3B}$ | $R^{a2}$ |
| C-88 | $R^{1D}$ | $R^{2B}$ | $R^{3B}$ | $R^{a2}$ |
| C-89 | $R^{1A}$ | $R^{2C}$ | $R^{3B}$ | $R^{a2}$ |
| C-90 | $R^{1B}$ | $R^{2C}$ | $R^{3B}$ | $R^{a2}$ |
| C-91 | $R^{1C}$ | $R^{2C}$ | $R^{3B}$ | $R^{a2}$ |
| C-92 | $R^{1D}$ | $R^{2C}$ | $R^{3B}$ | $R^{a2}$ |
| C-93 | $R^{1A}$ | $R^{2D}$ | $R^{3B}$ | $R^{a2}$ |
| C-94 | $R^{1B}$ | $R^{2D}$ | $R^{3B}$ | $R^{a2}$ |
| C-95 | $R^{1C}$ | $R^{2D}$ | $R^{3B}$ | $R^{a2}$ |
| C-96 | $R^{1D}$ | $R^{2D}$ | $R^{3B}$ | $R^{a2}$ |
| C-97 | $R^{1A}$ | $R^{2A}$ | $R^{3C}$ | $R^{a2}$ |
| C-98 | $R^{1B}$ | $R^{2A}$ | $R^{3C}$ | $R^{a2}$ |
| C-99 | $R^{1C}$ | $R^{2A}$ | $R^{3C}$ | $R^{a2}$ |
| C-100 | $R^{1D}$ | $R^{2A}$ | $R^{3C}$ | $R^{a2}$ |
| C-101 | $R^{1A}$ | $R^{2B}$ | $R^{3C}$ | $R^{a2}$ |
| C-102 | $R^{1B}$ | $R^{2B}$ | $R^{3C}$ | $R^{a2}$ |
| C-103 | $R^{1C}$ | $R^{2B}$ | $R^{3C}$ | $R^{a2}$ |
| C-104 | $R^{1D}$ | $R^{2B}$ | $R^{3C}$ | $R^{a2}$ |
| C-105 | $R^{1A}$ | $R^{2C}$ | $R^{3C}$ | $R^{a2}$ |
| C-106 | $R^{1B}$ | $R^{2C}$ | $R^{3C}$ | $R^{a2}$ |
| C-107 | $R^{1C}$ | $R^{2C}$ | $R^{3C}$ | $R^{a2}$ |
| C-108 | $R^{1D}$ | $R^{2C}$ | $R^{3C}$ | $R^{a2}$ |
| C-109 | $R^{1A}$ | $R^{2D}$ | $R^{3C}$ | $R^{a2}$ |
| C-110 | $R^{1B}$ | $R^{2D}$ | $R^{3C}$ | $R^{a2}$ |
| C-111 | $R^{1C}$ | $R^{2D}$ | $R^{3C}$ | $R^{a2}$ |
| C-112 | $R^{1D}$ | $R^{2D}$ | $R^{3C}$ | $R^{a2}$ |
| C-113 | $R^{1A}$ | $R^{2A}$ | $R^{3D}$ | $R^{a2}$ |
| C-114 | $R^{1B}$ | $R^{2A}$ | $R^{3D}$ | $R^{a2}$ |
| C-115 | $R^{1C}$ | $R^{2A}$ | $R^{3D}$ | $R^{a2}$ |
| C-116 | $R^{1D}$ | $R^{2A}$ | $R^{3D}$ | $R^{a2}$ |
| C-117 | $R^{1A}$ | $R^{2B}$ | $R^{3D}$ | $R^{a2}$ |
| C-118 | $R^{1B}$ | $R^{2B}$ | $R^{3D}$ | $R^{a2}$ |
| C-119 | $R^{1C}$ | $R^{2B}$ | $R^{3D}$ | $R^{a2}$ |
| C-120 | $R^{1D}$ | $R^{2B}$ | $R^{3D}$ | $R^{a2}$ |
| C-121 | $R^{1A}$ | $R^{2C}$ | $R^{3D}$ | $R^{a2}$ |
| C-122 | $R^{1B}$ | $R^{2C}$ | $R^{3D}$ | $R^{a2}$ |
| C-123 | $R^{1C}$ | $R^{2C}$ | $R^{3D}$ | $R^{a2}$ |
| C-124 | $R^{1D}$ | $R^{2C}$ | $R^{3D}$ | $R^{a2}$ |
| C-125 | $R^{1A}$ | $R^{2D}$ | $R^{3D}$ | $R^{a2}$ |
| C-126 | $R^{1B}$ | $R^{2D}$ | $R^{3D}$ | $R^{a2}$ |
| C-127 | $R^{1C}$ | $R^{2D}$ | $R^{3D}$ | $R^{a2}$ |
| C-128 | $R^{1D}$ | $R^{2D}$ | $R^{3D}$ | $R^{a2}$ |

In accordance with further aspects of this invention, this disclosure provides benzylamine compounds according to formula (I), wherein the compounds have following formula:

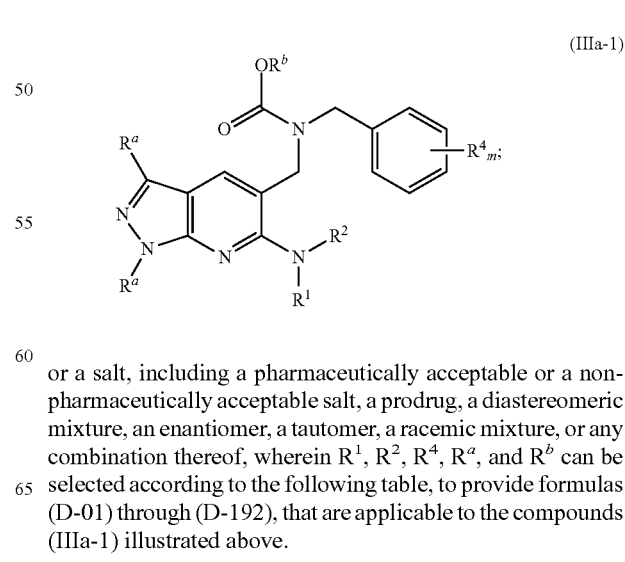

(IIIa-1)

or a salt, including a pharmaceutically acceptable or a non-pharmaceutically acceptable salt, a prodrug, a diastereomeric mixture, an enantiomer, a tautomer, a racemic mixture, or any combination thereof, wherein $R^1$, $R^2$, $R^4$, $R^a$, and $R^b$ can be selected according to the following table, to provide formulas (D-01) through (D-192), that are applicable to the compounds (IIIa-1) illustrated above.

TABLE 4

Substituent selections for compounds according to this invention, having substituents $R^1$, $R^2$, $R^4$, $R^a$, and $R^b$.

| Formula | $R^1$ | $R^2$ | $R^4$ | $R^a$ | $R^b$ |
|---|---|---|---|---|---|
| D-01 | $R^{1A}$ | $R^{2A}$ | $R^{4A}$ | $R^{a1}$ | $R^{b1}$ |
| D-02 | $R^{1B}$ | $R^{2A}$ | $R^{4A}$ | $R^{a1}$ | $R^{b1}$ |
| D-03 | $R^{1C}$ | $R^{2A}$ | $R^{4A}$ | $R^{a1}$ | $R^{b1}$ |
| D-04 | $R^{1D}$ | $R^{2A}$ | $R^{4A}$ | $R^{a1}$ | $R^{b1}$ |
| D-05 | $R^{1A}$ | $R^{2B}$ | $R^{4A}$ | $R^{a1}$ | $R^{b1}$ |
| D-06 | $R^{1B}$ | $R^{2B}$ | $R^{4A}$ | $R^{a1}$ | $R^{b1}$ |
| D-07 | $R^{1C}$ | $R^{2B}$ | $R^{4A}$ | $R^{a1}$ | $R^{b1}$ |
| D-08 | $R^{1D}$ | $R^{2B}$ | $R^{4A}$ | $R^{a1}$ | $R^{b1}$ |
| D-09 | $R^{1A}$ | $R^{2C}$ | $R^{4A}$ | $R^{a1}$ | $R^{b1}$ |
| D-10 | $R^{1B}$ | $R^{2C}$ | $R^{4A}$ | $R^{a1}$ | $R^{b1}$ |
| D-11 | $R^{1C}$ | $R^{2C}$ | $R^{4A}$ | $R^{a1}$ | $R^{b1}$ |
| D-12 | $R^{1D}$ | $R^{2C}$ | $R^{4A}$ | $R^{a1}$ | $R^{b1}$ |
| D-13 | $R^{1A}$ | $R^{2D}$ | $R^{4A}$ | $R^{a1}$ | $R^{b1}$ |
| D-14 | $R^{1B}$ | $R^{2D}$ | $R^{4A}$ | $R^{a1}$ | $R^{b1}$ |
| D-15 | $R^{1C}$ | $R^{2D}$ | $R^{4A}$ | $R^{a1}$ | $R^{b1}$ |
| D-16 | $R^{1D}$ | $R^{2D}$ | $R^{4A}$ | $R^{a1}$ | $R^{b1}$ |
| D-17 | $R^{1A}$ | $R^{2A}$ | $R^{4B}$ | $R^{a1}$ | $R^{b1}$ |
| D-18 | $R^{1B}$ | $R^{2A}$ | $R^{4B}$ | $R^{a1}$ | $R^{b1}$ |
| D-19 | $R^{1C}$ | $R^{2A}$ | $R^{4B}$ | $R^{a1}$ | $R^{b1}$ |
| D-20 | $R^{1D}$ | $R^{2A}$ | $R^{4B}$ | $R^{a1}$ | $R^{b1}$ |
| D-21 | $R^{1A}$ | $R^{2B}$ | $R^{4B}$ | $R^{a1}$ | $R^{b1}$ |
| D-22 | $R^{1B}$ | $R^{2B}$ | $R^{4B}$ | $R^{a1}$ | $R^{b1}$ |
| D-23 | $R^{1C}$ | $R^{2B}$ | $R^{4B}$ | $R^{a1}$ | $R^{b1}$ |
| D-24 | $R^{1D}$ | $R^{2B}$ | $R^{4B}$ | $R^{a1}$ | $R^{b1}$ |
| D-25 | $R^{1A}$ | $R^{2C}$ | $R^{4B}$ | $R^{a1}$ | $R^{b1}$ |
| D-26 | $R^{1B}$ | $R^{2C}$ | $R^{4B}$ | $R^{a1}$ | $R^{b1}$ |
| D-27 | $R^{1C}$ | $R^{2C}$ | $R^{4B}$ | $R^{a1}$ | $R^{b1}$ |
| D-28 | $R^{1D}$ | $R^{2C}$ | $R^{4B}$ | $R^{a1}$ | $R^{b1}$ |
| D-29 | $R^{1A}$ | $R^{2D}$ | $R^{4B}$ | $R^{a1}$ | $R^{b1}$ |
| D-30 | $R^{1B}$ | $R^{2D}$ | $R^{4B}$ | $R^{a1}$ | $R^{b1}$ |
| D-31 | $R^{1C}$ | $R^{2D}$ | $R^{4B}$ | $R^{a1}$ | $R^{b1}$ |
| D-32 | $R^{1D}$ | $R^{2D}$ | $R^{4B}$ | $R^{a1}$ | $R^{b1}$ |
| D-33 | $R^{1A}$ | $R^{2A}$ | $R^{4C}$ | $R^{a1}$ | $R^{b1}$ |
| D-34 | $R^{1B}$ | $R^{2A}$ | $R^{4C}$ | $R^{a1}$ | $R^{b1}$ |
| D-35 | $R^{1C}$ | $R^{2A}$ | $R^{4C}$ | $R^{a1}$ | $R^{b1}$ |
| D-36 | $R^{1D}$ | $R^{2A}$ | $R^{4C}$ | $R^{a1}$ | $R^{b1}$ |
| D-37 | $R^{1A}$ | $R^{2B}$ | $R^{4C}$ | $R^{a1}$ | $R^{b1}$ |
| D-38 | $R^{1B}$ | $R^{2B}$ | $R^{4C}$ | $R^{a1}$ | $R^{b1}$ |
| D-39 | $R^{1C}$ | $R^{2B}$ | $R^{4C}$ | $R^{a1}$ | $R^{b1}$ |
| D-40 | $R^{1D}$ | $R^{2B}$ | $R^{4C}$ | $R^{a1}$ | $R^{b1}$ |
| D-41 | $R^{1A}$ | $R^{2C}$ | $R^{4C}$ | $R^{a1}$ | $R^{b1}$ |
| D-42 | $R^{1B}$ | $R^{2C}$ | $R^{4C}$ | $R^{a1}$ | $R^{b1}$ |
| D-43 | $R^{1C}$ | $R^{2C}$ | $R^{4C}$ | $R^{a1}$ | $R^{b1}$ |
| D-44 | $R^{1D}$ | $R^{2C}$ | $R^{4C}$ | $R^{a1}$ | $R^{b1}$ |
| D-45 | $R^{1A}$ | $R^{2D}$ | $R^{4C}$ | $R^{a1}$ | $R^{b1}$ |
| D-46 | $R^{1B}$ | $R^{2D}$ | $R^{4C}$ | $R^{a1}$ | $R^{b1}$ |
| D-47 | $R^{1C}$ | $R^{2D}$ | $R^{4C}$ | $R^{a1}$ | $R^{b1}$ |
| D-48 | $R^{1D}$ | $R^{2D}$ | $R^{4C}$ | $R^{a1}$ | $R^{b1}$ |
| D-49 | $R^{1A}$ | $R^{2A}$ | $R^{4A}$ | $R^{a2}$ | $R^{b1}$ |
| D-50 | $R^{1B}$ | $R^{2A}$ | $R^{4A}$ | $R^{a2}$ | $R^{b1}$ |
| D-51 | $R^{1C}$ | $R^{2A}$ | $R^{4A}$ | $R^{a2}$ | $R^{b1}$ |
| D-52 | $R^{1D}$ | $R^{2A}$ | $R^{4A}$ | $R^{a2}$ | $R^{b1}$ |
| D-53 | $R^{1A}$ | $R^{2B}$ | $R^{4A}$ | $R^{a2}$ | $R^{b1}$ |
| D-54 | $R^{1B}$ | $R^{2B}$ | $R^{4A}$ | $R^{a2}$ | $R^{b1}$ |
| D-55 | $R^{1C}$ | $R^{2B}$ | $R^{4A}$ | $R^{a2}$ | $R^{b1}$ |
| D-56 | $R^{1D}$ | $R^{2B}$ | $R^{4A}$ | $R^{a2}$ | $R^{b1}$ |
| D-57 | $R^{1A}$ | $R^{2C}$ | $R^{4A}$ | $R^{a2}$ | $R^{b1}$ |
| D-58 | $R^{1B}$ | $R^{2C}$ | $R^{4A}$ | $R^{a2}$ | $R^{b1}$ |
| D-59 | $R^{1C}$ | $R^{2C}$ | $R^{4A}$ | $R^{a2}$ | $R^{b1}$ |
| D-60 | $R^{1D}$ | $R^{2C}$ | $R^{4A}$ | $R^{a2}$ | $R^{b1}$ |
| D-61 | $R^{1A}$ | $R^{2D}$ | $R^{4A}$ | $R^{a2}$ | $R^{b1}$ |
| D-62 | $R^{1B}$ | $R^{2D}$ | $R^{4A}$ | $R^{a2}$ | $R^{b1}$ |
| D-63 | $R^{1C}$ | $R^{2D}$ | $R^{4A}$ | $R^{a2}$ | $R^{b1}$ |
| D-64 | $R^{1D}$ | $R^{2D}$ | $R^{4A}$ | $R^{a2}$ | $R^{b1}$ |
| D-65 | $R^{1A}$ | $R^{2A}$ | $R^{4B}$ | $R^{a2}$ | $R^{b1}$ |
| D-66 | $R^{1B}$ | $R^{2A}$ | $R^{4B}$ | $R^{a2}$ | $R^{b1}$ |
| D-67 | $R^{1C}$ | $R^{2A}$ | $R^{4B}$ | $R^{a2}$ | $R^{b1}$ |
| D-68 | $R^{1D}$ | $R^{2A}$ | $R^{4B}$ | $R^{a2}$ | $R^{b1}$ |
| D-69 | $R^{1A}$ | $R^{2B}$ | $R^{4B}$ | $R^{a2}$ | $R^{b1}$ |
| D-70 | $R^{1B}$ | $R^{2B}$ | $R^{4B}$ | $R^{a2}$ | $R^{b1}$ |
| D-71 | $R^{1C}$ | $R^{2B}$ | $R^{4B}$ | $R^{a2}$ | $R^{b1}$ |
| D-72 | $R^{1D}$ | $R^{2B}$ | $R^{4B}$ | $R^{a2}$ | $R^{b1}$ |
| D-73 | $R^{1A}$ | $R^{2C}$ | $R^{4B}$ | $R^{a2}$ | $R^{b1}$ |
| D-74 | $R^{1B}$ | $R^{2C}$ | $R^{4B}$ | $R^{a2}$ | $R^{b1}$ |
| D-75 | $R^{1C}$ | $R^{2C}$ | $R^{4B}$ | $R^{a2}$ | $R^{b1}$ |
| D-76 | $R^{1D}$ | $R^{2C}$ | $R^{4B}$ | $R^{a2}$ | $R^{b1}$ |
| D-77 | $R^{1A}$ | $R^{2D}$ | $R^{4B}$ | $R^{a2}$ | $R^{b1}$ |
| D-78 | $R^{1B}$ | $R^{2D}$ | $R^{4B}$ | $R^{a2}$ | $R^{b1}$ |
| D-79 | $R^{1C}$ | $R^{2D}$ | $R^{4B}$ | $R^{a2}$ | $R^{b1}$ |
| D-80 | $R^{1D}$ | $R^{2D}$ | $R^{4B}$ | $R^{a2}$ | $R^{b1}$ |
| D-81 | $R^{1A}$ | $R^{2A}$ | $R^{4C}$ | $R^{a2}$ | $R^{b1}$ |
| D-82 | $R^{1B}$ | $R^{2A}$ | $R^{4C}$ | $R^{a2}$ | $R^{b1}$ |
| D-83 | $R^{1C}$ | $R^{2A}$ | $R^{4C}$ | $R^{a2}$ | $R^{b1}$ |
| D-84 | $R^{1D}$ | $R^{2A}$ | $R^{4C}$ | $R^{a2}$ | $R^{b1}$ |
| D-85 | $R^{1A}$ | $R^{2B}$ | $R^{4C}$ | $R^{a2}$ | $R^{b1}$ |
| D-86 | $R^{1B}$ | $R^{2B}$ | $R^{4C}$ | $R^{a2}$ | $R^{b1}$ |
| D-87 | $R^{1C}$ | $R^{2B}$ | $R^{4C}$ | $R^{a2}$ | $R^{b1}$ |
| D-88 | $R^{1D}$ | $R^{2B}$ | $R^{4C}$ | $R^{a2}$ | $R^{b1}$ |
| D-89 | $R^{1A}$ | $R^{2C}$ | $R^{4C}$ | $R^{a2}$ | $R^{b1}$ |
| D-90 | $R^{1B}$ | $R^{2C}$ | $R^{4C}$ | $R^{a2}$ | $R^{b1}$ |
| D-91 | $R^{1C}$ | $R^{2C}$ | $R^{4C}$ | $R^{a2}$ | $R^{b1}$ |
| D-92 | $R^{1D}$ | $R^{2C}$ | $R^{4C}$ | $R^{a2}$ | $R^{b1}$ |
| D-93 | $R^{1A}$ | $R^{2D}$ | $R^{4C}$ | $R^{a2}$ | $R^{b1}$ |
| D-94 | $R^{1B}$ | $R^{2D}$ | $R^{4C}$ | $R^{a2}$ | $R^{b1}$ |
| D-95 | $R^{1C}$ | $R^{2D}$ | $R^{4C}$ | $R^{a2}$ | $R^{b1}$ |
| D-96 | $R^{1D}$ | $R^{2D}$ | $R^{4C}$ | $R^{a2}$ | $R^{b1}$ |
| D-97 | $R^{1A}$ | $R^{2A}$ | $R^{4A}$ | $R^{a1}$ | $R^{b2}$ |
| D-98 | $R^{1B}$ | $R^{2A}$ | $R^{4A}$ | $R^{a1}$ | $R^{b2}$ |
| D-99 | $R^{1C}$ | $R^{2A}$ | $R^{4A}$ | $R^{a1}$ | $R^{b2}$ |
| D-100 | $R^{1D}$ | $R^{2A}$ | $R^{4A}$ | $R^{a1}$ | $R^{b2}$ |
| D-101 | $R^{1A}$ | $R^{2B}$ | $R^{4A}$ | $R^{a1}$ | $R^{b2}$ |
| D-102 | $R^{1B}$ | $R^{2B}$ | $R^{4A}$ | $R^{a1}$ | $R^{b2}$ |
| D-103 | $R^{1C}$ | $R^{2B}$ | $R^{4A}$ | $R^{a1}$ | $R^{b2}$ |
| D-104 | $R^{1D}$ | $R^{2B}$ | $R^{4A}$ | $R^{a1}$ | $R^{b2}$ |
| D-105 | $R^{1A}$ | $R^{2C}$ | $R^{4A}$ | $R^{a1}$ | $R^{b2}$ |
| D-106 | $R^{1B}$ | $R^{2C}$ | $R^{4A}$ | $R^{a1}$ | $R^{b2}$ |
| D-107 | $R^{1C}$ | $R^{2C}$ | $R^{4A}$ | $R^{a1}$ | $R^{b2}$ |
| D-108 | $R^{1D}$ | $R^{2C}$ | $R^{4A}$ | $R^{a1}$ | $R^{b2}$ |
| D-109 | $R^{1A}$ | $R^{2D}$ | $R^{4A}$ | $R^{a1}$ | $R^{b2}$ |
| D-110 | $R^{1B}$ | $R^{2D}$ | $R^{4A}$ | $R^{a1}$ | $R^{b2}$ |
| D-111 | $R^{1C}$ | $R^{2D}$ | $R^{4A}$ | $R^{a1}$ | $R^{b2}$ |
| D-112 | $R^{1D}$ | $R^{2D}$ | $R^{4A}$ | $R^{a1}$ | $R^{b2}$ |
| D-113 | $R^{1A}$ | $R^{2A}$ | $R^{4B}$ | $R^{a1}$ | $R^{b2}$ |
| D-114 | $R^{1B}$ | $R^{2A}$ | $R^{4B}$ | $R^{a1}$ | $R^{b2}$ |
| D-115 | $R^{1C}$ | $R^{2A}$ | $R^{4B}$ | $R^{a1}$ | $R^{b2}$ |
| D-116 | $R^{1D}$ | $R^{2A}$ | $R^{4B}$ | $R^{a1}$ | $R^{b2}$ |
| D-117 | $R^{1A}$ | $R^{2B}$ | $R^{4B}$ | $R^{a1}$ | $R^{b2}$ |
| D-118 | $R^{1B}$ | $R^{2B}$ | $R^{4B}$ | $R^{a1}$ | $R^{b2}$ |
| D-119 | $R^{1C}$ | $R^{2B}$ | $R^{4B}$ | $R^{a1}$ | $R^{b2}$ |
| D-120 | $R^{1D}$ | $R^{2B}$ | $R^{4B}$ | $R^{a1}$ | $R^{b2}$ |
| D-121 | $R^{1A}$ | $R^{2C}$ | $R^{4B}$ | $R^{a1}$ | $R^{b2}$ |
| D-122 | $R^{1B}$ | $R^{2C}$ | $R^{4B}$ | $R^{a1}$ | $R^{b2}$ |
| D-123 | $R^{1C}$ | $R^{2C}$ | $R^{4B}$ | $R^{a1}$ | $R^{b2}$ |
| D-124 | $R^{1D}$ | $R^{2C}$ | $R^{4B}$ | $R^{a1}$ | $R^{b2}$ |
| D-125 | $R^{1A}$ | $R^{2D}$ | $R^{4B}$ | $R^{a1}$ | $R^{b2}$ |
| D-126 | $R^{1B}$ | $R^{2D}$ | $R^{4B}$ | $R^{a1}$ | $R^{b2}$ |
| D-127 | $R^{1C}$ | $R^{2D}$ | $R^{4B}$ | $R^{a1}$ | $R^{b2}$ |
| D-128 | $R^{1D}$ | $R^{2D}$ | $R^{4B}$ | $R^{a1}$ | $R^{b2}$ |
| D-129 | $R^{1A}$ | $R^{2A}$ | $R^{4C}$ | $R^{a1}$ | $R^{b2}$ |
| D-130 | $R^{1B}$ | $R^{2A}$ | $R^{4C}$ | $R^{a1}$ | $R^{b2}$ |
| D-131 | $R^{1C}$ | $R^{2A}$ | $R^{4C}$ | $R^{a1}$ | $R^{b2}$ |
| D-132 | $R^{1D}$ | $R^{2A}$ | $R^{4C}$ | $R^{a1}$ | $R^{b2}$ |
| D-133 | $R^{1A}$ | $R^{2B}$ | $R^{4C}$ | $R^{a1}$ | $R^{b2}$ |
| D-134 | $R^{1B}$ | $R^{2B}$ | $R^{4C}$ | $R^{a1}$ | $R^{b2}$ |
| D-135 | $R^{1C}$ | $R^{2B}$ | $R^{4C}$ | $R^{a1}$ | $R^{b2}$ |
| D-136 | $R^{1D}$ | $R^{2B}$ | $R^{4C}$ | $R^{a1}$ | $R^{b2}$ |
| D-137 | $R^{1A}$ | $R^{2C}$ | $R^{4C}$ | $R^{a1}$ | $R^{b2}$ |
| D-138 | $R^{1B}$ | $R^{2C}$ | $R^{4C}$ | $R^{a1}$ | $R^{b2}$ |
| D-139 | $R^{1C}$ | $R^{2C}$ | $R^{4C}$ | $R^{a1}$ | $R^{b2}$ |
| D-140 | $R^{1D}$ | $R^{2C}$ | $R^{4C}$ | $R^{a1}$ | $R^{b2}$ |
| D-141 | $R^{1A}$ | $R^{2D}$ | $R^{4C}$ | $R^{a1}$ | $R^{b2}$ |
| D-142 | $R^{1B}$ | $R^{2D}$ | $R^{4C}$ | $R^{a1}$ | $R^{b2}$ |
| D-143 | $R^{1C}$ | $R^{2D}$ | $R^{4C}$ | $R^{a1}$ | $R^{b2}$ |
| D-144 | $R^{1D}$ | $R^{2D}$ | $R^{4C}$ | $R^{a1}$ | $R^{b2}$ |
| D-145 | $R^{1A}$ | $R^{2A}$ | $R^{4A}$ | $R^{a2}$ | $R^{b2}$ |
| D-146 | $R^{1B}$ | $R^{2A}$ | $R^{4A}$ | $R^{a2}$ | $R^{b2}$ |
| D-147 | $R^{1C}$ | $R^{2A}$ | $R^{4A}$ | $R^{a2}$ | $R^{b2}$ |
| D-148 | $R^{1D}$ | $R^{2A}$ | $R^{4A}$ | $R^{a2}$ | $R^{b2}$ |
| D-149 | $R^{1A}$ | $R^{2B}$ | $R^{4A}$ | $R^{a2}$ | $R^{b2}$ |
| D-150 | $R^{1B}$ | $R^{2B}$ | $R^{4A}$ | $R^{a2}$ | $R^{b2}$ |

TABLE 4-continued

Substituent selections for compounds according to this invention, having substituents $R^1$, $R^2$, $R^4$, $R^a$, and $R^b$.

| Formula | $R^1$ | $R^2$ | $R^4$ | $R^a$ | $R^b$ |
|---|---|---|---|---|---|
| D-151 | $R^{1C}$ | $R^{2B}$ | $R^{4A}$ | $R^{a2}$ | $R^{b2}$ |
| D-152 | $R^{1D}$ | $R^{2B}$ | $R^{4A}$ | $R^{a2}$ | $R^{b2}$ |
| D-153 | $R^{1A}$ | $R^{2C}$ | $R^{4A}$ | $R^{a2}$ | $R^{b2}$ |
| D-154 | $R^{1B}$ | $R^{2C}$ | $R^{4A}$ | $R^{a2}$ | $R^{b2}$ |
| D-155 | $R^{1C}$ | $R^{2C}$ | $R^{4A}$ | $R^{a2}$ | $R^{b2}$ |
| D-156 | $R^{1D}$ | $R^{2C}$ | $R^{4A}$ | $R^{a2}$ | $R^{b2}$ |
| D-157 | $R^{1A}$ | $R^{2D}$ | $R^{4A}$ | $R^{a2}$ | $R^{b2}$ |
| D-158 | $R^{1B}$ | $R^{2D}$ | $R^{4A}$ | $R^{a2}$ | $R^{b2}$ |
| D-159 | $R^{1C}$ | $R^{2D}$ | $R^{4A}$ | $R^{a2}$ | $R^{b2}$ |
| D-160 | $R^{1D}$ | $R^{2D}$ | $R^{4A}$ | $R^{a2}$ | $R^{b2}$ |
| D-161 | $R^{1A}$ | $R^{2A}$ | $R^{4B}$ | $R^{a2}$ | $R^{b2}$ |
| D-162 | $R^{1B}$ | $R^{2A}$ | $R^{4B}$ | $R^{a2}$ | $R^{b2}$ |
| D-163 | $R^{1C}$ | $R^{2A}$ | $R^{4B}$ | $R^{a2}$ | $R^{b2}$ |
| D-164 | $R^{1D}$ | $R^{2A}$ | $R^{4B}$ | $R^{a2}$ | $R^{b2}$ |
| D-165 | $R^{1A}$ | $R^{2B}$ | $R^{4B}$ | $R^{a2}$ | $R^{b2}$ |
| D-166 | $R^{1B}$ | $R^{2B}$ | $R^{4B}$ | $R^{a2}$ | $R^{b2}$ |
| D-167 | $R^{1C}$ | $R^{2B}$ | $R^{4B}$ | $R^{a2}$ | $R^{b2}$ |
| D-168 | $R^{1D}$ | $R^{2B}$ | $R^{4B}$ | $R^{a2}$ | $R^{b2}$ |
| D-169 | $R^{1A}$ | $R^{2C}$ | $R^{4B}$ | $R^{a2}$ | $R^{b2}$ |
| D-170 | $R^{1B}$ | $R^{2C}$ | $R^{4B}$ | $R^{a2}$ | $R^{b2}$ |
| D-171 | $R^{1C}$ | $R^{2C}$ | $R^{4B}$ | $R^{a2}$ | $R^{b2}$ |
| D-172 | $R^{1D}$ | $R^{2C}$ | $R^{4B}$ | $R^{a2}$ | $R^{b2}$ |
| D-173 | $R^{1A}$ | $R^{2D}$ | $R^{4B}$ | $R^{a2}$ | $R^{b2}$ |
| D-174 | $R^{1B}$ | $R^{2D}$ | $R^{4B}$ | $R^{a2}$ | $R^{b2}$ |
| D-175 | $R^{1C}$ | $R^{2D}$ | $R^{4B}$ | $R^{a2}$ | $R^{b2}$ |
| D-176 | $R^{1D}$ | $R^{2D}$ | $R^{4B}$ | $R^{a2}$ | $R^{b2}$ |
| D-177 | $R^{1A}$ | $R^{2A}$ | $R^{4C}$ | $R^{a2}$ | $R^{b2}$ |
| D-178 | $R^{1B}$ | $R^{2A}$ | $R^{4C}$ | $R^{a2}$ | $R^{b2}$ |
| D-179 | $R^{1C}$ | $R^{2A}$ | $R^{4C}$ | $R^{a2}$ | $R^{b2}$ |
| D-180 | $R^{1D}$ | $R^{2A}$ | $R^{4C}$ | $R^{a2}$ | $R^{b2}$ |
| D-181 | $R^{1A}$ | $R^{2B}$ | $R^{4C}$ | $R^{a2}$ | $R^{b2}$ |
| D-182 | $R^{1B}$ | $R^{2B}$ | $R^{4C}$ | $R^{a2}$ | $R^{b2}$ |
| D-183 | $R^{1C}$ | $R^{2B}$ | $R^{4C}$ | $R^{a2}$ | $R^{b2}$ |
| D-184 | $R^{1D}$ | $R^{2B}$ | $R^{4C}$ | $R^{a2}$ | $R^{b2}$ |
| D-185 | $R^{1A}$ | $R^{2C}$ | $R^{4C}$ | $R^{a2}$ | $R^{b2}$ |
| D-186 | $R^{1B}$ | $R^{2C}$ | $R^{4C}$ | $R^{a2}$ | $R^{b2}$ |
| D-187 | $R^{1C}$ | $R^{2C}$ | $R^{4C}$ | $R^{a2}$ | $R^{b2}$ |
| D-188 | $R^{1D}$ | $R^{2C}$ | $R^{4C}$ | $R^{a2}$ | $R^{b2}$ |
| D-189 | $R^{1A}$ | $R^{2D}$ | $R^{4C}$ | $R^{a2}$ | $R^{b2}$ |
| D-190 | $R^{1B}$ | $R^{2D}$ | $R^{4C}$ | $R^{a2}$ | $R^{b2}$ |
| D-191 | $R^{1C}$ | $R^{2D}$ | $R^{4C}$ | $R^{a2}$ | $R^{b2}$ |
| D-192 | $R^{1D}$ | $R^{2D}$ | $R^{4C}$ | $R^{a2}$ | $R^{b2}$ |

Also in accordance with further aspects of this invention, this disclosure provides benzylamine compounds according to formula (I), wherein the compounds have following formula:

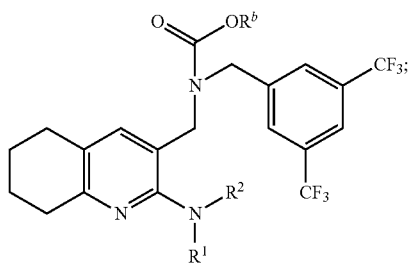

(IVa-1)

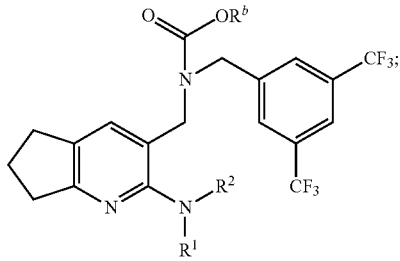

(Va-1)

or any combination thereof;

or a salt, including a pharmaceutically acceptable or a non-pharmaceutically acceptable salt, a prodrug, a diastereomeric mixture, an enantiomer, a tautomer, a racemic mixture, or any combination thereof, wherein $R^1$, $R^2$, and $R^b$ can be selected according to the following table, to provide formulas (E-01) through (E-32), that are applicable to the compounds (IVa-1) and (Va-1), illustrated above.

TABLE 5

Substituent selections for compounds according to this invention, having substituents $R^1$, $R^2$, and $R^b$.

| Formula | $R^1$ | $R^2$ | $R^b$ |
|---|---|---|---|
| E-01 | $R^{1A}$ | $R^{2A}$ | $R^{b1}$ |
| E-02 | $R^{1B}$ | $R^{2A}$ | $R^{b1}$ |
| E-03 | $R^{1C}$ | $R^{2A}$ | $R^{b1}$ |
| E-04 | $R^{1D}$ | $R^{2A}$ | $R^{b1}$ |
| E-05 | $R^{1A}$ | $R^{2B}$ | $R^{b1}$ |
| E-06 | $R^{1B}$ | $R^{2B}$ | $R^{b1}$ |
| E-07 | $R^{1C}$ | $R^{2B}$ | $R^{b1}$ |
| E-08 | $R^{1D}$ | $R^{2B}$ | $R^{b1}$ |
| E-09 | $R^{1A}$ | $R^{2C}$ | $R^{b1}$ |
| E-10 | $R^{1B}$ | $R^{2C}$ | $R^{b1}$ |
| E-11 | $R^{1C}$ | $R^{2C}$ | $R^{b1}$ |
| E-12 | $R^{1D}$ | $R^{2C}$ | $R^{b1}$ |
| E-13 | $R^{1A}$ | $R^{2D}$ | $R^{b1}$ |
| E-14 | $R^{1B}$ | $R^{2D}$ | $R^{b1}$ |
| E-15 | $R^{1C}$ | $R^{2D}$ | $R^{b1}$ |
| E-16 | $R^{1D}$ | $R^{2D}$ | $R^{b1}$ |
| E-17 | $R^{1A}$ | $R^{2A}$ | $R^{b2}$ |
| E-18 | $R^{1B}$ | $R^{2A}$ | $R^{b2}$ |
| E-19 | $R^{1C}$ | $R^{2A}$ | $R^{b2}$ |
| E-20 | $R^{1D}$ | $R^{2A}$ | $R^{b2}$ |
| E-21 | $R^{1A}$ | $R^{2B}$ | $R^{b2}$ |
| E-22 | $R^{1B}$ | $R^{2B}$ | $R^{b2}$ |
| E-23 | $R^{1C}$ | $R^{2B}$ | $R^{b2}$ |
| E-24 | $R^{1D}$ | $R^{2B}$ | $R^{b2}$ |
| E-25 | $R^{1A}$ | $R^{2C}$ | $R^{b2}$ |
| E-26 | $R^{1B}$ | $R^{2C}$ | $R^{b2}$ |
| E-27 | $R^{1C}$ | $R^{2C}$ | $R^{b2}$ |

TABLE 5-continued

Substituent selections for compounds according to this invention, having substituents $R^1$, $R^2$, and $R^b$.

| Formula | $R^1$ | $R^2$ | $R^b$ |
|---|---|---|---|
| E-28 | $R^{1D}$ | $R^{2C}$ | $R^{b2}$ |
| E-29 | $R^{1A}$ | $R^{2D}$ | $R^{b2}$ |
| E-30 | $R^{1B}$ | $R^{2D}$ | $R^{b2}$ |
| E-31 | $R^{1C}$ | $R^{2D}$ | $R^{b2}$ |
| E-32 | $R^{1D}$ | $R^{2D}$ | $R^{b2}$ |

Also in accordance with further aspects of this invention, this disclosure provides benzylamine compounds according to formula (I), wherein the compounds have following formula:

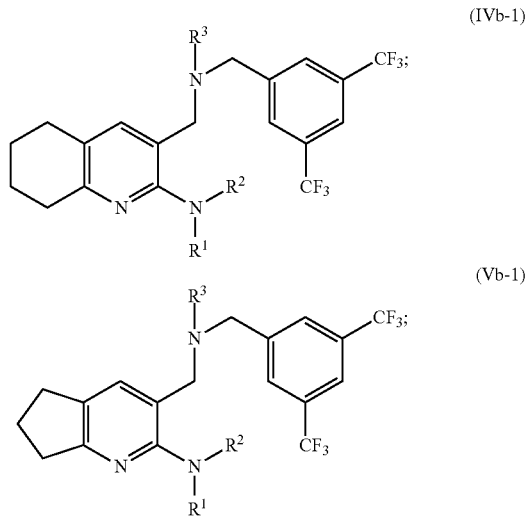

(IVb-1)

(Vb-1)

or any combination thereof;

or a salt, including a pharmaceutically acceptable or a non-pharmaceutically acceptable salt, a prodrug, a diastereomeric mixture, an enantiomer, a tautomer, a racemic mixture, or any combination thereof, wherein $R^1$, $R^2$, and $R^3$ can be selected according to the following table, to provide formulas (F-01) through (F-32), that are applicable to the compounds (IVb-1) and (Vb-1), illustrated above.

TABLE 6

Substituent selections for compounds according to this invention, having substituents $R^1$, $R^2$, and $R^3$.

| Formula | $R^1$ | $R^2$ | $R^3$ |
|---|---|---|---|
| F-01 | $R^{1A}$ | $R^{2A}$ | $R^{3A}$ |
| F-02 | $R^{1B}$ | $R^{2A}$ | $R^{3A}$ |
| F-03 | $R^{1C}$ | $R^{2A}$ | $R^{3A}$ |
| F-04 | $R^{1D}$ | $R^{2A}$ | $R^{3A}$ |
| F-05 | $R^{1A}$ | $R^{2B}$ | $R^{3A}$ |
| F-06 | $R^{1B}$ | $R^{2B}$ | $R^{3A}$ |
| F-07 | $R^{1C}$ | $R^{2B}$ | $R^{3A}$ |
| F-08 | $R^{1D}$ | $R^{2B}$ | $R^{3A}$ |
| F-09 | $R^{1A}$ | $R^{2C}$ | $R^{3A}$ |
| F-10 | $R^{1B}$ | $R^{2C}$ | $R^{3A}$ |
| F-11 | $R^{1C}$ | $R^{2C}$ | $R^{3A}$ |

TABLE 6-continued

Substituent selections for compounds according to this invention, having substituents $R^1$, $R^2$, and $R^3$.

| Formula | $R^1$ | $R^2$ | $R^3$ |
|---|---|---|---|
| F-12 | $R^{1D}$ | $R^{2C}$ | $R^{3A}$ |
| F-13 | $R^{1A}$ | $R^{2D}$ | $R^{3A}$ |
| F-14 | $R^{1B}$ | $R^{2D}$ | $R^{3A}$ |
| F-15 | $R^{1C}$ | $R^{2D}$ | $R^{3A}$ |
| F-16 | $R^{1D}$ | $R^{2D}$ | $R^{3A}$ |
| F-17 | $R^{1A}$ | $R^{2A}$ | $R^{3B}$ |
| F-18 | $R^{1B}$ | $R^{2A}$ | $R^{3B}$ |
| F-19 | $R^{1C}$ | $R^{2A}$ | $R^{3B}$ |
| F-20 | $R^{1D}$ | $R^{2A}$ | $R^{3B}$ |
| F-21 | $R^{1A}$ | $R^{2B}$ | $R^{3B}$ |
| F-22 | $R^{1B}$ | $R^{2B}$ | $R^{3B}$ |
| F-23 | $R^{1C}$ | $R^{2B}$ | $R^{3B}$ |
| F-24 | $R^{1D}$ | $R^{2B}$ | $R^{3B}$ |
| F-25 | $R^{1A}$ | $R^{2C}$ | $R^{3B}$ |
| F-26 | $R^{1B}$ | $R^{2C}$ | $R^{3B}$ |
| F-27 | $R^{1C}$ | $R^{2C}$ | $R^{3B}$ |
| F-28 | $R^{1D}$ | $R^{2C}$ | $R^{3B}$ |
| F-29 | $R^{1A}$ | $R^{2D}$ | $R^{3B}$ |
| F-30 | $R^{1B}$ | $R^{2D}$ | $R^{3B}$ |
| F-31 | $R^{1C}$ | $R^{2D}$ | $R^{3B}$ |
| F-32 | $R^{1D}$ | $R^{2D}$ | $R^{3B}$ |
| F-33 | $R^{1A}$ | $R^{2A}$ | $R^{3C}$ |
| F-34 | $R^{1B}$ | $R^{2A}$ | $R^{3C}$ |
| F-35 | $R^{1C}$ | $R^{2A}$ | $R^{3C}$ |
| F-36 | $R^{1D}$ | $R^{2A}$ | $R^{3C}$ |
| F-37 | $R^{1A}$ | $R^{2B}$ | $R^{3C}$ |
| F-38 | $R^{1B}$ | $R^{2B}$ | $R^{3C}$ |
| F-39 | $R^{1C}$ | $R^{2B}$ | $R^{3C}$ |
| F-40 | $R^{1D}$ | $R^{2B}$ | $R^{3C}$ |
| F-41 | $R^{1A}$ | $R^{2C}$ | $R^{3C}$ |
| F-42 | $R^{1B}$ | $R^{2C}$ | $R^{3C}$ |
| F-43 | $R^{1C}$ | $R^{2C}$ | $R^{3C}$ |
| F-44 | $R^{1D}$ | $R^{2C}$ | $R^{3C}$ |
| F-45 | $R^{1A}$ | $R^{2D}$ | $R^{3C}$ |
| F-46 | $R^{1B}$ | $R^{2D}$ | $R^{3C}$ |
| F-47 | $R^{1C}$ | $R^{2D}$ | $R^{3C}$ |
| F-48 | $R^{1D}$ | $R^{2D}$ | $R^{3C}$ |
| F-49 | $R^{1A}$ | $R^{2A}$ | $R^{3D}$ |
| F-50 | $R^{1B}$ | $R^{2A}$ | $R^{3D}$ |
| F-51 | $R^{1C}$ | $R^{2A}$ | $R^{3D}$ |
| F-52 | $R^{1D}$ | $R^{2A}$ | $R^{3D}$ |
| F-53 | $R^{1A}$ | $R^{2B}$ | $R^{3D}$ |
| F-54 | $R^{1B}$ | $R^{2B}$ | $R^{3D}$ |
| F-55 | $R^{1C}$ | $R^{2B}$ | $R^{3D}$ |
| F-56 | $R^{1D}$ | $R^{2B}$ | $R^{3D}$ |
| F-57 | $R^{1A}$ | $R^{2C}$ | $R^{3D}$ |
| F-58 | $R^{1B}$ | $R^{2C}$ | $R^{3D}$ |
| F-59 | $R^{1C}$ | $R^{2C}$ | $R^{3D}$ |
| F-60 | $R^{1D}$ | $R^{2C}$ | $R^{3D}$ |
| F-61 | $R^{1A}$ | $R^{2D}$ | $R^{3D}$ |
| F-62 | $R^{1B}$ | $R^{2D}$ | $R^{3D}$ |
| F-63 | $R^{1C}$ | $R^{2D}$ | $R^{3D}$ |
| F-64 | $R^{1D}$ | $R^{2D}$ | $R^{3D}$ |

In still a further aspect of the present invention, this disclosure provides benzylamine compounds, wherein the compound is selected from any of the compounds in the following tables, including any combination of the compounds provided in these tables. By the disclosure of these specific compounds, it is intended to include any salt, including a pharmaceutically acceptable or a non-pharmaceutically acceptable salt, any prodrug, and any stereoisomer, including diastereomeric mixtures, enantiomers, tautomers, racemic mixtures, or any combinations thereof, of the disclosed compounds. In each of the following tables, the Example number (Ex. No.) is provided for the preparation of that specific compound.

TABLE 7

Representative compounds in accordance with this invention, having the following structure.

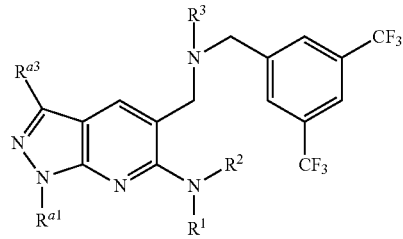

(IIIb-2-1)

| Ex. No. | Compound | R$^{a1}$ | R$^{a3}$ | R$^1$ | R$^2$ | R$^3$ |
|---|---|---|---|---|---|---|
| 1 | (5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-cyclobutylmethyl-ethyl-amine | Me | Me | Et | 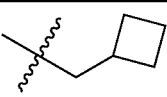 | 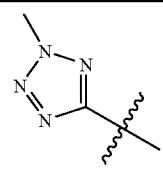 |
| 2 | (5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-bis-cyclopropylmethyl-amine | Me | Me | 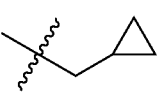 | 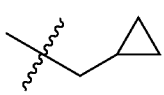 | 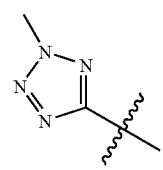 [SMILES: *c1nnn(C)n1] |
| 3 | (5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-cyclopropylmethyl-ethyl-amine | Me | Me | Et | 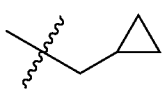 [SMILES: *CC1CC1] | 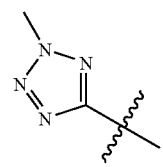 [SMILES: *c1nnn(C)n1] |
| 4 | (5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-cyclobutylmethyl-methyl-amine | Me | Me | Me | 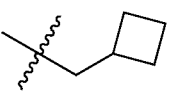 | 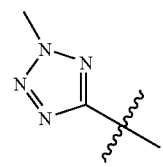 |
| 5 | (5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-cyclobutylmethyl-cyclopropylmethyl-amine | Me | Me | 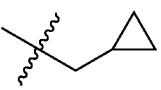 [SMILES: *CC1CC1] | 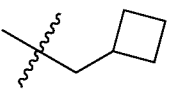 [SMILES: *CC1CCC1] | 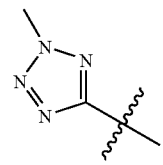 [SMILES: *c1nnn(C)n1] |
| 6 | (5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-(2,2-dimethyl-propyl)-ethyl-amine | Me | Me | Et | 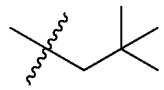 [SMILES: *CC(C)(C)C] | 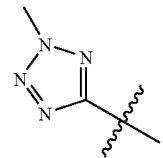 [SMILES: *c1nnn(C)n1] |
| 7 | (5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-ethyl-isopropyl-amine | Me | Me | Et | 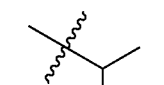 | 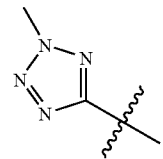 |

TABLE 7-continued

Representative compounds in accordance with this invention, having the following structure.

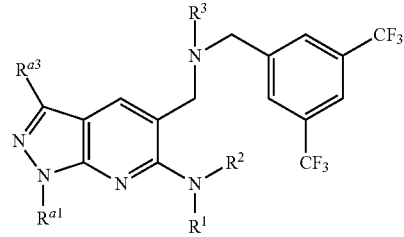

(IIIb-2-1)

| Ex. No. | Compound | R$^{a1}$ | R$^{a3}$ | R$^1$ | R$^2$ | R$^3$ |
|---|---|---|---|---|---|---|
| 8 | (5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-cyclopentyl-ethyl-amine | Me | Me | Et | 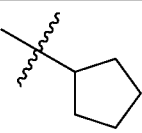 [SMILES: *C1CCCC1] | 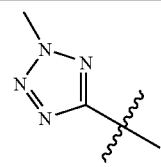 [SMILES: *c1nnn(C)n1] |
| 9 | (5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-cyclopentyl-cyclopropylmethyl-amine | Me | Me | 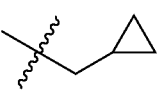 | 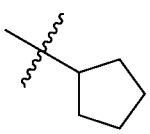 | 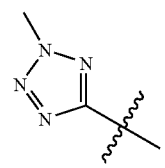 [SMILES: *c1nnn(C)n1] |
| 10 | (5-{[(3,5-bis-trifluoromethyl-benzyl)-(5-methyl-isoxazol-3-yl)-amino]-methyl}-1,3-dimethyl-1H-pyrazolo[3,4-b]pyridin-6-yl)-cyclobutylmethyl-ethyl-amine | Me | Me | Et | 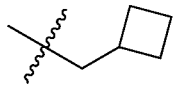 [SMILES: *CC1CCC1] | 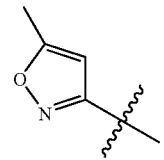 [SMILES: *c1cc(C)on1] |
| 11 | (5-{[(3,5-bis-trifluoromethyl-benzyl)-(5-methyl-isoxazol-3-yl)-amino]-methyl}-1,3-dimethyl-1H-pyrazolo[3,4-b]pyridin-6-yl)-bis-cyclopropylmethyl-amine | Me | Me | 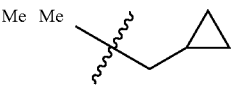 | 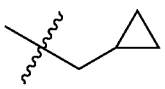 | 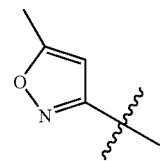 [SMILES: *c1cc(C)on1] |
| 12 | (5-{[(3,5-bis-trifluoromethyl-benzyl)-(2-methyl-2H-tetrazol-5-yl)-amino]-methyl}-1-methyl-1H-pyrazolo[3,4-b]pyridin-6-yl)-cyclobutylmethyl-ethyl-amine | Me | H | Et | 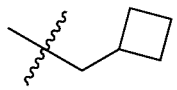 [SMILES: *CC1CCC1] | 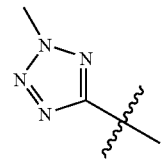 [SMILES: *c1nnn(C)n1] |
| 13 | (5-{[(3,5-bis-trifluoromethyl-benzyl)-(2-methyl-2H-tetrazol-5-yl)-amino]-methyl}-1-methyl-1H-pyrazolo[3,4-b]pyridin-6-yl)-bis-cyclopropylmethyl-amine | Me | H | 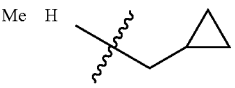 | 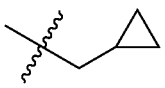 | 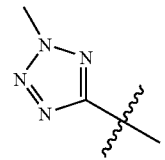 [SMILES: *c1nnn(C)n1] |
| 14 | (5-{[(3,5-bis-trifluoromethyl-benzyl)-(2-methyl-2H-tetrazol-5-yl)-amino]-methyl}-1-ethyl-1H-pyrazolo[3,4-b]-pyridin-6-yl)-bis-cyclopropylmethyl-amine | Et | H | 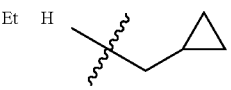 | 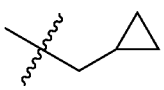 [SMILES: *CC1CC1] | 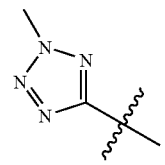 |

TABLE 7-continued

Representative compounds in accordance with this invention, having the following structure.

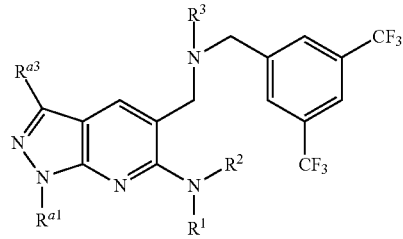

(IIIb-2-1)

| Ex. No. | Compound | $R^{a1}$ | $R^{a3}$ | $R^1$ | $R^2$ | $R^3$ |
|---|---|---|---|---|---|---|
| 15 | (5-{[(3,5-bis-trifluoromethyl-benzyl)-(2-methyl-2H-tetrazol-5-yl)-amino]-methyl}-1-ethyl-1H-pyrazolo[3,4-b]-yridin-6-yl)-cyclobutylmethyl-ethyl-amine | Et | H | Et | cyclobutylmethyl | 2-methyl-2H-tetrazol-5-yl |
| 22 | (5-{[(3,5-bis-trifluoromethyl-benzyl)-(4-trifluoromethyl-oxazol-2-yl)-amino]-methyl}-1,3-dimethyl-1H-pyrazolo[3,4-b]-pyridin-6-yl)-cyclopentylmethyl-ethyl-amine | Me | Me | Et | cyclopentylmethyl | 4-trifluoromethyl-oxazol-2-yl |
| 23 | (2-{[(3,5-bis-trifluoromethyl-benzyl)-(6-cyclopentylmethyl-ethyl-amino)-1,3-dimethyl-1H-pyrazolo[3,4-b]-pyridin-5-ylmethyl]-amino}-oxazol-4-carboxylic acid ethyl ester | Me | Me | Et | cyclopentylmethyl | 4-(ethoxycarbonyl)-oxazol-2-yl |
| 24 | (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopentylmethyl-ethyl-amine | Me | Me | Et | cyclopentylmethyl | 2-methyl-2H-tetrazol-5-yl |
| 25 | (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-diisobutyl-amine | Me | Me | isobutyl | isobutyl | 2-methyl-2H-tetrazol-5-yl |
| 26 | (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopropylmethyl-isobutyl-amine | Me | Me | cyclopropylmethyl | isobutyl | 2-methyl-2H-tetrazol-5-yl |
| 27 | cyclopropanecarboxylic acid (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopropylmethyl-amide | Me | Me | cyclopropylmethyl | cyclopropylcarbonyl | 2-methyl-2H-tetrazol-5-yl |

TABLE 7-continued

Representative compounds in accordance with this invention, having the following structure.

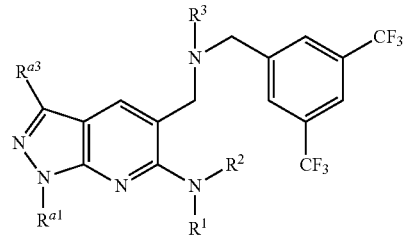

(IIIb-2-1)

| Ex. No. | Compound | $R^{a1}$ | $R^{a3}$ | $R^1$ | $R^2$ | $R^3$ |
|---|---|---|---|---|---|---|
| 28 | cyclopentanecarboxylic acid (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopropylmethyl-amide | Me | Me | 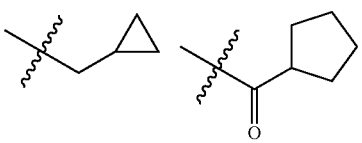 | 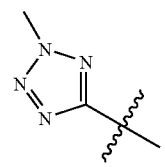 | 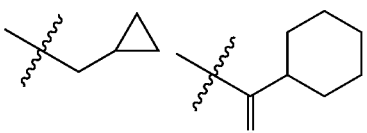 |
| 29 | cyclohexanecarboxylic acid (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopropylmethyl-amide | Me | Me | 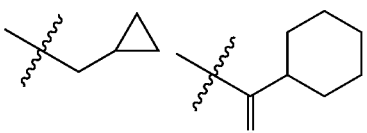 | 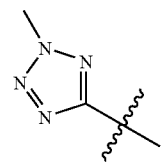 | 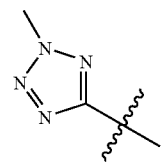 |
| 30 | N-(5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-N-cyclopropylmethyl-acetamide | Me | Me |  | 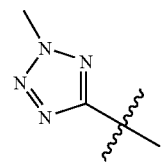 | 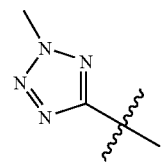 |
| 31 | N-(5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-3-chloro-N-cyclopropylmethyl-propionamide | Me | Me | 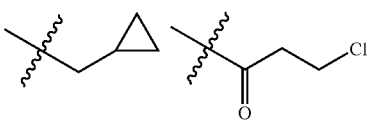 | 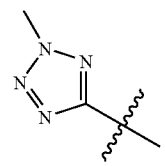 | 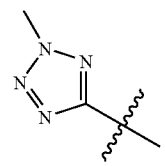 |
| 34 | (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-ethyl-(tetrahydro-furan-2ylmethyl)-amine | Me | Me | Et | 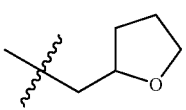 [SMILES: *CC1CCCO1] | 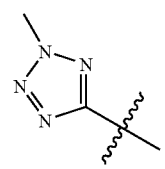 [SMILES: *c1nnn(C)n1] |

TABLE 8

Representative compounds in accordance with this invention, having the following structure.

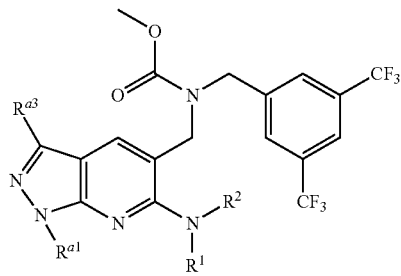

(IIIa-2)

| Ex. No. | Compound | $R^{a1}$ | $R^{a3}$ | $R^1$ | $R^2$ |
|---|---|---|---|---|---|
| 16 | (3,5-bis-trifluoromethyl-benzyl)-[6-(cyclopentylmethyl-ethyl-amino)-1,3-dimethyl-1H-pyrazolo[3,4-b]pyridine-5-ylmethyl]-carbamic acid methyl ester | Me | Me | Et | cyclopentylmethyl |

TABLE 9

Representative compounds in accordance with this invention, having the following structure.

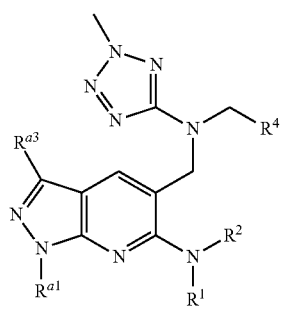

(IIIb-2-2)

| Ex. No. | Compound | $R^{a1}$ | $R^{a3}$ | $R^1$ | $R^2$ | $R^4$ |
|---|---|---|---|---|---|---|
| 17 | cyclopentylmethyl-ethyl-(5-{[(3,4,5-trifluoro-benzyl)-(2-methyl-2H-tetrazol-5-yl)-amino]-methyl}-1,3-dimethyl-1H-pyrazolo[3,4-b]pyridine-6-yl)-amine | Me | Me | Et | cyclopentylmethyl | 3,4,5-trifluorophenyl |

TABLE 9-continued

Representative compounds in accordance with this invention, having the following structure.

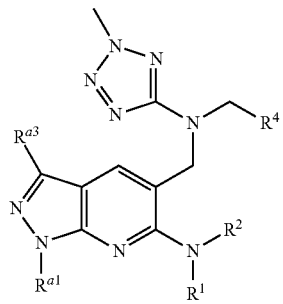

(IIIb-2-2)

| Ex. No. | Compound | R$^{a1}$ | R$^{a3}$ | R$^1$ | R$^2$ | R$^4$ |
|---|---|---|---|---|---|---|
| 18 | cyclopentylmethyl-ethyl-(5-{[(3,5-difluoro-benzyl)-(2-methyl-2H-tetrazol-5-yl)-amino]-methyl}-1,3-dimethyl-1H-pyrazolo[3,4-b]pyridin-6-yl)-amine | Me | Me | Et | 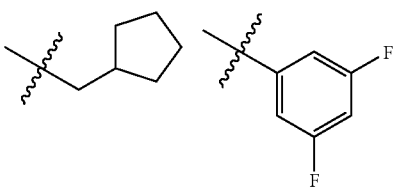 | |
| 19 | cyclopentylmethyl-(1,3-dimethyl-5-{[(2-methyl-2H-tetrazol-5-yl)-(3,5-dichlorobenzyl)-amino]-methyl}-1H-pyrazolo[3,4-b]pyridin-6-yl)-ethyl-amine | Me | Me | Et | 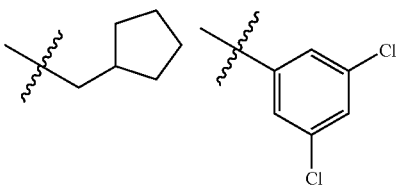 | |
| 20 | cyclopentylmethyl-ethyl-(5-{[(3-fluoro-5-trifluoromethyl-benzyl)-(2-methyl-2H-tetrazol-5-yl)-amino]-methyl}-1,3-dimethyl-1H-pyrazolo[3,4-b]pyridin-6-yl)-amine | Me | Me | Et | 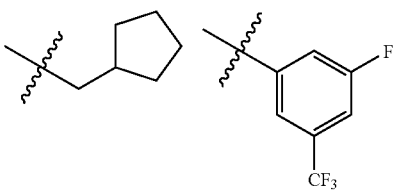 | |
| 21 | bis-cyclopropylmethyl-(5-{[(3,5-dichlorobenzyl)-(2-methyl-2H-tetrazol-5-yl)-amino]-methyl}-1,3-dimethyl-1H-pyrazolo[3,4-b]pyridin-6-yl)-amine | Me | Me | 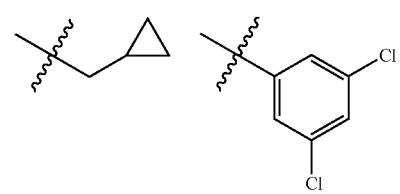 | | |

TABLE 10

Representative compounds in accordance with this invention, having the following structure.

(VIIIa-2)

| Ex. No. | Compound | $R^a$ | $R^1$ | $R^2$ |
|---|---|---|---|---|
| 32 | (3,5-bis-trifluoromethyl-benzyl)-[6-(cyclopentylmethyl-ethyl-amino)-3-methyl-isoxazolo[5,4-b]pyridine-5-ylmethyl}-carbamic acid methyl ester | Me | Et | cyclopentylmethyl |

TABLE 11

Representative compounds in accordance with this invention, having the following structure.

(VIIIb-2)

| Ex. No | Compound | $R^a$ | $R^1$ | $R^2$ | $R^3$ |
|---|---|---|---|---|---|
| 33 | (5-{[(3,5-bis-trifluoromethyl-benzyl)-(2-methyl-2H-tetrazol-5-yl)-amino]-methyl}-3-methyl-isoxazolo[5,4-b]pyridine-6-yl)-cyclopentylmethyl-ethyl-amine | Me | Et | cyclopentylmethyl | 2-methyl-2H-tetrazol-5-yl |

TABLE 12

Representative compounds in accordance with this invention, having the following structure.

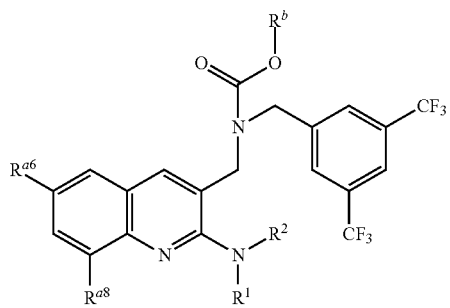

(IIa-2)

| Ex. No. | Compound | $R^{a6}$ | $R^{a8}$ | $R^1$ | $R^2$ | $R^b$ |
|---|---|---|---|---|---|---|
| 35 | (3,5-bis-trifluoromethyl-benzyl)-[2-(cyclopentylmethyl-ethyl-amino)-quinolin-3-ylmethyl]-carbamic acid methyl ester | H | H | Et | cyclopentylmethyl | Me |
| 41 | (3,5-bis-trifluoromethyl-benzyl)-[2-(butyl-ethyl-amino)-quinolin-3-ylmethyl]-carbamic acid ethyl ester | H | H | Et | butyl | Et |
| 42 | (3,5-bis-trifluoromethyl-benzyl)-[2-(cyclohexylmethyl-ethyl-amino)-quinolin-3-ylmethyl]-carbamic acid ethyl ester | H | H | Et | cyclohexylmethyl | Et |
| 43 | (3,5-bis-trifluoromethyl-benzyl)-[2-(cyclopentylmethyl-propyl-amino)-quinolin-3-ylmethyl]-carbamic acid ethyl ester | H | H | propyl | cyclopentylmethyl | Et |
| 44 | (3,5-bis-trifluoromethyl-benzyl)-[2-(cyclopropylmethyl-ethyl-amino)-quinolin-3-ylmethyl]-carbamic acid methyl ester | H | H | Et | cyclopropylmethyl | Me |
| 45 | (3,5-bis-trifluoromethyl-benzyl)-[2-(cyclobutylmethyl-ethyl-amino)-quinolin-3-ylmethyl]-carbamic acid methyl ester | H | H | Et | cyclobutylmethyl | Me |
| 46 | (3,5-bis-trifluoromethyl-benzyl)-[2-(cyclopentylmethyl-ethyl-amino)-6-methyl-quinolin-3-ylmethyl]-carbamic acid methyl ester | Me | H | Et | cyclopentylmethyl | Me |
| 47 | [2-(bis-cyclopropylmethyl-amino)-8-methyl-quinolin-3-ylmethyl]-(3,5-bis-trifluoromethyl-benzyl)-carbamic acid methyl ester | H | Me | cyclopropylmethyl | cyclopropylmethyl | Me |

TABLE 13

Representative compounds in accordance with this invention, having the following structure.

(IIb-2)

| Ex. No. | Compound | $R^{a6}$ | $R^{a8}$ | $R^1$ | $R^2$ | $R^3$ |
|---|---|---|---|---|---|---|
| 48 | (3,5-bis-trifluoromethyl-benzyl)[2-(cyclopentylmethyl-ethyl-amino)-quinolin-3-ylmethyl]-dithiocarbamic acid methyl ester | H | H | Et | cyclopentylmethyl | S-C(=O)-methyl (dithiocarbamate methyl ester) |
| 49 | 3-ethoxycarbonyl-1-(3,5-Bis-trifluoromethyl-benzyl)-1-[2-(cyclopentyl methyl-ethyl-amino)-quinolin-3-yl methyl]-thiourea | H | H | Et | cyclopentylmethyl | Et-O-C(=O)-NH-C(=S)- |
| 52 | (3-{[(3,5-bis-trifluoromethyl-benzyl)-(2-methyl-2H-tetrazol-5-yl)-amino]-methyl}-quinolin-2-yl)-cyclopentylmethyl-ethyl amine | H | H | Et | cyclopentylmethyl | 2-methyl-2H-tetrazol-5-yl |
| 54 | (3-{[3,5-bis-trifluoromethyl-benzyl)-(2-methyl-2H-tetrazole-5-yl)-amino]-methyl-}-quinolin-2-yl)-butyl-ethyl-amine | H | H | Et | butyl | 2-methyl-2H-tetrazol-5-yl |
| 55 | (3-{[3,5-bis-trifluoromethyl-benzyl)-(2-methyl-2H-tetrazole-5-yl)-amino]-methyl-}-quinolin-2-yl)-cyclopropylmethyl-ethyl-amine | H | H | Et | cyclopropylmethyl | 2-methyl-2H-tetrazol-5-yl |
| 56 | (3-{[3,5-bis-trifluoromethyl-benzyl)-(2-methyl-2H-tetrazole-5-yl)-amino]-methyl-}-quinolin-2-yl)-cyclobutylmethyl-ethyl-amine | H | H | Et | cyclobutylmethyl | 2-methyl-2H-tetrazol-5-yl |
| 57 | (3-{[3,5-bistrifluoromethyl-benzyl)-(2-methyl-2H-tetrazole-5-yl)-amino]-methyl-}-8-quinolin-2-yl)-bis-cyclopropylmethyl-amine | H | H | cyclopropylmethyl | cyclopropylmethyl | 2-methyl-2H-tetrazol-5-yl |

TABLE 13-continued

Representative compounds in accordance with this invention, having the following structure.

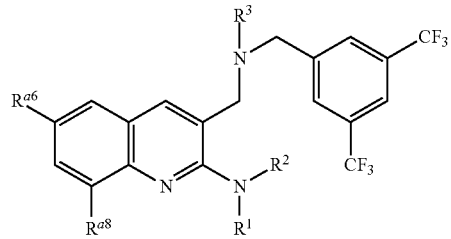

(IIb-2)

| Ex. No. | Compound | R$^{a6}$ | R$^{a8}$ | R$^1$ | R$^2$ | R$^3$ |
|---|---|---|---|---|---|---|
| 58 | (3-{[(3,5-bis-trifluoromethyl-benzyl)-(5-methyl-[1,3,4]oxadiazol-2-yl)-amino]-methyl}-quinolin-2-yl)-cyclopentylmethyl-ethyl-amine | H | H | Et | cyclopentylmethyl | 5-methyl-1,3,4-oxadiazol-2-yl |
| 59 | 1-(3,5 bistrifluoromethyl-benzyl)-1-[(2-cyclopentylmethyl-ethyl-amino)-quinoline-3-ylmethyl]-urea | H | H | Et | cyclopentylmethyl | C(=O)NH$_2$ |
| 61 | 1-(3,5-bis-trifluoromethyl-benzyl)-1-[(2-cyclopentylmethyl-ethyl-amino)-quinolin-3-yl methyl)]-O-ethyl isourea | H | H | Et | cyclopentylmethyl | C(=NH)OEt |
| 63 | (3-{[(3,5-bis-trifluoromethyl-benzyl)-(4-methyl-thiazol-2-yl)-amino]-methyl}-quinolin-2-yl)-cyclopentylmethyl-ethyl-amine | H | H | Et | cyclopentylmethyl | 4-methyl-thiazol-2-yl |
| 65 | (3-{[3,5-bis-trifluoromethyl-benzyl-(5-methyl-isoxazol-3-yl)-amino]-methyl}-quinolin-2-yl)-cyclobutylmethyl-ethyl-amine | H | H | Et | cyclobutylmethyl | 5-methyl-isoxazol-3-yl |
| 66 | (3-{[(3,5-bis-trifluoromethyl-benzyl)-pyrimidin-2-yl-amino]-methyl}-quinolin-2-yl)-cyclopentylmethyl-ethyl-amine | H | H | Et | cyclopentylmethyl | pyrimidin-2-yl |
| 67 | (3-{[(3,5-bis-trifluoromethyl-benzyl)-(4-methyl-oxazol-2-yl)-amino]-methyl}-quinolin-2-yl)-cyclopentylmethyl-ethyl-amine | H | H | Et | cyclopentylmethyl | 4-methyl-oxazol-2-yl |
| 68 | (3-{[(3,5-bis-trifluoromethyl-benzyl)-(4,5-dihydro-oxazol-2-yl)-amino]-methyl}-quinolin-2-yl)-cyclopentylmethyl-ethyl-amine | H | H | Et | cyclopentylmethyl | 4,5-dihydro-oxazol-2-yl |

TABLE 13-continued

Representative compounds in accordance with this invention, having the following structure.

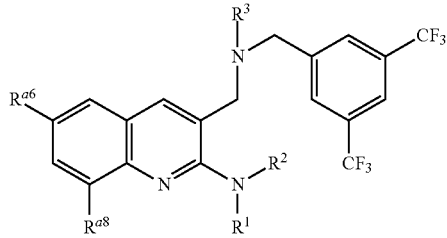
(IIb-2)

| Ex. No. | Compound | R$^{a6}$ | R$^{a8}$ | R$^1$ | R$^2$ | R$^3$ |
|---|---|---|---|---|---|---|
| 69 | (3-{[(3,5-bis-trifluoromethyl-benzyl)-pyridin-2-yl-amino]-methyl}-quinolin-2-yl)-cyclopentylmethyl-ethyl-amine | H | H | Et | 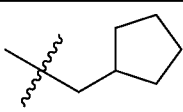 | 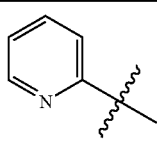 |
| 70 | (3-{[(3,5-bis-trifluoromethyl-benzyl)-(2-methyl-2H-tetrazol-5-ylmethy)-amino]-methyl}-quinolin-2-yl)-cyclopentylmethyl-ethyl-amine | H | H | Et | 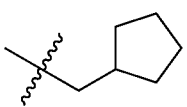 | 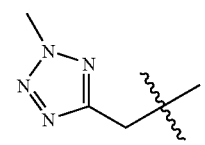 [SMILES: *Cc1nnn(C)n1] |
| 71 | (3-{[(3,5-bis-trifluoromethyl-benzyl)-(1-methyl-1H-tetrazol-5-ylmethyl)-amino]-methyl}-quinolin-2-yl)-cyclopentylmethyl-ethyl-amine | H | H | Et | 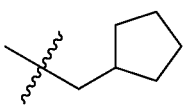 [SMILES: *CC1CCCC1] | 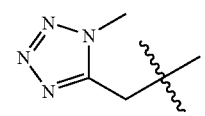 [SMILES: *Cc1nnnn1C] |

TABLE 14

Representative compounds in accordance with this invention, having the following structure.

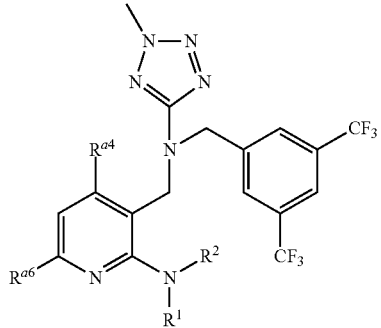
(VIb-2)

| Ex. No. | Compound | R$^{a4}$ | R$^{a6}$ | R$^1$ | R$^2$ |
|---|---|---|---|---|---|
| 73 | (3-{[3,5-bis-trifluoromethyl-benzyl)-(2-methyl-2H-tetrazole-5-yl)-amino]-methyl-}-pyridin-2-yl)-butyl-ethyl amine | H | H | Et | 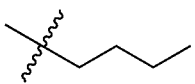 [SMILES: *CCCC] |
| 79 | (3-{[(3,5-bis-trifluoromethyl-benzyl)-(2-methyl-2H-tetrazole-5-yl)-amino]-methyl}-4,6-dimethyl-pyridin-2-yl)-bis-cyclopropylmethyl-amine | Me | Me | 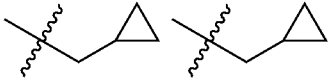 | |

TABLE 15

Representative compounds in accordance with this invention, having the following structure.

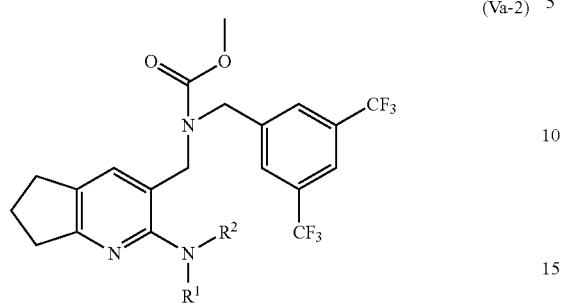

(Va-2)

| Ex. No. | Compound | R¹ | R² |
|---|---|---|---|
| 75 | (3,5-bis-trifluoromethyl-benzyl)-[2-(cyclopentylmethyl-ethyl-amino)-6,7-dihydro-5H-[1]pyridin-3-ylmethyl]-carbamic acid methyl ester | Et |  |

TABLE 16

Representative compounds in accordance with this invention, having the following structure.

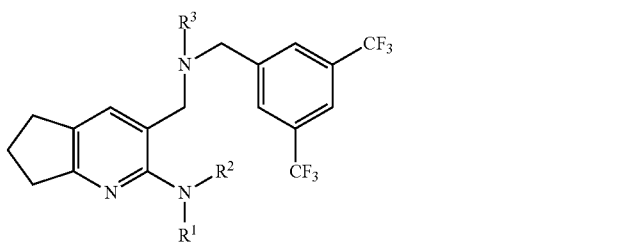

(Vb-2)

| Ex. No. | Compound | R¹ | R² | R³ |
|---|---|---|---|---|
| 76 | (3-{[(3,5-bis-trifluoromethyl-benzyl)-(2-methyl-2H-tetrazole-5-yl)-amino]-methyl}-6,7-dihydro-5H-[1]pyridine-2-yl)-cyclopentylmethyl-ethyl-amine | Et | cyclopentylmethyl | 2-methyl-2H-tetrazol-5-yl |

TABLE 17

Representative compounds in accordance with this invention, having the following structure.

(IVa-2)

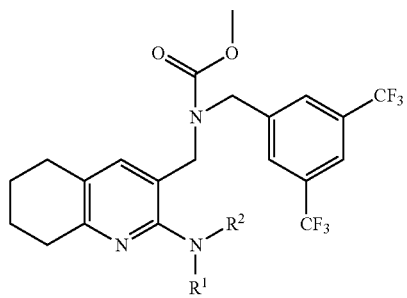

| Ex. No. | Compound | R¹ | R² |
|---|---|---|---|
| 74 | (3,5-bis-trifluoromethyl-benzyl)-[2-(cyclopentylmethyl-ethyl-amino)-5,6,7,8-tetrahydro-quinolin-3-ylmethyl]-carbamic acid methyl ester | Et | ⸽⸽CH₂-cyclopentyl |

TABLE 18

Representative compounds in accordance with this invention, having the following structure.

(IVb-2)

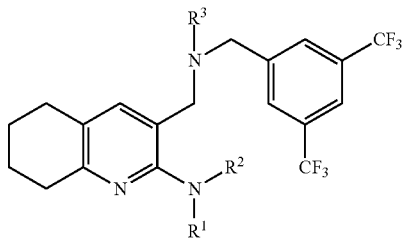

| Ex. No. | Compound | R¹ | R² | R³ |
|---|---|---|---|---|
| 77 | (3-{[3,5-bis trifluoromethyl-benzyl)-(2-methyl-2H-tetrazole-5-yl)-amino]-methyl}-5,6,7,8-tetrahydro-quinoline-2-yl)-cyclopentylmethyl-ethyl-amine | Et | ⸽⸽CH₂-cyclopentyl | 2-methyl-2H-tetrazol-5-yl |
| 78 | (3-{[3,5-bis trifluoromethyl-benzyl)-(5-methyl-[1,3,4]oxadiazol-2-yl)-amino]-methyl}-5,6,7,8-tetrahydro-quinoline-2-yl)-cyclopentylmethyl-ethyl-amine | Et | ⸽⸽CH₂-cyclopentyl | 5-methyl-[1,3,4]oxadiazol-2-yl |

Still another aspect of this invention provides benzylamine compounds according to formula (I), and compositions comprising benzylamine compounds, having the following formula:

(IX)

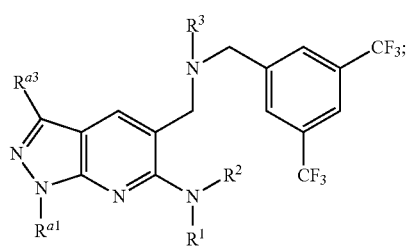

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^{a1}$ is Me or Et;
$R^{a3}$ is H, Me, or Et;

$R^1$ is Me, Et, [cyclopropylmethyl]; or [isobutyl];

$R^2$ is [cyclopropyl], [cyclopropylmethyl], [cyclobutylmethyl], [neopentyl], [isopropyl], [cyclopentylmethyl], [isobutyl], [cyclopropylcarbonyl], [cyclopentylcarbonyl], [cyclohexylcarbonyl], [acetyl], [3-chloropropanoyl], or [tetrahydrofuranylmethyl]; and $R^3$ is [1-methyltetrazol-5-yl], [5-methylisoxazol-3-yl], [4-(trifluoromethyl)oxazol-2-yl], or [ethyl oxazole-4-carboxylate].

Another aspect of this invention provides benzylamine compounds according to formula (I), and compositions comprising benzylamine compounds, having the following formula:

(X)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^{a1}$ is Me or Et;
$R^{a3}$ is H, Me, or Et;

$R^1$ is Me, Et, [cyclopropylmethyl]; or [isobutyl];

$R^2$ is [cyclopropyl], [cyclopropylmethyl], [cyclobutylmethyl], [neopentyl], [isopropyl], [cyclopentylmethyl], [isobutyl], [cyclopropylcarbonyl], [cyclopentylcarbonyl], [cyclohexylcarbonyl], [acetyl], [3-chloropropanoyl], or [tetrahydrofuranylmethyl];

$R^3$ is [1-methyltetrazol-5-yl], [5-methylisoxazol-3-yl], [4-(trifluoromethyl)oxazol-2-yl], or [ethyl oxazole-4-carboxylate], or -continued

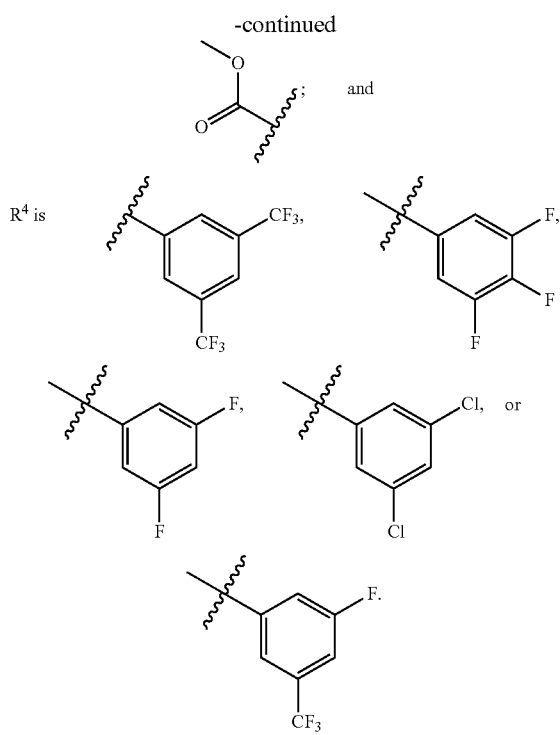

R⁴ is

Yet another aspect of this invention provides benzylamine compounds according to formula (I), and compositions comprising benzylamine compounds, having the following formula:

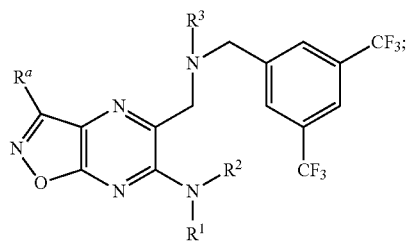

(XI)

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^a$ is H, Me, or Et;

$R^1$ is Me, Et, or

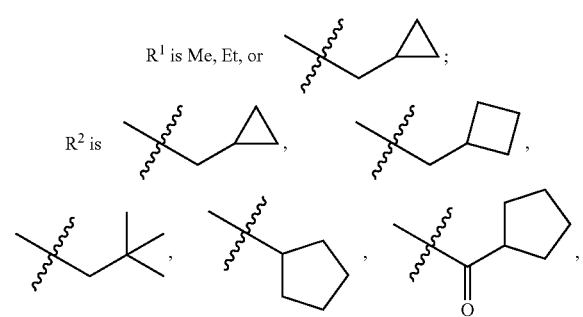

$R^2$ is

-continued

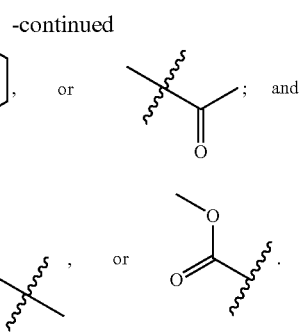

$R^3$ is

Still a further aspect of this invention provides benzylamine compounds according to formula (I), and compositions comprising benzylamine compounds, having the following formula:

(XII)

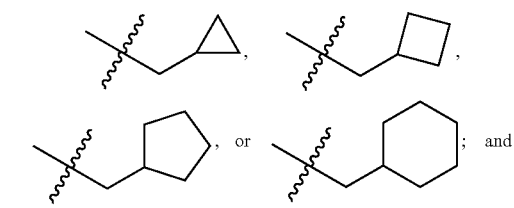

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^{a6}$ is H, Me, or Et;

$R^{a8}$ is H, Me, or Et;

$R^1$ is Me, Et, Pr, Bu, or

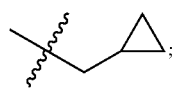

$R^2$ is Et, Pr, Bu, and $R^b$ is Me or Et.

Yet a further aspect of this invention provides benzylamine compounds according to formula (I), and compositions comprising benzylamine compounds, having the following formula:

(XIII)

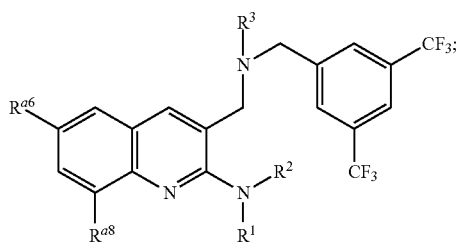

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^{a6}$ is H, Me, or Et;
$R^{a8}$ is H, Me, or Et;

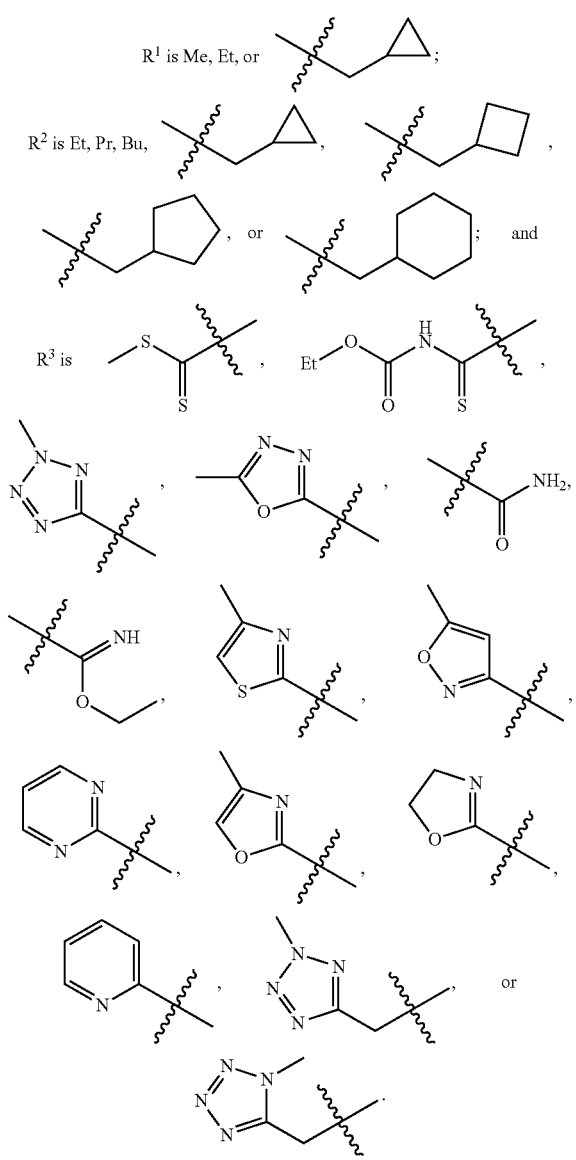

Yet still another aspect of this invention provides benzylamine compounds according to formula (I), and compositions comprising benzylamine compounds, having the following formula:

(XIV)

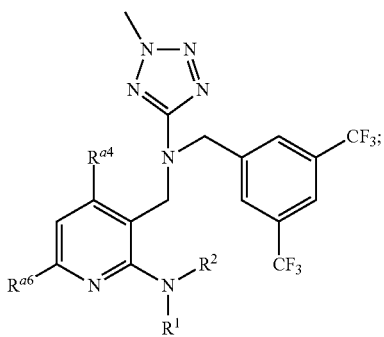

or a salt, including a pharmaceutically acceptable or a non-pharmaceutically acceptable salt, a prodrug, a diastereomeric mixture, an enantiomer, a tautomer, a racemic mixture, or any combination thereof, wherein:

$R^{a4}$ is H, Me, or Et;
$R^{a6}$ is H, Me, or Et;

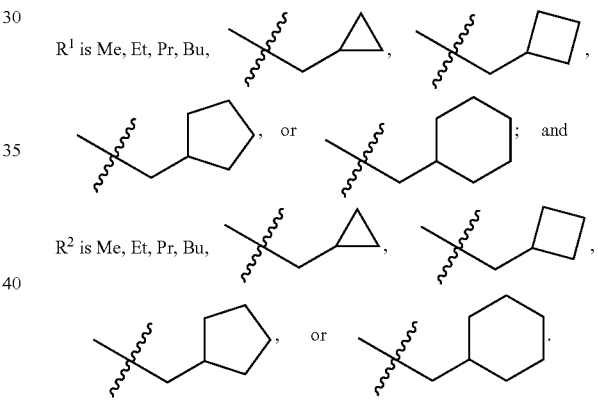

Still another aspect of this invention provides benzylamine compounds according to formula (I), and compositions comprising benzylamine compounds, having the following formula:

(XV)

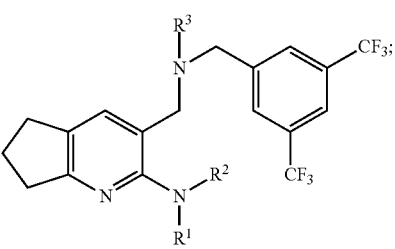

or a salt, including a pharmaceutically acceptable or a non-pharmaceutically acceptable salt, a prodrug, a diastereomeric mixture, an enantiomer, a tautomer, a racemic mixture, or any combination thereof, wherein:

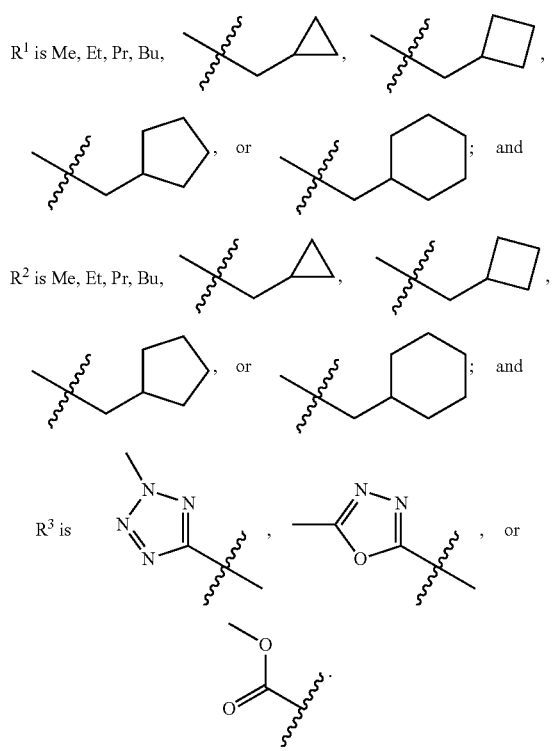

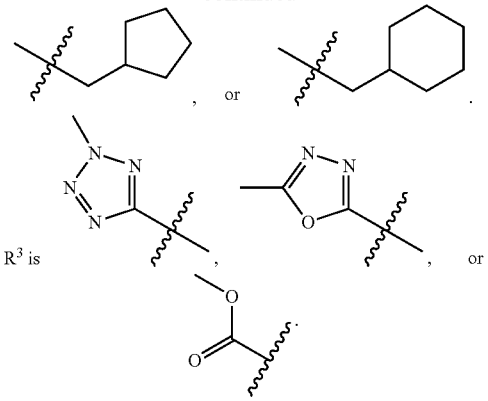

Another aspect of this invention provides benzylamine compounds according to formula (I), and compositions comprising benzylamine compounds, having the following formula:

(XVI)

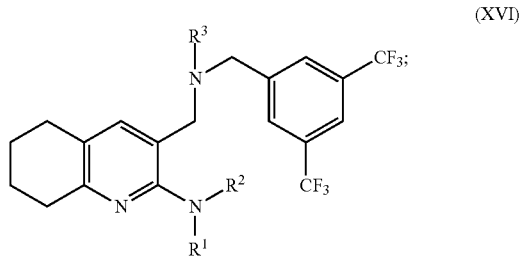

or a salt, including a pharmaceutically acceptable or a non-pharmaceutically acceptable salt, a prodrug, a diastereomeric mixture, an enantiomer, a tautomer, a racemic mixture, or any combination thereof, wherein:

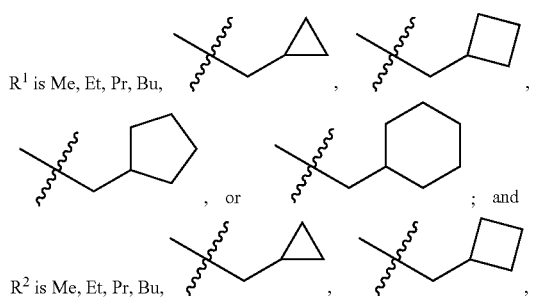

Another aspect of this invention provides benzylamine compounds according to formula (I), and compositions comprising benzylamine compounds wherein the compound is:

(5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-cyclobutylmethyl-ethyl-amine;

(5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-bis-cyclopropylmethyl-amine;

(5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-cyclopropylmethyl-ethyl-amine;

(5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-cyclobutylmethyl-methyl-amine;

(5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-cyclobutylmethyl-cyclopropylmethyl-amine;

(5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-(2,2-dimethyl-propyl)-ethyl-amine;

(5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-ethyl-isopropyl-amine;

(5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-cyclopentyl-ethyl-amine;

(5-{[(3,5-bis-trifluoromethyl-benzyl)-(2-methyl-2H-tetrazole-5-yl)-amino]-methyl}-1,3-dimethyl-1H-pyrazolo[3,4-b]pyridin-6-yl)-cyclopentyl-cyclopropylmethyl-amine;

(5-{[(3,5-bis-trifluoromethyl-benzyl)-(5-methyl-isoxazol-3-yl)-amino]-methyl}-1,3-dimethyl-1H-pyrazolo[3,4-b]pyridin-6-yl)-cyclobutylmethyl-ethyl-amine;

(5-{[(3,5-bis-trifluoromethyl-benzyl)-(5-methyl-isoxazol-3-yl)-amino]-methyl}-1,3-dimethyl-1H-pyrazolo[3,4-b]pyridin-6-yl)-bis-cyclopropylmethyl-amine;

(5-{[(3,5-bis-trifluoromethyl-benzyl)-(2-methyl-2H-tetrazol-5-yl)-amino]-methyl}-1-methyl-1H-pyrazolo[3,4-b]pyridin-6-yl)-cyclobutylmethyl-ethyl-amine;

(5-{[(3,5-bis-trifluoromethyl-benzyl)-(2-methyl-2H-tetrazol-5-yl)-amino]-methyl}-1-methyl-1H-pyrazolo[3,4-b]pyridin-6-yl)-bis-cyclopropylmethyl-amine;

(5-{[(3,5-bis-trifluoromethyl-benzyl)-(2-methyl-2H-tetrazol-5-yl)-amino]-methyl}-1-ethyl-1H-pyrazolo[3,4-b]-pyridin-6-yl)-bis-cyclopropylmethyl-amine;

(5-{[(3,5-bis-trifluoromethyl-benzyl)-(2-methyl-2H-tetrazol-5-yl)-amino]-methyl}-1-ethyl-1H-pyrazolo[3,4-b]-yridin-6-yl)-cyclobutylmethyl-ethyl-amine;

(5-{[(3,5-bis-trifluoromethyl-benzyl)-(4-trifluoromethyl-oxazol-2-yl)-amino]-methyl}-1,3-dimethyl-1H-pyrazolo[3,4-b]-pyridin-6-yl)-cyclopentylmethyl-ethyl-amine;

(2-{[(3,5-bis-trifluoromethyl-benzyl)-(6-cyclopentylmethyl-ethyl-amino)-1,3-dimethyl-1H-pyrazolo[3,4-b]-pyridin-5-ylmethyl]-amino}-oxazol-4-carboxylic acid ethyl ester;

(5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopentylmethyl-ethyl-amine;

(5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-diisobutyl-amine;

(5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopropylmethyl-isobutyl-amine;

cyclopropanecarboxylic acid (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopropylmethyl-amide;

cyclopentanecarboxylic acid (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopropylmethyl-amide;

cyclohexanecarboxylic acid (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopropylmethyl-amide;

N-(5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-N-cyclopropylmethyl-acetamide;

N-(5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-3-chloro-N-cyclopropylmethyl-propionamide;

(5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-ethyl-tetrahydro-furan-2ylmethyl)-amine;

(3,5-bis-trifluoromethyl-benzyl)-[6-(cyclopentylmethyl-ethyl-amino)-1,3-dimethyl-1H-pyrazolo[3,4-b]pyridine-5-ylmethyl]-carbamic acid methyl ester;

cyclopentylmethyl-ethyl-(5-{[(3,4,5-trifluoro-benzyl)-(2-methyl-2H-tetrazol-5-yl)-amino]-methyl}-1,3-dimethyl-1H-pyrazolo[3,4-b]pyridine-6-yl)-amine;

cyclopentylmethyl-ethyl-(5-{[(3,5-difluoro-benzyl)-(2-methyl-2H-tetrazol-5-yl)-amino]-methyl}-1,3-dimethyl-1H-pyrazolo[3,4-b]pyridin-6-yl)-amine;

cyclopentylmethyl-(1,3-dimethyl-5-{[(2-methyl-2H-tetrazol-5-yl)-(3,5-dichlorobenzyl)-amino]-methyl}-1H-pyrazolo[3,4-b]pyridin-6-yl)-ethyl-amine;

cyclopentylmethyl-ethyl-(5-{[(3-fluoro-5-trifluoromethyl-benzyl)-(2-methyl-2H-tetrazol-5-yl)-amino]-methyl}-1,3-dimethyl-1H-pyrazolo[3,4-b]pyridin-6-yl)-amine;

bis-cyclopropylmethyl-(5-{[(3,5-dichlorobenzyl)-(2-methyl-2H-tetrazol-5-yl)-amino]-methyl}-1,3-dimethyl-1H-pyrazolo[3,4-b]pyridin-6-yl)-amine;

(3,5-bis-trifluoromethyl-benzyl)-[6-(cyclopentylmethyl-ethyl-amino)-3-methyl-isoxazolo[5,4-b]pyridine-5-ylmethyl]-carbamic acid methyl ester;

(5-{[(3,5-bis-trifluoromethyl-benzyl)-(2-methyl-2H-tetrazol-5-yl)-amino]-methyl}-3-methyl-isoxazolo[5,4-b]pyridine-6-yl)-cyclopentylmethyl-ethyl-amine;

(3,5-bis-trifluoromethyl-benzyl)-[2-(cyclopentylmethyl-ethyl-amino)-quinolin-3-ylmethyl]-carbamic acid methyl ester;

(3,5-bis-trifluoromethyl-benzyl)-[2-(butyl-ethyl-amino)-quinolin-3-ylmethyl]-carbamic acid ethyl ester;

(3,5-bis-trifluoromethyl-benzyl)-[2-(cyclohexylmethyl-ethyl-amino)-quinolin-3-ylmethyl]-carbamic acid ethyl ester;

(3,5-bis-trifluoromethyl-benzyl)-[2-(cyclopentylmethyl-propyl-amino)-quinolin-3-ylmethyl]-carbamic acid ethyl ester;

(3,5-bis-trifluoromethyl-benzyl)-[2-(cyclopropylmethyl-ethyl-amino)-quinolin-3-ylmethyl]-carbamic acid methyl ester;

(3,5-bis-trifluoromethyl-benzyl)-[2-(cyclobutylmethyl-ethyl-amino)-quinolin-3-ylmethyl]-carbamic acid methyl ester;

(3,5-bis-trifluoromethyl-benzyl)-[2-(cyclopentylmethyl-ethyl-amino)-6-methyl-quinolin-3-ylmethyl]-carbamic acid methyl ester;

[2-(bis-cyclopropylmethyl-amino)-8-methyl-quinolin-3-yl-methyl]-(3,5-bis-trifluoromethyl-benzyl)-carbamic acid methyl ester;

(3,5-bis-trifluoromethyl-benzyl)[2-(cyclopentylmethyl-ethyl-amino)-quinolin-3-ylmethyl]-dithiocarbamic acid methyl ester;

3-ethoxycarbonyl-1-(3,5-Bis-trifluoromethyl-benzyl)-1-[2-(cyclopentyl methyl-ethyl-amino)-quinolin-3-yl methyl]-thiourea;

(3-{[(3,5-bis-trifluoromethyl-benzyl)-(2-methyl-2H-tetrazol-5-yl)-amino]-methyl}-quinolin-2-yl)-cyclopentylmethyl-ethyl-amine;

(3-{[3,5-bis-trifluoromethyl-benzyl)-(2-methyl-2H-tetrazole-5-yl)-amino]-methyl-}-quinolin-2-yl)-butyl-ethyl-amine;

(3-{[3,5-bis-trifluoromethyl-benzyl)-(2-methyl-2H-tetrazole-5-yl)-amino]-methyl-}-quinolin-2-yl)-cyclopropyl-methyl-ethyl-amine;

(3-{[3,5-bis-trifluoromethyl-benzyl)-(2-methyl-2H-tetrazole-5-yl)-amino]-methyl-}-quinolin-2-yl)-cyclobutylmethyl-ethyl-amine;

(3-{[3,5-bistrifluoromethyl-benzyl)-(2-methyl-2H-tetrazole-5-yl)-amino]-methyl-}-8-quinolin-2-yl)-bis-cyclopropylmethyl-amine;

(3-{[(3,5-bis-trifluoromethyl-benzyl)-(5-methyl-[1,3,4]oxadiazol-2-yl)-amino]-methyl}-quinolin-2-yl)-cyclopentylmethyl-ethyl-amine;

1-(3,5 bistrifluoromethyl-benzyl)-1-[(2-cyclopentylmethyl-ethyl-amino)-quinoline-3-ylmethyl]-urea;

1-(3,5-bis-trifluoromethyl-benzyl)-1-[(2-cyclopentylmethyl-ethyl-amino)-quinolin-3-yl methyl)]-O-ethyl isourea;

(3-{[3,5-bis-trifluoromethyl-benzyl)-(4-methyl-thiazol-2-yl)-amino]-methyl}-quinolin-2-yl)-cyclopentylmethyl-ethyl-amine;

(3-{[3,5-bis-trifluoromethyl-benzyl-(5-methyl-isoxazol-3-yl)-amino]-methyl}-quinolin-2-yl)-cyclobutylmethyl-ethyl-amine;

(3-{[(3,5-bis-trifluoromethyl-benzyl)-pyrimidin-2-yl-amino]-methyl}-quinolin-2-yl)-cyclopentylmethyl-ethyl-amine;

(3-{[(3,5-bis-trifluoromethyl-benzyl)-(4-methyl-oxazol-2-yl)-amino]-methyl}-quinolin-2-yl)-cyclopentylmethyl-ethyl-amine;

(3-{[(3,5-bis-trifluoromethyl-benzyl)-(4,5-dihydro-oxazol-2-yl)-amino]-methyl}-quinolin-2-yl)-cyclopentylmethyl-ethyl-amine;

(3-{[(3,5-bis-trifluoromethyl-benzyl)-pyridin-2-yl-amino]-methyl}-quinolin-2-yl)-cyclopentylmethyl-ethyl-amine;

(3-{[(3,5-bis-trifluoromethyl-benzyl)-(2-methyl-2H-tetrazol-5-ylmethyl)-amino]-methyl}-quinolin-2-yl)-cyclopentylmethyl-ethyl-amine;
(3-{[(3,5-bis-trifluoromethyl-benzyl)-(1-methyl-1H-tetrazol-5-ylmethyl)-amino]-methyl}-quinolin-2-yl)-cyclopentylmethyl-ethyl-amine;
(3-{[3,5-bis-trifluoromethyl-benzyl)-(2-methyl-2H-tetrazole-5-yl)-amino]-methyl-}-pyridin-2-yl)-butyl-ethyl amine;
(3-{[(3,5-bis-trifluoromethyl-benzyl)-(2-methyl-2H-tetrazole-5-yl)-amino]-methyl}-4,6-dimethyl-pyridin-2-yl)-bis-cyclopropylmethyl-amine;
(3,5-bis-trifluoromethyl-benzyl)-[2-(cyclopentylmethyl-ethyl-amino)-6,7-dihydro-5H-[1]pyridin-3-ylmethyl]-carbamic acid methyl ester;
(3-{[(3,5-bis-trifluoromethyl-benzyl)-(2-methyl-2H-tetrazole-5-yl)-amino]-methyl}-6,7-dihydro-5H-[1]pyridine-2-yl)-cyclopentylmethyl-ethyl-amine;
(3,5-bis-trifluoromethyl-benzyl)-[2-(cyclopentylmethyl-ethyl-amino)-5,6,7,8-tetrahydro-quinolin-3-ylmethyl]-carbamic acid methyl ester;
(3-{[3,5-bis trifluoromethyl-benzyl)-(2-methyl-2H-tetrazole-5-yl)-amino]-methyl}-5,6,7,8-tetrahydro-quinoline-2-yl)-cyclopentylmethyl-ethyl-amine;
(3-{[3,5-bis trifluoromethyl-benzyl)-(5-methyl-[1,3,4]oxadiazol-2-yl)-amino]-methyl}-5,6,7,8-tetrahydro-quinoline-2-yl)-cyclopentylmethyl-ethyl-amine; or
any combination thereof.

The present invention also encompasses any combination of compounds provided herein, including any salts, including pharmaceutically acceptable and non-pharmaceutically acceptable salts, or any mixture thereof. The present invention also encompasses any stereoisomers of compounds provided herein, including any combination of stereoisomers.

In this aspect of the present invention, compounds provided herein can be chiral or achiral, or they may exist as racemic mixtures, diastereomers, pure enantiomers, a prodrug, a tautomer or any mixture thereof. For chiral compounds, separate enantiomers, separate diastereomers, and any mixture of enantiomers, diastereomers, or both are encompassed herein, such as, for example, (R), (S), or a mixture of (R) and (S) isomers. In this aspect, individual optical isomers or a particular desired isomer may be obtained by using chiral reagents to obtain a single isomeric form in a resolution process wherever applicable, or by conducting the reaction in the presence of reagents or catalysts in their single enantiomeric or diasteromeric form.

Unless otherwise specified, any compound illustrated herein, including any compound of formula (I), is intended to include all possible positional isomers or regioisomers that could be encompassed by a given formula, including all possible positional isomers that arise from the position of a heteroatom or heterogroup within a heterocyclic ring. For example, when ring A of formula (I) is pyridine, the possible positional isomers include

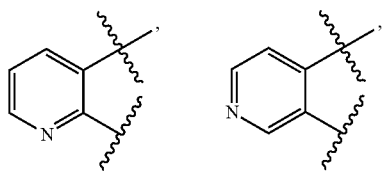

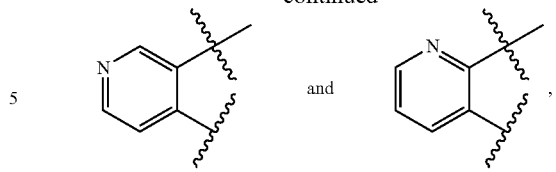

and each of these isomers is intended to be included in formula (I) when ring A is pyridine. Similarly, when ring A is pyrazolopyridine, the possible positional isomers include

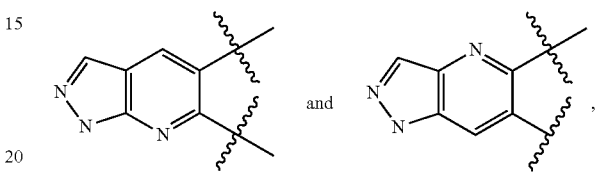

and each of these isomers is intended to be included in formula (I) when ring A is pyrazolopyridine. Further, when ring A is bicyclic system the invention also contemplates other isomers of such ring systems, for example when ring A is indole, the possible isomers include

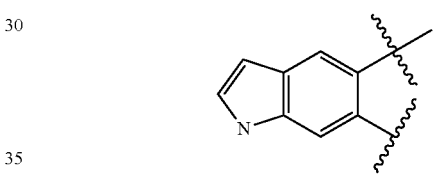

and

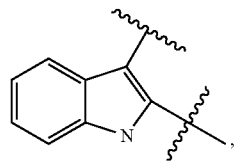 [SMILES: *c1[nH]c2ccccc2c1*]

and each of these isomers is intended to be included in formula (I) when ring A is indole.

In one aspect, methods for the resolution of racemic compounds include, but are not limited to: using microbial resolution; resolving the diastereomeric salts formed with chiral acids such as mandelic acid, camphorsulfonic acid, tartaric acid, lactic acid, and the like wherever applicable; or resolving the diastereomeric salts formed with chiral bases such as brucine, cinchona alkaloids and their derivatives; and the like. Commonly used methods are compiled in Jaques, et al. in *Enantiomers, Racemates and Resolution*; Wiley-Interscience, 1981. For example, where appropriate, compounds of formula (I) can be resolved by treating with chiral amines, aminoacids, or aminoalcohols derived from aminoacids; by using conventional reaction conditions to convert an acid into an amide; by separation of diastereomers by fractional crystallization or by chromatography; or by preparing the stereoisomers of formula (I) by hydrolyzing the pure diastereomeric amide.

As used herein, the terms "pharmaceutically acceptable" salt or "pharmacologically acceptable" salt refers generally to a salt or complex of the compound or compounds in which the compound can be either anionic or cationic, and have associated with it a counter cation or anion, respectively, that is generally considered suitable for human or animal consumption. For example, a pharmaceutically acceptable salt can refer to a salt of a compound disclosed herein that forms upon reaction or complexation with an acid whose anion is generally considered suitable for human or animal consumption. In this aspect, pharmacologically acceptable salts include salts with organic acids or inorganic acids. Examples of pharmacologically acceptable salts include, but are not limited to, hydrochloride, hydrobromide, hydroiodide, sulfate, phosphate, propionate, lactate, maleate, malate, succinate, tartarate, and the like.

Salts may also be formed by deprotonating an acid moiety of the compound, such as a carboxylic acid moiety, OH, or NH, and the like, using a base such as an organic base, an inorganic base, an organometallic base, a Lewis base, a Brønsted base, or any combination thereof. In cases where compounds carry an acidic moiety, suitable pharmaceutically acceptable salts can include alkali metal salts, alkaline earth metal salts, or salts with organic basis, and the like. In this aspect, examples of alkali metal salts include, but are not limited to, sodium and potassium salts, and examples of salts with organic basis include, but are not limited to, meglumine salts, and the like. The pharmacologically acceptable salts can be prepared by conventional means. Additional examples of pharmaceutically acceptable salts, and methods of preparing such salts, are found, for example, in Berg et. al., J. Pharma. Sci, 66, 1-19 (1977).

In a further aspect, this invention also provides a composition comprising at least one compound as disclosed herein, including a composition comprising a pharmaceutically acceptable carrier and at least one compound as disclosed herein. In this aspect, the at least one compound can be present as a neutral compound, as a salt, or as any combination thereof. This invention also encompasses a composition comprising at least one compound as disclosed herein, and optionally comprising a pharmaceutically acceptable additive selected from a carrier, an auxiliary, a diluent, an excipient, a preservative, a solvate, or any combination thereof. In another aspect, this invention encompasses a pharmaceutical composition comprising at least one compound as disclosed herein, and optionally further comprising an agent selected from a chemotherapeutic agent, an immunosuppressive agent, a cytokine, a cytotoxic agent, an anti-inflammatory agent, an antidyspilidemic agent, an antirheumatic agent, a cardiovascular agent, or any combination thereof.

Further, this invention encompasses a pharmaceutical composition, comprising at least one compound as disclosed herein, and optionally comprising a pharmaceutically acceptable additive selected from a carrier, an auxiliary, a diluent, an excipient, a preservative, a solvate, or any combination thereof, wherein the pharmaceutical composition is in the form of a tablet, a capsule, a syrup, a cachet, a powder, a granule, a solution, a suspension, an emulsion, a bolus, a lozenge, a suppository, a cream, a gel, a paste, a foam, a spray, an aerosol, a microcapsule, a liposome, or a transdermal patch.

Prodrugs

In another aspect of this invention, alternatively, the compounds can be formulated and administered in a prodrug form. In general, prodrugs comprise functional derivatives of the claimed compounds which are capable of being enzymatically activated or converted into the more active parent form.

Thus, in the treatment methods of the present invention, the term "administering" encompasses the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in Wihnan, 14 *Biochem. Soc. Trans.* 375-82 (1986); Stella et al., Prodrugs: A Chemical Approach to Targeted Drug Delivery, in *Directed Drug Delivery* 247-67 (1985).

Thus, in one aspect, "prodrugs" of the compounds disclosed herein refers to species that have chemically- or metabolically-cleavable groups wherein, under physiological conditions, the species become, provide, release, or are transformed into the compounds disclosed herein. In this manner, prodrugs can release the pharmaceutically in vivo active compounds disclosed herein. For example, prodrugs of present invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine or other 5-fluorouridine prodrugs which may be converted into the more active species, and the like. In another aspect, prodrugs of present invention include, but are not limited to derivatives of carboxylic acid, sulfonamide, amine, hydroxyl, and the like, including other functional groups and including any combination thereof.

In another aspect, this invention provides a pharmaceutical composition, comprising one or more compounds of any formula in any combination described above and optionally comprising a pharmaceutically acceptable additive selected from a carrier, an auxiliary, a diluent, an excipient, a preservative, a solvate, or any combination thereof. In a related aspect, this invention affords a method of treating a condition or disease state such as dyslipidemia, atherosclerosis, peripheral vascular disease, hypertryglyceridemia, hypercholesterolemia, hyperbetalipoproteinemia, hypoalphalipoprotenemia, cardiovascular disorders such as angina, ischemia, stroke, myocardial infarction (MI), reperfusion injury, restenosis and hypertension, and diabetic vascular diseases such as diabetic retinopathy, and endotoxemia, comprising administering an effective amount of at least one compound as disclosed herein.

Synthetic Methods

General reaction schemes are provided herein that detail the synthetic approaches to the benzylamine compounds disclosed herein. Thus, compounds in accordance with this disclosure could be prepared as shown in the specific Schemes and/or as illustrated in the Examples by using standard synthetic methods and starting materials, which are either commercially available or can be synthesized from commercially available precursors using synthetic methods known in the art, or variations thereof as appreciated by those skilled in the art. Each variable in the following schemes refer to any group consistent with the description of the compounds provided herein. In each synthetic scheme or example provided, substitutents in any structure that are illustrated in the scheme or example that are not specified are selected as disclosed according to the general formulas of the compounds provided herein.

The following general procedures could be used in the reactions schemes and in the Examples provided herein.

Halogenation could be carried out by using reagents such as phosphorus oxychloride (POCl₃), thionyl chloride (SOCl₂), and the like, for example, at a temperature from about 80° C. to about 120° C., for about 4 to about 8 hours, followed by pH adjustment of resultant mixture to a pH from about 6 to about 7.

Amination could be carried out by using amines in presence of a solvent chosen from acetone, acetonitrile, dimethylformamide, dimethylacetamide and the like, with or without a base. Suitable bases include triethylamine, N,N-diisopropyl ethyl amine, potassium carbonate, sodium carbonate, sodium hydride, and the like. The reaction temperature was typically from about 20° C. to about 120° C., and the duration of the reaction was typically in the range of from about 4 hours to about 20 hours.

Thus one further aspect of the invention relates to the processes of preparing compounds of formulas provided herein. Any compound of any formula disclosed herein can be obtained using procedures provided in the reaction Schemes, as well as procedures provided in the Examples, by selecting suitable starting materials and following analogous procedures. Thus, any compound of any formula disclosed or exemplified herein, can be obtained by using the appropriate starting materials and appropriate reagents, with the desired substitutions, and following procedures analogous to those described herein. Therefore, it will be readily understood by one of ordinary skill, that the reaction schemes disclosed herein can be adapted to prepare any compound of this disclosure, therefore any discussion of a particular step in a reaction scheme is intended to reflect one method or one set of considitions that can be used to carry out that step. This discussion of a particular step is not intended to be limiting, but rather exemplary, of one particular method and set of conditions by which that step can be effected.

In one aspect of this invention, compounds of formula (I) according to this invention could be prepared as illustrated in at least one of the following Schemes 1-5. In some cases, the relevant reagents and starting materials were commercially available. In other cases, the relevant reagents and starting materials were made by standard synthetic procedures in organic and heterocyclic chemistry, and known by one of ordinary skill in the relevant art. These techniques were analogous to the synthesis of known structurally similar intermediates or starting materials and the procedures described in preparations and examples below. For example the following references disclosed the exact procedures or analogues procedures for the preparation of many of the intermediates described in Schemes 1-5: Synlett., 2001, No: 2, 251-253; Synthesis 2001, 1185-1196; Journal of Heterocyclic Chemistry, 1987, 351-355; Journal of Organic Chemistry Vol: 30, 1965, 3593-3596; Journal of Heterocyclic Chemistry 1982, 809-811. Such known procedures include the reduction of aldehydes, cyanation, alkylation of amines, benzylation, acylation of amines, sulfonylation of amines, reductive amination, hydrolysis of nitriles, esterification of carboxylic acids and carboxylic acids to amide conversions, and the like.

Thus, in the following representative synthetic schemes, the starting materials were either commercially available or readily prepared using well known procedures, using starting materials and/or reagents having the appropriate substitution. As the context of any scheme or Example demands or allows, substitutents in any structure that are not specified are selected as provided herein in the general description of the disclosed compounds.

In one aspect, compounds according to the present invention could be prepared according to the following scheme.

Scheme 1

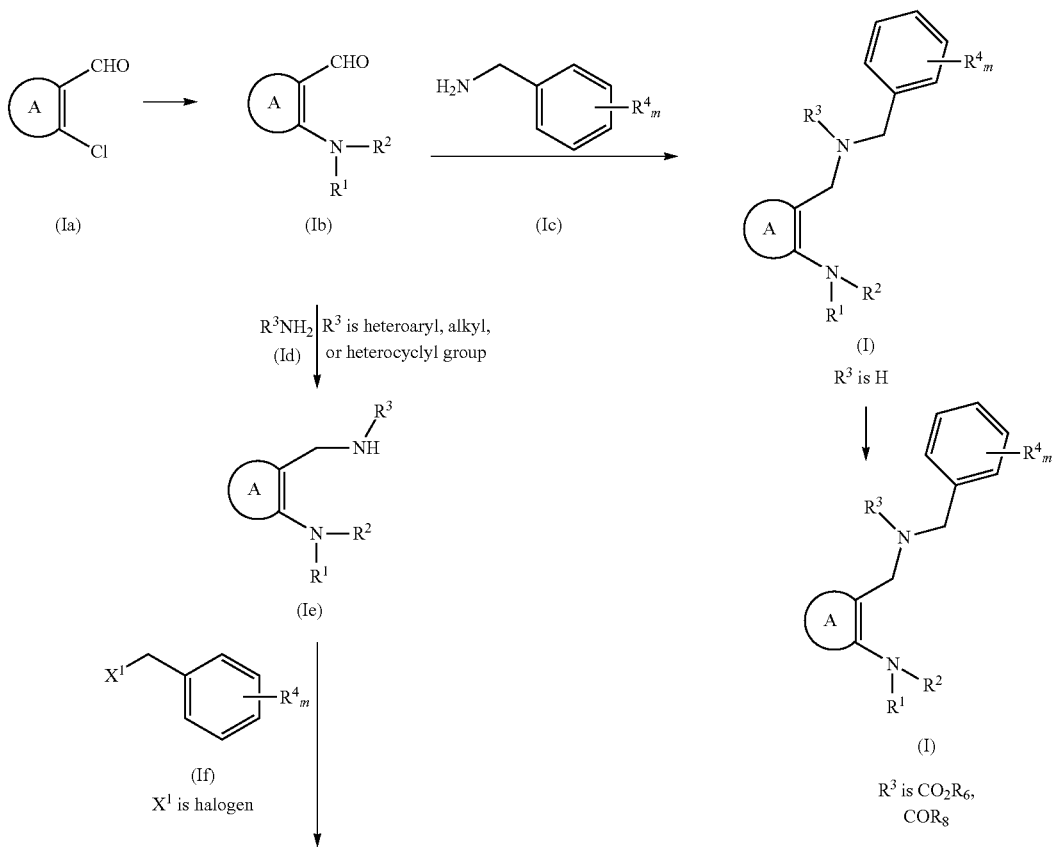

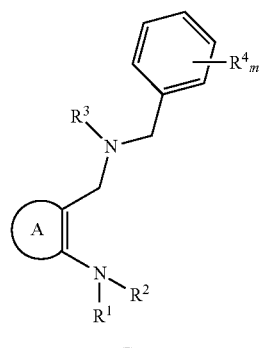

(I)

R³ is heteroaryl, alkyl,
or heterocyclyl group

Representative steps of Scheme 1 include the following. The compound of formula (Ia) could be converted to a compound of formula (Ib) by an amination reaction using HNR¹R², in a polar solvent such as N,N-dimethylformamide (DMF) and a base such as sodium carbonate or potassium carbonate. The reaction could also be carried out in the presence of a solvent such as acetonitrile, tetrahydrofuran, or toluene. The base could also be selected from cesium carbonate, potassium tertiary butoxide, and the like.

Reductive amination of compound of formula (Ib) with a compound of formula (Ic), in presence of a reducing agent such as Na(CN)BH₃, Na(OAc)₃BH, NaBH₄ and the like, in a (C₁-C₁₀) alcohol solvent such as methanol, ethanol, propanol, isopropanol, and the like, or a chlorinated solvent such as dichloromethane, chloroform, 1,2-dichloroethane, and the like, along with an acid such as acetic acid or diluted hydrochloric acid, yields a compound of formula (I), wherein R³ is typically hydrogen. In one aspect, the temperature of the reaction could be maintained from about 25° C. to about 35° C., and the duration of the reaction typically could range from about 30 minutes to about 5 hours.

The compound of formula (I), where R³ is hydrogen, could be converted to a compound of formula (I), wherein R³ is typically CO₂R⁶ or COR⁸, wherein R⁶ and R⁸ are as defined herein, by reacting with a compound of formula X¹CO₂R⁶ or X¹COR⁸, where X¹ can be halogen, in the presence of a base such as potassium carbonate in a solvent such as tetrahydrofuran. The reaction could also be carried out in the presence of acetone, acetonitrile, and the like. In one aspect, the temperature of the reaction could be maintained from about 25° C. to about 55° C., and the duration of the reaction typically could range from about 20 minutes to about 5 hours.

Reductive amination of compounds of formula (Ib) with a compound of formula (Id) wherein R³ can be heteroaryl, alkyl, heterocyclyl; in presence of reducing agents like Na(CN)BH₃, Na(OAc)₃BH, NaBH₄ and the like, in (C₁-C₁₀) alcohol solvent medium such as ethanol, propanol, isopropanol, and the like, along with an acid like acetic acid or diluted hydrochloric acid, could yield a compound of formula (Ie). In one aspect, the temperature of the reaction could be maintained from about 25° C. to about 35° C., and the duration of the reaction typically could range from about 30 minutes to about 5 hours.

The compound of formula (Ie) could be reacted with a compound of formula (If) wherein X¹ can be leaving group such as halogen, mesyloxy, tosyl, and the like, to obtain a compound of formula (I), where R³ can be akyl, heteroaryl, heterocyclyl, in the presence of a base like sodium hydride or potassium hydride. The reaction could be carried in a solvent such as N,N-dimethylformamide, acetonitrile, tetrahydrofuran, toluene and the like. In one aspect, the temperature of the reaction could be maintained from about 25° C. to about 55° C., and the duration of the reaction typically could range from about 20 minutes to about 5 hours.

In another aspect, compounds according to the present invention could be prepared according to the following scheme.

Scheme 2

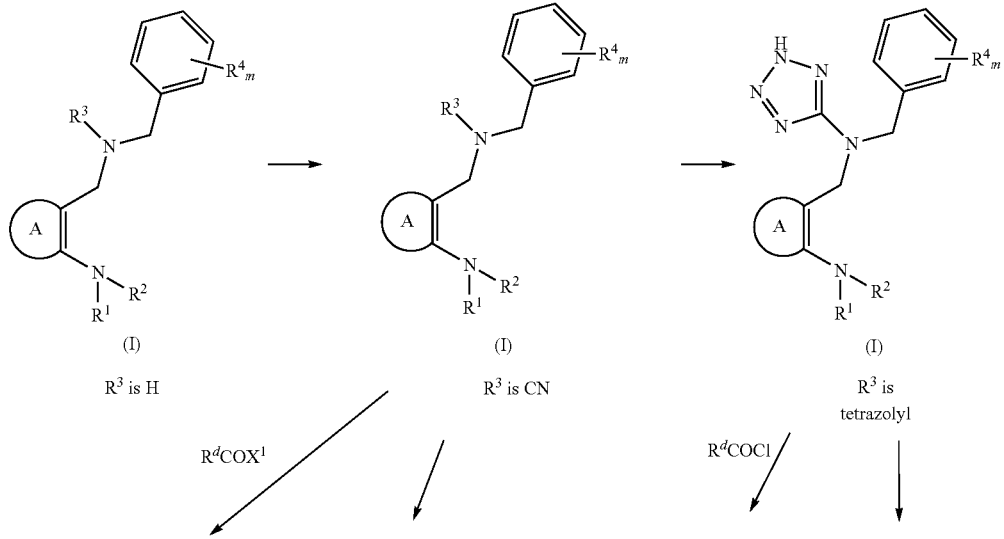

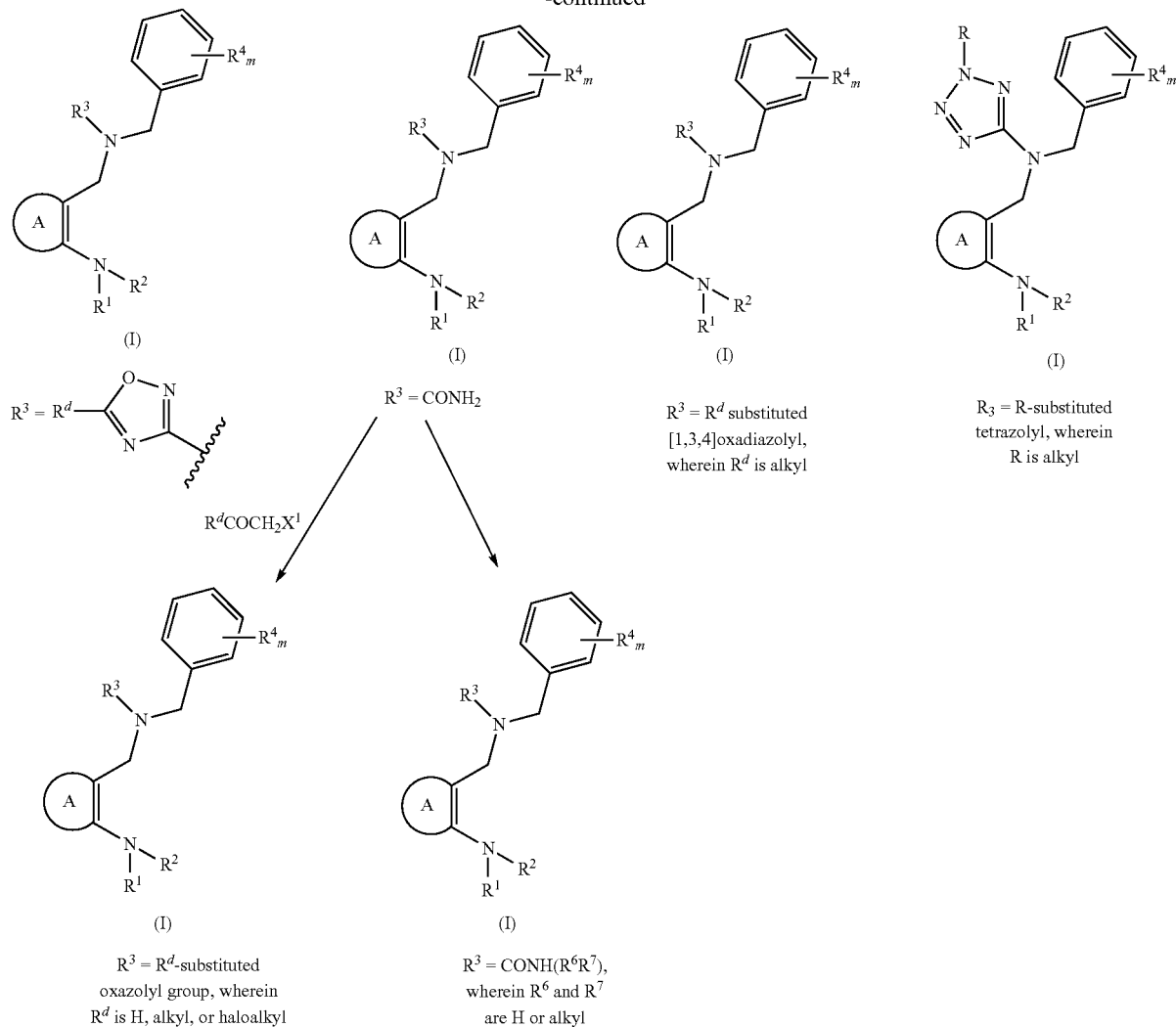

In this scheme, the compound of formula (I), where $R^3$ can be hydrogen could be converted to a compound of formula (I), where $R^3$ can be CN group, in the presence of cyanogen bromide (CNBr), by using a suitable solvent such as dimethylformamide, acetonitrile, a ($C_1$-$C_{10}$) alcohol, or the like, along with a base such as sodium bicarbonate, sodium carbonate, potassium carbonate, cesium carbonate, potassium bicarbonate, and the like. In one aspect, the temperature of the reaction could be maintained from about 25° C. to about 55° C., and the duration of the reaction typically could range from about 20 minutes to about 5 hours.

The compound of formula (I), where $R^3$ can be a cyano (CN) group, can be converted to a compound of formula (I), where $R^3$ is a tetrazoloyl group by reacting the cyano compound with sodium azide or potassium azide, in the presence zinc salts such as $ZnBr_2$. Suitable solvents for this reaction include N,N-dimethylformamide, acetonitrile, ($C_1$-$C_{10}$) alcohols, and the like.

Compounds of formula (I) where $R^3$ is tetrazolyl could be converted into a compound of formula (I) where $R^3$ is an alkyl-substituted tetrazolyl, by reacting the tetrazolyl compound with alkylating reagents such as alkyl halides or dialkyl sulphates, in the presence of a base such as sodium hydroxide, potassium hydroxide, potassium carbonate, sodium hydride and the like, along with a phase-transfer catalyst such as tetraalkylammoniumhalide or tetraarylammoiumhalide, in a solvent medium such as water, dimethylformamide, acetonitrile, and the like.

Compounds of formula (I), where $R^3$ is tetrazolyl, could be converted to a compound of formula (I) where $R^3$ is an alkyl substituted [1,3,4]oxadiazolyl, by reacting the tetrazolyl compound with the corresponding acid chloride in a solvent such as pyridine. In one aspect, the temperature of the reaction could be maintained from about 120° C. to about 140° C., and the duration of the reaction typically could range from about 2 hours to about 6 hours.

Compounds of formula (I), where $R^3$ is a cyano (CN) group, could be hydrolyzed in the presence of a base such as KOH, NaOH, and the like, along with a catalytic amount of $H_2O_2$, typically at a temperature in the range from about 25 to about 100° C. for a period of time from about 30 minutes to about 6 hours, to yield a compound of formula (I) where $R^3$ is $CONH_2$.

Compounds of formula (I) wherein $R^3$ is a $CONH_2$ group, could be converted to a compound of formula (I) where $R^3$ is $CONR^6R^7$, and wherein $R^6$ and $R^7$ independently can be hydrogen or an alkyl as specified herien, by reacting alkyl halides, in the presence of a base such as sodium hydroxide, potassium hydroxide, potassium carbonate, and the like, along with a phase transfer catalyst such as tetraalkylammoniumhalide, tetraalkylammonium hydrogen sulphate, or tetraarylammoiumhalide, in a solvent such as benzene, toluene, and the like.

Compounds of formula (I) where $R^3$ can be a $CONH_2$ group, could also be reacted with a compound of general formula $R^d COCH_2 X^1$, wherein $R^d$ can be hydrogen, alkyl, or haloalkyl, and $X^1$ can be a leaving group such as halogen, in the presence of an alcoholic solvent such as tert-butanol, isopropanol, and the like. In one aspect, the temperature of the reaction could be maintained from about 60° C. to about 120° C., to yield a compound of formula (I) where $R^3$ can be an $R^d$-substituted oxazolyl group.

Compounds of formula (I) wherein $R^3$ is a cyano (CN) group, could be reacted with hydroxylamine in a solvent such as 1,4-dioxane, toluene, and the like, followed by the addition of a compound of general formula $R^d COX^1$, wherein $R^d$ can be an alkyl and $X^1$ can be halogen, along with a base such as pyridine, to yield a compound of formula (I), wherein $R^3$ can be an $R^d$-substituted 1,2,4-oxadiazolyl group.

In yet another aspect, compounds according to the present invention could be prepared according to the following scheme.

Scheme 3

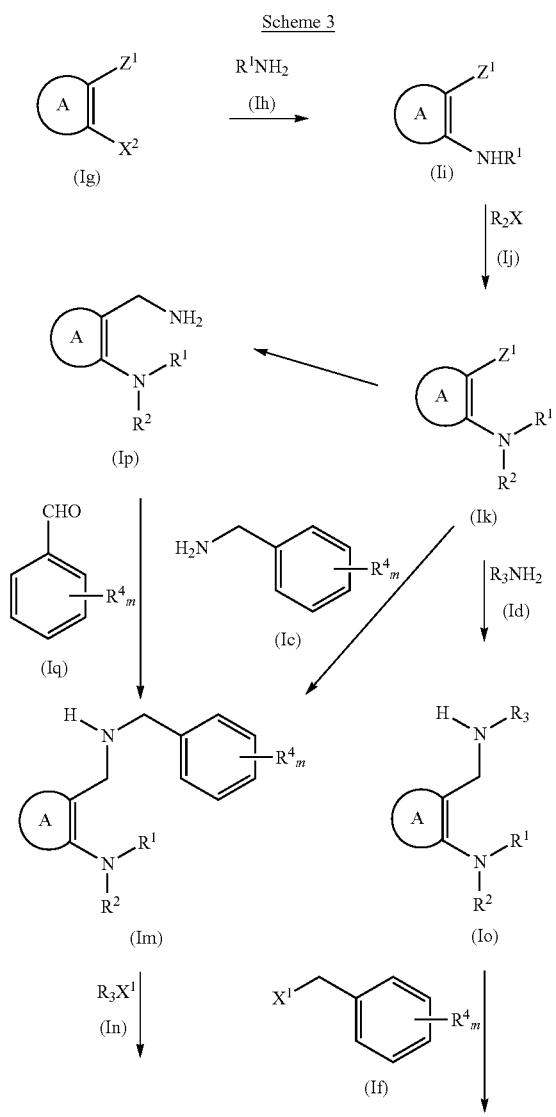

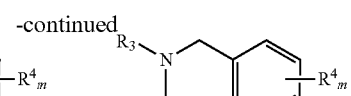
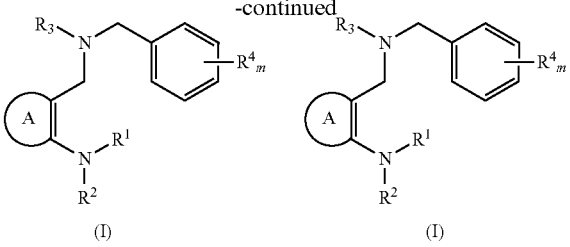

$R^1$ is alkyl; $R^2$ is alkyl, acyl;
$R^3$ is alkyl, H, $CO_2R_6$, $COR_8$,
$SO_2R_8$, $CONR_6R_7$, $CSNR_6R_7$ $R^1$ is alkyl; $R^2$ is alkyl, acyl;
$R^3$ is 5-7 member heteroaryl In this scheme, syntheses can begin with a compound of formula (Ig) wherein $Z^1$ can be an aldehyde, acetal, or CN, and $X^2$ can be a halogen, which could be reacted with a nucleophile of formula (Ih), wherein $R^1$ can be alkyl, to obtain a compound of formula (Ii), by using the methodology known to one of ordinary skill from the literature (see below). For example, formation of a secondary amine from a substituted chloropyridine and the primary amine(ethylamine hydrochloride) could be carried out in the presence of a base such as N,N-diisopropyl-N-ethylamine, and a solvent such as ethanol. The base could also be selected from other tertiary amines such as triethyl amine (TEA), tributyl amine, and the like. The reaction could also be carried out in the presence of a solvent which includes, but is not limited to, n-butanol, tertiary butanol, N,N-dimethylformamide (DMF), dimethoxyethane, and the like. The temperature of the reaction could be maintained from about 50° C. to the boiling point of the solvent used. The duration of the reaction could be in the range from about 3 to about 16 hours [Cappelli, A. et. al. *Journal of Medicinal Chemistry*, 47(10): pp. 2574-2586 (2004); Izumi, T., et. al. *Bioorganic & Medicinal Chemistry*, 11: 2541-2550 (pp. 2003)].

The compound of formula (Ik) could be obtained by the alkylation or acylation of a compound of formula (Ii) with a compound of formula (Ij), wherein $R^2$ can be an alkyl, a haloalkyl, or $COR^8$, in the presence of a base such as potassium carbonate, in a polar solvent such as tetrahydrofuran, diethyl ether, and the like. In one aspect, the temperature of the reaction could be maintained from about 0° C. to about 100° C., and the duration of the reaction typically could range from about 1 hour to about 8 hours.

The compound of formula (Ip) could be prepared by reducing a compound of formula (Ik), wherein $Z^1$ can be a cyano (CN) group, by using an appropriate reducing agent such as lithium aluminium hydride (LAH), sodium bis(2-methoxyethoxy)aluminumhydride (Red-Al®), and the like, which could be carried out in an appropriate solvent such as tetrahydrofuran, diethylether, and the like. In one aspect, the temperature of the reaction could be maintained from about 0° C. to about 60° C., and the duration of the reaction typically could range from about 1 hour to about 14 hours.

The compound of formula (Ip) could be converted to a compound of formula (Im) by reductive amination with a compound of formula (Iq). The reaction could be conducted in the presence of acetic acid, a solvent such as methanol, and a reducing agent such as sodium cyanoborohydride. The reaction could also be carried out in the presence of diluted hydrochloric acid. The solvent used could also be selected from ($C_1$-$C_{10}$) alcohols such as ethanol, propanol, isopropanol, and the like, or mixtures thereof. The reaction could also be conducted using other reducing agents such as sodium triacetoxyborohydride, and the like. In one aspect, the temperature of the reaction could be maintained from about 25° C. to about 35° C., and the duration of the reaction typically could range from about 30 minutes to about 5 hours.

The compound of formula (Ik), an aldehyde or acetal, could be converted to a compound of formula (Im) by reductive amination with a compound of formula (Ic). The reaction could be conducted in the presence of acetic acid, a solvent such as methanol, and a reducing agent such as sodium cyanoborohydride. The reaction could also be carried out in the presence of diluted hydrochloric acid. The solvent used could also be selected from a ($C_1$-$C_{10}$) alcohol such as ethanol, propanol, isopropanol, and the like, or mixtures thereof. The reaction could also be conducted using other reducing agents such as sodium triacetoxyborohydride, and similar reducing agents. Typically, the temperature of the reaction could be maintained between about 25° C. and about 35° C., and the duration of the reaction typically could be from about 30 minutes to about 5 hours.

The compound of formula (Im) is converted to a compound of formula (I) wherein typically, $R^3$ can be $CO_2R^6$, $COR^8$, $SO_2R^8$, $CONR^6R^7$, or alkyl, by acylation with a compound of formula (In), wherein $X^1$ can be a leaving group such as halogen, mesyloxy and the like. For example, compound (Im) could be reacted with ethyl chloroformate in the presence of a base such as potassium carbonate and a solvent such as tetrahydrofuran at ambient temperature. The reaction could also be carried out with other acylating agent such as methyl chloroformate, and the like. The reaction could also be carried out in the presence of different solvents, including but not limited to, acetone, acetonitrile, and the like. In one aspect, the temperature of the reaction could be maintained from about 22° C. to about 50° C., and the duration of the reaction typically could range from about 4 hours to about 12 hours.

The compound of formula (Ik) wherein $Z^1$ can be an aldehyde or acetal, could also be converted to a compound of formula (Io) by reductive amination with a compound of formula (Id) wherein $R^3$ can be alkyl, heteroaryl, heterocyclyl, in the presence of acetic acid, a solvent such as methanol, and an appropriate reducing agent such as sodium cyanoborohydride. The reaction could also be carried out in the presence of diluted hydrochloric acid. The solvent used could also be selected from ($C_1$-$C_{10}$) alcohols such as ethanol, propanol, isopropanol, and the like or their mixtures thereof. In one aspect, the temperature of the reaction could be maintained from about 25° C. to about 50° C., and the duration of the reaction typically could range from about 1 hour to about 6 hours.

The compound of formula (Io) could be converted to a compound of formula (I) wherein $R^3$ can be a 5-7 membered heteroaryl group, by a benzylation reaction with a compound of formula (If), wherein $X^1$ can be a leaving group such as halogen, mesyloxy, and the like, in the presence of a base such as sodium hydride and a solvent such as N,N-dimethylformamide. The base could also be selected from bases including potassium hydride, and the like. The reaction could also be carried out in the presence of a solvent, including for example, acetonitrile, tetrahydrofuran, toluene, and the like. Typically, the temperature of the reaction could be in the range from about 25° C. to about 60° C.

In still another aspect, compounds according to the present invention could be prepared according to the following scheme.

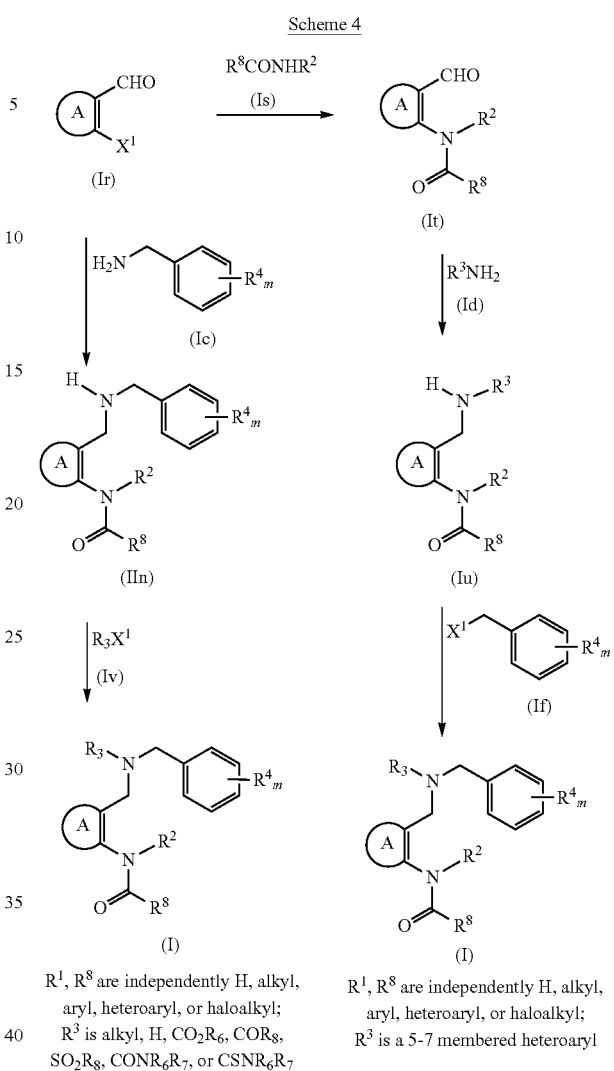

Scheme 4

$R^1$, $R^8$ are independently H, alkyl, aryl, heteroaryl, or haloalkyl;
$R^3$ is alkyl, H, $CO_2R_6$, $COR_8$, $SO_2R_8$, $CONR_6R_7$, or $CSNR_6R_7$ $R^1$, $R^8$ are independently H, alkyl, aryl, heteroaryl, or haloalkyl;
$R^3$ is a 5-7 membered heteroaryl In this scheme, a palladium catalyzed cross-coupling amidation reaction could be used to produce compound of formula (It). For example, formation of compound of formula (It) from the heteroaryl halide (Ir), wherein $X^1$ can be halogen, and amide (Is), wherein $R^8$ and $R^2$ can be alkyl or aryl, could be accomplished in the presence of a palladium catalyst such as tris(dibenzylideneacetone)dipalladium, a phosphorus ligand such as 4,5-bis(diphenylphosphino)-9,9-dimethylxanthene (Xantphos™), and a base such as cesium carbonate, in a suitable solvent, such as toluene. The reaction could also be carried out in the presence of a solvent including toluene, xylene, dimethylformamide, tetrahydrofuran, 1,4-dioxane and the like, as well as mixtures thereof. Further, the reaction could be carried out in the presence of from about 1 mol % to about 10 mol % of a suitable Pd catalyst such as Pd(OAc)$_2$, Pd(DIPHOS)$_2$, Pd(PPh$_3$)$_4$ and the like. The reaction could also be carried out in the presence of a ligand, such as 2-dicyclohexylphoshino-2',4',6'-tri-1-propyl-1,1'-biphenyl (XPHOS), 1,1-bis(diphenylphosphine)ferrocene (DPPF), 2,2'-bis(diphenylphosphanyl)-1,1'-biphenyl (BINAP), 1,2-bis(diphenylphosphine)ethane (DIPHOS), and the like. Further, other bases could be employed, such as sodium carbonate, potassium carbonate, sodium acetate, and the like. The temperature of the reaction could typically be in the range from about 50° C. to about 125° C. [see: Yin, J; Buchwald, S. L. *Organic Letters*, 2 (8): pp. 1101-1104 (2000)].

The compound of formula (It) could be converted to a compound of formula (Iv) by reductive amination with a compound of formula (Ic) in the presence of acetic acid, a suitable solvent such as methanol, and a reducing agent such as sodium cyanoborohydride. The reaction could also be carried out in the presence of diluted hydrochloric acid. The solvent used could also be selected from $(C_1-C_{10})$ alcohols such as ethanol, propanol, isopropanol and the like or mixtures thereof. In one aspect, the temperature of the reaction could be maintained from about 25° C. to about 35° C., and the duration of the reaction typically could range from about 30 minutes to about 5 hours.

The compound of formula (Iv) could be converted to a compound of formula (I) wherein $R^3$ can be $CO_2R^6$, $COR^8$, $SO_2R^8$, $CONR^6R^7$, or an alkyl, and Y can be N, by acylation with a compound of formula (In), wherein $X^1$ can be halogen, in the presence of a base such as potassium carbonate, and a solvent such as terahydrofuran. The reaction could also be carried out in the presence of other suitable solvents, including acetone, acetonitrile, and the like. In one aspect, the temperature of the reaction could be maintained from about 22° C. to about 50° C., and the duration of the reaction typically could range from about 4 hours to about 12 hours.

The compound of formula (It) is converted to a compound of formula (Iu) by reductive amination with a compound of formula (Id) wherein $R^3$ can be a 5-7 membered heteroaryl group, in the presence of acetic acid, a solvent such as methanol, and a reducing agent such as sodium cyanoborohydride. The reaction could also be carried out in the presence of diluted hychloric acid. The solvent used could also be selected from $(C_1-C_{10})$ alcohols such as ethanol, propanol, isopropanol, and the like, or mixtures thereof. In one aspect, the temperature of the reaction could be maintained from about 25° C. to about 50° C., and the duration of the reaction typically could range from about 1 hour to about 6 hours.

The compound of formula (Iu) could be converted to a compound of formula (I) by benzylation with a compound of formula (If) wherein $X^1$ can be a leaving group such as halogen, mesyloxy, and the like, in the presence of a base such as sodium hydride and a solvent such as dimethylformamide. The base could also be selected from potassium hydride, other hydrides, and the like. The reaction could also be conducted in the presence of a solvent, which includes acetonitrile, tetrahydrofuran, toluene and the like. Typically, the temperature of the reaction could be in the range from about 25° C. to about 60° C.

In yet another aspect, the present invention provides a general process for the preparation of compound of formula (I), wherein $R^1$ can be $(CHR^x)_nR^5$, wherein n is 1 and all other substituents are as defined above. This general process is depicted in the following scheme.

Scheme 5

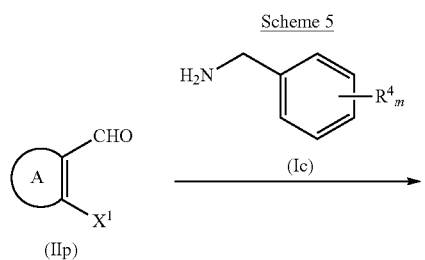

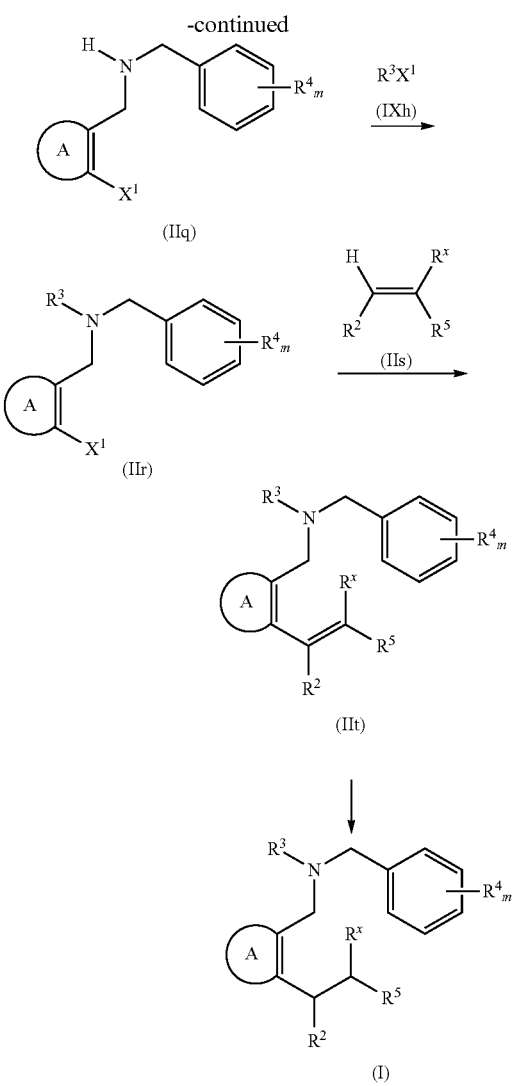

$R^x$, $R^2$, and $R^5$ are independently H, alkyl, aryl, heteroaryl, or alkoxy;
$R^3$ is alkyl, H, $CO_2R^6$, $COR^8$, $SO_2R^8$, $CONR^6R^7$, or $CSNR^6R^7$ In this scheme, the compound of formula (IIp) could be converted to a compound of formula (IIq) by reductive amination with a compound of formula (Ic) in the presence of acetic acid, a solvent such as methanol, and a reducing agent such as sodium cyanoborohydride. The reaction could also be carried out in the presence of diluted hydrochloric acid. The solvent used could also be selected from $(C_1-C_{10})$ alcohol such as ethanol, propanol, isopropanol, and the like, or their mixtures thereof. In one aspect, the temperature of the reaction could be maintained from about 25° C. to about 35° C., and the duration of the reaction typically could range from about 30 minutes to about 5 hours.

The compound of formula (IIq) could be converted to a compound of formula (1 hr), wherein $R^3$ can be $CO_2R^6$, by acylation with a compound of formula (IXh), in the presence of a base such as potassium carbonate, and a solvent such as tetrahydrofuran. The reaction could also be carried out in the presence of other suitable solvents, such as tetrahydrofuran, acetone, acetonitrile, and the like. In one aspect, the temperature of the reaction could be maintained from about 22° C. to about 50° C., and the duration of the reaction typically could range from about 4 hours to about 12 hours.

The Heck-type carbon-carbon bond formation reaction could be conducted between a compound of formula (IIr) and a compound of formula (IIs), wherein $R^x$, $R^2$, and $R^5$, independently can be selected from hydrogen, alkyl, aryl, heteroaryl, cyano, carbalkoxy, or alkoxy. Synthetic methods include, for example, formation of compound of formula (IIt) from the heteroaryl halide (IIr) and an olefin (IIs) in the presence of a palladium catalyst such as palladium acetate, a phosphorus ligand such as triphenylphosphine, a base such as triethylamine (TEA), and a suitable solvent, such as tetrahydrofuran. The reaction could also be carried out in the presence of other suitable solvents, such as toluene, xylene, N,N-dimethylformamide, diethyl ether, 1,4-dioxane, and the like. Further, this reaction could be carried out in the presence of from about 1 mol % to about 10 mol % of palladium catalyst, which include but are not limited to, $PdCl_2$, $Pd_2(dba)_3$, $Pd(PPh_3)_4$, and the like. The reaction could also be accomplished in the presence of a ligand, which includes tributylphosphine, triarylphosphine, DPPF, BINAP, DIPHOS, and the like. Further, the reaction could be carried out in the presence of other bases, which include sodium carbonate, potassium carbonate, sodium acetate, and the like. Typically, the temperature of the reaction could be in the range from about 50° C. to about 125° C. [see: Franzen, R., *Canadian Journal of Chemistry*, 78: pp. 957-962 (2000); Negishi, E. et al., *Chemical Review*, Vol. 96: pp. 365-394 (1996)].

The compound of formula (I), wherein $R^1$ can be $(CHR^x)_n R^5$, where n is 1, and all other substituents and abbreviations are as defined herein, could be obtained by reduction of a compound of formula (IIt). Synthetic methods of reduction include, but are not lmited to, catalytic hydrogenation, wherein catalyst include approximately a 5-10% palladium on carbon, Raney-nickel, sodium (or other appropriate metal(s)) amalgam, in the presence of hydrogen (typically from about 1 psi to about 50 psi), in a polar solvent such as ethanol, tetrahydrofuran, and the like. Typically, the temperature of the reaction could be in the range of about 25° C. to about 60° C.

In a further aspect, compounds of formula (I) wherein $R^1$ is $(CH_2)_n R^d CO_2 R^e$ and $R^2$ is alkyl, and unspecified substitutents are selected as disclosed above for formula (I), can be prepared by following an analogous procedure as described in Schemes 1 through 5, using precursors, starting materials, and reagents having the appropriate substitutions.

In still another aspect, compounds according to the present invention could be prepared according to the following scheme.

Scheme 6

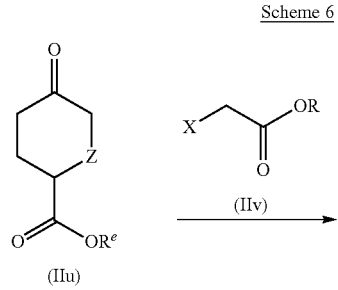

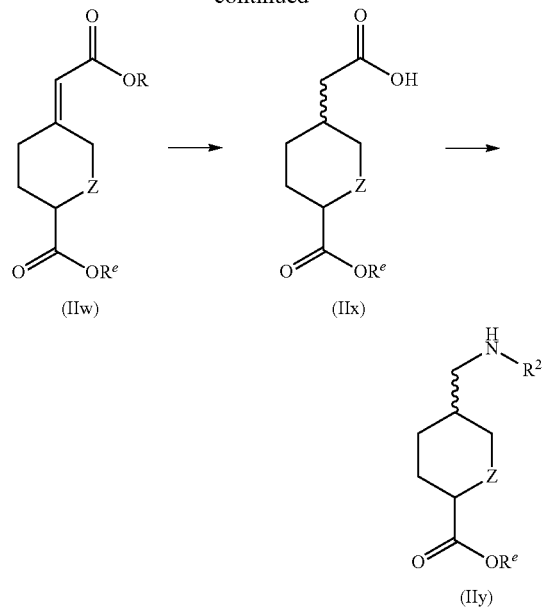

In this scheme, compounds of formula (IIy) could be prepared by starting from a compound of formula (IIu), wherein Z is: $(CH_2)_r$ and r is an integer from 0 to 2, inclusive, N, or O; and $R^e$ is defined according to formula (I); by procedures known to one of ordinary skill. The applicable synthetic methods include, for example, the following sequence of reaction steps: 1) Wittig reaction; 2) reduction; 3) hydrolysis of the ester; and 4) conversion to the amine.

Compound of formula (IIy) could be reacted with a compound of formula (Ia) or (Ig) of Scheme 1 or Scheme 3 to obtain the corresponding compound of formula (I).

Further, compounds of the formulas provided herein, including, but not limited to, compounds of formula (I), (Ia), (Ia'), (II), (IIa), (IIb), (IIc), (III), (IIIa), (IIIb), (IIIc), (IV), (IVa), (IVb), (IVc), (V), (Va), (Vb), (Vc), (VI), (VIa), (VIb), (VIc), (VII), (VIIa), (VIIb), (VIIc), (VIII), (VIIIa), (VIIIb), (VIIIc), (II-1), (IIa-1), (IIb-1), (III-1), (IIIa-1), (IIIb-1), (IV-1), (IVa-1), (IVb-1), (V-1), (Va-1), (Vb-1), (VI-1), (VIa-1), (VIb-1), (VII-1), (VIIa-1), (VIIb-1), (VIII-1), (VIIIa-1), and (VIIIb-1), and the like, can be prepared by following analogous procedures with the appropriate starting materials and reagents, as described in Schemes 1 through 6.

In another aspect of this invention, the compounds provided in the following table could be synthesized according to at least one of Schemes 1 through 6, as disclosed herein.

TABLE 19

Representative compounds that can be prepared according to at least one of Schemes 1 through 6.

| Entry | Compound |
|---|---|
| 1. | (5-{[(3,5-difluorobenzyl)-(2-methyl-2H-tetrazol-5yl)-amino]-methyl}-1,3-dimethyl-1H-pyrazolo[3,4-b]pyridin-6-yl)-dimethyl-amine |
| 2. | Ethyl-(1-ethyl-5-{[(3-fluoro-5-trifluoromethylbenzyl)-(2-methyl-2H-tetrazol-5-yl)amino]methyl}-3-methyl-1H-pyrazolo[3,4-b]pyridin-6-yl)-methyl-amine |
| 3. | (5-{[(3,5-bis-trifluoromethylbenzyl)-(2-methyl-2H-tetrazol-5-yl)-amino]-methyl}-1,3-dimethyl-1H-pyrazolo[3,4-b]pyridin-6-yl)-dimethyl-amine |

TABLE 19-continued

Representative compounds that can be prepared according to at least one of Schemes 1 through 6.

Entry  Compound 4. (5-{[(3,5-bis-trifluoromethylbenzyl)-(2-methyl-2H-tetrazol-5-yl)-amino]-methyl}-1-methyl-1H-pyrazolo[3,4-b]pyridin-6-yl)-dimethyl-amine
5. (5-{[(3,5-difluorobenzyl)-(2-methyl-2H-tetrazol-5yl)-amino]-methyl}-1-ethyl-3-methyl-1H-pyrazolo[3,4-b]pyridin-6-yl)-ethyl-methyl-amine
6. ethyl-(1-ethyl-5-{[(3-fluoro-5-trifluoromethylbenzyl)-(2-methyl-2H-tetrazol-5-yl)-amino]-methyl}-3-methyl-1H-pyrazolo[3,4b]pyridin-6-yl)-methyl-amine
7. (5-{[(3,5-bis-trifluoromethylbenzyl)-(2-methyl-2H-tetrazol-5-yl)-amino]-methyl}-1-ethyl-3-methyl-1H-pyrazolo[3,4-b]pyridin-6-yl)-ethyl-methyl-amine
8. (5-{[(3,5-bis-trifluoromethylbenzyl)-(2-methyl-2H-tetrazol-5-yl)-amino]-methyl}-1-ethyl-1H-pyrazolo[3,4-b]pyridin-6-yl)-ethyl-methyl-amine
9. (5-{[(3-bis-trifluoromethyl-benzyl)-(2-methyl-2H-tetrazol-5-yl)-amino]-methyl}-1,3-diethyl-1H-pyrazolo[3,4-b]pyridin-6-yl)-ethyl-methyl-amine
10. (1,3-diethyl-5-{[(3-fluoro-5-trifluoromethyl-benzyl)-(2-methyl-2H-tetrazol-5-yl)-amino]-methyl}-1H-pyrazolo[3,4-b]pyridin-6-yl)-ethyl-methyl-amine
11. (5-{[(3,5-bis-trifluoromethylbenzyl)-(2-methyl-2H-tetrazol-5-yl)-amino]-methyl}-1,3-diethyl-1H-pyrazolo[3,4-b]pyridin-6-yl)-ethyl-methyl-amine
12. (5-{[(3,5-bis-trifluoromethylbenzyl)-(2-methyl-2H-tetrazol-5-yl)-amino]-methyl}-1-ethyl-1H-pyrazolo[3,4-b]pyridin-6-yl)-ethyl-methyl-amine
13. (6-{[(3,5-difluorobenzyl)-(2-methyl-2H-tetrazol-5-yl)-amino]-methyl}-2,3-dimethyl-3H-imidazo[4,5-b]pyridin-5-yl)-dimethyl-amine
14. (6-{[(3-fluoro-5-trifluoromethylbenzyl)-(2-methyl-2H-tetrazol-5-yl)-amino]-methyl}-2,3-dimethyl-3H-imidazo[4,5-b]pyridin-5-yl)-dimethyl-amine
15. (6-{[(3,5-bis-trifluoromethylbenzyl)-(2-methyl-2H-tetrazol-5-yl)-amino]-methyl}-2,3-dimethyl-3H-imidazo[4,5-b]pyridin-5-yl)-dimethyl-amine
16. (6-{[(3,5-bis-trifluoromethyl-benzyl)-(2-methyl-2H-tetrazol-5-yl)-amino]-methyl}-2,3-dimethyl-3H-imidazo[4,5-b]pyridin-5-yl)-dimethyl-amine
17. (6-{[(3,5-difluorobenzyl)-(2-methyl-2H-tetrazol-5-yl)-amino]-methyl}-3-ethyl-2-methyl-3H-imidazo[4,5-b]pyridin-5-yl)-ethyl-methyl-amine
18. ethyl-(3-ethyl-6-{[(3-fluoro-5-trifluoromethylbenzyl)-(2-methyl-2H-tetrazol-5-yl)-amino]-methyl}-2-methyl-3H-imidazo[4,5-b]pyridin-5-yl)-methyl-amine
19. (6-{[(3,5-bis-trifluoromethylbenzyl)-(2-methyl-2H-tetrazol-5-yl)-amino]-methyl}-3-ethyl-2-methyl-3H-imidazo[4,5-b]pyridin-5-yl)-ethyl-methyl-amine
20. (6-{[(3,5-bis-trifluoromethylbenzyl)-(2-methyl-2H-tetrazol-5-yl)-amino]-methyl}-3-ethyl-3H-imidazo[4,5-b]pyridin-5-yl)-ethyl-methyl-amine
21. (6-{[(3,5-bis-trifluoromethylbenzyl)-(2-methyl-2H-tetrazol-5-yl)-amino]-methyl}-2,3-diethyl-3H-imidazo[4,5-b]pyridin-5-yl)-ethyl-methyl-amine
22. (2,3-diethyl-6-{[(3-fluoro-5-triflumethylbenzyl)-(2-methyl-2H-tetrazol-5-yl)-amino]-methyl}-3H-imidazo[4,5-b]pyridin-5-yl)-ethyl-methyl-amine
23. (6-{[(3,5-bis-trifluoromethylbenzyl)-(2-methyl-2H-tetrazol-5-yl)-amino]-methyl}-2,3-diethyl-3H-imidazo[4,5-b]pyridin-5-yl)-ethyl-methyl-amine
24. (6-{[(3,5-bis-trifluoromethylbenzyl)-(2-methyl-2H-tetrazol-5-yl)-amino]-methyl}-3-ethyl-3H-imidazo[4,5-b]pyridin-5-yl)-ethyl-methyl-amine
25. (5-{[(3,5-difluorobenzyl)-(2-methyl-2H-tetrazol-5-yl)-amino]-methyl}-1,2-dimethyl-1H-pyrrolo[2,3-b]pyridin-6-yl)-dimethyl-amine
26. (5-{[(3-fluoro-5-trifluoromethylbenzyl)-(2-methyl-2H-tetrazol-5-yl)-amino]-methyl}-1,2dimethyl-1H-pyrrolo[2,3-b]pyridin-6-yl)-dimethyl-amine
27. (5-{[(3,5-bis-trifluoromethylbenzyl)-(2-methyl-2H-tetrazol-5-yl)-amino]-methyl}-1,2-dimethyl-1H-pyrrolo[2,3-b]pyridin-6-yl)-dimethyl-amine
28. (5-{[(3,5-bis-trifluoromethyl-benzyl)-(2-methyl-2H-tetrazol-5-yl)-amino]-methyl}-1-methyl-1H-pyrrolo[2,3-b]pyridin-6-yl)-dimethyl-amine
29. (5-{[(3,5-difluorobenzyl)-(2-methyl-2H-tetrazol-5-yl)-amino]-methyl}-1-ethyl-2-methyl-1H-pyrrolo[2,3-b]pyridin-6-yl)-ethyl-methyl-amine
30. ethyl-(1-ethyl-5-{[(3-fluoro-5-trifluoromethyl-benzyl)-(2-methyl-2H-tetrazol-5-yl)-amino]-methyl}-2-methyl-1H-pyrrolo[2,3-b]pyridin-6-yl)-methyl-amine
31. (5-{[(3,5-bis-trifluoromethylbenzyl)-(2-methyl-2H-tetrazol-5-yl)-amino]-methyl}-1-ethyl-2-methyl-1H-pyrrolo[2,3b]pyridin-6-yl)-ethyl-methyl-amine
32. (5-{[(3,5-bis-trifluoromethylbenzyl)-(2-methyl-2H-tetrazol-5-yl)-amino]-methyl}-1-ethyl-1H-pyrrolo[2,3-b]pyridin-6-yl)ethyl-methyl-amine
33. (5-{[(3,5-bis-trifluoromethylbenzyl)-(2-methyl-2H-tetrazol-5-yl)-amino]-methyl}-1,2-diethyl-1H-pyrrolo[2,3-b]pyridin-6-yl)-ethyl-methyl-amine
34. (1,2-diethyl-5-{[(3-fluoro-5-trifluoromethylbenzyl)-(2-methyl-2H-tetrazol-5-yl)-amino]-methyl}-1H-pyrrolo[2,3-b]pyridin-6-yl)-ethyl-methyl-amine
35. (5-{[(3,5-bis-trifluoromethylbenzyl)-(2-methyl-2H-tetrazol-5-yl)-amino]-methyl}-1,2-diethyl-1H-pyrrolo[2,3-b]pyridin-6-yl)-ethyl-methyl-amine
36. (5-{[(3,5-bis-trifluoromethylbenzyl)-(2-methyl-2H-tetrazol-5-yl)-amino]-methyl}-1-ethyl-1H-pyrrolo[2,3-b]pyridin-6-yl)ethyl-methyl-amine Methods of Treating Diseases Compounds disclosed herein to control CETP activity can be used for preventing or treating a variety of conditions or diseases such as ones associated with lipoprotein metabolism. Without being held to a particular theory, it is believed that CETP activity can affect the level of circulating cholesterol-containing HDL. Increased CETP can produce a decrease in HDL-C levels relative to LDL-C and/or VLDL-C levels. For example, CETP plays a role in transferring cholesteryl ester from HDL to VLDL and LDL, and thereby in altering the relative profile of circulating lipoproteins to one which is associated with an increased risk of cardiovascular disease (for example, decreased levels of HDL-C and increased levels of VLDL-C and LDL-C). Further, increased levels of CETP activity can be predictive of increased risk of cardiovascular disease. Modulation or inhibition of CETP activity, therefore, can be a prophylactic or therapeutic method for modulating the relative levels of lipoproteins to reduce or prevent the progression of, to induce regression of, or reduce risk of development of a variety of conditions or diseases including cardiovascular diseases, such as atherosclerosis.

Effective amounts are administered to the subject in dosages and formulations that are safe and effective, including, but not limited to, the ranges taught herein. As disclosed herein, compositions comprising at least one compound having a formula as disclosed herein, and/or their pharmaceutically-acceptable salts, can be used in conjunction with other prophylactic or therapeutic agents or in methods optionally comprising steps such as altered patient activities, including, but not limited to, changes in exercise or diet.

In one aspect, the present invention provides a method of treating or preventing a condition or disease in a mammalian subject, the method comprising administering to the subject a composition comprising a prophylactically- or therapeutically-effective amount of at least one compound having a formula as disclosed herein, and/or their pharmaceutically-acceptable salts. In various aspects, the condition or disease is dyslipidemia, atherosclerosis, a peripheral vascular disease, hypertryglyceridemia, hypercholesterolemia, hyperbetalipoproteinemia, hypoalphalipoproteinemia, a cardiovascular disorder (i.e., angina, ischemia, stroke, myocardial infarction (MI), reperfusion injury, restenosis, hypertension) or diabetic vascular diseases (i.e., diabetic retinopathy, endotoxemia).

In one other aspect, the present invention provides a method of decreasing or inhibiting CETP activity in a mammalian subject, the method comprising administering to the subject an amount of a composition comprising at least one compound having a formula as disclosed herein, and/or their pharmaceutically-acceptable salts, wherein the amount is sufficient to decrease or inhibit CETP activity in the subject.

In still another aspect, the present invention provides a method of increasing high density lipoprotein (HDL) in a mammalian subject, the method comprising administering to the subject an amount of a composition comprising at least one compound having a formula as disclosed herein, and/or their pharmaceutically-acceptable salts, wherein the amount is sufficient to increase high density lipoprotein (HDL) in the subject.

In another aspect, the present invention provides a method of elevating the ratio of circulating HDL to circulating LDL, VLDL, or total cholesterol in a mammalian subject, the method comprising administering to the subject a prophylactically- or therapeutically-effective amount of at least one compound having a formula as disclosed herein, and/or their pharmaceutically-acceptable salts.

In yet another aspect, the present invention provides a method of altering catabolism of HDL-cholesterol to decrease development of atherosclerotic lesions in a mammalian subject, the method comprising administering to the subject an amount of a composition comprising at least one compound having a formula as disclosed herein, and/or their pharmaceutically-acceptable salts, wherein the amount is sufficient to alter the catabolism of HDL-cholesterol thereby leading to decreased development of atherosclerotic lesions.

In still another aspect, the present invention provides a method of decreasing low density lipoprotein (LDL) in a mammalian subject, the method comprising administering to the subject an amount of a composition comprising at least one compound having a formula as disclosed herein, and/or their pharmaceutically-acceptable salts, wherein the amount is sufficient to decrease low density lipoprotein (LDL).

In another aspect, the present invention provides a method of treating or preventing atherosclerosis in a mammalian subject, the method comprising administering to the subject a prophylactically- or therapeutically-effective amount of at least one compound having a formula as disclosed herein, and/or their pharmaceutically-acceptable salts.

In yet another aspect, the present invention provides a method of treating or preventing hyperlipidemia in a mammalian subject, the method comprising administering to the subject a prophylactically- or therapeutically-effective amount of at least one compound having a formula as disclosed herein, and/or their pharmaceutically-acceptable salts.

In another aspect of the present invention, this invention provides a method of treating or preventing a CETP-mediated disorder in a mammalian subject, the method comprising administering to the subject a prophylactically- or therapeutically-effective amount of at least one compound having a formula as disclosed herein, and/or their pharmaceutically-acceptable salts.

In yet another aspect, the present invention provides a method of treating or preventing dyslipidemia, atherosclerosis, a peripheral vascular disease, hypertryglyceridemia, hypercholesterolemia, hyperbetalipoproteinemia, hypoalphalipoproteinemia, a cardiovascular disorder, a diabetic vascular disease, or endotoxemia. In one aspect, the cardiovascular disorder is angina, ischemia, stroke, myocardial infarction (MI), reperfusion injury, restenosis or hypertension.

The compounds of the present invention are useful in the treatment and/or prophylaxis of the above said diseases in combination/concomittant with one or more LDL-cholesterol lowering agents such as HMG CoA reductase inhibitors; cholesterol absorption inhibitors; antiobesity drugs; lipoprotein disorder treatment drugs; hypoglycemic agents: insulin; biguanides; sulfonylureas; thiazolidinediones; dual PPAR agonists; and/or mixtures thereof. The compounds of the present invention in combination with HMG CoA reductase inhibitors, microsomal triglyceride transfer protein (MTP)/ApoB secretion inhibitors, cholesterol absorption inhibitors, antiobesity drugs, hypoglycemic agents can be administered together or within in such a period of time so as to act synergistically.

In one aspect, the present invention provides a prophylactic or therapeutic composition comprising at least one compound having a formula as disclosed herein, and/or their pharmaceutically-acceptable salts and, optionally an antihypertensive agent. Hypertension can be characterized as persistently high blood pressure. Illustratively, an adult having a systolic blood pressure that is persistently at least about 140 mmHg or a diastolic blood pressure that is at least about 90 mmHg can be classified as hypertensive. Hyperlipidemic conditions such as atherosclerosis can have an affect on hypertension.

The dosage regimen utilizing, the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Compounds and compositions of the present invention can be administered by any appropriate route, including, for example, orally, parenterally, intravenously, intradermally, intramuscularly, subcutaneously, sublingually, transdermally, bronchially, pharyngolaryngeal, intranasally, topically such as by a cream or ointment, rectally, intraarticular, intracisternally, intrathecally, intravaginally, intraperitoneally, intraocularly, by inhalation, bucally or as an oral or nasal spray.

Oral dosages of compositions of the present invention, when used for the indicated effects, will range from about 0.01 mg per kg of body weight per day (mg/kg/day) to about 100 mg/kg/day. Advantageously, compounds of the present invention can be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be substantially continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or betalactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Pharmaceutical Compositions

In one aspect, the present invention provides a composition comprising at least one compound as disclosed herein.

In another aspect, this invention provides a pharmaceutical composition, comprising:

at least one compound as disclosed herein; and optionally comprising a pharmaceutically acceptable additive selected from a carrier, an auxiliary, a diluent, an excipient, a preservative, a solvate, or any combination thereof.

In yet another aspect, this invention provides a pharmaceutical composition, comprising:

at least one compound as disclosed herein; and optionally comprising a pharmaceutically acceptable additive selected from a carrier, an auxiliary, a diluent, an excipient, a preservative, a solvate, or any combination thereof;

wherein the pharmaceutical composition is in the form of a tablet, a capsule, a syrup, a cachet, a powder, a granule, a solution, a suspension, an emulsion, a bolus, a lozenge, a suppository, a cream, a gel, a paste, a foam, a spray, an aerosol, a microcapsule, a liposome, or a transdermal patch.

In still another aspect, this invention provides a pharmaceutical composition, comprising:

at least one compound as disclosed herein;

optionally comprising a pharmaceutically acceptable additive selected from a carrier, an auxiliary, a diluent, an excipient, a preservative, a solvate, or any combination thereof; and further comprising an agent selected from a chemotherapeutic agent, an immunosuppressive agent, a cytokine, a cytotoxic agent, an anti-inflammatory agent, an antirheumatic agent, an antidyspilidemic agent, a cardiovascular agent, or any combination thereof.

Accordingly, in addition to the compounds disclosed herein, the pharmaceutical compositions of the present invention can further comprise at least one of any suitable auxiliary such as, but not limited to, diluent, binder, stabilizer, buffers, salts, lipophilic solvents, preservative, adjuvant, or the like. In one aspect of the present invention, pharmaceutically acceptable auxiliaries are employed. Examples and methods of preparing such sterile solutions are well known in the art and can be found in well known texts such as, but not limited to, REMINGTON'S PHARMACEUTICAL SCIENCES (Gennaro, Ed., 18th Edition, Mack Publishing Co. (1990)). Pharmaceutically acceptable carriers can be routinely selected that are suitable for the mode of administration, solubility and/or stability of the compound.

Pharmaceutical Compositions for Oral Administration

For oral administration in the form of a tablet or capsule, a compound can be combined with an oral, non-toxic pharmaceutically acceptable inert carrier such as ethanol, glycerol, water, and the like. Moreover, when desired or necessary, suitable binders, lubricants, disintegrating agents, and coloring agents may also be incorporated into the mixture. Suitable binders include, without limitation, starch; gelatin; natural sugars such as glucose or beta-lactose; corn sweeteners; natural and synthetic gums such as acacia, tragacanth, or sodium alginate, carboxymethylcellulose; polyethylene glycol; waxes; and the like. Lubricants used in these dosage forms include, without limitation, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The pharmaceutical preparations contain at least one compound of the present invention represented by any formula disclosed herein, and/or a pharmaceutically acceptable salt thereof, in an amount effective to inhibit CETP activity and prevent or treat the various conditions or diseases attributable to CETP activity. One skilled in the art can easily determine such an effective amount. The preparations optionally can contain other ingredients including, for example, an antihypertensive drug.

Formulations of the present invention suitable for oral administration can be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, and the like.

Routes of Administration

The invention further relates to the administration of at least one compound disclosed herein by the following routes, including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means.

Dosages

A composition comprising at least one compound of the present invention can be administered at a frequency and for a period of time effective to achieve a therapeutic effect, which should be understood in the context of a regimen of repeated administration at such a frequency and over such a period. In some aspects, a composition is administered at a frequency and for a period of time effective to increase a HSPG expression. In some aspects, a composition can be administered in a single daily dose, or a total daily dosage can be administered in divided doses of two, three, or four times daily. Typically and most conveniently, a composition is administered at least once daily, but in certain situations less frequent, e.g., twice weekly or weekly, administration can be effective. For greatest benefit, administration should continue for a prolonged period, for example at least about 3 months, or at least about 6 months, or at least about 1 year, or at least about 2 years, or at least about 3 years. In one aspect, administration continues from a time of initiation for substantially the remainder of the mammal's life.

The selection and/or amounts of individual compounds can, if desired vary over the period of administration. In one aspect, a single composition of this invention is administered to a mammal for the entire period of administration. In other aspects, different compositions comprising at least one compound are administered to the mammal at different times.

The dosages of compounds can be adjusted on a per body weight basis and may thus be suitable for any subject regardless of the subject's size.

In one aspect of this invention, daily oral dose comprises a total compound amount of at least about 0.0001 mg per kg body weight, illustratively about 0.0001 mg to about 1000 mg, about 0.001 mg to about 100 mg, about 0.01 mg to about 10 mg, about 0.1 mg to about 5 mg, or about 1 to about 3 mg per kg body weight.

In another aspect, a daily intravenous injection comprises a total compound amount of at least about 0.0001 mg per kg body weight, illustratively about 0.0001 mg to about 0.5 mg, about 0.001 mg to about 0.25, or about 0.01 to about 0.03 mg per kg body weight.

Illustratively, a tablet for oral administration can be manufactured to comprise a total compound amount of about 0.001 mg, about 0.1 mg, about 0.2 mg, about 0.5 mg, about 1 mg, about 2 mg, about 5 mg, about 10 mg, about 15 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 800 mg, about 900 mg, or about 1000 mg.

In one aspect, a composition comprises an active ingredient content of at least about 0.01% by weight of the composition, illustratively about 0.01% to about 99%, about 0.05% to about 90%, about 0.1% to about 80%, about 0.5% to about 50% by weight of the composition. The amount of active ingredient that can be combined with other materials to produce a single dosage form varies depending upon the subject treated and the particular mode of administration.

An effective amount of the drug is ordinarily supplied at a dosage level of from about 0.1 mg/kg to about 20 mg/kg of body weight per day. In one aspect, the range is from about 0.2 mg/kg to about 10 mg/kg of body weight per day. In another aspect, the range is from about 0.5 mg/kg to about 10 mg/kg of body weight per day. The compounds can be administered on a regimen of about 1 to about 10 times per day.

Co-administration or sequential administration of the compounds of the present invention and other therapeutic agents can be employed, such as chemotherapeutic agents, immunosuppressive agents, cytokines, cytotoxic agents, nucleolytic compounds, radioactive isotopes, receptors, and prodrug activating enzymes, which can be naturally occurring or produced by recombinant methods. The combined administration includes co-administration, using separate formulations or a single pharmaceutical formulation, and consecutive administration in either order, wherein preferably there is a time period while both (or all) active therapeutic agents simultaneously exert their biological activities.

It is to be understood that this invention is not limited to the particular methodology, syntheses, formulations, protocols, cell lines, constructs, and reagents described herein and as such can vary. It is also to be understood that the terminology used herein is for the purpose of describing particular aspects only, and is not intended to limit the scope of the present invention.

All publications, patents, and other references mentioned herein are provided for the purpose of describing and disclosing, for example, the constructs and methodologies that are described in these references, which might be used in connection with the presently described invention.

DEFINITIONS AND TERMINOLOGY

The groups defined for various symbols used in the formulas of this disclosure, as well as the optional substituents defined on those groups, can be defined as follows. Unless otherwise specified, any recitation of the number of carbon atoms in a particular group is intended to refer to the unsubstituted "base" group, therefore, any substituent recited on a base group is described by its own definition, including its own limitation of the number of carbon atoms. Unless otherwise specified, all structural isomers of a given structure, for example, all enantiomers, diasteriomers, and regioisomers, are included within this definition.

The terms "halogen" or "halo" includes fluorine, chlorine, bromine, or iodine.

The term "alkyl" group is used to refer to both linear and branched alkyl groups. Exemplary alkyl groups include, but are not limited to, methyl, ethyl, propyl, butyl, pentyl, hexyl, heptyl, octyl, nonyl, or decyl, and the like. Unless otherwise specified, an alkyl group has from 1 to 12 carbon atoms. Also unless otherwise specified, all structural isomers of a given structure, for example, all enantiomers and all diasteriomers, are included within this definition. For example, unless otherwise specified, the term propyl is meant to include n-propyl and iso-propyl, while the term butyl is meant to include n-butyl, iso-butyl, t-butyl, sec-butyl, and so forth.

The term "aryl" refers to an optionally substituted monocylic or polycyclic aromatic ring system of 6 to 14 carbon atoms. Exemplary groups include phenyl, naphthyl, 1,2,3,4-tetrahydronaphthalene, indane, fluorene, and the like. Unless otherwise specified, an aryl group typically has from 6 to 14 carbon atoms.

"Aralkyl" refers to an aryl substituted alkyl group, wherein the aryl group and the alkyl group are defined herein. Typically, the aryl group can have from 6 to 14 carbon atoms, and the alkyl group can have up to 10 carbon atoms. Exemplary aralkyl groups include, but are not limited to, benzyl, phenylethyl, phenylpropyl, phenylbutyl, propyl-2-phenylethyl and the like.

The term "haloalkyl" refers to a group containing at least one halogen and an alkyl portion as define above, that is, a haloalkyl is a substituted alkyl group that is substituted with one or more halogens. Unless otherwise specified, all structural isomers of a given structure, for example, all enantiomers and all diasteriomers, are included within this definition. Exemplary haloalkyl groups include fluoromethyl, chloromethyl, fluoroethyl, chloroethyl, trifluoromethyl, and the like. Unless otherwise specified, a haloalkyl group has from 1 to 12 carbon atoms.

A "cycloalkyl" group refers to a cyclic alkyl group which can be mono or polycyclic. Exemplary cycloalkyl groups include cyclopropyl, cyclobutyl, cyclopentyl, cyclohexyl, cycloheptyl, cyclooctyl, cyclononyl, and cyclodecyl. Unless otherwise specified, a cycloalkyl group has from 3 to 12 carbon atoms.

An "alkoxy" group refers to an —O(alkyl) group, where alkyl is as defined herein. Therefore, unless otherwise specified, all isomers of a given structure are included within a definition. Exemplary alkyl groups include methoxy, ethoxy, n-propoxy, iso-propoxy, n-butoxy, iso-butoxy, t-butoxy, and the like. Unless otherwise specified, an alkoxy group has from 1 to 12 carbon atoms. Unless otherwise specified, all structural isomers of a given structure, for example, all enantiomers and all diasteriomers, are included within this definition. For example, unless otherwise specified, the term propoxy is meant to include n-propoxy and iso-propoxy.

An "aryloxy" group refers to an —O(aryl) group, where aryl is as defined herein. Thus, the aryl portion of an aryloxy group can be substituted or unsubstituted. Exemplary aryloxy groups include, but are not limited to, phenoxy, naphthyl, and the like. Unless otherwise specified, an aryloxy group typically has from 6 to 14 carbon atoms.

"Haloalkoxy" refers to an alkoxy group with a halo substituent, where alkoxy and halo groups are as defined above. Exemplary haloalkoxy groups include fluoromethoxy, chloromethoxy, trifluoromethoxy, trichloroethoxy, fluoroethoxy, chloroethoxy, trifloroethoxy, perfluoroethoxy (—OCF$_2$CF$_3$), trifluoro-t-butoxy, hexafluoro-t-butoxy, perfluoro-t-butoxy (—OC(CF$_3$)$_3$), and the like. Unless otherwise specified, an haloalkoxy group typically has from 1 to 12 carbon atoms.

"Alkylthio" refers to an —S(alkyl) goup, where alkyl group is as defined above. Exemplary alkyl groups include methylthio, ethylthio, propylthio, butylthio, iso-propylthio, iso-butylthio, and the like. Unless otherwise specified, an alkylthio group typically has from 1 to 12 carbon atoms.

"Heteroaryl" is an aromatic monocyclic or polycyclic ring system of 4 to 10 carbon atoms, having at least one heteroatom or heterogroup selected from —O—, >N—, —S—, >NH or NR, and the like, wherein R is a substituted or unsubstituted alkyl, aryl, or acyl, as defined herein. In this aspect, >NH or NR are considered to be included when the heteroatom or heterogroup can be >N—. Exemplary heteroaryl groups include as pyrazinyl, isothiazolyl, oxazolyl, pyrazolyl, pyrrolyl, triazolyl, tetrazolyl, oxatriazolyl, oxadiazolyl, pyridazinyl, thienopyrimidyl, furanyl, indolyl, isoindolyl, benzo[1,3]dioxolyl, 1,3-benzoxathiole, quinazolinyl, isoquinolinyl, quinolinyl, pyridyl, 1,2,3,4-tetrahydro-isoquinolinyl, 1,2,3,4-tetrahydro-quinolinyl pyridyl, thiophenyl, and the like. Unless otherwise specified, a heteroaryl group typically has from 4 to 10 carbon atoms. Moreover, the heteroaryl group can be bonded to the heterocyclic core structure at a ring carbon atom, or, if applicable for a N-substituted heteroaryl such as pyrrole, can be bonded to the heterocyclic core structure through the heteroatom that is formally deprotonated to form a direct heteroatom-pyrimdine ring bond.

"Heterocyclyl" is a non-aromatic, saturated or unsaturated, monocyclic or polycyclic ring system of 3 to 10 member having at least one heteroatom or heterogroup selected from —O—, >N—, —S—, >NR, >SO$_2$, >CO, and the like, wherein R is hydrogen or a substituted or an unstubstituted alkyl, aryl, or acyl, as defined herein. Exemplary heterocyclyl groups include aziridinyl, imidazolidinyl, 2,5-dihydro-[1,2,4]oxadiazolenyl, oxazolidinyl, isooxazolidinyl, pyrrolidinyl, piperdinyl, piperazinyl, morpholinyl, thiomorpholinyl, thiazolidinyl, 1,3-dioxolanyl, 1,4-dioxanyl, 2,5-dihydro-1H-imidazolyl, and the like. Unless otherwise specified, a heterocyclyl group typically has from 2 to 10 carbon atoms. A heterocyclyl group can be bonded through a heteroatom that is formally deprotonated or a heterocyclyl group can be bonded through a carbon atom of the heterocyclyl group.

"Heterocycloalkyl" refers to the saturated subset of a heterocyclyl, that is, a non-aromatic, saturated monocyclic or polycyclic ring system of 3 to 10 members having at least one heteroatom or heterogroup selected from —O—, >N—, —S—, >NR, >SO$_2$, >CO, and the like, wherein R is hydrogen or a substituted or an unstubstituted alkyl, aryl, or acyl, as defined herein. Exemplary heterocycloalkyl groups include aziridinyl, piperdinyl, piperazinyl, morpholinyl, thiazolidinyl, 1,3-dioxolanyl, 1,4-dioxanyl, and the like. Unless otherwise specified, a heterocycloalkyl group typically has from 2 to 10 carbon atoms, or in another aspect, from 2 to 6 carbon atoms. A heterocycloalkyl group can be bonded through a heteroatom that is formally deprotonated or a heterocycloalkyl group can be bonded through a carbon atom of the heterocycloalkyl group.

A "heteroaryloxy" group refers to an aryloxy-type analog of a heteroaryl group. Thus, a heteroaryloxy group is intended to describe a heteroaryl group as defined herein, that is bonded to an oxygen atom, to form a formal [O-heteroaryl] moiety. Unless otherwise specified, a heteroaryloxy group typically comprises from 4 to 10 carbon atoms.

A "cyclic" moiety, including a monocyclic moiety or a bicyclic moiety, unless otherwise specified, is intended to be inclusive of all the cyclic groups disclosed herein, for example, a heteroaryl group, a heterocyclyl group, a heterocycloalkyl group, and/or a heteroaryloxy group.

An "alkoxycarbonyl" group refers to a —C(O)O(alkyl) group, wherein the alkyl portion of the alkoxycarbonyl group is defined as herein. Examples of alkoxycarbonyl groups include, but are not limited to, methoxycarbonyl, ethoxycarbonyl, t-butoxycarbonyl and the like.

An "alkenyl" group is an aliphatic hydrocarbon group comprising an alkene functionality, regardless of the regiochemistry of the alkene functionality within the aliphatic hydrocarbon group. Unless otherwise specified, an alkenyl group typically has from 2 to 12 carbon atoms, and in another aspect, is a C$_2$-C$_{10}$ alkenyl group. Exemplary alkenyl groups include ethenyl, propenyl, butenyl, and the like, including all regiochemistries, thus, "butenyl" includes 1-butenyl, 2-butenyl, and 3-butenyl.

An "alkynyl" group is an aliphatic hydrocarbon group comprising an alkyne functionality, regardless of the regiochemistry of the alkyne functionality within the aliphatic hydrocarbon group. Unless otherwise specified, an alkynyl group typically has from 2 to 12 carbon atoms, and in another aspect, is a C$_2$-C$_{10}$ alkynyl group. Exemplary alkynyl groups include ethynyl, propynyl, butynyl, and the like, including all regiochemistries. Thus, "butynyl" includes 1-butynyl, 2-butynyl, and 3-butynyl.

An "alkoxyalkyl" group is an alkoxy-substituted alkyl group, wherein an alkoxy group and an alkyl group are defined herein. Unless otherwise specified, an alkoxyalkyl group typically has from 2 to 20 carbon atoms. In one aspect, an alkoxyalkyl group can be a (C$_1$-C$_{10}$)alkoxy group bonded to a (C$_1$-C$_{10}$)alkyl group, where alkoxy and alkyl groups are as defined here, including all stereochemistries and all regiochemistries. Exemplary alkoxyalkyl groups include methoxymethyl, methoxyethyl, methoxypropyl, ethoxymethyl, ethoxyethyl, methoxyisopropyl, ethoxyisobutyl, and the like.

An "aminoalkyl" group, as used herein, refers to an amino-substituted alkyl group, wherein an alkyl is defined herein. Unless otherwise specified, an aminoalkyl group can typically have from 1 to 12 carbon atoms, therefore, a typical aminoalkyl group can be an amino (C$_1$-C$_{12}$)alkyl, including all regiochemistries. Exemplary aminoalkyl groups include, but are not limited to, aminomethyl, aminoethyl, aminopropyl, and the like.

A "cycloalkyl-substitued alkyl" group, also termed a "cycloalkylalkyl" group, refers to an alkyl group that is substituted with a cycloalkyl substituent, wherein alkyl and cycloalkyl are defined herein. Thus, the cycloalkyl group portion can be a mono or polycyclic alkyl group. Unless otherwise specifed, a cycloalkylalkyl group can have up to 20 carbon atoms, regardless of how the carbon atoms are distributed between the alkyl portion and the cycloalkyl portion of the group, and including all possible sterochemistries and all regiochemistries. For example, in one aspect, a cycloalkyl-substituted alkyl can comprise a (C$_3$-C$_{10}$)cycloalkyl bonded to a C$_1$-C$_{10}$ alkyl group, wherein the cycloalkyl portion can be mono or polycyclic. Exemplary cycloalkylalkyl groups include, but are not limited to, cyclopropylmethyl, cyclopropylethyl, cyclopropylpropyl, cyclobutylmethyl, cyclobutylethyl, cyclobutylpropyl, cyclopentylmethyl, cyclopentylethyl, cyclopentylpropyl, cyclohexylmethyl, cyclohexylethyl, cyclohexylpropyl, cycloheptylmethyl, cycloheptylethyl, cyclooctylmethyl, cyclooctylethyl, cyclooctylpropyl, and the like.

A "cycloalkoxy" group, also refered to as a "cycloalkyloxy" group, refers herein to an —O(cycloalkyl) substituent, that is, an alkoxide-type moiety comprising a cycloalkyl group, wherein a cycloalkyl is defined herein. Thus, the cycloalkyl group portion can be a mono or polycyclic alkyl group, and unless otherwise specifed, a cycloalkylalkyl group can have up to 20 carbon atoms. In one aspect, a cycloalkoxy group can be a $(C_3\text{-}C_{10})$cycloalkyl-O— group. Exemplary cycloalkoxy groups include cyclopropoxy, cyclobutoxy, cyclopentoxy, cyclohexoxy, and the like.

An "acyl" group refers to a $(C_1\text{-}C_{10})$alkyl-CO— group, wherein the $(C_1\text{-}C_{10})$alkyl group is used in this structure to refer to the alkyl-linker moiety bonded both to the CO group, and to another chemical group. Examples of acyl groups include, but are not limited to, methylcarbonyl, ethylcarbonyl, propylcarbonyl, isopropylcarbonyl, and the like.

An "alkenylene" group refers to a $(C_2\text{-}C_{10})$ hydrocarbon linker comprising at least one C=C double bond within the $C_2\text{-}C_{10}$ chain. Examples of alkenylene groups include, but are not limited to, —CH=CH—, —CH$_2$—CH=CH, —CH$_2$—CH=CH—CH$_2$—, —CH$_2$—CH=CH—CH=CH—, and the like. Thus, unless otherwise specified, an alkenylene group has from 2 to 10 carbon atoms.

A "haloalkoxyalkyl" group refers to a haloalkyl-O—$(C_1\text{-}C_{10})$alkyl group, that is, a haloalkoxy-substituted alkyl group, wherein haloalkoxy and alkyl are defined herein. Unless otherwise specifed, a cycloalkylalkyl group can have up to 20 carbon atoms, regardless of how the carbon atoms are distributed between the haloalkoxy portion and the alkyl portion of the group, and including all possible sterochemistries and all regiochemistries. In one aspect, for example, a haloalkoxyalkyl is haloalkyl-O—$(C_1\text{-}C_{10})$alkyl, where group can be $(C_1\text{-}C_{10})$haloalkyl group bonded to a $(C_1\text{-}C_{10})$alkyl moiety. Exemplary haloalkoxyalkyl groups include trifluoromethoxymethyl, chloromethoxyethyl, flouroethoxyethyl, chloroethoxyethyl, trilfluoromethoxypropyl, hexafluoroethoxyethyl and the like.

A "monoalkylamino" group refers to an amino group that is substituted with a single alkyl group, that is, a mono($C_1$-$C_{20}$)alkylamino group. Unless otherewise specified, a monoalkylamino group can have up to 20 carbon atoms. In one aspect, a monoalkylamino group can be a $(C_1\text{-}C_{10})$alkyl-substitued amino group. Exemplary monoalkylamino groups include methylamino, ethylamino, propylamino, isopropylamino, and the like.

A "dialkylamino" group refers to an amino group that is substituted with two, independently-selected, alkyl groups, that is, a di($C_1$-$C_{10}$)alkylamino group. Unless otherewise specified, a dialkylamino group can have up to 20 carbon atoms. Exemplary dialkylamino groups include dimethylamino, diethylamino, and the like.

Further, the meaning of certain additional terms and phrases employed in the specification, can be defined as follows.

As used herein, the term "compound" includes both the singular and the plural, and includes any single entity or combined entities that have at least the affect disclosed herein and combinations, fragments, analogs or derivatives of such entities.

As used herein, the term "substance" refers broadly to any material of a particular kind or constitution. Examples of a "substance" can include, without limitation, a chemical element, a molecule, a compound, a mixture, a composition, an emulsion, a chemotherapeutic agent, a pharmacological agent, a hormone, an antibody, a growth factor, a cellular factor, a nucleic acid, a protein, a peptide, a peptidomimetic, a nucleotide, a carbohydrate, and combinations, fragments, analogs or derivatives of such entities.

The terms "treatment", "treating", "treat", and the like are used herein to refer generally to any process, application, therapy, etc., wherein a mammal is subject to medical attention with the object of obtaining a desired pharmacological and/or physiological effect for improving the mammal's condition or disease, directly or indirectly. The effect can be therapeutic in terms of a partial or complete stabilization or cure for a disease and/or adverse effect attributable to the disease. The effect also can include, for example, inhibition of disease symptom (i.e., arresting its development) or relieving disease symptom (i.e., causing regression of the disease or symptom).

A used herein, the term "therapeutically-effective amount" refers to that amount of at least one compound as disclosed herein, or their pharmaceutically-acceptable salts thereof, that is sufficient to bring about the biological or medical effect that is being sought in a mammal, system, tissue, or cell.

The term "preventing", "prevent", "prevention", and the like are used herein to refer generally to any process, application, therapy, etc., wherein a mammal is subject to medical attention with the object of obtaining a desired pharmacological and/or physiological effect for preventing onset of clinically evident condition or disease or preventing onset of a preclinically evident stage of a condition or disease. The effect can be prophylactic in terms of completely or partially preventing or reducing the risk of occurance of a condition or disease or symptom thereof.

A used herein, the term "prophylactically-effective amount" refers to that amount of a drug or pharmaceutical agent that will prevent or reduce the risk of occurrence of the biological or medical effect that is sought to be prevented in the cell, tissue, system, or mammal.

As used herein, the term "activation" refers to any alteration of a signaling pathway or biological response including, for example, increases above basal levels, restoration to basal levels from an inhibited state, and stimulation of the pathway above basal levels.

Generally a skill in the art is known that valance must be conserved for all the stable molecules. Therefore, the necessary implication that hydrogen atoms are necessary and available to complete the valance in all structures including Formula I unless expressly indicated otherwise.

Publications and patents mentioned herein are disclosed for the purpose of describing, for example, the constructs and methodologies that are provided in the publications and patents, which might be used in connection with the present invention. Nothing herein is to be construed as an admission that the inventors are not entitled to antedate such publications, patents, or other disclosure by virtue of prior invention.

To the extent that any definition or usage provided by any document incorporated herein by reference conflicts with the definition or usage provided herein, the definition or usage provided herein controls.

When Applicants disclose or claim a range of any type, for example a range of temperatures, a range of numbers of atoms, a molar ratio, or the like, Applicants' intent is to disclose or claim individually each possible number that such a range could reasonably encompass, as well as any sub-ranges and combinations of sub-ranges encompassed therein.

For example, when the Applicants disclose or claim a chemical moiety having a certain number of carbon atoms, Applicants' intent is to disclose or claim individually every possible number that such a range could encompass, consistent with the disclosure herein. For example, the disclosure that R is selected independently from an alkyl group having up to 12 carbon atoms, or in alternative language a $C_1$ to $C_{12}$ alkyl group, as used herein, refers to an R group that can be selected independently from a hydrocarbyl group having 1, 2, 3, 4, 5, 6, 7, 8, 9, 10, 11, or 12 carbon atoms, as well as any range between these two numbers for example a $C_3$ to $C_8$ alkyl group, and also including any combination of ranges between these two numbers for example a $C_3$ to $C_5$ and $C_7$ to $C_{10}$ hydrocarbyl group. In another example, by the disclosure that the molar ratio typically spans the range from about 0.1 to about 1.1, Applicants intend to recite that the molar ratio can be selected from about 0.1:1, about 0.2:1, about 0.3:1, about 0.4:1, about 0.5:1, about 0.6:1, about 0.7:1, about 0.8:1, about 0.9:1, about 1.0:1, or about 1.1:1.

Applicants reserve the right to proviso out or exclude any individual members of any such group, including any sub-ranges or combinations of sub-ranges within the group, that may be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, compounds, ligands, structures, or groups thereof, or any members of a claimed group, if for any reason Applicants choose to claim less than the full measure of the disclosure, for example, to account for a reference that Applicants may be unaware of at the time of the filing of the application.

The following references disclose certain heterocyclic compounds.

TABLE 20

References disclosing heterocyclic compounds.

| Publication or Pat. No. | Title |
|---|---|
| WO2005097806 | Preparation of heterocyclic piperidine derivatives as inhibitor of cholesterol ester transfer protein |
| WO2005095395 | Preparation of 1,2,3,4-tetrahydro-1,5-naphthyridin-4-amines as cholesteryl ester transfer protein inhibitors |
| WO2005095409 | Preparation of 1,2,3,4-tetrahydroquinolin-4-amines as cholesteryl ester transfer protein inhibitors |
| WO2005030185 | Method using cholesteryl ester transfer protein (CETP) inhibitors for inhibiting remnant lipoprotein production |
| US2004039018 | Use of cholesteryl ester transfer protein (CETP) inhibitors and antihypertensive agents and optional HMG-CoA reductase inhibitors for the treatment of cardiovascular conditions |
| WO2000017165 | Preparation of 4-amino-substituted 2-substituted 1,2,3,4-tetrahydroquinolines as CEPT inhibitors |
| US2004053842 | Therapeutic use and pharmaceutical compositions of cholesterol ester transfer protein (CETP) inhibitors and optional HMG-CoA reductase inhibitors and/or antihypertensive agents |
| WO2003000295 | Self-emulsifying formulations of cholesteryl ester transfer protein inhibitors and surfactants |
| WO2002011710 | Pharmaceutical compositions of cholesteryl ester transfer protein inhibitors |
| US2003198674 | Controlled release dosage forms containing cholesteryl ester transfer protein inhibitor |
| WO2003063832 | Pharmaceutical compositions comprising a solid amorphous dispersion of CETP inhibitors |
| US2003104063 | Pharmaceutical compositions containing a solid dispersion of a poorly-soluble drug in a matrix and a solubility-enhancing polymer |
| US2003054037 | Pharmaceutical compositions of adsorbates of amorphous drug |
| US2003170309 | Pharmaceutical compositions containing polymer and drug assemblies |
| US2003072801 | Pharmaceutical compositions comprising concentration-enhancing polymers |
| US2004185102 | Dosage forms comprising a CETP inhibitor and an HMG-CoA reductase inhibitor |
| WO2005000811 | Preparation of 3-aminopyrrolidines as inhibitors of monoamine uptake |
| US2005049239 | Preparation of aroylpiperidines and related compounds as selective inhibitors of the type 2 glycine transporter (GlyT2) |
| WO2005021525 | Preparation of aroylpiperidines and related compounds as selective inhibitors of the type 2 glycine transporter (GlyT2) |
| WO2004078169 | Use of EP2 selective receptor agonists in medical treatment of pulmonary hypertension and other conditions |
| WO2004078128 | Preparation of pyridine-containing diaryl ureas useful in the treatment of cancer and other disorders |
| WO2004073709 | Preparation of tertiary amino compounds as antimicrobial agents |
| WO2003087088 | Preparation of pyridone and pyrimidone compounds as inhibitors of the enzyme Lp-PLA2 |

TABLE 20-continued

References disclosing heterocyclic compounds.

| Publication or Pat. No. | Title |
|---|---|
| WO2003030909 | Preparation of 2- and 4-aminopyrimidines N-substituted by a bicyclic ring for use as kinase inhibitors in the treatment of cancer |
| WO2002090349 | Pyridylmethylanthranilamide N-oxides as inhibitors of VEGFR II kinase |
| WO2002070462 | Preparation of aminodicarboxylic acids for the treatment of cardiovascular diseases |
| WO2002068417 | Heteropolycyclic compounds, particularly pyridyl- and phenyl-substituted 1,2,4-oxadiazoles and analogs, and their use as metabotropic glutamate receptor antagonists for inhibiting neuronal damage |
| WO2002042273 | Preparation of aromatic acid derivatives useful as serine protease inhibitors |
| WO2002022584 | Preparation of substituted heterocyclic aryl-alkyl-aryl compounds as thrombin inhibitors |
| WO2001085671 | Preparation of (heterocyclyl)anthranylamides as inhibitors of vascular endothelial growth factor receptors |
| WO2001060458 | Piperazine inhibitors of prenyl-protein transferase for antitumor use |
| WO2001060369 | Piperazine inhibitors of prenyl-protein transferase for antitumor therapy |
| WO2001056560 | Preparation of substituted amino acids as neutral sphingomyelinase inhibitors |
| WO2001022954 | Indolyl-3-glyoxylic acid derivatives comprising therapeutically valuable properties |
| WO2001000623 | Method of producing nitroguanidine and nitroenamine derivatives |
| JP2001163779 | Prostaglandin receptor agonists and prodrugs for treatment of male erectile disorder |
| EP1108426 | Prostaglandin receptor agonists and prodrugs for treatment of male erectile disorder |
| DE19962300 | Preparation of N-(pyridin-4-yl) [1-(4-aminobenzyl)indol-3-yl]glyoxylamides as antitumor agents |
| US2001014690 | Preparation of N-(pyridin-4-yl) [1-(4-aminobenzyl)indol-3-yl]glyoxylamides as antitumor agents |
| U.S. Pat. No. 6,432,987 | Preparation of N-(pyridin-4-yl) [1-(4-aminobenzyl)indol-3-yl]glyoxylamides as antitumor agents |
| CA2395259 | Preparation of N-(pyridin-4-yl) [1-(4-aminobenzyl)indol-3-yl]glyoxylamides as antitumor agents |
| WO2001047913 | Preparation of N-(pyridin-4-yl) [1-(4-aminobenzyl)indol-3-yl]glyoxylamides as antitumor agents |
| DE19930075 | Preparation of aminoarylsulfonamides as antivirals |
| WO2001002350 | Preparation of aminoarylsulfonamides as antivirals |
| WO2000050398 | Preparation of phenyl and pyridinyl derivatives as NK-1 receptor antagonists |
| U.S. Pat. No. 6,121,271 | Preparation of naphtho[2,3-b]heteroar-4-yl derivatives for treating metabolic disorders related to insulin resistance or hyperglycemia |
| DE19845202 | Hair growth atimulant |
| WO2000019969 | Hair growth atimulant |
| WO9951224 | Preparation of indolylglyoxylamides as antitumor agents |
| WO9919300 | Preparation of prostaglandin agonists and their use to treat bone disorders |
| U.S. Pat. No. 6,008,362 | Elevation of HDL cholesterol by 2-(4-chloro-1-aryl-butylidene)-hydrazinecarbothioamides |
| U.S. Pat. No. 5,977,170 | Preparation of 4-[(aminothioxomethyl)hydrazono]-4-arylbutyl carbamates as elevators of HDL cholesterol |
| JP11209366 | Preparation of chromans and pharmaceuticals for treatment of heart failure |
| WO9857928 | Elevation of HDL cholesterol by 2-(4-chloro-1-aryl-butylidene)hydrazinecarbothioamides |
| WO9857927 | Elevation of HDL cholesterol by 4-[(aminothioxomethyl)hydrazono]-4-arylbutyl carbamates |
| WO9857925 | Elevation of HDL cholesterol by 2-[(aminothioxomethyl)hydrazono]-2-arylethyl carbamates |
| WO9827053 | Preparation of sulfonamide and carboxamide derivatives as drugs |
| WO9809946 | Preparation of new, N-substituted indole-3-glyoxylamides as antiasthmatics, antiallergic agents and immunosuppressants/immunomodulators |

TABLE 20-continued

References disclosing heterocyclic compounds.

| Publication or Pat. No. | Title |
|---|---|
| DE19615262 | Phenylglycinol amides as antiatherosclerotic agents |
| EP802188 | Phenylglycinol amides as antiatherosclerotic agents |
| WO9616650 | Antibacterial or bactericide comprising 2-aminothiazole derivative and salts thereof |
| U.S. Pat. No. 5,491,152 | ACAT-inhibiting derivatives of cyclic ethers and sulfides for the treatment of atherosclerosis |
| JP08092225 | Preparation of O-(1,2,4-triazol-5-yl)glycolamide derivatives as herbicides |
| JP08092224 | Preparation of 3,5-diphenyl-1,2,4-triazole derivatives as insecticides and acaricides |
| WO9505363 | Amidine derivatives with nitric oxide synthetase activities |
| U.S. Pat. No. 5,422,355 | Antidepressant (arylalkyl)amines as GABA autoreceptor agonists |
| DD294706 | Antidepressant (arylalkyl)amines as GABA autoreceptor agonists |
| U.S. Pat. No. 5,086,073 | Antidepressant (arylalkyl)amines as GABA autoreceptor agonists |
| U.S. Pat. No. 5,260,331 | Antidepressant (arylalkyl)amines as GABA autoreceptor agonists |
| JP07285962 | Preparation of (pyridyloxy)pyrazole derivatives as herbicides |
| WO9413636 | Preparation of N-carbamoyl-2-[(aminoalkyl)carbamoylalkoxy]azetidinones and analogs as elastase inhibitors |
| U.S. Pat. No. 5,348,953 | Preparation of azetidinones as antiinflammatory and antidegenerative agents |
| CN1068815 | Preparation of azetidinones as antiinflammatory and antidegenerative agent |
| ZA9204659 | Preparation of azetidinones as antiinflammatory and antidegenerative agent |
| AU9218582 | Preparation of azetidinones as antiinflammatory and antidegenerative agent |
| AU660026 | Preparation of azetidinones as antiinflammatory and antidegenerative agent |
| WO9413636 | Preparation of azetidinones as antiinflammatory and antidegenerative agent |
| EP604798 | N-arylhydrazine derivatives as insecticides and acaricides |
| EP585500 | Diaryl piperazineacetamides as antimuscarinic agents |
| WO9405648 | Diaryl piperazineacetamides as antimuscarinic agents |
| WO9310099 | Pyrazoleglycolamide derivatives as agrochemicals |
| EP553016 | Preparation of naphthalene amides and sulfonamides, their pharmaceutical formulations, and their affinity for serotoninergic receptors |
| JP01104052 | Preparation of pyridine derivatives as leukotriene antagonists and vasodilators |

Applicants reserve the right to proviso out or to restrict from any claim currently presented, or from any claim that may be presented in this or any further application based upon this disclosure, including claims drawn any genus or subgenus disclosed herein, any compound or group of compounds disclosed in any reference, including any reference provided herein.

The following acronyms, abbreviations, terms and definitions have been used throughout this disclosure. The following acronyms, abbreviations, terms and definitions have been used throughout the experimental section. Acronyms and abbreviations: THF (tetrahydrofuran), DMF (N,N-dimethylformamide), IPA (iso-propanol), TBAB (tetra-n-butylammonium bromide), DCM (dichloromethane), DCE (dichloroethane), EDCI [1-(3-dimethylaminopropyl)-3-ethylcarbodiimide hydrochloride], DIBAL (diisobutyl aluminum hydride), TBAB (tetrabutylammonium bromide), LAH (lithium aluminum hydride), g or gm (grams), L (liter), mL (milliliters), mp (melting point), rt or RT (room temperature), aq (aqueous), min (minute), h or hr (hour), atm (atmosphere), conc. (concentrated), MS or mass spec (mass spectroscopy/spectrometry), NMR (nuclear magnetic resonance), IR (infrared spectroscopy), RB (round bottom), RBF (round bottom flask). In addition to these abbreviations, standard chemical abbreviations for chemical moieties, such as Me for methyl, Et for ethyl, and the like, are used throughout. NMR abbreviations: br (broad), apt (apparent), s (singlet), d (doublet), t (triplet), q (quartet), dq (doublet of quartets), dd (doublet of doublets), dt (doublet of triplets), m (multiplet).

General Synthetic Procedures.

Room temperature is defined as an ambient temperature range, typically from about 20° C. to about 35° C. An ice bath (crushed ice and water) temperature is defined as a range, typically from about −5° C. to about 0° C. Temperature at reflux is defined as ±15° C. of the boiling point of the primary reaction solvent. Overnight is defined as a time range of from about 8 to about 16 hours. Vacuum filtration (water aspirator) is defined as occurring over a range of pressures, typically from about 5 mm Hg to about 15 mm Hg. Dried under vacuum is defined as using a high vacuum pump at a range of pressures, typically from about 0.1 mm Hg to about 5 mm Hg. Neutralization is defined as a typical acid-based neutralization method and measured to a pH range of from about pH 6 to about pH 8, using pH-indicating paper. Brine is defined as a saturated aqueous sodium chloride. Nitrogen atmosphere is defined as positive static pressure of nitrogen gas passed through a Drierite™ column with an oil bubbler system. Concentrated ammonium hydroxide is defined as an approximately 15 M solution. Melting points were measured against a mercury thermometer and are not corrected.

All eluents for column or thin layer chromatography were prepared and reported as volume:volume (v:v) solutions. The solvents, reagents, and the quantities of solvents and/or reagents used for reaction work-up or product isolation can be those that typically would be used by one of ordinary skill in organic chemical synthesis, as would be determined for the specific reaction or product to be isolated. For example: 1) crushed ice quantity typically ranged from about 10 g to about 1000 g depending on reaction scale; 2) silica gel quantity used in column chromatography depended on material quantity, complexity of mixture, and size of chromatography column employed and typically ranged from about 5 g to about 1000 g; 3) extraction solvent volume typically ranged from about 10 mL to about 500 mL, depending upon the reaction size; 4) washes employed in compound isolation ranged from about 10 mL to about 100 mL of solvent or aqueous reagent, depending on scale of reaction; and 5) drying reagents (potassium carbonate, sodium carbonate or magnesium sulfate) ranged from about 5 g to about 100 g depending on the amount of solvent to be dried and its water content.

Spectroscopic and Other Instrumental Procedures

NMR.

The $^1$H spectra described herein were obtained using Varian Gemini 200 MHz spectrometers. Spectrometer field strength and NMR solvent used for a particular sample are indicated in the examples, or on any NMR spectra that are shown as Figures. Typically, $^1$H NMR chemical shifts are reported as δ values in parts per million (ppm) downfield from tetramethylsilane (TMS) (δ=0 ppm) as an internal standard. Solid or liquid samples were dissolved in an appropriate NMR solvent (typically CDCl$_3$ or DMSO-d$_6$), placed in a NMR sample tube, and data were collected according to the spectrometer instructional manuals. Most samples were analyzed in Variable Temperature mode, typically at about 55° C., though some data for some samples were collected with the probe at ambient probe temperature. NMR data were processed using the software provided by Varian, VNMR 6.1 G version.

The present invention is further illustrated by the following examples, which are not to be construed in any way as imposing limitations upon the scope of this disclosure, but rather are intended to be illustrative only. On the contrary, it is to be clearly understood that resort may be had to various other embodiments, modifications, and equivalents thereof which, after reading the description herein, may suggest themselves to one of ordinary skill in the art without departing from the spirit of the present invention. Thus, the skilled artisan will appreciate how the experiments and Examples may be further implemented as disclosed by variously altering the following examples, substituents, reagents, or conditions. In the following examples, in the disclosure of any measurements, including temperatures, pressures, times, weights, percents, concentrations, ranges, chemical shifts, frequencies, molar ratios, and the like, it is to be understood that such measurements are respectively, "about."

EXAMPLES

Example 1

Synthesis of (5-{[(3,5-bis-trifluoromethyl-benzyl)-(2-methyl-2H-tetrazole-5-yl)-amino]methyl}-1,3-dimethyl-1H-pyrazolo[3,4-b]pyridin-6-yl)-cyclobutylmethyl-ethyl-amine

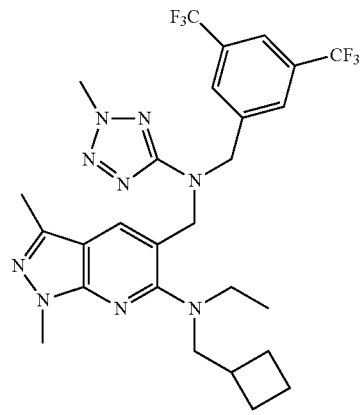 [SMILES: CCN(CC1CCC1)c1nc2c(cc1CN(Cc1cc(C(F)(F)F)cc(C(F)(F)F)c1)c1nnn(C)n1)c(C)nn2C]

Step (i): Synthesis of 6-chloro-1,3-dimethyl-1H-pyrazolo[3,4-b]pyridine-5-carbaldehyde

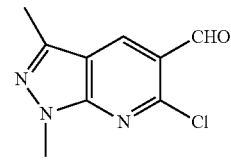

A mixture of acetic anhydride (6.62 mL, 70 mmol) and 2,5-dimethyl-2H-pyrazol-3-ylamine (5.0 g, 45 mmol) was heated while stirring at 90-100° C. for 4 h. After evaporation of volatiles in vacuo, phosphorus oxychloride (18.5 mL, 200 mmol) was added and the mixture was heated while stirring at 90-95° C. for 3 h. Thereafter, anhydrous DMF (9.2 mL, 120 mmol) was added slowly over the period of 30 min while maintaining the internal temperature of the mixture at 90-95° C. After stirring for an additional 2 h, the reaction mixture was cooled to RT and poured over crushed ice (100-120 g). The precipitated solid was filtered off, washed with water and dried in vacuo. The yellowish solid product was subsequently dissolved in methylene chloride (100 mL), washed with water, dried over sodium sulfate, and the solvent was evaporated in vacuo to give the desired product as light yellow solid (4.1 g), yield: 44%, mp: 152-153° C.

¹H NMR (300 MHz, CDCl₃): δ 10.48 (s, 1H), 8.60 (s, 1H), 4.07 (s, 3H), 2.59 (s, 3H).

Step (ii): Synthesis of cyclobutylmethyl-ethyl-amine

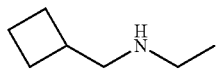

Cyclobutanecarbonyl chloride (4.0 mL, 35 mmol) was added slowly to an ice-cooled solution of ethylamine [20 mL, 2M solution in tetrahydrofuran (THF)] and triethylamine (4.85 mL, 35 mmol) in anhydrous methylene chloride (25 mL) at 0-5° C. under nitrogen. After stirring for 20 min the mixture was warmed to 20-25° C. and stirred for an additional 5-7 h. The reaction was quenched by pouring the mixture into 5-10% aqueous sodium bicarbonate. The organic layer was separated, washed with brine, dried over sodium sulfate, and the solvent was evaporated to give cyclobutanecarboxylic acid ethylamide as a pale yellow liquid, which solidified upon standing at RT.

Thereafter, lithium aluminum hydride (30 mL, 2M solution in THF) was added slowly to a solution of cyclobutanecarboxylic acid ethylamide (4.45 g, 35 mmol) in anhydrous THF (10 mL) under a nitrogen atmosphere. After stirring for 1 h at 20° C., the reaction was gently refluxed for 3 h. After cooling to RT, the reaction was quenched with 1N aqueous sodium hydroxide, filtered, and the precipitate was washed with diethyl ether. The combined filtrates were concentrated to afford cyclobutylmethyl-ethyl-amine as a colorless liquid (2.0 g), yield: 50%.

¹H NMR (300 MHz, CDCl₃,): δ 2.61-2.54 (m, 4H), 2.47-2.39 (m, 1H), 2.04-1.56 (m, 6H), 1.22 (bs, 1H), 1.07 (t, J=6.9 Hz, 3H).

Step (iii): Synthesis of 6-(cyclobutylmethyl-ethyl-amino)-1,3-dimethyl-1H-pyrazolo[3,4-b]pyridine-5-carbaldehyde

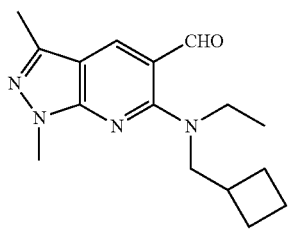 [SMILES: CCN(CC1CCC1)c1nc2c(cc1C=O)c(C)nn2C]

Potassium carbonate (0.83 g, 6 mmol) was added to a solution of 6-chloro-1,3-dimethyl-1H-pyrazolo[3,4-b]pyridine-5-carbaldehyde (1.04 g, 5.0 mmol) and cyclobutylmethyl-ethyl-amine (0.8 g, 7.0 mmol) in anhydrous DMF (8 mL) under nitrogen. After stirring for 0.5 h at RT, the reaction mixture was heated for 14 h at 80° C. Thereafter, the reaction was cooled to RT, water (30 mL) and ethyl acetate (30 mL) were added, and the organic layer was separated from the aqeous mixture. The organic extract was washed with brine, dried over sodium sulfate and the solvent was evaporated in vacuo. The residue was purified by chromatography using silica gel (200-400 mesh) and eluted with 20-60% hexane: ethyl acetate to afford the title compound as a pale yellow liquid (1.23 g), yield: 87%.

¹H NMR (300 MHz, CDCl₃): δ 9.99 (s, 1H), 8.32 (s, 1H), 3.91 (s, 3H), 3.52-3.44 (m, 4H), 2.79-2.65 (m, 1H), 2.48 (s, 3H), 2.04-1.60 (m, 6H), 1.25 (t, J=7.04 Hz, 3H).

Step (iv): Synthesis of {5-[(3,5-bis-trifluoromethyl-benzylamino)-methyl]-1,3-dimethyl-1H-pyrazolo[3,4-b]pyridin-6-yl}-cyclobutylmethyl-ethyl-amine

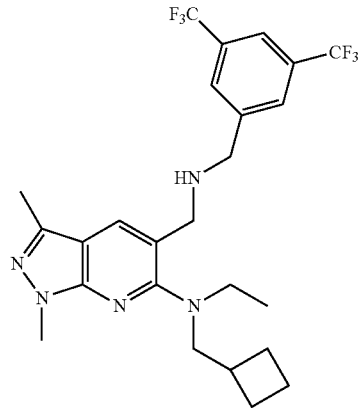 [SMILES: CCN(CC1CCC1)c1nc2c(cc1CNCc1cc(C(F)(F)F)cc(C(F)(F)F)c1)c(C)nn2C]

To a solution of 6-(cyclobutylmethyl-ethyl-amino)-1,3-dimethyl-1H-pyrazolo[3,4-b]pyridine-5-carbaldehyde (0.38 g, 1.3 mmol) and bis-trifluoromethyl-benzylamine (0.32 g, 1.3 mmol) in anhydrous MeOH (5.0 mL) was added glacial acetic acid (0.2 mL) and the resulting mixture was stirred for 20 min at RT. Sodium cyanoborohydride (0.245 g, 4 mmol) was added slowly and the reaction was stirred overnight at RT. After evaporation of the volatiles in vacuo, water (30 mL) and ethyl acetate (30 mL) were added to the residue, and the organic layer was allowed to separate. The organic layer was collected and washed with brine, dried over sodium sulfate, and the solvent was evaporated in vacuo. The residue was purified by chromatography using silica gel (200-400 mesh) and eluted with 1-5% CH₂Cl₂:MeOH to afford the title compound as a colorless liquid (0.265 g), yield: 40%.

¹H NMR (300 MHz, CDCl₃): δ 7.96-7.88 (m, 4H), 4.34 (s, 2H), 4.19 (s, 2H), 4.01 (s, 3H), 3.27-3.21 (m, 4H), 2.54 (s, 3H), 2.49-2.38 (m, 1H), 1.87-1.46 (m, 6H), 1.06 (t, J=7.04 Hz, 3H).

Step (v): Synthesis of (5-{[(3,5-bis-trifluoromethyl-benzyl)-(2-methyl-2H-tetrazole-5-yl)-amino]methyl}-1,3-dimethyl-1H-pyrazolo[3,4-b]pyridine-6-yl)-cyclobutylmethyl-ethyl-amine

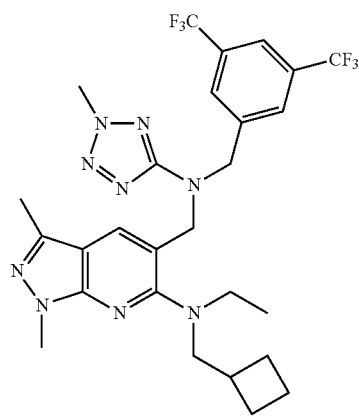 [SMILES: CCN(CC1CCC1)c1nc2c(cc1CN(Cc1cc(C(F)(F)F)cc(C(F)(F)F)c1)c1nnn(C)n1)c(C)nn2C]

Anhydrous potassium carbonate (0.138 g, 1 mmol) was added to a solution of {5-[3,5-bis-trifluoromethyl-benzylamino)-methyl]-1,3-dimethyl-1H-pyrazolo[3,4-b]pyridin-6-yl}-cyclobutylmethyl-ethyl-amine (0.25 g, 0.49 mmol) and cyanogen bromide (0.106 g, 1 mmol) in anhydrous MeOH at RT. After stirring for 2 h, the volatiles were evaporated in vacuo. Water (30 mL) and ethyl acetate (30 mL) were added to the residue and the organic layer was separated from the aqueous mixture. The organic extract was washed with brine, dried over sodium sulfate, and the solvent was evaporated in vacuo.

The crude residue was dissolved in anhydrous DMF (4.5 mL) and to this solution, sodium azide (0.195 g, 3.0 mmol) and ammonium chloride (0.16 g, 3.0 mmol) were added at RT. After stirring for 15 min at RT, the reaction mixture was heated at 95° C. for 5 h. Thereafter, the reaction mixture was cooled to RT, water (30 mL) and ethyl acetate (30 mL) were added, and the organic layer was separated, washed with brine, dried over sodium sulfate, and the solvent was evaporated in vacuo. Aqueous NaOH (1N) was added at RT to dissolve the residue. To this solution were added sequentially methylene chloride (6 mL), dimethyl sulfate (0.1 mL, 1 mmol), tetrabutylammonium bromide (0.01-0.02 g), and the resulting mixture was stirred overnight. The organic layer was then separated and the aqueous layer was back extracted with methylene chloride (2×20 mL). The combined organic extracts were washed with brine, and the solvent was evaporated in vacuo. The residue was purified by chromatography using silica gel (200-400 mesh) and eluted with 5-20% hexane:EtOAc to afford the title compound as a colorless thick liquid (0.06 g), yield: 21%

Purity: 99.58% (HPLC: YMC C8, 30:70 [$KH_2PO_4$ (0.01 M, pH 3.2):$CH_3CN$], $R_t$ 24.01 min).

$^1$H NMR (300 MHz, $CDCl_3$): δ 7.71 (s, 1H), 7.64-7.59 (m, 3H), 4.76 (s, 2H), 4.58 (s, 2H), 4.22 (s, 3H), 3.95 (s, 3H), 3.21 (d, J=7.26 Hz, 2H), 3.14 (q, J=7.04 Hz, 2H), 2.56-2.48 (m, 1H), 2.39 (s, 3H), 1.91-1.78 (m, 4H), 1.58-1.52 (m, 2H), 1.06 (t, J=7.04 Hz, 3H).

MS (ESI) m/z 596 (M+1)$^+$.

Example 2

Synthesis of (5-{[(3,5-bis-trifluoromethyl-benzyl)-(2-methyl-2H-tetrazole-5-yl)-amino]methyl}-1,3-dimethyl-1H-pyrazolo[3,4-b]pyridin-6-yl)-bis-cyclopropylmethyl-amine

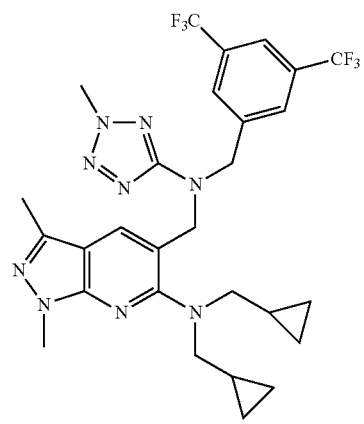 [SMILES: Cc1nn(C)c2nc(N(CC3CC3)CC3CC3)c(CN(Cc3cc(C(F)(F)F)cc(C(F)(F)F)c3)c3nnn(C)n3)cc12]

The title compound was obtained as a colorless thick liquid following the procedure as described in Example 1, using bis-cyclopropylmethyl-amine (prepared following the literature method disclosed in U.S. Pat. No. 3,546,295) instead of cyclobutylmethyl-ethyl-amine in step (iii) (0.17 g), yield: 28%.

Purity: 98.29% (HPLC: YMC C8, 30:70 [$KH_2PO_4$ (0.01 M, pH 3.2):$CH_3CN$], $R_t$ 20.72 min)

$^1$H NMR (300 MHz, $CDCl_3$): δ 7.70-7.59 (m, 4H), 4.86 (s, 2H), 4.62 (s, 2H), 4.21 (s, 3H), 3.96 (s, 3H), 3.12 (d, J=6.58 Hz, 4H), 2.39 (s, 3H), 0.99-0.87 (m, 2H), 0.38-0.33 (m, 4H), 0.07-0.032 (m, 4H).

MS (ESI) m/z 608 (M+1)$^+$.

Example 3

Synthesis of (5-{[(3,5-bis-trifluoromethyl-benzyl)-(2-methyl-2H-tetrazole-5-yl)-amino]methyl}-1,3-dimethyl-1H-pyrazolo[3,4-b]pyridin-6-yl)-cyclopropylmethyl-ethyl-amine

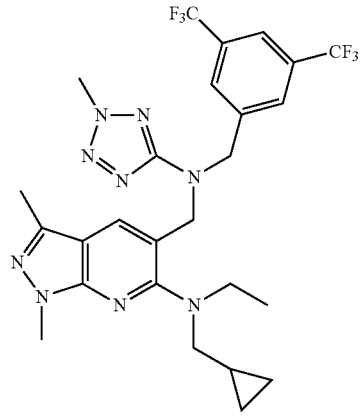 [SMILES: CCN(CC1CC1)c1nc2c(cc1CN(Cc1cc(C(F)(F)F)cc(C(F)(F)F)c1)c1nnn(C)n1)c(C)nn2C]

The title compound was obtained as a colorless thick liquid following the procedure as described in Example 1, using cyclopropylmethyl-ethyl-amine (prepared as disclosed in U.S. Pat. No. 3,546,295) instead of cyclobutylmethyl-ethyl-amine in step (iii) (0.2 g), yield: 37%.

Purity: 98.19% (HPLC: YMC C8, 30:70 [$KH_2PO_4$ (0.01 M, pH 3.2):$CH_3CN$], $R_t$ 16.17 min)

$^1$H NMR (300 MHz, $CDCl_3$): δ 7.71-7.61 (m, 4H), 4.80 (s, 2H), 4.59 (s, 2H), 4.22 (s, 3H), 3.96 (s, 3H), 3.30 (q, J=7.04 Hz, 2H), 3.03 (d, J=6.59 Hz, 2H), 2.40 (s, 3H), 1.07 (t, J=7.04 Hz, 3H), 0.99-0.88 (m, 1H), 0.40-0.35 (m, 2H), 0.07-0.049 (m, 2H).

MS (ESI) m/z 582 (M+1)$^+$.

Example 4

Synthesis of (5-{[(3,5-bis-trifluoromethyl-benzyl)-(2-methyl-2H-tetrazole-5-yl)-amino]methyl}-1,3-dimethyl-1H-pyrazolo[3,4-b]pyridin-6-yl)-cyclobutylmethyl-methyl-amine

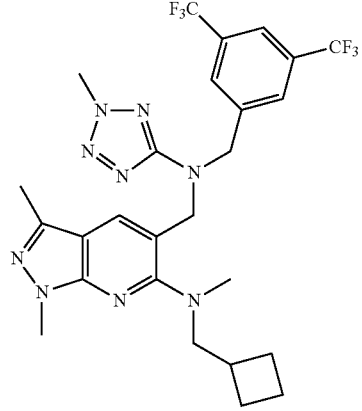 [SMILES: Cc1nn(C)c2nc(N(C)CC3CCC3)c(CN(Cc3cc(C(F)(F)F)cc(C(F)(F)F)c3)c3nnn(C)n3)cc12]

The title compound was obtained as a colorless thick liquid following the procedure as described in Example 1, using cyclobutylmethyl-methyl-amine (obtained as a colorless liquid following the procedure as described in Example 1, step (ii), using methylamine, instead of ethylamine), instead of cyclobutylmethyl-ethyl-amine in step (iii) (0.23 g), yield: 31%.

Purity 98.78% (HPLC: YMC C8, 30:70 [KH$_2$PO$_4$ (0.01 M, pH 3.2):CH$_3$CN], R$_t$ 18.6 min)

$^1$H NMR (300 MHz, CDCl$_3$): δ 7.71-7.58 (m, 4H), 4.76 (s, 2H), 4.56 (s, 2H), 4.22 (s, 3H), 3.95 (s, 3H), 3.12 (d, J=7.04 Hz, 2H), 2.78 (s, 3H), 2.58-2.44 (m, 1H), 2.39 (s, 3H), 1.98-1.55 (m, 6H).

MS (ESI) m/z 582 (M+1)$^+$.

Example 5

Synthesis of (5-{[(3,5-bis-trifluoromethyl-benzyl)-(2-methyl-2H-tetrazole-5-yl)-amino]methyl}-1,3-dimethyl-1H-pyrazolo[3,4-b]pyridin-6-yl)-cyclobutylmethyl-cyclopropylmethyl-amine

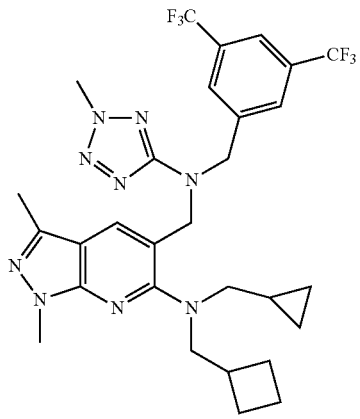 [SMILES: Cc1nn(C)c2nc(N(CC3CCC3)CC3CC3)c(CN(Cc3cc(C(F)(F)F)cc(C(F)(F)F)c3)c3nnn(C)n3)cc12]

The title compound was obtained as a light yellow solid following the procedure as described in Example 1, by using cyclobutylmethyl-cyclopropylmethyl-amine, instead of cyclobutylmethyl-ethyl-amine in step (iii) (0.106 g), yield: 15%, mp 84-85° C.

Purity: 95.76% (HPLC: YMC C8, 30:70 [KH$_2$PO$_4$ (0.01 M, pH 3.2):CH$_3$CN], R$_t$ 25.44 min).

$^1$H NMR (300 MHz, CDCl$_3$): δ 7.69 (s, 1H), 7.63-7.58 (m, 3H), 4.82 (s, 2H), 4.60 (s, 2H), 4.21 (s, 3H), 3.95 (s, 3H), 3.32 (d, J=7.04 Hz, 2H), 2.97 (d, J=6.59 Hz, 2H), 2.54-2.43 (m, 1H), 2.38 (s, 3H), 1.86-1.50 (m, 6H), 0.92-0.86 (m, 1H), 0.41-0.35 (m, 2H), 0.066-0.016 (m, 2H).

MS (ESI) m/z 622 (M+1)$^+$.

Example 6

Synthesis of (5-{[(3,5-bis-trifluoromethyl-benzyl)-(2-methyl-2H-tetrazole-5-yl)-amino]methyl}-1,3-dimethyl-1H-pyrazolo[3,4-b]pyridin-6-yl)-(2,2-dimethyl-propyl)-ethyl-amine

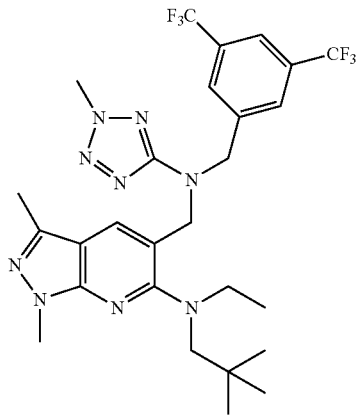 [SMILES: CCN(CC(C)(C)C)c1nc2c(cc1CN(Cc1cc(C(F)(F)F)cc(C(F)(F)F)c1)c1nnn(C)n1)c(C)nn2C]

The title compound was obtained as a colorless solid following the procedure as described in Example 1, using 2,2-dimethyl-propyl-ethyl-amine, instead of cyclobutylmethyl-ethyl-amine in step (iii) (0.28 g), yield: 41%, mp 72-73° C.

Purity: 95.57% (HPLC: YMC C8, 30:70 [KH$_2$PO$_4$ (0.01 M, pH 3.2):CH$_3$CN], R$_t$ 21.15 min)

$^1$H NMR (300 MHz, CDCl$_3$): δ 7.74 (s, 1H), 7.64-7.59 (m, 3H), 4.83 (s, 2H), 4.68 (s, 2H), 4.22 (s, 3H), 3.95 (s, 3H), 3.38 (s, 2H), 3.01 (q, J=7.04 Hz, 2H), 2.40 (s, 3H), 1.02 (t, J=7.04 Hz, 3H), 0.63 (s, 9H).

MS (ESI) m/z 598 (M+1)$^+$.

Example 7

Synthesis of (5-{[(3,5-bis-trifluoromethyl-benzyl)-(2-methyl-2H-tetrazole-5-yl)-amino]methyl}-1,3-dimethyl-1H-pyrazolo[3,4-b]pyridin-6-yl)-ethyl-isopropyl-amine

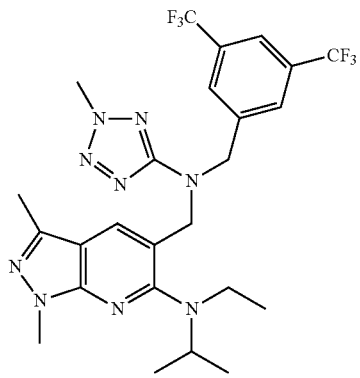 [SMILES: CCN(c1nc2c(cc1CN(Cc1cc(C(F)(F)F)cc(C(F)(F)F)c1)c1nnn(C)n1)c(C)nn2C)C(C)C]

The title compound was obtained as a colorless thick liquid following the procedure as described in Example 1, using ethyl-isopropylamine, instead of cyclobutylmethyl-ethyl-amine in step (iii) (0.23 g), yield: 38%.

Purity 99.05% (HPLC: YMC C8, 30:70 [KH$_2$PO$_4$ (0.01 M, pH 3.2):CH$_3$CN], R$_t$ 17.9 min).

$^1$H NMR (300 MHz, CDCl$_3$): δ 7.72-7.61 (m, 4H), 4.77 (s, 2H), 4.58 (s, 2H), 4.22 (s, 3H), 3.96 (s, 3H), 3.48-3.32 (m, 3H), 2.40 (s, 3H), 1.08 (d, J=5.67 Hz, 6H), 0.95 (t, J=6.82 Hz, 3H).

MS (ESI) m/z 570 (M+1)$^+$.

Example 8

Synthesis of (5-{[(3,5-bis-trifluoromethyl-benzyl)-(2-methyl-2H-tetrazole-5-yl)-amino]methyl}-1,3-dimethyl-1H-pyrazolo[3,4-b]pyridin-6-yl)-cyclopentyl-ethyl-amine

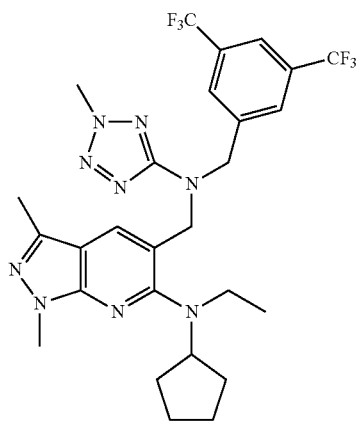 [SMILES: CCN(c1nc2c(cc1CN(Cc1cc(C(F)(F)F)cc(C(F)(F)F)c1)c1nnn(C)n1)c(C)nn2C)C1CCCC1]

The title compound was obtained as a colorless solid following the procedure as described in Example 1, using cyclopentyl-ethylamine instead of cyclobutylmethyl-ethyl-amine in step (iii) (0.14 g), yield: 30%, mp 43-44° C.

Purity 95.57% (HPLC: YMC C8, 20:80 [$KH_2PO_4$ (0.01 M, pH 3.2):$CH_3CN$], $R_t$ 5.81 min)

$^1H$ NMR (300 MHz, $CDCl_3$): δ 7.70-7.59 (m, 4H), 4.77 (s, 2H), 4.56 (s, 2H), 4.19 (s, 3H), 3.92 (s, 3H), 3.75-3.69 (m, 1H), 3.22 (q, J=7.04 Hz, 2H), 2.37 (s, 3H), 1.76-1.32 (m, 8H), 0.90 (t, J=7.04 Hz, 3H).

MS (ESI) m/z 596 (M+1)$^+$.

Example 9

Synthesis of (5-{[(3,5-bis-trifluoromethyl-benzyl)-(2-methyl-2H-tetrazole-5-yl)-amino]methyl}-1,3-dimethyl-1H-pyrazolo[3,4-b]pyridin-6-yl)-cyclopentyl-cyclopropylmethyl-amine

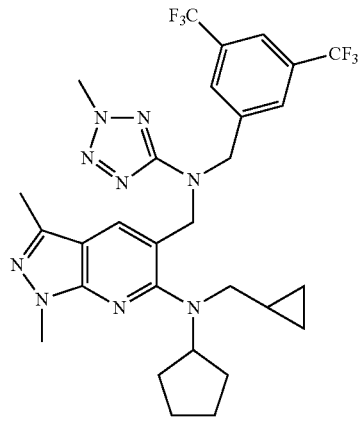 [SMILES: Cc1nn(C)c2nc(N(CC3CC3)C3CCCC3)c(CN(Cc3cc(C(F)(F)F)cc(C(F)(F)F)c3)c3nnn(C)n3)cc12]

The title compound was obtained as a colorless liquid following the procedure as described in Example 1, using cyclopentyl-cyclopropylmethylamine instead of cyclobutylmethyl-ethyl-amine in step (iii) (0.25 g), yield: 46%.

Purity 86.56% (HPLC: YMC C8, 20:80 [$KH_2PO_4$ (0.01 M, pH 3.2):$CH_3CN$], $R_t$ 9.10 min)

$^1H$ NMR (300 MHz, $CDCl_3$): δ 7.72-7.64 (m, 4H), 4.87 (s, 2H), 4.61 (s, 2H), 4.21 (s, 3H), 3.97 (s, 3H), 3.76-3.70 (m, 1H), 3.05 (d, J=6.58 Hz, 2H), 2.40 (s, 3H), 1.80-1.42 (m, 8H), 0.88-0.74 (m, 1H), 0.25-0.21 (m, 2H), (−0.084)-(−0.102) (m, 2H).

MS (ESI) m/z 622 (M+1)$^+$.

Example 10

Synthesis of (5-{[(3,5-bis-trifluoromethyl-benzyl)-(5-methyl-isoxazol-3-yl)-amino]-methyl}-1,3-dimethyl-1H-pyrazolo[3,4-b]pyridin-6-yl)-cyclobutylmethyl-ethyl-amine

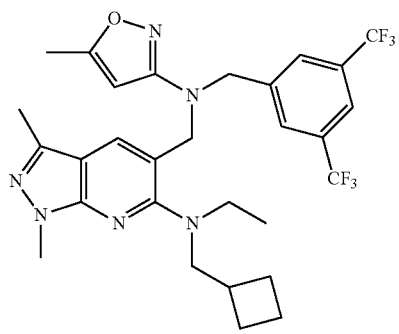 [SMILES: CCN(CC1CCC1)c1nc2c(cc1CN(Cc1cc(C(F)(F)F)cc(C(F)(F)F)c1)c1cc(C)on1)c(C)nn2C]

Step (i): Synthesis of cyclobutylmethyl-{1,3-dimethyl-5-[(5-methyl-isoxazol-3-ylamino)-methyl]-1H-pyrazolo[3,4-b]pyridin-6-yl}-ethyl-amine

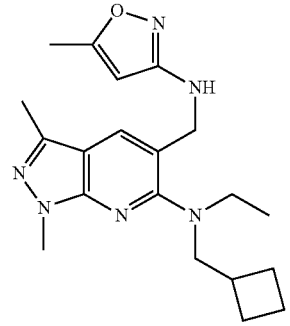 [SMILES: CCN(CC1CCC1)c1nc2c(cc1CNc1cc(C)on1)c(C)nn2C]

5-Methyl-isoxazol-3-ylamine (0.37 g, 3.8 mmol) was added to a solution of 6-(cyclobutylmethyl-ethyl-amino)-1,3-dimethyl-1H-pyrazolo[3,4-b]pyridine-5-carbaldehyde (0.54 g, 1.9 mmol) in anhydrous chloroform (20 mL) and acetic acid (0.2 mL) under nitrogen. After stirring for 15 min at RT, sodium triacetoxyborohydride (1.20 g, 5.7 mmol) was added slowly and this mixture was stirred at RT overnight. After evaporation of chloroform in vacuo, water (30 mL) and ethyl acetate (30 mL) were added to the residue. The organic layer was separated, washed with brine, dried over sodium sulfate, and concentrated to give title compound, which was taken on without further purification.

Step (ii): Synthesis of (5-{[(3,5-bis-trifluoromethyl-benzyl)-(5-methyl-isoxazol-3-yl)-amino]-methyl}-1,3-dimethyl-1H-pyrazolo[3,4-b]pyridin-6-yl)-cyclobutylmethyl-ethyl-amine

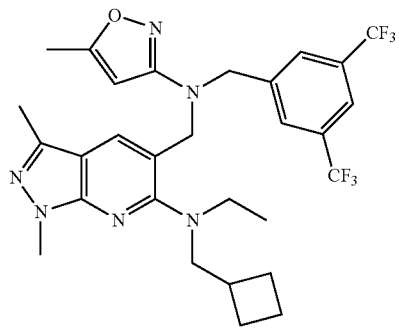 [SMILES: CCN(CC1CCC1)c1nc2c(cc1CN(Cc1cc(C(F)(F)F)cc(C(F)(F)F)c1)c1cc(C)on1)c(C)nn2C]

Sodium hydride [0.06 g, (60% dispersion in mineral oil)] was added to a solution of cyclobutylmethyl-{1,3-dimethyl-5-[(5-methyl-isoxazol-3-ylamino)-methyl]-1H-pyrazolo[3,4-b]pyridin-6-yl}-ethyl-amine (0.225 g, 0.6 mmol) in anhydrous DMF (3 mL) while stirring at RT. After this mixture was stirred for 1 h, 3,5-bis-trifluoromethybenzyl bromide (0.13 mL, 0.7 mmol) was added slowly and stirring was continued for an additional 12 h. Ethyl acetate (30 mL) and water (30 mL) were added, and the layers were separated. The aqueous layer was back-extracted with ethyl acetate (2×30 mL). The combined organic extracts were washed with brine, dried over sodium sulfate, and concentrated in vacuo. The crude residue was purified by chromatography using silica gel (200-400 mesh) and eluted with 25-50% hexane:ethyl acetate to yield the title compound as a colorless thick liquid (0.10 g), yield: 29%.

Purity: 98.52% (HPLC: YMC C8, 30:70 [KH$_2$PO$_4$ (0.01 M, pH 3.2):CH$_3$CN], R$_t$ 29.71 min).

$^1$H NMR (300 MHz, CDCl$_3$): δ 7.73 (s, 1H), 7.68-7.65 (m, 3H), 5.51 (s, 1H), 4.54 (s, 2H), 4.48 (s, 2H), 3.95 (s, 3H), 3.20 (d, J=7.04 Hz, 2H), 3.10 (q, J=7.04 Hz, 2H), 2.52-2.43 (m, 1H), 2.42 (s, 3H), 2.31 (s, 3H), 1.85-1.56 (m, 6H), 1.05 (t, J=7.04 Hz, 3H). MS (ESI) m/z 595 (M+1)$^+$.

Example 11

Synthesis of (5-{[(3,5-bis-trifluoromethyl-benzyl)-(5-methyl-isoxazol-3-yl)-amino]-methyl}-1,3-dimethyl-1H-pyrazolo[3,4-b]pyridin-6-yl)-bis-cyclopropylmethyl-amine

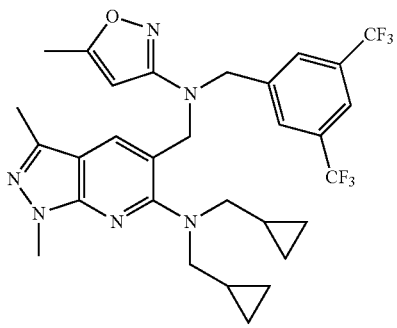 [SMILES: Cc1cc(N(Cc2cc(C(F)(F)F)cc(C(F)(F)F)c2)Cc2cc3c(C)nn(C)c3nc2N(CC2CC2)CC2CC2)no1]

The title compound was obtained as a colorless thick liquid following the procedure as described in Example 10, with the exceptions as follow: 1) step (i): using 6-(bis-cyclopropylmethylamino)-1,3-dimethyl-1H-pyrazolo[3,4-b]pyridine-5-carbaldehyde, instead of 6-(cyclobutylmethyl-ethyl-amino)-1,3-dimethyl-1H-pyrazolo[3,4-b]pyridine-5-carbaldehyde; 2) step (ii): using sodium tert-butoxide and anhydrous THF instead of sodium hydride and DMF, respectively (0.03 g), yield: 19%.

Purity: 92.72% (HPLC: YMC C8, 30:70 [KH$_2$PO$_4$ (0.01 M, pH 3.2):CH$_3$CN], R$_t$ 26.04 min).

$^1$H NMR (300 MHz, CDCl$_3$): δ 7.72-7.66 (m, 4H), 5.53 (s, 1H), 4.59 (s, 2H), 4.57 (s, 2H), 3.96 (s, 3H), 3.08 (d, J=6.59 Hz, 4H), 2.42 (s, 3H), 2.30 (s, 3H), 0.81-0.94 (m, 2H), 0.38-0.34 (m, 4H), 0.066-0.0314 (m, 4H).

MS (ESI) m/z 607 (M+1)$^+$.

Example 12

Synthesis of (5-{1[(3,5-bis-trifluoromethyl-benzyl)-(2-methyl-2H-tetrazol-5-yl)-amino]methyl}-1-methyl-1H-pyrazolo[3,4-b]pyridin-6-yl)-cyclobutylmethyl-ethyl-amine

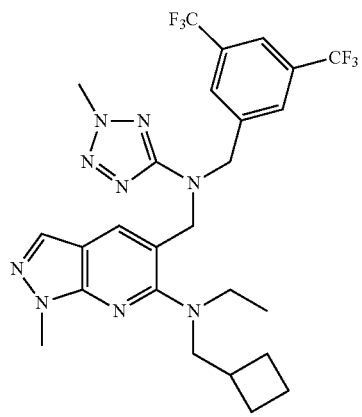 [SMILES: CCN(CC1CCC1)c1nc2c(cnn2C)cc1CN(Cc1cc(C(F)(F)F)cc(C(F)(F)F)c1)c1nnn(C)n1]

Step (i): Synthesis of 6-chloro-1-methyl-1H-pyrazolo[3,4-b]pyridine-5-carbaldehyde

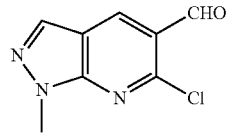

Hydrazine hydrate (9.7 mL, 200 mmol) was added over 10 min to a vigorously stirred solution of acrylonitrile (13.5 mL, 205 mmol) in absolute EtOH (105 mL) at 5-10° C. After the addition was complete, the reaction was stirred for 24 h at RT and then cooled to 5-10° C. before the slow addition of paraformaldehyde (6.4 g, 220 mmol). The resulting mixture continued to be stirred at RT for an additional 3 h. Evaporation of ethanol in vacuo yielded a viscous yellow oil, which was diluted with 1-propanol (30 mL). To this solution was added solid NaOH (0.2 g) and this mixture was heated at reflux for 4 h. After evaporation of the volatiles, the dark brown oil was filtered through silica gel and washed with 1-5% CH$_2$Cl$_2$:MeOH. The combined filtrates were evaporated to yield a pale yellow liquid. The liquid compound was dissolved in acetic anhydride (15.2 mL) and heated at 100° C. for 3 h. Thereafter, the reaction mixture was cooled to RT, phosphorus oxychloride (49.0 mL, 540 mmol) followed by DMF (31.0 mL) were added slowly over the period of 30 min. After stirring this mixture at RT for 30 min the reaction was heated at 100° C. for 5 h, then cooled to RT and slowly poured over ice-water and extracted with CH$_2$Cl$_2$ (3×50 mL). The combined organic extracts were dried over sodium sulfate and filtered, and concentrated in vacuo. The crude product was purified by silica gel chromatography and eluted with 1-5% CH$_2$Cl$_2$:MeOH to give 6-chloro-1-methyl-1H-pyrazolo[3,4-b]pyridine-5-carbaldehyde as a light yellow oil (1.8 g), yield: 6%).

$^1$H NMR (300 MHz, CDCl$_3$): δ 10.5 (s, 1H), 8.67 (s, 1H), 8.16 (s, 1H), 4.15 (s, 3H).

Step (ii): Synthesis of (5-{[(3,5-bis-trifluoromethyl-benzyl)-(2-methyl-2H-tetrazol-5-yl)-amino]methyl}-1-methyl-1H-pyrazolo[3,4-b]pyridin-6-yl)-cyclobutylmethyl-ethyl-amine

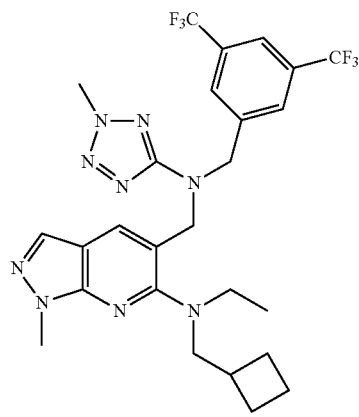 [SMILES: CCN(CC1CCC1)c1nc2c(cnn2C)cc1CN(Cc1cc(C(F)(F)F)cc(C(F)(F)F)c1)c1nnn(C)n1]

The title compound was obtained as a colorless thick liquid following the procedure as described in Example 1, with the exception of using 6-chloro-1-methyl-1H-pyrazolo[3,4-b]pyridine-5-carbaldehyde for 6-chloro-1,3-dimethyl-1H-pyrazolo[3,4-b]pyridine-5-carbaldehyde in step (iii) (0.49 g), yield: 42%.

Purity 98.82% (HPLC: YMC C8, 20:80 [KH$_2$PO$_4$ (0.01 M, pH 3.2):CH$_3$CN], R$_t$ 9.08 min)

$^1$H NMR (300 MHz, CDCl$_3$): δ 7.71-7.69 (m, 3H), 7.61 (s, 2H), 4.76 (s, 2H), 4.59 (s, 2H), 4.21 (s, 3H), 4.02 (s, 3H), 3.22 (d, J=7.04 Hz, 2H), 3.18 (q, J=7.04 Hz, 2H), 2.52-2.48 (m, 1H), 1.87-1.70 (m, 4H), 1.61-1.50 (m, 2H), 1.06 (t, J=7.04 Hz, 3H).

MS (ESI) m/z 582 (M+1)$^+$.

Example 13

Synthesis of (5-{[(3,5-bis-trifluoromethyl-benzyl)-(2-methyl-2H-tetrazol-5-yl)-amino]methyl}-1-methyl-1H-pyrazolo[3,4-b]pyridin-6-yl)-bis-cyclopropylmethyl-amine

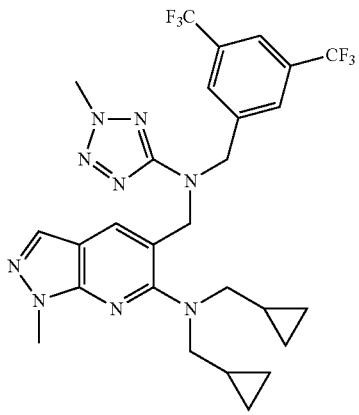 [SMILES: Cn1nnc(N(Cc2cc(C(F)(F)F)cc(C(F)(F)F)c2)Cc2cc3cnn(C)c3nc2N(CC2CC2)CC2CC2)n1]

The title compound was obtained as a light yellow oil following the procedure as described in Example 1, with the exception of using bis-cyclopropylmethyl-amine, instead of cyclobutylmethyl-ethylamine, and 6-chloro-1-methyl-1H-pyrazolo[3,4-b]pyridine-5-carbaldehyde, instead of 6-chloro-1,3-dimethyl-1H-pyrazolo[3,4-b]pyridine-5-carbaldehyde in step (iii) (0.31 g), yield: 60%.

Purity: 97.38% (HPLC: YMC C8, 30:70 [KH$_2$PO$_4$ (0.01 M, pH 3.2):CH$_3$CN], R$_t$ 31.25 min)

$^1$H NMR (300 MHz, CDCl$_3$): δ 7.74-7.67 (m, 3H), 7.60 (s, 2H), 4.82 (s, 2H), 4.60 (s, 2H), 4.19 (s, 3H), 4.01 (s, 3H), 3.11 (d, J=6.59 Hz, 4H), 0.97-0.87 (m, 2H), 0.38-0.32 (m, 4H), 0.059-0.006 (m, 4H).

MS (ESI) m/z 594 (M+1)$^+$.

Example 14

Synthesis of (5-{[(3,5-bis-trifluoromethyl-benzyl)-(2-methyl-2H-tetrazol-5-yl)-amino]methyl}-1-ethyl-1H-pyrazolo[3,4-b]pyridin-6-yl)-bis-cyclopropylmethyl-amine

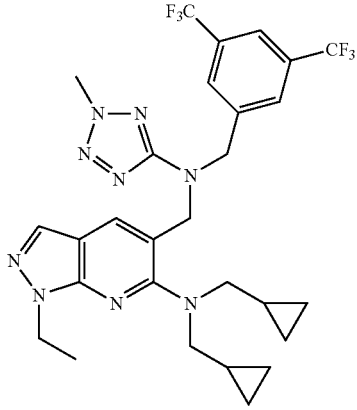 [SMILES: CCn1ncc2cc(CN(Cc3cc(C(F)(F)F)cc(C(F)(F)F)c3)c3nnn(C)n3)c(N(CC3CC3)CC3CC3)nc21]

The title compound was obtained as a colorless oil following the procedure as described in Example 1, with the exception of using bis-cyclopropylmethyl-amine, instead of cyclobutylmethyl-ethylamine, and 6-chloro-1-ethyl-1H-pyrazolo[3,4-b]pyridine-5-carbaldehyde, instead of 6-chloro-1,3-dimethyl-1H-pyrazolo[3,4-b]pyridine-5-carbaldehyde in step (iii) (0.37 g), yield: 45%.

Purity: 96.36% (HPLC: YMC C8, 20:80 [KH$_2$PO$_4$ (0.01 M, pH 3.2):CH$_3$CN], R$_t$ 26.80 min)

$^1$H NMR (300 MHz, CDCl$_3$): δ 7.78-7.64 (m, 5H), 4.85 (s, 2H), 4.63 (s, 2H), 4.50 (q, J=7.27 Hz, 2H), 4.21 (s, 3H), 3.12 (d, J=6.36 Hz, 4H), 1.56 (t, J=7.27 Hz, 3H), 0.97-0.87 (m, 2H), 0.37-0.34 (m, 4H), 0.065-0.035 (m, 4H).

MS (ESI) m/z 608 (M+1)$^+$.

Example 15

Synthesis of (5-{[(3,5-bis-trifluoromethyl-benzyl)-(2-methyl-2H-tetrazol-5-yl)-amino]methyl}-1-ethyl-1H-pyrazolo[3,4-b]pyridin-6-yl)-cyclobutylmethyl-ethyl-amine

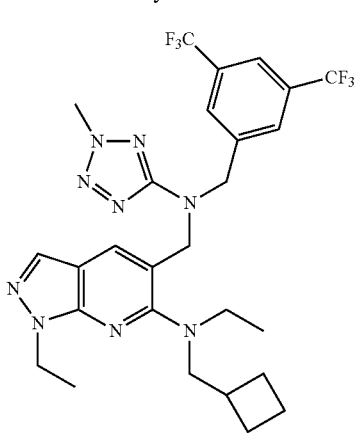

The title compound was obtained as a colorless powder following the procedure as described in Example 1, with the exception of using 6-chloro-1-ethyl-1H-pyrazolo[3,4-b]pyridine-5-carbaldehyde, instead of 6-chloro-1,3-dimethyl-1H-pyrazolo[3,4-b]pyridine-5-carbaldehyde in step (iii) (0.36 g), yield: 36%.

Mp 76-77° C.

Purity 97.85% (HPLC: YMC C8, 20:80 [KH$_2$PO$_4$ (0.01 M, pH 3.2):CH$_3$CN], R$_t$ 9.81 min)

$^1$H NMR (300 MHz, CDCl$_3$): δ 7.74-7.71 (m, 3H), 7.63 (s, 2H), 4.77 (s, 2H), 4.61 (s, 2H), 4.46 (q, J=7.27 Hz, 2H), 4.21 (s, 3H), 3.23-3.14 (m, 4H), 2.56-2.48 (m, 1H), 1.87-1.47 (m, 9H), 1.06 (t, J=7.04 Hz, 3H).

MS (ESI) m/z 596 (M+1)$^+$.

Example 16

Synthesis of (3,5-bis-trifluoromethyl-benzyl)-[6-(cyclopentylmethyl-ethyl-amino)-1,3-dimethyl-1H-pyrazolo[3,4-b]pyridine-5-ylmethyl]-carbamic acid methyl ester

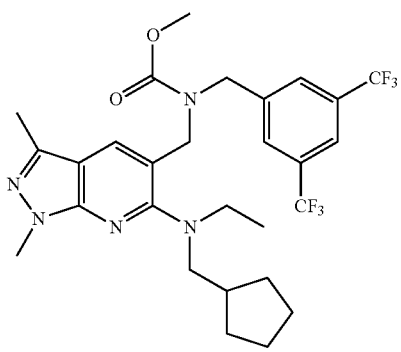

Step (i): Synthesis of N-(2,5-dimethyl-2H-pyrazol-3-yl)-acetamide

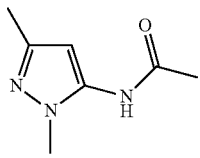

Pyridine (7.1 mL, 90 mmol) was added to a solution of 2,5-dimethyl-2H-pyrazol-3-ylamine (10 g, 90 mmol) in acetic anhydride (46 mL) at 0° C. and the resulting mixture was stirred at room temperature for 30 min. The solvent was removed under vacuum to yield the title compound as a brownish liquid (13.7 g), yield: 100%.

$^1$H NMR (400 MHz, CDCl$_3$): δ 7.91 (bs, 1H), 5.98 (s, 1H), 3.67-3.56 (m, 3H), 2.19-2.11 (m, 6H).

ES-MS m/z 154 (M$^+$+1, 100%).

Step (ii): Synthesis of 6-chloro-1,3-dimethyl-1H-pyrazolo[3,4-b]pyridine-5-carbaldehyde

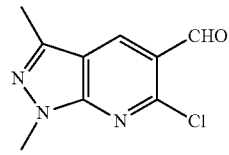

A mixture of N-(2,5-dimethyl-2H-pyrazol-3-yl)-acetamide (13.7 g, 89 mmol) and phosphorus oxychloride (68.4 mL, 44.5 mmol, distilled prior to use) was heated to 90-95° C. with stirring under nitrogen atmosphere for 2 h followed by the slow addition of DMF (19.6 mL, 26.7 mmol) at the same temperature for 20 min. After stirring for 3 h, the reaction was cooled to 0° C. and crushed ice was slowly added and continued stirring for 30 min. The resultant solid was filtered off, washed with water and petroleum ether to yield a light yellow solid (7.8 g), yield: 43%.

$^1$H NMR (400 MHz, CDCl$_3$): δ 10.48 (s, 1H), 8.60 (s, 1H), 4.07 (s, 3H), 2.59 (s, 3H).

CI-MS m/z 210 (M$^+$+1, 100%).

Step (iii): Synthesis of 6-(cyclopentylmethyl-ethyl-amino)-1,3-dimethyl-1H-pyrazolo[3,4-b]pyridine-5-carbaldehyde

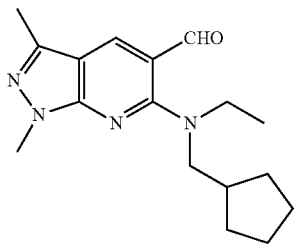 [SMILES: CCN(CC1CCCC1)c1nc2c(cc1C=O)c(C)nn2C]

A suspension of 6-chloro-1,3-dimethyl-1H-pyrazolo[3,4-b]pyridine-5-carbaldehyde (5 g, 0.023 mol) and potassium carbonate (9.9 g, 0.0717 mol) in DMF (75 mL) was stirred for 20 min at RT. Cyclopentylmethyl ethyl amine (4.25 g, 33.0 mmol) was then added and the reaction was refluxed for 8 h. After cooling the reaction to RT, water (500 mL) was added to the reaction mixture and extracted with ethyl acetate (3×400 mL) and the combined organic layers were dried and concentrated. The residue was purified by silica gel (100-200 mesh) column chromatography. Elution with 10% ethyl acetate in hexanes gave the pure product as a colorless, gummy mass (76%).

$^1$H NMR (400 MHz, CDCl$_3$): δ 10.01 (s, 1H), 8.32 (s, 1H), 3.92 (s, 3H), 3.55-3.44 (m, 4H), 2.49 (s, 3H), 2.32-2.30 (m, 1H), 1.71-1.47 (m, 8H), 1.18 (t, J=14.0 Hz, 3H).

ES-MS m/z 301 (M$^+$+1, 80%).

Step (iv): Synthesis of {5-[(3,5-bis-trifluoromethyl-benzylamino)-methyl]-1,3-dimethyl-1H-pyrazolo[3,4-b]pyridin-6-yl}-cyclopentylmethyl-ethyl-amine

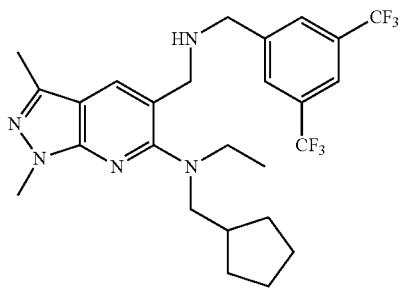 [SMILES: CCN(CC1CCCC1)c1nc2c(cc1CNCc1cc(C(F)(F)F)cc(C(F)(F)F)c1)c(C)nn2C]

A mixture of 6-(cyclopentylmethyl-ethyl-amino)-1,3-dimethyl-1H-pyrazolo[3,4-b]pyridine-5-carbaldehyde (5.3 g, 17.0 mmol) and 3,5-bis-trifluoromethylbenzylamine (4.7 g, 0.019 mol) in MeOH and acetic acid (2 drops) was stirred at RT for 30 min. After cooling to 0° C., sodium cyanoborohydride (2.2 g, 35.0 mmol) was added slowly over a period of about 10 min. After stirring at RT for 30 min, the reaction mixture was concentrated in vacuo. Water (50 mL) was added to the residue and stirred for 30 min. The solid was filtered off, washed with water followed by petroleum ether, and dried in vacuo to yield colorless solid (72%).

$^1$H NMR (400 MHz, CDCl$_3$): δ 7.89-7.86 (m, 4H), 4.19-4.08 (m, 4H), 3.99 (s, 3H), 3.27-3.20 (m, 4H), 2.52 (s, 3H), 2.06-1.98 (m, 1H), 1.62-1.41 (m, 8H), 1.11 (t, J=14.0 Hz, 3H).

ES-MS m/z 528 (M$^+$+1, 100%).

Step (v): Synthesis of (3,5-bis-trifluoromethyl-benzyl)-[6-(cyclopentylmethyl-ethyl-amino)-1,3-dimethyl-1H-pyrazolo[3,4-b]pyridine-5-ylmethyl]-carbamic acid methyl ester

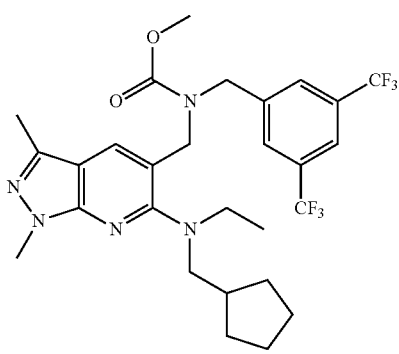 [SMILES: CCN(CC1CCCC1)c1nc2c(cc1CN(Cc1cc(C(F)(F)F)cc(C(F)(F)F)c1)C(=O)OC)c(C)nn2C]

A mixture of {5-[(3,5-bis-trifluoromethyl-benzylamino)-methyl]-1,3-dimethyl-1H-pyrazolo[3,4-b]pyridin-6-yl}-cyclopentylmethyl-ethyl-amine (0.25 g, 0.47 mmol) and potassium carbonate (0.19 g, 1.4 mmol) in THF (10 mL) was stirred for 20 min at RT. Thereafter, methyl chloroformate (0.55 mL, 0.7 mmol) was added and stirring was continued overnight. To this mixture was added water (100 mL) and the product was extracted with ethyl acetate (3×100 mL). The organic extracts were combined and concentrated and the residue was purified by column chromatography over 230-400 mesh silica gel. Elution with 20% ethyl acetate in hexanes gave the pure product as a colorless, gummy mass (55%).

$^1$H NMR (400 MHz, CDCl$_3$): δ 7.73-7.54 (m, 4H), 4.64-4.36 (m, 4H), 3.95 (s, 3H), 3.88 (s, 3H), 3.13-3.08 (m, 4H), 2.45 (s, 3H), 2.10-2.04 (m, 1H), 1.56-1.25 (m, 8H), 1.03 (t, J=14.0 Hz, 3H).

ES-MS m/z: 586 (M$^+$+1, 100%).

IR (neat) cm$^{-1}$: 3498, 2957, 2346, 2185, 1623, 1457, 1370, 1278, 1191, 1133, 907.

Example 17

Synthesis of cyclopentylmethyl-ethyl-(5-{[(3,4,5-trifluoro-benzyl)-(2-methyl-2H-tetrazol-5-yl)-amino]-methyl}-1,3-dimethyl-1H-pyrazolo[3,4-b]pyridine-6-yl)-amine Step (i): Synthesis of cyclopentylmethyl-ethyl-{5-[(3,4,5-difluoro-benzylamino)-methyl]-1,3-dimethyl-1H-pyrazolo[3,4-b]pyridine-6-yl}-amine

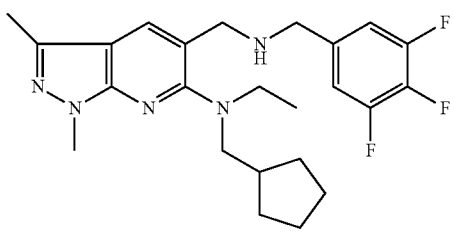 [SMILES: CCN(CC1CCCC1)c1nc2c(cc1CNCc1cc(F)c(F)c(F)c1)c(C)nn2C]

6-(Cyclopentylmethyl-ethyl-amino)-1,3-dimethyl-1H-pyrazolo[3,4-b]pyridine-5-carbaldehyde (0.30 g, 1.00 mmol), obtained in step (iii) of Example 16, 3,4,5-trifluorobenzylamine (0.161 g, 1.0 mmol) and acetic acid (0.120 g, 2.0 mmol) were added to a 25 mL round-bottomed flask, followed by 5 mL of MeOH. This mixture was stirred at 25-35° C. for 15 min Sodium cyanoborohydride (0.189 g, 3.0 mmol) was then added portion-wise. After this mixture was stirred at RT for 1 h, MeOH was removed in vacuo and water was added to the crude mixture. The mixture was extracted with ethyl acetate (3×50 mL), and the combined organic layers were washed with saturated sodium bicarbonate solution, brine, and dried over sodium sulfate. Evaporation of the solvent provided the product as oil (0.44 g), yield: 90%.

$^1$H NMR (200 MHz, CDCl$_3$): δ 7.98 (s, 1H), 7.09 (t, J=6.2 Hz, 2H), 4.27 (s, 2H), 3.99 (s, 3H), 3.95 (s, 2H), 3.20-3.16 (m, 4H), 2.54 (s, 3H), 2.48-2.42 (m, 1H), 1.87-1.42 (m, 8H), 1.05 (t, J=7.3 MHz, 3H), 0.88-0.85 (m, 1H).

MS m/z (CI-MS): 432 (M$^+$+1, 100%).

IR (cm$^{-1}$): 2928, 1612

Step (ii): Synthesis of [6-(cyclopentylmethyl-ethyl-amino)-1,3-dimethyl-1H-pyrazolo[3,4-b]pyridine-5-ylmethyl-(3,4,5-trifluoro-benzyl)-cyanamide

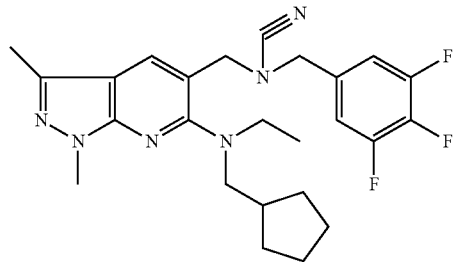 [SMILES: CCN(CC1CCCC1)c1nc2c(cc1CN(C#N)Cc1cc(F)c(F)c(F)c1)c(C)nn2C]

To a solution of cyclopentylmethyl-ethyl-{5-[(3,4,5-difluoro-benzylamino)-methyl]-1,3-dimethyl-1H-pyrazolo[3,4-b]pyridine-6-yl}-amine (0.450 g, 1.0 mmol) in MeOH (15 mL) under an N$_2$ atmosphere was added sodium bicarbonate (0.168 g, 2.0 mmol), followed by cyanogen bromide (0.126 g, 1.20 mmol), and this mixture was stirred for 0.5 h at RT. The reaction mixture was then concentrated under vacuum and the residue was dissolved in water and extracted with ethyl acetate (3×20 mL). The combined organic extracts were dried over sodium sulfate and concentrated to afford the crude product. The crude product was purified by column chromatography over 100-200 mesh silica gel, using 10% ethyl acetate and petroleum ether to yield the title compound as an oil (59%).

$^1$H NMR (400 MHz, CDCl$_3$): δ 7.88 (s, 1H), 6.90-6.86 (m, 2H), 4.29 (s, 2H), 3.97 (s, 5H), 3.21-3.14 (m, 4H), 2.56-2.48 (m, 4H), 1.95-1.72 (bs, 4H), 1.53-1.12 (m, 4H), 1.07 (t, J=7.2 Hz, 3H).

MS m/z (CI-MS): 457 (M$^+$−16, 100%).

Step (iii): Synthesis of cyclopentylmethyl-ethyl-(5-{[(3,4,5-trifluoro-benzyl)-(1H-tetrazol-5-yl)-amino]-methyl}-1,3-dimethyl-1H-pyrazolo[3,4-b]pyridine-6-yl)-amine

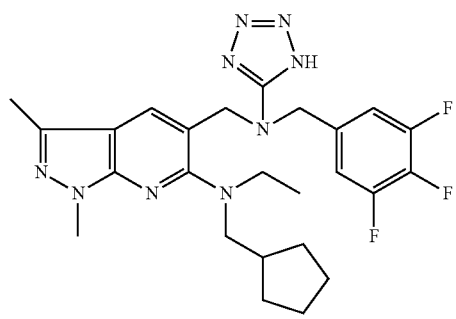 [SMILES: CCN(CC1CCCC1)c1nc2c(cc1CN(Cc1cc(F)c(F)c(F)c1)c1nnn[nH]1)c(C)nn2C]

To a stirred suspension of [6-(cyclopentylmethyl-ethyl-amino)-1,3-dimethyl-1H-pyrazolo[3,4-b]pyridine-5-ylmethyl-(3,4,5-trifluoro-benzyl)-cyanamide (0.280 g, 0.590 mmol) and ammonium chloride (0.160 g, 2.95 mmol) in dry DMF (10 mL) was added sodium azide (0.195 g, 2.95 mmol) and the reaction mixture was heated at 100° C. overnight. After the reaction mixture was cooled to RT, ice water was added, and this mixture was stirred for 30 min, and then extracted with ethyl acetate (3×50 mL). The combined organic layers were dried over sodium sulfate and evaporated to yield the product as oil (90%).

$^1$H NMR (400 MHz, CDCl$_3$): δ 8.01 (s, 1H), 7.55 (s, 1H), 7.02-6.98 (m, 1H), 4.81 (s, 2H), 4.50 (s, 2H), 3.98 (s, 3H), 3.38 (q, J=7.0 Hz, 2H), 3.27 (d, J=7.0 Hz, 2H), 2.46 (s, 3H), 1.99-1.95 (m, 1H), 1.89-1.57 (bs, 8H), 1.20 (t, J=7.1 Hz, 3H).

MS m/z (CI-MS): 500 (M$^+$–13, 100%).

Step (iv): Synthesis of cyclopentylmethyl-ethyl-(5-{[(3,4,5-trifluoro-benzyl)-(2-methyl-2H-tetrazol-5-yl)-amino]-methyl}-1,3-dimethyl-1H-pyrazolo[3,4-b]pyridine-6-yl)-amine

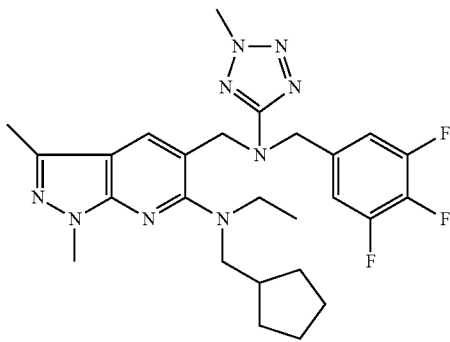 [SMILES: CCN(CC1CCCC1)c1nc2c(cc1CN(Cc1cc(F)c(F)c(F)c1)c1nnn(C)n1)c(C)nn2C]

To a suspension of cyclopentylmethyl-ethyl-(5-{[(3,4,5-trifluoro-benzyl)-(1H-tetrazol-5-yl)-amino]-methyl}-1,3-dimethyl-1H-pyrazolo[3,4-b]pyridine-6-yl)-amine (0.420 g, 0.818 mmol) in water (4 mL) was added sodium hydroxide (0.065 g, 1.630 mmol), and the resulting mixture was stirred for 15 min at RT. Thereafter, DCM (5 mL), dimethyl sulfate (0.113 g, 0.90 mmol), and tetrabutylammonium bromide (0.013 g, 0.050 mmol) were added sequentially to the reaction mixture. The reaction was stirred for 0.5 h at RT. The organic layer was separated from aqueous layer, the aqueous layer was back-extracted with DCM (3×10 mL), and the combined organic layers were washed with brine, dried over sodium sulfate and concentrated. The residue was purified by column chromatography over 100-200 mesh silica gel using 5% EtOAc and petroleum ether, to afford cyclopentylmethyl-ethyl-(5-{[(3,4,5-difluoro-benzyl)-(2-methyl-2H-tetrazol-5-yl)-amino]-methyl}-1,3-dimethyl-1H-pyrazolo[3,4-b]pyridine-6-yl)-amine as a pale yellow solid (45%), mp: 100° C.

$^1$H NMR (400 MHz, CDCl$_3$): δ 7.63 (s, 1H), 6.82-6.78 (m, 2H), 4.71 (s, 2H), 4.41 (s, 2H), 4.20 (s, 3H), 3.96 (s, 3H), 3.24-3.13 (m, 4H), 2.54-2.51 (m, 1H), 2.42 (s, 3H), 1.90-1.81 (m, 2H), 1.79-1.62 (m, 2H), 1.60-1.43 (m, 4H), 1.05 (t, J=6.9 Hz, 3H).

MS m/z (CI-MS) 514 (M$^+$–13, 100%).
IR (cm$^{-1}$): 2926, 1528.

Example 18

Synthesis of cyclopentylmethyl-ethyl-(5-{[(3,5-difluoro-benzyl)-(2-methyl-2H-tetrazol-5-yl)-amino]-methyl}-1,3-dimethyl-1H-pyrazolo[3,4-b]pyridin-6-yl)-amine

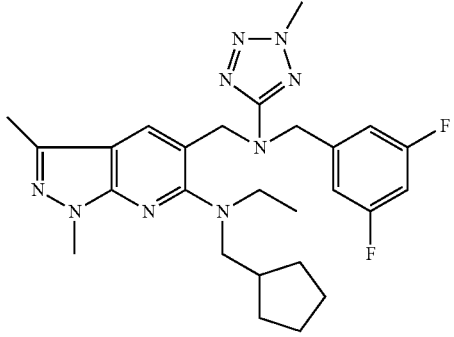 [SMILES: CCN(CC1CCCC1)c1nc2c(cc1CN(Cc1cc(F)cc(F)c1)c1nnn(C)n1)c(C)nn2C]

The title compound was obtained following the procedure as described in Example 17, using 3,5-difluorobenzylamine, instead of 3,4,5-trifluorobenzylamine in step (i).

Purity: 96.93%.

$^1$H NMR (300 MHz, CDCl$_3$): δ 7.62 (s, 1H), 6.70-6.62 (m, 3H), 4.73 (s, 2H), 4.49 (s, 2H), 4.21 (s, 3H), 3.98 (s, 3H), 3.19-3.11 (m, 4H), 2.42 (s, 3H), 1.61-1.42 (m, 8H), 1.08-1.02 (m, 3H).

MS m/z (CI-MS) 510 (M$^+$+1, 100%).
IR (KBr, cm$^{-1}$): 2932, 2864, 1599.

Example 19

Synthesis of cyclopentylmethyl-(1,3-dimethyl-5-{[(2-methyl-2H-tetrazol-5-yl)-(3,5-dichlorobenzyl)-amino]-methyl}-1H-pyrazolo[3,4-b]pyridin-6-yl)-ethyl-amine

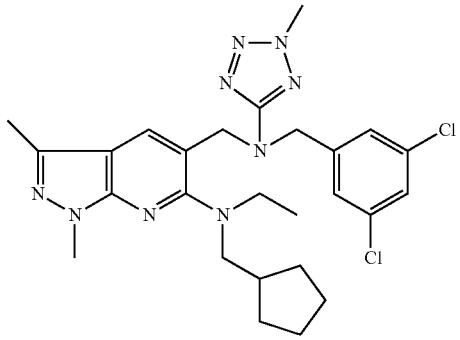 [SMILES: CCN(CC1CCCC1)c1nc2c(cc1CN(Cc1cc(Cl)cc(Cl)c1)c1nnn(C)n1)c(C)nn2C]

The title compound was obtained following the procedure as described in Example 17, using 3,5-dichlorobenzylamine, instead of 3,4,5-trifluorobenzylamine in step (i).

Purity: 95.0%.

$^1$H NMR (400 MHz, CDCl$_3$): δ 7.57 (s, 1H), 7.17 (s, 1H), 7.02 (s, 2H), 4.73 (s, 2H) 4.46 (s, 2H), 4.21 (s, 3H), 3.95 (s, 2H), 4.67 (s, 3H), 3.18-3.12 (m, 4H), 2.41 (s, 3H), 1.58-1.43 (m, 8H), 1.10-1.02 (m, 4H).

MS m/z (CI-MS) 541 (M$^+$, 100%).

Example 20

Synthesis of cyclopentylmethyl-ethyl-(5-{[(3-fluoro-5-trifluoromethyl-benzyl)-(2-methyl-2H-tetrazol-5-yl)-amino]-methyl}-1,3-dimethyl-1H-pyrazolo[3,4-b]pyridin-6-yl)-amine

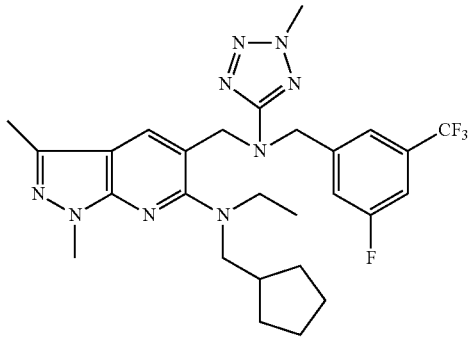 [SMILES: CCN(CC1CCCC1)c1nc2c(cc1CN(Cc1cc(F)cc(C(F)(F)F)c1)c1nnn(C)n1)c(C)nn2C]

The title compound was obtained following the procedure as described in Example 1, using 3-fluoro-5-trifluoromethyl-benzylamine, instead of 3,5-bis-trifluorobenzylamine in step (iv) and cyclopropylmethyl-ethyl-amine instead of cyclobutylmethyl-ethyl-amine in step (iii).

Purity: 95.72%.

$^1$H NMR (400 MHz, CDCl$_3$): δ 7.61 (s, 1H), 7.18-7.09 (m, 3H), 4.76 (s, 2H), 4.55 (s, 2H), 4.21 (s, 3H), 3.95 (s, 3H), 3.17-3.11 (m, 4H), 2.40 (s, 3H), 1.58-1.41 (m, 8H), 1.19-1.02 (m, 3H).

MS m/z (CI-MS) 560 (M$^+$+1, 100%).
IR (KBr, cm$^{-1}$): 2954, 2867, 1610, 1583, 1344, 1132.

Example 21

Synthesis of bis-cyclopropylmethyl-(5-{[(3,5-dichlorobenzyl)-(2-methyl-2H-tetrazol-5-yl)-amino]-methyl}-1,3-dimethyl-1H-pyrazolo[3,4-b]pyridin-6-yl)-amine

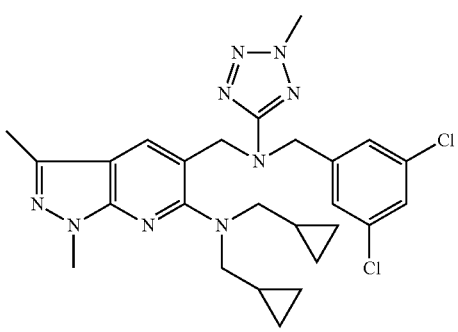 [SMILES: Cc1nn(C)c2nc(N(CC3CC3)CC3CC3)c(CN(Cc3cc(Cl)cc(Cl)c3)c3nnn(C)n3)cc12]

The title compound was prepared following the experimental procedure for Example 1, except using bis-cyclopropylmethyl-ethylamine, instead of cyclobutyl methyl ethylamine in step (iii) of Example 1, and 3,5-dichlorobenzylamine, instead of bis-trifluoromethyl-benzylamine in step (iv) of Example 1.

$^1$H NMR (400 MHz, CDCl$_3$): δ 7.64 (s, 1H), 7.16 (s, 1H), 7.15 (s, 2H), 4.81 (s, 2H), 4.46 (s, 2H), 4.22 (s, 3H), 3.97 (s, 3H), 3.13-3.12 (m, 4H), 2.42 (s, 3H), 0.98-0.94 (m, 2H), 0.40-0.38 (m, 4H), 0.097-0.058 (m, 4H).

MS m/z (ES-MS) 540 (M$^+$+1, 100%).

IR (cm$^{-1}$): 3384, 2925, 1582.

Example 22

Synthesis of (5-{[(3,5-bis-trifluoromethyl-benzyl)-(4-trifluoromethyl-oxazol-2-yl)-amino]-methyl}-1,3-dimethyl-1H-pyrazolo[3,4-b]-pyridin-6-yl)-cyclopentylmethyl-ethyl-amine

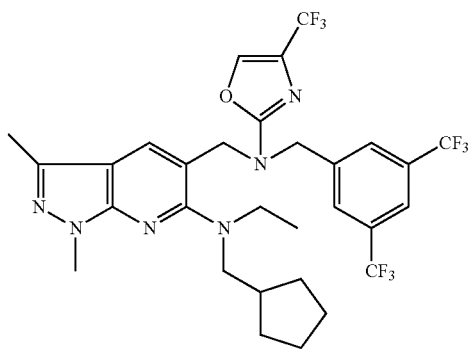 [SMILES: CCN(CC1CCCC1)c1nc2c(cc1CN(Cc1cc(C(F)(F)F)cc(C(F)(F)F)c1)c1nc(C(F)(F)F)co1)c(C)nn2C]

Step (i): Synthesis of 1-(3,5-bis-trifluoromethyl-benzyl)-1-[6-(cyclopentylmethyl-ethyl-amino)-1,3-dimethyl-1H-pyrazolo[3,4-b]pyridine-5-ylmethyl]-urea

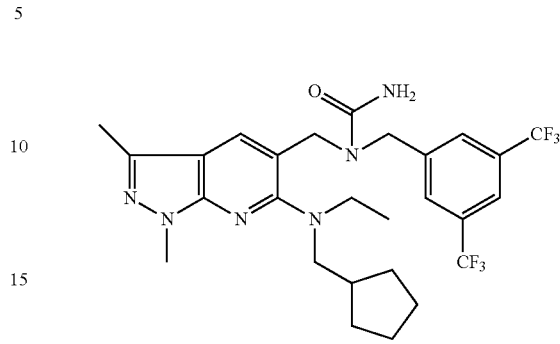

To a stirred solution of [6-(cyclopentylmethyl-ethyl-amino)-1,3-dimethyl-1H-pyrazolo[3,4-b]pyridine-5-ylmethyl-(3,5-bis-trifluoromethyl-benzyl)-cyanamide (0.50 g, 0.880 mmol) in ethanol (15 mL) were added H$_2$O$_2$ (1.5 mL) and a saturated aqueous solution of KOH (0.70 g, 11.97 mmol) at 0° C. This mixture was slowly heated to reflux. After 2 h the reaction mixture was cooled to RT, water (10 mL) was added, and the product was extracted with ethyl acetate (3×40 mL). The combined organic layers were dried over sodium sulfate and evaporated to yield the crude residue. The crude was purified by column chromatography over 100-200 mesh silica gel using 10% ethyl acetate and petroleum ether to yield the title compound as a sticky oil (60%).

$^1$H NMR (400 MHz, CDCl$_3$): δ 7.73 (s, 1H), 7.58 (s, 3H), 4.77 (s, 2H), 4.57 (s, 2H), 3.95 (s, 3H), 3.15-3.10 (m, 4H), 2.42 (s, 3H), 1.54-1.40 (m, 8H), 1.06-1.03 (m, 4H)

IR (cm$^{-1}$): 3198, 2955, 1668, 1278, 1130.

Step (ii): Synthesis of (5-{[(3,5-bis-trifluoromethyl-benzyl)-(4-trifluoromethyl-oxazol-2-yl)-amino]-methyl}-1,3-dimethyl-1H-pyrazolo[3,4-b]-pyridin-6-yl)-cyclopentylmethyl-ethyl-amine

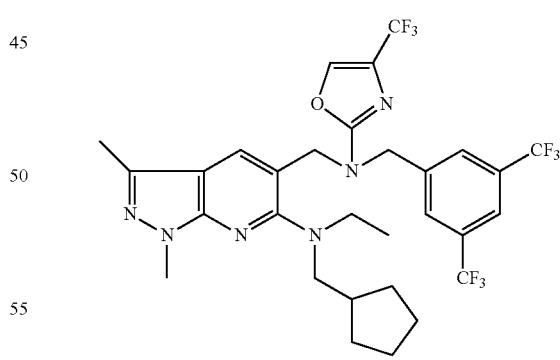

To a stirred solution of 1-(3,5-bis-trifluoromethyl-benzyl)-1-[6-(cyclopentylmethyl-ethyl-amino)-1,3-dimethyl-1H-pyrazolo[3,4-b]pyridine-5-ylmethyl]-urea (0.250 g, 0.430 mmol) in tert-butanol (10 mL) was added 1,1,1-trifluoromethyl acetyl bromide (0.20 g, 0.480 mmol). This mixture was refluxed for 3 h and then cooled to RT. After concentration in vacuo, water (10 mL) was added to the residue, and the product was extracted with ethyl acetate (3×25 mL). The combined organic layers were dried over sodium sulfate and concentrated under vacuum to afford the crude residue, which was purified by column chromatography over 100-200 mesh silica gel using 5% ethyl acetate and petroleum ether, to yield the title compound as a white solid (20%), mp: 139° C.

$^1$H NMR (400 MHz, CDCl$_3$): δ 7.74 (s, 1H), 7.61 (s, 2H), 7.57 (s, 1H), 4.77 (s, 2H), 4.57 (s, 2H), 3.95 (s, 3H), 3.14-3.12 (m, 4H), 2.41 (s, 3H), 1.54-1.52 (m, 8H), 1.07-1.03 (m, 4H).

MS m/z (ES-MS) 663 (M$^+$+1, 100%).

IR (cm$^{-1}$): 2938, 1640, 1279, 1136.

Example 23

Synthesis of (2-{[(3,5-Bis-trifluoromethyl-benzyl)-(6-cyclopentylmethyl-ethyl-amino)-1,3-dimethyl-1H-pyrazolo[3,4-b]-pyridin-5-ylmethyl]-amino}-oxazol-4-carboxylic acid ethyl ester

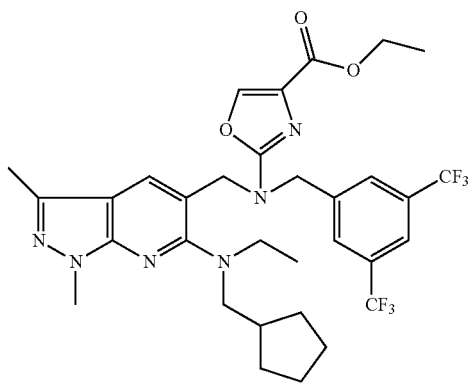 [SMILES: CCOC(=O)c1coc(N(Cc2cc(C(F)(F)F)cc(C(F)(F)F)c2)Cc2cc3c(C)nn(C)c3nc2N(CC)CC2CCCC2)n1]

To a ice-cooled solution of 1-(3,5-bis-trifluoromethyl-benzyl)-1-[6-(cyclopentylmethyl-ethyl-amino)-1,3-dimethyl-1H-pyrazolo[3,4-b]pyridine-5-ylmethyl]-urea (1.20 gm, 2.10 mmol) in ethanol (10 mL) was added 3-bromo-2-oxo-propionic acid ethyl ester (0.612 g, 3.150 mmol). This mixture was stirred while allowing the temperature to reach RT, after which the reaction mixture was refluxed for 8 h, and then cooled to RT. After evaporation of the reaction volatiles, water (10 mL) was added, and the product was extracted with ethyl acetate (3×50 mL). The combined organic layers were dried over sodium sulfate and evaporated to get the crude residue, which was purified by column chromatography over 100-200 mesh silica gel using 5% ethyl acetate and petroleum ether, to yield the title product as a yellow paste (6%).

$^1$H NMR (400 MHz, CDCl$_3$): δ 7.85 (s, 1H), 7.76 (s, 1H), 7.59 (s, 1H), 4.79 (s, 2H), 4.62 (s, 2H), 4.39 (q, J=7.3 Hz, 2H), 3.95 (s, 3H), 3.14-3.08 (m, 4H), 2.41 (s, 3H), 2.07-2.04 (m, 1H), 1.62-1.20 (m, 11H), 1.03 (t, J=6.9 Hz, 3H).

MS m/z (ES-MS) 667 (M$^+$+1, 100%).

IR (cm$^{-1}$): 2925, 1612, 1278, 1137.

Example 24

Synthesis of (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopentylmethyl-ethyl-amine

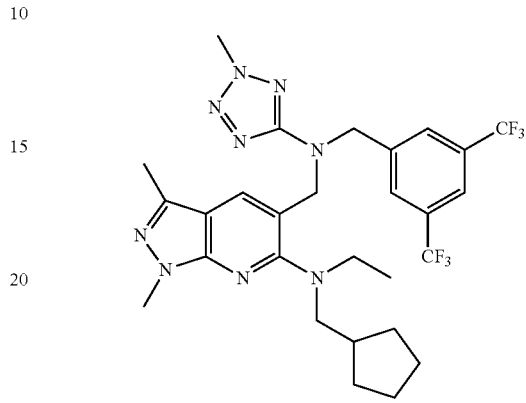

The title compound was obtained as a light orange solid following the procedure as described in Example 1, by using cyclopentylmethyl-ethyl-amine, instead of cyclobutylmethyl-ethyl-amine in step (iii) (56%), mp: 84-86° C.

Purity: 99%.

$^1$H NMR (400 MHz, CDCl$_3$): δ 7.70-7.61 (m, 4H), 4.79 (s, 2H), 4.61 (s, 2H), 4.22 (s, 3H), 3.95 (s, 3H), 3.17-3.11 (m, 4H), 2.39 (s, 3H), 2.13-2.04 (m, 1H), 1.58-1.40 (m, 8H), 1.06 (t, J=14.0 Hz, 3H).

ES-MS m/z: 610 (M$^+$+1, 100%).

IR (neat) cm$^{-1}$: 3447, 2955, 2866, 1610, 1582, 1563, 1403, 1361, 1281, 1170, 1131, 900, 706, 682.

Example 25

Synthesis of (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-diisobutyl-amine

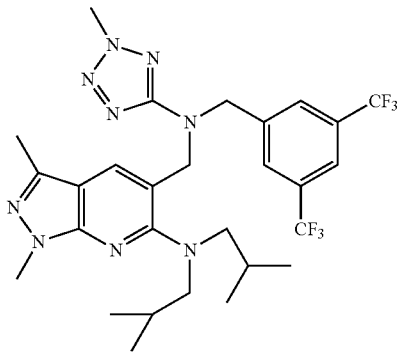 [SMILES: Cc1nn(C)c2nc(N(CC(C)C)CC(C)C)c(CN(Cc3cc(C(F)(F)F)cc(C(F)(F)F)c3)c3nnn(C)n3)cc12]

The title compound was obtained as a gummy liquid following the procedure as described in Example 1, using diisobutyl-amine, instead of cyclobutylmethyl-ethyl-amine in step (iii) (0.395 g), yield: 38%.

Purity: 95%.

$^1$H NMR (400 MHz, CDCl$_3$): δ 7.69 (s, 1H), 7.58 (s, 2H), 7.55 (s, 1H), 4.81 (s, 2H), 4.61 (s, 2H), 4.22 (s, 3H), 3.93 (s, 3H), 3.02-3.00 (m, 4H), 2.37 (s, 3H), 1.92-1.82 (m, 2H), 0.77-0.74 (m, 12H).

CI-MS m/z 611 (M$^+$+1, 100%).

IR (neat) cm$^{-1}$: 2959, 2871, 1612, 1582, 1563, 1514, 1466, 1404, 1380, 1279, 1175, 1138, 1050, 758.

Example 26

Synthesis of (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopropylmethyl-isobutyl-amine

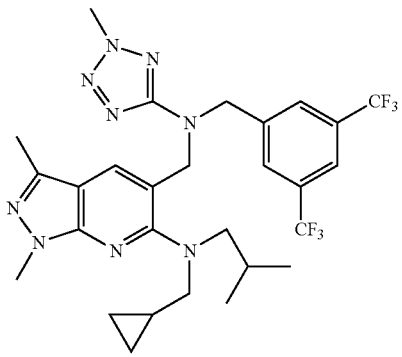 [SMILES: Cc1nn(C)c2nc(N(CC(C)C)CC3CC3)c(CN(Cc3cc(C(F)(F)F)cc(C(F)(F)F)c3)c3nnn(C)n3)cc12]

The title compound was obtained as a colorless solid following the procedure as described in Example 1, using cyclopropylmethyl-isobutyl-amine, instead of cyclobutylmethyl-ethyl-amine in step (iii) (0.35 g), yield: 40%, mp: 99-101° C.

Purity: 99%.

$^1$H NMR (400 MHz, CDCl$_3$): δ 7.69-7.59 (m, 4H), 4.84 (s, 2H), 4.63 (s, 2H), 4.22 (s, 3H), 3.95 (s, 3H), 3.19 (d, J=7.2 Hz, 2H), 2.95 (d, J=6.4 Hz, 2H), 2.38 (s, 3H), 1.84-1.82 (m, 1H), 1.81-1.68 (m, 1H), 0.79-0.78 (m, 6H), 0.41-0.39 (m, 2H), 0.02-0.00 (m, 2H).

ES-MS m/z 610 (M$^+$+1, 100%).

IR (neat) cm$^{-1}$: 2928, 1611, 1582, 1380, 1278, 1175, 1136, 902.

Example 27

Synthesis of cyclopropanecarboxylic acid (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopropylmethyl-amide

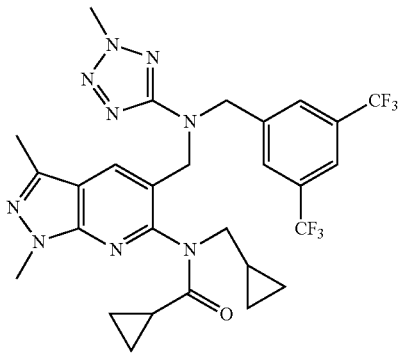 [SMILES: Cc1nn(C)c2nc(N(CC3CC3)C(=O)C3CC3)c(CN(Cc3cc(C(F)(F)F)cc(C(F)(F)F)c3)c3nnn(C)n3)cc12]

Step (i): Synthesis of 3,5-bis-trifluoromethyl-benzyl)-(6-chloro-1,3-dimethyl-1H-pyrazolo[3,4-b]pyridin-5-ylmethyl)-amine

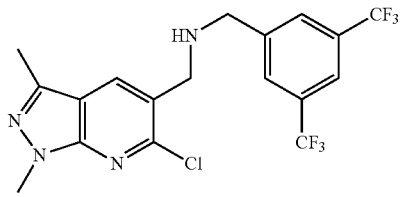 [SMILES: Cc1nn(C)c2nc(Cl)c(CNCc3cc(C(F)(F)F)cc(C(F)(F)F)c3)cc12]

A mixture of 6-chloro-1,3-dimethyl-1H-pyrazolo[3,4-b]pyridine-5-carbaldehyde (6.3 g, 30 mmol) and 3,5-bis-trifluoromethylbenzylamine (7.3 g, 30 mmol) in MeOH (75 mL) and acetic acid (2 drops) was stirred at room temperature for 30 minutes. The reaction was then cooled to 0° C. and sodium cyanoborohydride (3.7 g, 50 mmol) was added slowly over a period of 10 minutes. After being stirred for 2 h at RT, the reaction mixture was concentrated, water (50 mL) was added to the residue, and the resulting mixture was stirred for 30 min. The solid product was filtered off, washed with water and petroleum ether, and dried under vacuum to afford a colorless solid (9.2 g), yield: 70%.

$^1$H NMR (400 MHz, CDCl$_3$): δ 7.94 (s, 1H), 7.86 (s, 2H), 7.77 (s, 1H), 4.04-3.97 (m, 7H), 2.54 (s, 3H).

CI-MS m/z 437 (M$^+$+1, 100%).

Step (ii): Synthesis of (3,5-bis-trifluoromethyl-benzyl)-(6-chloro-1,3-dimethyl-1H-pyrazolo[3,4-b]pyridin-5-ylmethyl)-cyanamide

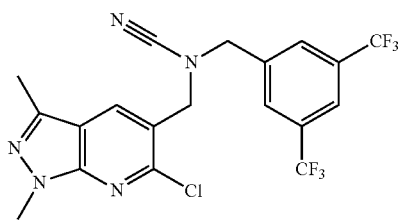 [SMILES: Cc1nn(C)c2nc(Cl)c(CN(C#N)Cc3cc(C(F)(F)F)cc(C(F)(F)F)c3)cc12]

A mixture of compound 3,5-bis-trifluoromethyl-benzyl)-(6-chloro-1,3-dimethyl-1H-pyrazolo[3,4-b]pyridin-5-ylmethyl)-amine (9.0 g, 0.02 mol), cyanogen bromide (2.60 g, 0.024 mole), and sodium hydrogen carbonate (3.50 g, 0.04 mole) in methanol (150 mL) was stirred at RT for 30 minutes. The reaction mixture was then concentrated, water (100 mL) was added to the residue, and this mixture was stirred for another 30 min. The resultant solid was filtered off, washed with water followed by petroleum ether, and finally dried under vacuum to yield a colorless solid (8.70 g), yield: 91%.

$^1$H NMR (400 MHz, CDCl$_3$): δ 7.95 (s, 1H), 7.87 (s, 1H), 7.79 (s, 2H), 4.42-4.40 (m, 4H), 4.05 (s, 3H), 2.54 (s, 3H).

CI-MS m/z 462 (M$^+$+1, 30%).

Step (iii): Synthesis of (3,5-bis-trifluoromethyl-benzyl)-(6-chloro-1,3-dimethyl-1H-pyrazolo[3,4-b]pyridin-5-ylmethyl)-(2H-tetrazol-5-yl)-amine

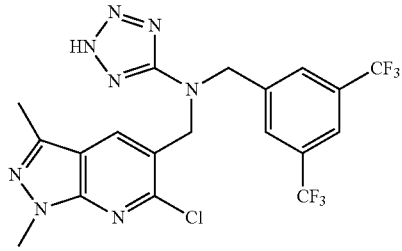 [SMILES: Cc1nn(C)c2nc(Cl)c(CN(Cc3cc(C(F)(F)F)cc(C(F)(F)F)c3)c3nn[nH]n3)cc12]

A mixture of (3,5-bis-trifluoromethyl-benzyl)-(6-chloro-1,3-dimethyl-1H-pyrazolo[3,4-b]pyridin-5-ylmethyl)-cyanamide (8.5 g, 10 mmol), sodium azide (1.4 g, 20 mmol), and zinc bromide (4.1 g, 10 mmol) in water (300 mL) was refluxed for 3 h. The reaction mixture was cooled to RT, 5% hydrochloric acid (50 mL) and ethyl acetate (500 mL) were added, and the resulting mixture was stirred for 20 min, after which time the organic layer was separated. This process was repeated 3 more times with ethyl acetate (3×500 mL). The combined organic layers were dried and concentrated, and the residue was purified by column chromatography over 230-400 mesh silica gel. Elution of the column with 15% ethyl acetate in hexanes gave the pure product as a colorless solid (8.3 g), yield: 90%.

$^1$H NMR (400 MHz, CDCl$_3$): δ 7.85 (s, 1H), 7.67-7.72 (m, 3H), 4.87-4.89 (m, 4H), 4.01 (s, 3H), 2.48 (s, 3H).

CI-MS m/z 504 (M$^+$+1, 100%).

Step (iv): Synthesis of (3,5-bis-trifluoromethyl-benzyl)-(6-chloro-1,3-dimethyl-1H-pyrazolo[3,4-b]pyridin-5-ylmethyl)-(2-methyl-2H-tetrazol-5-yl)-amine

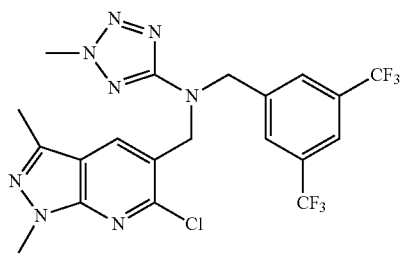 [SMILES: Cc1nn(C)c2nc(Cl)c(CN(Cc3cc(C(F)(F)F)cc(C(F)(F)F)c3)c3nnn(C)n3)cc12]

A mixture of (3,5-bis-trifluoromethyl-benzyl)-(6-chloro-1,3-dimethyl-1H-pyrazolo[3,4-b]pyridin-5-ylmethyl)-(2H-tetrazol-5-yl)-amine (8.5 g, 10 mmol) and sodium hydride (0.81 g, 30 mmol) in DMF (150 mL) was stirred at 0° C. for 20 minutes. Thereafter, methyl iodide (3.5 g, 20 mmol) was added and the resulting mixture was stirred at 0-10° C. for 30 minutes. Water (100 mL) was added to the reaction mixture, which was then extracted with ethyl acetate (3×100 mL). The combined organic layers were dried over sodium sulfate and concentrated. The residue was purified by column chromatography over 230-400 mesh silica gel. Elution of the column with 10% acetone in hexanes gave the pure product as a colorless solid (6.3 g), yield: 75%.

$^1$H NMR (400 MHz, CDCl$_3$): δ 7.66-7.85 (m, 4H), 4.84-4.89 (m, 4H), 4.20 (s, 3H), 4.02 (s, 3H), 2.48 (s, 3H).

CI-MS m/z 504 (M$^+$+1, 100%).

Step (v): Synthesis of (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopropylmethyl-amine

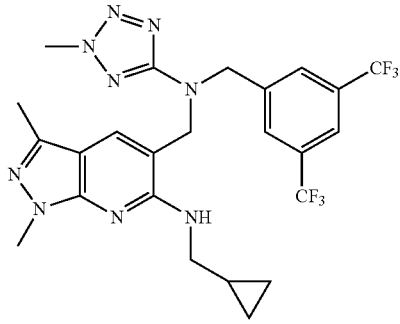 [SMILES: Cc1nn(C)c2nc(NCC3CC3)c(CN(Cc3cc(C(F)(F)F)cc(C(F)(F)F)c3)c3nnn(C)n3)cc12]

A mixture of (3,5-bis-trifluoromethyl-benzyl)-(6-chloro-1,3-dimethyl-1H-pyrazolo[3,4-b]pyridin-5-ylmethyl)-(2-methyl-2H-tetrazol-5-yl)-amine (0.5 g, 0.9 mmol), potassium tertiary butoxide (0.43 g, 3 mmol), cyclopropylmethyl amine (0.275 g, 3 mmol), and Pd(OAc)$_2$ (0.01 g, 0.004 mmol), BINAP (0.03 g, 0.04 mmol) was prepared in a 10 mL pressure vial. The pressure vial was placed in the focused microwave oven (CEM Discovery) and irradiated for 20 min at 110° C. by using 250 Watt microwave power. After this mixture was cooled to RT, ethyl acetate (100 mL) was added to the vial. The organic layer was washed with water (3×100 mL) and dried and concentrated. The resultant oil was purified by column chromatography using silica gel (230-400 mesh) and eluting the column with 10% ethyl acetate in hexane afforded a colorless solid (0.485 g), yield: 90%.

$^1$H NMR (400 MHz, CDCl$_3$): δ 7.69 (s, 1H), 7.54 (s, 2H), 7.32 (s, 1H), 5.80 (bs, 1H), 4.67-4.62 (m, 4H), 4.21 (s, 3H), 3.88 (s, 3H), 3.33-3.27 (m, 2H), 2.40 (s, 3H), 1.02-0.92 (m, 1H), 0.46-0.37 (m, 2H), 0.17-0.12 (m, 2H).

ES-MS m/z 554 (M$^+$+1, 100%).

Step (vi): Synthesis of cyclopropanecarboxylic acid (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopropylmethyl-amide

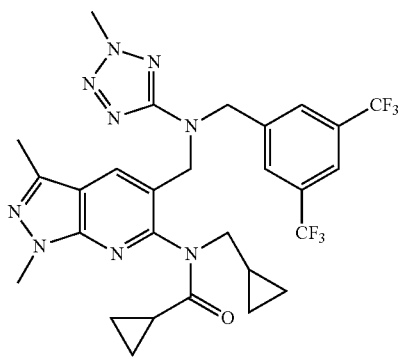 [SMILES: Cc1nn(C)c2nc(N(CC3CC3)C(=O)C3CC3)c(CN(Cc3cc(C(F)(F)F)cc(C(F)(F)F)c3)c3nnn(C)n3)cc12]

A mixture of (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopropylmethyl-amine (0.25 g, 0.45 mmol), triethylamine (0.13 g, 1.3 mmol), and cyclopropanecarbonyl chloride (0.28 g, 2.7 mmol) in THF (5 mL) was prepared in 10 mL reaction vessel and irradiated with 250 Watt microwave power, under 250 psi at 80° C. for 2 h. The vessel was cooled to RT and the reaction mixture was diluted with ethyl acetate (100 mL). The ethyl acetate layer was washed with water (3×100 mL), the organic layer was separated out, dried over sodium sulfate, and concentrated. The resulting oil was purified by column chromatography using silica gel (230-400 mesh) and eluting the column with 1% methanol in dichloromethane afforded a colorless solid (0.147 g), yield: 52.5%, mp 120-122° C.

Purity: 98%.

$^1$H NMR (400 MHZ, CDCl$_3$): δ 7.78-7.71 (m, 4H), 5.04-4.78 (m, 4H), 4.17 (s, 3H), 4.05 (s, 3H), 3.71 (d, J=5.104 Hz, 2H), 2.49 (s, 3H), 2.38 (s, 3H), 1.84-1.82 (m, 1H), 1.81-1.68 (m, 1H), 0.79-0.78 (m, 6H), 0.41-0.39 (m, 2H), 0.02-0.00 (m, 2H).

ES-MS m/z 622 (M$^+$+1, 100%).

IR (neat) cm$^{-1}$: 3445, 2925, 1648, 1590, 1380, 1278, 1181, 1134, 709, 682.

Example 28

Synthesis of cyclopentanecarboxylic acid (5-{[(3,5-bis-trifluoromethyl-benzyl)-(2methyl-2H-tetrazol-5-yl)-amino]-methyl}-1,3-dimethyl-1H-pyrazolo[3,4-b]pyridin-6-yl)-cyclopropylmethyl-amide

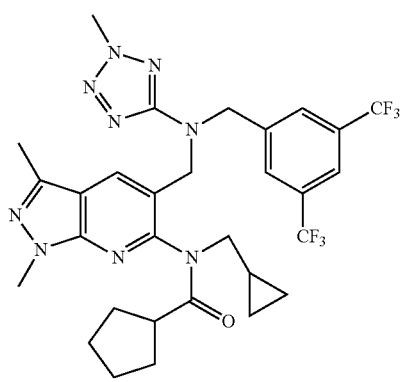 [SMILES: Cc1nn(C)c2nc(N(CC3CC3)C(=O)C3CCCC3)c(CN(Cc3cc(C(F)(F)F)cc(C(F)(F)F)c3)c3nnn(C)n3)cc12]

The title compound (purity 99%) was obtained as a colorless solid following the procedure as described in Example 27, using cyclopentanecarbonyl chloride, instead of cyclopropanecarbonyl chloride in step (vi) (0.085 g), yield: 48.2%, mp 88-90° C.

Purity: 99%.

$^1$H NMR (400 MHz, CDCl$_3$): δ 7.78-7.70 (m, 4H), 4.88-4.74 (m, 4H), 4.16 (s, 3H), 4.03 (s, 3H), 3.78-3.73 (m, 2H), 3.49-3.44 (m, 1H), 2.50 (s, 3H), 2.23-2.21 (m, 1H), 1.87-1.25 (m, 8H), 0.96 (m, 2H), 0.33-0.29 (m, 2H).

ES-MS m/z 650 (M$^+$+1, 100%).

IR (neat) cm$^{-1}$: 3444, 2954, 1657, 1565, 1392, 1365, 1279, 1180, 1130, 1021, 897.

Example 29

Synthesis of cyclohexanecarboxylic acid (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-cyclopropylmethyl-amide

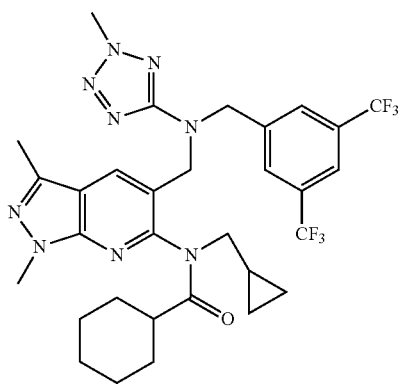 [SMILES: Cc1nn(C)c2nc(N(CC3CC3)C(=O)C3CCCCC3)c(CN(Cc3cc(C(F)(F)F)cc(C(F)(F)F)c3)c3nnn(C)n3)cc12]

The title compound was obtained as a colorless liquid following the procedure as described in Example 27, using cyclohexanecarbonyl chloride, instead of cyclopropanecarbonyl chloride in step (vi) (0.13 g), yield: 72%.

Purity: 96%.

$^1$H NMR (400 MHz, CDCl$_3$): δ 7.79-7.70 (m, 4H), 4.94-4.75 (m, 4H), 4.17 (s, 3H), 4.02 (s, 3H), 3.73-3.68 (m, 2H), 3.52-3.46 (m, 1H), 2.51 (s, 3H), 2.36-2.29 (m, 2H), 1.95-1.18 (m, 9H), 0.96-0.92 (m, 2H), 0.32-0.27 (m, 2H).

ES-MS m/z 664 (M$^+$+1, 100%).

IR (neat) cm$^{-1}$: 2933, 2857, 1726, 1659, 1581, 1380, 1279, 1174, 1135, 1021, 895, 707, 682.

Example 30

Synthesis of N-(5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-N-cyclopropylmethyl-acetamide

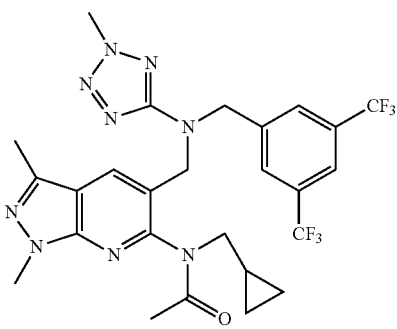 [SMILES: CC(=O)N(CC1CC1)c1nc2c(cc1CN(Cc1cc(C(F)(F)F)cc(C(F)(F)F)c1)c1nnn(C)n1)c(C)nn2C]

The title compound was obtained as a colorless liquid following the procedure as described in Example 27, using acetyl chloride, instead of cyclopropanecarbonyl chloride in step (vi) (0.15 g), yield: 93%.

Purity: 98%.
¹H NMR (400 MHz, CDCl₃): δ 7.80-7.71 (m, 4H), 4.95-4.70 (m, 4H), 4.17 (s, 3H), 4.04 (s, 3H), 3.80-3.43 (m, 2H), 2.51 (s, 3H), 2.27 (m, 1H), 1.80 (s, 3H), 0.99-0.86 (m, 2H), 0.35-0.30 (m, 2H).
ES-MS m/z 596 (M⁺+1, 100%).
IR (neat) cm⁻¹: 3457, 2928, 1664, 1580, 1380, 1279, 1174, 1135, 1021, 903, 756, 682.

Example 31

Synthesis of N-(5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-3-chloro-N-cyclopropylmethyl-propionamide

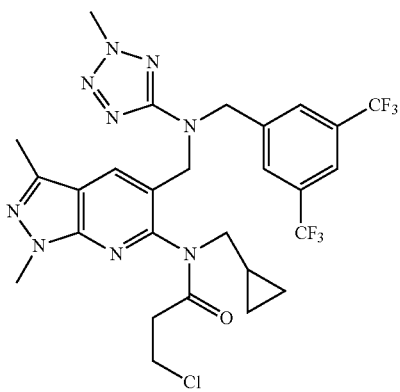 [SMILES: Cc1nn(C)c2nc(N(CC3CC3)C(=O)CCCl)c(CN(Cc3cc(C(F)(F)F)cc(C(F)(F)F)c3)c3nnn(C)n3)cc12]

The title compound was obtained as a colorless liquid following the procedure as described in Example 27, using chloropropionyl chloride, instead of cyclopropanecarbonyl chloride in step (vi) (0.066 g), yield: 38%.
Purity: 97%.
¹H NMR (400 MHz, CDCl₃): δ 7.79-7.71 (m, 4H), 4.99-4.64 (m, 4H), 4.18 (s, 3H), 4.03 (s, 3H), 3.86-3.37 (m, 4H), 2.60-2.33 (m, 6H), 1.00-0.83 (m, 2H), 0.39-0.31 (m, 2H).
ES-MS m/z 644 (M⁺+1, 100%).
IR (neat) cm⁻¹: 2927, 2361, 1664, 1579, 1403, 1380, 1279, 1174, 1135, 1021, 903, 756, 682.

Example 32

Synthesis of (3,5-bis-trifluoromethyl-benzyl)-[6-(cyclopentylmethyl-ethyl-amino)-3-methyl-isoxazolo[5,4-b]pyridine-5-ylmethyl}-carbamic acid methyl ester

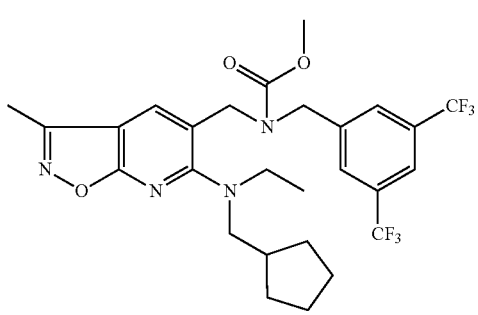 [SMILES: CCN(CC1CCCC1)c1nc2onc(C)c2cc1CN(Cc1cc(C(F)(F)F)cc(C(F)(F)F)c1)C(=O)OC]

The title compound was prepared following the experimental procedure for Example 16 except using 3-methyl-isoxazol-5-ylamine, instead of 1,3-dimethyl-pyrazol-5-ylamine in step (i) (65%).
Purity 93.66% (HPLC: Symmetry Shield RP8, [0.01M KH₂PO₄:CH₃CN], 210 nM, R, 9.174 min)
¹H NMR (400 MHz, CDCl₃): δ 7.78 (s, 1H), 7.63-7.52 (m, 3H), 4.57-4.51 (m, 2H), 4.42-4.38 (m, 2H), 3.89 (s, 3H), 3.20-3.16 (m, 4H), 2.48 (s, 3H), 2.16-2.07 (m, 1H), 1.52-1.42 (m, 8H), 1.05 (t, J=7.0 Hz, 3H).
(ES-MS) m/z 573 (M⁺+1, 100%)

Example 33

Synthesis of (5-{[(3,5-bis-trifluoromethyl-benzyl)-(2-methyl-2H-tetrazol-5-yl)-amino]-methyl}-3-methyl-isoxazolo[5,4-b]pyridine-6-yl)-cyclopentylmethyl-ethyl-amine

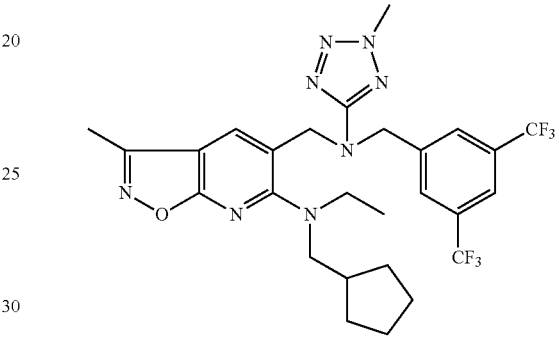

The title compound was prepared following the experimental procedure for Example 24 except using {5-[(3,5-bis-trifluoromethyl-benzylamino)-methyl]-3-methyl-isoxazolo[5,4-b]pyridine-6-yl}-cyclopentylmethyl-ethyl-amine, instead of {5-[(3,5-bis-trifluoromethyl-benzylamino)-methyl]-1,3-dimethyl-1H-pyrazolo[3,4-b]pyridine-6-yl}-cyclopentylmethyl-ethyl-amine (60%).
Purity 98% (HPLC: Symmetry Shield RP8, [0.01M KH₂PO₄:CH₃CN], 210 nM, R, 9.165 min)
¹H NMR (400 MHz, CDCl₃): δ 7.75 (s, 1H), 7.64-7.63 (m, 3H), 4.74 (s, 2H), 4.63 (s, 2H), 4.22 (s, 3H), 3.24-3.19 (m, 4H), 2.42 (s, 3H), 2.15-2.04 (m, 1H), 1.59-1.41 (m, 6H), 1.07 (t, J=7.0 Hz, 3H), 1.04-0.99 (m, 2H).
(ES-MS) m/z 597 (M⁺+1, 100%).

Example 34

Synthesis of (5-{[(3,5-bis-trifluoromethyl-benzyl)-(2-methyl-2H-tetrazol-5-yl)-amino]-methyl}-1,3-dimethyl-1H-pyrazolo[3,4-b]pyridin-6-yl)-ethyl-(tetrahydro-furan-2ylmethyl)-amine

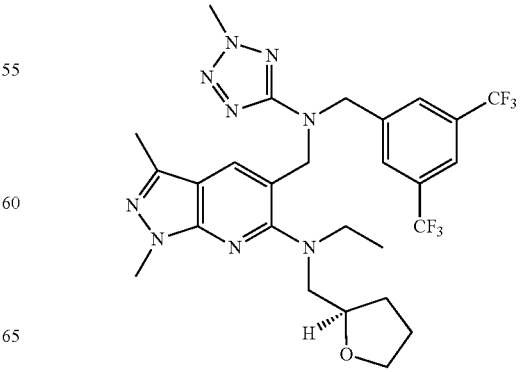

The title compound was obtained as a colorless thick liquid following the procedure as described in Example 1, by using (S)-ethyl-(tetrahydro-furan-2-ylmethyl)-amine, instead of cyclobutylmethyl-ethyl-amine in step (iii) (0.21 g), yield: 55%.

Purity: 95.02% (HPLC: YMC C8, 20:80 [KH$_2$PO$_4$ (0.01 M, pH 3.2):CH$_3$CN], R$_t$ 4.41 min)

$^1$H NMR (300 MHz, CDCl$_3$): δ 7.69-7.65 (m, 4H), 4.83 (s, 2H), 4.66 (s, 2H), 4.21 (s, 3H), 4.01-3.98 (m, 1H), 3.94 (s, 3H), 3.79-3.74 (m, 1H), 3.65-3.59 (m, 1H), 3.41-3.34 (m, 2H), 3.22-3.14 (m, 2H), 3.16 (s, 3H), 1.86-1.76 (m, 4H), 1.08 (t, J=6.81 Hz, 3H).

MS (ESI) m/z 612 (M+1)$^+$.

Example 35

Synthesis of (3,5-bis-trifluoromethyl-benzyl)-[2-(cyclopentylmethyl-ethyl-amino)-quinolin-3-ylmethyl]-carbamic acid methyl ester Step (i): Synthesis of 2-chloroquinoline-3-carbaldehyde

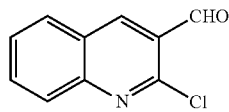

Dimethylformamide (9.13 grams, 0.125 mol) was cooled to 0° C. in a flask equipped with a drying tube, and phosphorous oxychloride (53.7 grams, 0.35 mol) was added drop-wise with stirring. To this solution was added acetanilide (6.55 grams, 0.05 mol) and the mixture was heated under reflux for 16 hours at 65° C. Excess phosphorous oxychloride was distilled off, water was added, and the solution was extracted with ethyl acetate. The solvent was evaporated and the crude purified over silica gel (100-200 mesh) using 2% ethyl acetate/petroleum ether. Yield: 68%, mp: 145° C.;

$^1$H NMR (CDCl$_3$, 400 MHz): δ 10.5 (s, 1H); 8.78 (s, 1H), 8.12-7.90 (m, 3H); 7.70 (t, J=7.3 Hz, 1H);

Mass m/z (EI-MS): 192 (M+1, 100%).

Step (ii): Synthesis of N-cyclopentylmethyl ethylamine

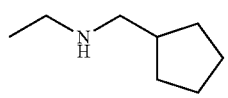

N-Cyclopentenoyl-ethylamine was prepared from cyclopentenoic acid (2 grams, 17.5 mmol) and oxallyl chloride (2.2 grams, 17.5 mmol) after stirring at 25-35° C. for 8-12 hours. To this was added a benzene solution of ethylamine (2.1 grams, 48.7 mmol) at 0° C., and this reaction mixture was stirred for 3 hours at 25-35° C., after which time the solvent was evaporated under vacuum to yield N-cyclopentenoyl-ethylamine (1.7 grams), yield: 68.9%. A solution of N-cyclopentenoyl-ethylamine (1.7 grams, 13.3 mmol) in anhydrous tetrahydrofuran (THF) (10 mL) under a nitrogen atmosphere, and lithium aluminum hydride (LiAlH$_4$; 1.3 grams, 36.1 mmol) was added to the solution. After being stirred for 1 hour at 25-35° C., the reaction mixture was gently refluxed for 8 hours. The reaction mixture was quenched with saturated sodium sulfate solution, filtered, and the precipitate washed with diethyl ether (Et$_2$O). The filtrate was concentrated to afford N-cyclopentylmethyl ethylamine (0.6 g), yield: 40%.

$^1$H NMR (CDCl$_3$): δ 5.41 (bs, 1H), 3.34-3.21 (m, 2H), 2.50-2.39 (m, 1H), 1.86-1.55 (m, 8H), 1.12 (t, J=7.2 Hz, 3H); CI-MS (/z): 127 (MW, 20%), 126 (M−1, 100%).

Step (iii): Synthesis of 2-(cyclopentylmethyl-ethyl-amino)-quinolin-3-carbaldehyde

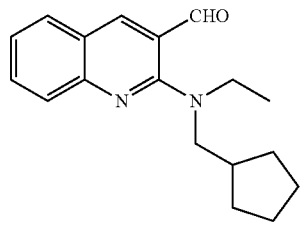 [SMILES: CCN(CC1CCCC1)c1nc2ccccc2cc1C=O]

2-Chloroquinoline-3-carbaldehyde (0.27 grams, 1.40 mmol) and potassium carbonate (0.579 grams, 1.4 mmol) were added to a 25 mL two-necked round bottomed flask. To this flask was added 3 mL of N,N-dimethylformamide (DMF), followed by the drop-wise addition of a dimethylformamide solution of cyclopentyl methyl ethyl amine (0.214 grams, 1.69 mmol). The resulting mixture was refluxed for 2 hours and then cooled to 25-35° C., after which the mixture was poured onto crushed ice (10 mL), and extracted with ethyl acetate (3×50 mL). The organic layer was washed with brine and dried over sodium sulfate. The solvent was evaporated in vacuo to provide the product as a yellow oil. Yield: 0.355 g (89%);

$^1$H NMR (CDCl$_3$, 400 MHz): δ 10.14 (s, 1H); 8.44 (s, 1H); 7.80-7.74 (m, 2H); 7.67-7.63 (m, 1H); 7.34-7.30 (m, 1H), 3.55-3.47 (m, 4H), 2.37-2.29 (m, 1H), 1.73-1.72 (m, 2H), 1.70-1.46 (m, 3H), 1.20-1.11 (m, 6H);

m/z (EI-MS): 282 (M+1, 40%), 213 (100%);

IR (cm$^{-1}$):3385, 2948, 1691.

Step (iv): Synthesis of {3-[(3,5-bis-trifluoromethyl-benzylamino)-methyl]-quinolin-2-yl}-cyclopentylmethyl-ethyl-amine

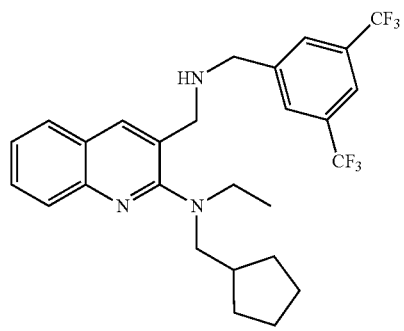 [SMILES: CCN(CC1CCCC1)c1nc2ccccc2cc1CNCc1cc(C(F)(F)F)cc(C(F)(F)F)c1]

2-(Cyclopentylmethyl-ethyl-amino)-quinolin-3-carbaldehyde (0.355 grams, 1.25 mmol), obtained in step (iii), 3,5-bis-trifluoromethylbenzylamine (0.305 grams, 1.25 mmol), and acetic acid (0.151 grams, 2.51 mmol) were added to a 25 mL round-bottomed flask, followed by 4 mL of methanol, and the mixture was stirred at 25-35° C. for 15 minutes. Sodium cyanoborohydride (0.237 grams, 3.77 mmol) was then added portion-wise. Stirring at room temperature was continued for another 1 hour, after which time the methanol was removed under vacuum, and water was added to the crude mixture. This mixture was extracted with ethyl acetate (3×50 mL), and the combined organic layers washed with saturated sodium bicarbonate solution, then brine, and then dried over sodium sulfate. The solvent was evaporated to provide the product as an oily residue, which was purified over silica gel (100-200) using 4% ethyl acetate/petroleum ether. Yield: 155 mg (56%).

$^1$H NMR (CDCl$_3$, 400 MHz): δ 7.96 (s, 1H); 7.85 (d, J=8.5 Hz, 1H); 7.81 (s, 2H); 7.76 (s, 1H); 7.68 (q, J$_1$=8.0 Hz, J$_2$=1.3 Hz, 1H), 7.58 (m, 1H); 7.37-7.35 (m, 1H); 3.96 (s, 2H), 3.84 (s, 2H), 3.30-3.24 (m, 4H), 2.17-2.12 (m, 1H), 1.64-1.09 (m, 11H);

m/z (EI-MS): 509 (M$^+$, 40%), 282 (100%);

IR (cm$^{-1}$): 3357, 2929, 2851.

Step (v): Synthesis of (3,5-bis-trifluoromethyl-benzyl)-[2-(cyclopentylmethyl-ethyl-amino)-quinolin-3-ylmethyl]-carbamic acid methyl ester

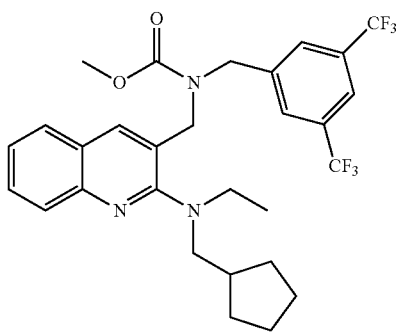 [SMILES: CCN(CC1CCCC1)c1nc2ccccc2cc1CN(Cc1cc(C(F)(F)F)cc(C(F)(F)F)c1)C(=O)OC]

{3-[(3,5-Bis-trifluoromethyl-benzylamino)-methyl]-quinolin-2-yl}-cyclopentyl-methyl-ethyl-amine (0.155 g, 0.304 mmol), obtained in step (iv), and K$_2$CO$_3$ (0.126 g, 0.913 mmol) were added to a two-necked round-bottomed flask under a nitrogen atmosphere. Dry tetrahydrofuran (3 to 4 mL) was added to the flask, and the mixture was stirred at room temperature for 30 minutes. Methylchloroformate (0.035 grams, 0.456 mmol) was then added dropwise, and the reaction mixture was stirred at 25-35° C. for 8-12 hours. After this time, the solvent was removed in vacuo, water added to it, and the mixture extracted with ethyl acetate. The organic layer was dried over sodium sulfate and concentrated under vacuum to get the crude title compound, which was purified over silica gel (100-200 mesh ASTM) using 3% ethyl acetate/petroleum ether. The desired compound was obtained as a yellow sticky compound having purity of 96.70%.

Yield: 115 mg (90%);

$^1$H NMR (CDCl$_3$, 400 MHz): δ 7.86-7.79 (m, 1H); 7.75-7.73 (m, 2H); 7.65-7.63 (m, 2H); 7.60-7.57 (m, 2H); 7.45-7.32 (m, 1H); 4.67 (s, 2H); 4.49 (s, 2H); 3.88 (s, 3H); 3.20-3.13 (m, 4H); 2.14-2.11 (m, 1H), (1.67-1.40 (m, 5H); 1.32-1.20 (m, 2H); 1.17-1.04 (m, 3H) 0.89-0.82 (m, 1H); m/z (ES-MS): 568 (M+1,100%); IR (cm$^{-1}$): 2955, 1710, 1279.

Example 36

Synthesis of (3,5-bis-trifluoromethyl-benzyl)-(2-diethylamino-quinolin-3-ylmethyl)-carbamic acid methyl ester

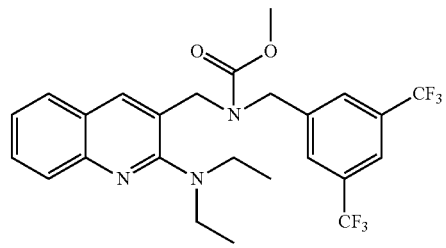 [SMILES: CCN(CC)c1nc2ccccc2cc1CN(Cc1cc(C(F)(F)F)cc(C(F)(F)F)c1)C(=O)OC]

The title compound was synthesized following the same procedure used for Example 35 except diethylamine was used instead of cyclopentylmethyl ethyl amine in step (iii), and the product was obtained as a colorless sticky compound (0.14 g), purity: 60%, of purity 95.45% (HPLC: Alltima C18, [0.01M KH$_2$PO$_4$:CH$_3$CN], 215 nM, R$_t$ 10.589 min)

IR (neat, cm$^{-1}$): 2970, 1708, 1279, 1135;

$^1$H NMR (CDCl$_3$, 400 MHz): δ 7.86 (d, J=8.3 Hz, 1H), 7.75 (d, J=5.6 Hz, 2H), 7.67-7.58 (m, 4H), 7.37 (t, J=7.3 Hz, 1H), 4.55 (s, 2H), 4.45 (s, 2H), 3.89 (s, 3H), 3.21 (q, J=14.0 Hz, 4H), 1.06 (t, J=6.9 Hz, 6H);

m/z (ES-MS): 514 (M$^+$, 100%)

Example 37

Synthesis of (3,5-bis-trifluoromethyl-benzyl)-(2-pyrrolidin-1-yl-quinolin-3-ylmethyl)-carbamic acid methyl ester

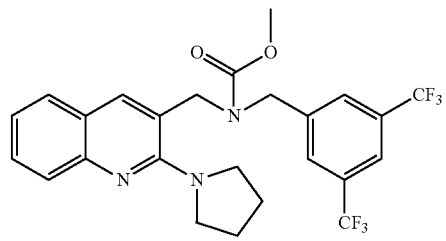 [SMILES: COC(=O)N(Cc1cc(C(F)(F)F)cc(C(F)(F)F)c1)Cc1cc2ccccc2nc1N1CCCC1]

The title compound was obtained as an oil following the procedure as described in Example 35, using pyrrolidine instead of cyclopentyl methyl ethylamine in step (iii) (0.25 g, 59%) of 95.12% purity (HPLC: Inertsil ODS 3V, [0.01M KH$_2$PO$_4$:CH$_3$CN], 215 nM, R$_t$ 12.410 min).

IR (neat, cm$^{-1}$): 3395, 2959, 2872, 1708;

$^1$H NMR (CDCl$_3$, 400 MHz): δ 7.75-7.73 (m, 2H), 7.60-7.51 (m, 6H), 4.62 (br s, 2H), 4.48 (br s, 2H), 3.86 (s, 3H), 3.55-3.50 (m, 4H), 1.93-1.89 (m, 4H);

m/z (ES-MS): 512 (M$^+$+1, 100%)

Example 38

Synthesis of (3,5-bis-trifluoromethyl-benzyl)-(2-piperidin-1-yl-quinolin-3-ylmethyl)-carbamic acid methyl ester

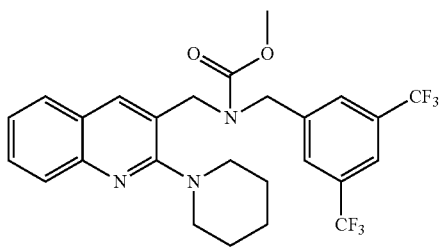 [SMILES: COC(=O)N(Cc1cc(C(F)(F)F)cc(C(F)(F)F)c1)Cc1cc2ccccc2nc1N1CCCCC1]

The title compound was synthesized following the same procedure described in Example 35, except using piperidine in step (iii) instead of cyclopentylmethyl ethyl amine. The product was obtained as a colorless, sticky compound (0.07 g), yield: 63% of purity 93.56% product (HPLC: Inertsil ODS 3V, [0.01M $KH_2PO_4$:$CH_3CN$], 215 nM, $R_t$ 10.569 min).

IR (neat, $cm^{-1}$): 3384, 2933, 2855, 1709;

$^1$H NMR ($CDCl_3$, 400 MHz): δ 7.94-7.80 (m, 2H), 7.72 (s, 1H), 7.66-7.51 (m, 4H), 7.38-7.35 (m, 1H), 4.58 (s, 2H), 4.44 (s, 2H), 3.89 (s, 3H), 3.09-3.08 (m, 4H), 1.60 (s, 4H), 1.54 (s, 2H);

m/z (ES-MS): 526 ($M^+$+1, 100%).

Example 39

Synthesis of (3,5-bis-trifluoromethyl-benzyl)-[2-(4-cyclohexylmethyl-piperazin-1-yl)-quinolin-3-ylmethyl]-carbamic acid ethyl ester

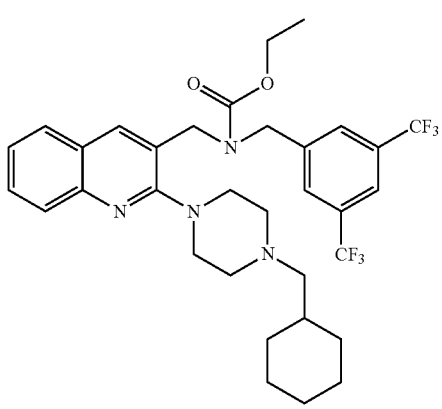 [SMILES: CCOC(=O)N(Cc1cc(C(F)(F)F)cc(C(F)(F)F)c1)Cc1cc2ccccc2nc1N1CCN(CC2CCCCC2)CC1]

Step (i): Synthesis of 2-(4-cyclohexylmethyl-piperazin-1-yl)-quinoline-3-carbaldehyde

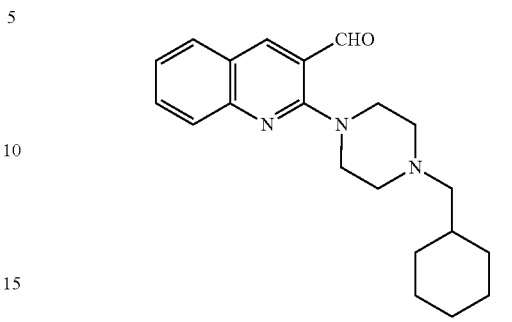

1-(Cyclohexylmethyl)piperazine (0.42 mL, 2.2 mmol) was added to a mixture of 2-chloro-3-quinolinecarboxaldehyde (0.383 g, 2.0 mmol) and potassium carbonate (0.7 g, 5.0 mmol) in anhydrous DMF (4 mL) at ambient temperature under a nitrogen atmosphere. After being stirred for 20 minutes, the reaction mixture was heated at 110° C. for 4.5 h. After cooling to room temperature this mixture was diluted with water (40 mL) and extracted with ethyl acetate (3×30 mL). The combined organic extracts were washed with brine, dried over sodium sulfate, filtered, and then concentrated under vacuum to give a pale brown crude product. Purification by silica gel column chromatography and eluting with 2.5% methanol in dichloromethane afforded the title compound (0.56 g), yield: 86%.

Mp 95-96° C.;

$^1$H NMR ($CDCl_3$, 300 MHz): δ 10.17 (s, 1H), 8.48 (s, 1H), 7.81 (t, J=8.2 Hz, 2H), 7.67 (m, 1H), 7.36 (m, 1H), 3.51 (t, J=5.1 Hz, 4H), 2.61 (t, J=4.8 Hz, 4H), 2.22 (d, J=7.2 Hz, 2H), 1.84-1.68 (m, 6H), 1.31-1.13 (m, 3H), 0.96-0.82 (m, 2H).

m/z MS: 338 ($M^+$+1, 100%)

Step (ii): Synthesis of (3,5-bis-trifluoromethyl-benzyl)-[2-(4-cyclohexylmethyl-piperazin-1-yl)-quinolin-3-ylmethyl]-amine

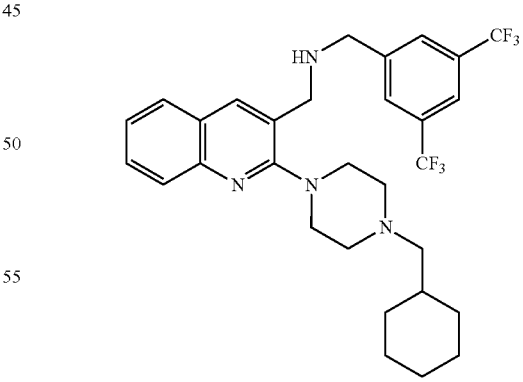

3,5-Bis(trifluoromethyl)benzylamine (0.305 g, 1.25 mmol) was added to a solution of 2-(4-cyclohexylmethyl-piperazin-1-yl)-quinoline-3-carbaldehyde (0.4 g, 1.23 mmol) in methanol followed by acetic acid (0.15 mL) at ambient temperature under nitrogen atmosphere. After stirring 1 h, sodium cyanoborohydride (0.237 g, 3.77 mmol) was added carefully, and the reaction was stirred at RT for overnight. The reaction mixture was evaporated to dryness, and water (30 mL) and ethyl acetate (30 mL) were added to the residue, and this was then extracted with ethyl acetate (2×30 mL). The combined organic phases were washed with brine, dried over sodium sulfate, filtered, and concentrated under vacuum to afford a pale yellow crude product. Purification by silica gel column chromatography and eluting with 2.5% methanol/dichloromethane afforded the title compound (0.468 g), yield: 67%.

Mp 54-55° C.;

$^1$H NMR (CDCl$_3$, 300 MHz): δ 8.11 (s, 1H), 7.84 (s, 1H), 7.80-7.68 (m, 4H), 7.64-7.58 (m, 1H), 7.45-7.39 (m, 1H), 4.09 (d, J=11.4 Hz, 2H), 3.85-3.72 (m, 4H), 3.46-3.27 (m, 4H), 2.85 (d, J=6.6 Hz, 2H), 2.05 (br s, D$_2$O exchangeable, 1H), 1.84-1.68 (m, 7H), 1.37-1.03 (m, 6H).

m/z MS: 565 (M$^+$+1)

Step (ii): Synthesis of (3,5-bis-trifluoromethyl-benzyl)-[2-(4-cyclohexylmethyl-piperazin-1-yl)-quinolin-3-ylmethyl]-carbamic acid ethyl ester

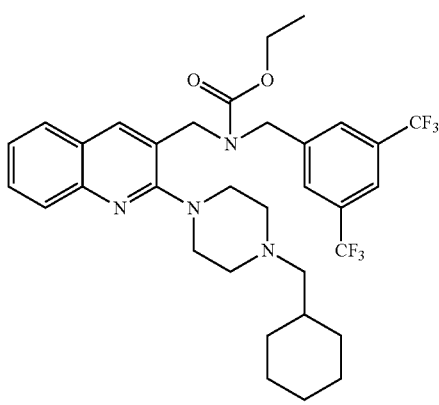 [SMILES: CCOC(=O)N(Cc1cc(C(F)(F)F)cc(C(F)(F)F)c1)Cc1cc2ccccc2nc1N1CCN(CC2CCCCC2)CC1]

Anhydrous potassium carbonate (0.17 g, 1.23 mmol) was added to a solution of (3,5-bis-trifluoromethyl-benzyl)-[2-(4-cyclohexylmethyl-piperazin-1-yl)-quinolin-3-yl-methyl]-amine (0.23 g, 0.4 mmol) in anhydrous THF (5 mL). After stirring 0.5 h, ethyl chloroformate (0.06 mL, 0.6 mmol) was added slowly under a nitrogen atmosphere. After stirring at RT for overnight, water (25 mL) was added, and the mixture was extracted with ethyl acetate (3×25 mL). The combined organic phases were washed with brine, dried over sodium sulfate, filtered, and concentrated in vacuo to give a colorless liquid. Purification by silica gel chromatography and eluting with 10-30% ethyl acetate/hexane afforded the desired final product as a viscous liquid (0.206 g), yield: 81%.

Purity 94.87% (HPLC: 30:70 [KH$_2$PO$_4$ (0.01 M, pH 3.2): CH$_3$CN], R$_t$ 4.22 min).

$^1$H NMR (CDCl$_3$, 300 MHz): δ 7.87-7.82 (m, 2H), 7.72 (s, 1H), 7.67-7.46 (m, 4H), 7.42-7.35 (m, 1H), 4.68-4.30 (m, 6H), 3.56-3.21 (m, 4H), 2.54-2.38 (m, 4H), 2.18-2.09 (m, 1H), 1.85-1.48 (m, 6H), 1.35 (t, J=7.2 Hz, 3H), 1.28-1.09 (m, 4H), 0.99-0.82 (m, 2H).

m/z MS 637 (M$^+$+1, 100%).

Example 40

Synthesis of [2-(benzyl-ethyl-amino)-quinolin-3-ylmethyl]-(3,5-bis-trifluoromethyl-benzyl)-carbamic acid ethyl ester

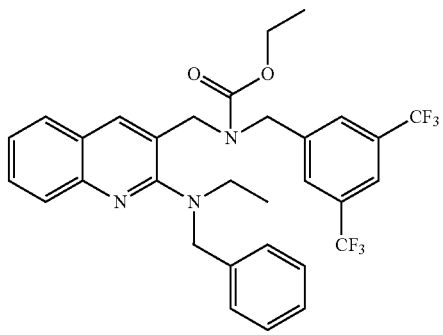 [SMILES: CCOC(=O)N(Cc1cc(C(F)(F)F)cc(C(F)(F)F)c1)Cc1cc2ccccc2nc1N(CC)Cc1ccccc1]

The title compound was prepared following the experimental procedure for Example 39, except using N-ethyl-benzylamine instead of 1-(cyclohexylmethyl)piperazine in Step (i) and was obtained as a viscous liquid (0.218 g), yield: 96%.

Purity 97.93% (HPLC: 30:70 [KH$_2$PO$_4$ (0.01 M, pH 3.2): CH$_3$CN], R$_t$ 99.72 min).

$^1$H NMR (CDCl$_3$, 300 MHz): δ 7.91 (s, 1H), 7.88 (s, 1H), 7.75 (s, 1H), 7.66-7.51 (m, 4H), 7.40 (t, J=7.5 Hz, 1H), 7.26-7.16 (m, 5H), 4.72-4.29 (m, 8H), 3.23 (q, J=6.9 Hz, 2H), 1.38-1.23 (m, 3H), 1.10 (t, J=6.9 Hz, 3H).

m/z MS: 590 (M$^+$+1).

Example 41

Synthesis of (3,5-bis-trifluoromethyl-benzyl)-[2-(butyl-ethyl-amino)-quinolin-3-ylmethyl]-carbamic acid ethyl ester

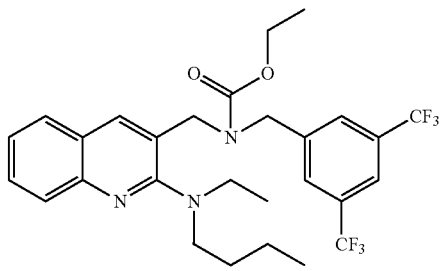 [SMILES: CCCCN(CC)c1nc2ccccc2cc1CN(Cc1cc(C(F)(F)F)cc(C(F)(F)F)c1)C(=O)OCC]

The target compound was prepared following the experimental procedure for Example 39, except using N-ethyl-butylamine instead of 1-(cyclohexylmethyl)piperazine in Step (i) and obtained as a viscous liquid (0.223 g), yield: 97.4%.

Purity 98.83% (HPLC: 30:70 [KH$_2$PO$_4$ (0.01 M, pH 3.2): CH$_3$CN], R$_t$ 52.25 min).

$^1$H NMR (CDCl$_3$, 300 MHz): δ 7.89-7.79 (m, 2H), 7.74 (s, 1H), 7.68-7.56 (m, 4H), 7.36 (t, J=7.2 Hz, 1H), 4.65-4.26 (m, 6H), 3.23-3.15 (m, 4H), 1.52-1.19 (m, 7H), 1.07 (t, J=7.2 Hz, 3H), 0.835 (t, J=7.2 Hz, 3H).

m/z MS: 556 (M$^+$+1).

Example 42

Synthesis of (3,5-bis-trifluoromethyl-benzyl)-[2-(cyclohexylmethyl-ethyl-amino)-quinolin-3-ylmethyl]-carbamic acid ethyl ester

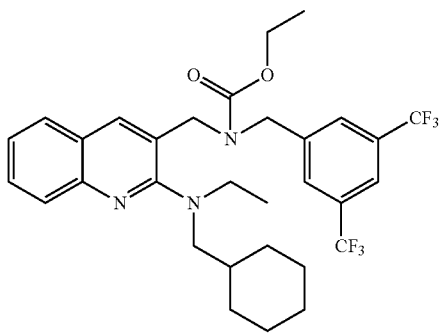 [SMILES: CCOC(=O)N(Cc1cc(C(F)(F)F)cc(C(F)(F)F)c1)Cc1cc2ccccc2nc1N(CC)CC1CCCCC1]

Step (i): Synthesis of N-cyclohexylmethyl-ethylamine

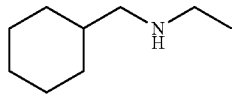

Acetyl chloride (1.1 mL, 15.4 mmol) was added slowly to an ice cooled solution of cyclohexylmethyl amine (1.3 mL, 10 mmol) in pyridine (4 mL) under a nitrogen atmosphere. After stirring at 0-5° C. for 1 h, the reaction mixture was maintained at ambient temperature for 6 h. This mixture was then poured into water (20 mL) and extracted with ethyl acetate (3×25 mL). The combined organic phases were washed with 1N HCl (2×10 mL) and then with a saturated sodium bicarbonate solution (10 mL). The organic layer was dried over sodium sulfate, filtered, and concentrated in vacuo to give N-acetyl-cyclohexyl-ethyl-amine (1.50 g), yield: 98%. A solution of N-acetyl-cylohexyl-ethyl-amine (0.8 g, 5.0 mmol) in anhydrous THF (10 mL) was prepared under nitrogen, and lithium aluminum hydride (1.0 M solution in ether, 10 mmol) was added to the solution. After stirring for 6 h at RT, the reaction mixture was poured into water (30 mL) and stirred for 1 h. The inorganic salts were then filtered and washed with water (10 mL) and ethyl acetate (3×25 mL). The combined filtrate was collected and the organic phase was separated. The organic layer was washed with brine, dried over sodium sulfate, filtered, and concentrated in vacuo to afford the title compound (0.4 g), yield: 56%.

$^1$H NMR (CDCl$_3$, 300 MHz): δ 2.62 (q, J=7.2 Hz, 2H), 2.42 (d, J=6.6 Hz, 2H), 1.74-1.63 (m, 5H), 1.50-1.38 (m, 1H), 1.28-1.15 (m, 4H), 1.09 (t, J=7.2 Hz, 3H), 0.94-0.84 (m, 2H).

Step (ii): Synthesis of (3,5-bis-trifluoromethyl-benzyl)-[2-(cyclohexylmethyl-ethyl-amino)-quinolin-3-ylmethyl]-carbamic acid ethyl ester The target compound was prepared following the experimental procedure for Example 39, except using N-cyclohexylmethyl-ethylamine instead of 1-(cyclohexylmethyl)piperazine, as a colorless viscous liquid (0.268 g); yield, 98.89%. Purity 99.32% (HPLC: 20:80 [KH$_2$PO$_4$ (0.01 M, pH 3.2):CH$_3$CN], R$_t$ 118.83 min).

$^1$H NMR (CDCl$_3$, 300 MHz): δ 7.84 (m, 2H), 7.72 (s, 1H), 7.64-7.54 (m, 4H), 7.35 (t, J=7.2 Hz, 1H), 4.71-4.28 (m, 6H), 3.23-3.08 (m, 4H), 1.68-1.52 (m, 7H), 1.37-1.25 (m, 2H), 1.17-0.99 (m, 6H), 0.87-0.71 (m, 2H).

m/z MS: 596 (M$^+$+1, 100%)

Example 43

Synthesis of (3,5-bis-trifluoromethyl-benzyl)-[2-(cyclopentylmethyl-propyl-amino)-quinolin-3-ylmethyl]-carbamic acid ethyl ester

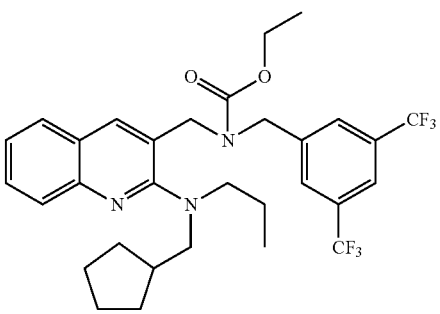 [SMILES: CCCN(CC1CCCC1)c1nc2ccccc2cc1CN(Cc1cc(C(F)(F)F)cc(C(F)(F)F)c1)C(=O)OCC]

The title compound was prepared following the experimental procedure of Example 39, by using cyclopentylmethyl propylamine instead of 1-(cyclohexylmethyl)piperazine in step (i) as a colorless viscous liquid (0.155 g), yield: 88%.

Purity: 98.21% (HPLC: 20:80 [KH$_2$PO$_4$ (0.01 M, pH 3.2): CH$_3$CN], R$_t$ 89.41 min).

$^1$H NMR (CDCl$_3$, 300 MHz): δ 7.88-7.81 (m, 2H), 7.72 (s, 1H), 7.68-7.56 (m, 4H), 7.39-7.31 (m, 1H), 4.71-4.28 (m, 6H), 3.27-3.05 (m, 4H), 1.61-1.28 (m, 12H), 1.11-0.95 (m, 2H), 0.79 (t, J=7.5 Hz, 3H).

m/z (ES-MS): 596 (M$^+$+1)

Example 44

Synthesis of (3,5-bis-trifluoromethyl-benzyl)-[2-(cyclopropylmethyl-ethyl-amino)-quinoline-3-ylmethyl]-carbamic acid methyl ester

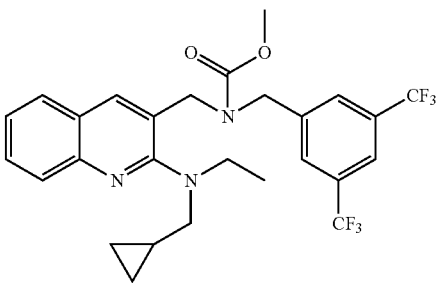 [SMILES: CCN(CC1CC1)c1nc2ccccc2cc1CN(Cc1cc(C(F)(F)F)cc(C(F)(F)F)c1)C(=O)OC]

The title compound was prepared following the experimental procedure for Example 35, by using cyclopropylmethyl ethylamine instead of cyclopentylmethyl ethylamine in Step (iii) as a colorless viscous liquid (0.085 g), yield: 54.48%.

Purity 98.05% (HPLC: 20:80 [KH$_2$PO$_4$ (0.01 M, pH 3.2): CH$_3$CN], R$_t$ 26.75 min).

$^1$H NMR (CDCl$_3$, 300 MHz): δ 7.88-7.79 (m, 2H), 7.74 (s, 1H), 7.67-7.57 (m, 4H), 7.39-7.37 (m, 1H), 4.68-4.38 (m, 4H); 3.88 (s, 3H); 3.32 (q, J=7.0 Hz, 2H); 3.06 (d, J=6.6 Hz, 2H), 1.08 (t, J=7.0 Hz, 3H), 0.93-0.89 (m, 1H), 0.42-0.34 (m, 2H), 0.09-0.05 (m, 2H).

m/z MS (ESI) 540 (M$^+$+1).

Example 45

Synthesis of (3,5-bis-trifluoromethyl-benzyl)-[2-(cyclobutylmethyl-ethyl-amino)-quinoline-3-ylmethyl]-carbamic acid methyl ester

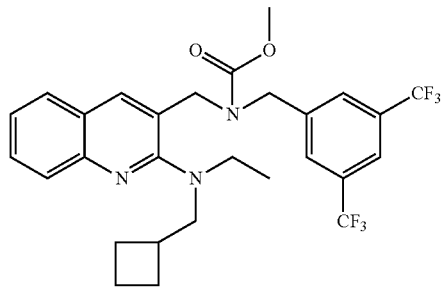 [SMILES: CCN(CC1CCC1)c1nc2ccccc2cc1CN(Cc1cc(C(F)(F)F)cc(C(F)(F)F)c1)C(=O)OC]

The title compound was prepared following the experimental procedure for Example 35, by using cyclobutylmethyl ethylamine instead of cyclopentyl methyl ethylamine in Step (iii) as a colorless viscous liquid (0.13 g), yield: 97%.

Purity 100.0% (HPLC: 20:80 [KH$_2$PO$_4$ (0.01 M, pH 3.2): CH$_3$CN], R$_t$ 39.77 min).

$^1$H NMR (CDCl$_3$, 300 MHz): δ 7.86-7.84 (m, 2H), 7.73 (s, 1H), 7.66-7.57 (m, 4H), 7.39-7.25 (m, 1H), 4.64-4.36 (m, 4H); 3.88 (s, 3H); 3.25 (d, J=7.2 Hz, 2H)); 3.14 (q, J=7.0 Hz, 2H), 2.62-2.44 (m, 1H), 1.86-1.69 (m, 4H), 1.55-1.51 (m, 2H), 1.07 (t, J=7.0 Hz, 3H).

m/z (ES-MS) 554 (M$^+$+1).

Example 46

Synthesis of (3,5-bis-trifluoromethyl-benzyl)-[2-(cyclopentylmethyl-ethyl-amino)-6-methyl-quinolin-3-ylmethyl]-carbamic acid methyl ester

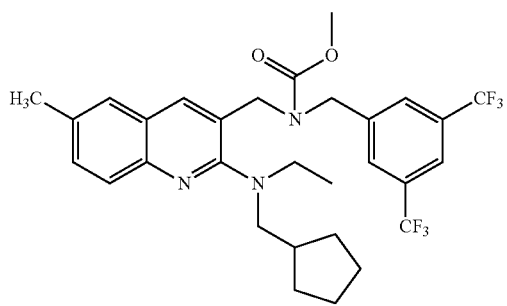 [SMILES: CCN(CC1CCCC1)c1nc2ccc(C)cc2cc1CN(Cc1cc(C(F)(F)F)cc(C(F)(F)F)c1)C(=O)OC]

The title compound was synthesized by following the same experimental procedure as mentioned in Example 35, except using p-tolyl acetamide in step (i) instead of acetanilide to yield it as a viscous liquid (0.02 g), yield: 18%, of purity 99.59% (HPLC: Symmetry Shield RP8, 22:70 [0.01M KH$_2$PO$_4$:CH$_3$CN], 220 nM, R$_t$ 8.212 min).

$^1$H NMR (CDCl$_3$, 400 MHz): δ 7.77-7.72 (m, 4H), 7.65-7.56 (m, 1H), 7.44-7.42 (m, 2H), 4.67-4.58 (br s, 2H), 4.49-4.37 (br s, 2H), 3.88 (s, 3H), 3.18-3.11 (m, 4H), 2.48 (s, 3H), 2.13-2.09 (m, 1H), 1.54-1.40 (m, 8H), 1.04 (t, J=6.9 Hz, 3H)

m/z (CI-MS): 581 (M$^+$, 100%)

Example 47

Synthesis of [2-(bis-cyclopropylmethyl-amino)-8-methyl-quinolin-3-ylmethyl]-(3,5-bis-trifluoromethyl-benzyl)-carbamic acid methyl ester Step (i): Synthesis of bis-cyclopropylmethyl-amine (i) a. Synthesis of cyclopropanecarboxylic acid cyclopropylmethyl-amide

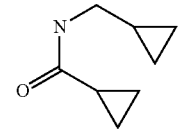

Cyclopropyl carboxylic acid (1.0 g, 11.63 mmol) was added to a 50 mL two neck round bottom flask, along with DCM (25 mL). This mixture was cooled to 0° C., EDCI (4.15 g, 13.95 mmol) was added portionwise to the mixture with stirring under nitrogen atmosphere, and the temperature was maintained for 0.5 h. After this time, hydroxybenzotriazole (1.88 g, 13.95 mmol) was added to the 0° C. mixture which was stirred for 10 min, then triethylamine (1.7 g, 11.63 mmol) was added, and stirring of the mixture was continued at the same temperature for another 0.5 h. Then, cyclopropylmethylamine (0.825 g, 11.63 mmol) was added, and the reaction was allowed to reach RT, and stirring was continued overnight. The solvent was then removed in vacuo, and the crude residue was purified by passing through a column over 60-120 silica gel, eluting with dichloromethane, to afford the title compound (1.6 g), yield: 87%.

$^1$H NMR (CDCl$_3$, 200 MHz): δ 5.75 (br s, NH, D$_2$O exchangeable), 3.17-3.16 (m, 2H), 1.00-0.80 (m, 4H), 0.77-0.67 (m, 2H), 0.56-0.43 (m, 2H), 0.24-0.16 (m, 2H)

m/z (CI-MS): 139 (M+, 100%)

(i) b. Synthesis of bis-cyclopropylmethyl-amine

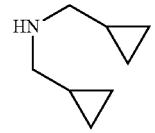

To a suspension of lithium aluminum hydride (1.3 g, 9.35 mmol) in 10 mL dry ether, a solution of N-cyclopentenoyl-ethylamine (1.7 g, 13.3 mmol) in dry ether (10 mL) was added under a nitrogen atmosphere. This reaction was stirred at RT for 8 h and the reaction mixture was then quenched with saturated sodium sulfate solution, filtered, and the precipitate was washed with diethyl ether. The filtrate was concentrated to afford the title amine (0.8 g), yield: 69%.

¹H NMR (CDCl₃, 200 MHz): δ 5.75 (br s, NH, D₂O exchangeable), 3.16-3.09 (m, 2H), 2.50-2.4 (m, 2H), 0.56-0.43 (m, 4H), 0.24-0.21 (m, 3H), 0.21-0.13 (m, 3H)

m/z (ES-MS): 139 (M⁺+14, 100%)

Step (ii): Synthesis of [2-(bis-cyclopropylmethyl-amino)-8-methyl-quinolin-3-ylmethyl]-(3,5-bis-trifluoromethyl-benzyl)-carbamicacid methyl ester

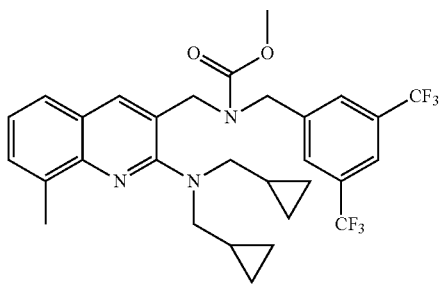 [SMILES: COC(=O)N(Cc1cc(C(F)(F)F)cc(C(F)(F)F)c1)Cc1cc2cccc(C)c2nc1N(CC1CC1)CC1CC1]

The title compound was synthesized by using the same procedure as in Example 35, except using o-tolyl acetanilide in step (i) instead of acetanilide and bis-cyclopropylmethyl amine in step (iii), which yielded the desired product as a light yellow, viscous liquid (0.05 g), yield: 40%, of purity 98.8% (HPLC: Symmetry Shield RP8, [0.01M KH₂PO₄:CH₃CN], 217 nM, R$_t$ 12.719 min).

¹H NMR (CDCl₃, 400 MHz): δ 7.7 (s, 1H), 7.68-7.44 (m, 3H), 7.27-7.24 (m, 2H), 4.78-4.65 (m, 2H), 4.47-4.4 (m, 2H), 3.8 (s, 3H), 3.16-3.14 (d, J=7 Hz, 2H), 2.7 (s, 3H), 1.55 (s, 3H), 1.01-0.9 (m, 1H), 0.38-0.34 (m, 4H), 0.07-0.05 (m, 4H);

m/z (CI-MS): 579 (M⁺, 100%)

Example 48

Synthesis of (3,5-bis-trifluoromethyl-benzyl) [2-(cyclopentylmethyl-ethyl-amino)-quinolin-3-ylmethyl]-dithiocarbamic acid methyl ester

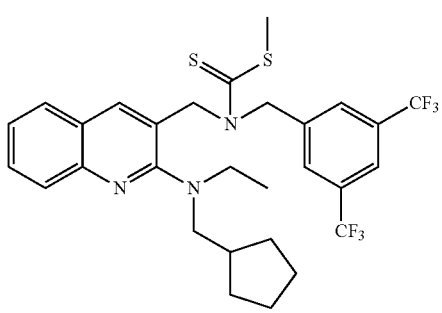 [SMILES: CCN(CC1CCCC1)c1nc2ccccc2cc1CN(Cc1cc(C(F)(F)F)cc(C(F)(F)F)c1)C(=S)SC]

To a suspension of sodium hydride (0.023 g, 0.98 mmol) in dry THF (15 mL) at 0° C., in a 25 mL round bottom flask, was added {3-[(3,5-bis-trifluoromethyl-benzylamino)-methyl]-quinolin-2-yl}-cyclopentylmethyl-ethyl-amine (0.25 g, 0.44 mmol), obtained in step (iv) of Example 35. This reaction mixture was stirred for 10 minutes at the same temperature, carbon disulphide (0.112 g, 0.98 mmol) was added dropwise, followed by the addition of methyl iodide (0.208 g, 1.47 mmol). The reaction was allowed to reach RT and stirring was continued for 0.5 h. Water was then added to the reaction, which was then extracted with ethyl acetate. The combined organic layer was washed with brine solution and dried over sodium sulfate. The solvent was evaporated to afford the title compound (0.250 g), yield: 87%, of purity 98.59% (HPLC: Symmetry Shield RP8, [0.01M KH₂PO₄:CH₃CN], 217 nM, R$_t$ 12.221 min).

IR (neat, cm⁻¹) 2953, 1378, 1278;

¹H NMR (CDCl₃, 400 MHz): δ 7.88-7.86 (m, 1H), 7.77-7.59 (m, 6H), 7.39-7.36 (s, 2H), 5.37 (br s, 2H), 5.07 (br s, 2H), 3.2-3.12 (m, 4H), 2.77-2.76 (m, 3H), 2.15-2.07 (t, J=7.5 Hz, 1H), 1.55-1.40 (m, 7H), 1.07 (t, J=6.9 Hz, 3H);

m/z (ES-MS): 645 (M⁺+1, 100%)

Example 49

Synthesis of 3-ethoxycarbonyl-1-(3,5-bis-trifluoromethyl-benzyl)-1-[2-(cyclopentyl methyl-ethyl-amino)-quinolin-3-yl methyl]-thiourea

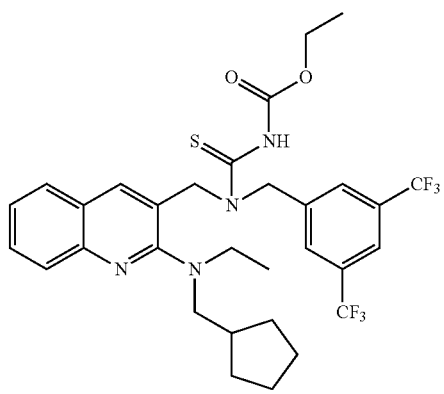 [SMILES: CCOC(=O)NC(=S)N(Cc1cc(C(F)(F)F)cc(C(F)(F)F)c1)Cc1cc2ccccc2nc1N(CC)CC1CCCC1]

{3-[(3,5-Bis-trifluoromethyl-benzylamino)-methyl]-quinolin-2-yl}-cyclopentyl-methyl-ethyl-amine (0.5 g, 0.982 mmol), obtained in step (iv) of Example 35, and ethoxycarbonyl isothiocyanate (0.141 g, 1.08 mmol) were added to a 50 mL round bottom flask, and chloroform was added to this mixture. The reaction was refluxed under a nitrogen atmosphere for 0.5 h, after which time the reaction mixture was concentrated under vacuum to afford the title compound (0.4 g), yield: 65%, of purity 93.7% (HPLC: Symmetry Shield RP8, [0.01M KH₂PO₄:CH₃CN], 215 nM, R$_t$ 9.337 min).

IR (neat, cm⁻¹) 3418, 2921, 1137

¹H NMR (CDCl₃, 400 MHz): δ 10.10 (br s, 1H), 7.92-7.9 (m, 1H), 7.75-7.67 (m, 6H), 7.51-7.28 (m, 1H), 5.14 (br s, 2H), 4.89 (br s, 2H), 4.31 (q, J=7.2 Hz, 2H), 3.22 (br s, 4H), 2.04 (q, J=7.5 Hz, 1H), 1.53 (m, 4H), 1.48-1.34 (m, 3H), 1.25 (m, 4H), 1.00 (t, J=7.2 Hz, 3H).

m/z (ES-MS) 641 (M⁺+1, 100%)

Example 50

Synthesis of [(3,5-bis-trifluoromethyl-benzyl)-(2-pent-1-ynyl-quinolin-3-ylmethyl)-amino]-acetic acid tert-butyl ester

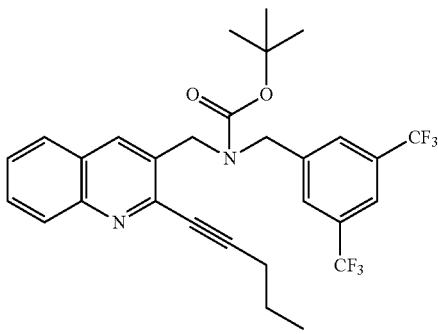 [SMILES: CCCC#Cc1nc2ccccc2cc1CN(Cc1cc(C(F)(F)F)cc(C(F)(F)F)c1)C(=O)OC(C)(C)C]

Step (i): Synthesis of (3,5-bis-trifluoromethyl-benzyl)-(2-chloro-quinolin-3-ylmethyl)-amine

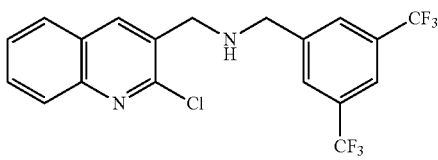 [SMILES: FC(F)(F)c1cc(CNCc2cc3ccccc3nc2Cl)cc(C(F)(F)F)c1]

3,5-Bis-(trifluoromethylbenzylamine) (6.31 g, 26 mmol) and acetic acid (1.5 mL, 36.4 mmol) were added to 2-chloro-3-quinoline carboxaldehyde (5.01 g, 26 mmol) that was dissolved in anhydrous THF (100 mL). The resulting mixture was stirred at room temperature for 1 h. Sodium triacetoxyborohydride (7.71 g, 26 mmol) was then added to the solution and this mixture was stirred at room temperature overnight. Afterwards, the mixture was diluted with ether, and was washed two times with water and one time with brine. The organic phase was collected, dried over potassium carbonate, and concentrated by rotary evaporation. The resulting sample was dried under vacuum and purified (Biotage Horizon HPFC chromatography system, SiO$_2$, 70:30 hexanes:ethyl acetate) to give an off-white solid (9.5 g), yield: 87%, of 97.7% purity (HPLC: Inertsil ODS-3V C18, 30:70 [KH$_2$PO$_4$ (0.01M, pH 3.2): CH$_3$CN], 264 nm, R$_t$ 12.2 min.).

Mp 74° C.;

$^1$H NMR (300 MHz, CDCl$_3$, TMS): δ 8.23 (s, 1H), 7.79-8.02 (m, 3H), 7.70-7.75 (m, 3H), 7.54-7.59 (m, 1H), 4.09 (s, 2H), 4.02 (s, 2H).

Step (ii): Synthesis of [(3,5-bis-trifluoromethyl-benzyl)-(2-chloro-quinolin-3-ylmethyl)-amino]-acetic acid tert-butyl ester

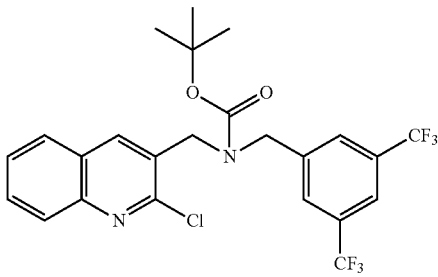 [SMILES: CC(C)(C)OC(=O)N(Cc1cc(C(F)(F)F)cc(C(F)(F)F)c1)Cc1cc2ccccc2nc1Cl]

(3,5-bis-trifluoromethyl-benzyl)-(2-chloro-quinolin-3-ylmethyl)-amine (972 mg, 2.3 mmol), obtained in step (i), was dissolved in THF (10 mL) and then di-tert-butyl dicarbonate (587 mg, 2.53 mmol) and triethylamine (0.32 mL, 2.3 mmol) were added. The resulting mixture was stirred at room temperature overnight and then concentrated on the rotary evaporator to remove the THF. The crude sample was diluted with dichloromethane and was washed two times with water and one time with brine. The organic phase was dried over potassium carbonate, concentrated by rotary evaporation and was dried overnight under vacuum (1.1 g, 90%) to yield [(3,5-bis-trifluoromethyl-benzyl)-(2-chloro-quinolin-3-ylmethyl)-amino]-acetic acid tert-butyl ester, an off-white solid, of 98.4% purity (HPLC: Inertsil ODS-3V C18, 20:80 [KH$_2$PO$_4$ (0.01M, pH 3.2):CH$_3$CN], 264 nm, R$_t$ 20.9 min), mp 84° C.

$^1$H NMR (300 MHz, CDCl$_3$, TMS): δ 8.02 (apt d, J=8.4 Hz, 2H), 7.56-7.80 (br m, 6H), 4.64 (br s, 4H), 1.48 (s, 9H).

Step (iii): Synthesis of [(3,5-bis-trifluoromethyl-benzyl)-(2-pent-1-ynyl-quinolin-3-ylmethyl)-amino]-acetic acid tert-butyl ester

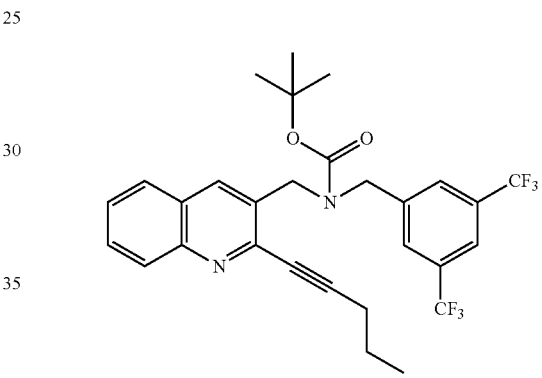

[(3,5-Bis-trifluoromethyl-benzyl)-(2-chloro-quinolin-3-ylmethyl)-amino]-acetic acid tert-butyl ester (530 mg, 1 mmol), obtained in step (ii), was dissolved in anhydrous DMF (5 mL) and anhydrous THF (2 mL) followed by the addition of PdCl$_2$(PPh$_3$)$_2$ (36.7 mg, 0.05 mmol), triethylamine (0.57 mL, 4.15 mmol), copper iodide (11 mg, 0.05 mmol), and 1-pentyne (0.12 mL, 1.2 mmol) to the THF solution. The reaction vessel was wrapped in aluminum foil, and the resulting mixture was stirred at room temperature overnight. Afterwards, this sample was diluted with ethyl acetate, and filtered through Celite™. The Celite™ was washed with ethyl acetate, and the filtrate was washed two times with water and one time with brine. The organic phase was dried, filtered, and concentrated by rotary evaporation. The resulting sample was dried overnight under vacuum and the crude residue was purified (Biotage Horizon HPFC chromatography system, SiO$_2$, 80:20 hexanes:ethyl acetate) to give the title compound as a brown oil (458 mg), yield: 83%, with 91.3% purity (HPLC: Inertsil ODS-3V C18, 20:80 [KH$_2$PO$_4$ (0.01M, pH 3.2):CH$_3$CN], 264 nm, R$_t$ 28.6 min).

$^1$H NMR (300 MHz, CDCl$_3$, TMS): δ 8.00-8.08 (m, 1H), 7.67-7.76 (br m, 4H), 7.51-7.56 (m, 1H), 4.54-4.86 (br m, 4H, rotamers), 2.40 (t, J=7.2 Hz, 2H), 1.56-1.61 (m, 2H), 1.50 (s, 9H), 0.95 (t, J=7.5 Hz, 3H).

Example 51

Synthesis of [(3,5-bis-trifluoromethyl-benzyl)-(2-pentyl-quinolin-3-ylmethyl)-amino]-acetic acid tert-butyl ester

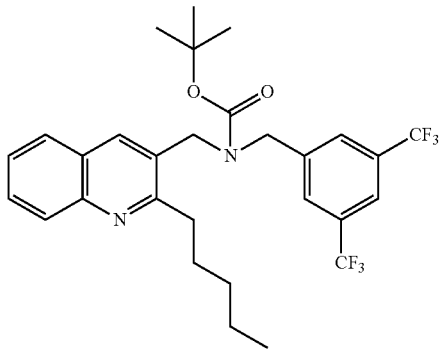 [SMILES: CCCCCc1nc2ccccc2cc1CN(Cc1cc(C(F)(F)F)cc(C(F)(F)F)c1)C(=O)OC(C)(C)C]

The compound obtained in Example 16, [(3,5-bis-trifluoromethyl-benzyl)-(2-pent-1-ynyl-quinolin-3-ylmethyl)-amino]-acetic acid tert-butyl ester (163 mg, 0.3 mmol) was dissolved in ethanol (3 mL), and palladium [10% on carbon powder (50 mg)] was added. The resulting mixture was stirred under $H_2$ (using a balloon) for 3 h. The sample was diluted in ethanol and filtered through Celite™. The Celite™ was washed with ethanol, the filtrate was concentrated by rotary evaporation, and the resulting sample was dried overnight under vacuum and the crude was purified (Biotage Horizon HPFC chromatography system, $SiO_2$, 80:20 hexanes:ethyl acetate) to give the titled product as a colorless oil (75 mg), yield: 45%, of 96.3% purity (HPLC: Inertsil ODS-3V C18, 20:80 [$KH_2PO_4$ (0.01M, pH 3.2):$CH_3CN$], 264 nm, $R_t$ 49.0 min)

$^1$H NMR (300 MHz, $CDCl_3$, TMS): δ 8.04 (d, J=8.4 Hz, 1H), 7.64-7.78 (br m, 6H), 7.47-7.52 (m, 1H), 4.59 (br s, 4H), 2.88 (t, J=8.1 Hz, 2H), 1.68-1.78 (m 2H), 1.51 (s, 9H), 1.29-1.45 (br m, 4H), 0.87 (t, J=6.9 Hz, 3H).

Example 52

Synthesis of (3-{[3,5-bis-trifluoromethyl-benzyl)-(2-methyl-2H-tetrazole-5-yl)-amino]-methyl}-quinoline-2-yl)-cyclopentylmethyl-ethyl amine

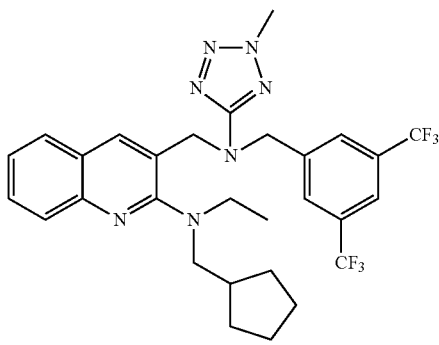 [SMILES: CCN(CC1CCCC1)c1nc2ccccc2cc1CN(Cc1cc(C(F)(F)F)cc(C(F)(F)F)c1)c1nnn(C)n1]

Step (i): Synthesis of (3,5-bis-trifluoromethyl-benzyl)-[2-(cyclopentylmethyl-ethyl-amino)-quinolin-4-yl]-cyanamide

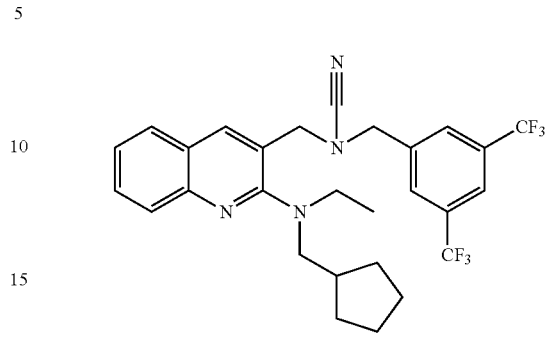

To a solution of {3-[(3,5-bis-trifluoromethyl-benzylamino)-methyl]-quinolin-2-yl}-cyclopentylmethyl-ethyl-amine (0.372 g, 0.73 mmol), obtained in step (iv) of Example 35, in MeOH (10 mL), under a $N_2$ atmosphere, was added sodium bicarbonate (0.122 g, 1.46 mmol), followed by the addition of cyanogen bromide (0.138 g, 1.31 mmol). The reaction mixture was stirred at RT for 4 h. The solvent was then removed under vacuum to give the crude residue which was dissolved in water, extracted with ethyl acetate, and dried over sodium sulfate. The solvent was evaporated and concentrated in vacuo to afford (3,5-bis-trifluoromethyl-benzyl)-[2-(cyclopentyl-methyl-ethyl-amino)-quinoline-4-yl]-cyanamide (0.4 g), yield: 99%.

IR (KBr, $cm^{-1}$): 3424, 2952, 2214, 1280;
$^1$H NMR ($CDCl_3$, 400 MHz): δ 8.11 (s, 1H), 7.88-7.83 (m, 3H), 7.79-7.69 (m, 2H), 7.66-7.62 (m, 1H), 7.42-7.38 (m, 1H), 4.42 (s, 2H), 4.21 (s, 2H), 3.21-3.16 (m, 4H), 2.16-2.09 (m, 1H), 1.60-1.56 (m, 6H), 1.11-1.02 (m, 5H);
m/z (ES-MS): 535 ($M^+$+1, 100%)

Step (ii): Synthesis of (3-{[(3,5-bis-trifluoromethyl-benzyl)-(1H-tetrazol-5-yl)-amino]-methyl}-quinolin-2-yl)-cyclopentylmethyl-ethyl-amine

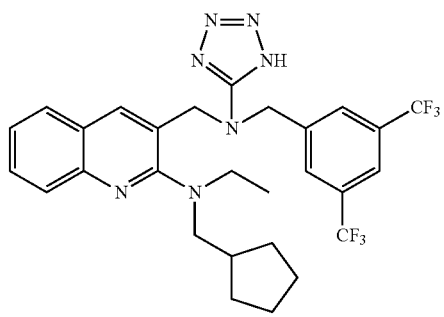 [SMILES: CCN(CC1CCCC1)c1nc2ccccc2cc1CN(Cc1cc(C(F)(F)F)cc(C(F)(F)F)c1)c1nnn[nH]1]

(3,5-Bis-trifluoromethyl-benzyl)-[2-(cyclopentylmethyl-ethyl-amino)-quinolin-4-yl]-cyanamide (0.368 g, 0.689 mmol), sodium azide (0.049 g, 0.758 mmol), and zinc bromide (0.155 g, 0.689 mmol) were added to a round bottom flask under a $N_2$ atmosphere. To this reaction mixture, water (8 mL) was added, and the resulting mixture was refluxed for 24 h with vigorous stirring. Afterwards, the reaction mixture was cooled to RT and a mixture of HCl (3N, 0.92 mL) and ethyl acetate was added. The vigorous stirring was continued until no solid was separated out and the aqueous layer had reached a pH of 1. The organic layer was separated and concentrated under vacuum. A solution of sodium hydroxide (0.25 N, 6.25 mL) was added to the residue and was stirred for 30 minutes until the residue was dissolved, and a suspension of zinc hydroxide was formed. The suspension was filtered and washed with NaOH (1N), and the filtrate was acidified with 3N HCl dropwise to afford (3-{[(3,5-bis-trifluoromethyl-benzyl)-(1H-tetrazol-5-yl)-amino]-methyl}-quinolin-2-yl)-cyclopentylmethyl-ethyl-amine as a yellow solid (0.140 g), yield: 35%.

IR (KBr, cm$^{-1}$) 3442, 2923, 1631, 1280;

$^1$H NMR (CDCl$_3$, 400 MHz): δ 8.62 (s, 1H), 7.87 (s, 1H), 7.79-7.73 (m, 3H), 7.73-7.64 (m, 2H), 7.51-7.43 (m, 2H), 4.89 (s, 2H), 4.80 (s, 2H), 3.68 (s, 4H), 2.16 (s, 1H) 1.56-1.06 (m, 11H);

m/z (ES-MS): 578 (M$^+$+1, 100%)

Step (iii): Synthesis of (3-{[3,5-bis trifluoromethyl-benzyl)-(2-methyl-2H-tetrazole-5-yl)-amino]-methyl}-quinoline-2-yl)-cyclopentamethyl-ethyl amine

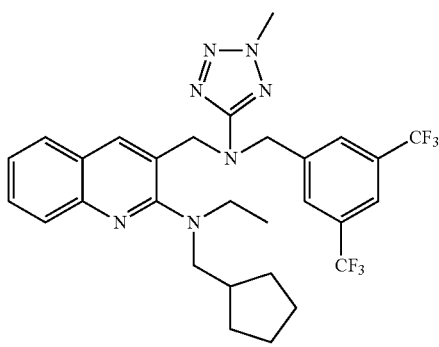 [SMILES: CCN(CC1CCCC1)c1nc2ccccc2cc1CN(Cc1cc(C(F)(F)F)cc(C(F)(F)F)c1)c1nnn(C)n1]

To a suspension of (3-{[(3,5-bis-trifluoromethyl-benzyl)-(1H-tetrazol-5-yl)-amino]-methyl}-quinolin-2-yl)-cyclopentylmethyl-ethyl-amine (0.133 g, 0.230 mmol in water (4 mL) was added sodium hydroxide (0.009 g, 0.230 mmol), and this mixture was stirred for 15 min at RT, followed by the addition of dichloromethane (4 mL). To this reaction mixture was added dimethyl sulfate (0.030 g, 0.241 mmol), followed by the addition of tetrabutylammonium bromide (0.003 g, 0.011 mmol). This mixture was stirred for 24 h. The organic layer was separated from aqueous layer, the aqueous layer was extracted with DCM (3×10 mL), the combined organic layer was washed with brine and dried over sodium sulfate, and concentrated under vacuum to afford the crude residue. This residue was purified by column chromatography over 100-200 mesh silica gel using 8% ethyl acetate and petroleum ether to afford (3-{[(3,5-bis-trifluoromethyl-benzyl)-(2-methyl-2H-tetrazole-5-yl)-amino]-methyl-}-quinoline-2-yl)-cyclopentyl-methyl-ethyl amine (0.030 g), yield: 22%.

Mp 97° C.;

Purity 96.97% (HPLC: Inertsil ODS 3V, 20:80 [0.01M KH$_2$PO$_4$:CH$_3$CN], 216 nM, R$_t$ 10.668 min);

IR (neat, cm$^{-1}$) 3385, 2954, 1581;

$^1$H NMR (CDCl$_3$, 400 MHz): δ 7.85 (d, J=8.3 Hz, 1H), 7.78 (s, 1H), 7.71 (s, 1H), 7.66 (s, 2H), 7.56 (d, J=7.8 Hz, 2H), 7.32 (t, J=6.8 Hz, 1H), 4.82 (s, 2H), 4.67 (s, 2H), 4.21 (s, 3H), 3.24-3.15 (m, 4H), 2.16-2.12 (m, 1H), 1.56-1.50 (m, 4H), 1.40-1.04 (m, 3H)

m/z (ES-MS): 592 (M$^+$+1, 100%)

Example 53

Synthesis of (3-{[(3,5-bis-trifluoromethyl-benzyl)-(1-methyl-1H-tetrazol-5-yl)-amino]-methyl}-quinolin-2-yl)-cyclopentylmethyl-ethyl-amine

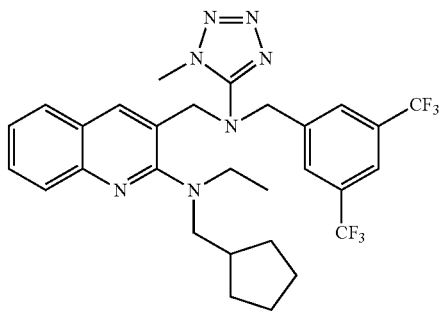 [SMILES: CCN(CC1CCCC1)c1nc2ccccc2cc1CN(Cc1cc(C(F)(F)F)cc(C(F)(F)F)c1)c1nnnn1C]

The regioisomer of Example 52, (3-{[3,5-bis-trifluoromethyl-benzyl)-(1-methyl-1H-tetrazole-5-yl)-amino]-methyl}-quinoline-2-yl)-cyclopentylmethyl-ethyl amine was separated from the same reaction mixture after purification of the crude by column chromatography over 100-200 mesh silica gel and eluting with 18% ethyl acetate in petroleum ether (0.2 g), yield: 7%.

Mp 110° C.;

Purity 99.21% (HPLC: Symmetry Shield RP8, [0.01M KH$_2$PO$_4$:CH$_3$CN], 216 nM, R$_t$ 7.809 min);

$^1$H NMR (DMSO-d$_6$, 400 MHz): δ 8.21 (s, 1H), 8.03 (s, 3H), 7.80-7.78 (d, J=8 Hz, 1H), 7.73-7.71 (d, J=8.0 Hz, 7H), 7.61-7.57 (m, 1H), 7.39-7.35 (m, 1H), 4.8 (s, 4H), 3.88 (s, 3H), 3.15-3.09 (m, 4H), 2.02-2.00 (m, 1H), 1.49-1.32 (m, 6H), 1.3-0.9 (m, 5H);

m/z (CI-MS): 591 (M$^+$, 100%)

Example 54

Synthesis of (3-{[3,5-bis-trifluoromethyl-benzyl)-(2-methyl-2H-tetrazole-5-yl)-amino]-methyl}-quinoline-2-yl)-butyl-ethyl amine

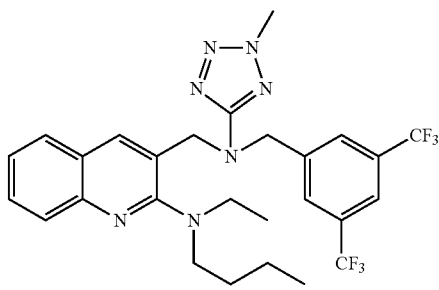 [SMILES: CCCCN(CC)c1nc2ccccc2cc1CN(Cc1cc(C(F)(F)F)cc(C(F)(F)F)c1)c1nnn(C)n1]

The title compound was prepared following the experimental procedure of Example 52, by using (3-{[(3,5-bis-trifluoromethyl-benzylamino)-methyl]-quinolin-2-yl)-butyl-ethyl-amine instead of {3-[(3,5-bis-trifluoromethyl-benzylamino)-methyl]-quinolin-2-yl}-cyclopentylmethyl-ethyl-amine in step (i) (0.04 g), yield: 11%, as a thick, colorless liquid.

Purity 97.51% (HPLC: 20:80 [KH$_2$PO$_4$ (0.01 M, pH 3.2): CH$_3$CN], R$_t$ 35.82 min).
$^1$H NMR (CDCl$_3$, 300 MHz): δ 7.86-7.82 (m, 2H), 7.72 (s, 1H) 7.66 (s, 1H), 7.60-7.54 (m, 3H), 7.37-7.27 (m, 1H), 4.80 (s, 2H), 4.64 (s, 2H), 4.22 (s, 3H), 3.26-3.16 (m, 4H), 1.53-1.41 (m, 2H), 1.31-1.17 (m, 2H), 1.10 (t, J=6.81 Hz, 3H), 0.86 (t, J=7.27 Hz, 3H).
m/z (ES-MS): 566 (M$^+$+1).

Example 55

Synthesis of (3-{[3,5-bis-trifluoromethyl-benzyl)-(2-methyl-2H-tetrazole-5-yl)-amino]-methyl}-quinoline-2-yl)-cyclopropylmethyl-ethyl amine

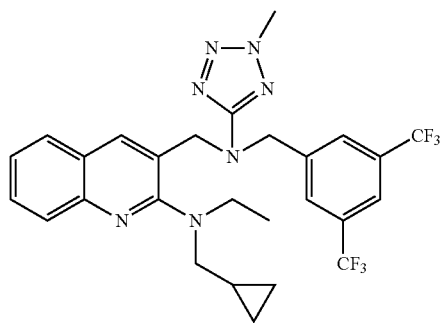 [SMILES: CCN(CC1CC1)c1nc2ccccc2cc1CN(Cc1cc(C(F)(F)F)cc(C(F)(F)F)c1)c1nnn(C)n1]

The title compound was prepared following the experimental procedure of Example 52, by using {3-[(3,5-bis-trifluoromethyl-benzylamino)-methyl]-quinolin-2-yl}-cyclopropylmethyl-ethyl-amine instead of {3-[(3,5-bis-trifluoromethyl-benzylamino)-methyl]-quinolin-2-yl}-cyclopentylmethyl-ethyl-amine in step (i) as a colorless, thick liquid (0.045 g), yield: 29.6%.
Purity 98.35% (HPLC: 30:70 [KH$_2$PO$_4$ (0.01 M, pH 3.2): CH$_3$CN], R$_t$ 43.92 min).
$^1$H NMR (CDCl$_3$, 300 MHz): δ 7.87 (s, 1H), 7.84 (s, 1H), 7.71 (s, 1H) 7.67 (s, 1H), 7.60-7.55 (m, 3H), 7.36-7.27 (m, 1H), 4.84 (s, 2H), 4.65 (s, 2H), 4.22 (s, 3H), 3.89 (q, J=7.27 Hz, 2H), 3.10 (d, J=6.58 Hz, 2H), 1.10 (t, J=7.27 Hz, 3H), 0.97-0.93 (m, 1H), 0.42-0.36 (m, 2H), 0.13-0.07 (m, 2H);
m/z (ES-MS): 564 (M$^+$+1).

Example 56

Synthesis of (3-{[3,5-bis-trifluoromethyl-benzyl)-(2-methyl-2H-tetrazole-5-yl)-amino]-methyl}-quinoline-2-yl)-cyclobutylmethyl-ethyl amine

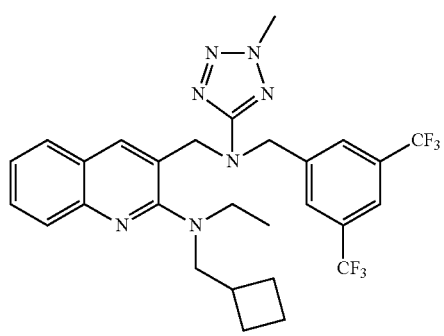 [SMILES: CCN(CC1CCC1)c1nc2ccccc2cc1CN(Cc1cc(C(F)(F)F)cc(C(F)(F)F)c1)c1nnn(C)n1]

The title compound was prepared following the experimental procedure of Example 52, by using {3-[(3,5-bis-trifluoromethyl-benzylamino)-methyl]-quinolin-2-yl}-cyclobutylmethyl-ethyl-amine instead of {3-[(3,5-bis-trifluoromethyl-benzylamino)-methyl]-quinolin-2-yl}-cyclopentylmethyl-ethyl-amine in step (i) as a colorless, thick liquid (0.064 g), yield: 27.3%.
Purity 99.53% (HPLC: 30:70 [KH$_2$PO$_4$ (0.01 M, pH 3.2): CH$_3$CN], R$_t$ 78.12 min).
$^1$H NMR (CDCl$_3$, 300 MHz): δ 7.87-7.79 (m, 2H), 7.71 (s, 1H), 7.66 (s, 1H), 7.60-7.55 (m, 3H), 7.36-7.27 (m, 1H), 4.83 (s, 2H), 4.66 (s, 2H), 4.22 (s, 3H), 3.28 (d, J=6.58 Hz, 2H), 3.15 (q, J=7.27 Hz, 2H), 2.59-2.49 (m, 1H), 1.92-1.69 (m, 4H), 1.62-1.51 (m, 2H), 1.08 (t, J=7.27 Hz, 3H);
m/z (ES-MS) 578 (M$^+$+1).

Example 57

Synthesis of (3-{[3,5-bis-trifluoromethyl-benzyl)-(2-methyl-2H-tetrazole-5-yl)-amino]-methyl}-8-methyl-quinolin-2-yl)-bis-cyclopropylmethyl-amine

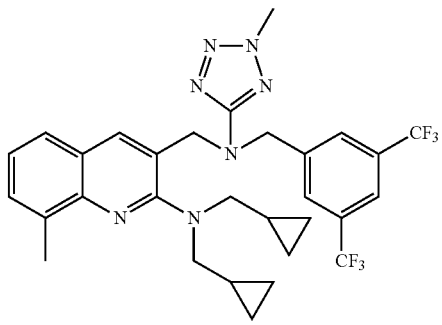 [SMILES: Cc1cccc2cc(CN(Cc3cc(C(F)(F)F)cc(C(F)(F)F)c3)c3nnn(C)n3)c(N(CC3CC3)CC3CC3)nc12]

The title compound was prepared as an oil by following the same synthetic procedures as in Example 52, except using {3-[(3,5-bis-trifluoromethyl-benzylamino)-methyl]-8-methyl-quinolin-2-yl}-bis-cyclopropylmethyl-amine in step (i) instead of {3-[(3,5-bis-trifluoromethyl-benzylamino)-methyl]-quinolin-2-yl}-cyclopentylmethyl-ethyl-amine (0.07 g), yield: 52%.
Purity: 95.53% (HPLC: Symmetry Shield RP8, [0.01M KH$_2$PO$_4$:CH$_3$CN], 217 nM, R$_t$ 9.538 min).
IR (neat, cm$^{-1}$) 3079, 2925, 1582;
$^1$H NMR (CDCl$_3$, 400 MHz): δ 7.82 (s, 1H), 7.69-7.67 (m, 2H), 7.44-7.41 (m, 1H), 7.23-7.2 (m, 3H), 4.91 (s, 2H), 4.65 (s, 2H), 4.21 (s, 3H), 3.29-3.19 (m, 4H), 2.71 (s, 3H), 1.01-1.00 (m, 2H), 0.99-0.83 (m, 2H), 0.39-0.34 (m, 3H), 0.08-0.07 (m, 3H).
m/z (ES-MS): 604 (M$^+$+1, 100%)

Example 58

Synthesis of (3-{[(3,5-bis-trifluoromethyl-benzyl)-(5-methyl-[1,3,4]oxadiazol-2-yl)-amino]-methyl}-quinolin-2-yl)-cyclopentylmethyl-ethyl-amine

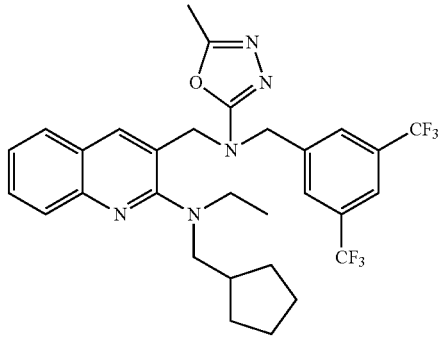 [SMILES: CCN(CC1CCCC1)c1nc2ccccc2cc1CN(Cc1cc(C(F)(F)F)cc(C(F)(F)F)c1)c1nnc(C)o1]

(3-{[(3,5-Bis-trifluoromethyl-benzyl)-(1H-tetrazol-5-yl)-amino]-methyl}-quinolin-2-yl)-cyclopentylmethyl-ethyl-amine (0.30 g, 0.519 mmol), obtained in step (ii) of Example 52, was added to dry pyridine (5 mL) and the solution was cooled to 0° C., followed by the addition of acetyl chloride (0.143 g, 1.8 mmol). This reaction mixture was refluxed for 3 h, after which time it was allowed to reach RT, diluted with water, and then basified with sodium hydroxide. Pyridine was removed as an azeotrope and the residue was dissolved in ethyl acetate and purified by column chromatography to afford (3-{[(3,5-bis-trifluoromethyl-benzyl)-(5-methyl-[1,3,4]oxadiazol-2-yl)-amino]-methyl}-quinolin-2-yl)-cyclopentylmethyl-ethyl-amine (0.110 g), yield: 36%, of purity 96.91%.

Mp 126-127° C.; IR (KBr, cm$^{-1}$) 3445, 2962, 1638;

$^1$H NMR (CDCl$_3$, 400 MHz): δ 7.99 (s, 1H), 7.92 (s, 3H), 7.75-7.70 (m, 2H), 7.60-7.56 (m, 1H), 7.38-7.33 (m, 1H), 4.81 (s, 2H), 4.74 (s, 2H), 3.24-3.08 (m, 4H), 2.33 (s, 3H), 2.08-2.02 (m, 1H), 1.45 (br s, 4H), 1.42 (br s, 1H), 1.01-0.97 (m, 3H);

m/z (CI-MS): 592 (M$^+$+1, 100%)

Example 59

Synthesis of 1-(3,5-bis-trifluoromethyl-benzyl)-1-(cyclopentylmethyl-ethyl-amino)-quinoline-3-ylmethyl]-urea

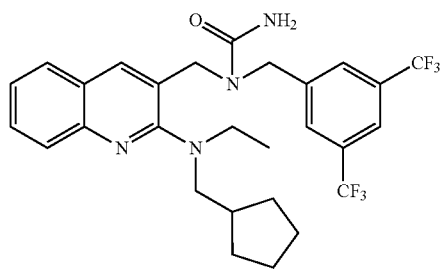 [SMILES: CCN(CC1CCCC1)c1nc2ccccc2cc1CN(Cc1cc(C(F)(F)F)cc(C(F)(F)F)c1)C(N)=O]

(3,5-Bis-trifluoromethyl-benzyl)-[2-(cyclopentylmethyl-ethyl-amino)-quinolin-4-yl]-cyanamide (0.10 g., 0.19 mmol), obtained in step (i) of Example 52, was added to a round bottom flask under a nitrogen atmosphere, hydrogen peroxide (325 micro liter) was added, followed by the addition of potassium hydroxide (0.147 g, 0.18 mmol). The reaction mixture was stirred at 40° C. for 2 h and then allowed to cool to RT. Water was added to the reaction mixture, which was then extracted with ethyl acetate. The combined organic layer was washed with brine solution and dried over sodium sulfate. The solvent was evaporated to afford the title compound (0.1 g), yield: 37%, of purity 91.00%.

Mp: 92-94° C.;

IR (neat, cm$^{-1}$) 3356, 2927, 1658 1602;

$^1$H NMR (CDCl$_3$, 400 MHz): δ 7.88 (d, J=7.5 Hz, 2H), 7.67-7.62 (m, 2H), 7.73 (s, 2H), 7.78 (s, 1H), 7.40 (t, J=6.9 Hz, 1H), 5.12 (s, 2H), 4.69 (s, 2H), 4.51 (s, 2H), 3.21-3.14 (m, 4H), 2.16-2.00 (m, 1H), 1.59-1.22 (m, 8H), 1.07 (t, J=6.9 Hz, 3H);

m/z (CI-MS): 553 (M$^+$+1, 100%)

Example 60

Synthesis of (3-{[(3,5-bis-trifluoromethyl-benzyl)-(4-trifluoromethy-oxazol-2-yl)-amino]-methyl}-quinolin-2-yl)-cyclopentylmethyl-ethyl-amine

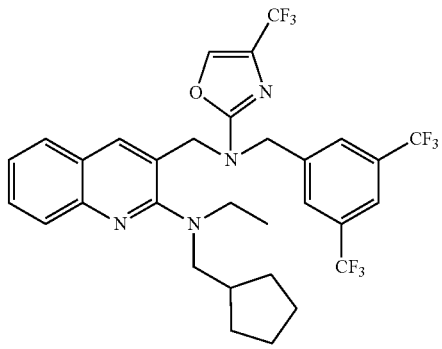 [SMILES: CCN(CC1CCCC1)c1nc2ccccc2cc1CN(Cc1cc(C(F)(F)F)cc(C(F)(F)F)c1)c1nc(C(F)(F)F)co1]

1-(3,5-Bis-trifluoromethyl-benzyl)-1-(cyclopentylmethyl-ethyl-amino)-quinoline-3-ylmethyl]-urea (0.1 g, 0.181 mmol), Example 59, and 3-bromo-1,1,1-trifluoro propane-2-one (0.032 g, 0.181 mmol) were added to a 50 mL two neck round bottom flask, followed by the addition of tert-butanol (10 mL). This reaction mixture was refluxed under a nitrogen atmosphere for 12 h, then concentrated under vacuum. Water was then added to this mixture, the aqueous solution was extracted with ethyl acetate (3×10 mL), and the combined organic layer was washed with brine. The organic solvent was dried over sodium sulfate and concentrated under vacuum to afford the title compound (0.03 g), yield: 27%, of purity 93.7%.

IR (neat, cm$^{-1}$): 3420, 2928, 2857;

$^1$H NMR (CDCl$_3$, 400 MHz): δ 7.86 (d, J=8.4 Hz, 1H), 7.79 (s, 1H), 7.74 (s, 2H), 7.67 (s, 2H), 7.36 (t, J=8 Hz, 3H), 4.8 (s, 2H), 4.63 (s, 2H), 3.16-3.14 (m, 4H), 2.15-2.09 (m, 1H), 1.55-1.45 (m, 4H), 1.39-1.25 (m, 4H), 1.07 (t, J=7.3 Hz, 3H);

m/z (CI-MS): 645 (M$^+$+1, 100%)

Example 61

Synthesis of 1-(3,5-bis-trifluoromethyl-benzyl)-1-(2-cyclopentylmethyl-ethyl-amino)-quinolin-3-yl methyl)-2-ethyl isourea

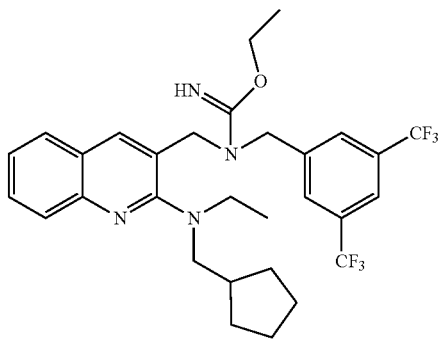 [SMILES: CCOC(=N)N(Cc1cc(C(F)(F)F)cc(C(F)(F)F)c1)Cc1cc2ccccc2nc1N(CC)CC1CCCC1]

1-(3,5-Bis-trifluoromethyl-benzyl)-1-(cyclopentylmethyl-ethyl-amino)-quinoline-3-ylmethyl]-urea (0.1 g, 0.181 mmol), Example 59, and triethoxy tetrafluoroborate (0.034 g, 0.181 mmol) were added to a 25 mL two neck round bottom flask under argon atmosphere, after which 4 mL of DCE was added to the mixture. This reaction mixture was stirred at RT for 12 h, after which the suspension was filtered, and the resulting precipitate was washed with DCE (20 mL), and dried under vacuum to afford the title compound (0.1 g), yield: 95.2%, of purity 96.42%.

Mp 158-160° C.;

IR (neat, cm$^{-1}$) 3382, 1279, 1003;

$^{1}$H NMR (CDCl$_{3}$, 400 MHz): δ 9.23 (s, 1H), 8.14 (s, 1H), 8.03-7.98 (m, 3H), 7.95-7.87 (m, 1H), 7.69-7.65 (m, 1H), 7.49-7.45 (m, 1H), 4.87 (br s, 2H), 4.71-4.68 (br s, 2H), 4.6-4.46 (br s, 2H), 4.35-4.32 (br s, 2H), 3.12-3.16 (br s, 4H), 2.01-1.90 (s, 1H), 1.43 (br s, 4H), 1.33-1.29 (m, 3H), 1.01 (s, 3H);

m/z (ES-MS): 581 (M$^{+}$, 100%)

Example 62

Synthesis of 1-(3,5-bis-trifluoromethyl-benzyl)-1-[2-(cyclopentylmethyl-ethyl-amino)-quinolin-3-yl methyl]-thiourea

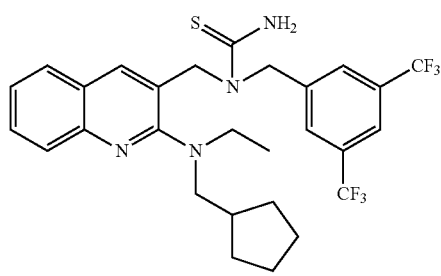

3-Ethoxycarbonyl-1-(3,5-bis-trifluoromethyl-benzyl)-1-[2-(cyclopentylmethyl-ethyl-amino)-quinolin-3-yl methyl]-thiourea (0.3 g, 0.468 mmol), obtained in Example 49, and 2N sodium hydroxide (20 mL) were added to a 50 mL round bottom flask. The reaction mixture was refluxed for 12 h, neutralized with 6N hydrochloric acid, and the aqueous solution was extracted with ethyl acetate (3×20 mL). The combined organic layer was washed with brine, dried over sodium sulfate, and concentrated under vacuum to afford the title compound (0.2 g), yield: 75.2%, of purity 97.5%.

Mp: 98° C.;

IR (neat, cm$^{-1}$) 3287, 2926, 1179;

$^{1}$H NMR (CDCl$_{3}$, 400 MHz): δ 7.90 (m, 4H), 7.67-7.63 (m, 2H), 7.45-7.41 (m, 1H), 6.35 (br s, 2H), 5.4 (br s, 2H), 4.71 (br s, 2H), 3.21-3.16 (m, 4H), 2.13-2.09 (m, 1H), 1.61-1.42 (m, 8H), 1.07 (t, J=6.9 Hz, 3H)

m/z (ES-MS): 569 (M$^{+}$+1, 100%)

Example 63

Synthesis of (3-{[3,5-bis-trifluoromethyl-benzyl)-(4-methyl-thiazol-2-yl)-amino]-methyl}-quinolin-2-yl)-cyclopentylmethyl-ethyl-amine

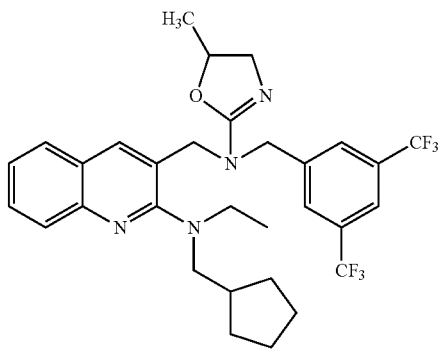 [SMILES: CCN(CC1CCCC1)c1nc2ccccc2cc1CN(Cc1cc(C(F)(F)F)cc(C(F)(F)F)c1)C1=NCC(C)O1]

1-(3,5-Bis-trifluoromethyl-benzyl)-1-[2-(cyclopentylmethyl-ethyl-amino)-quinolin-3-yl methyl]-thiourea (0.1 g, 0.176 mmol), obtained in Example 62, and chloroacetone (0.048 g, 0.528 mmol) were added to a 50 mL round bottom flask and tert-butanol was then added. The reaction was refluxed under a nitrogen atmosphere for 12 h, after which time the reaction mixture was concentrated under vacuum, and water was added. The aqueous solution was extracted with ethyl acetate (3×10 mL), and the combined organic layer was washed with brine, dried over sodium sulfate, and concentrated under vacuum to afford the title compound (0.04 g), yield: 40%, of purity 93.3%.

IR (neat, cm$^{-1}$):2952, 1278, 1135;

$^{1}$H NMR (CDCl$_{3}$, 400 MHz): δ 7.86 (m, 2H), 7.73 (m, 3H), 7.61-7.58 (m, 2H), 7.35-7.26 (m, 1H), 6.14-6.13 (m, 1H), 4.46-4.74 (m, 4H), 3.22 (d, J=6.2 Hz, 2H), 3.16 (q, J=7.2 Hz, 2H), 2.31 (s, 3H), 2.17-2.13 (m, 1H), 1.54-1.41 (m, 8H), 1.07 (t, J=7.1 Hz, 3H);

m/z (ES-MS): 607 (M$^{+}$+1, 100%)

Example 64

Synthesis of cyclopentylmethyl-(3-{[3,5-bis-trifluoromethyl-benzyl)-(5-methyl-4,5-dihydro-oxazol-2-yl)-amino]-methyl}-quinolin-2-yl)-ethyl-amine (3,5-Bis-trifluoromethyl-benzyl)-[2-(cyclopentylmethyl-ethyl-amino)-quinolin-4-yl]-cyanamide (0.10 g, 0.184 mmol), obtained in step (i) of Example 52, 1-amino-2-propanol (0.018 g, 0.257 mmol), and cadmium acetate (0.02 g) were added to a 50 mL round bottom flask. This reaction mixture was heated to 100° C. for 0.5 h, cooled to RT, and a saturated sodium chloride solution was added. The aqueous solution was extracted with dichloromethane (3×10 mL), and the combined organic layer was washed with brine, dried over sodium sulfate, and concentrated under vacuum to afford the title compound (0.9 g), yield: 83%, of purity 97.7%.

IR (neat, cm$^{-1}$): 2926, 1654, 1278;

$^1$H NMR (CDCl$_3$, 400 MHz): δ 7.87 (m, 2H), 7.71 (s, 1H), 7.66-7.59 (m, 3H), 7.58-7.37 (m, 1H), 7.36-7.32 (m, 1H), 4.93-4.87 (m, 1H), 4.68-4.34 (m, 4H), 4.08-4.02 (m, 1H), 3.53-3.46 (m, 1H), 3.24-3.1 (m, 4H), 2.16-2.1 (m, 1H), 1.57-1.4 (m, 7H), 1.39-1.26 (m, 4H), 1.04 (t, J=7.2 Hz, 3H)

m/z (CI-MS) 592 (M$^+$, 100%)

Example 65

Synthesis of (3-{[3,5-bis-trifluoromethyl-benzyl-(5-methyl-isoxazol-3-yl)-amino]-methyl}-quinolin-2-yl)-cyclobutylmethyl-ethyl-amine

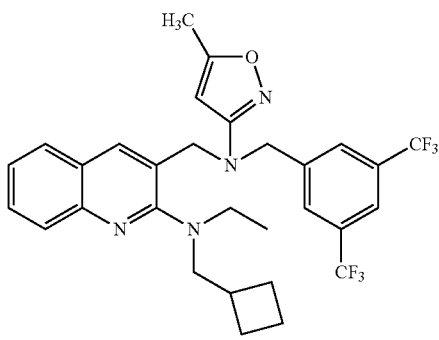 [SMILES: CCN(CC1CCC1)c1nc2ccccc2cc1CN(Cc1cc(C(F)(F)F)cc(C(F)(F)F)c1)c1cc(C)on1]

Step (i): Synthesis of cyclobutylmethyl-ethyl-{3-[(5-methyl-isoxazol-3-ylamino)-methyl]-quinolin-2-yl}-amine

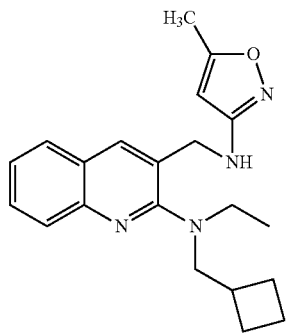 [SMILES: CCN(CC1CCC1)c1nc2ccccc2cc1CNc1cc(C)on1]

5-Methyl-isoxazol-3-ylamine (0.098 g, 1 mmol) was added to a solution of 2-(cyclobutylmethyl-ethyl-amino)-quinoline-3-carbaldehyde (0.268 g, 1 mmol) in anhydrous methanol (5 mL) and acetic acid (0.15 mL) under nitrogen. After being stirred for 15 minutes at ambient temperature, sodium cyanoborohydride (0.19 g, 3 mmol) was added slowly, and the reaction mixture was stirred overnight. Afterwards, the solvent was evaporated in vacuo, and water (30 mL) and ethyl acetate (30 mL) were added to the residue. The organic layer was separated, washed with brine, dried over sodium sulfate, filtered, and concentrated in vacuo. The residue was purified by chromatography on silica gel, eluting with 1-5% methanol in dichloromethane, to afford the title compound (0.150 g), yield: 43%.

$^1$H NMR (CDCl$_3$, 300 MHz): δ 8.01 (s, 1H), 7.86 (d, J=8.63 Hz, 1H), 7.71-7.54 (m, 2H), 7.39-7.33 (m, 1H), 5.44 (s, 1H), 4.51 (s, 2H), 3.39 (d, J=7.27 Hz, 2H), 3.27 (q, J=7.04 Hz, 2H), 2.67-2.58 (m, 1H), 2.27 (s, 3H), 2.09-1.61 (m, 6H), 1.16 (t, J=7.04 Hz, 3H).

Step (ii): Synthesis of (3-{[3,5-bis-trifluoromethyl-benzyl-(5-methyl-isoxazol-3-yl)-amino]-methyl}-quinolin-2-yl)-cyclobutylmethyl-ethyl-amine

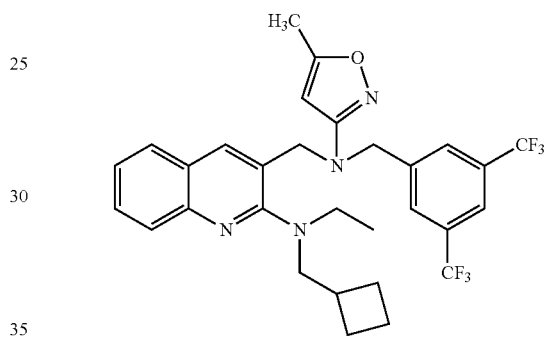

Sodium methoxide (0.108 g, 2.0 mmol) was added to an anhydrous tetrahydrofuran (6 mL) solution of cyclobutylmethyl-ethyl-{3-[(5-methyl-isoxazol-3-ylamino)-methyl]-quinolin-2-yl}-amine (0.14 g, 0.4 mmol), with stirring, at ambient temperature. After this mixture was stirred for 15 minutes, 3,5-bis-trifluoromethybenzyl bromide (0.08 mL, 0.4 mmol) was added slowly, and stirring was continued overnight. Ethyl acetate (30 mL) and water (30 mL) were added, and the layers were separated. The aqueous layer was back-extracted with ethyl acetate (2×30 mL), and the combined organic extracts were washed with brine, dried over sodium sulfate, and concentrated in vacuo. The crude residue was purified by chromatography on silica gel and eluted with 10-70% hexane in ethyl acetate to afford the title compound (0.045 g), yield: 20%.

Purity 96.79% (HPLC: 30:70 [KH$_2$PO$_4$ (0.01 M, pH 3.2): CH$_3$CN], R$_t$ 23.37 min).

$^1$H NMR (CDCl$_3$, 300 MHz): δ 7.88-7.83 (m, 2H), 7.52-7.68 (m, 3H), 7.64-7.55 (m, 2H), 7.38-7.33 (m, 1H), 5.51 (s, 1H), 4.60 (s, 2H), 4.53 (s, 2H), 3.27 (d, J=7.04 Hz, 2H), 3.15 (q, J=7.04 Hz, 2H), 2.59-2.51 (m, 1H), 2.31 (s, 3H), 1.81-1.62 (m, 6H), 1.08 (t, J=7.04 Hz, 3H).

m/z (ES-MS): 577 (M$^+$+1).

Example 66

Synthesis of (3-{1[(3,5-bis-trifluoromethyl-benzyl)-pyrimidin-2-yl-amino]-methyl}-quinolin-2-yl)-cyclopentylmethyl-ethyl-amine

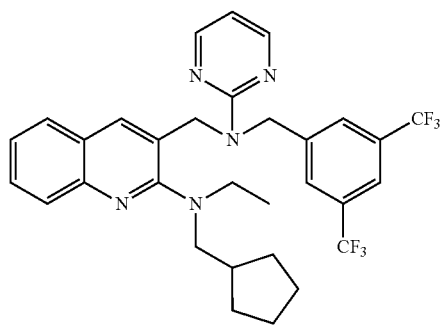

{3-[(3,5-Bis-trifluoromethyl-benzylamino)-methyl]-quinolin-2-yl}-cyclopentylmethyl-ethyl-amine (0.96 g, 1.88 mmol), obtained in step (iv) of Example 35, 2-bromopyrimidine (0.1 g, 0.26 mmol) and potassium carbonate (0.26 g, 1.88 mmol) were added to a tube with DMSO (1 mL) and heated in microwave at 150° C. for 2 h. The crude residue was purified over silica gel (60-120 mesh), eluting with 5% ethyl acetate in hexane, to afford the title compound (0.035 g), yield: 30%, of purity 97.53%.

IR (neat, cm$^{-1}$), 2929, 2857, 1586;
$^1$H NMR (CDCl$_3$, 400 MHz): δ 8.43-8.38 (m, 2H), 7.85 (d, J=8.9 Hz, 1H), 7.67-7.62 (m, 1H), 7.70 (s, 2H), 7.68 (s, 2H), 7.57-7.51 (m, 2H), 7.31-7.27 (m, 1H), 6.69-6.67 (m, 1H), 5.29 (s, 2H), 5.02 (s, 2H), 3.27-3.17 (m, 4H), 2.95-2.88 (m, 1H), 1.43-1.4 (m, 3H), 1.29-1.25 (m, 4H), 1.1-1.06 (m, 4H);
m/z (CI-MS): 587 (M$^+$, 100%)

Example 67

Synthesis of (3-{[(3,5-bis-trifluoromethyl-benzyl)-(4-methyl-oxazol-2-yl)-amino]-methyl}-quinolin-2-yl)-cyclopentylmethyl-ethyl-amine

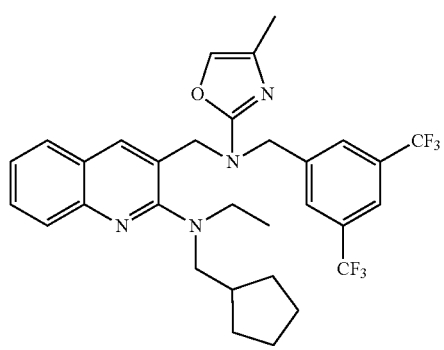 [SMILES: CCN(CC1CCCC1)c1nc2ccccc2cc1CN(Cc1cc(C(F)(F)F)cc(C(F)(F)F)c1)c1nc(C)co1]

(3,5-Bis-trifluoromethyl-benzyl)-[2-(cyclopentylmethyl-ethyl-amino)-quinolin-4-yl]-cyanamide (0.1 g, 0.184 mmol), obtained in step (i) of Example 52, and 2N sodium hydroxide (0.08 g, 0.22 mmol) were added to a 50 mL round bottom flask with dioxane (10 mL), and hydroxyacetone (0.013 g, 0.18 mmol) was added dropwise at RT. The reaction mixture was refluxed for 2 to 4 h, after which time the reaction was cooled to RT and water was added. The aqueous solution was extracted with ethyl acetate (3×10 mL), and the combined organic layer was washed with brine, dried over sodium sulfate, and concentrated under vacuum to afford the title compound (0.03 g), yield: 27%, of purity 97.4%.

IR (neat, cm$^{-1}$) 2928, 1627, 1596;
$^1$H NMR (CDCl$_3$, 400 MHz): δ 7.86-7.82 (m, 2H), 7.71 (s, 1H), 7.64-7.61 (m, 2H), 7.59-7.55 (m, 2H), 7.35-7.31 (m, 1H), 7.02 (d, J=1.3 Hz, 1H), 4.75 (s, 2H), 4.59 (s, 2H), 3.21-3.19 (m, 2H), 3.17-3.12 (m, 2H), 2.14 (s, 3H), 1.41-1.38 (m, 3H), 1.07-1.03 (m, 5H), 0.89-0.83 (m, 3H);
m/z (CI-MS): 590 (M$^+$, 100%)

Example 68

Synthesis of (3-{[(3,5-bis-trifluoromethyl-benzyl)-(4,5-dihydro-oxazol-2-yl)-amino]-methyl}-quinolin-2-yl)-cyclopentylmethyl-ethyl-amine

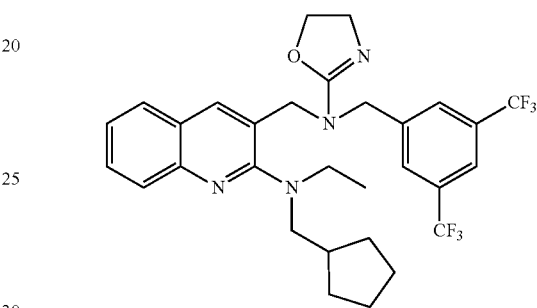

(3,5-Bis-trifluoromethyl-benzyl)-[2-(cyclopentylmethyl-ethyl-amino)-quinolin-4-yl]-cyanamide (0.5 g, 0.936 mmol), obtained in step (i) of Example 52, 2-amino-ethanol (1.2 mL, 1.3 mmol), and cadmium acetate (0.02 g) were added to a 50 mL round bottom flask. This reaction mixture was heated to 100° C. for 0.5 h, after which time the reaction was cooled to RT, and a saturated sodium chloride solution was added to the mixture. The aqueous solution was extracted with DCM (3×10 mL), and the combined organic layer was washed with brine, and the solvent was dried over sodium sulfate and concentrated under vacuum to afford the title compound (0.1 g), yield: 18%, of purity 97.5%.

$^1$H NMR (CDCl$_3$, 400 MHz): δ 7.87-7.83 (m, 2H), 7.71 (s, 1H), 7.65-7.60 (m, 2H), 7.59-7.55 (m, 1H), 7.36-7.32 (m, 1H), 4.62 (s, 2H), 4.50-4.45 (m, 4H), 3.98-3.93 (m, 2H), 3.19-3.09 (m, 4H), 2.09-2.04 (m, 1H), 1.60-1.40 (m, 8H), 1.11-0.92 (m, 3H)
m/z (CI-MS): 578 (M$^+$, 100%)

Example 69

Synthesis of (3-{[(3,5-bis-trifluoromethyl-benzyl)-pyridin-2-yl-amino]-methyl}-quinolin-2-yl)-cyclopentylmethyl-ethyl-amine

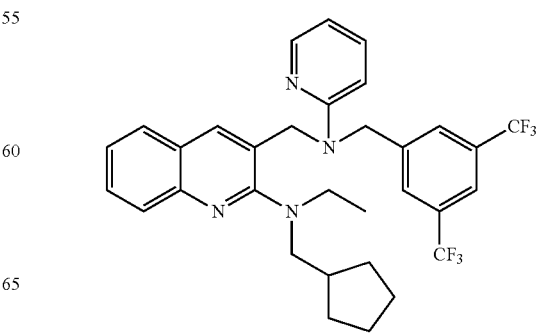

The title compound of purity 97.45% was synthesized by following the same experimental procedure of Example 65, except using 2-(cyclopentylmethyl-ethyl-amino)-quinolin-3-carbaldehyde instead of 2-(cyclobutylmethyl-ethyl-amino)-quinoline-3-carbaldehyde, and using 2-amino pyridine instead of 5-methyl-isoxazol-3-ylamine, in step (i) (0.10 g), yield: 31%.

$^1$H NMR (CDCl$_3$, 400 MHz): δ 8.24 (d, 1H), 8.23 (d, 1H), 7.87-7.73 (m, 4H), 7.58-7.54 (m, 2H), 7.45-7.41 (m, 1H), 7.33-7.31 (m, 1H), 6.69-6.66 (m, 1H), 6.43-6.4 (d, J=2 Hz, 1H), 4.9 (s, 2H), 4.7 (s, 2H), 3.27-3.25 (d, J=8.0 Hz, 2H), 3.2-3.1 (m, 2H), 2.18-2.14 (m, 1H), 1.6-1.4 (m, 8H), 1.71 (m, 3H)

m/z (CI-MS): 586 (M$^+$, 100%)

Example 70

Synthesis of (3-{[(3,5-bis-trifluoromethyl-benzyl)-(2-methyl-2H-tetrazol-5-ylmethyl)-amino]-methyl}-quinolin-2-yl)-cyclopentylmethyl-ethyl-amine Step (i): Synthesis of (3-{[3,5-bis trifluoro methyl-benzyl)-[2-(cylopentylmethyl-ethyl-amino)-quinolin-3-ylmethyl]-amino}-acetonitrile

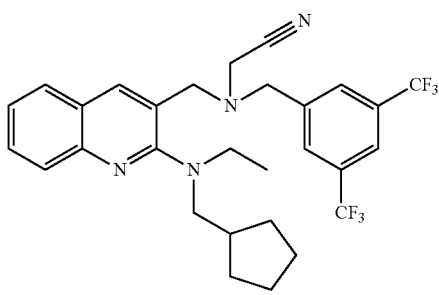 [SMILES: CCN(CC1CCCC1)c1nc2ccccc2cc1CN(CC#N)Cc1cc(C(F)(F)F)cc(C(F)(F)F)c1]

Under a N$_2$ atmosphere, potassium carbonate (0.4 g, 2.94 mmol) was added to a solution of {3-[(3,5-bis-trifluorom-ethyl-benzylamino)-methyl]-quinolin-2-yl}-cyclo-pentylm-ethyl-ethyl-amine (0.5 g, 0.98 mmol), obtained in step (iv) of Example 35, in MeOH (10 mL), followed by the addition of chloroacetonitrile (0.64 g, 0.98 mmol). This reaction mixture was stirred at RT for 4 h. Afterwards, the solvent was removed under vacuum to give the crude residue which was dissolved in water, extracted with ethyl acetate, and dried over sodium sulfate. The solvent was evaporated and concentrated under vacuum to afford the title compound (0.25 g), yield: 47%.

$^1$H NMR (CDCl$_3$, 400 MHz): δ 8.16 (s, 1H), 7.86-7.82 (m, 4H), 7.70-7.67 (m, 1H), 7.62-7.6 (m, 1H), 7.38-7.34 (m, 1H), 3.92 (s, 2H), 3.45 (s, 2H), 3.34-3.28 (m, 4H), 2.22-2.17 (m, 1H), 1.66-1.45 (br s, 8H), 1.26 (t, J=7.1 Hz, 3H)

m/z (ES-MS): 549 (M$^+$+1, 100%), 510 (M$^+$−40, 40%)

Step (ii): Synthesis of (3-{[(3,5-bis-trifluoromethyl-benzyl)-(1H-tetrazol-5-ylmethyl)-amino]-methyl}-quinolin-2-yl)-cyclopentylmethyl-ethyl-amine

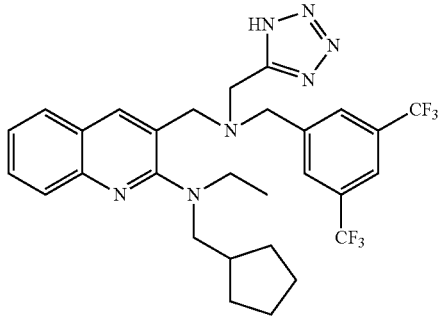 [SMILES: CCN(CC1CCCC1)c1nc2ccccc2cc1CN(Cc1cc(C(F)(F)F)cc(C(F)(F)F)c1)Cc1nnn[nH]1]

(3-{[3,5-Bis-trifluoromethyl-benzyl)-[2-(cylopentylm-ethyl-ethyl-amino)-quinolin-3-ylmethyl]-amino}-acetonitrile (0.26 g, 0.474 mmol), obtained in Example 19, sodium azide (0.154 g, 2.37 mmol), and ammonium chloride (0.126 g, 2.37 mmol) were added to a 50 mL round bottom flask with dry DMF (10 mL). This reaction was refluxed under a nitrogen atmosphere for 1 h. The reaction mixture was then cooled to RT, the aqueous solution was extracted with ethyl acetate (3×10 mL), and the combined organic layer was washed with brine. The solvent was then dried over sodium sulfate and concentrated under vacuum to afford the title compound (0.25 g), yield: 92%.

m/z (ES-MS): 592 (M$^+$+1, 100%)

Step (iii): Synthesis of (3-{[(3,5-bis-trifluoromethyl-benzyl)-(2-methyl-2H-tetrazol-5-ylmethyl)-amino]-methyl}-quinolin-2-yl)-cyclopentylmethyl-ethyl-amine

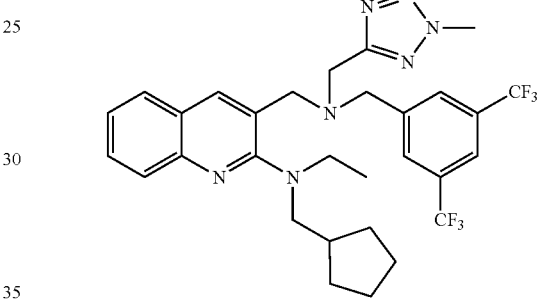

To a suspension of (3-{[(3,5-bis-trifluoromethyl-benzyl)-(2H-tetrazol-5-ylmethyl)-amino]-methyl}-quinolin-2-yl)-cyclopentylmethyl-ethyl-amine (0.25 g, 0.423 mmol) in water (4 mL) was added sodium hydroxide (0.033 g, 0.846 mmol), the resulting mixture was stirred for 15 min at RT, and then DCM (4 mL) was added. Dimethyl sulfate (0.058 g, 0.465 mmol) was then added to this mixture, followed by tetrabutylammonium bromide (0.006 g, 0.021 mmol), and stirring of the resulting mixture was continued for 15 min. The organic layer was then separated from aqueous layer, the aqueous layer was extracted with DCM (3×10 mL), and the combined organic layer was washed with brine, dried over sodium sulfate, and concentrated under vacuum to afford a residue. This residue was purified by column chromatography over 100-200 mesh silica gel using 4% ethyl acetate in petroleum ether, to give the title compound (0.08 g), yield: 31.3%.

Purity 98.38% (HPLC: Symmetry Shield RP8, [0.01M KH$_2$PO$_4$:CH$_3$CN], 216 nM, R$_t$ 11.207 min).

IR (neat, cm$^{-1}$), 3382, 1278, 1134;

$^1$H NMR (CDCl$_3$, 400 MHz): δ 8.36 (s, 1H), 7.89 (s, 2H), 7.83-7.81 (m, 1H), 7.71-7.68 (m, 1H), 7.57-7.53 (m, 1H), 7.36-7.32 (m, 1H), 4.33 (s, 3H), 3.99 (s, 2H), 3.86 (s, 2H), 3.78 (s, 2H), 3.27-3.18 (m, 4H), 2.18-2.13 (m, 1H), 1.63-1.51 (br s, 4H), 1.51-1.42 (br s, 2H), 1.29-1.27 (br s, 2H), 1.1 (t, J=7.0 Hz, 3H);

m/z (ES-MS): 605 (M+, 100%).

Example 71

Synthesis of (3-{[(3,5-bis-trifluoromethyl-benzyl)-(1-methyl-1H-tetrazol-5-ylmethyl)-amino]-methyl}-quinolin-2-yl)-cyclopentylmethyl-ethyl-amine

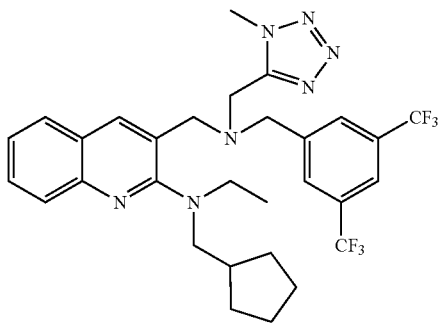 [SMILES: CCN(CC1CCCC1)c1nc2ccccc2cc1CN(Cc1cc(C(F)(F)F)cc(C(F)(F)F)c1)Cc1nnnn1C]

The regioisomer of Example 70, (3-{[(3,5-bis-trifluoromethyl-benzyl)-(1-methyl-1H-tetrazol-5-ylmethyl)-amino]-methyl}-quinolin-2-yl)-cyclopentylmethyl-ethyl-amine was separated from the same reaction mixture after purification of the crude residue by column chromatography over 100-200 mesh silica gel using 15% ethyl acetate in petroleum ether (0.03 g), yield: 17%.

Purity 96.69% (HPLC: Symmetry Shield RP8, [0.01M $KH_2PO_4$:$CH_3CN$], 216 nM, $R_t$ 8.715 min);

$^1$H NMR ($CDCl_3$, 400 MHz): δ 8.13 (s, 1H), 7.85-7.79 (m, 4H), 7.67-7.62 (m, 1H), 7.61-7.58 (m, 1H), 7.39-7.35 (m, 1H), 3.86-3.84 (m, 6H), 3.73 (s, 3H), 3.25-3.22 (m, 4H), 2.18-2.14 (m, 1H), 1.62-1.42 (br s, 8H), 1.1 (t, J=6.9 Hz, 3H);

m/z (ES-MS): 605 ($M^+$, 100%)

Example 72

Synthesis of (3-{[(3,5-bis-trifluoromethyl-benzyl)-(2-methyl-2H-tetrazole-5-yl)-amino]-methyl-}-8-ethyl-quinolin-2-yl)-bis-cyclopropylmethyl-amine

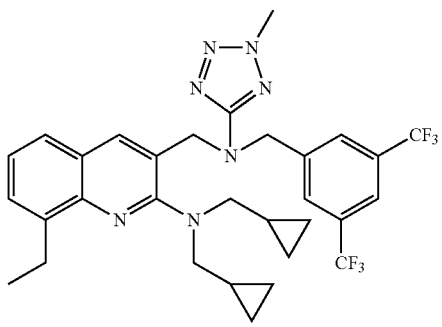 [SMILES: CCc1cccc2cc(CN(Cc3cc(C(F)(F)F)cc(C(F)(F)F)c3)c3nnn(C)n3)c(N(CC3CC3)CC3CC3)nc12]

The title compound was synthesized following the same synthetic procedures disclosed in Example 52, except using {3-[(3,5-bis-trifluoromethyl-benzylamino)-methyl]-8-ethyl-quinolin-2-yl}-bis-cyclopropylmethyl-amine in step (i) instead of {3-[(3,5-bis-trifluoromethyl-benzylamino)-methyl]-quinolin-2-yl}-cyclopentylmethyl-ethyl-amine, to provide this compound as an oil (0.60 g), yield: 54%.

Purity 94.23% (HPLC: Symmetry Shield RP8, [0.01M $KH_2PO_4$:$CH_3CN$], 220 nM, $R_t$ 10.391 min).

IR (neat, $cm^{-1}$): 2928, 1582, 1279, 1138;

$^1$H NMR ($CDCl_3$, 400 MHz): δ 7.84 (s, 1H), 7.71-7.69 (m, 3H), 7.43-7.42 (m, 2H), 7.28-7.24 (m, 1H), 4.92 (s, 2H), 4.68 (s, 2H), 4.21 (s, 3H), 3.20-3.18 (m, 6H), 1.36 (t, J=7.5 Hz, 3H), 1.02-0.95 (m, 2H), 0.38-0.04 (m, 4H);

m/z (CI-MS): 616 ($M^+$–1, 100%).

Example 73

Synthesis of (3-{[3,5-bis-trifluoromethyl-benzyl)-(2-methyl-2H-tetrazole-5-yl)-amino]-methyl}-pyridin-2-yl)-butyl-ethyl amine

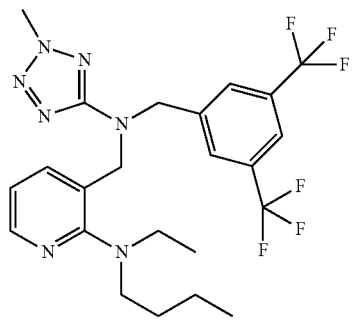 [SMILES: CCCCN(CC)c1ncccc1CN(Cc1cc(C(F)(F)F)cc(C(F)(F)F)c1)c1nnn(C)n1]

The title compound was prepared as a colorless, thick liquid following the experimental procedure of Example 52, except using {3-[(3,5-bis-trifluoromethyl-benzylamino)-methyl]-pyridin-2-yl}-butyl-ethyl-amine instead of {3-[(3,5-bis-trifluoromethyl-benzylamino)-methyl]-quinolin-2-yl}-cyclopentylmethyl-ethyl-amine in step (i).

Purity 95.67% (HPLC: 30:70 [$KH_2PO_4$ (0.01 M, pH 3.2): $CH_3CN$], $R_t$ 38.37 min).

$^1$H NMR (300 MHz, $CDCl_3$); δ 8.25 (d, J=3.17 Hz, 1H), 7.75 (s, 1H), 7.65 (s, 2H), 7.46 (d, J=6.8 Hz, 1H), 6.89-6.82 (m, 1H), 4.69 (s, 2H); 4.59 (s, 2H), 4.20 (s, 3H), 3.15-3.03 (m, 4H), 1.39-1.32 (m, 2H), 1.25-1.14 (m, 2H), 1.01 (t, J=7.04 Hz, 3H), 0.84 (t, J=7.27 Hz, 3H);

MS m/z (ESI) 516 ($M^+$+1, 100%).

Example 74

Synthesis of (3,5-bis-trifluoromethyl-benzyl)-[2-(cyclopentylmethyl-ethyl-amino)-5,6,7,8-tetrahydro-quinolin-3-ylmethyl]-carbamic acid methyl ester

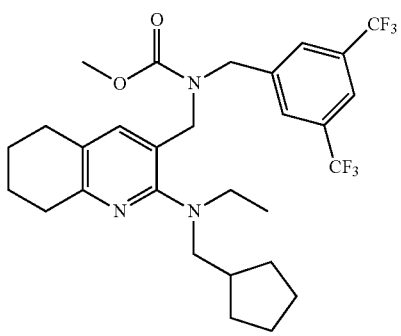 [SMILES: CCN(CC1CCCC1)c1nc2c(cc1CN(Cc1cc(C(F)(F)F)cc(C(F)(F)F)c1)C(=O)OC)CCCC2]

Step (i): Synthesis of sodium salt of 2-formyl cyclohexanone

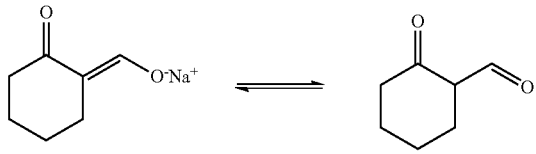

Sodium (2.8 g) was added into 300 mL of dry ether in a 1-L round bottom flask, and the suspension was cooled to 0° C. by using an acetone-dry ice bath. To this cooled suspension was added a mixture of ethyl formate (0.21 mol) and cyclohexanone (0.204 mol) in dry ether (100 mL). The temperature of the reaction mixture was allowed to reach room temperature, and stirring was continued overnight. The crude suspension was filtered, and the precipitate was dried under vacuum for 2 h to yield (2-oxo-cyclohexylidene) sodium methanolate (16.0 g), yield: 82%.

m/z (ES-MS): 126 ($M^++1$, 100%), 125 ($M^+-1$, 30%), 97 ($M^+$-CHO, 50%).

Step (ii): Synthesis of 2-oxo-1,2,5,6,7,8-hexahydro-quinoline-3-carbonitrile

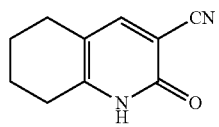 [SMILES: N#Cc1cc2c([nH]c1=O)CCCC2]

To a solution of sodium salt of 2-formylcyclohexanone (16.0 g, 10.8 mmol) in toluene (300 mL) was added cyanoacetamide (22.00 g, 0.237 mol), and the reaction was allowed to stir at room temperature for 1 h. After this time, a 2M solution of piperidine acetate in dichloromethane (25 mL) was added, and the reaction was refluxed for 24 h. The reaction mixture was then cooled to 0° C., and acidified with acetic acid. The resulting suspension was filtered and the precipitate was washed with toluene. The filtrate was concentrated to give a sticky residue, which was was treated with diethyl ether followed by ethyl acetate, to provide 2-oxo-1,2,5,6,7,8-hexahydro-quinoline-3-carbonitrile as a fine solid (6.00 g), yield: 31.8%.

m/z (CI-MS): 175 ($M^++1$, 100%)
IR ($cm^{-1}$): 2227 (CN), 1664 (CO).

Step (iii): 2-Chloro-5,6,7,8-tetrahydro-quinoline-3-carbonitrile

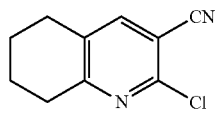 [SMILES: N#Cc1cc2c(nc1Cl)CCCC2]

To 2-oxo-1,2,5,6,7,8-hexahydroquinoline-3-carbonitrile (6.0 g, 34.4 mmol) was added phosphorus oxychloride (20 mL), this mixture was stirred at RT for 1 h, and then refluxed for 12 h. Excess phosphorous oxychloride was distilled off, and the residue was poured into ice cooled water. The aqueous solution was basified with saturated sodium bicarbonate solution, and the precipitate that formed was filtered off. The precipitate was purified by column chromatography eluting with 2% ethyl acetate and petroleum ether to afford 2-chloro-5,6,7,8-tetrahydro-quinoline-3-carbonitrile (5.00 g), yield: 75%.

$^1$H NMR (CDCl$_3$, 400 MHz): δ 7.67 (s, 1H), 3.00-2.97 (m, 2H), 2.94-2.83 (m, 2H), 1.99-1.94 (m, 4H);
m/z (EI-MS): 193 ($M^++1$, 100%)

Step (iv): Synthesis of 2-(cyclopentylmethyl-ethyl-amino)-5,6,7,8-tetrahydro-quinoline-3-carbonitrile

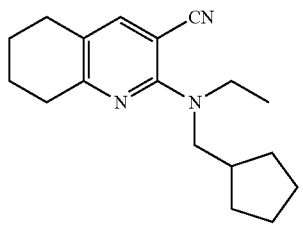 [SMILES: CCN(CC1CCCC1)c1nc2c(cc1C#N)CCCC2]

Dry dioxane (15 mL) was added to a mixture of 2-chloro-5,6,7,8-tetrahydro-quinoline-3-carbonitrile (3.0 g, 15.62 mmol), potassium carbonate (8.6 g, 62.5 mmol), CuI (5 mol %, 0.064 g), and trans-1,2-cyclohexanediamine (5 mol %, 0.089 g) under an argon atmosphere. A solution of N-cyclopentyl-ethylamine (2.3 g, 18.75 mmol) in dioxane was them added to the stirred reaction mixture, which was then refluxed for 24 h. After this time, the solvent was evaporated under vacuum, and the residue was purified by column chromatography over silica gel (100-200 mesh), eluted with 2% ethyl acetate and petroleum ether, to afford 2-(cyclopentylmethyl-ethyl-amino)-5,6,7,8-tetrahydro-quinoline-3-carbonitrile (0.3 g), yield: 10%.

$^1$H-NMR: (CDCl$_3$, 200 MHz) δ 7.39 (s, 1H), 3.69 (q, 2H), 3.58 (d, 2H), 2.75 (t, 2H), 2.58 (t, 2H), 2.38-2.22 (m, 1H), 1.9-1.4 (m, 8H), 1.32-1.15 (m, 7H).
m/z (ES-MS): 284 ($M^++1$, 100%)

Step (v): Synthesis of (3-aminomethyl-5,6,7,8-tetrahydro-quinoline-2-yl)-cyclopentylmethyl-ethylamine

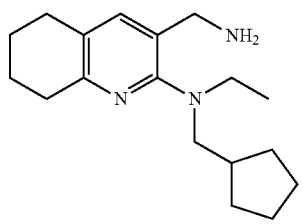 [SMILES: CCN(CC1CCCC1)c1nc2c(cc1CN)CCCC2]

To a suspension of LAH (0.600 g, 16 mmol) in THF (15 mL), was added a solution of 2-(cyclopentylmethyl-ethylamino)-5,6,7,8-tetrahydro-quinoline-3-carbonitrile (0.300 g, 1.06 mmol) in dry THF. This reaction mixture was gently refluxed for 14 h. The unreacted LAH was then quenched with a saturated solution of sodium sulfate, and the residue was filtered off and washed with diethyl ether. The washings were collected, dried over sodium sulfate, and the solvent was evaporated to provide (3-aminomethyl-5,6,7,8-tetrahydro-quinoline-2-yl)-cyclopentylmethyl-ethylamine (0.2 g), yield: 65%.

$^1$H NMR (CDCl$_3$, 200 MHz): δ 7.22 (s, 1H), 3.83 (s, 2H), 3.09-3.03 (m, 4H), 2.78 (t, J=6.4 Hz, 2H), 2.68 (t, J=6.0 Hz, 2H), 2.05-1.92 (m, 1H), 1.86-1.76 (m, 4H), 1.60-1.44 (m, 6H), 1.18-1.14 (m, 2H), 1.05 (t, J=6.9 Hz, 3H).

m/z (ES-MS): 288 (M$^+$+1, 100%), 271 (M$^+$−17)

Step (vi): Synthesis of {3-[(3,5-bis-trifluoromethyl-benzylamino)-methyl]-5,6,7,8-tetrahydro-quinolin-2-yl}-cyclopentylmethyl-ethylamine

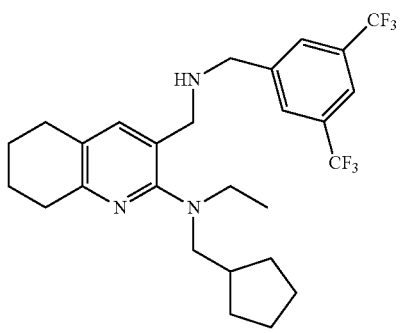 [SMILES: CCN(CC1CCCC1)c1nc2c(cc1CNCc1cc(C(F)(F)F)cc(C(F)(F)F)c1)CCCC2]

To a solution of 3,5-bis-trifluoromethyl benzaldehyde (0.185 g, 0.76 mmol) in MeOH (3 mL) was added (3-aminomethyl-5,6,7,8-tetrahydro-quinoline-2-yl)-cyclopentylmethyl-ethylamine (0.2 g, 0.69 mmol), followed by the addition of acetic acid (0.08 mL, 1.39 mmol). This reaction mixture was stirred at RT for 1 h, after which time sodium cyanoborohydride (0.172 g, 2.78 mmol) was added, and stirring was continued for another 8 h. The solvent was then evaporated under vacuum and water was added, followed by extraction of the product with ethyl acetate. The organic layer was washed with saturated sodium bisulfite solution, the organic layer was separated and dried over sodium sulfate, and the solvent was evaporated to give the {3-[(3,5-bis-trifluoromethyl-benzylamino)-methyl]-5,6,7,8-tetrahydro-quinolin-2-yl}-cyclopentylmethyl-ethyl amine (0.250 g), yield: 70%.

$^1$H NMR (CDCl$_3$, 200 MHz): δ 7.76 (br s, 1H), 7.64-7.56 (m, 2H), 6.99 (s, 1H), 4.54 (br s, 4H), 2.97-2.93 (m, 4H), 2.76 (t, J=6.0 Hz, 2H), 2.64 (t, J=6.2 Hz, 2H), 2.00-1.96 (m, 1H), 1.86-1.68 (m, 4H), 1.55-1.38 (m, 6H), 1.24-1.22 (m, 2H), 0.97 (t, J=6.9 Hz, 3H);

m/z (ES MS): 514 (M$^+$+1)

Step (vii): Synthesis of (3,5-bis-trifluoromethyl-benzyl)-[2-(cyclopentylmethyl-ethyl-amino)-5,6,7,8-tetrahydro-quinolin-3-ylmethyl]-carbamic acid methyl ester

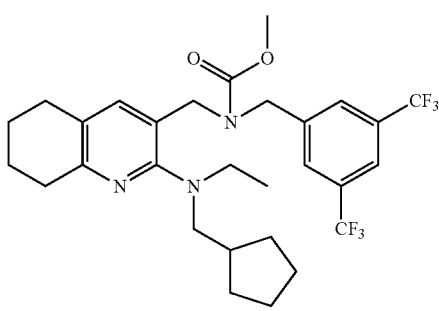 [SMILES: CCN(CC1CCCC1)c1nc2c(cc1CN(Cc1cc(C(F)(F)F)cc(C(F)(F)F)c1)C(=O)OC)CCCC2]

To a suspension of potassium carbonate (0.269 g, 1.949 mmol) in dry THF (5 mL) was added a THF solution (10 mL) of {3-[(3,5-bis-trifluoromethyl-benzylamino)-methyl]-5,6,7,8-tetrahydro-quinolin-2-yl}-cyclopentylmethyl-ethylamine (0.25 g, 0.3 mmol), which was then stirred for 1 h. Methyl chloroformate (0.137 g, 1.46 mmol) was then added and stirring was was continued at RT for 8 h. The solvent was then evaporated, water was added, and the product was extracted with ethyl acetate. The organic layer was dried over sodium sulfate and the solvent was evaporated to afford a residue. This crude residue was purified over silica gel (100-200 mesh) and eluted with 2% ethyl acetate and petroleum ether to afford (3,5-bis-trifluoromethyl-benzyl)-[2-(cyclopentylmethyl-ethyl-amino)-5,6,7,8-tetrahydro-quinolin-3-ylmethyl]-carbamic acid methyl ester as light green, pasty compound (0.05 g), yield: 15%.

$^1$H NMR (CDCl$_3$, 200 MHz): δ 7.76 (s, 1H), 7.64-7.56 (m, 2H), 7.08-6.97 (m, 1H), 4.54-4.45 (m, 4H), 3.93-3.83 (s, 3H), 2.97-2.93 (m, 4H), 2.77 (t, J=5.9 Hz, 2H), 2.64 (t, J=6.3 Hz, 2H), 2.00-1.96 (m, 1H), 1.86-1.68 (m, 4H), 1.55-1.38 (m, 6H), 1.24-1.22 (m, 2H), 0.95 (t, J=6.9 Hz, 3H);

m/z (ES-MS): 572 (M$^+$+1, 100%).

Example 75

Synthesis of (3,5-bis-trifluoromethyl-benzyl)-[2-(cyclopentylmethyl-ethyl-amino)-6,7-dihydro-5H-[1]pyridin-3-ylmethyl]-carbamic acid methyl ester

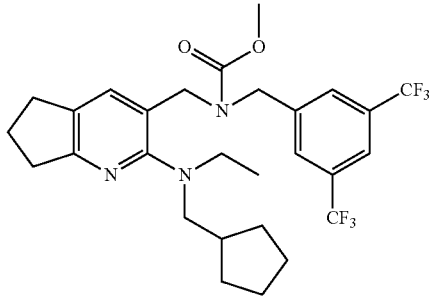 [SMILES: CCN(CC1CCCC1)c1nc2c(cc1CN(Cc1cc(C(F)(F)F)cc(C(F)(F)F)c1)C(=O)OC)CCC2]

The title compound of purity 96% was prepared by following the same experimental procedure as provided in Example 74, except using cyclopentanone instead of cyclohexanone in step (i) (0.03 g), yield: 13%.

$^1$H NMR (CDCl$_3$, 200 MHz): δ 7.75 (s, 1H), 7.64-7.56 (m, 2H), 7.17 (br s, 1H), 4.59-4.45 (m, 4H), 3.84 (s, 3H), 2.98-2.81 (m, 8H), 2.16-1.92 (m, 3H), 1.57-1.25 (m, 8H), 0.95 (t, J=6.9 Hz, 3H)

m/z (ES-MS): 558 (M$^+$+1, 100%)

Example 76

Synthesis of (3-{[(3,5-bis-trifluoromethyl-benzyl)-(2-methyl-2H-tetrazole-5-yl)-amino]-methyl}-,6,7-dihydro-5H-[1]pyridine-2-yl)-cyclopentylmethyl-ethyl-amine

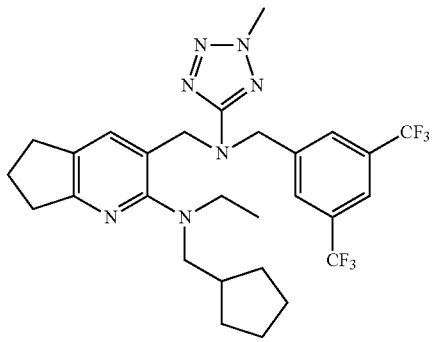 [SMILES: CCN(CC1CCCC1)c1nc2c(cc1CN(Cc1cc(C(F)(F)F)cc(C(F)(F)F)c1)c1nnn(C)n1)CCC2]

Step (i): Synthesis of (3,5-bis-trifluoromethyl-benzyl)-[2-(cyclopentylmethyl-ethyl-amino)-6,7-tetrahydro-5H-[1]pyridine-3-ylmethyl]-cyanamide

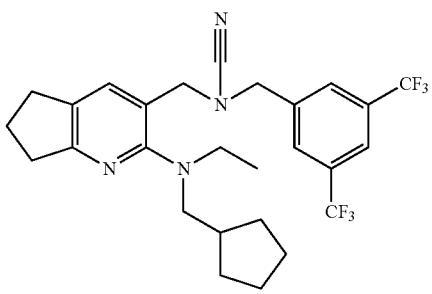 [SMILES: CCN(CC1CCCC1)c1nc2c(cc1CN(C#N)Cc1cc(C(F)(F)F)cc(C(F)(F)F)c1)CCC2]

A solution of {3-[(3,5-bis-trifluoromethyl-benzylamino)-methyl]-6,7-dihydro-5H-[1]-pyridin-2-yl}-cyclopentylmethyl-ethylamine (1.20 g, 2.4 mmol), prepared as {3-[(3,5-bis-trifluoromethyl-benzylamino)-methyl]-5,6,7,8-tetrahydro-quinolin-2-yl}-cyclopentylmethyl-ethylamine in step (vi) of Example 2, was prepared in DMF (10 mL) was added potassium carbonate (0.995 g, 7.21 mmol), followed by the addition of cyanogen bromide (0.303 g, 2.88 mmol). This reaction mixture was stirred at room temperature overnight, after which time crushed ice was added, and the resulting aqueous layer was extracted with ethyl acetate, and washed with brine. The organic layer was dried over sodium sulfate, and the solvent was evaporated under vacuum to afford the title compound (1.20 g), yield: 95%.

$^1$H NMR (CDCl$_3$, 400 MHz): δ 8.01 (s, 1H), 7.84-7.77 (m, 3H), 4.98 (s, 2H), 4.85 (s, 2H), 3.88-3.83 (m, 2H), 3.10-3.03 (m, 2H), 2.95-2.85 (m, 4H), 2.16-2.11 (m, 3H), 1.59-1.43 (m, 6H), 1.27-1.24 (m, 2H), 0.99 (t, J=6.9 Hz, 3H);

m/z (ES-MS) 525 (M$^+$+1, 100%)

Step (ii): Synthesis of (3-{[(3,5-bis-trifluoromethyl-benzyl)-(2H-tetrazol-5-yl)-amino]-methyl}-6,7-dihydro-5H-[1]pyridin-2-yl)-cyclopentylmethyl-ethyl-amine

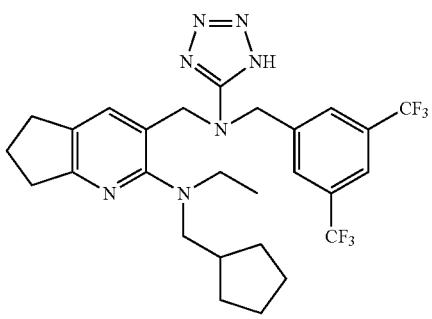 [SMILES: CCN(CC1CCCC1)c1nc2c(cc1CN(Cc1cc(C(F)(F)F)cc(C(F)(F)F)c1)c1nnn[nH]1)CCC2]

(3,5-Bis-trifluoromethyl-benzyl)-[2-(cyclopentylmethyl-ethyl-amino)-6,7-tetrahydro-5H-[1]pyridine-3-ylmethyl]-cyanamide (0.8 g, 1.526 mmol), obtained in step (i), sodium azide (0.496 g, 7.633 mmol), and ammonium chloride (0.408 g, 7.633 mmol) were added to a 50 mL round bottom flask, along with dry DMF (10 mL). This mixture was refluxed under nitrogen atmosphere for 1 hour, after which it was cooled to RT, and ice-cooled water (15 mL) was added. This aqueous solution was extracted with ethyl acetate (3×10 mL).

The combined organic layer was washed with brine, and the solvent was dried over sodium sulfate and concentrated under vacuum to afford the title compound (0.800 g), yield: 92.4%

$^1$H NMR (CDCl$_3$, 400 MHz): δ 8.01 (s, 1H), 7.84-7.80 (m, 2H), 7.73 (s, 1H), 4.98 (s, 2H), 4.85 (s, 2H), 4.45 (s, 2H), 4.15-4.1 (m, 4H), 3.35 (q, J=7.0 Hz, 2H), 3.06 (d, J=7.0 Hz, 2H), 2.16-2.07 (m, 1H), 1.58-1.46 (m, 6H), 1.29-1.27 (m, 2H), 1.08 (t, J=6.9 Hz, 3H);

m/z (CI-MS) 567 (M$^+$, 100%)

Step (iii): Synthesis of (3-{[(3,5-bis-trifluoromethyl-benzyl)-(2-methyl-2H-tetrazole-5-yl)-amino]-methyl}-6,7-dihydro-5H-[1]pyridine-2-yl)-cyclopentyl-methyl-ethyl-amine

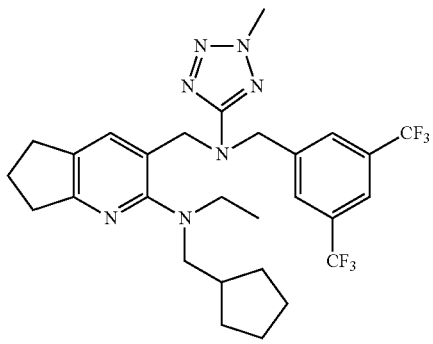 [SMILES: CCN(CC1CCCC1)c1nc2c(cc1CN(Cc1cc(C(F)(F)F)cc(C(F)(F)F)c1)c1nnn(C)n1)CCC2]

To an aqueous suspension of (3-{[(3,5-bis-trifluoromethyl-benzyl)-(2H-tetrazol-5-yl)-amino]-methyl}-6,7-dihydro-5H-[1]pyridin-2-yl)-cyclopentylmethyl-ethyl-amine (0.800 g, 1.446 mmol) obtained in step (ii), in 8 mL of water, was added sodium hydroxide (0.115 g, 2.890 mmol), and this mixture was stirred for 15 min at RT, followed by the addition of DCM (8 mL). Dimethyl sulfate (0.200 g, 1.591 mmol) was then added, followed by the addition of tetrabutylammonium bromide (0.023 g, 0.072 mmol). This mixture was stirred for 0.5 h, after which the organic layer was separated from the aqueous layer, the aqueous layer was extracted with DCM (3×10 mL), and the combined organic layer was washed with brine, dried over sodium sulfate, and then concentrated under vacuum to afford the title compound (0.500 g), yield: 61%.

Purity: 96.34% (HPLC: Symmetry Shield RP8, [0.01M KH$_2$PO$_4$:CH$_3$CN], 210 nM, R$_t$ 8.728 min).

$^1$H NMR (CDCl$_3$, 400 MHz): δ 7.84 (s, 1H), 7.81 (s, 1H), 7.74 (s, 1H), 7.65 (s, 1H), 4.76 (s, 2H), 4.64 (s, 2H), 4.19 (s, 3H), 3.02-2.96 (m, 4H), 2.91 (t, J=7.1 Hz, 2H), 2.75 (t, J=7.0 Hz, 2H), 2.10-2.05 (m, 2H), 2.04-1.93 (m, 1H), 1.52-1.41 (m, 6H), 1.26-1.22 (m, 2H), 0.97 (t, J=6.9 Hz, 3H);

m/z (CI-MS) 581 (M$^+$, 100%)

Example 77

Synthesis of (3-{[3,5-bis trifluoromethyl-benzyl)-(2-methyl-2H-tetrazole-5-yl)-amino]-methyl}-5,6,7,8-tetrahydro-quinoline-2-yl)-cyclopentylmethyl-ethyl-amine

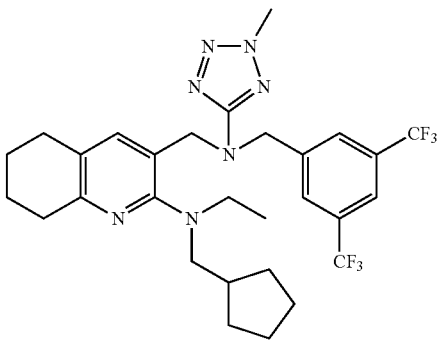 [SMILES: CCN(CC1CCCC1)c1nc2c(cc1CN(Cc1cc(C(F)(F)F)cc(C(F)(F)F)c1)c1nnn(C)n1)CCCC2]

The title compound was prepared by following the procedure as provided in Example 76, except using {3-[(3,5-bis-trifluoromethyl-benzylamino)-methyl]-5,6,7,8-tetrahydro-quinolin-2-yl}-cyclopentylmethyl-ethylamine instead of {3-[(3,5-bis-trifluoromethyl-benzylamino)-methyl]-6,7-dihydro-5H-[1]pyridine-2-yl}-cyclopentylmethyl-ethyl-amine in step (i) (0.04 g), yield: 35%.

$^1$H NMR (CDCl$_3$, 400 MHz): δ 7.74 (s, 1H), 7.65 (s, 2H), 7.03 (s, 1H), 4.72 (s, 2H), 4.63 (s, 2H), 4.19 (s, 3H), 3.00-2.95 (m, 4H), 2.76 (t, J=6.0 Hz, 2H), 2.54 (t, J=5.9 Hz, 2H), 2.00-1.96 (m, 1H), 1.86-1.80 (m, 2H), 1.75-1.68 (m, 2H), 1.55-1.38 (m, 6H), 1.24-1.22 (m, 2H), 0.97 (t, J=7.0 Hz, 3H);

m/z (ES-MS) 596 (M$^+$+1, 100%);

IR (cm$^{-1}$) 3385, 2954, 1581.

Example 78

Synthesis of (3-{[3,5-bis trifluoromethyl-benzyl)-(5-methyl-[1,3,4]oxadiazol-2-yl)-amino]-methyl}-5,6,7,8-tetrahydroquinoline-2-yl)-cyclopentylmethyl-ethyl-amine

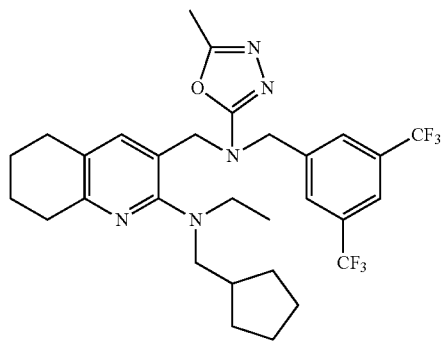 [SMILES: CCN(CC1CCCC1)c1nc2c(cc1CN(Cc1cc(C(F)(F)F)cc(C(F)(F)F)c1)c1nnc(C)o1)CCCC2]

(3-{[3,5-Bis-trifluoromethyl-benzyl)-(2H-tetrazol-5-yl)-amino]-methyl}-5,6,7,8-tetrahydro-quinoline-2-yl)-cyclopentylmethyl-ethyl-amine (0.2 g, 0.344 mmol), was added to dry pyridine (5 mL), the solution was cooled to 0° C., acetyl chloride (0.094 g, 1.2 mmol) was added, and the reaction was then refluxed for 3 h. Afterwards, the reaction was allowed to cool to RT, was diluted with water, and then was basified with sodium hydroxide. The pyridine was removed as an azeotrope and the residue was dissolved in ethyl acetate and purified by column chromatography to afford the title compound (0.110 g), yield: 40%. Purity 94.8% (HPLC: Symmetry Shield RP8, [0.01M KH$_2$PO$_4$:CH$_3$CN], 210 nM, R$_t$ 8.214 min).

$^1$H NMR (CDCl$_3$, 400 MHz): δ 7.73 (s, 1H), 7.65 (s, 2H), 7.05 (s, 1H), 4.64 (s, 2H), 4.59 (s, 2H), 2.99-2.94 (m, 4H), 2.77 (t, J=6.0 Hz, 2H), 2.58 (t, J=6.0 Hz, 2H), 2.43 (s, 2H), 2.01-1.8 (m, 1H), 1.84-1.77 (m, 2H), 1.77-1.73 (m, 2H), 1.53-1.43 (m, 8H), 1.03 (t, J=7.0 Hz, 3H)

m/z (CI-MS) 595 (M$^+$, 100%);

IR (neat, cm$^{-1}$) 2931, 1279, 1139.

Example 79

Synthesis of (3-{[(3,5-bis-trifluoromethyl-benzyl)-(2-methyl-2H-tetrazol-5-yl)-amino]-methyl}-5,6-dimethyl-pyridin-2-yl)-bis-cyclopropylmethyl-amine

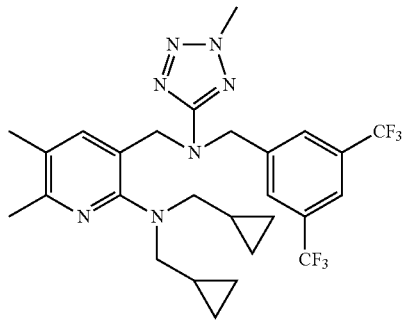 [SMILES: Cc1cc(CN(Cc2cc(C(F)(F)F)cc(C(F)(F)F)c2)c2nnn(C)n2)c(N(CC2CC2)CC2CC2)nc1C]

Step (i): Synthesis of sodium salt of 3-formyl-2-butanone

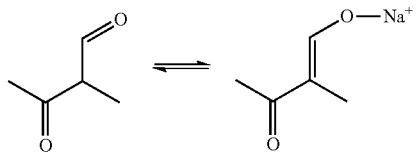

Sodium (5.80 g) was added to 300 mL of dry ether in a 1 L round bottom flask and the suspension was cooled to 0° C. using an acetone-dry ice bath. To this cooled suspension was added a mixture of ethyl formate (0.256 mol) and 2-butanone (0.232 mol) in dry ether (100 mL). This mixture was allowed to warm to RT and stirring was continued overnight. The crude suspension was then filtered and the precipitate was dried under vacuum for 2 h to yield the title compound (21.0 g), yield: 79.2%.

$^1$H NMR (CDCl$_3$, 200 MHz): δ 9.11 (s, 1H), 2.50-2.19 (m, 3H), 1.39 (s, 3H), 0.98-0.91 (t, J=14.0 Hz, 3H);

m/z (CI-MS): 114 (M+, 100%);

IR (neat, cm$^{-1}$): 3384, 1584.

Step (ii): Synthesis of 2-oxo-1,2,dihydro-5,6-dimethylpyridine-3-carbonitrile

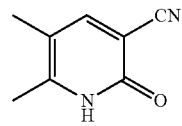

Cyano acetamide (3.78 g, 0.237 mol) was added to a solution of the sodium salt of 3-formyl-2-butanone (5.00 g, 40.9 mmol) in water (100 mL), and this reaction was allowed to stir at room temperature for 1 h. Afterwards, a 2 M solution of piperidine acetate in water (10 mL) was added, and the reaction mixture was allowed to reflux for 24 h. This mixture was allowed to cool and was acidified with acetic acid. The suspension was filtered and the precipitate was washed with toluene. The filtrate was collected and was concentrated to afford a sticky residue, which was washed with diethyl ether followed by ethyl acetate, to afford the title compound (2.00 g), yield: 33%, as a light brown solid.

Mp: 103° C.

$^1$H NMR (DMSO-d$_6$, 200 MHz): δ 12.44 (s, 1H), 7.94 (s, 1H), 2.23 (s, 3H), 1.98 (s, 3H) m/z (CI-MS): 148 (M$^+$, 100%)

Step (iii): Synthesis of 2-Chloro-5,6-dimethyl pyridin-3-carbonitrile

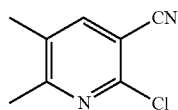

Phosphorus oxychloride (15 mL) was added to 2-oxo-1,2-dihydro-5,6-dimethyl pyridine-3-carbonitrile (2.00 g, 13.5 mmol) in a two neck 50 mL round bottom flask, and this mixture was stirred at RT for 1 h, and then refluxed for 12 h. Afterwards, the excess phosphorous oxychloride was distilled off, and the residue was poured into ice cooled water. The aqueous solution was basified with saturated sodium bicarbonate solution, and the precipitate that formed was filtered off to afford the title compound (1.50 g), yield: 66.7%.

mp: 110° C.

$^1$H NMR (DMSO-d$_6$, 200 MHz): δ 7.94 (s, 1H), 2.55 (s, 3H), 2.31 (s, 3H);

m/z (CI-MS) 167 (M$^+$+1, 100%);

IR (Neat, cm$^{-1}$): 3420, 2231

Step (iv): Synthesis of 2-(bis-cyclopropylmethyl-amino)-5,6-dimethylpyridine-3-carbonitrile

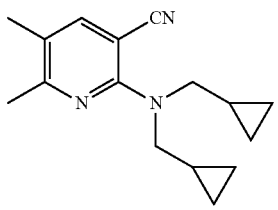 [SMILES: Cc1cc(C#N)c(N(CC2CC2)CC2CC2)nc1C]

DMF (5 mL) was added to a mixture of 2-chloro-5,6-dimethyl pyridin-3-carbonitrile (1.50 g, 9.0 mmol), obtained in step (iii), and potassium carbonate (3.70 g, 26.8 mmol). A solution of bis-cyclopropylmethyl-amine (1.2 g, 9.6 mmol) in DMF was added slowly to the stirred reaction mixture, and then the reaction was refluxed for 24 h. The reaction was then cooled to RT and poured onto crushed ice which was then extracted with ethyl acetate (3×20 mL). The combined organic layer was washed with brine, dried over sodium sulfate, and the solvent was evaporated under vacuum to afford title compound (0.500 g), yield: 22.7%.

$^1$H NMR (CDCl$_3$, 400 MHz): δ 7.40 (s, 1H), 3.62 (d, J=6.7 Hz, 4H), 2.13 (s, 3H), 1.19-1.11 (m, 2H), 0.54-0.49 (m, 4H), 0.29-0.25 (m, 4H).

m/z (CI-MS): 256 (M$^+$+1, 100%)

Step (v): Synthesis of 2-(bis-cyclopropylmethyl-amino)-5,6-dimethylpyridine-3-carbaldehyde

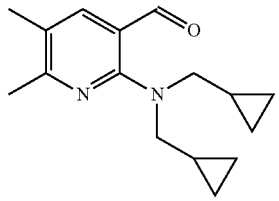 [SMILES: Cc1cc(C=O)c(N(CC2CC2)CC2CC2)nc1C]

2-(Bis-cyclopropylmethyl-amino)-5,6-dimethylpyridine-3-carbonitrile (0.5 g, 1.96 mmol), obtained in step (iv), was added to a 50 mL two neck round bottom flask with dry THF. The reaction mixture was cooled to 0° C. and a 20% (w/v) solution of DIBAL (1.8 g, 12.9 mmol) in THF was added to this mixture drop-wise. This mixture was maintained at 0° C. and stirred for 1 h. After this time, the reaction was allowed to reach RT, 1N HCl (10 mL) was added, and the product was extracted with ethyl acetate (3×10 mL). The organic layer was washed with brine, dried over sodium sulfate, and the solvent was evaporated under vacuum to afford the title compound (0.2 g), yield: 40%.

$^1$H NMR (CDCl$_3$, 400 MHz): δ 10.1 (s, 1H), 7.71 (s, 1H), 3.37 (d, J=6.4 Hz, 4H), 2.42 (s, 3H), 2.22 (s, 3H), 1.07-1.05 (m, 2H), 0.49-0.44 (m, 4H), 0.16-0.07 (m, 4H);

m/z (CI-MS): 259 (M$^+$+1, 100%);

IR (Neat, cm$^{-1}$): 3078, 2925, 1601.

Step (vi): Synthesis of {3-[(3,5-bis-trifluoromethyl-benzylamino)-methyl]-5,6-dimethyl-pyridin-2-yl}-bis-cyclopropylmethyl-amine

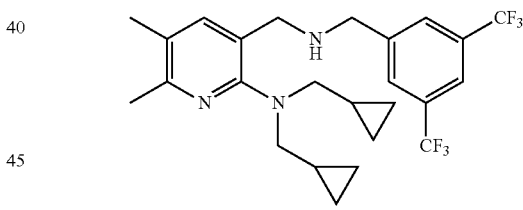

To a solution of 2-(bis-cyclopropylmethyl-amino)-5,6-dimethylpyridine-3-carbaldehyde (0.2 g, 0.775 mmol), obtained in step (v), and 3,5-bis-trifluoromethyl benzyl amine (0.18 g, 0.74 mmol) in MeOH (3 mL), was added acetic acid (0.093 mL, 1.5 mmol). This reaction mixture was stirred at RT for 1 h and then sodium cyanoborohydride (0.096 g, 1.5 mmol) was added. This mixture was stirred for another 2 h, after which time the solvent was evaporated under vacuum, water was added, and the product was extracted with ethyl acetate. The organic layer was washed with a saturated sodium bicarbonate solution, dried over sodium sulfate, and the solvent was evaporated to give the title compound (0.300 g), yield: 81%.

$^1$H NMR (CDCl$_3$, 400 MHz): δ 7.99 (s, 2H), 7.90 (s, 1H), 7.01 (s, 1H), 4.27 (s, 2H), 4.21 (s, 2H), 3.30 (d, J=6.5 Hz, 4H), 2.41 (s, 3H), 2.22 (s, 3H), 0.73-0.67 (m, 1H), 0.48-0.43 (m, 4H), 0.07-0.01 (m, 4H);

m/z (CI-MS), 486 (M$^+$+1, 100%);

IR (Neat, cm$^{-1}$): 2926, 2329.

Step (vii): Synthesis of [2-(bis-cyclopropylmethyl-amino)-5,6-dimethyl-pyridin-3-ylmethyl]-(3,5-bis-trifluoromethyl-benzyl-cyanamide

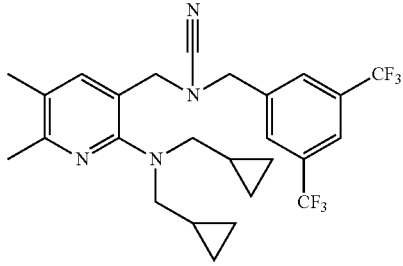 [SMILES: Cc1cc(CN(C#N)Cc2cc(C(F)(F)F)cc(C(F)(F)F)c2)c(N(CC2CC2)CC2CC2)nc1C]

To a solution of {3-[(3,5-bis-trifluoromethyl-benzylamino)-methyl]-5,6-dimethyl-pyridin-2-yl}-bis-cyclopropylmethyl-amine (0.300 g, 0.600 mmol), obtained in step (vi), was added sodium bicarbonate (0.15 g, 1.7 mmol) under N₂ atmosphere, followed by the addition of cyanogen bromide (0.13 g, 1.2 mmol). This mixture was stirred at room temperature for 0.5 h, then concentrated under vacuum. Water was then added, and the aqueous layer was extracted with ethyl acetate, washed with brine, and dried over sodium sulfate. The solvent was evaporated under vacuum to afford the title compound (0.297 g), yield: 95%.

$^1$H NMR (CDCl₃, 400 MHz): δ 7.85 (s, 1H), 7.71 (s, 2H), 7.38 (s, 1H), 4.36 (s, 2H), 4.25 (s, 2H), 2.91 (d, J=6.5 Hz, 4H), 2.42 (s, 3H), 2.23 (s, 3H), 0.91-0.74 (m, 6H), 0.35-0.31 (m, 4H)

m/z (CI-MS): 511 (M⁺+1, 100%)

Step (viii): Synthesis of (3-{[(3,5-bis-trifluoromethyl-benzyl)-(2H-tetrazol-5-yl)-amino]-methyl}-5,6-dimethyl-pyridin-2-yl)-bis-cyclopropylmethyl-amine

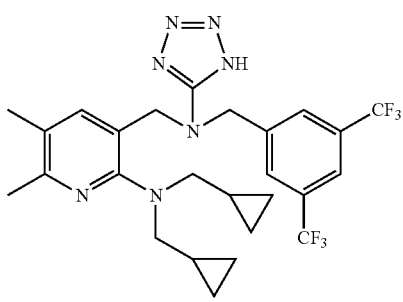 [SMILES: Cc1cc(CN(Cc2cc(C(F)(F)F)cc(C(F)(F)F)c2)c2nnn[nH]2)c(N(CC2CC2)CC2CC2)nc1C]

[2-(Bis-cyclopropylmethyl-amino)-5,6-dimethyl-pyridin-3-ylmethyl]-(3,5-bis-trifluoromethyl-benzyl-cyanamide (0.297 g, 0.58 mmol), obtained in step (vii), sodium azide (0.18 g, 2.7 mmol), and ammonium chloride (0.15 g, 2.7 mmol) were added to a 50 mL round bottom flask. Along with dry DMF (10 mL). The reaction was refluxed under a nitrogen atmosphere for 1 h, then allowed to cool to RT. Ice-cooled water (10 mL) was then added to the reaction mixture in DMF, and the aqueous solution was extracted with ethyl acetate (3×20 mL), and the combined organic layer was washed with brine, dried over sodium sulfate, and concentrated under vacuum to afford the title compound. This compounds was used in the next step without purification (0.3 g), yield: 93.7% m/z (CI-MS) 557 (M⁺+1, 100%)

Step (ix): Synthesis of (3-{[(3,5-bis-trifluoromethyl-benzyl)-(2-methyl-2H-tetrazole-5-yl)-amino]-methyl}-5,6-dimethyl-pyridin-2-yl)-bis-cyclopropylmethyl-amine

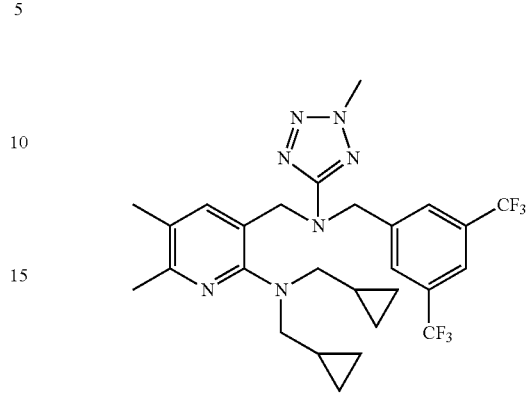

To a suspension of (3-{[(3,5-bis-trifluoromethyl-benzyl)-(2H-tetrazol-5-yl)-amino]-methyl}-5,6-dimethyl-pyridin-2-yl)-bis-cyclopropylmethyl-amine (0.3 g, 0.54 mmol), obtained in step (viii), in water (4 mL) was added sodium hydroxide (0.04 g, 1.0 mmol), and this mixture was stirred for 15 min at RT, followed by the addition of DCM (4 mL). Dimethyl sulfate (0.13 g, 1.03 mmol) was then added to this mixture, followed by the addition of tetrabutylammonium bromide (0.008 g, 0.024 mmol). The mixture was then stirred for 0.5 h, after which the organic layer was separated from the aqueous layer which was extracted with DCM (3×10 mL). The combined organic layer was washed with brine, dried over sodium sulfate, and then concentrated under vacuum to afford the title compound as light yellow oil (0.200 g), yield: 66.6%.

Purity 96.2% (HPLC: Symmetry Shield RP8, [0.01M KH₂PO₄:CH₃CN], 210 nM, R$_t$ 8.823 min).

$^1$H NMR (CDCl₃, 400 MHz): δ 7.72 (s, 1H), 7.66 (s, 2H), 7.17 (s, 1H), 4.83 (s, 2H), 4.64 (s, 2H), 4.18 (s, 3H), 2.93 (d, J=6.7 Hz, 4H), 2.37 (s, 3H), 2.11 (s, 3H), 0.90-0.80 (m, 2H), 0.33-0.29 (m, 4H), 0.01-0.00 (m, 4H)

m/z (CI-MS) 567 (M⁺–1, 100%)

IR (Neat, cm⁻¹) 2982, 1581

Example 80

Synthesis of (3-{[(3,5-bis-trifluoromethyl-benzyl)-(2-methyl-2H-tetrazole-5-yl)-amino]-methyl}-4,6-dimethyl-pyridin-2-yl)-bis-cyclopropylmethyl-amine

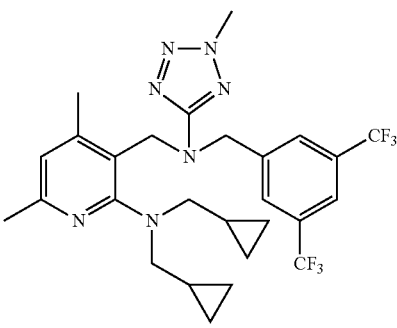 [SMILES: Cc1cc(C)c(CN(Cc2cc(C(F)(F)F)cc(C(F)(F)F)c2)c2nnn(C)n2)c(N(CC2CC2)CC2CC2)n1]

The title compound was prepared by following the experimental procedure provided in Example 79, except using pentane-2,4-dione instead of 2-butanone in step (i) (0.2 g) yield: 39.1%.

Purity 97% (HPLC: Symmetry Shield RP8, [0.01M KH$_2$PO$_4$:CH$_3$CN], 210 nM, R$_t$ 8.946 min).

$^1$H NMR (CDCl$_3$, 400 MHz): δ 7.63 (s, 1H), 7.45 (s, 2H), 6.59 (s, 1H), 5.00 (s, 2H), 4.49 (s, 2H), 4.18 (s, 3H), 2.97 (d, J=6.7 Hz, 4H), 2.37 (s, 3H), 2.07 (s, 3H), 0.90-0.83 (m, 2H), 0.36-0.30 (m, 4H), 0.04-0.01 (m, 4H);

m/z (CI-MS) 567 (M$^+$, 100%)

IR (Neat, cm$^{-1}$): 3079, 2856

Example 81

Synthesis of (3,5-bis-trifluoromethyl-benzyl)-[3-(cyclopentylmethyl-ethyl-amino)-pyrazin-2-ylmethyl]-carbamic acid methyl ester Step (i): Synthesis of 3-bromo-pyrazine-2-carboxylic acid methyl ester

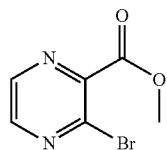

Copper bromide (1.36 g, 6.1 mmol) and t-butyl nitrite (0.78 g, 7.6 mmol) were added to a 50 mL round bottom flask along with acetonitrile (2 mL), and this mixture was heated at 60° C. for 5 min. After this time, 3-amino-pyrazine-2-carboxylic acid methyl ester (0.8 g, 5.09 mmol) was added portion-wise, with stirring, and stirring was continued at the same temperature for another 10 min. The reaction mixture was then cooled to RT, poured into 100 mL of dilute HCL (2N), and then extracted with diethyl ether (3×50 mL). The combined organic layer was washed with dilute HCl, dried over sodium sulfate, and then concentrated under vacuum to afford the title compound (0.139 g), yield: 12%.

$^1$H NMR (CDCl$_3$, 400 MHz): δ 8.58 (m, 2H), 4.04 (s, 3H));

m/z (CI-MS) 217 (M$^+$);

IR (neat, cm$^{-1}$): 3385, 2955, 1742

Step (ii): Synthesis of 2-(cyclopentylmethyl-ethyl-amino)-pyrazine-2-carboxylic acid methyl ester

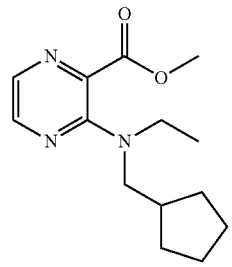 [SMILES: CCN(CC1CCCC1)c1nccnc1C(=O)OC]

3-Bromo-pyrazine-2-carboxylic acid methyl ester (0.893 g, 4.11 mmol), obtained from a scale-up reaction of step (i), and potassium carbonate (1.7 g, 12.3 mmol) were added to a 50 mL two neck round bottom flask. To this flask, 10 mL of DMF was added, followed by the dropwise addition of a DMF solution of N-cyclopentylmethyl ethyl amine (0.627 g, 4.93 mmol). This mixture was refluxed overnight, after which it was allowed to cool to RT, poured onto crushed ice (10 mL), and extracted with ethyl acetate (3×50 mL). The organic layer was washed with brine, dried over sodium sulfate, and the solvent was evaporated under vacuum to give the title compound (0.468 g), yield: 43%.

$^1$H NMR (CDCl$_3$, 400 MHz): δ 8.11 (m, 1H), 7.87 (m, 1H), 3.96 (s, 3H), 3.46-3.39 (m, 4H), 2.29-2.25 (m, 1H), 1.71-1.60 (m, 3H), 1.19-1.15 (m, 3H), 0.88-0.83 (m, 5H)

m/z (CI-MS): 264 (M$^+$+1, 100%);

IR (cm$^{-1}$): 3749, 3421, 2951.

Step (iii): Synthesis of 3-(cyclopentylmethyl-ethyl-amino)-pyrazine-2-carbaldehyde

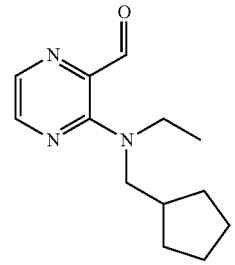 [SMILES: CCN(CC1CCCC1)c1nccnc1C=O]

2-(Cyclopentylmethyl-ethyl-amino)-pyrazine-2-carboxylic acid methyl ester (0.468 g, 1.77 mmol), obtained in step (ii), was added to a 50 mL two neck round bottom flask, along with dry DCM. The reaction mixture was cooled to −70° C., DIBAL (20% solution in toluene, 0.252 g, 1.77 mmol) was added dropwise to the mixture with stirring, and stirred was continued at the same temperature for 1 h. This mixture was allowed to warm to RT, was quenched with a saturated ammonium chloride solution, and was extracted with DCM (3×30 mL). The combined organic layer was washed with brine, dried over sodium sulfate, and the solvent was evaporated under vacuum to afford title compound (0.082 g), yield: 20%.

$^1$H NMR (CDCl$_3$, 400 MHz): δ 9.95 (s, 1H), 8.16 (d, J=2.1 Hz, 1H), 8.01 (d, J=2.1 Hz, 1H), 3.59-3.52 (m, 4H), 2.27-2.16 (m, 1H), 1.68-1.48 (m, 8H), 1.19-1.10 (m, 3H);

m/z (CI-MS): 234 (M$^+$+1, 100%);

IR (neat, cm$^{-1}$): 3384, 2952, 1692.

Step (iv): Synthesis of {3-[(3,5-bis-trifluoromethyl-benzylamino)-methyl]-pyrazin-2-yl}-cyclopentylmethyl-ethyl-amine

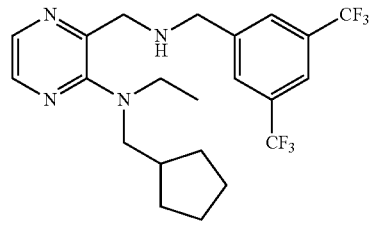 [SMILES: CCN(CC1CCCC1)c1nccnc1CNCc1cc(C(F)(F)F)cc(C(F)(F)F)c1]

3-(Cyclopentylmethyl-ethyl-amino)-pyrazine-2-carbaldehyde (0.082 g, 0.351 mmol), obtained in step (iii), 3,5-bis-trifluoromethylbenzylamine (0.085 g, 0.351 mmol), and acetic acid (0.042 g, 0.70 mmol) were added to a 25 mL round bottom flask. Methanol (4 mL) was added and this mixture was stirred at RT for 15 min. Sodium cyanoborohydride (0.066 g, 1.05 mmol) was then added portionwise and stirring was continued at RT for another 1 hour. The methanol was removed under vacuum, water was added to the crude mixture, and the productr was extracted with ethyl acetate (3×25 mL). The combined organic layer was washed with saturated sodium bicarbonate solution, then brine, dried over sodium sulfate, and the solvent was evaporated to afford the title amine (0.163 g), yield: 90%.

m/z (CI-MS): 461 ($M^+$+1, 100%);
IR (neat, $cm^{-1}$):2955, 2868, 1278

Step (v): Synthesis of (3,5-bis-trifluoromethyl-benzyl)-[3-(cyclopentylmethyl-ethyl-amino)-pyrazin-2-ylmethyl]-carbamic acid methyl ester

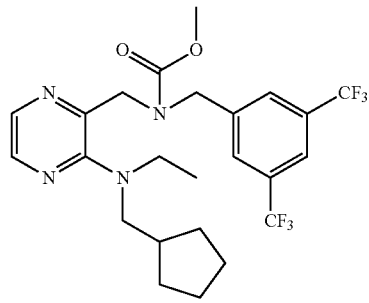 [SMILES: CCN(CC1CCCC1)c1nccnc1CN(Cc1cc(C(F)(F)F)cc(C(F)(F)F)c1)C(=O)OC]

{3-[(3,5-Bis-trifluoromethyl-benzylamino)-methyl]-pyrazin-2-yl}-cyclopentyl-methyl-ethyl-amine (0.155 g, 0.33 mmol), obtained in step (iv), and $K_2CO_3$ (0.139 g, 1.0 mmol) were added to a two neck round bottom flask under $N_2$ atmosphere. Dry THF (3 to 4 mL) was added to the flask, and this mixture was stirred at RT for 30 min. Methylchloroformate (0.038 g, 0.404 mmol) was then added dropwise to the mixture, and the reaction was allowed to stir at RT overnight. The solvent was the removed under vacuum, water was added, and the product, was extracted with ethyl acetate. The organic layer was dried over sodium sulfate and concentrated under vacuum to afford title compound (0.020 g), yield: 12%

$^1$H NMR (CDCl$_3$, 400 MHz): δ 8.07-8.06 (m, 2H), 7.75 (s, 1H), 7.70 (s, 1H), 7.62 (s, 1H), 4.64-4.49 (m, 4H), 3.73 (s, 3H), 3.13-3.09 (m, 4H), 2.06-1.98 (m, 1H), 1.37-1.30 (m, 6H), 1.30-1.18 (m, 5H);

m/z (CI-MS): 518 ($M^+$, 100%);
IR (neat, $cm^{-1}$): 3313, 2950, 1548.

Example 82

Determination of In Vitro Activity

An in vitro fluorescence-based assay to identify CETP inhibitors was developed from modifications of the protocols outlined in Bisgaier et al., J Lipid Res., 34(9): 1625-34 (1993) and Epps et al., Chem Phys Lipids., 77(1): 51-63 (1995). Acceptor and donor lipid microemulsions were prepared according to Bisgaier et al., 1993, except that the buffer was prepared with 0.67 ug/mL human HDL (Calbiochem). Donor microemulsions contained the fluorescent cholesteryl ester analog BODIPY-CE (Molecular Probes), characterized by excitation and emission maxima at 503 nm and 518 nm, respectively. The CETP-mediated transfer of fluorescent cholesteryl ester to acceptor particles was monitored over a 2-hour time period using the FAM filter set (excitation 492 nm, emission 516 nm) in an MX3000P fluorescent plate reader (Stratagene). Recombinant CETP enzyme (Cardiovascular Targets) was used at 0.14 ng/μl, final concentration, to achieve lipid transfer. CETP inhibition by compounds was compared to DMSO controls and graphed as a percentage of the control CETP activity over 2 hours. The $IC_{50}$ curves for CETP inhibition were generated from the activity profiles. Active compounds were also tested for CETP inhibition as above, but in the presence of 3% human serum albumin, fraction V (Calbiochem).

Using this protocol, compounds given in Examples 35, 41, 42, 43, 44, 45, 46, 48, 49, 53, 58, 59, 61, 63, 66, 68, 69, 70, 71, 73 and 75 were shown to exhibit a CETP activity with an $IC_{50}$ of less than or equal to 5 μM; compounds given in Examples 1, 2, 3, 4, 5, 6, 7 8, 10, 11, 12, 13, 14, 15, 18, 19, 20, 21, 22, 24, 27, 32, 33, 52, 54, 55, 56, 57, 65, 67, 74, 77, 76 and 78 have shown CETP activity with an $IC_{50}$ of less than or equal to 1 μM.

We claim:
1. A compound having the formula:

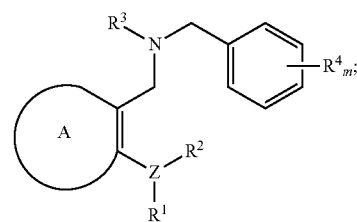

(I)

or a salt, a diastereomeric mixture, an enantiomer, a tautomer, or a racemic mixture thereof, or any combination thereof, wherein:

A is a substituted or an unsubstituted quinoline moiety having the formula:

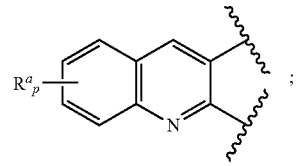

wherein $R^a$, in each occurrence, is selected independently from: 1) a halogen; a hydroxyl, or a cyano; 2) an alkyl or an alkoxy, any of which having up to 12 carbon atoms; or 3) $CO_2R^6$; and p is an integer from 0 to 3, inclusive;

$R^1$ and $R^2$ are selected independently from: 1) hydrogen; 2) a substituted or an unsubstituted alkyl, cycloalkyl, haloalkyl, aryl, heterocyclyl, heteroaryl, any of which having up to 12 carbon atoms, wherein any heterocyclyl or heteroaryl comprises at least one heteroatom or heterogroup selected independently from O, N, S, $NR^{10}$, $SO_2$, or CO; 3) $CO_2R^6$, $COR^8$, $SO_2R^8$, $SO_2NR^6R^7$, or $CONR^6R^7$; or 4) $(CHR^x)_nR^5$ or $(CH_2)_nR^dCO_2R^e$, wherein n, in each occurrence, is 1, 2, or 3; $R^x$, in each occurrence, is selected independently from an alkyl or an alkoxy, either of which having up to 12 carbon atoms, or hydrogen; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen;

or $R^1$ and $R^2$ together with the diradical Z to which they are attached form a substituted or an unsubstituted monocyclic or bicyclic moiety comprising up to 12 carbon atoms, and optionally comprising 1, 2, or 3 heteroatoms or heterogroups in addition to Z, selected independently from O, N, S, $NR^{10}$, $SO_2$, or CO;

$R^3$ is selected from: 1) cyano; 2) a substituted alkyl having up to 12 carbon atoms; 3) a substituted or an unsubstituted aryl, or a substituted or an unsubstituted 5-, 6-, or 7-membered heterocyclyl or heteroaryl, any of which having up to 12 carbon atoms, comprising 1, 2, or 3 heteroatoms or heterogroups selected independently from O, N, S, $NR^{10}$, $SO_2$, or CO; or 4) $CO_2R^6$, $COR^8$, $SO_2R^8$, $SO_2NR^6R^7$, $CONR^6R^7$, $C(S)NR^6R^7$, $C(S)NHC(O)OR^8$, or $C(S)SR^8$; or 5) a substituted or an unsubstituted group selected from 4,5-dihydro-oxazolyl, tetrazolyl, isoxazolyl, pyridyl, pyrimidinyl, oxadiazolyl, thiazolyl, or oxazolyl; wherein any optional substituents is selected independently from a) an alkyl or a haloalkyl, any of which having up to 12 carbon atoms; or b) $CO_2R^9$, wherein $R^9$ is an alkyl having up to 12 carbon atoms; wherein when $R^3$ is an aryl, a heterocyclyl, or a heteroaryl, $R^3$ is optionally substituted with up to three substituents selected independently from a halide, a hydroxyl, a cyano, an alkoxy having up to 12 carbon atoms, or $R^{11}$;

$R^4$, in each occurrence, is selected independently from: 1) halogen, cyano, or hydroxy; 2) an alkyl, a cycloalkyl, a cycloalkoxy, an alkoxy, a haloalkyl, or a haloalkoxy, any of which having up to 12 carbon atoms; 3) a substituted or an unsubstituted aryl, aralkyl, aryloxy, heteroaryl, or heteroaryloxy, any of which having up to 12 carbon atoms, wherein any heteroaryl or heteroaryloxy comprises at least one heteroatom or heterogroup selected independently from O, N, S, or $NR^{10}$; or 4) $CO_2R^6$, $COR^8$, $SO_2R^8$, $SO_2NR^6R^7$, $CONR^6R^7$, or $(CH_2)_qNR^6R^7$, wherein q is an integer from 0 to 5, inclusive; m is an integer from 0 to 3, inclusive;

or $R^4{}_m$ is a fused cyclic moiety comprising from 3 to 5 additional ring carbon atoms, inclusive, and optionally comprising at least one heteroatom or heterogroup selected independently from O, N, S, $NR^{10}$, $SO_2$, or CO;

$R^5$, in each occurrence, is selected independently from: 1) an alkoxy, a haloalkoxy, or a cycloalkyl, any of which having up to 12 carbon atoms; 2) a substituted or an unsubstituted aryl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO; 3) hydroxyl, $NR^6R^7$, $CO_2R^6$, $COR^8$, or $SO_2R^8$; or 4) a substituted or an unsubstituted heterocycloalkyl comprising from 3 to 7 ring carbon atoms, and from 1 to 3 heteroatoms or heterogroups, inclusive, selected independently from O, N, S, $NR^{10}$, $SO_2$, or CO;

$R^6$ and $R^7$, in each occurrence, are selected independently from: 1) hydrogen; 2) an alkyl, a cycloalkyl, or a haloalkyl, any of which having up to 12 carbon atoms; or 3) a substituted or an unsubstituted aryl, aralkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO; or $R^6$ and $R^7$ together with the nitrogen atom to which they are attached form a substituted or an unsubstituted cyclic moiety having from 3 to 7 ring carbon atoms, and optionally comprising 1, 2, or 3 heteroatoms in addition to the nitrogen atom to which $R^6$ and $R^7$ are bonded, selected independently from O, N, S, or $NR^{10}$;

$R^8$, in each occurrence, is selected independently from: 1) an alkyl, a cycloalkyl, or a haloalkyl, any of which having up to 12 carbon atoms; or 2) a substituted or an unsubstituted aryl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

$R^{10}$, in each occurrence, is selected independently from: 1) hydrogen; or 2) an alkyl, a cycloalkyl, a haloalkyl, an aryl, or an aralkyl, any of which having up to 12 carbon atoms;

Z is N; or the $ZR^1$ moiety is S, CO, or $SO_2$;

$R^{11}$ is selected independently from:
1) an alkyl, a haloalkyl, a cycloalkyl, or an alkoxycarbonyl, any of which having up to 12 carbon atoms;
2) a substituted or an unsubstituted heteroaryl or heterocyclyl, any of which having up to 12 carbon atoms, comprises at least one heteroatom or heterogroup selected independently from O, N, S, $NR^{10}$, $SO_2$, or CO, wherein any substituted heteroaryl or heterocyclyl is substituted with up to three substituents selected independently from an alkyl having up to 12 carbon atoms or a hydroxyl; or
3) —CO—$Z^2$—$R^{13}$, —CO—$R^{12}$, —CO—$Z^2$—$(CH_2)_r$—CO—$Z^2$—$R^{13}$, —$NR^{15}R^{16}$, —$Z^2$—CO—$(CH_2)_r$—$Z^2$—$R^{13}$, —$Z^2$—CO—$(CH_2)_r$—CO—$Z^2$—$R^{13}$, —O—$(CH_2)_r$—CO—$Z^2$—$R^{13}$, —O—$(CH_2)_r$—$R^{14}$, —O—$R^{12}$—$(CH_2)_r$—$R^{13}$, —O—$R^{14}$—CO—O—$R^{13}$, —O—$(CH_2)_r$—$R^{12}$, —O—$(CH_2)_r$—NR'R", —O—$(CH_2)_r$—$CO_2$—$(CH_2)_r$—$R^{13}$, —O—$(CH_2)_r$—CONR'R", —O—$(CH_2)_r$—$SR^8$, —O—$(CH_2)_r$—$CO_2$—$R^{13}$, —O—$(CH_2)_r$—O—$(CH_2)_r$—$OR^{13}$, —O—$(CH_2)_r$—CONH—$(CH_2)_r$—$OR^{13}$, —O—$(CH_2)_r$—$SO_2R^8$, —O—$(CH_2)_r$—$R^{13}$, —O—$(CH_2)_r$—$OR^{13}$, —S—$(CH_2)_r$—CONR'R", —$SO_2$—$(CH_2)_r$—$OR^{13}$, —$SO_2$—$(CH_2)_r$—CONR'R", —$(CH_2)_r$—O—CO—$R^8$, —$(CH_2)_r$—$R^{12}$, —$(CH_2)_r$—$R^{13}$, —$(CH_2)_r$—CO—$Z^2$—$R^{13}$, —$(CH_2)_r$—$Z^2$—$R^{13}$, or -alkenylene-$CO_2$—$(CH_2)_r$—$R^{13}$;

r, in each occurrence, is independently 1, 2, or 3;

$R^{12}$, in each occurrence, is independently selected from a substituted or an unsubstituted heterocyclyl having up to 12 carbon atoms, comprising at least one heteroatom or heterogroup selected independently from O, N, S, $NR^{10}$, $SO_2$, or CO, wherein any substituted heterocyclyl is substituted with up to three substituents selected independently from an acyl, an alkyl, or an alkoxycarbonyl, any of which having up to 12 carbon atoms, or —COOH;

$R^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from O, N, S, $NR^{10}$, $SO_2$, or CO;

$R^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from O, N, S, $NR^{10}$, $SO_2$, or CO;

$Z^2$, in each occurrence, is selected independently from $NR^{10}$ or O;

R' and R", in each occurrence, are independently selected from hydrogen or an alkyl having up to 12 carbon atoms; and $R^{15}$ and $R^{16}$, in each occurrence, are independently selected from: 1) hydrogen; 2) an alkyl having up to 12 carbon atoms; or 3) —$(CH_2)_r$—O—$R^{13}$, —$(CH_2)_r$—$R^{14}$, —$COR^{13}$, —$(CH_2)_r$—CO—$Z^2$—$R^{13}$, —$CO_2R^{13}$, —$CO_2$—$(CH_2)_r$—$R^{13}$, —$CO_2$—$(CH_2)_r$—$R^{12}$, —$CO_2$—$(CH_2)_r$—CO—$Z^2$—$R^{13}$, —$CO_2$—$(CH_2)_r$—$OR^{13}$, —CO—$(CH_2)_r$—O—$(CH_2)_r$—O—$(CH_2)_r$—$R^{13}$, —CO—$(CH_2)_r$—$O(CH_2)_r$—$OR^{13}$, or —CO—NH—$(CH_2)_r$—$OR^{13}$; or $R^{15}$ and $R^{16}$ together with the nitrogen atom to which they are attached form a substituted or an unsubstituted cyclic moiety comprising up to 12 carbon atoms, optionally comprising at least one additional heteroatom or heterogroup selected independently from O, N, S, $NR^{10}$, $SO_2$, or CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from O, N, S, or $NR^{10}$; or 3) $COOR^{13}$, —$Z^2$—$(CH_2)_r$—$R^{13}$, —$COR^{13}$, —$CO_2$—$(CH_2)_r$—$R^{13}$, —$CO(CH_2)_r$—O—$R^{13}$, —$(CH_2)_r$—$CO_2$—$R^{13}$, —$SO_2R^8$, —$SO_2NR'R''$, or —NR'R";

wherein the —$(CH_2)_r$— linking moiety, in any occurrence, is optionally substituted with at least one group selected independently from hydroxyl, amino, or an alkyl having up to 3 carbon atoms;

when $R^1$ and $R^2$ do not form a monocyclic or bicyclic moiety, $R^1$ and $R^2$ are optionally substituted with 1 or 2 substituents, and when substituted, the substituents are selected independently from: 1) an alkyl, a cycloalkyl, a haloalkyl, an alkoxy, an aryl, a heteroaryl, or a heterocyclyl, any of which having up to 12 carbon atoms, wherein any heteroaryl or heterocyclyl comprises at least one heteroatom or heterogroup selected independently from O, N, S, $NR^{10}$, $SO_2$, or CO; or 2) halogen, cyano, or hydroxyl;

when $R^1$ and $R^2$ together with the diradical Z to which they are attached form a monocyclic or a bicyclic moiety, the cyclic moiety is optionally substituted with at least one substituent selected independently from: 1) halogen, cyano, or hydroxyl; 2) an alkyl, a haloalkyl, a cycloalkyl, an alkoxy, a cycloalkyl-substituted alkyl, an alkoxyalkyl, a cycloalkoxy, a haloalkoxy, an aryl, an aryloxy, an aralkyl, a heteroaryl or a heteroaryloxy, any of which having up to 12 carbon atoms, wherein any heteroaryl or heteroaryloxy comprises at least one heteroatom or heterogroup selected independently from O, N, S, or $NR^{10}$; or 3) $CO_2R^6$, $COR^8$, $SO_2R^8$, $SO_2NR^6R^7$, or $CONR^6R^7$;

$R^4$, $R^6$, $R^7$, and $R^8$ are optionally substituted with at least one substituent, and when substituted, the substituents are selected independently from: 1) halide, hydroxy, cyano, or $NR^6R^7$; or 2) an alkyl or an alkoxy, any of which having up to 12 carbon atoms;

and $R^5$ is optionally substituted with at least one substituent, and when substituted, the substituents are selected independently from: 1) halide, hydroxy, cyano, or $NR^6R^7$; or 2) an alkyl having up to 12 carbon atoms.

2. The compound according to claim 1, wherein Z is N.

3. The compound according to claim 1, wherein:

$R^1$ and $R^2$ are selected independently from: an alkyl having up to 6 carbon atoms; a cycloalkyl having up to 6 carbon atoms; $COR^8$; $(CH_2)_nR^5$, or $(CH_2)_nR^dCO_2R^e$, wherein n, in each occurrence, is 1 or 2;

or $R^1$ and $R^2$ together with the diradical Z to which they are attached form a substituted or an unsubstituted monocyclic or bicyclic moiety comprising up to 12 carbon atoms, and optionally comprising 1 or 2 heteroatoms or heterogroups selected independently from O, N, or $NR^{10}$; wherein any optional substituent on the cyclic moiety selected from: 1) a cycloalkyl having up to 6 carbon atoms; or 2) an alkyl having up to 2 carbon atoms.

4. The compound according to claim 1, wherein: $R^3$ is selected from:

1) cyano; 2) a substituted alkyl having up to 12 carbon atoms; 3) a substituted or an unsubstituted aryl, or a substituted or an unsubstituted 5-, 6-, or 7-membered heterocyclyl or heteroaryl, comprising 1, 2, or 3 heteroatoms or heterogroups selected independently from O, N, S, $NR^{10}$, $SO_2$, or CO, any of which having up to 12 carbon atoms; or 4) $CO_2R^6$, $COR^8$, $SO_2R^8$, $SO_2NR^6R^7$, $CONR^6R^7$, $C(S)NR^6R^7$, $C(S)NHC(O)OR^8$, or $C(S)SR^8$; or 5) a substituted or an unsubstituted group selected from 4,5-dihydro-oxazolyl, tetrazolyl, isoxazolyl, pyridyl, pyrimidinyl, oxadiazolyl, thiazolyl, or oxazolyl; wherein any optional substituents is selected independently from a) an alkyl or a haloalkyl, any of which having up to 12 carbon atoms; or b) $CO_2R^9$, wherein $R^9$ is an alkyl having up to 12 carbon atoms;

wherein when $R^3$ is an aryl, a heterocyclyl, or a heteroaryl, $R^3$ is optionally substituted with up to three substituents selected independently from a halide, a hydroxyl, a cyano, an alkoxy having up to 12 carbon atoms, or $R^{11}$;

$R^{11}$ is selected independently from:

1) an alkyl, a haloalkyl, a cycloalkyl, or an alkoxycarbonyl, any of which having up to 12 carbon atoms;

2) a substituted or an unsubstituted heteroaryl or heterocyclyl, any of which having up to 12 carbon atoms, comprises at least one heteroatom or heterogroup selected independently from O, N, S, $NR^{10}$, $SO_2$, or CO, wherein any substituted heteroaryl or heterocyclyl is substituted with up to three substituents selected independently from an alkyl having up to 12 carbon atoms or a hydroxyl; or 3) —CO—$Z^2$—$R^{13}$, —CO—$R^{12}$, —CO—$Z^2$—$(CH_2)_r$—CO—$Z^2$—$R^{13}$, —$NR^{15}R^{16}$, —$Z^2$—CO—$(CH_2)_r$—$Z^2$—$R^{13}$, —$Z^2$—CO—$(CH_2)_r$—CO—$Z^2$—$R^{13}$, —O—$(CH_2)_r$—CO—$Z^2$—$R^{13}$, —O—$(CH_2)_r$—$R^{14}$, —O—$R^{12}$—$(CH_2)_r$—$R^{13}$, —O—$R^{14}$—CO—O—$R^{13}$, —O—$(CH_2)_r$—$R^{12}$, —O—$(CH_2)_r$—NR'R", —O—$(CH_2)_r$—$CO_2$—$(CH_2)_r$—$R^{13}$, —O—$(CH_2)_r$—$SR^8$, —O—$(CH_2)_r$—$CO_2$—$R^{13}$, —O—$(CH_2)_r$—CONR'R", —O—$(CH_2)_r$—CONH—$(CH_2)_r$—$OR^{13}$, —O—$(CH_2)_r$—$SO_2R^8$, —O—$(CH_2)_r$—$R^{13}$, —O—$(CH_2)_r$—$OR^{13}$, —O—$(CH_2)_r$—O—$(CH_2)_r$—$OR^{13}$, —S—$(CH_2)_r$—CONR'R", —$SO_2$—$(CH_2)_r$—$OR^{13}$, —$SO_2$—$(CH_2)_r$—CONR'R", —$(CH_2)_r$—O—CO—$R^8$, —$(CH_2)_r$—$R^{12}$, —$(CH_2)_r$—$R^{13}$, —$(CH_2)_r$—CO—$Z^2$—$R^{13}$, —$(CH_2)_r$—$Z^2$—$R^{13}$, or -alkenylene-$CO_2$—$(CH_2)_r$—$R^{13}$;

r, in each occurrence, is independently 1, 2, or 3;

$R^{12}$, in each occurrence, is independently selected from a substituted or an unsubstituted heterocyclyl having up to 12 carbon atoms, comprising at least one heteroatom or heterogroup selected independently from O, N, S, $NR^{10}$, SO₂, or CO, wherein any substituted heterocyclyl is substituted with up to three substituents selected independently from an acyl, an alkyl, or an alkoxycarbonyl, any of which having up to 12 carbon atoms, or —COOH;

$R^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from O, N, S, $NR^{10}$, $SO_2$, or CO;

$R^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from O, N, S, $NR^{10}$, $SO_2$, or CO;

$Z^2$, in each occurrence, is selected independently from $NR^{10}$ or O;

R' and R", in each occurrence, are independently selected from hydrogen or an alkyl having up to 12 carbon atoms; and $R^{15}$ and $R^{16}$, in each occurrence, are independently selected from: 1) hydrogen; 2) an alkyl having up to 12 carbon atoms; or 3) —(CH₂)ᵣ—O—$R^{13}$, —(CH₂)ᵣ—$R^{14}$, —COR¹³, —(CH₂)ᵣ—CO—Z²—$R^{13}$, —CO₂$R^{13}$, —CO₂—(CH₂)ᵣ—$R^{13}$, —CO₂—(CH₂)ᵣ—$R^{12}$, —CO₂—(CH₂)ᵣ—O—Z²—$R^{13}$, —CO₂—(CH₂)ᵣ—OR¹³, —CO—(CH₂)ᵣ—O—(CH₂)ᵣ—O—(CH₂)ᵣ—$R^{13}$, —CO—(CH₂)ᵣ—O(CH₂)ᵣ—OR¹³, or —CO—NH—(CH₂)ᵣ—OR¹³;

or $R^{15}$ and $R^{16}$ together with the nitrogen atom to which they are attached form a substituted or an unsubstituted cyclic moiety comprising up to 12 carbon atoms, optionally comprising at least one additional heteroatom or heterogroup selected independently from O, N, S, $NR^{10}$, $SO_2$, or CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from O, N, S, or $NR^{10}$; or 3) COOR¹³, —Z²—(CH₂)ᵣ—$R^{13}$, —COR¹³, —CO₂—(CH₂)ᵣ—$R^{13}$, —CO(CH₂)ᵣ—O—$R^{13}$, —(CH₂)ᵣ—CO₂—$R^{13}$, —SO₂R⁸, —SO₂NR'R", or —NR'R"; and wherein the —(CH₂)ᵣ— linking moiety, in any occurrence, is optionally substituted with at least one group selected independently from hydroxyl, amino, or an alkyl having up to 3 carbon atoms.

5. The compound according to claim 1, wherein: $R^4$, in each occurrence, is selected independently from: 1) a halogen or cyano; or 2) an alkyl or a haloalkyl, either of which having up to 4 carbon atoms; and m is 2 or 3.

6. A compound having the formula:

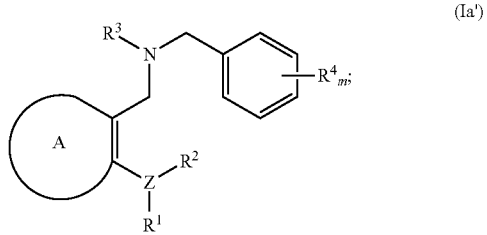

(Ia')

or a salt, a diastereomeric mixture, an enantiomer, a tautomer, or a racemic mixture thereof, or any combination thereof, wherein:

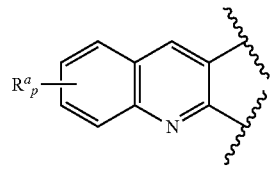

A is:

wherein $R^a$, in each occurrence, is selected independently from: 1) a halogen; a hydroxyl, or a cyano; 2) an alkyl or an alkoxy, any of which having up to 12 carbon atoms; or 3) $CO_2R^6$; and p is an integer from 0 to 3, inclusive;

$R^1$ and $R^2$ are selected independently from: 1) a substituted or an unsubstituted alkyl, cycloalkyl, haloalkyl, aryl, heterocyclyl, heteroaryl, any of which having up to 12 carbon atoms, wherein any heterocyclyl or heteroaryl comprises at least one heteroatom or heterogroup selected independently from O, N, S, $NR^{10}$, $SO_2$, or CO; 2) $CO_2R^6$, $COR^8$, $SO_2R^8$, $SO_2NR^6R^7$, or $CONR^6R^7$; or 3) $(CHR^x)_nR^5$ or $(CH_2)_nR^dCO_2R^e$, wherein n, in each occurrence, is 1, 2, or 3; $R^x$, in each occurrence, is selected independently from an alkyl or an alkoxy, either of which having up to 12 carbon atoms, or hydrogen; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen;

or $R^1$ and $R^2$ together with the diradical Z to which they are attached form a substituted or an unsubstituted monocyclic or bicyclic moiety comprising up to 12 carbon atoms, and optionally comprising 1, 2, or 3 heteroatoms or heterogroups in addition to Z, selected independently from O, N, S, $NR^{10}$, $SO_2$, or CO;

$R^3$ is selected from: 1) cyano; 2) a substituted or an unsubstituted aryl, or a substituted or an unsubstituted 5-, 6-, or 7-membered heterocyclyl or heteroaryl, any of which having up to 12 carbon atoms, comprising 1, 2, or 3 heteroatoms or heterogroups selected independently from O, N, S, $NR^{10}$, $SO_2$, or CO; or 3) $CO_2R^6$, $COR^8$, $SO_2R^8$, $SO_2NR^6R^7$, $CONR^6R^7$, $C(S)NR^6R^7$, $C(S)NHC(O)OR^8$, or $C(S)SR^8$; or 4) a substituted or an unsubstituted group selected from 4,5-dihydro-oxazolyl, tetrazolyl, isoxazolyl, pyridyl, pyrimidinyl, oxadiazolyl, thiazolyl, or oxazolyl; wherein any optional substituents is selected independently from a) an alkyl or a haloalkyl, any of which having up to 12 carbon atoms; or b) $CO_2R^9$, wherein $R^9$ is an alkyl having up to 12 carbon atoms;

wherein when $R^3$ is an aryl, a heterocyclyl, or a heteroaryl, $R^3$ is optionally substituted with up to three substituents selected independently from a halide, a hydroxyl, a cyano, an alkoxy having up to 12 carbon atoms, or $R^{11}$;

$R^4$, in each occurrence, is selected independently from: 1) halogen, cyano, or hydroxy; 2) an alkyl, a cycloalkyl, a cycloalkoxy, an alkoxy, a haloalkyl, or a haloalkoxy, any of which having up to 12 carbon atoms; 3) a substituted or an unsubstituted aryl, aralkyl, aryloxy, heteroaryl, or heteroaryloxy, any of which having up to 12 carbon atoms, wherein any heteroaryl or heteroaryloxy comprises at least one heteroatom or heterogroup selected independently from O, N, S, or $NR^{10}$; or 4) $CO_2R^6$, $COR^8$, $SO_2R^8$, $SO_2NR^6R^7$, $CONR^6R^7$, or $(CH_2)_q NR^6R^7$, wherein q is an integer from 0 to 5, inclusive;

m is an integer from 0 to 3, inclusive;

or $R^4_m$ is a fused cyclic moiety comprising from 3 to 5 additional ring carbon atoms, inclusive, and optionally comprising at least one heteroatom or heterogroup selected independently from O, N, S, $NR^{10}$, $SO_2$, or CO;

$R^5$, in each occurrence, is selected independently from: 1) an alkoxy, a haloalkoxy, or a cycloalkyl, any of which having up to 12 carbon atoms; 2) a substituted or an unsubstituted aryl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO; 3) hydroxyl, $NR^6R^7$, $CO_2R^6$, $COR^8$, or $SO_2R^8$; or 4) a substituted or an unsubstituted heterocycloalkyl comprising from 3 to 7 ring carbon atoms, and from 1 to 3 heteroatoms or heterogroups, inclusive, selected independently from O, N, S, $NR^{10}$, $SO_2$, or CO;

$R^6$ and $R^7$, in each occurrence, are selected independently from: 1) hydrogen; 2) an alkyl, a cycloalkyl, or a haloalkyl, any of which having up to 12 carbon atoms; or 3) a substituted or an unsubstituted aryl, aralkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO; or $R^6$ and $R^7$ together with the nitrogen atom to which they are attached form a substituted or an unsubstituted cyclic moiety having from 3 to 7 ring carbon atoms, and optionally comprising 1, 2, or 3 heteroatoms in addition to the nitrogen atom to which $R^6$ and $R^7$ are bonded, selected independently from O, N, S, or $NR^{10}$;

$R^8$, in each occurrence, is selected independently from: 1) an alkyl, a cycloalkyl, or a haloalkyl, any of which having up to 12 carbon atoms; or 2) a substituted or an unsubstituted aryl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

$R^{10}$, in each occurrence, is selected independently from: 1) hydrogen; or 2) an alkyl, a cycloalkyl, a haloalkyl, an aryl, or an aralkyl, any of which having up to 12 carbon atoms;

Z is N $R^{11}$ is selected independently from:

1) an alkyl, a haloalkyl, a cycloalkyl, or an alkoxycarbonyl, any of which having up to 12 carbon atoms;

2) a substituted or an unsubstituted heteroaryl or heterocyclyl, any of which having up to 12 carbon atoms, comprises at least one heteroatom or heterogroup selected independently from O, N, S, $NR^{10}$, $SO_2$, or CO, wherein any substituted heteroaryl or heterocyclyl is substituted with up to three substituents selected independently from an alkyl having up to 12 carbon atoms or a hydroxyl; or 3) —CO—$Z^2$—$R^{13}$, —CO—$R^{12}$, —CO—$Z^2$—$(CH_2)_r$—CO—$Z^2$—$R^{13}$, —$NR^{15}R^{16}$, —$Z^2$—CO—$(CH_2)_r$—$Z^2$—$R^{13}$, —$Z^2$—CO—$(CH_2)_r$—CO—$Z^2$—$R^{13}$, —O—$(CH_2)_r$—CO—$Z^2$—$R^{13}$, —O—$(CH_2)_r$—$R^{14}$, —O—$R^{12}$—$(CH_2)_r$—$R^{13}$, —O—$R^{14}$—CO—O—$R^{13}$, —O—$(CH_2)_r$—$R^{12}$, —O—$(CH_2)_r$—NR'R", —O—$(CH_2)_r$—$CO_2$—$(CH_2)_r$—$R^{13}$, —O—$(CH_2)_r$—CONR'R", —O—$(CH_2)_r$—$SR^8$, —O—$(CH_2)_r$—$CO_2$—$R^{13}$, —O—$(CH_2)_r$—O—$(CH_2)_r$—$OR^{13}$, —O—$(CH_2)_r$—CONH—$(CH_2)_r$—$OR^{13}$, —O—$(CH_2)_r$—$SO_2R^8$, —O—$(CH_2)_r$—$R^{13}$, —O—$(CH_2)_r$—$OR^{13}$, —S—$(CH_2)_r$—CONR'R", —$SO_2$—$(CH_2)_r$—$OR^{13}$, —$SO_2$—$(CH_2)_r$—CONR'R", —$(CH_2)_r$—O—CO—$R^8$, —$(CH_2)_r$—$R^{12}$, —$(CH_2)_r$—$R^{13}$, —$(CH_2)_r$—CO—$Z^2$—$R^{13}$, —$(CH_2)_r$—$Z^2$—$R^{13}$, or -alkenylene-$CO_2$—$(CH_2)_r$—$R^{13}$;

r, in each occurrence, is independently 1, 2, or 3;

$R^{12}$, in each occurrence, is independently selected from a substituted or an unsubstituted heterocyclyl having up to 12 carbon atoms, comprising at least one heteroatom or heterogroup selected independently from O, N, S, $NR^{10}$, $SO_2$, or CO, wherein any substituted heterocyclyl is substituted with up to three substituents selected independently from an acyl, an alkyl, or an alkoxycarbonyl, any of which having up to 12 carbon atoms, or —COOH;

$R^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from O, N, S, $NR^{10}$, $SO_2$, or CO;

$R^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from O, N, S, $NR^{10}$, $SO_2$, or CO;

$Z^2$, in each occurrence, is selected independently from $NR^{10}$ or O;

R' and R", in each occurrence, are independently selected from hydrogen or an alkyl having up to 12 carbon atoms; and $R^{15}$ and $R^{16}$, in each occurrence, are independently selected from: 1) hydrogen; 2) an alkyl having up to 12 carbon atoms; or 3) —$(CH_2)_r$—O—$R^{13}$, —$(CH_2)_r$—$R^{14}$, —$COR^{13}$, —$(CH_2)_r$—CO—$Z^2$—$R^{13}$, —$CO_2R^{13}$, —$CO_2$—$(CH_2)_r$—$R^{13}$, —$CO_2$—$(CH_2)_r$—$R^{12}$, —$CO_2$—$(CH_2)_r$—CO—$Z^2$—$R^{13}$, —$CO_2$—$(CH_2)_r$—$OR^{13}$, —CO—$(CH_2)_r$—O—$(CH_2)_r$—O—$(CH_2)_r$—$R^{13}$, —CO—$(CH_2)_r$—O$(CH_2)_r$—$OR^{13}$, or —CO—NH—$(CH_2)_r$—$OR^{13}$; or $R^{15}$ and $R^{16}$ together with the nitrogen atom to which they are attached form a substituted or an unsubstituted cyclic moiety comprising up to 12 carbon atoms, optionally comprising at least one additional heteroatom or heterogroup selected independently from O, N, S, $NR^{10}$, $SO_2$, or CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from O, N, S, or $NR^{10}$; or 3) $COOR^{13}$, —$Z^2$—$(CH_2)_r$—$R^{13}$, —$COR^{13}$, —$CO_2$—$(CH_2)_r$—$R^{13}$, —$CO(CH_2)_r$—O—$R^{13}$, —$(CH_2)_r$—$CO_2$—$R^{13}$, —$SO_2R^8$, —$SO_2NR'R"$, or —NR'R";

wherein the —$(CH_2)_r$— linking moiety, in any occurrence, is optionally substituted with at least one group selected independently from hydroxyl, amino, or an alkyl having up to 3 carbon atoms;

when $R^1$ and $R^2$ do not form a monocyclic or bicyclic moiety, $R^1$ and $R^2$ are optionally substituted with 1 or 2 substituents, and when substituted, the substituents are selected independently from: 1) an alkyl, a cycloalkyl, a haloalkyl, an alkoxy, an aryl, a heteroaryl, or a heterocyclyl, any of which having up to 12 carbon atoms, wherein any heteroaryl or heterocyclyl comprises at least one heteroatom or heterogroup selected independently from O, N, S, $NR^{10}$, $SO_2$, or CO; or 2) halogen, cyano, or hydroxyl;

when $R^1$ and $R^2$ together with the diradical Z to which they are attached form a monocyclic or a bicyclic moiety, the cyclic moiety is optionally substituted with at least one substituent selected independently from: 1) halogen, cyano, or hydroxyl; 2) an alkyl, a haloalkyl, a cycloalkyl, an alkoxy, a cycloalkyl-substituted alkyl, an alkoxyalkyl, a cycloalkoxy, a haloalkoxy, an aryl, an aryloxy, an aralkyl, a heteroaryl or a heteroaryloxy, any of which having up to 12 carbon atoms, wherein any heteroaryl or heteroaryloxy comprises at least one heteroatom or heterogroup selected independently from O, N, S, or $NR^{10}$; or 3) $CO_2R^6$, $COR^8$, $SO_2R^8$, $SO_2NR^6R^7$, or $CONR^6R^7$;

$R^4$, $R^6$, $R^7$, and $R^8$ are optionally substituted with at least one substituent, and when substituted, the substituents are selected independently from: 1) halide, hydroxy, cyano, or $NR^6R^7$; or 2) an alkyl or an alkoxy, any of which having up to 12 carbon atoms;

and $R^5$ is optionally substituted with at least one substituent, and when substituted, the substituents are selected independently from: 1) halide, hydroxy, cyano, or $NR^6R^7$; or 2) an alkyl having up to 12 carbon atoms.

7. The compound according to claim 6, wherein Z is N.

8. The compound according to claim 6, wherein:

$R^1$ and $R^2$ are selected independently from: 1) an alkyl having up to 6 carbon atoms; 2) a cycloalkyl having up to 6 carbon atoms; 3) $COR^8$; or 4) $(CH_2)_n R^5$ or $(CH_2)_n R^d CO_2 R^e$, wherein n, in each occurrence, is 1 or 2; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen;

or $R^1$ and $R^2$ together with the diradical Z to which they are attached form a substituted or an unsubstituted monocyclic or bicyclic moiety comprising up to 12 carbon atoms, and optionally comprising 1 or 2 heteroatoms or heterogroups selected independently from O, N, or $NR^{10}$; wherein any optional substituent on the cyclic moiety selected from: 1) a cycloalkyl having up to 6 carbon atoms; or 2) an alkyl having up to 2 carbon atoms.

9. The compound according to claim 6, wherein:

$R^3$ is selected from: 1) cyano; 2) a substituted or an unsubstituted aryl, or a substituted or an unsubstituted 5-, 6-, or 7-membered heterocyclyl or heteroaryl, comprising 1, 2, or 3 heteroatoms or heterogroups selected independently from O, N, S, $NR^{10}$, $SO_2$, or CO, any of which having up to 12 carbon atoms; or 3) $CO_2R^6$, $COR^S$, $SO_2R^8$, $SO_2NR^6R^7$, $CONR^6R^7$, $C(S)NR^6R^7$, $C(S)NHC(O)OR^8$, or $C(S)SR^8$; or 4) a substituted or an unsubstituted group selected from 4,5-dihydro-oxazolyl, tetrazolyl, isoxazolyl, pyridyl, pyrimidinyl, oxadiazolyl, thiazolyl, or oxazolyl; wherein any optional substituents is selected independently from a) an alkyl or a haloalkyl, any of which having up to 12 carbon atoms; or b) $CO_2R^9$, wherein $R^9$ is an alkyl having up to 12 carbon atoms;

wherein when $R^3$ is an aryl, a heterocyclyl, or a heteroaryl, $R^3$ is optionally substituted with up to three substituents selected independently from a halide, a hydroxyl, a cyano, an alkoxy having up to 12 carbon atoms, or $R^{11}$;

$R^{11}$ is selected independently from:

1) an alkyl, a haloalkyl, a cycloalkyl, or an alkoxycarbonyl, any of which having up to 12 carbon atoms;

2) a substituted or an unsubstituted heteroaryl or heterocyclyl, any of which having up to 12 carbon atoms, comprises at least one heteroatom or heterogroup selected independently from O, N, S, $NR^{10}$, $SO_2$, or CO, wherein any substituted heteroaryl or heterocyclyl is substituted with up to three substituents selected independently from an alkyl having up to 12 carbon atoms or a hydroxyl; or 3) —CO—$Z^2$—$R^{13}$, —CO—$R^{12}$, —CO—$Z^2$—$(CH_2)_r$—CO—$Z^2$—$R^{13}$, —$NR^{15}R^{16}$, —$Z^2$—CO—$(CH_2)_r$—$Z^2$—$R^{13}$, —$Z^2$—CO—$(CH_2)_r$—CO—$Z^2$—$R^{13}$, —O—$(CH_2)_r$—CO—$Z^2$—$R^{13}$, —O—$(CH_2)_r$—$R^{14}$, —O—$R^{12}$—$(CH_2)_r$—$R^{13}$, —O—$R^{14}$—CO—O—$R^{13}$, —O—$(CH_2)_r$—$R^{12}$, —O—$(CH_2)_r$—NR'R'', —O—$(CH_2)_r$—$CO_2$—$(CH_2)_r$—$R^{13}$, —O—$(CH_2)_r$—$SR^8$, —O—$(CH_2)_r$—$CO_2$—$R^{13}$, —O—$(CH_2)_r$—CONR'R'', —O—$(CH_2)_r$—CONH—$(CH_2)_r$—$OR^{13}$, —O—$(CH_2)_r$—$SO_2R^8$, —O—$(CH_2)_r$—$R^{13}$, —O—$(CH_2)_r$—$OR^{13}$, —O—$(CH_2)_r$—O—$(CH_2)_r$—$OR^{13}$, —S—$(CH_2)_r$—CONR'R'', —$SO_2$—$(CH_2)_r$—$OR^{13}$, —$SO_2$—$(CH_2)_r$—CONR'R'', —$(CH_2)_r$—O—CO—$R^8$, —$(CH_2)_r$—$R^{12}$, —$(CH_2)_r$—$R^{13}$, —$(CH_2)_r$—CO—$Z^2$—$R^{13}$, —$(CH_2)_r$—$Z^2$—$R^{13}$, or -alkenylene-$CO_2$—$(CH_2)_r$—$R^{13}$;

r, in each occurrence, is independently 1, 2, or 3;

$R^{12}$, in each occurrence, is independently selected from a substituted or an unsubstituted heterocyclyl having up to 12 carbon atoms, comprising at least one heteroatom or heterogroup selected independently from O, N, S, $NR^{10}$, $SO_2$, or CO, wherein any substituted heterocyclyl is substituted with up to three substituents selected independently from an acyl, an alkyl, or an alkoxycarbonyl, any of which having up to 12 carbon atoms, or —COOH;

$R^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from O, N, S, $NR^{10}$, $SO_2$, or CO;

$R^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from O, N, S, $NR^{10}$, $SO_2$, or CO;

$Z^2$, in each occurrence, is selected independently from $NR^{10}$ or O;

R' and R'', in each occurrence, are independently selected from hydrogen or an alkyl having up to 12 carbon atoms; and $R^{15}$ and $R^{16}$, in each occurrence, are independently selected from: 1) hydrogen; 2) an alkyl having up to 12 carbon atoms; or 3) —$(CH_2)_r$—O—$R^{13}$, —$(CH_2)_r$—$R^{14}$, —$COR^{13}$, —$(CH_2)_r$—CO—$Z^2$—$R^{13}$, —$CO_2R^{13}$, —$CO_2$—$(CH_2)_r$—$R^{13}$, —$CO_2$—$(CH_2)_r$—$R^{12}$, —$CO_2$—$(CH_2)_r$—CO—$Z^2$—$R^{13}$, —$CO_2$—$(CH_2)_r$—$OR^{13}$, —CO—$(CH_2)_r$—O—$(CH_2)_r$—O—$(CH_2)_r$—$R^{13}$, —CO—$(CH_2)_r$—O$(CH_2)_r$—$OR^{13}$, or —CO—NH—$(CH_2)_r$—$OR^{13}$;

or $R^{15}$ and $R^{16}$ together with the nitrogen atom to which they are attached form a substituted or an unsubstituted cyclic moiety comprising up to 12 carbon atoms, optionally comprising at least one additional heteroatom or heterogroup selected independently from O, N, S, $NR^{10}$, $SO_2$, or CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from O, N, S, or $NR^{10}$; or 3) $COOR^{13}$, $-Z^2-(CH_2)_r-R^{13}$, $-COR^{13}$, $-CO_2-(CH_2)_r-R^{13}$, $-CO(CH_2)_r-O-R^{13}$, $-(CH_2)_r-CO_2-R^{13}$, $-SO_2R^8$, $-SO_2NR'R''$, or $-NR'R''$; and wherein the $-(CH_2)_r-$ linking moiety, in any occurrence, is optionally substituted with at least one group selected independently from hydroxyl, amino, or an alkyl having up to 3 carbon atoms.

10. The compound according to claim 6, wherein: $R^4$, in each occurrence, is selected independently from: 1) halogen or cyano; or 2) an alkyl or a haloalkyl, any of which having up to 4 carbon atoms; and m is 2 or 3.

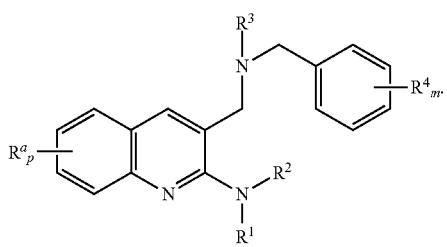

11. The compound according to claim 6, having the formula:

(II);

or a salt, a diastereomeric mixture, an enantiomer, a tautomer, or a racemic mixture thereof, or any combination thereof, wherein:

$R^1$ and $R^2$ are selected independently from: 1) a substituted or an unsubstituted alkyl or a substituted or an unsubstituted cycloalkyl, either of which having up to 12 carbon atoms; 2) $COR^8$ or $CO_2R^6$; or 3) $(CH_2)_nR^5$ or $(CH_2)_n R^d CO_2R^e$, wherein n, in each occurrence, is 1 or 2; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen;

$R^3$ is selected from: 1) cyano; 2) a substituted or an unsubstituted, 5-, 6-, or 7-membered heterocyclyl or heteroaryl, any of which having up to 12 carbon atoms, comprising 1, 2, or 3 heteroatoms or heterogroups selected independently from O, N, S, $NR^{10}$, $SO_2$, or CO; or 3) $CO_2R^6$, $C(S)SR^8$, or $C(S)NHC(O)OR^8$; or 4) a substituted or an unsubstituted group selected from 4,5-dihydro-oxazolyl, tetrazolyl, isoxazolyl, pyridyl, pyrimidinyl, oxadiazolyl, thiazolyl, or oxazolyl; wherein any optional substituents is selected independently from a) an alkyl or a haloalkyl, any of which having up to 12 carbon atoms; or b) $CO_2R^9$, wherein $R^9$ is an alkyl having up to 12 carbon atoms;

$R^4$, in each occurrence, is selected independently from: 1) halogen or cyano; or 2) an alkyl or a haloalkyl, either of which having up to 12 carbon atoms; m is an integer from 0 to 3, inclusive;

$R^5$, in each occurrence, is selected independently from: 1) a cycloalkyl having up to 12 carbon atoms; or (2) a substituted or an unsubstituted aryl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

$R^6$ is selected from: 1) hydrogen; 2) an alkyl, a cycloalkyl, or a haloalkyl, any of which having up to 12 carbon atoms; or 3) a substituted or an unsubstituted aryl, aralkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

$R^8$, in each occurrence, is selected independently from an alkyl, a cycloalkyl, or a haloalkyl, any of which having up to 12 carbon atoms or a substituted or an unsubstituted aryl, heteroaryl, or heterocyclyl, any of which having up to 12 carbon atoms, wherein any heteroaryl or heterocyclyl comprises at least one heteroatom or heterogroup selected independently from O, N, S, $NR^{10}$, $SO_2$, or CO;

$R^{10}$, in each occurrence, is selected independently from: 1) hydrogen; or 2) an alkyl, a cycloalkyl, a haloalkyl, an aryl, or an aralkyl, any of which having up to 12 carbon atoms;

$R^a$, in each occurrence, is selected independently from: 1) halogen, hydroxyl, or cyano; 2) an alkyl, or an alkoxy, any of which having up to 12 carbon atoms; or 3) $CO_2R^6$; and p is an integer from 0 to 3, inclusive.

12. The compound according to claim 11, having the formula:

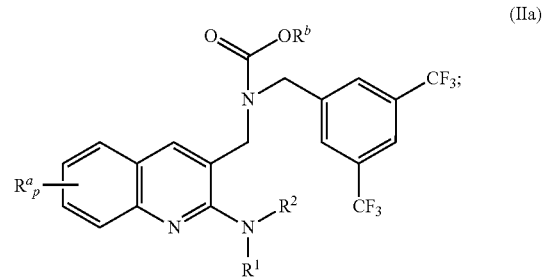

or a salt, a diastereomeric mixture, an enantiomer, a tautomer, or a racemic mixture thereof, or any combination thereof, wherein: $R^b$ is selected independently from: 1) hydrogen; or 2) an alkyl or a cycloalkyl, either of which having up to 12 carbon atoms.

13. The compound according to claim 6 having the formula:

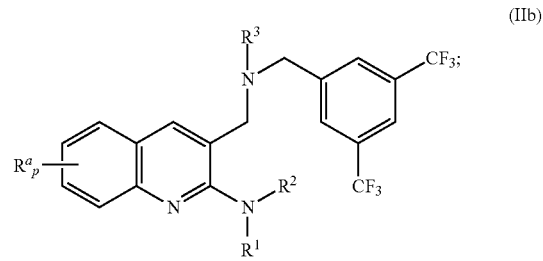

or a salt, a diastereomeric mixture, an enantiomer, a tautomer, or a racemic mixture thereof, or any combination thereof, wherein:

$R^1$ and $R^2$ are selected independently from: 1) a substituted or an unsubstituted alkyl, cycloalkyl, haloalkyl, aryl, heterocyclyl, any of which having up to 12 carbon atoms, wherein any heterocyclyl comprises at least one heteroatom or heterogroup selected independently from O, N, $NR^{10}$, or CO; 2) $COR^8$, or 3) $(CH)_n R^5$, wherein n, in each occurrence, is 1, 2, or 3; $R^x$, in each occurrence, is selected independently from an alkyl or an alkoxy, either of which having up to 12 carbon atoms, or hydrogen;

or $R^1$ and $R^2$ together with the nitrogen atom to which they are attached form a substituted or an unsubstituted monocyclic or bicyclic moiety comprising up to 12 carbon atoms, and optionally comprising 1, 2, or 3 heteroatoms or heterogroups in addition to N, selected independently from O, N, —$NR^{10}$ or CO;

$R^3$ is selected from a substituted or an unsubstituted group selected from tetrazolyl, 1,3,4-oxadiazolyl, oxazolyl, pyrimidinyl, 4,5-dihydro-oxazolyl, pyridyl, thiazolyl, or isoxazolyl; wherein any optional substituent on $R^3$ is selected independently from an alkyl or a haloalkyl, any of which having up to 12 carbon atoms;

$R^5$, in each occurrence, is selected independently from: 1) an alkoxy, a haloalkoxy, or a cycloalkyl, any of which having up to 12 carbon atoms; 2) a substituted or an unsubstituted aryl, or heterocyclyl any of which having up to 12 carbon atoms, wherein any heterocyclyl comprises at least one heteroatom or heterogroup selected independently from O, N, $NR^{10}$, or CO; 3) hydroxyl, $NR^6R^7$, $COR^8$, or 4) a substituted or an unsubstituted heterocycloalkyl comprising from 3 to 7 ring carbon atoms, and from 1 to 3 heteroatoms or heterogroups, inclusive, selected independently from O, N, $NR^{10}$, or CO;

$R^6$ and $R^7$, in each occurrence, are selected independently from: 1) hydrogen; 2) an alkyl, a cycloalkyl, or a haloalkyl, any of which having up to 12 carbon atoms; or 3) a substituted or an unsubstituted aryl, aralkyl, heterocyclyl, any of which having up to 12 carbon atoms, wherein any heterocyclyl comprises at least one heteroatom or heterogroup selected independently from O, N, $NR^{10}$, or CO; or $R^6$ and $R^7$ together with the nitrogen atom to which they are attached form a substituted or an unsubstituted cyclic moiety having from 3 to 7 ring carbon atoms, and optionally comprising 1, 2, or 3 heteroatoms in addition to the nitrogen atom to which $R^6$ and $R^7$ are bonded, selected independently from O, N, or $NR^{10}$;

$R^8$, in each occurrence, is selected independently from: 1) an alkyl, a cycloalkyl, or a haloalkyl, any of which having up to 12 carbon atoms; or 2) a substituted or an unsubstituted aryl, heterocyclyl, or heteroaryl, any of which having up to 12 carbon atoms, wherein any heterocyclyl or heteroaryl comprises at least one heteroatom or heterogroup selected independently from O, N, $NR^{10}$, or CO;

$R^{10}$, in each occurrence, is selected independently from: 1) hydrogen; or 2) an alkyl, a cycloalkyl, a haloalkyl, an aryl, or an aralkyl, any of which having up to 12 carbon atoms;

when $R^1$ and $R^2$ do not form a monocyclic or bicyclic moiety, $R^1$ and $R^2$ are optionally substituted with 1 or 2 substituents, and when substituted, the substituents are selected independently from: 1) an alkyl, a cycloalkyl, a haloalkyl, an alkoxy, an aryl, a heteroaryl, or a heterocyclyl, any of which having up to 12 carbon atoms, wherein any heterocyclyl comprises at least one heteroatom or heterogroup selected independently from O, N, $NR^{10}$, or CO; or 2) halogen, cyano, or hydroxyl;

when $R^1$ and $R^2$ together with the nitrogen atom to which they are attached form a monocyclic or a bicyclic moiety, the cyclic moiety is optionally substituted with at least one substituent selected independently from: 1) halogen, cyano, or hydroxyl; 2) an alkyl, a haloalkyl, a cycloalkyl, an alkoxy, a cycloalkyl-substituted alkyl, an alkoxyalkyl, a cycloalkoxy, a haloalkoxy, an aryl, an aryloxy, or an aralkyl, any of which having up to 12 carbon atoms;

$R^4$, $R^6$, $R^7$, and $R^8$ are optionally substituted with at least one substituent, and when substituted, the substituents are selected independently from: 1) halide, hydroxy, cyano, or $NR^6R^7$; or 2) an alkyl or an alkoxy, any of which having up to 12 carbon atoms;

$R^5$ is optionally substituted with at least one substituent, and when substituted, the substituents are selected independently from: 1) halide, hydroxy, cyano, or $NR^6R^7$; or 2) an alkyl having up to 12 carbon atoms;

wherein $R^a$, in each occurrence, is selected independently from: 1) a halogen; a hydroxyl, or a cyano; 2) an alkyl or an alkoxy, any of which having up to 12 carbon atoms; or 3) $CO_2R^6$; and p is an integer from 0 to 3, inclusive.

14. The compound according to claim 13, having the formula:

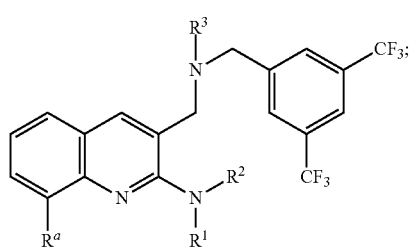

(IIc)

or a salt, a diastereomeric mixture, an enantiomer, a tautomer, or a racemic mixture thereof, or any combination thereof, wherein: $R^a$ is selected from methyl, ethyl, or methoxy.

15. A compound wherein the compound is selected from:

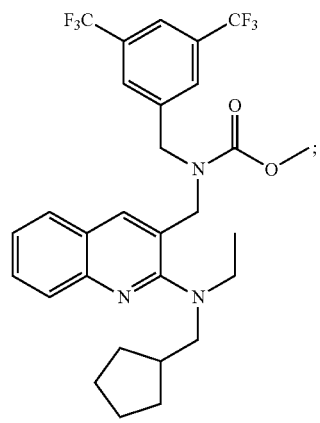

223
-continued
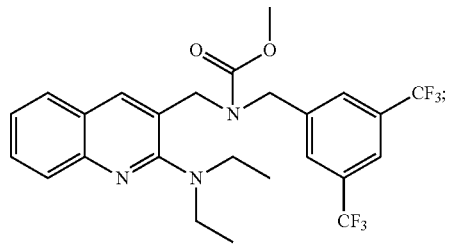
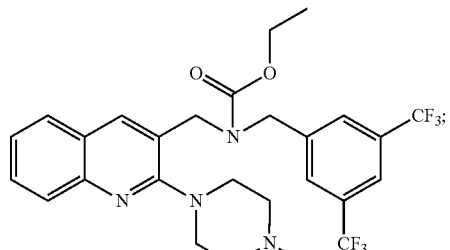
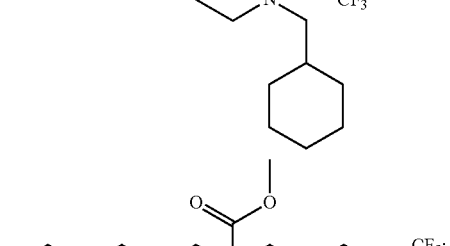
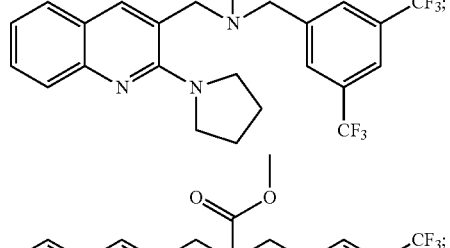
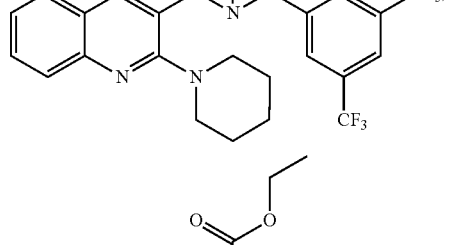
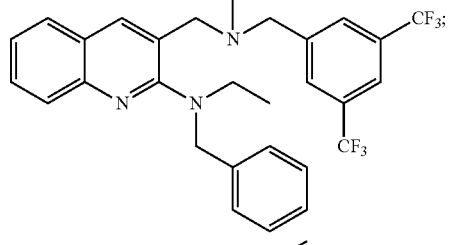
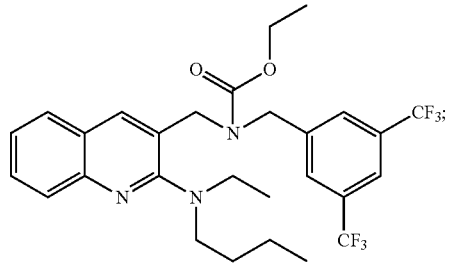
224
-continued
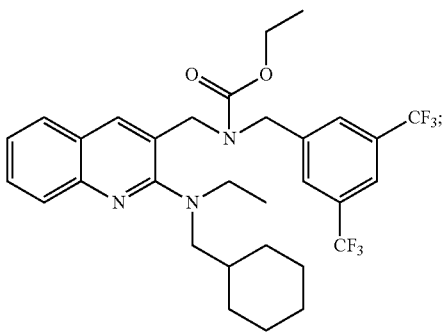
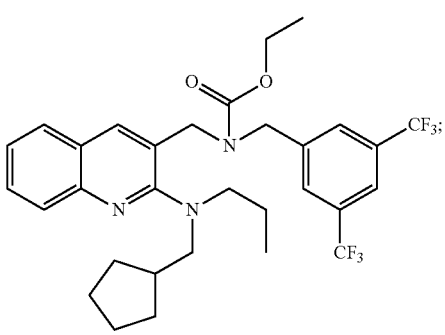
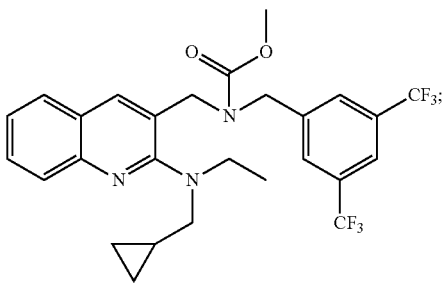
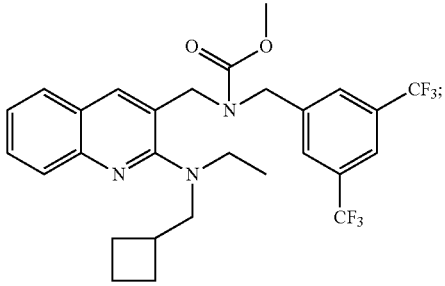
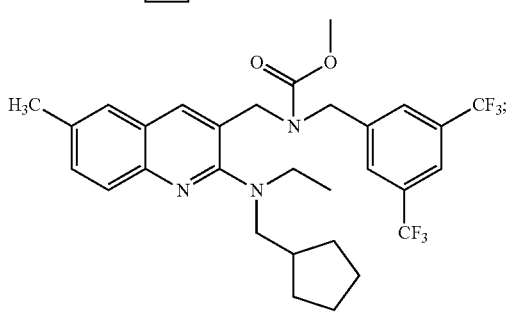

225
-continued
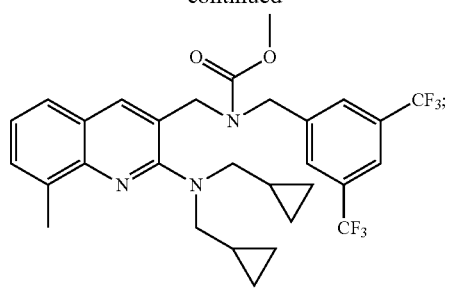
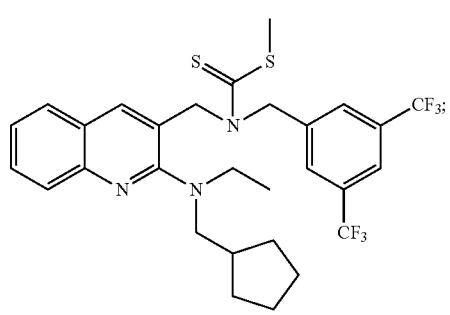
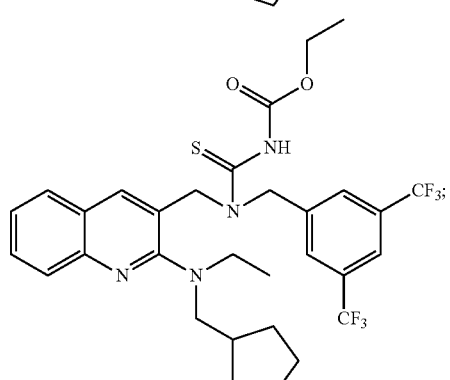
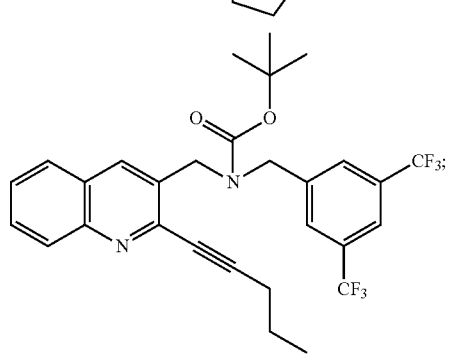
226
-continued
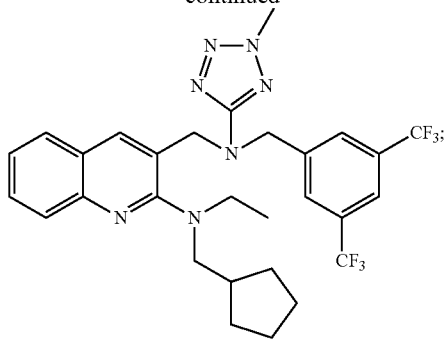
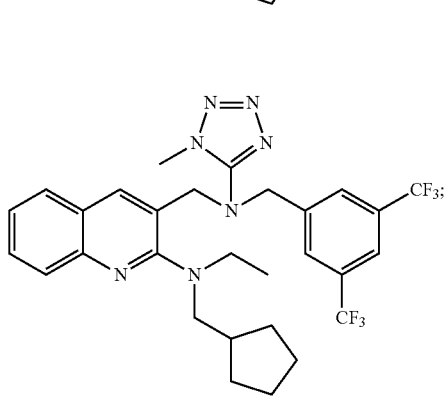
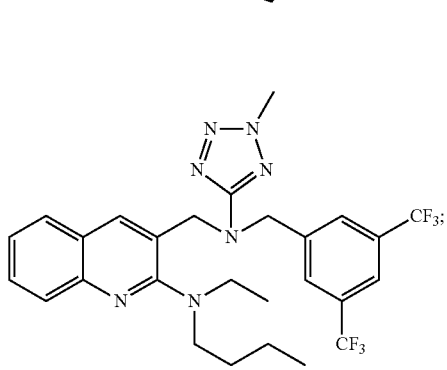
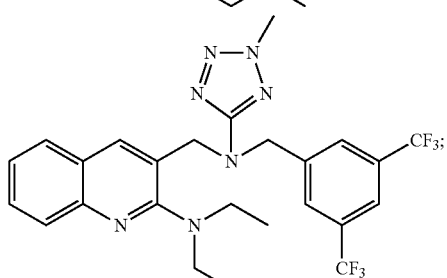

227

-continued

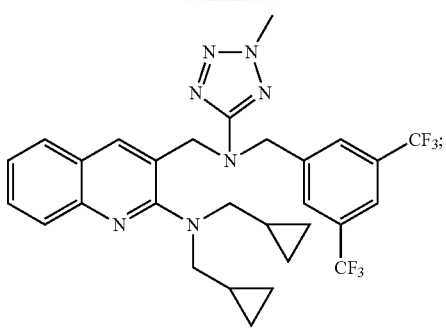

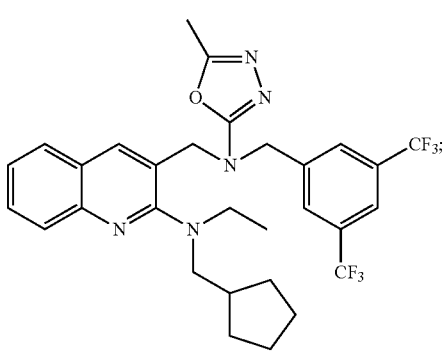

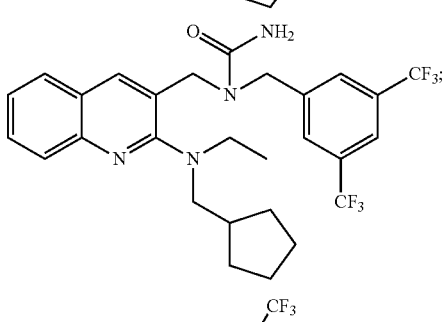

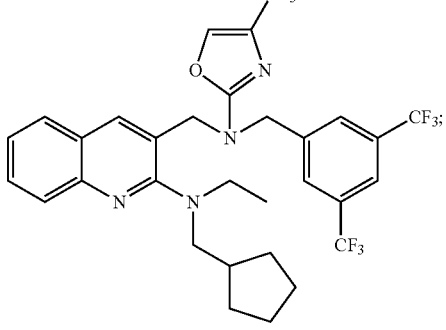

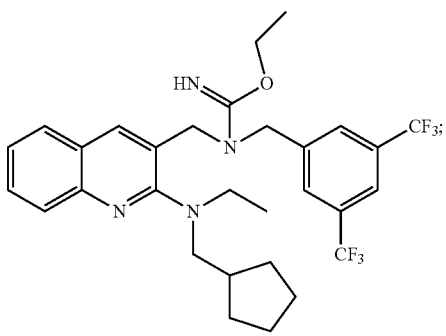

228

-continued

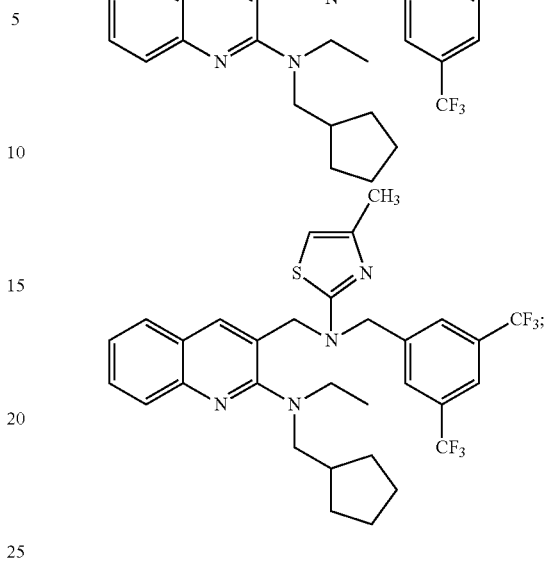

and combinations thereof.

16. A pharmaceutical composition comprising a pharmaceutically acceptable carrier and at least one compound having the formula:

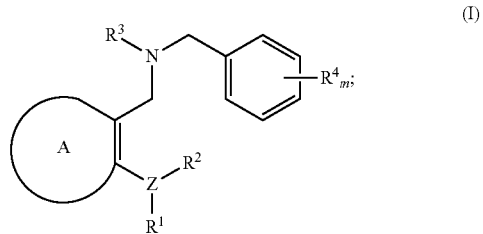

(I)

or a salt, a diastereomeric mixture, an enantiomer, a tautomer, or a racemic mixture thereof, or any combination thereof, wherein:

A is a substituted or an unsubstituted quinoline moiety having the formula:

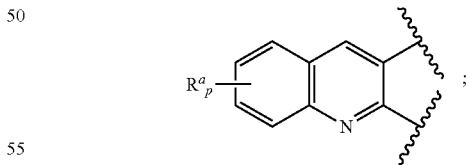

wherein $R^a$, in each occurrence, is selected independently from: 1) a halogen; a hydroxyl, or a cyano; 2) an alkyl or an alkoxy, any of which having up to 12 carbon atoms; or 3) $CO_2R^6$; and p is an integer from 0 to 3, inclusive;

$R^1$ and $R^2$ are selected independently from: 1) hydrogen; 2) a substituted or an unsubstituted alkyl, cycloalkyl, haloalkyl, aryl, heterocyclyl, heteroaryl, any of which having up to 12 carbon atoms, wherein any heterocyclyl or heteroaryl comprises at least one heteroatom or heterogroup selected independently from O, N, S, $NR^{10}$, SO$_2$, or CO; 3) CO$_2$R$^6$, COR$^8$, SO$_2$R$^8$, SO$_2$NR$^6$R$^7$, or CONR$^6$R$^7$; or 4) (CHR$^x$)$_n$R$^5$ or (CH$_2$)$_n$R$^d$CO$_2$R$^e$, wherein n, in each occurrence, is 1, 2, or 3; R$^x$, in each occurrence, is selected independently from an alkyl or an alkoxy, either of which having up to 12 carbon atoms, or hydrogen; R$^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, NR$^{10}$, SO$_2$, or CO; and R$^e$, in each occurrence, is selected independently from an alkyl or a cycloalkyl, either of which having up to 12 carbon atoms, or hydrogen;

or R$^1$ and R$^2$ together with the diradical Z to which they are attached form a substituted or an unsubstituted monocyclic or bicyclic moiety comprising up to 12 carbon atoms, and optionally comprising 1, 2, or 3 heteroatoms or heterogroups in addition to Z, selected independently from O, N, S, NR$^{10}$, SO$_2$, or CO;

R$^3$ is selected from: 1) hydrogen or cyano; 2) a substituted alkyl having up to 12 carbon atoms; 3) a substituted or an unsubstituted aryl, or a substituted or an unsubstituted 5-, 6-, or 7-membered heterocyclyl or heteroaryl, any of which having up to 12 carbon atoms, comprising 1, 2, or 3 heteroatoms or heterogroups selected independently from O, N, S, NR$^{10}$, SO$_2$, or CO; or 4) CO$_2$R$^6$, COR$^8$, SO$_2$R$^8$, SO$_2$NR$^6$R$^7$, CONR$^6$R$^7$, C(S)NR$^6$R$^7$, C(S)NHC(O)OR$^8$, or C(S)SR$^8$; or 5) a substituted or an unsubstituted group selected from 4,5-dihydro-oxazolyl, tetrazolyl, isoxazolyl, pyridyl, pyrimidinyl, oxadiazolyl, thiazolyl, or oxazolyl; wherein any optional substituent is selected independently from: a) an alkyl or haloalkyl, any of which having up to 12 carbon atoms; or b) CO$_2$R$^9$, wherein R$^9$ is an alkyl having up to 12 carbon atoms;

wherein when R$^3$ is an aryl, a heterocyclyl, or a heteroaryl, R$^3$ is optionally substituted with up to three substituents selected independently from a halide, a hydroxyl, a cyano, an alkoxy having up to 12 carbon atoms, or R$^{11}$;

R$^4$, in each occurrence, is selected independently from: 1) halogen, cyano, or hydroxy; 2) an alkyl, a cycloalkyl, a cycloalkoxy, an alkoxy, a haloalkyl, or a haloalkoxy, any of which having up to 12 carbon atoms; 3) a substituted or an unsubstituted aryl, aralkyl, aryloxy, heteroaryl, or heteroaryloxy, any of which having up to 12 carbon atoms, wherein any heteroaryl or heteroaryloxy comprises at least one heteroatom or heterogroup selected independently from O, N, S, or NR$^{10}$; or 4) CO$_2$R$^6$, COR$^8$, SO$_2$R$^8$, SO$_2$NR$^6$R$^7$, CONR$^6$R$^7$, or (CH$_2$)$_q$NR$^6$R$^7$, wherein q is an integer from 0 to 5, inclusive;

m is an integer from 0 to 3, inclusive;

or R$^4_m$ is a fused cyclic moiety comprising from 3 to 5 additional ring carbon atoms, inclusive, and optionally comprising at least one heteroatom or heterogroup selected independently from O, N, S, NR$^{10}$, SO$_2$, or CO;

R$^5$, in each occurrence, is selected independently from: 1) an alkoxy, a haloalkoxy, or a cycloalkyl, any of which having up to 12 carbon atoms; 2) a substituted or an unsubstituted aryl, heterocyclyl, or heteroaryl, any of which having up to 12 carbon atoms, wherein any heterocyclyl or heteroaryl comprises at least one heteroatom or heterogroup selected independently from O, N, S, NR$^{10}$, SO$_2$, or CO; 3) hydroxyl, NR$^6$R$^7$, CO$_2$R$^6$, COR$^8$, or SO$_2$R$^8$; or 4) a substituted or an unsubstituted heterocycloalkyl comprising from 3 to 7 ring carbon atoms, and from 1 to 3 heteroatoms or heterogroups, inclusive, selected independently from O, N, S, NR$^{10}$, SO$_2$, or CO;

R$^6$ and R$^7$, in each occurrence, are selected independently from: 1) hydrogen; 2) an alkyl, a cycloalkyl, or a haloalkyl, any of which having up to 12 carbon atoms; or 3) a substituted or an unsubstituted aryl, aralkyl, heterocyclyl, or heteroaryl, any of which having up to 12 carbon atoms, wherein any heterocyclyl or heteroaryl comprises at least one heteroatom or heterogroup selected independently from O, N, S, NR$^{10}$, SO$_2$, or CO;

or R$^6$ and R$^7$ together with the nitrogen atom to which they are attached form a substituted or an unsubstituted cyclic moiety having from 3 to 7 ring carbon atoms, and optionally comprising 1, 2, or 3 heteroatoms in addition to the nitrogen atom to which R$^6$ and R$^7$ are bonded, selected independently from O, N, S, or NR$^{10}$;

R$^8$, in each occurrence, is selected independently from: 1) an alkyl, a cycloalkyl, or a haloalkyl, any of which having up to 12 carbon atoms; or 2) a substituted or an unsubstituted aryl, heterocyclyl, or heteroaryl, any of which having up to 12 carbon atoms, wherein any heterocyclyl or heteroaryl comprises at least one heteroatom or heterogroup selected independently from O, N, S, NR$^{10}$, SO$_2$, or CO;

R$^{10}$, in each occurrence, is selected independently from: 1) hydrogen; or 2) an alkyl, a cycloalkyl, a haloalkyl, an aryl, or an aralkyl, any of which having up to 12 carbon atoms;

Z is N; or the ZR$^1$ moiety is S, CO, or SO$_2$;

R$^{11}$ is selected independently from:

1) an alkyl, a haloalkyl, a cycloalkyl, or an alkoxycarbonyl, any of which having up to 12 carbon atoms;

2) a substituted or an unsubstituted heteroaryl or heterocyclyl, any of which having up to 12 carbon atoms, comprises at least one heteroatom or heterogroup selected independently from O, N, S, NR$^{10}$, SO$_2$, or CO, wherein any substituted heteroaryl or heterocyclyl is substituted with up to three substituents selected independently from an alkyl having up to 12 carbon atoms or a hydroxyl; or 3) —CO—Z$^2$—R$^{13}$, —CO—R$^{12}$, —CO—Z$^2$—(CH$_2$)$_r$—CO—Z$^2$—R$^{13}$, —NR$^{15}$R$^{16}$, —Z$^2$—CO—(CH$_2$)$_r$—Z$^2$—R$^{13}$, —Z$^2$—CO—(CH$_2$)$_r$—CO—Z$^2$—R$^{13}$, —O—(CH$_2$)$_r$—CO—Z$^2$—R$^{13}$, —O—(CH$_2$)$_r$—R$^{14}$, —O—R$^{12}$—(CH$_2$)$_r$—R$^{13}$, —O—R$^{14}$—CO—O—R$^{13}$, —O—(CH$_2$)$_r$—R$^{12}$, —O—(CH$_2$)$_r$—NR'R'', —O—(CH$_2$)$_r$—CO$_2$—(CH$_2$)$_r$—R$^{13}$, —O—(CH$_2$)$_r$—SR$^8$, —O—(CH$_2$)$_r$—CO$_2$—R$^{13}$, —O—(CH$_2$)$_r$—CON'R'', —O—(CH$_2$)$_r$—CONH—(CH$_2$)$_r$—OR$^{13}$, —O—(CH$_2$)$_r$—SO$_2$R$^8$, —O—(CH$_2$)$_r$—R$^{13}$, —O—(CH$_2$)$_r$—OR$^{13}$, —O—(CH$_2$)$_r$—O—(CH$_2$)$_r$—OR$^{13}$, —S—(CH$_2$)$_r$—CONR'R'', —SO$_2$—(CH$_2$)$_r$—OR$^{13}$, —SO$_2$—(CH$_2$)$_r$—CON'R'', —(CH$_2$)$_r$—O—CO—R$^8$, —(CH$_2$)$_r$—R$^{12}$, —(CH$_2$)$_r$—R$^{13}$, —(CH$_2$)$_r$—CO—Z$^2$—R$^{13}$, —(CH$_2$)$_r$—Z$^2$—R$^{13}$, or -alkenylene-CO$_2$—(CH$_2$)$_r$—R$^{13}$;

r, in each occurrence, is independently 1, 2, or 3;

R$^{12}$, in each occurrence, is independently selected from a substituted or an unsubstituted heterocyclyl having up to 12 carbon atoms, comprising at least one heteroatom or heterogroup selected independently from O, N, S, NR$^{10}$, SO$_2$, or CO, wherein any substituted heterocyclyl is substituted with up to three substituents selected independently from an acyl, an alkyl, or an alkoxycarbonyl, any of which having up to 12 carbon atoms, or —COOH;

R$^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from O, N, S, $NR^{10}$, $SO_2$, or CO;

$R^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from O, N, S, $NR^{10}$, $SO_2$, or CO;

$Z^2$, in each occurrence, is selected independently from $NR^{10}$ or O;

R' and R", in each occurrence, are independently selected from hydrogen or an alkyl having up to 12 carbon atoms; and $R^{15}$ and $R^{16}$, in each occurrence, are independently selected from: 1) hydrogen; 2) an alkyl having up to 12 carbon atoms; or 3) $-(CH_2)_r-O-R^{13}$, $-(CH_2)_r-R^{14}$, $-COR^{13}$, $-(CH_2)_r-CO-Z^2-R^{13}$, $-CO_2R^{13}$, $-CO_2-(CH_2)_r-R^{13}$, $-CO_2-(CH_2)_r-R^{12}$, $-CO_2-(CH_2)_r-CO-Z^2-R^{13}$, $-CO_2-(CH_2)_r-OR^{13}$, $-CO-(CH_2)_r-O-(CH_2)_r-O-(CH_2)_r-R^{13}$, $-CO-(CH_2)_r-O(CH_2)_r-OR^{13}$, or $-CO-NH-(CH_2)_r-OR^{13}$;

or $R^{15}$ and $R^{16}$ together with the nitrogen atom to which they are attached form a substituted or an unsubstituted cyclic moiety comprising up to 12 carbon atoms, optionally comprising at least one additional heteroatom or heterogroup selected independently from O, N, S, $NR^{10}$, $SO_2$, or CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from O, N, S, or $NR^{10}$; or 3) $COOR^{13}$, $-Z^2-(CH_2)_r-R^{13}$, $-COR^{13}$, $-CO_2-(CH_2)_r-R^{13}$, $-CO(CH_2)_r-O-R^{13}$, $-(CH_2)_r-CO_2-R^{13}$, $-SO_2R^8$, $-SO_2NR'R''$, or $-NR'R''$;

wherein the $-(CH_2)_r-$ linking moiety, in any occurrence, is optionally substituted with at least one group selected independently from hydroxyl, amino, or an alkyl having up to 3 carbon atoms;

when $R^1$ and $R^2$ do not form a monocyclic or bicyclic moiety, $R^1$ and $R^2$ are optionally substituted with 1 or 2 substituents, and when substituted, the substituents are selected independently from: 1) an alkyl, a cycloalkyl, a haloalkyl, an alkoxy, an aryl, a heteroaryl, or a heterocyclyl, any of which having up to 12 carbon atoms, wherein any heteroaryl or heterocyclyl comprises at least one heteroatom or heterogroup selected independently from O, N, S, $NR^{10}$, $SO_2$, or CO; or 2) halogen, cyano, or hydroxyl;

when $R^1$ and $R^2$ together with the diradical Z to which they are attached form a monocyclic or a bicyclic moiety, the cyclic moiety is optionally substituted with at least one substituent selected independently from: 1) halogen, cyano, or hydroxyl; 2) an alkyl, a haloalkyl, a cycloalkyl, an alkoxy, a cycloalkyl-substituted alkyl, an alkoxyalkyl, a cycloalkoxy, a haloalkoxy, an aryl, an aryloxy, an aralkyl, a heteroaryl or a heteroaryloxy, any of which having up to 12 carbon atoms, wherein any heteroaryl or heteroaryloxy comprises at least one heteroatom or heterogroup selected independently from O, N, S, or $NR^{10}$; or 3) $CO_2R^6$, $COR^8$, $SO_2R^8$, $SO_2NR^6R^7$, or $CONR^6R^7$;

$R^4$, $R^6$, $R^7$, and $R^8$ are optionally substituted with at least one substituent, and when substituted, the substituents are selected independently from: 1) halide, hydroxy, cyano, or $NR^6R^7$; or 2) an alkyl or an alkoxy, any of which having up to 12 carbon atoms;

and $R^5$ is optionally substituted with at least one substituent, and when substituted, the substituents are selected independently from: 1) halide, hydroxy, cyano, or $NR^6R^7$; or 2) an alkyl having up to 12 carbon atoms.

17. The pharmaceutical composition according to claim 16, further comprising: optionally, a pharmaceutically acceptable auxiliary; optionally, a pharmaceutically acceptable preservative; optionally, a pharmaceutically acceptable excipient; and optionally, a pharmaceutically acceptable diluent.

18. The pharmaceutical composition according to claim 16, wherein the composition is in the form of a tablet, a capsule, a cachet, a powder, a granule, a solution, a suspension, an emulsion, a bolus, a lozenge, a suppository, a pessary, a tampon, a cream, a gel, a paste, a foam, a spray, an aerosol, a microcapsule, a liposome, a transdermal patch, a pastille, a paste, or a mouthwash.

19. A pharmaceutical composition comprising a pharmaceutically acceptable carrier and at least one compound that has the formula:

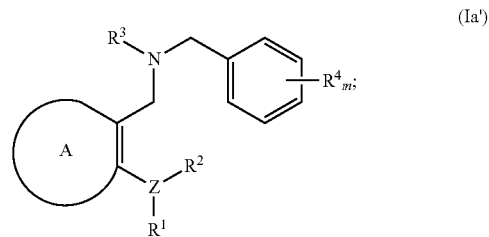

(Ia')

or a salt, a diastereomeric mixture, an enantiomer, a tautomer, or a racemic mixture thereof, or any combination thereof, wherein:

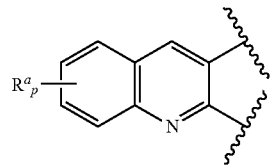

A is:

wherein $R^a$, in each occurrence, is selected independently from: 1) a halogen; a hydroxyl, or a cyano; 2) an alkyl or an alkoxy, any of which having up to 12 carbon atoms; or 3) $CO_2R^6$; and p is an integer from 0 to 3, inclusive;

$R^1$ and $R^2$ are selected independently from: 1) a substituted or an unsubstituted alkyl, cycloalkyl, haloalkyl, aryl, heterocyclyl, heteroaryl, any of which having up to 12 carbon atoms, wherein any heterocyclyl or heteroaryl comprises at least one heteroatom or heterogroup selected independently from O, N, S, $NR^{10}$, $SO_2$, or CO; 2) $CO_2R^6$, $COR^8$, $SO_2R^8$, $SO_2NR^6R^7$, or $CONR^6R^7$; or 3) $(CHR^x)_nR^5$ or $(CH_2)_nR^dCO_2R^e$, wherein n, in each occurrence, is 1, 2, or 3; $R^x$, in each occurrence, is selected independently from an alkyl or an alkoxy, either of which having up to 12 carbon atoms, or hydrogen; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen;

or $R^1$ and $R^2$ together with the diradical Z to which they are attached form a substituted or an unsubstituted monocyclic or bicyclic moiety comprising up to 12 carbon atoms, and optionally comprising 1, 2, or 3 heteroatoms or heterogroups in addition to Z, selected independently from O, N, S, $NR^{10}$, $SO_2$, or CO;

$R^3$ is selected from: 1) hydrogen or cyano; 2) a substituted or an unsubstituted aryl, or a substituted or an unsubstituted 5-, 6-, or 7-membered heterocyclyl or heteroaryl, any of which having up to 12 carbon atoms, comprising 1, 2, or 3 heteroatoms or heterogroups selected independently from O, N, S, $NR^{10}$, $SO_2$, or CO; or 3) $CO_2R^6$, $COR^8$, $SO_2R^8$, $SO_2NR^6R^7$, $CONR^6R^7$, $C(S)NR^6R^7$, $C(S)NHC(O)OR^8$, or $C(S)SR^8$; or 4) a substituted or an unsubstituted group selected from 4,5-dihydro-oxazolyl, tetrazolyl, isoxazolyl, pyridyl, pyrimidinyl, oxadiazolyl, thiazolyl, or oxazolyl; wherein any optional substituent is selected independently from: a) an alkyl or haloalkyl, any of which having up to 12 carbon atoms; or b) $CO_2R^9$, wherein $R^9$ is an alkyl having up to 12 carbon atoms;

wherein when $R^3$ is an aryl, a heterocyclyl, or a heteroaryl, $R^3$ is optionally substituted with up to three substituents selected independently from a halide, a hydroxyl, a cyano, an alkoxy having up to 12 carbon atoms, or $R^{11}$;

$R^4$, in each occurrence, is selected independently from: 1) halogen, cyano, or hydroxy; 2) an alkyl, a cycloalkyl, a cycloalkoxy, an alkoxy, a haloalkyl, or a haloalkoxy, any of which having up to 12 carbon atoms; 3) a substituted or an unsubstituted aryl, aralkyl, aryloxy, heteroaryl, or heteroaryloxy, any of which having up to 12 carbon atoms, wherein any heteroaryl or heteroaryloxy comprises at least one heteroatom or heterogroup selected independently from O, N, S, $NR^{10}$; or 4) $CO_2R^6$, $COR^8$, $SO_2R^8$, $SO_2NR^6R^7$, $CONR^6R^7$, or $(CH_2)_qNR^6R^7$, wherein q is an integer from 0 to 5, inclusive;

m is an integer from 0 to 3, inclusive;

$R^5$, in each occurrence, is selected independently from: 1) an alkoxy, a haloalkoxy, or a cycloalkyl, any of which having up to 12 carbon atoms; 2) a substituted or an unsubstituted aryl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO; 3) hydroxyl, $NR^6R^7$, $CO_2R^6$, $COR^8$, or $SO_2R^8$; or 4) a substituted or an unsubstituted heterocycloalkyl comprising from 3 to 7 ring carbon atoms, and from 1 to 3 heteroatoms or heterogroups, inclusive, selected independently from O, N, S, $NR^{10}$, $SO_2$, or CO;

$R^6$ and $R^7$, in each occurrence, are selected independently from: 1) hydrogen; 2) an alkyl, a cycloalkyl, or a haloalkyl, any of which having up to 12 carbon atoms; or 3) a substituted or an unsubstituted aryl, aralkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

or $R^6$ and $R^7$ together with the nitrogen atom to which they are attached form a substituted or an unsubstituted cyclic moiety having from 3 to 7 ring carbon atoms, and optionally comprising 1, 2, or 3 heteroatoms in addition to the nitrogen atom, to which $R^6$ and $R^7$ are bonded, selected independently from O, N, S, or $NR^{10}$;

$R^8$, in each occurrence, is selected independently from: 1) an alkyl, a cycloalkyl, or a haloalkyl, any of which having up to 12 carbon atoms; or 2) a substituted or an unsubstituted aryl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

$R^{10}$, in each occurrence, is selected independently from: 1) hydrogen; or 2) an alkyl, a cycloalkyl, a haloalkyl, an aryl, or an aralkyl, any of which having up to 12 carbon atoms;

Z is N; or the $ZR^1$ moiety is S, CO, or $SO_2$;

$R^{11}$ is selected independently from:

1) an alkyl, a haloalkyl, a cycloalkyl, or an alkoxycarbonyl, any of which having up to 12 carbon atoms;

2) a substituted or an unsubstituted heteroaryl or heterocyclyl, any of which having up to 12 carbon atoms, comprises at least one heteroatom or heterogroup selected independently from O, N, S, $NR^{10}$, $SO_2$, or CO, wherein any substituted heteroaryl or heterocyclyl is substituted with up to three substituents selected independently from an alkyl having up to 12 carbon atoms or a hydroxyl; or 3) $-CO-Z^2-R^{13}$, $-CO-R^{12}$, $-CO-Z^2-(CH_2)_r-CO-Z^2-R^{13}$, $-NR^{15}R^{16}$, $-Z^2-CO-(CH_2)_r-Z^2-R^{13}$, $-Z^2-CO-(CH_2)_r-CO-Z^2-R^{13}$, $-O-(CH_2)_r-CO-Z^2-R^{13}$, $-O-(CH_2)_r-R^{14}$, $-O-R^{12}-(CH_2)_r-R^{13}$, $-O-R^{14}-CO-O-R^{13}$, $-O-(CH_2)_r-R^{12}$, $-O-(CH_2)_r-NR'R''$, $-O-(CH_2)_r-CO_2-(CH_2)_r-R^{13}$, $-O-(CH_2)_r-SR^8$, $-O-(CH_2)_r-CO_2-R^{13}$, $-O-(CH_2)_r-CONR'R''$, $-O-(CH_2)_r-CONH-(CH_2)_r-OR^{13}$, $-O-(CH_2)_r-SO_2R^8$, $-O-(CH_2)_r-R^{13}$, $-O-(CH_2)_r-OR^{13}$, $-O-(CH_2)_r-O-(CH_2)_r-OR^{13}$, $-S-(CH_2)_r-CONR'R''$, $-SO_2-(CH_2)_r-OR^{13}$, $-SO_2-(CH_2)_r-CONR'R''$, $-(CH_2)_r-O-CO-R^8$, $-(CH_2)_r-R^{12}$, $-(CH_2)_r-R^{13}$, $-(CH_2)_r-CO-Z^2-R^{13}$, $-(CH_2)_r-Z^2-R^{13}$, or -alkenylene-$CO_2-(CH_2)_r-R^{13}$;

r, in each occurrence, is independently 1, 2, or 3;

$R^{12}$, in each occurrence, is independently selected from a substituted or an unsubstituted heterocyclyl having up to 12 carbon atoms, comprising at least one heteroatom or heterogroup selected independently from O, N, S, $NR^{10}$, $SO_2$, or CO, wherein any substituted heterocyclyl is substituted with up to three substituents selected independently from an acyl, an alkyl, or an alkoxycarbonyl, any of which having up to 12 carbon atoms, or $-COOH$;

$R^{13}$, in each occurrence, is independently selected from: 1) hydrogen; or 2) a cycloalkyl, an aryl, a haloalkyl, a heterocyclyl, or an alkyl group optionally substituted with at least one hydroxyl, any of which having up to 12 carbon atoms, wherein any heterocyclyl comprises at least one heteroatom or heterogroup selected independently from O, N, S, $NR^{10}$, $SO_2$, or CO;

$R^{14}$, in each occurrence, is independently selected from a heterocyclyl, a cycloalkyl, or an aryl, any of which having up to 12 carbon atoms, wherein any heterocyclyl comprises at least one heteroatom or heterogroup selected independently from O, N, S, $NR^{10}$, $SO_2$, or CO;

$Z^2$, in each occurrence, is selected independently from $NR^{10}$ or O;

R' and R", in each occurrence, are independently selected from hydrogen or an alkyl having up to 12 carbon atoms; and $R^{15}$ and $R^{16}$, in each occurrence, are independently selected from: 1) hydrogen; 2) an alkyl having up to 12 carbon atoms; or 3) —$(CH_2)_r$—O—$R^{13}$, —$(CH_2)_r$—$R^{14}$, —$COR^{13}$, —$(CH_2)_r$—CO—$Z^2$—$R^{13}$, —$CO_2R^{13}$, —$CO_2$—$(CH_2)_r$—$R^{13}$, —$CO_2$—$(CH_2)_r$—$R^{12}$, —$CO_2$—$(CH_2)_r$—CO—$Z^2$—$R^{13}$, —$CO_2$—$(CH_2)_r$—$OR^{13}$, —CO—$(CH_2)_r$—O—$(CH_2)_r$—O—$(CH_2)_r$—$R^{13}$, —CO—$(CH_2)_r$—$O(CH_2)_r$—$OR^{13}$, or —CO—NH—$(CH_2)_r$—$OR^{13}$;

or $R^{15}$ and $R^{16}$ together with the nitrogen atom to which they are attached form a substituted or an unsubstituted cyclic moiety comprising up to 12 carbon atoms, optionally comprising at least one additional heteroatom or heterogroup selected independently from O, N, S, $NR^{10}$, $SO_2$, or CO; wherein any substituted cyclic moiety is substituted with up to three substituents selected independently from: 1) hydroxyl; 2) an alkyl or a heteroaryl, any of which having up to 12 carbon atoms, wherein any heteroaryl comprises at least one heteroatom or heterogroup selected independently from O, N, S, or $NR^{10}$; or 3) $COOR^{13}$, —$Z^2$—$(CH_2)_r$—$R^{13}$, —$COR^{13}$, —$CO_2$—$(CH_2)_r$—$R^{13}$, —$CO(CH_2)_r$—O—$R^{13}$, —$(CH_2)_r$—$CO_2$—$R^{13}$, —$SO_2R^8$, —$SO_2NR'R''$, or —NR'R'';

wherein the —$(CH_2)_r$— linking moiety, in any occurrence, is optionally substituted with at least one group selected independently from hydroxyl, amino, or an alkyl having up to 3 carbon atoms;

when $R^1$ and $R^2$ do not form a monocyclic or bicyclic moiety, $R^1$ and $R^2$ are optionally substituted with 1 or 2 substituents, and when substituted, the substituents are selected independently from: 1) an alkyl, a cycloalkyl, a haloalkyl, an alkoxy, an aryl, a heteroaryl, or a heterocyclyl, any of which having up to 12 carbon atoms, wherein any heteroaryl or heterocyclyl comprises at least one heteroatom or heterogroup selected independently from O, N, S, $NR^{10}$, $SO_2$, or CO; or 2) halogen, cyano, or hydroxyl;

when $R^1$ and $R^2$ together with the diradical Z to which they are attached form a monocyclic or a bicyclic moiety, the cyclic moiety is optionally substituted with at least one substituent selected independently from: 1) halogen, cyano, or hydroxyl; 2) an alkyl, a haloalkyl, a cycloalkyl, an alkoxy, a cycloalkyl-substituted alkyl, an alkoxyalkyl, a cycloalkoxy, a haloalkoxy, an aryl, an aryloxy, an aralkyl, a heteroaryl or a heteroaryloxy, any of which having up to 12 carbon atoms, wherein any heteroaryl or heteroaryloxy comprises at least one heteroatom or heterogroup selected independently from O, N, S, or $NR^{10}$; or 3) $CO_2R^6$, $COR^8$, $SO_2R^8$, $SO_2NR^6R^7$, or $CONR^6R^7$;

$R^4$, $R^6$, $R^7$, and $R^8$ are optionally substituted with at least one substituent, and when substituted, the substituents are selected independently from: 1) halide, hydroxy, cyano, or $NR^6R^7$; or 2) an alkyl or an alkoxy, any of which having up to 12 carbon atoms; and $R^5$ is optionally substituted with at least one substituent, and when substituted, the substituents are selected independently from: 1) halide, hydroxy, cyano, or $NR^6R^7$; or 2) an alkyl having up to 12 carbon atoms.

20. The pharmaceutical composition according to claim 19,

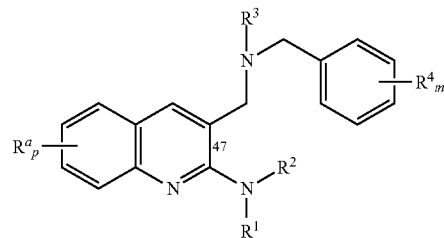

wherein the at least one compound has the formula:
(II);
or a salt, a diastereomeric mixture, an enantiomer, a tautomer, or a racemic mixture thereof, or any combination thereof, wherein:

$R^1$ and $R^2$ are selected independently from: 1) a substituted or an unsubstituted alkyl or a substituted or an unsubstituted cycloalkyl, either of which having up to 12 carbon atoms; 2) $COR^8$ or $CO_2R^6$; or 3) $(CH_2)_nR^5$ or $(CH_2)_nR^dCO_2R^e$, wherein n, in each occurrence, is 1 or 2; $R^d$, in each occurrence, is selected independently from an alkyl, a cycloalkyl, an aryl, a heterocyclyl, or a heteroaryl, any of which having up to 12 carbon atoms, wherein any heterocyclyl or heteroaryl comprises at least one heteroatom or heterogroup selected independently from O, N, S, $NR^{10}$, $SO_2$, or CO; and $R^e$, in each occurrence, is selected independently from an alkyl or a cycloalkyl, either of which having up to 12 carbon atoms, or hydrogen;

$R^3$ is selected from: 1) hydrogen or cyano; 2) a substituted or an unsubstituted, 5-, 6-, or 7-membered heterocyclyl or heteroaryl, any of which having up to 12 carbon atoms, comprising 1, 2, or 3 heteroatoms or heterogroups selected independently from O, N, S, $NR^{10}$, $SO_2$, or CO; or 3) $CO_2R^6$, $C(S)SR^8$, or $C(S)NHC(O)OR^8$; or 5) a substituted or an unsubstituted group selected from 4,5-dihydro-oxazolyl, tetrazolyl, isoxazolyl, pyridyl, pyrimidinyl, oxadiazolyl, thiazolyl, or oxazolyl; wherein any optional substituent is selected independently from: a) an alkyl or haloalkyl, any of which having up to 12 carbon atoms; or b) $CO_2R^9$, wherein $R^9$ is an alkyl having up to 12 carbon atoms;

$R^4$, in each occurrence, is selected independently from: 1) halogen or cyano; or 2) an alkyl or a haloalkyl, either of which having up to 12 carbon atoms; m is an integer from 0 to 3, inclusive;

$R^5$, in each occurrence, is selected independently from: 1) a substituted or an unsubstituted aryl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

$R^6$ is selected from: 1) hydrogen; 2) an alkyl, a cycloalkyl, or a haloalkyl, any of which having up to 12 carbon atoms; or 3) a substituted or an unsubstituted aryl, aralkyl, heterocyclyl, or heteroaryl, any of which having up to 12 carbon atoms, wherein any heterocyclyl or heteroaryl comprises at least one heteroatom or heterogroup selected independently from O, N, S, $NR^{10}$, $SO_2$, or CO;

$R^8$, in each occurrence, is selected independently from an alkyl, a cycloalkyl, or a haloalkyl, any of which having up to 12 carbon atoms or a substituted or an unsubstituted aryl, heteroaryl, or heterocyclyl, any of which having up to 12 carbon atoms, wherein any heteroaryl or heterocyclyl comprises at least one heteroatom or heterogroup selected independently from O, N, S, $NR^{10}$, $SO_2$, or CO;

$R^{10}$, in each occurrence, is selected independently from: 1) hydrogen; or 2) an alkyl, a cycloalkyl, a haloalkyl, an aryl, or an aralkyl, any of which having up to 12 carbon atoms;

$R^a$, in each occurrence, is selected independently from: 1) halogen, hydroxyl, or cyano; 2) an alkyl, or an alkoxy, any of which having up to 12 carbon atoms; or 3) $CO_2R^6$; and p is an integer from 0 to 3, inclusive.

21. The pharmaceutical composition according to claim 19, wherein the at least one compound has the formula:

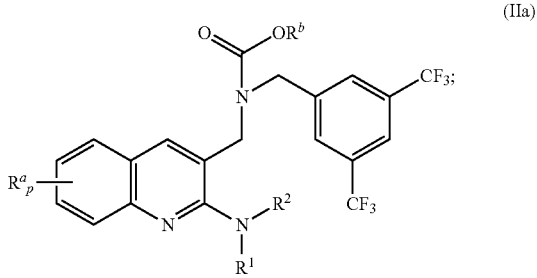

(IIa)

or a salt, a diastereomeric mixture, an enantiomer, a tautomer, or a racemic mixture thereof, or any combination thereof, wherein: $R^b$ is selected independently from: 1) hydrogen; or 2) an alkyl or a cycloalkyl, either of which having up to 12 carbon atoms.

22. A pharmaceutical composition comprising a pharmaceutically acceptable carrier and at least one compound having the formula:

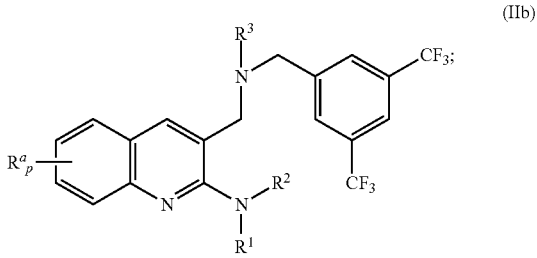

(IIb)

or a salt, a diastereomeric mixture, an enantiomer, a tautomer, or a racemic mixture thereof, or any combination thereof, wherein:

$R^1$ and $R^2$ are selected independently from: 1) a substituted or an unsubstituted alkyl, cycloalkyl, haloalkyl, aryl, heterocyclyl, any of which having up to 12 carbon atoms, wherein any heterocyclyl comprises at least one heteroatom or heterogroup selected independently from O, N, $NR^{10}$, or CO; 2) $COR^8$, or 3) $(CHR^x)_nR^5$, wherein n, in each occurrence, is 1, 2, or 3; $R^x$, in each occurrence, is selected independently from an alkyl or an alkoxy, either of which having up to 12 carbon atoms, or hydrogen;

or $R^1$ and $R^2$ together with the nitrogen atom to which they are attached form a substituted or an unsubstituted monocyclic or bicyclic moiety comprising up to 12 carbon atoms, and optionally comprising 1, 2, or 3 heteroatoms or heterogroups in addition to Z, selected independently from O, N, —$NR^{10}$ or CO;

$R^3$ is selected from a substituted or an unsubstituted group selected from tetrazolyl, 1,3,4-oxadiazolyl, oxazolyl, pyrimidinyl, 4,5-dihydro-oxazolyl, pyridyl, thiazolyl, or isoxazolyl; wherein any optional substituent on $R^3$ is selected independently from an alkyl or a haloalkyl, any of which having up to 12 carbon atoms;

$R^5$, in each occurrence, is selected independently from: 1) an alkoxy, a haloalkoxy, or a cycloalkyl, any of which having up to 12 carbon atoms; 2) a substituted or an unsubstituted aryl, or heterocyclyl any of which having up to 12 carbon atoms, wherein any heterocyclyl comprises at least one heteroatom or heterogroup selected independently from O, N, $NR^{10}$, or CO; 3) hydroxyl, $NR^6R^7$, $COR^8$, or 4) a substituted or an unsubstituted heterocycloalkyl comprising from 3 to 7 ring carbon atoms, and from 1 to 3 heteroatoms or heterogroups, inclusive, selected independently from O, N, $NR^{10}$, or CO;

$R^6$ and $R^7$, in each occurrence, are selected independently from: 1) hydrogen; 2) an alkyl, a cycloalkyl, or a haloalkyl, any of which having up to 12 carbon atoms; or 3) a substituted or an unsubstituted aryl, aralkyl, heterocyclyl, any of which having up to 12 carbon atoms, wherein any heterocyclyl comprises at least one heteroatom or heterogroup selected independently from O, N, $NR^{10}$, or CO; or $R^6$ and $R^7$ together with the nitrogen atom to which they are attached form a substituted or an unsubstituted cyclic moiety having from 3 to 7 ring carbon atoms, and optionally comprising 1, 2, or 3 heteroatoms in addition to the nitrogen atom to which $R^6$ and $R^7$ are bonded, selected independently from O, N, or $NR^{10}$;

$R^8$, in each occurrence, is selected independently from: 1) an alkyl, a cycloalkyl, or a haloalkyl, any of which having up to 12 carbon atoms; or 2) a substituted or an unsubstituted aryl, heterocyclyl, or heteroaryl, any of which having up to 12 carbon atoms, wherein any heterocyclyl or heteroaryl comprises at least one heteroatom or heterogroup selected independently from O, N, $NR^{10}$, or CO;

$R^{10}$, in each occurrence, is selected independently from: 1) hydrogen; or 2) an alkyl, a cycloalkyl, a haloalkyl, an aryl, or an aralkyl, any of which having up to 12 carbon atoms;

Z is N;

when $R^1$ and $R^2$ do not form a monocyclic or bicyclic moiety, $R^1$ and $R^2$ are optionally substituted with 1 or 2 substituents, and when substituted, the substituents are selected independently from: 1) an alkyl, a cycloalkyl, a haloalkyl, an alkoxy, an aryl, a heteroaryl, or a heterocyclyl, any of which having up to 12 carbon atoms, wherein any heterocyclyl comprises at least one heteroatom or heterogroup selected independently from O, N, $NR^{10}$, or CO; or 2) halogen, cyano, or hydroxyl;

when $R^1$ and $R^2$ together with the nitrogen atom to which they are attached form a monocyclic or a bicyclic moiety, the cyclic moiety is optionally substituted with at least one substituent selected independently from: 1) halogen, cyano, or hydroxyl; 2) an alkyl, a haloalkyl, a cycloalkyl, an alkoxy, a cycloalkyl-substituted alkyl, an alkoxyalkyl, a cycloalkoxy, a haloalkoxy, an aryl, an aryloxy, or an aralkyl, any of which having up to 12 carbon atoms;

$R^4$, $R^6$, $R^7$, and $R^8$ are optionally substituted with at least one substituent, and when substituted, the substituents are selected independently from: 1) halide, hydroxy, cyano, or $NR^6R^7$; or 2) an alkyl or an alkoxy, any of which having up to 12 carbon atoms;

$R^5$ is optionally substituted with at least one substituent, and when substituted, the substituents are selected independently from: 1) halide, hydroxy, cyano, or $NR^6R^7$; or 2) an alkyl having up to 12 carbon atoms; and wherein $R^a$, in each occurrence, is selected independently from: 1) a halogen; a hydroxyl, or a cyano; 2) an alkyl or an alkoxy, any of which having up to 12 carbon atoms; or 3) $CO_2R^6$; and p is an integer from 0 to 3, inclusive.

23. The pharmaceutical composition according to claim 22, wherein the at least one compound has the formula: or a salt, a diastereomeric mixture, an enantiomer, a tautomer, or a racemic mixture thereof, or any combination thereof, wherein: $R^a$ is selected from methyl, ethyl, or methoxy.

24. A pharmaceutical composition comprising a pharmaceutically acceptable carrier and at least one compound, wherein the compound is:

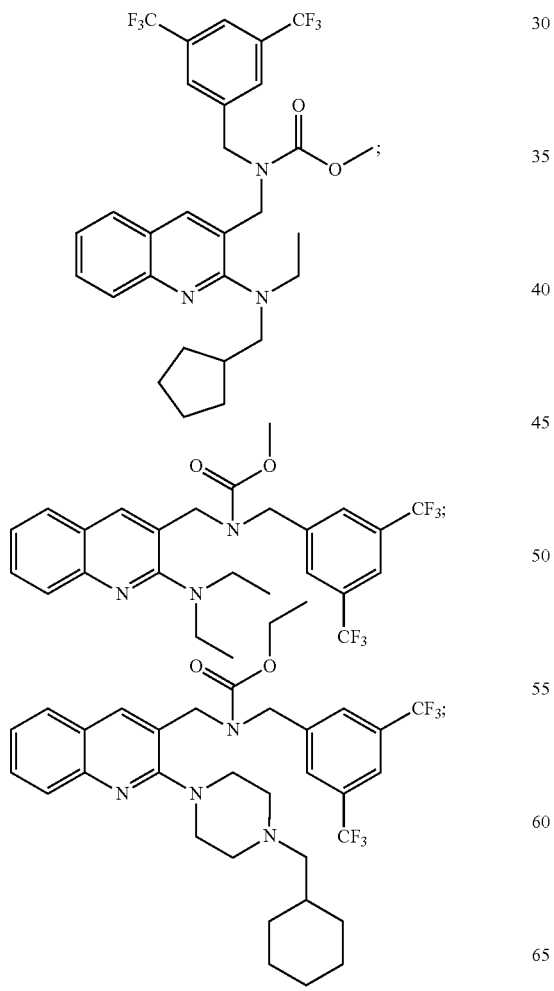

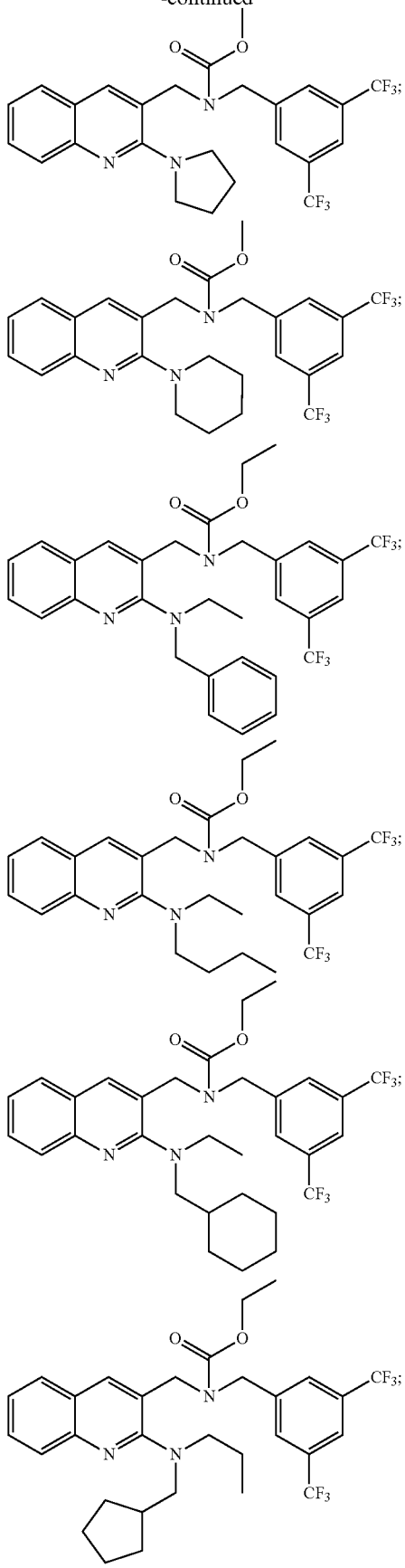

-continued
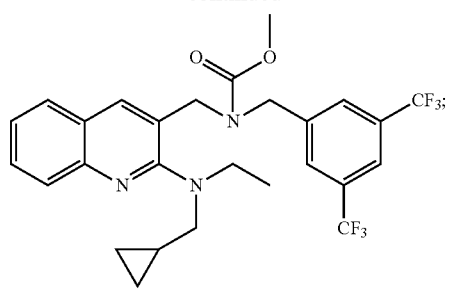
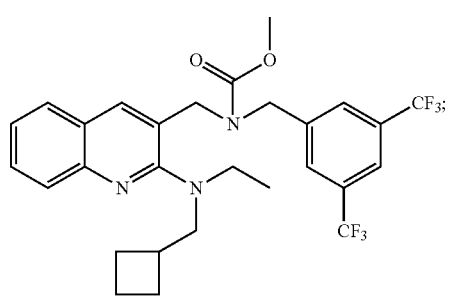
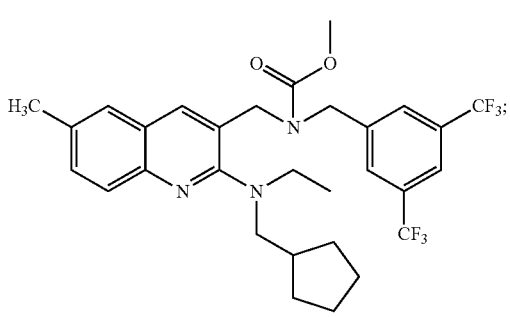
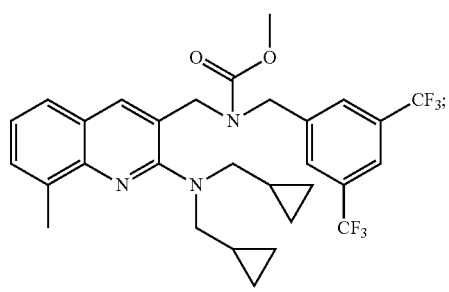
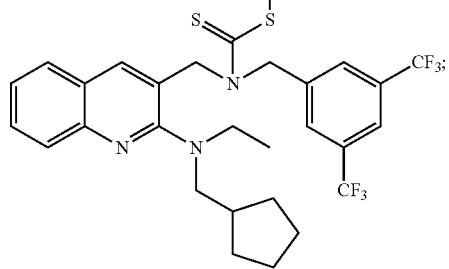
-continued
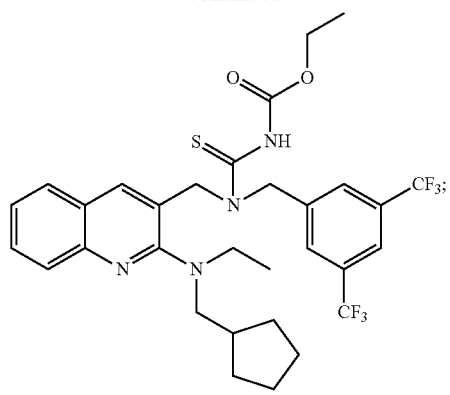
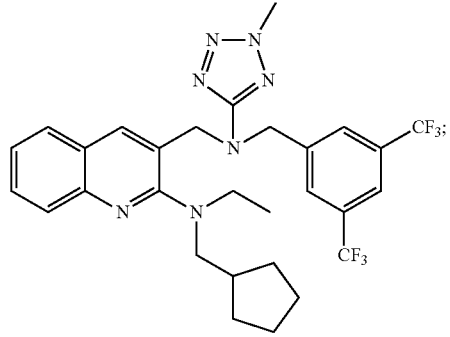
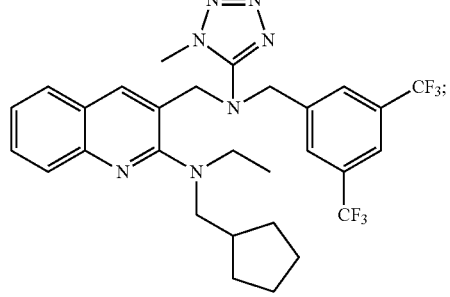
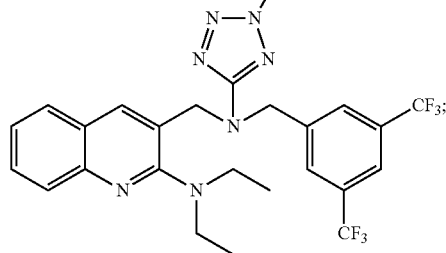
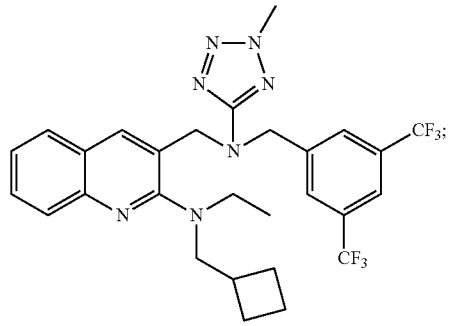

-continued

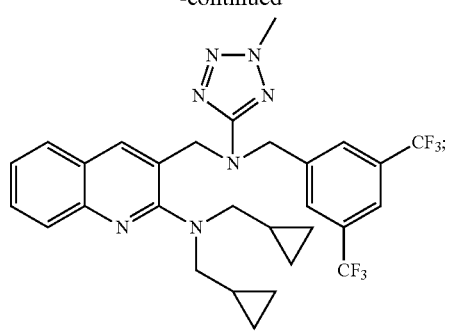

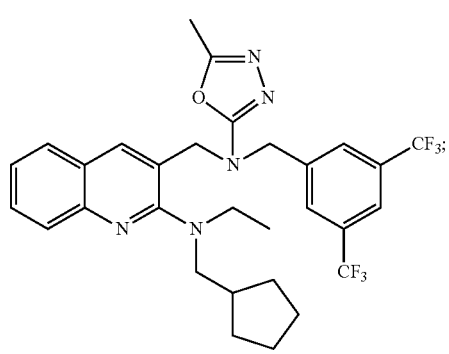

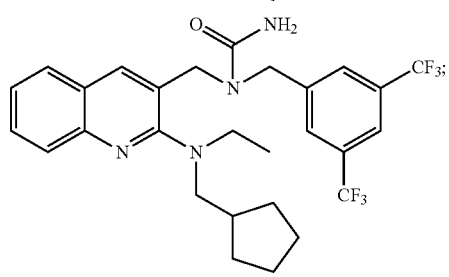

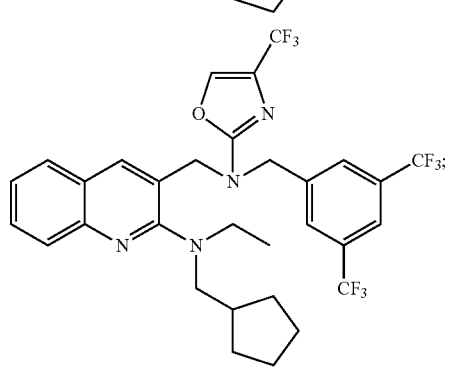

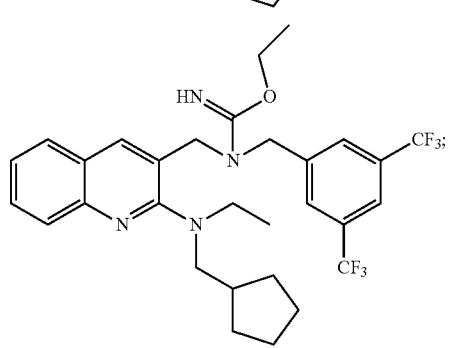

-continued

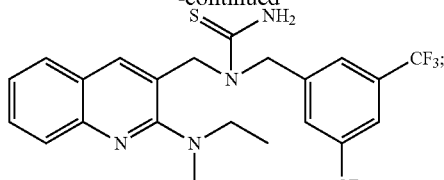

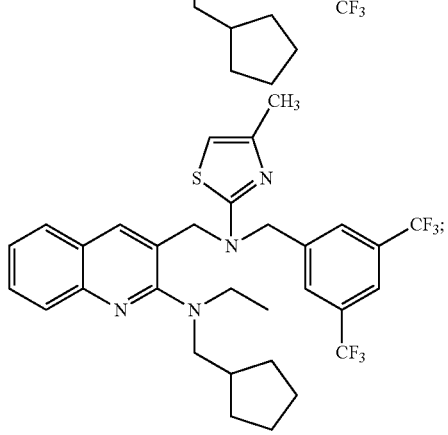

and combinations thereof.

25. The pharmaceutical composition according to claim 24, further comprising:
optionally, a pharmaceutically acceptable auxiliary;
optionally, a pharmaceutically acceptable preservative;
optionally, a pharmaceutically acceptable excipient; and
optionally, a pharmaceutically acceptable diluent.

26. The pharmaceutical composition according to claim 25, wherein the composition is in the form of a tablet, a capsule, a cachet, a powder, a granule, a solution, a suspension, an emulsion, a bolus, a lozenge, a suppository, a pessary, a tampon, a cream, a gel, a paste, a foam, a spray, an aerosol, a microcapsule, a liposome, a transdermal patch, a pastille, a paste, or a mouthwash.

27. A compound selected from the group consisting of:

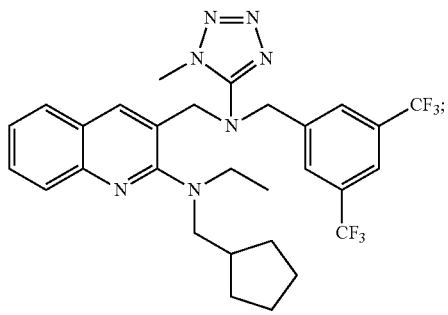

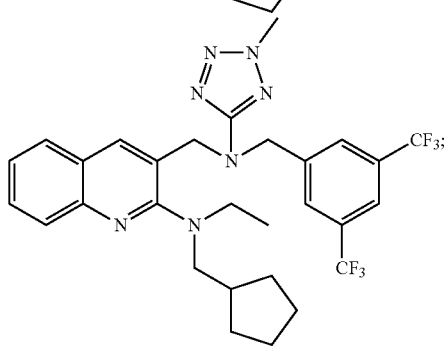

-continued
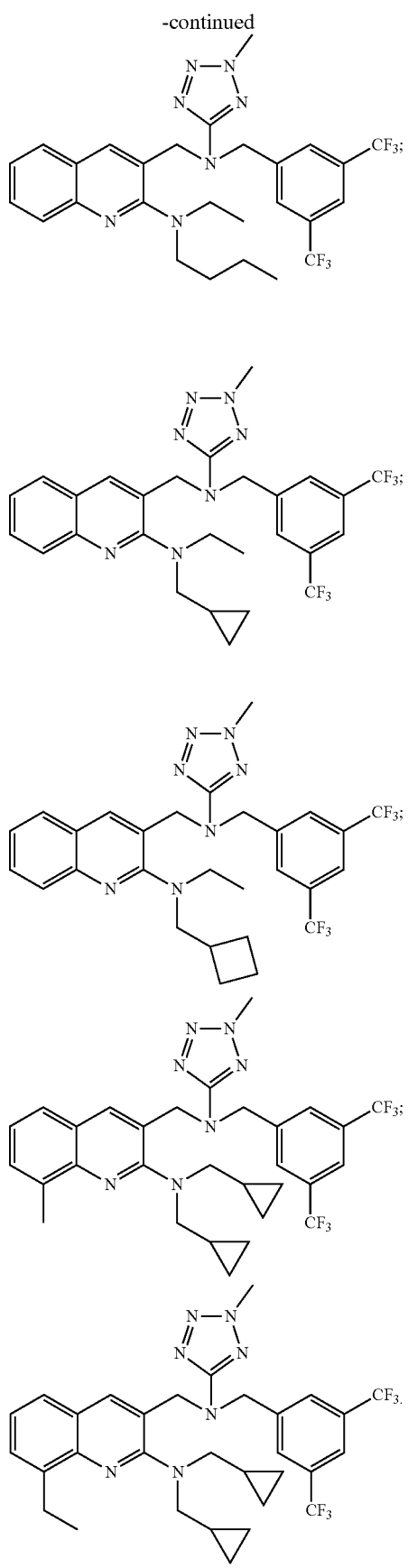
28. A pharmaceutical composition comprising one or more compounds selected from the group consisting of:
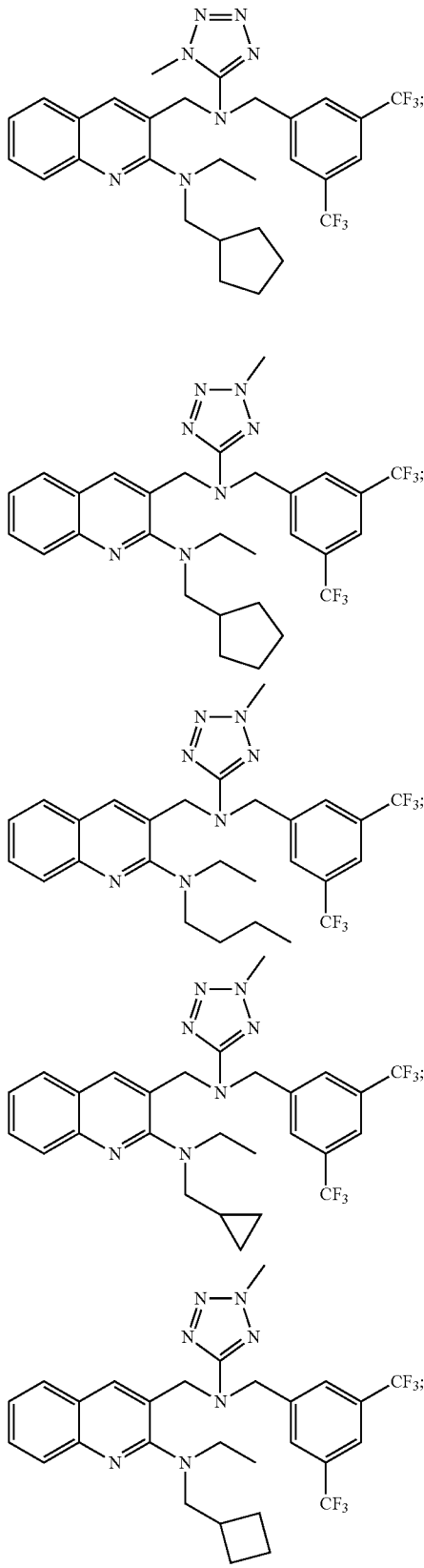

-continued
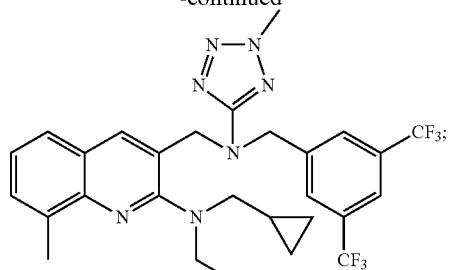
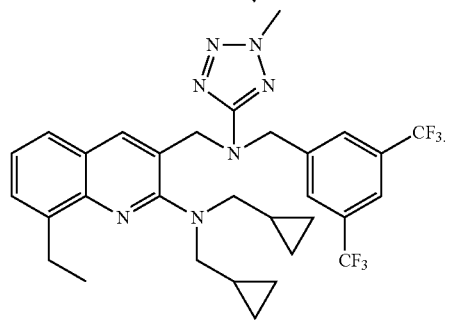
* * * * *